(12) United States Patent
Patron et al.

(10) Patent No.: US 10,392,371 B2
(45) Date of Patent: Aug. 27, 2019

(54) COMPOUNDS USEFUL AS MODULATORS OF TRPM8

(71) Applicant: Senomyx, Inc., San Diego, CA (US)

(72) Inventors: Andrew P. Patron, San Diego, CA (US); Alain Noncovich, San Diego, CA (US); Timothy Davis, San Diego, CA (US); Chad Priest, San Diego, CA (US); Joseph R. Fotsing, San Diego, CA (US); Jane Ung, San Diego, CA (US); Catherine Tachdjian, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 15/764,204

(22) PCT Filed: Sep. 21, 2016

(86) PCT No.: PCT/US2016/052777
§ 371 (c)(1),
(2) Date: Mar. 28, 2018

(87) PCT Pub. No.: WO2017/058594
PCT Pub. Date: Apr. 6, 2017

(65) Prior Publication Data
US 2018/0273517 A1   Sep. 27, 2018
US 2019/0177308 A9   Jun. 13, 2019

Related U.S. Application Data

(60) Provisional application No. 62/236,080, filed on Oct. 1, 2015.

(51) Int. Cl.
*C07D 409/12* (2006.01)
*A61K 9/00* (2006.01)
*A61K 31/4155* (2006.01)
*A23L 33/10* (2016.01)
*A23L 2/52* (2006.01)
*B65D 65/38* (2006.01)
*B65D 81/18* (2006.01)

(52) U.S. Cl.
CPC ............ *C07D 409/12* (2013.01); *A23L 2/52* (2013.01); *A23L 33/10* (2016.08); *A61K 9/0014* (2013.01); *A61K 31/4155* (2013.01); *B65D 65/38* (2013.01); *B65D 81/18* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,419,543 A | 12/1968 | Mold et al. |
| 3,488,419 A | 1/1970 | McCune et al. |
| 4,157,384 A | 6/1979 | Browning et al. |
| 4,459,425 A | 7/1984 | Amano et al. |
| 5,009,893 A | 4/1991 | Cherukuri et al. |
| 5,112,598 A | 5/1992 | Biesalski |
| 5,286,500 A | 2/1994 | Synosky et al. |
| 5,372,824 A | 12/1994 | Record et al. |
| 5,556,611 A | 9/1996 | Biesalski |
| 5,698,155 A | 12/1997 | Grosswald et al. |
| 5,698,181 A | 12/1997 | Luo |
| 5,725,865 A | 3/1998 | Mane et al. |
| 5,821,450 A | 10/1998 | Fedida |
| 5,843,466 A | 12/1998 | Mane et al. |
| 6,196,348 B1 | 3/2001 | Yano et al. |
| 6,328,982 B1 | 12/2001 | Shiroyama et al. |
| 6,468,576 B1 | 10/2002 | Sher et al. |
| 6,627,233 B1 | 9/2003 | Wolf et al. |
| 7,030,273 B1 | 4/2006 | Sun |
| 2002/0077367 A1 | 6/2002 | Amano et al. |
| 2002/0142015 A1 | 10/2002 | Kumamoto et al. |
| 2002/0156327 A1 | 10/2002 | Amano et al. |
| 2003/0072842 A1 | 4/2003 | Johnson et al. |
| 2003/0161802 A1 | 8/2003 | Flammer et al. |
| 2005/0004214 A1 | 1/2005 | Dewis et al. |
| 2005/0084506 A1 | 4/2005 | Tachdjian et al. |
| 2005/0176598 A1 | 8/2005 | Bergquist et al. |
| 2005/0222256 A1 | 10/2005 | Erman et al. |
| 2006/0159734 A1 | 7/2006 | Shudo |
| 2006/0159819 A1 | 7/2006 | Witkewitz et al. |
| 2006/0210482 A1 | 9/2006 | Cassara |
| 2006/0263411 A1 | 11/2006 | Tachdjian et al. |
| 2007/0225378 A1 | 9/2007 | Ishida et al. |
| 2008/0008665 A1 | 1/2008 | Ramji et al. |
| 2008/0107742 A1 | 5/2008 | Hare |
| 2008/0175800 A1 | 7/2008 | Schoening et al. |
| 2008/0176945 A1 | 7/2008 | Galopin et al. |
| 2008/0253974 A1 | 10/2008 | Galopin et al. |
| 2008/0300314 A1 | 12/2008 | Galopin et al. |
| 2008/0311232 A1 | 12/2008 | Furrer et al. |
| 2008/0319055 A1 | 12/2008 | Cole et al. |
| 2009/0054520 A1 | 2/2009 | Surburg et al. |
| 2009/0098066 A1 | 4/2009 | Galopin et al. |
| 2009/0105237 A1 | 4/2009 | Bell et al. |
| 2009/0111834 A1 | 4/2009 | Tachdjian et al. |
| 2009/0148938 A1 | 6/2009 | Gravina et al. |
| 2009/0163572 A1 | 6/2009 | Bom |
| 2009/0220662 A1 | 9/2009 | Tachdjian et al. |
| 2009/0312384 A1 | 12/2009 | Furrer et al. |

(Continued)

FOREIGN PATENT DOCUMENTS

EP    1332772 A2    8/2003
EP    2014333 A1    1/2009

(Continued)

OTHER PUBLICATIONS

International Report on Patentability for International Patent Application No. PCT/US2016/052777, dated Apr. 12, 2018, 9 pages.

(Continued)

*Primary Examiner* — Karl J Puttlitz
(74) *Attorney, Agent, or Firm* — Armstrong Teasdale LLP

(57) ABSTRACT

Provided herein are compounds which are useful as cooling sensation compounds.

22 Claims, No Drawings

(56) References Cited

U.S. PATENT DOCUMENTS

| | | |
|---|---|---|
| 2010/0035938 A1 | 2/2010 | Bell et al. |
| 2010/0086498 A1 | 4/2010 | Haught et al. |
| 2010/0104547 A1 | 4/2010 | Logsdon |
| 2010/0197713 A1 | 8/2010 | Furrer et al. |
| 2010/0226871 A1 | 9/2010 | Fraser et al. |
| 2010/0297038 A1 | 11/2010 | Furrer |
| 2011/0070329 A1 | 3/2011 | Kazimierski et al. |
| 2011/0081393 A1 | 4/2011 | Komatsuki et al. |
| 2011/0091531 A1 | 4/2011 | Furrer et al. |
| 2011/0135627 A1 | 6/2011 | Lamotta et al. |
| 2011/0182833 A1 | 7/2011 | Furrer et al. |
| 2011/0305657 A1 | 12/2011 | Kueper et al. |
| 2012/0095042 A1 | 4/2012 | Furrer |
| 2012/0129827 A1 | 5/2012 | Kazimierski et al. |
| 2012/0201763 A1 | 8/2012 | Tachdjian et al. |
| 2012/0226047 A1 | 9/2012 | Shigemura et al. |
| 2012/0263659 A1 | 10/2012 | Subkowski et al. |
| 2013/0102981 A1 | 4/2013 | Perring et al. |
| 2013/0202543 A1 | 8/2013 | Kueper et al. |
| 2013/0323388 A1 | 12/2013 | Talsma et al. |
| 2013/0324557 A1 | 12/2013 | Priest et al. |
| 2014/0186272 A1 | 7/2014 | Yelm et al. |
| 2014/0335224 A1 | 11/2014 | Asche et al. |
| 2014/0341821 A1 | 11/2014 | Saji et al. |
| 2014/0343158 A1 | 11/2014 | Fusco |
| 2015/0093339 A1 | 4/2015 | Tachdjian et al. |
| 2015/0094365 A1 | 4/2015 | Krohn et al. |
| 2015/0104498 A1 | 4/2015 | Angel et al. |
| 2016/0339026 A1* | 11/2016 | Noncovich .......... A61K 31/515 |
| 2017/0087199 A1* | 3/2017 | Patron .................... A61K 36/81 |

FOREIGN PATENT DOCUMENTS

| | | | |
|---|---|---|---|
| EP | 2787051 | A1 | 10/2014 |
| WO | 0205802 | A1 | 1/2002 |
| WO | 02091849 | A1 | 11/2002 |
| WO | 2004037764 | A1 | 5/2004 |
| WO | 2011147455 | A1 | 12/2011 |
| WO | 2011159935 | A1 | 12/2011 |
| WO | 2012061698 | * | 5/2012 |
| WO | 2012061698 | A2 | 5/2012 |
| WO | 2012101244 | A1 | 8/2012 |
| WO | 2013092711 | A1 | 6/2013 |
| WO | 2014090293 | A1 | 6/2014 |
| WO | 2014130582 | A1 | 8/2014 |

OTHER PUBLICATIONS tended European Search Report for EP Patent Application No. 16852328.0, dated Jan. 30, 2019, 9 pages.

* cited by examiner

COMPOUNDS USEFUL AS MODULATORS OF TRPM8

CROSS-REFERENCE TO RELATED APPLICATIONS

This application is the national stage entry of PCT/US2016/052777, filed on Sep. 21, 2016, which claims the benefit of priority to U.S. Provisional Application No. 62/236,080, filed Oct. 1, 2015, which are incorporated by reference in their entirety herein.

BACKGROUND

Field

The present invention relates to compounds useful as cooling agents.

Background Description

Modulators of the Melastatin Transient Receptor Potential Channel (TRPM8) are known to have a cooling effect. TRPM8 is a channel involved in the chemesthetic sensation, such as cool to cold temperatures as well as the sensation of known cooling agents, such as Menthol and Icilin. However, many of the currently known TRPM8 modulators have deficiencies with regard to strength and/or duration of effect, skin and/or mucosa irritation, odor, taste, solubility, and/or toxicity.

SUMMARY

The present disclosure relates to compounds useful as cooling agents. In some embodiments, the compounds are modulators of TRPM8. Some embodiments include compounds, ingestible compositions, personal care products, and pharmaceutical compositions, and the use and preparation thereof. In particular, some embodiments, relate to specific pyrazolyl and thiophenyl substituted acetamide compounds as disclosed herein.

Some embodiments include a compound selected from

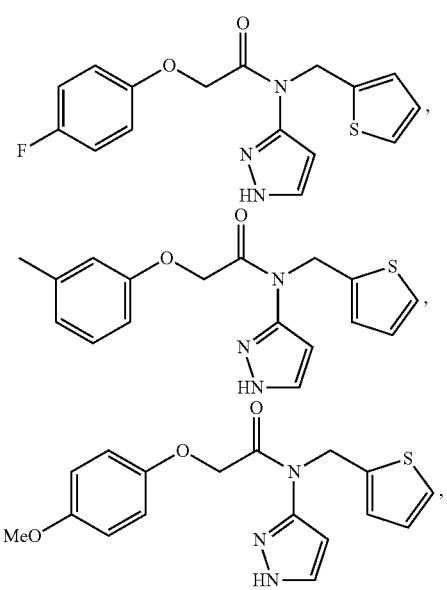

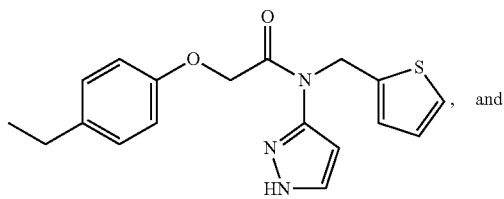

, and

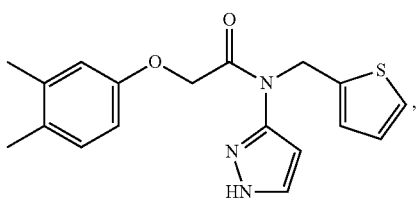

or a salt or solvate thereof.

In some embodiments the compound can have the structure

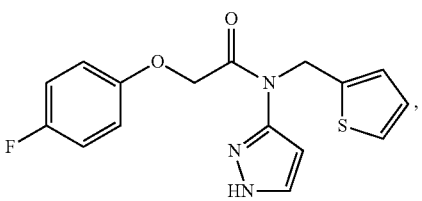

or a salt thereof.

In some embodiments the compound has the structure

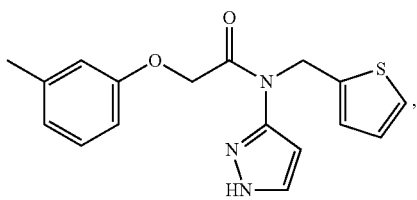 [SMILES: Cc1cccc(OCC(=O)N(Cc2cccs2)c2cc[nH]n2)c1]

or a salt thereof.

In some embodiments the compound can have the structure

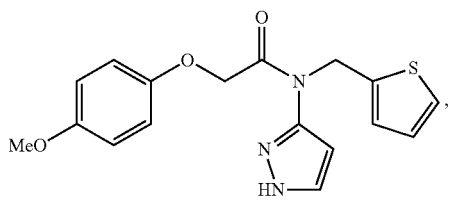 [SMILES: COc1ccc(OCC(=O)N(Cc2cccs2)c2cc[nH]n2)cc1]

or a salt thereof.

In some embodiments the compound can have the structure

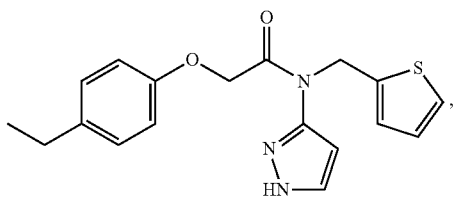 [SMILES: CCc1ccc(OCC(=O)N(Cc2cccs2)c2cc[nH]n2)cc1]

or a salt thereof.

In some embodiments the compound can have the structure

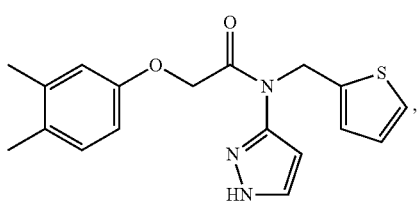 [SMILES: Cc1ccc(OCC(=O)N(Cc2cccs2)c2cc[nH]n2)cc1C]

or a salt thereof.

In some embodiments, a composition is provided, comprising any one of the above compounds and at least one carrier.

In some embodiments, the composition can be an ingestible composition or personal care product.

In some embodiments, the composition can be a food or beverage.

In some embodiments, the composition can be a topical personal care product.

In some embodiments, the composition can be in form of a solid, semi-solid, plaster, solution, suspension, lotion, cream, foam, gel, paste, or emulsion.

In some embodiments, a compound disclosed herein in the composition can be in a concentration ranging from about 0.0001 ppm to 100,000 ppm.

In some embodiments, the compound disclosed herein in the composition can be in a concentration ranging from about 1 ppm to 500 ppm.

In some embodiments, the composition can be a textile product or a packaging material.

Some embodiments include a method of modulating transient receptor potential channel melastatin member 8 (TRPM8) comprising contacting the receptor with a compound of the present disclosure, or a salt or solvate thereof. In some embodiments, the compound can be a TRPM8 receptor agonist.

Some embodiments include a method of modulating the cooling sensation of a composition comprising combining the composition with a compound of the present disclosure, or a salt or solvate thereof, to form a modified composition.

Some embodiments include a method of inducing a cooling sensation in a human or animal comprising contacting the human or animal with a compound of the present disclosure, or a salt or solvate thereof.

DETAILED DESCRIPTION

Some embodiments provide a compound selected from the compounds listed in Table 1, or a salt thereof.

TABLE 1

| Compound Number | Structure |
|---|---|
| 101 | 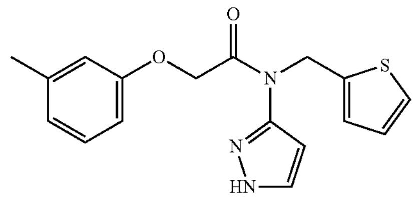 [SMILES: Cc1cccc(OCC(=O)N(Cc2cccs2)c2cc[nH]n2)c1] |
| 102 | 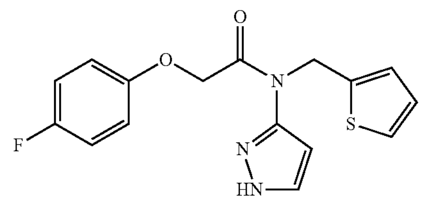 [SMILES: O=C(COc1ccc(F)cc1)N(Cc1cccs1)c1cc[nH]n1] |
| 103 | 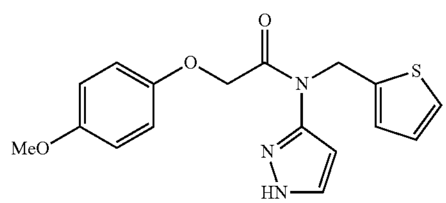 [SMILES: COc1ccc(OCC(=O)N(Cc2cccs2)c2cc[nH]n2)cc1] |
| 104 | 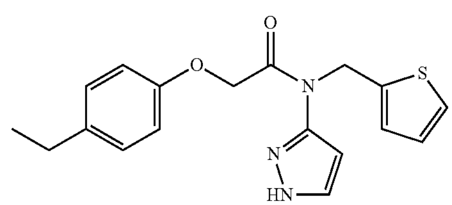 [SMILES: CCc1ccc(OCC(=O)N(Cc2cccs2)c2cc[nH]n2)cc1] |
| 105 | 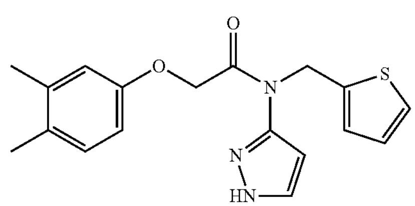 [SMILES: Cc1ccc(OCC(=O)N(Cc2cccs2)c2cc[nH]n2)cc1C] |

In some embodiments, the compound can have the structure of Compound 101, or a salt thereof:

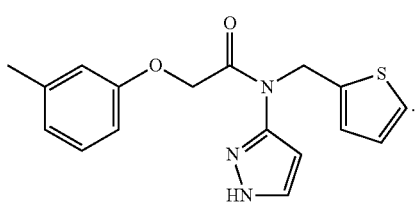 [SMILES: Cc1cccc(OCC(=O)N(Cc2cccs2)c2cc[nH]n2)c1]

In some embodiments, the compound can have the structure of Compound 102, or a salt thereof:

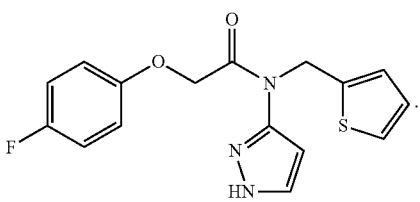 [SMILES: O=C(COc1ccc(F)cc1)N(Cc1cccs1)c1cc[nH]n1]

In some embodiments, the compound can have the structure of Compound 103, or a salt thereof:

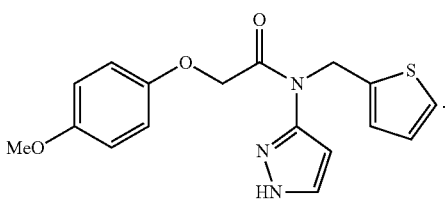 [SMILES: COc1ccc(OCC(=O)N(Cc2cccs2)c2cc[nH]n2)cc1]

In some embodiments, the compound can have the structure of Compound 104, or a salt thereof:

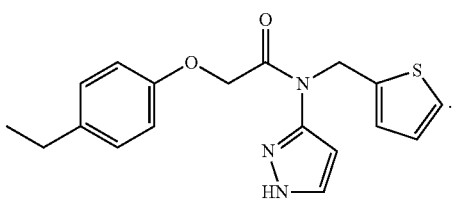 [SMILES: CCc1ccc(OCC(=O)N(Cc2cccs2)c2cc[nH]n2)cc1]

In some embodiments, the compound can have the structure of Compound 105, or a salt thereof:

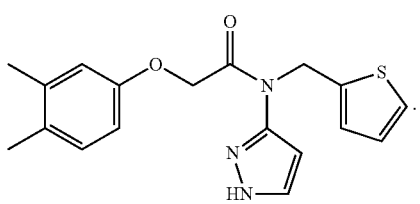 [SMILES: Cc1ccc(OCC(=O)N(Cc2cccs2)c2cc[nH]n2)cc1C]

In some embodiments, a composition is provided, comprising any one Compounds 101-105 and at least one carrier.

In some embodiments, a personal product is provided comprising a compound selected from Compounds 101-105, or a salt thereof.

In some embodiments, the composition comprising a compound selected from Compounds 101-105 can be an ingestible composition or a personal care composition.

In some embodiments, the composition comprising a compound selected from Compounds 101-105 can be an ingestible composition that is a food or beverage.

In some embodiments, the composition comprising a compound selected from Compounds 101-105 can be a topical personal care product.

In some embodiments, the composition comprising a compound selected from Compounds 101-105 can be in form of a solid, semi-solid, plaster, solution, suspension, lotion, cream, foam, gel, paste, emulsion, or a combination thereof.

In some embodiments, the composition can comprise a compound selected from Compounds 101-105 in a concentration ranging from about 0.0001 ppm to 100,000 ppm.

In some embodiments, the composition can comprise a compound selected from Compounds 101-105 in a concentration ranging from about 1 ppm to 500 ppm.

In some embodiments, the composition comprising a compound selected from Compounds 101-105 can be a textile product or a packaging material.

In some embodiments, a method of modulating transient receptor potential channel melastatin member 8 (TRPM8) is provided, comprising contacting the receptor with a compound comprising a compound selected from Compounds 101-105, or a salt or solvate thereof. In some embodiments, the method can be in vitro or in vivo. In some embodiments of the method of modulating TRPM8, the compound comprising a compound selected from Compounds 101-105 can be a TRPM8 receptor agonist.

In some embodiments, a method of modulating the cooling sensation of a composition is provided, comprising combining the composition with a compound selected from Compounds 101-105, or a salt or solvate thereof, to form a modified composition.

In some embodiments, a method of inducing a cooling sensation in a human or animal is provided, comprising contacting the human or animal with a compound selected from Compounds 101-105, or a salt or solvate thereof.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

Compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

"Solvate" refers to the compound formed by the interaction of a solvent and a compound described herein or salt thereof. Suitable solvates are physiologically acceptable solvates including hydrates.

The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

A "personal care product", as used herein, refers to any product that is used by or useful for a person or animal, optionally in contact with the person or animal during its intended use, e.g., in surface contact such as skin or mucosa contact with the person or animal during its intended use.

As used herein, an "ingestible composition" includes any substance that, either alone or together with another substance, can be taken by mouth whether intended for consumption or not. The ingestible composition includes both "food or beverage products" and "non-edible products". By "food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

An "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A "flavor" herein refers to the perception of taste in a subject, which include sweet, sour, salty, bitter and umami (also known as savory). The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "modulator" herein refers to a compound that can regulate the activity of TRPM8. Such regulation includes activating TRPM8, blocking TRPM8, or potentiating/reducing the activation of TRPM8. That is, the modulators include agonists, antagonists, enhancers, and etc.

The term "chemesthesis" or "chemesthetic sensation" herein refers to the sensibility of bodily surface, e.g., the skin and/or mucosal surfaces which arise either when the bodily surface is exposed to heat or coldness or when chemical compounds activate receptors associated with senses that mediate pain, touch, and thermal/cold perception. Particularly, these chemical-induced reactions do not fit into the traditional sense categories of taste and smell. Examples of chemesthetic sensations include the burn-like irritation from chili pepper, the coolness of menthol in mouthwashes and topical analgesic creams, the stinging or tingling of carbonation in the nose and mouth, and the tear-induction of onions. That is, chemesthetic sensations can arise by direct chemical activation of ion channels on sensory nerve fibers, e.g. TRPM8. Because chemoresponsive nerve fibers are present in all types of skin, chemesthetic sensations can be aroused from anywhere on the body's surface as well as from mucosal surfaces in the nose, mouth, eyes, etc.

A "chemesthetic sensation modifier" or "chemesthetic sensation modifying agent" herein refers to a compound, or a salt or solvate thereof, that modulates, including enhancing or potentiating, inducing, or blocking, the chemesthetic sensation in an animal or a human.

A "chemesthetic sensation modulating amount" herein refers to an amount of a compound of the present invention that is sufficient to alter (either induce, increase, or decrease) the chemesthetic sensation in a personal product, sufficiently to be perceived by an animal or human subject. In many embodiments of the invention, at least about 0.001 ppm of the present compound would need to be present in order for most animal or human subjects to perceive a modulation of the chemesthetic sensation in a personal product comprising the present compound. A broad range of concentration that would typically be employed in order to economically provide a desirable degree of chemesthetic sensation modulation can be from about 0.001 ppm to 1000 ppm, or from about 0.01 ppm to about 500 ppm, or from about 0.05 ppm to about 300 ppm, or from about 0.1 ppm to about 200 ppm, or from about 0.5 ppm to about 150 ppm, or from about 1 ppm to about 100 ppm.

A "chemesthetic sensation inducing amount" or "chemesthetic sensation increasing amount" herein refers to an amount of a compound that is sufficient to induce or increase a chemesthetic sensation as perceived by an animal or a human. A broad range of a chemesthetic sensation inducing/increasing amount can be from about 0.001 ppm to 100 ppm, or a narrow range from about 0.1 ppm to about 10 ppm. Alternative ranges of chemesthetic sensation inducing/increasing amounts can be from about 0.01 ppm to about 30 ppm, from about 0.05 ppm to about 15 ppm, from about 0.1 ppm to about 5 ppm, or from about 0.1 ppm to about 3 ppm.

By "oral care composition" is meant a personal care product or other product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

The term "dentifrice", as used herein, includes paste, gel, or liquid formulations unless otherwise specified. The dentifrice composition may be a single phase composition or may be a combination of two or more separate dentifrice compositions. The dentifrice composition may be in any desired form, such as deep striped, surface striped, multi-layered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes safe and effective materials and conventional additives such as used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Herein, the terms "tartar" and "calculus" are used interchangeably and refer to mineralized dental plaque biofilms.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

Compositions

The compounds of the present disclosure can be used as modulators, e.g., agonists, of the TRPM8 receptor in personal products for modulating, e.g., inducing, chemesthetic sensations, particularly the cold or cool sensations.

The present compounds are important to the flavorings and fragrance industry because they can increase or induce/generate a cooling or cold sensation which is often associated with freshness and cleanliness. The present disclosure provides compositions comprising combinations of compounds, including one or more of Compounds 101-105, that provide a cooling sensation and/or are modulators of TRPM8 with other compounds necessary to the production of such items as medicaments, including without limitation tablets, capsules, other dry dosing forms, parenteral forms, topical forms, inhalable dosing forms, and orally administered dissolved forms; foodstuffs and confections; beverages including alcoholic beverages; perfumes, deodorizers, and deodorants; personal care products; oral health products; home and consumer products; probiotic compositions; and smoking articles.

The pleasant cooling sensation provided by Compounds 101-105 contributes to the appeal and acceptability of the products. For example, oral care products such as dentifrices and mouthwashes are formulated with coolants because they provide breath freshening effects and a clean, cool, fresh feeling in the mouth.

As modulators of the TRPM8 receptor, the present compounds also have repellent effect on insects, therapeutic effect in antitumor treatments (e.g. an influencing of prostate tumors), activity in the treatment of inflammatory pain/hyperalgesia, and efficacy (as TRPM8 antagonists) in the treatment of bladder syndrome or overactive bladder.

Some embodiments provide compositions, which comprise one or more of Compounds 101-105 and at least one carrier. The composition can be in any physical form, such as a solid, semi-solid, plaster, solution, suspension, lotion, cream, foam, gel, paste, emulsion, or a combination thereof. Examples of the composition include, but are not limited to, a pharmaceutical composition, an ingestible composition, a chemesthetic concentrate, a personal care product, and a combination thereof. In one embodiment, the composition comprises a chemesthetic sensation modulating amount of the present compound. In another embodiment of the present invention, the composition comprises a chemesthetic sensation inducing amount of the present compound. In certain embodiments, the chemesthetic sensation is a cold or cooling sensation. In one embodiment of the composition, the present compound is in a concentration ranging from about 0.0001 ppm to 100,000 ppm. In another embodiment of the composition, the present compound is in a concentration ranging from about 0.001 ppm to 10,000 ppm. In another embodiment of the composition, the present compound is in a concentration ranging from about 0.01 ppm to 1,000 ppm. In another embodiment of the composition, the present compound is in a concentration ranging from about 0.1 ppm to 500 ppm. In another embodiment of the composition, the present compound is in a concentration ranging from about 1 ppm to 500 ppm. In another embodiment of the composition, the present compound is in a concentration ranging from about 10 ppm to 500 ppm. In another embodiment of the composition, the present compound is in a concentration ranging from about 1 ppm to 400 ppm.

In some embodiments, compounds as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French *vanilla*, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

In one embodiment, a chemesthetic concentrate formulation is provided. The present chemesthetic concentrate formulation can be in a form selected from the group consisting of liquid including solution and suspension, solid, foamy material, paste, gel, cream, and a combination thereof, such as a liquid containing certain amount of solid contents. In one embodiment, the chemesthetic concentrate formulation is in form of a liquid including aqueous-based and nonaqueous-based. The present chemesthetic concentrate formulation can be carbonated or non-carbonated.

The chemesthetic concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the chemesthetic concentrate formulation is formulated to have a low water activity for extended shelf life. Water activity is the ratio of the vapor pressure of water in a formulation to the vapor pressure of pure water at the same temperature. In one embodiment, the chemesthetic concentrate formulation has a water activity of less than about 0.85. In another embodiment, the chemesthetic concentrate formulation has a water activity of less than about 0.80. In another embodiment, the chemesthetic concentrate formulation has a water activity of less than about 0.75.

In one embodiment, the chemesthetic concentrate formulation has the present compound in a concentration that is at least 2 times of the concentration of the compound in a ready-to-use composition. In one embodiment, the chemesthetic concentrate formulation has the present compound in a concentration that is at least 5 times of the concentration of the compound in a ready-to-use composition. In one embodiment, the chemesthetic concentrate formulation has the present compound in a concentration that is at least 10 times of the concentration of the compound in a ready-to-use composition. In one embodiment, the chemesthetic concentrate formulation has the present compound in a concentration that is at least 15 times of the concentration of the compound in a ready-to-use composition. In one embodiment, the chemesthetic concentrate formulation has the present compound in a concentration that is at least 20 times of the concentration of the compound in a ready-to-use composition. In one embodiment, the chemesthetic concentrate formulation has the present compound in a concentration that is at least 30 times of the concentration of the compound in a ready-to-use composition. In one embodiment, the chemesthetic concentrate formulation has the present compound in a concentration that is at least 40 times of the concentration of the compound in a ready-to-use composition. In one embodiment, the chemesthetic concentrate formulation has the present compound in a concentration that is at least 50 times of the concentration of the compound in a ready-to-use composition. In one embodiment, the chemesthetic concentrate formulation has the present compound in a concentration that is at least 60 times of the concentration of the compound in a ready-to-use composition. In one embodiment, the chemesthetic concentrate formulation has the present compound in a concentration that is up to 100 times of the concentration of the compound in a ready-to-use composition.

Some embodiments provide a textile product. Examples of the textile product includes, but are not limited to, shirts, pants, socks, towels, and etc. The present compound can be applied to the textile product in any suitable methods known to one skilled in the art. For example, the present compound can be associated with the textile by spin-coating, imprinting, in the form of microencapsulation, direct incorporation into the textile material (e.g. extruding), covalent coupling of suitable derivatives of the modulators (via suitable spacer/linker groups, with the help of which the molecule is reversibly or irreversibly bonded to the packaging material).

Some embodiments provide packaging materials. Examples of the packaging materials include paper and plastic wrapping, which may be in various processing forms including fibers, fabrics, and moldings. The present compound can be applied to the packaging material in any suitable methods known to one skilled in the art. For example, the present compound can be associated with the packaging material by spin-coating, imprinting, in the form of microencapsulation, direct incorporation into the packaging material (e.g. extruding), covalent coupling of suitable derivatives of the modulators (via suitable spacer/linker groups, with the help of which the molecule is reversibly or irreversibly bonded to the packaging material.

The compounds of the present invention can be used for modulating transient receptor potential channel melastatin member 8 (TRPM8) by contacting the receptor with a compound of the present invention. This modulation process can be carried out either in vitro or in vivo. In one embodiment, the compound is a TRPM8 receptor agonist.

The compounds of the present invention can also be formulated into a precursor of the above-described compositions. By "precursor", it is meant a substance or composition from which another composition, such as those described above, is formed. For example, the present compounds may be provided as a concentrated formulation or composition which may be further mixed or diluted to form another composition suitable for consumption or personal use.

The present compounds can be used to modify the chemesthetic sensation of a composition by contacting the present compounds with the composition to form a taste-modified composition. In one embodiment, the present compounds can convey or impart a cooling taste to a composition.

In one embodiment, the present invention provides a method of modulating the cold or cooling sensation of a composition comprising combining the composition with a compound of the present invention to form a modified composition.

In one embodiment, the present invention provides a method of inducing a cold or cooling sensation in a human or animal by contacting the human or animal with a compound of the present invention.

Combinations

The chemestetic effect of Compounds 101-105 disclosed herein can be enhanced through the combination of one or more of Compounds 101-105 with one or more natural or synthetic cooling agents. Through such a combination, a synergistic effect can be achieved whereby the chemestetic effect of the combination is greater than the sum of chemestetic effects of each individual agent used in the combination.

Examples of natural and synthetic cooling agents are well-known in the art. Several suitable cooling agents useful for combination with Compounds 101-105 disclosed herein are described in U.S. 2013/0324557, WO 2014/130582, U.S. Pat. No. 7,923,585, U.S. 2008/0319055, U.S. Pat. No. 7,893,110, U.S. 2009/0105237, U.S. 2009/0098066, U.S. 2010/0035938, U.S. Pat. Nos. 8,263,046, 7,959,958, U.S. 2008/0300314, U.S. 2009/0312384, U.S. Pat. Nos. 8,309, 598, 7,935,848, U.S. 2010/0297038, U.S. Pat. Nos. 8,377, 422, 8,664,261, U.S. 2011/0091531, U.S. 2013/0323388, U.S. 2014/0341821, U.S. 2010/0086498, U.S. 2014/0186272, U.S. Pat. No. 6,884,906, U.S. 2011/0070329, U.S. Pat. Nos. 8,575,349, 5,725,865, 5,843,466, WO 2011/147455, U.S. Pat. No. 8,007,771, WO 2004/037764, U.S. Pat. No. 6,627,233, WO 2011/159935, U.S. Pat. Nos. 7,767, 243, 7,662,576, 5,372,824, 5,009,893, 5,698,181, 7,189,760, 7,030,273, WO 02/091849, U.S. Pat. Nos. 5,286,500, 3,488, 419, 6,515,188, 6,407,293, 4,459,425, 3,419,543, U.S. 2006/0210482, U.S. Pat. Nos. 6,328,982, 7,025,999, EP 1332772, U.S. Pat. No. 4,157,384, WO 2014/090293, U.S. 2008/0175800, U.S. Pat. Nos. 8,344,025, 8,927,605, U.S. 2011/0305657, U.S. 2013/0202543, and U.S. 2014/0335224, which are incorporated by reference herein in their entireties.

Other suitable cooling agents suitable for combination with Compounds 101-105 are known in the art and include, but are not limited to: 5-methyl-2-(propane-2-yl)cyclohexyl-N-ethyloxamate, N-ethyl-p-menthane carboxamide (WS-3, also referred to as menthane-3-carboxylic acid-N-ethyl amide), N-2,3-trimethyl-2-isopropyl butane amide (WS-23), menthyl lactate (Frescolat® ML), menthone glycerine acetal (Frescolat® MGA), mono-menthyl succinate (Physcool®), mono-menthyl glutarate, O-menthyl-glycerine, menthyl-N,N-dimethyl succinamate, N-(4-cyano methyl phenyl)-p-menthane carboxamide, N-(2 (pyridin-2-yl)ethyl)-3-p-menthane carboxamide menthol and menthol derivatives (e.g. L-menthol, D-menthol, racemic menthol, isomenthol, neoisomenthol, neomenthol) menthyl ether (e.g. (I-menthoxy)-1,2-propanediol, (1-menthoxy)-2-methyl-1,2-propanediol, 1-menthyl-methyl ether), menthyl ester (e.g. menthyl formiate, menthyl acetate, menthyl isobutyrate, menthyl lactates, L-menthyl-L-lactate, L-menthyl-D-lactate, menthyl-(2-methoxy)acetate, menthyl-(2-methoxy ethoxy)acetate, menthyl pyroglutamate), N-(4-cyano methyl phenyl)-p-menthane carboxamide, N-(2-(pyridin-2-yl)ethyl)-3-p-menthane carboxamides, menthyl carbonates (e.g. menthyl propylene glycol carbonate, menthyl ethylene glycol carbonate, menthyl glycerine carbonate or mixtures thereof), menthane carboxylic acid amide (e.g. menthane carboxylic acid-N-ethylamid [WS3], N-alpha.-(menthane-carbonyl) glycine ethyl ester [WS5], menthane carboxylic acid-N-(4-cyanophenyl)amide, menthane carboxylic acid-N-(alkoxyalkyl)amide), menthone and menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide [WS23]), isopulegol or its esters (1-(−)-isopulegol, 1-(−)-isopulegol acetate), menthane derivatives (e.g. p-menthane-3,8-diol), N-(4-cyano methyl phenyl)-p-menthane carboxamides, N-(2-(pyridin-2-yl)ethyl)-3-p-menthane carboxamides, cubebol or synthetic or natural mixtures containing cubebol, pyrrolidone derivates of cycloalkyl dione derivatives (e.g. 3-methyl-2(1-pyrrolidinyl)-2-cyclopentene-1-one) or tetrahydropyrimidine-2-ones (e.g. Icilin or related compounds such as those described in WO 2004/026840), N-(4-cyano methyl phenyl)-p-menthane carboxamide, N-(2-(pyridin-2-yl)ethyl)-3-p-menthane carboxamides, menthyl ether (e.g. (I-menthoxy)-1,2-propanediol, (I-menthoxy)-2-methyl-1,2-propanediol), more polar menthyl esters (e.g. menthyl lactates, L-menthyl-L-lactate, L-menthyl-D-lactate, menthyl-(2-methoxy)acetate, menthyl-(2-methoxy ethoxy)acetate, menthyl pyroglutamate), menthyl carbonates (e.g. menthyl propylene glycol carbonate, menthyl ethylene glycol carbonate, menthyl glycerine carbonate), the semi-esters of menthols with a dicarboxylic acid or the derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), 3,4-methylendioxycinnamic acid-N-cyclohexyl-N-2-pyridylamide, isopropyl-(5-methoxy-2-pyridin-2-yl-pyrimidin-4-yl)-amine, 3,4,6,7,11b,12-hexahydro-3,3-dimethyl-spiro[13H-dibenzo[a,f]quinolizine-1-3,2'-[1,3]dithiolan]-1(2H)-one, 5,6,10b,11-tetrahydro-3-methyl-spiro[12H-benzo[a]furo[3,4-f] quinolizine-1-2,2'-[1,3]dithiolan]-1(3H)-one. Most preferred as cooling compounds are compounds selected from the group consisting of 5-methyl-2-(propane-2-yl)cyclohexyl-N-ethyloxamate, N-ethyl-p-menthane carboxamide (WS-3, also referred to as menthane-3-carboxylic acid-N-ethyl amide), menthyl lactate (Frescolat® ML), menthone glycerine acetal (Frescolat® MGA), N-(4-cyano methyl phenyl)-p-menthane carboxamide and (I-menthoxy)-1,2-propanediol.

In some other embodiments, the additional cooling agent or agents can comprise one or more compounds shown in Table 2 or a salt or solvate thereof.

TABLE 2

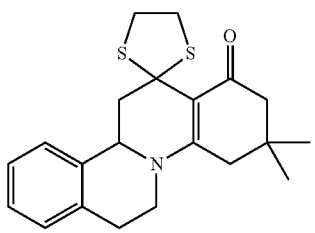 [SMILES: CC1(C)CC(=O)C2=C(C1)N1CCc3ccccc3C1CC21SCCS1]

TABLE 2-continued

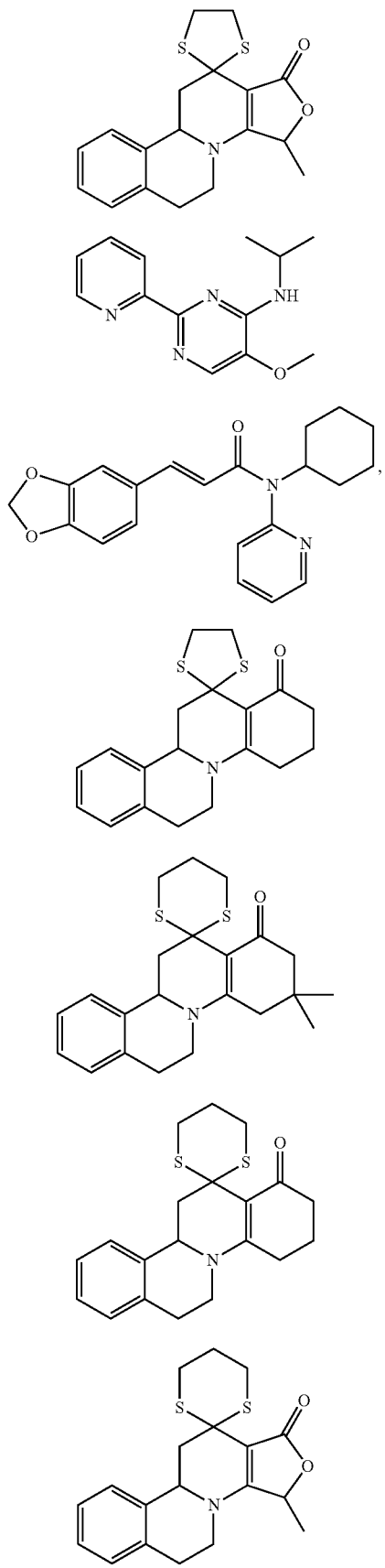

TABLE 2-continued
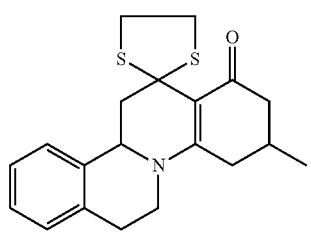 [SMILES: CC1CC(=O)C2=C(C1)N1CCc3ccccc3C1CC21SCCS1]
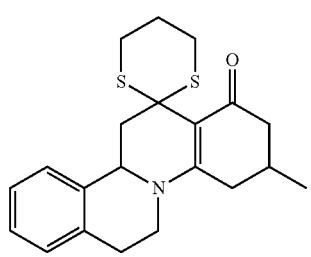 [SMILES: CC1CC(=O)C2=C(C1)N1CCc3ccccc3C1CC21SCCCS1]
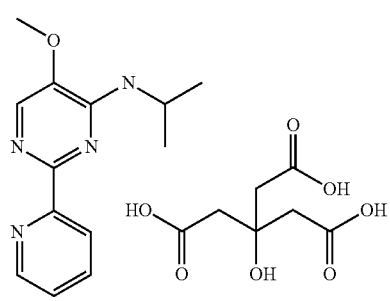
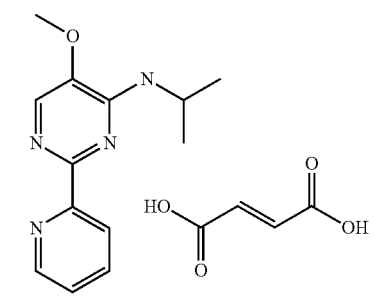
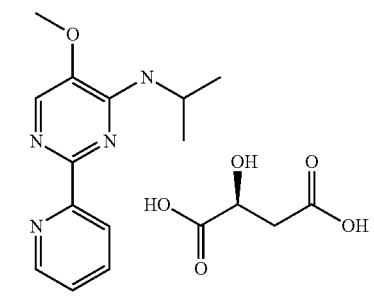
TABLE 2-continued
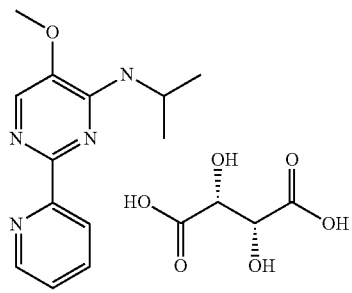
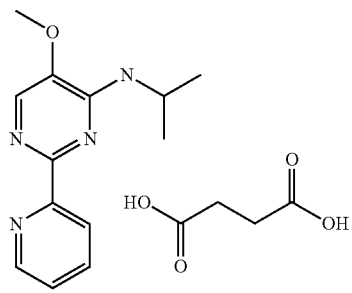
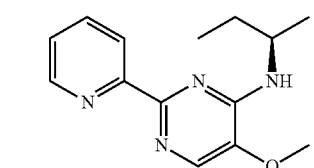
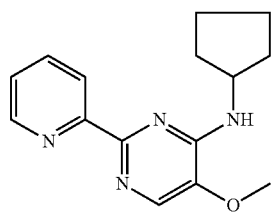 [SMILES: COc1cnc(-c2ccccn2)nc1NC1CCCC1]
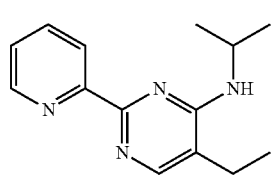 [SMILES: CCc1cnc(-c2ccccn2)nc1NC(C)C]
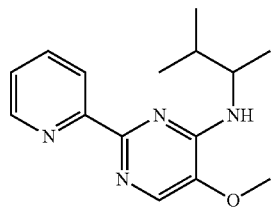 [SMILES: COc1cnc(-c2ccccn2)nc1NC(C)C(C)C]
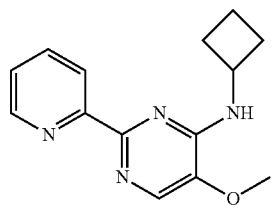 [SMILES: COc1cnc(-c2ccccn2)nc1NC1CCC1]

TABLE 2-continued
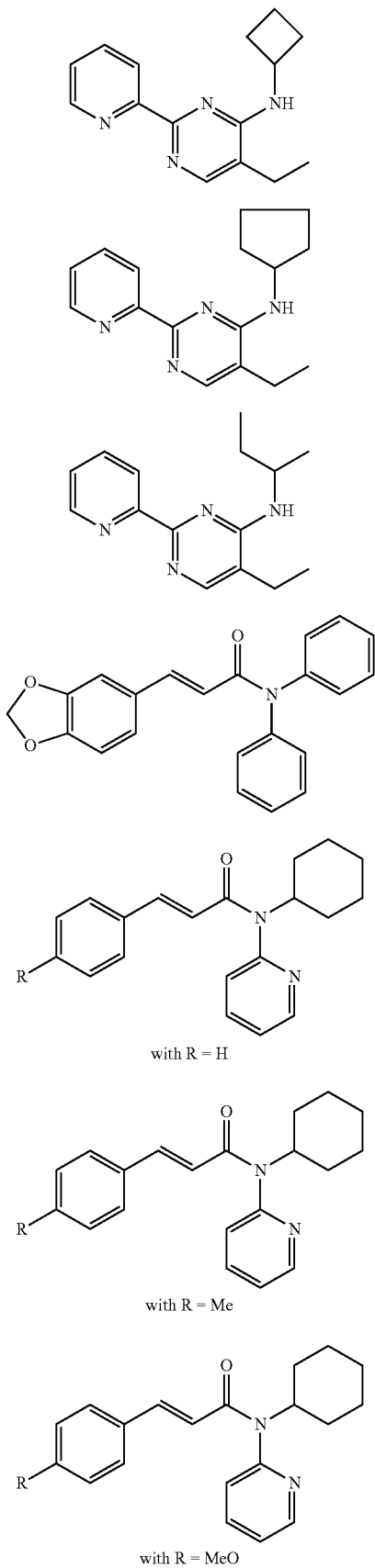
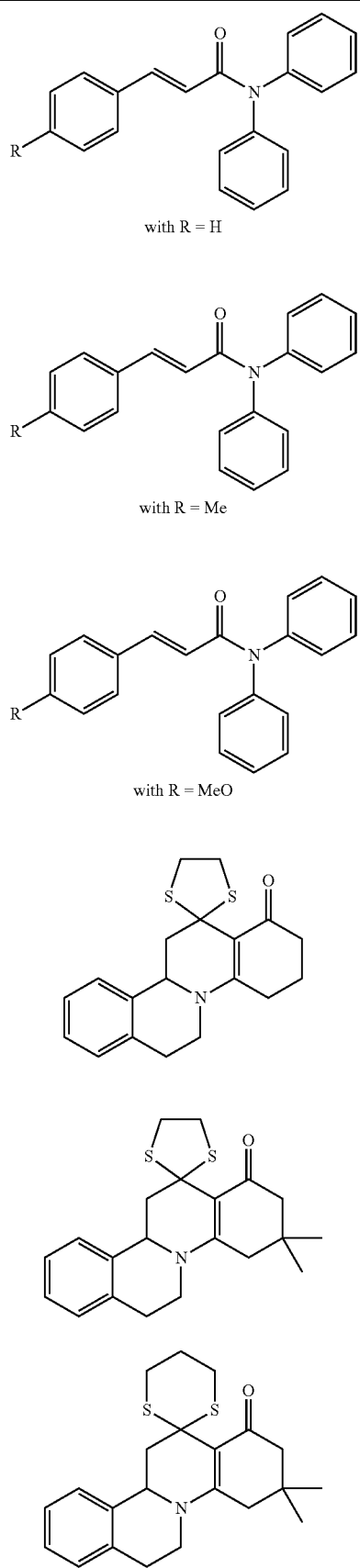
with R = H
with R = Me
with R = MeO

TABLE 2-continued
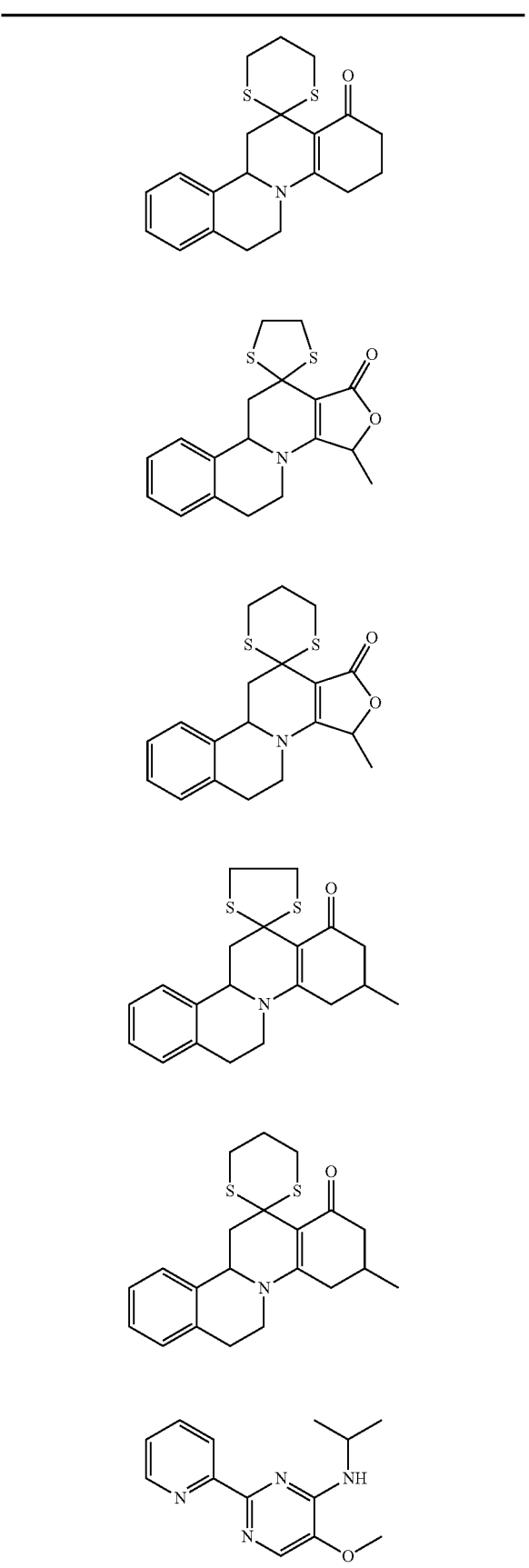
TABLE 2-continued
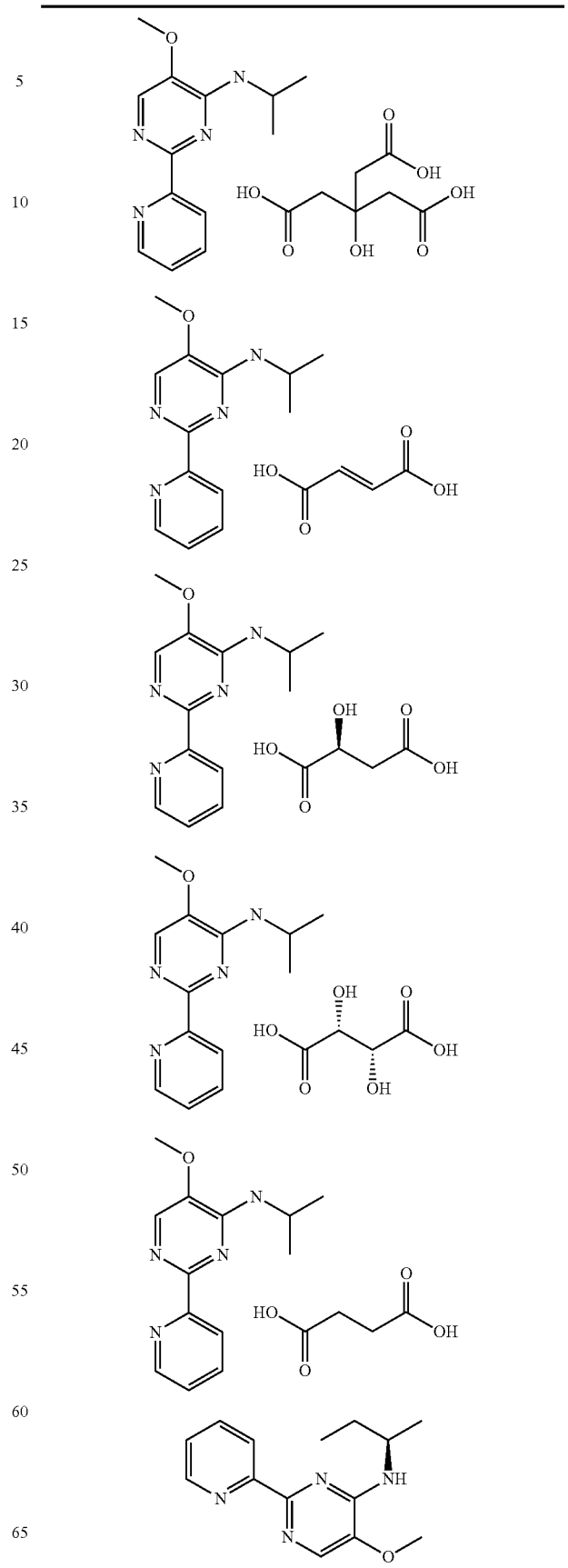

TABLE 2-continued
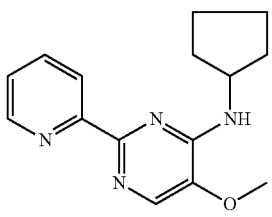 [SMILES: COc1cnc(-c2ccccn2)nc1NC1CCCC1]
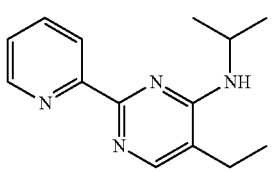 [SMILES: CCc1cnc(-c2ccccn2)nc1NC(C)C]
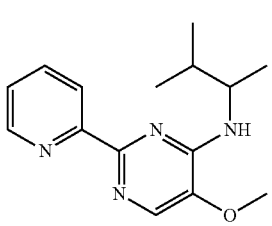 [SMILES: COc1cnc(-c2ccccn2)nc1NC(C)C(C)C]
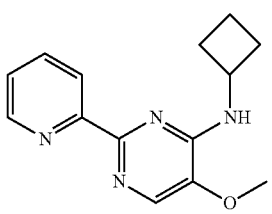 [SMILES: COc1cnc(-c2ccccn2)nc1NC1CCC1]
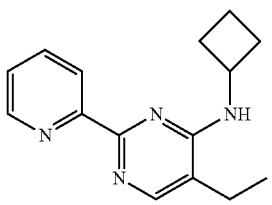 [SMILES: CCc1cnc(-c2ccccn2)nc1NC1CCC1]
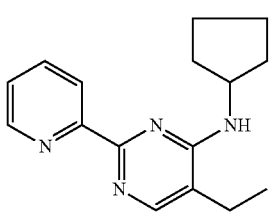 [SMILES: CCc1cnc(-c2ccccn2)nc1NC1CCCC1]
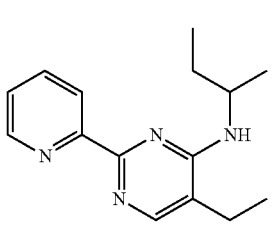 [SMILES: CCc1cnc(-c2ccccn2)nc1NC(C)CC]
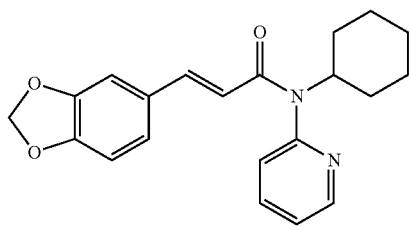 [SMILES: O=C(/C=C/c1ccc2c(c1)OCO2)N(c1ccccn1)C1CCCCC1]
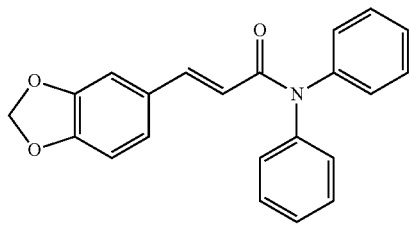 [SMILES: O=C(/C=C/c1ccc2c(c1)OCO2)N(c1ccccc1)c1ccccc1]
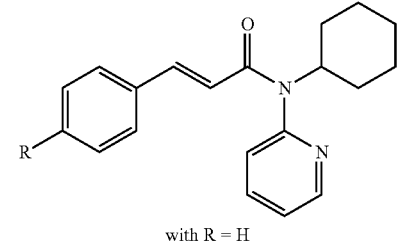
with R = H
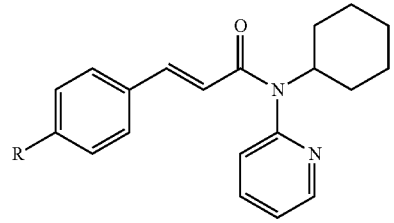
with R = Me
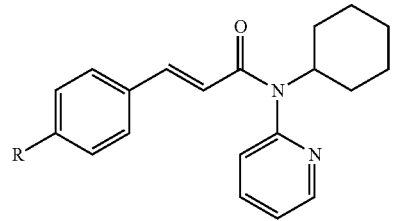
with R = MeO
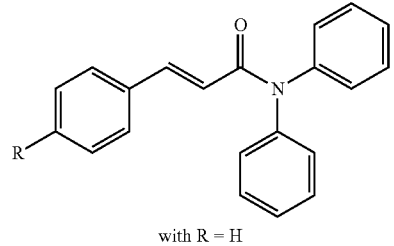
with R = H TABLE 2-continued

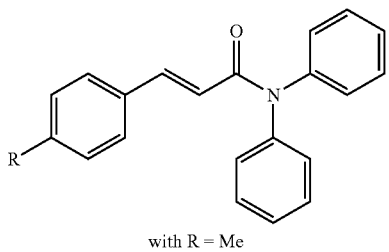

with R = Me

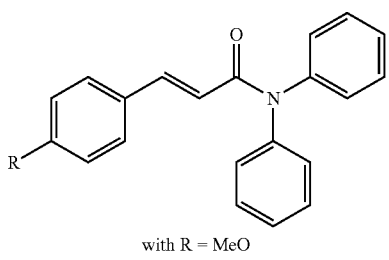

with R = MeO

In some further embodiments, the additional cooling agent or agents comprise one or more of 2-Isopropyl-N,2,3-trimethylbutyramide; N-Ethyl-p-menthane-3-carboxamide; Ethyl 3-(p-menthane-3-carboxamido)acetate; 1R,2S,5R)—N-(4-Methoxyphenyl)-p-menthanecarboxamide; N-Ethyl-2,2-diisopropylbutanamide; N-Cyclopropyl-5-methyl-2-isopropylcyclohexanecarboxamide; N-(1,1-Dimethyl-2-hydroxyethyl)-2,2-diethylbutanamide); Menthoxyethanol; N-(4-cyanomethylphenyl)-p-menthanecarboxamide; N-(2-(Pyridin-2-yl)ethyl)-3-p-menthanecarboxamide; N-(2-Hydroxyethyl)-2-isopropyl-2,3-dimethylbutanamide; N-(4-(carbamoylmethyl)phenyl)-menthylcarboxamide; (1R,2S,5R)—N-(4-Methoxyphenyl)-p-menthanecarboxamide; (2S,5R)—N-[4-(2-Amino-2-oxoethyl)phenyl]-p-menthanecarboxamide; 2-[(2-p-Menthoxy)ethoxy]ethanol; (2,6-Diethyl-5-isopropyl-2-methyltetrahydropyran; trans-4-tert-Butylcyclohexanol; 2-(p-tolyloxy)-N-(1H-pyrazol-5-yl)-N-((thiophen-2-yl)methyl)acetamide; Racemic N-isopropyl-5-methylcyclohexyl)cyclopropanecarboxamide; (−)-Menthol; (−)-Isopulegol; (−)-Menthyl lactate; 3-((−)-Menthoxy)propane-1,2-diol; (−)-Menthyl ethylene glycol carbonate; (−)-Menthone 1,2-glycerol ketal; DL-Menthone 1,2-glycerol ketal; (−)-Menthyl succinate; (−)-Menthyl 1&2 propylene glycol carbonates; (−)-Menthyl 1&2 propylene glycol carbonates; (−)-Menthyl glutarate; (+)-cis & (−)-trans p-menthane-3,8-diol; (−)-Menthyl pyrrolidone carboxylate; N,N-Dimethyl (−)-menthyl succinamide; (−)-Menthone (S)-lactic acid ketal; (−)-Menthyl (S)-3-hydroxybutyrate; (−)-Menthyl acetoacetate; (1R,2S,5R)—N-(4-(cyanomethyl)phenyl) menthylcarboxamide; (1R,4S,5R,6R,7S,10R)-7-isopropyl-4,10-dimethyl-tricyclo[4.4.0.0(1,5)]decan-4-ol; (1R,2S,5R)—N-(2-(pyridin-2-yl)ethyl)menthylcarboxamide; N-(2-Hydroxyethyl)-2,3-dimethyl-2-isopropylbutanamide; Di-(−)-menthyl glutarate; (1R,2S,5R)—N-(4-(carbamoylmethyl)phenyl)-menthylcarboxamide; 2-[2-(p-menthan-3-yloxy)ethoxy]ethanol, also known as (1R,2S,5R)-2-[2-(2-Isopropyl-5-methyl-cyclohexyloxy)ethoxy]-ethanol; (1R,2R,4R)-1-(2-Hydroxy-4-methylcyclohexyl) ethanone; 2-(p-tolyloxy)-N-(1H-pyrazol-5-yl)-N-((thiophen-2-yl)methyl)acetamide; N-(2-hydroxyethyl)-2,3-dimethyl-2-isopropylbutyramide; ((1R,2S,5R)—N-(4-Methoxyphenyl)-p-menthanecarboxamide); (−)-Menthoxypropane-1,2-diol; 3-(1-Menthoxy)-2-methylpropane-1,2-diol; (−)-Isopulegol; (−)-Isopulegol; menthyl lactate and menthoxypropanediol; (cis)-p-Menthane-3,8-diol; (trans)-p-Menthane-3,8-diol; 2,3-dihydroxy-p-menthane; 3,3,5-trimethylcyclohexanone glycerol ketal; menthyl pyrrolidone carboxylate; (1R,3R,4S)-3-menthyl-3,6-dioxaheptanoate; (1R,2S,5R)-3-menthyl methoxyacetate; (1R,2S,5R)-3-menthyl 3,6,9-trioxadecanoate; (1R,2S,5R)-3-menthyl 3.6,9-trioxadecanoate; (1R,2S,5R)-3-menthyl (2-hydroxyethoxy)acetate; (1R,2S,5R)-menthyl 11-hydroxy-3,6,9-trioxaundecanoate; p-menthane carboxamidesl; (−)-Menthoxypropane-1,2-diol; 6-isopropyl-3,9-dimethyl-1,4-dioxaspiro[4.5]decan-2-one; N-benzo[1,3] dioxol-5-yl-3-p-menthanecarboxamide; N-benzooxazol-4-yl-3-p-menthanecarboxamide; N-4-([1,2,4]triazol-1-yl)-phenyl-3-p-menthanecarboxamide & N-4-(pyrazol-1-yl)-phenyl-3-p-menthanecarboxamide; N-(1-isopropyl-1,2-dimethylpropyl)-1,3-benzodioxole-5-carboxamide; L-Phenylephrine p-menthane carboxamide; 2,2,5,6,6-pentamethyl-2,3,6,6a-tetrahydropentalen-3a(1H)-ol; 5-(2-hydroxy-2-methylpropyl)-3,4,4-trimethylcyclopent-2-en-1-one; (2S,5R)-2-isopropyl-5-methyl-N-(2-(pyridin-4-yl)ethyl)cyclohexanecarboxamide; 5-methyl-2-(propane-2-yl)cyclohexyl-N-ethyloxamate; (1R,2S,5R)-5-methyl-2-(propane-2-yl)cyclohexyl-N-ethyloxamate; 2,4-decadienoic acid-N-isobutylamide; N-[[5-methyl-2-(1-methylethyl)cyclohexyl]-carbonylglycine ethyl ester; menthyl-3-hydroxy butyrate; menthyl-3-oxo butyrate; menthyl-3-oxo pentanoate; menthyl lactate; menthone glycerine acetal, menthol glycol carbonate; menthol propyleneglycol carbonate; menthol glycerin carbonate; 1-menthyl-3-hydroxy butyrate; trans-pellitorin; cis-pellitorin; peppermint oil; 1,2-propylene glycol and/or diethyl malonate; N-ethyl-p-menthane-3-carboxamide; trimethyl isopropyl butanamide; 1S,2S,5R)—N-(4-(cyanomethyl)phenyl)-2-isopropyl-5-methylcyclohexanecarboxamide; (1S,2S,5R)-2-isopropyl-5-methylcyclohexyl-2(S)-acetoxypropanoate; 1-lsopropyl-4-methyl-bicyclo[2.2.21oct-5-ene-2,3-dicarbinol; 4-methoxy-N-phenyl-N-[2-(pyridin-2-yl)ethyl]benzamide; 4-methoxy-N-phenyl-N-[2-(pyridin-2-yl)ethyl]benzenesulfonamide; 4-chloro-N-phenyl-N-[2-(pyridin-2-yl)ethyl]benzenesulfonamide; 4-cyano-N-phenyl-N-[2-(pyridin-2-yl)ethyl]benzenesulfonamide; 2,6-diethyl-5-isopropyl-2-methyl tetrahydropyran; 6-ethyl-5-isopropenyl-2-methyl-2-vinyltetrahydropyran; 2.6-dimethyl-5-isopropyl-2-ethyltetrahydropyran; 2.6-dimethyl-5-isopropenyl-2-vinyltetrahydropyran; 2.6-diethyl-5-sec.-butyl-2-methyltetrahydropyran; 2.6-dimethyl-5-sec.-butyl-2-ethyltetrahydropyran, 4-((benzhydrylamino)methyl)-2-methoxyphenol; 4-((bis(4-methoxyphenyl)-methylamino)-methyl)-2-methoxyphenol; 4-((1,2-diphenylethylamino) methyl)-2-methoxyphenol; 4-((benzhydryloxy)methyl)-2-methoxyphenol; 4-((9H-fluoren-9-ylamino)methyl)-2-methoxyphenol; 4-((benzhydrylamino)methyl)-2-ethoxyphenol; 1-(4-methoxyphenyl)-2-(1-methyl-1H-benzo[d]imidazol-2-yl)vinyl4-methoxybenzoate; 2-(1-isopropyl-6-methyl-1H-benzo[d]imidazol-2-yl)-1-(4-methoxyphenyl)vinyl4-methoxybenzoate; (Z)-2-(1-isoprop yl-5-methyl-1H-benzo[d]imidazol-2-yl)-1-(4-methoxy-phenyl)vinyl-4-methoxybenzoate; N-(1-methyl-1-isopropylbutyl) benzamide; fenchyl; D-bornyl; L-bornyl, exo-norbornyl; 2-methylisobornyl; 2-ethylfenchyl; 2-methylbornyl; cis-pinan-2-yl; verbanyl; isobornyl; menthyl oxamate and derivatives thereof; 4-oxo-4-((1R,2R,4R)-1,7,7-trimethylbicyclo[2.2.1]heptan-2-yloxy)butanoic acid; L-menthyl 3-oxobutyrate; L-menthyl 3-oxopentanoate; 3,4-methylenedioxycinnamic acid, N,N-diphenylamide; (−)-(1R,2R,4S)-dihydroumbellulol; (1R,2R,5R)—N-ethyl-5-methyl-2-

(prop-1-en-2-yl)cyclohexanecarboxamide; 3-menthoxy-1-propanol; 1-menthoxy-2-propanol; 1-[2-hydroxyphenyl]-4-[2-nitrophenyl-]-1,2,3,6-tetrahydropyrimidine-2-one); 4-methyl-3-(1-pyrrolidinyl)-2[5H]-furanone; 5-methyl-4-(1-pyrrolidinyl)-3-[2H]-furanone; 4,5-dimethyl-3-(1-pyrrolidinyl)-2[5H]-furanone; menthyl oxamate; menthyl N-methyl oxamate; menthyl N,N-dimethyl oxamate; menthyl N-ethyl oxamate; menthyl N,N-diethyl oxamate; menthyl N-propyl oxamate; menthyl N,N-dipropyl oxamate; menthyl N-isopropyl oxamate; menthyl N,N-diisopropyl oxamate; menthyl N-cyclopropyl oxamate; menthyl N-butyl oxamate; morpholin-4-yl-oxo-acetic acid; (1R,2S,5R)-2-isopropyl-5-methylcyclohexyl ester; menthyl N-(2-methoxyethyl)oxamate; menthyl N-(3-methoxypropanol) oxamate; menthyl N-(2-hydroxyethyl)oxamate; L-menthyl N-methyl oxamate; D-menthyl N-methyl oxamate; rac-menthyl N-methyl oxamate; L-menthyl N-ethyl oxamate; D-menthyl N-ethyl oxamate; rac-menthyl N-ethyl oxamate; and menthyl N-(3-hydroxypropyl)oxamate.

It is sometimes advantageous to include an agent causing a cooling sensation in the delivery of a pharmaceutical compound, whether to improve the flavor of oral liquid or powder forms, to improve the sensation of taking tablet or capsule forms, to modulate sensation at injection sites for injectable forms, to modulate sensation in the sinus or lung for inhalable forms, or for other reasons known in the art. Therefore, in some embodiments, the cooling compounds and combinations thereof are further combined with a pharmaceutical excipient. Examples of pharmaceutical excipients are known in the art and include those listed on the U.S. FDA list of inactive drug ingredients (available at http://www.fda.gov/Drugs/InformationOnDrugs/ucm113978.htm, Last accessed Oct. 31, 2015). Examples of pharmaceutical excipients suitable for combination with the cooling compounds disclosed above include but are not limited to: Alpha-Terpineol; Alpha-Tocopherol; Alpha-Tocopherol Acetate; Alpha-Tocopherol Acetate, Dl-; Alpha-Tocopherol, Dl-; Beta-Carotene; Beta-Cyclodextrin Sulfobutyl Ether Sodium; Beta-Ionone; 1-(Phenylazo)-2-Naphthylamine; 1,2,6-Hexanetriol; 1,2-Dimyristoyl-Sn-Glycero-3-(Phospho-S-(1-Glycerol)); 1,2-Dimyristoyl-Sn-Glycero-3-Phosphocholine; 1,2-Dioleoyl-Sn-Glycero-3-Phosphocholine; 1,2-Dipalmitoyl-Sn-Glycero-3-(Phospho-Rac-(1-Glycerol)); 1,2-Distearoyl-Sn-Glycero-3-(Phospho-Rac-(1-Glycerol)); 1,2-Distearoyl-Sn-Glycero-3-Phosphocholine; 1-Aminocyclohexanecarboxylic Acid, C-11; 1-O-Tolylbiguanide; 2212 Fine Black; 2-Ethyl-1,6-Hexanediol; *Acacia; Acacia* Syrup; Acesulfame; Acesulfame Potassium; Acetaminophen; Acetic Acid; Acetic Anhydride; Acetone; Acetone Sodium Bisulfite; Acetonitrile; Acetophenone; Acetylated Lanolin Alcohols; Acetylcysteine; Acetyltributyl Citrate; Acetyltryptophan, Dl-; Acid Blue 9 Ammonium; Acid Orange 20; Acrylates Copolymer; Acryl-Eze 93018509 White; Acryl-Eze 93053823 Orange; Acryl-Eze 93084719 Pink; Acryl-Eze 93084720 Pink; Acrylic Acid-Isooctyl Acrylate Copolymer; Acrylic Adhesive 788; Activated Charcoal; Adcote 72a103; Adhesive Tape; Adipic Acid; Advantia Prime 190100ba01 White; Aerotex Resin 3730; Agar; Air; Alanine; Albumin Aggregated; Albumin Colloidal; Albumin Human; Albumins; Alcloxa; Alcohol; Alfadex; Algeldrate; Alginic Acid; Alkyl Ammonium Sulfonic Acid Betaine; Alkyl Aryl Sodium Sulfonate; Allantoin; Almond Oil; *Althaea Officinalis* Root; Aluminum Acetate; Aluminum Hydroxide; Aluminum Hydroxide—Sucrose, Hydrated; Aluminum Monostearate; Aluminum Oxide; Aluminum Polyester; Aluminum Silicate; Aluminum Silicate Pentahydrate; Aluminum Starch Octenylsuccinate; Aluminum Stearate; Aluminum Subacetate; Aluminum Sulfate Anhydrous; Aluminum Sulfate Tetradecahydrate; Alzamer-39; Alzamer-50; Amaranth; Amberlite; Amberlite Xe-58; Amberlite Xe-88; Amerchol C; Amerchol-Cab; Aminobenzoate Sodium; Aminomethylpropanol; Ammonia; Ammonio Methacrylate Copolymer; Ammonio Methacrylate Copolymer Type A; Ammonio Methacrylate Copolymer Type B; Ammonium Acetate; Ammonium Calcium Alginate; Ammonium Chloride; Ammonium Glycyrrhizate; Ammonium Lauryl Sulfate; Ammonium Nonoxynol-4 Sulfate; Ammonium Phosphate, Dibasic; Ammonium Salt Of C-12-C-15 Linear Primary Alcohol Ethoxylate; Ammonium Sulfate; Ammonyx; Amphoteric-9; Amyl Acetate; Anethole; Anhydrous Citric Acid; Anhydrous Dextrose; Anhydrous Dibasic Calcium Phosphate; Anhydrous Lactose; Anhydrous Trisodium Citrate; Anidrisorb 85/70; Anise; Anise Oil; Anoxid Sbn; Antifoam; Antifoam Dc; Antifoam M; Antipyrine; Apaflurane; Apricot Kernel Oil Peg-6 Esters; Aquacel 126; Aquacoat; Aquacoat Ecd; Aquacoat Ecd-30; Aquaphor; Aquarius Bkt14090 Yellow; Aquarius Bp17066 Blue; Arginine; Arlacel; Ascorbic Acid; Ascorbyl Palmitate; Aspartame; Aspartic Acid; Attapulgite; Balsam Peru; Barium Sulfate; Beeswax, Synthetic; Beheneth-10; Bentonite; Benzaldehyde; Benzalkonium Chloride; Benzenesulfonic Acid; Benzethonium Chloride; Benzododecinium Bromide; Benzoic Acid; Benzoin Resin; Benzyl Acetate; Benzyl Alcohol; Benzyl Benzoate; Benzyl Chloride; Benzyl Violet; Betadex; Betanaphthol; Betose; Bibapcitide; Bismuth Subcarbonate; Bismuth Subgallate; Black Currant; Black Ink; Boric Acid; Brocrinat; Brown Iron Oxide; Buffered Soda; Butane; Butyl Alcohol; Butyl Ester Of Methyl Vinyl Ether/Maleic Anhydride Copolymer (125000 Mw); Butyl Stearate; Butylated Hydroxyanisole; Butylated Hydroxytoluene; Butylene Glycol; Butylparaben; Butyric Acid; $C_{12-15}$ Alkyl Lactate; $C_{20-40}$ Pareth-24; Caffeine; Calcium; Calcium Acetate; Calcium Alginate And Ammonium Alginate; Calcium Ascorbate; Calcium Carbonate; Calcium Carrageenan Sulfate; Calcium Chloride; Calcium Citrate; Calcium Cyclamate; Calcium Gluceptate; Calcium Hydroxide; Calcium Lactate; Calcium Phosphate Dibasic Dihydrate-Sucrose Agglomerate; Calcium Phosphate, Dibasic Monohydrate; Calcium Phosphate, Unspecified Form; Calcium Polycarbophil; Calcium Pyrophosphate; Calcium Salicylate; Calcium Silicate; Calcium Stearate; Calcium Sulfate Anhydrous; Calcium Sulfate Dihydrate; Calcium Sulfate Hemihydrate; Calcium Sulfate, Unspecified Form; Calcobutrol; Caldiamide Sodium; Caloxetate Trisodium; Calteridol Calcium; Canada Balsam; Candelilla Wax; Candesartan Cilexetil; Canola Oil; Caprylic/Capric Mono/Diglycerides; Caprylic/Capric/Stearic Triglyceride; Caprylic/Capric/Succinic Triglyceride; Caprylocaproyl Macrogolglycerides; *Capsicum* Oleoresin; Captan; Caramel; Carbomer 1382; Carbomer Copolymer Type B (Allyl Pentaerythritol Crosslinked); Carbomer Homopolymer Type A (Allyl Pentaerythritol Crosslinked); Carbomer Homopolymer Type B (Allyl Pentaerythritol Crosslinked); Carbomer Homopolymer Type B (Allyl Pentaerythritol Or Allyl Sucrose Crosslinked); Carbomer Homopolymer Type C (Allyl Pentaerythritol Crosslinked); Carbon Dioxide; Carbon Tetrachloride; Carboxy Vinyl Copolymer; Carboxymethyl Starch; Carboxymethylamylopectin Sodium; Carboxymethylcellulose; Carboxymethylcellulose Calcium; Carboxymethylcellulose Sodium, Unspecified Form; Carboxypolymethylene; Carmine; Carmine 50; Carnauba Wax; Carrageenan; Carrageenan Calcium; Carrageenan Sodium; Carvone, (-)-; Castor Oil; Cedar Leaf Oil; Cellaburate; Cellacefate; Cellulose Acetate; Cellulose Acetate Ca-320s; Cellulose Acetate Ca-398-10; Cellulose Microcrystalline/

Carboxymethylcellulose Sodium; Cellulose, Microcrystalline; Cellulose, Oxidized; Cellulosic Polymers; Ceresin; Ceteareth-12; Ceteareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Cetylpyridinium Chloride; Chemoderm 6401b; Cherry; Cherry Juice; Chinese Cinnamon Oil; Chlorobutanol; Chlorobutanol Hemihydrate; Chlorocresol; Chloroform; Chloroxylenol; Cholesterol; Choleth; Choleth-24; *Chondrus Crispus* Carrageenan; Chromacote T 2700gn; Chromacote T 2716y; Chroma-Kote T2956-Y Yellow; Ciclopirox Olamine; Cinnamaldehyde; Cinnamon; Cinnamon Oil; Citric Acid Monohydrate; *Citrus Sinensis* Flower Oil; Clove Oil; Coateric Ypa-6-7430 White; Cocamide Ether Sulfate; Cocamine Oxide; Coco Betaine; Coco Diethanolamide; Coco Monoethanolamide; Cocoa; Cocoa Butter; Coco-Caprylate/Caprate; Coco-Glycerides; Coconut Oil; Coconut Oil—Lecithin; Coconut Oil/Palm Kernel Oil Glycerides, Hydrogenated; Coffee Bean; Cola Nut; Collagen; Color Hs 290008cr01 White; Color Icg-U-10251 Brown; Coloring Suspension; Compressible Sugar; Copovidone K25-31; Coriander Oil; Corn Glycerides; Corn Oil; Corn Oil Peg-6 Esters; Corn Syrup; Cottonseed Oil; Cream Base; Creatine; Creatinine; Cresol; Croscarmellose; Croscarmellose Sodium; Crospovidone (15 Mpa·S At 5%); Crystal Gum; Cupric Sulfate; Cupric Sulfate Anhydrous; Cutina; Cyclamic Acid; Cyclomethicone; Cyclomethicone 5; Cyclomethicone/Dimethicone Copolyol; Cysteine; Cysteine Hydrochloride; Cysteine Hydrochloride Anhydrous; Cysteine, Dl-; D&C Black No. 2; D&C Blue No. 1 Lake; D&C Blue No. 1—Aluminum Lake; D&C Blue No. 2 Lake; D&C Blue No. 4; D&C Blue No. 6; D&C Blue No. 9; D&C Brown No. 1; D&C Green No. 3 Lake; D&C Green No. 5; D&C Green No. 6; D&C Orange No. 4; D&C Red No. 21—Aluminum Lake; D&C Red No. 22; D&C Red No. 27; D&C Red No. 27 Lake; D&C Red No. 27—Aluminum Lake; D&C Red No. 28; D&C Red No. 28-Aluminum Lake; D&C Red No. 30; D&C Red No. 30 Lake; D&C Red No. 33; D&C Red No. 33 Lake; D&C Red No. 36; D&C Red No. 39; D&C Red No. 4 Lake; D&C Red No. 40 Lake; D&C Red No. 6; D&C Red No. 6 Barium Lake; D&C Red No. 6 Lake; D&C Red No. 7; D&C Red No. 7 Lake; D&C Violet No. 2 Lake; D&C Yellow No. 10; D&C Yellow No. 10 Lake; D&C Yellow No. 10-Aluminum Lake; D&C Yellow No. 10—Aluminum Lake; D&C Yellow No. 11; D&C Yellow No. 5—Aluminum Lake; D&C Yellow No. 6 Lake; Daubert 1-5 Pestr (Matte) 164z; Dc Antifoam Af Trituration 1% On Sucrose; Decyl Methyl Sulfoxide; Dehydag Wax Sx; Dehydroacetic Acid; Dehymuls E; Denatonium Benzoate; Deoxycholic Acid; Dexbrompheniramine Maleate; Dextran; Dextran 40; Dextrates; Dextrins Modified; Dextrose Monohydrate; Dextrose, Unspecified Form; Diacetylated Monoglycerides; Diastase, Malt; Diatomaceous Earth; Diatrizoic Acid; Diazolidinyl Urea; Dibasic Calcium Phosphate Dihydrate; Dibutyl Phthalate; Dibutyl Sebacate; Dichlorobenzyl Alcohol; Dichlorodifluoromethane; Dichlorofluoromethane; Dichlorotetrafluoroethane; Diethanolamine; Diethyl Phthalate; Diethyl Pyrocarbonate; Diethyl Sebacate; Diethylaminoethyl Stearamide Phosphate; Diethylene Glycol Monoethyl Ether; Diethylhexyl Phthalate; Dihydroxyaluminum Aminoacetate; Dihydroxyaluminum Sodium Carbonate; Diisopropanolamine; Diisopropyl Adipate; Diisopropyl Dilinoleate; Diisopropylbenzothiazyl-2-Sulfenamide; Dimethicone; Dimethicone 100; Dimethicone 1000; Dimethicone 20; Dimethicone 350; Dimethicone Mdx4-4210; Dimethiconol/Trimethylsiloxysilicate Crosspolymer (40/60 W/W; 1000000 Pa·S); Dimethyl Isosorbide; Dimethyl Phthalate; Dimethyl Sulfoxide; Dimethylaminoethyl Methacrylate—Butyl Methacrylate—Methyl Methacrylate Copolymer; Dimethyldioctadecylammonium Bentonite; Dimethylsiloxane/Methylvinylsiloxane Copolymer; Dinoseb-Ammonium; Dipalmitoylphosphatidylglycerol, Dl-; Dipentenedimercaptan; Dipropylene Glycol; Disodium Citrate Sesquihydrate; Disodium Cocoamphodiacetate; Disodium Hydrogen Citrate; Disodium Laureth Sulfosuccinate; Disodium Lauryl Sulfosuccinate; Disodium Oleamido Monoethanolamine Sulfosuccinate; Disodium Sulfosalicylate; Disofenin; Distearoylphosphatidylcholine, Dl-; Divinylbenzene Styrene Copolymer; Dmdm Hydantoin; Docosanol; Docusate Sodium; Docusate Sodium/Sodium Benzoate; Dri Klear; Dri Klear 042; Dri Klear Lv 609527; Dry Flo; Dry-Clear Lv; Duro-Tak 280-2516; Duro-Tak 387-2516; Duro-Tak 80-1196; Duro-Tak 87-2070; Duro-Tak 87-2194; Duro-Tak 87-2287; Duro-Tak 87-2296; Duro-Tak 87-2888; Duro-Tak 87-2979; Dusting Powder; Dye Beige P-1437; Dye Black Lb-1171; Dye Black Lb-442; Dye Black Lb-636; Dye Black Lb-9972; Dye Black Oxide; Dye Blue Lake Blend Lb-1245; Dye Blue Lake Blend Lb-1939; Dye Blue Lake Blend Lb-332; Dye Blue Lakolene; Dye Blue Lb-781; Dye Brown Lake; Dye Brown Lake Blend; Dye Brown Lake Blend Lb-1685; Dye Brown Lake Blend Lb-1792; Dye Brown Lb-292; Dye Brown Lb-464; Dye Burnt Umber; Dye Caramel 105; Dye Caramel Acid Proof 100; Dye Carmine 09349; Dye Casing 27-75; Dye Chroma-Teric Deb-5037-Ore; Dye Chroma-Teric T3000-We; Dye Chroma-Teric Yellow T3277-Ye; Dye Chroma-Tone; Dye Chroma-Tone Pddb-8906w; Dye Chroma-Tone-P Ddb-8746-Or; Dye Dc Red Lake; Dye Dc Red Lb No. 9570; Dye Dc Red Lb Wj-9570; Dye Diolack 00f32892 Yellow; Dye Emerald Green Lb; Dye Emerald Green Lb-9207; Dye Fdc Black Lb260; Dye Fdc Blue No. 10; Dye Fdc Blue No. 40 Ht Lake; Dye Fdc Brown R Lb-56069; Dye Fdc Green Lb-1174; Dye Fdc Green Lb-3323; Dye Fdc Green Lb-9583; Dye Fdc Lb483; Dye Fdc Orange Lb-452; Dye Fdc Purple Lb588; Dye Fdc Purple Lb-694; Dye Grape; Dye Gray No. 2982; Dye Green 70363; Dye Green Al Lb-265; Dye Green Aluminum Lb; Dye Green Lake Blend Lb-1236; Dye Green Lake Blend Lb-1441; Dye Green Lake Blend Lb-1644; Dye Green Lake Blend Lb-333; Dye Green Lb; Dye Green Lb-1594; Dye Green Lb-1616; Dye Green Lb-279; Dye Green Lb-482; Dye Green Lb-555; Dye Green Lb-603; Dye Green Lb-820; Dye Green Lb-883; Dye Green Pb-1543; Dye Green Pb-1763; Dye Green Pb-1766; Dye Green Pms-579; Dye Green Pr-1333; Dye Green Pr-1339; Dye Lavender; Dye Lavender Lake Blend Lb-1603; Dye Lavender Lb-1356; Dye Mint Green; Dye Ochre 3506; Dye Orange 54172; Dye Orange Lake Blend 3810; Dye Orange Lake Blend Lb-1439; Dye Orange Lake Blend Lb-1944; Dye Orange Lb-1387; Dye Orange Lb-715; Dye Orange Pb-1657; Dye Orange Pb-2148; Dye Peach Lb-1576; Dye Pink; Dye Purple Lake; Dye Purple Lb-1902; Dye Purple Lb-562; Dye Purple Lb-639; Dye Purple Lb-694; Dye Red Cotolene-P; Dye Red Lake Blend 6053-R; Dye Red Pb-1595; Dye Red R07058; Dye Salmon Lb-1668; Dye Spectraspray Blue 50726; Dye Swedish Orange No. 2191; Dye Tan Pb-1388; Dye Tetrarome Orange; Dye Turquoise Lb-1430; Dye Violet; Dye White Coateric Ypa-6-7089; Dye White Cotolene-P; Dye White Tc-1032; Dye Wild Cherry 7598; Dye Yellow 70362; Dye Yellow Lake Blend Lb-1769; Dye Yellow Lb 104; Dye Yellow Lb 9706; Dye Yellow Lb-111; Dye Yellow Lb-1577; Dye Yellow Lb-1637; Dye Yellow Lb-282; Dye Yellow No. 62; Dye Yellow Pb1345; Dye Yellow Pb-1381; Dye Yellow Wd-2014; Edetate Calcium Disodium; Edetate Disodium;

Edetate Disodium Anhydrous; Edetate Sodium; Edetic Acid; Egg Phospholipids; Eiderdown Soap; Entsufon; Entsufon Sodium; Epilactose; Epitetracycline Hydrochloride; Erythorbic Acid; Erythritol; Essence Bouquet 9200; Essence Fritzbro Orange; Essence Lemon; Essence Orange; Ethanolamine Hydrochloride; Ether; Ethyl Acetate; Ethyl Acrylate And Methyl Methacrylate Copolymer (2:1; 750000 Mw); Ethyl Maltol; Ethyl Oleate; Ethyl Vanillate; Ethyl Vanillin; Ethylcellulose (10 Mpa·S); Ethylcellulose (20 Mpa·S); Ethylcellulose (4 Mpa·S); Ethylcellulose (45 Mpa·S); Ethylcellulose (50 Mpa·S); Ethylcellulose (7 Mpa·S); Ethylcelluloses; Ethylene; Ethylene Glycol; Ethylene Glycol Monoethyl Ether; Ethylenediamine; Ethylenediamine Dihydrochloride; Ethylene-Propylene Copolymer; Ethylene-Vinyl Acetate Copolymer (15% Vinyl Acetate); Ethylene-Vinyl Acetate Copolymer (28% Vinyl Acetate); Ethylene-Vinyl Acetate Copolymer (9% Vinylacetate); Ethylene-Vinyl Acetate Copolymers; Ethylhexyl Hydroxystearate; Ethylparaben; Eucalyptol; *Eucalyptus* Oil; Eugenol; Exametazime; Ext. D&C Yellow No. 7; Fat, Edible; Fat, Hard; Fatty Acid Esters; Fatty Acid Esters, Saturated; Fatty Acid Glycerides; Fatty Acid Pentaerythriol Ester; Fatty Acids; Fatty Alcohol Citrate; Fatty Alcohols; Fd&C Blue No. 1; Fd&C Blue No. 1 Lake; Fd&C Blue No. 1—Aluminum Lake; Fd&C Blue No. 2; Fd&C Blue No. 2—Aluminum Lake; Fd&C Green No. 3; Fd&C Red No. 3; Fd&C Red No. 30—Aluminum Lake; Fd&C Red No. 3—Aluminum Lake; Fd&C Red No. 4; Fd&C Red No. 40; Fd&C Red No. 40—Aluminum Lake; Fd&C Yellow No. 5; Fd&C Yellow No. 5—Aluminum Lake; Fd&C Yellow No. 6; Fd&C Yellow No. 6-Aluminum Lake; Fd&C Yellow No. 6—Aluminum Lake; Feculose; Ferric Chloride; Ferric Oxide Brown; Ferric Oxide Green; Ferric Oxide Orange; Ferric Oxide Pink; Ferric Oxide Red; Ferric Oxide Yellow; Ferrosoferric Oxide; Ferrous Fumarate; Ferrous Oxide; *Ferula* Assa-Foetida Resin; Film Coating Solution, Aqueous Im-163; Firmenich 51.226/T; Flavor 18317; Flavor 57000 Iu; Flavor 57820/A; Flavor 89-186; Flavor 89-259; Flavor Anise 29653; Flavor Aniseed 501007 Bp0551; Flavor Apple Watermelon Pfc 9887; Flavor Apricot 23067; Flavor Apricot 24829; Flavor Apricot Peach; Flavor Aromalok 182608; Flavor Aromalok 262453; Flavor Banana 11090; Flavor Banana 15223; Flavor Banana 501013 Ap0551; Flavor Banana 59256c; Flavor Banana 71507; Flavor Banana 74546; Flavor Banana 8763; Flavor Banana 9.19081; Flavor Banana Durarome 860.095 Td09.91; Flavor Banana Fmc 23406; Flavor Banana Fn-6713; Flavor Banana Sa84; Flavor Bba-47769; Flavor Berry *Citrus* Blend 8409; Flavor Berry *Citrus* Blend 9621; Flavor Berry *Citrus* Blend 9756; Flavor Berry Fruit Punch 135846; Flavor Bitter Mask 9885; Flavor Bitterness Modifier 15555; Flavor Bitterness Modifier 36734; Flavor Bitterness Modifier 367343; Flavor Black Cherry 501027 Ap0551; Flavor Black Cherry 825.083; Flavor Blood Orange 51.226t; Flavor Blood Orange Sa; Flavor Bubble Gum 15864; Flavor Bubble Gum 175303; Flavor Bubble Gum 3266p; Flavor Bubble Gum Mc-4938; Flavor Burnt Sugar 680537; Flavor Burnt Sugar 687817; Flavor Burnt Sugar 994535; Flavor Butter *Vanilla*; Flavor Buttermint 24020; Flavor Butterscotch 61oo5-U; Flavor Butterscotch F-1785; Flavor C&K Mixed Fruit A13688; Flavor Candied Sugar 510155u; Flavor Cheri Beri Pcd-5580; Flavor Cheri-Beri Pfc-8573; Flavor Cheri-Beri Pfc-8580; Flavor Cherry 104613; Flavor Cherry 107026; Flavor Cherry 11539; Flavor Cherry 11929; Flavor Cherry 1566; Flavor Cherry 181612; Flavor Cherry 213; Flavor Cherry 231494; Flavor Cherry 3321; Flavor Cherry 338614; Flavor Cherry 349; Flavor Cherry 461566; Flavor Cherry 500910u; Flavor Cherry 57.679/A; Flavor Cherry 590271a; Flavor Cherry 594 S.D.; Flavor Cherry 598384; Flavor Cherry 825.382; Flavor Cherry 825.476wc; Flavor Cherry 842; Flavor Cherry 8513; Flavor Cherry A-22872; Flavor Cherry Beri Pfc-8573; Flavor Cherry Berry F-1194; Flavor Cherry Blend 770; Flavor Cherry Burgundy 11650; Flavor Cherry Cream 14850; Flavor Cherry Dp300684; Flavor Cherry Durarome 860.097 Td10.91; Flavor Cherry E.P. Modified 151; Flavor Cherry Ep-3699; Flavor Cherry F-232; Flavor Cherry Fi-8568; Flavor Cherry Fmc 22872; Flavor Cherry Fmc 8513; Flavor Cherry Fona 825.662; Flavor Cherry H&R Pharma 004; Flavor Cherry Iff 13530912; Flavor Cherry L-1233; Flavor Cherry Maraschino S-3531; Flavor Cherry Mint 5073a; Flavor Cherry N-2755; Flavor Cherry Nv-1489; Flavor Cherry Pfc-9768; Flavor Cherry Pistachio Pfc-8450; Flavor Cherry R-6556; Flavor Cherry *Vanilla* Compound A77487; Flavor Cherry Wixon 3566; Flavor Cherry Wl-1093; Flavor Cherry Wl-18022; Flavor Cherry Wl-4658; Flavor Cherry-Anise Pfc-9758; Flavor Chloroform 103589; Flavor Chocolate P727; Flavor Cinnamon; Flavor Cinnamon Sd 516; Flavor Cinnamon Veko 3726; Flavor *Citrus* Fn-7176; Flavor *Citrus*/Fruit Freeze 1100609500; Flavor Coconut 41; Flavor Coconut F-3893; Flavor Coconut Toasted 1323pg; Flavor Cola Fmc 15740; Flavor Cool *Vanilla* Bp18114; Flavor Cool *Vanilla* Bp18257; Flavor Cotton Candy 30-92-0011; Flavor Cotton Candy F-9967; Flavor Cough Syrup 110257; Flavor Cough Syrup 134681; Flavor Cough Syrup 819; Flavor Cream Ep-17688; Flavor Cream Soda; Flavor Creamy *Vanilla* 16345; Flavor Creme 46971; Flavor Creme De Menthe 14677; Flavor Creme De *Vanilla* 28156; Flavor Curacao; Flavor Curacao 50.397a; Flavor Custard 52.940/A Fir; Flavor Df-119; Flavor Df-1530; Flavor E-472; Flavor Enhancer; Flavor F-5397a; Flavor F-9843; Flavor Felton 6-R-9; Flavor Fig 827118; Flavor Fona 815.019wc; Flavor Fritzsche 21028-D; Flavor Fritzsche 46215; Flavor Fritzsche 73959; Flavor Fritzsche 75021; Flavor Fruit 01-10428; Flavor Fruit 84.6422; Flavor Fruit Fn-6714; Flavor Fruit Gum 912; Flavor Fruit Mint 75588; Flavor Fruit N&A Ws-605398; Flavor Fruit Punch 14761fm; Flavor Fruit Punch No. 28140; Flavor Fruit Punch No. 716; Flavor Fruit Tak 20008; Flavor Golden Punch; Flavor Grape 054158; Flavor Grape 10273; Flavor Grape 13403873; Flavor Grape 486939; Flavor Grape 501040a; Flavor Grape 501417c; Flavor Grape 59.145/Apo5.51; Flavor Grape 59.266/Apo5.51; Flavor Grape 61.13252; Flavor Grape 6175; Flavor Grape F&F 231460; Flavor Grape Firmenich 587.444; Flavor Grape Firmenich 597.303/C; Flavor Grape Givaudan 433160; Flavor Grape Iff 13549478; Flavor Grape Manheimer 522463; Flavor Grape Micron Zd-3876; Flavor Grape Nector Pfc-8599; Flavor Grape Pfc 8439; Flavor Grape Pfc-9711; Flavor Grape Pfc-9924; Flavor Grape St6835/09; Flavor Guarana Fmc-15417; Flavor Haverstroo Zd 49284; Flavor Iff Fp 69 F; Flavor Kiwi S-718; Flavor Lemon 812; Flavor Lemon Fmc-10471; Flavor Lemon Givaudan 74940-74; Flavor Lemon Lime Sd 935; Flavor Lemon Mint 862.547; Flavor Lemon Mint Fritzsche 54369; Flavor Lemon N&A 397; Flavor Lemon Spray V3938-1n1; Flavor Magnasweet 110; Flavor Mandarin 15228-71; Flavor Maque Tree 377(Bush); Flavor Mask Rbt-Nv-7759; Flavor Masker Fn-6819; Flavor Masker Fn-6820; Flavor Masking 35321; Flavor Masking Agent 141.18074; Flavor Masking Tak-031431; Flavor Mcp Lemon Duramone 4409a; Flavor Mcp Lime Duramone 6419; Flavor Menthol 875.017; Flavor Menthol Mint Pfc-9926; Flavor Menthol Tak-020184; Flavor Menthol Veralock; Flavor Mint 287; Flavor Mint 501359; Flavor Mint 51296 Tp0551; Flavor Mint Sn027513;

Flavor Mixed Fruit Pfc-9970; Flavor Orange 002.120; Flavor Orange 13334; Flavor Orange 249792; Flavor Orange 501071 Ap0551; Flavor Orange 57.458/Ap05.51; Flavor Orange 607217; Flavor Orange 739k (Pb82); Flavor Orange 74016-71; Flavor Orange 9/79j839; Flavor Orange Banana Wl-18093; Flavor Orange Blood Silician Fn-12235; Flavor Orange G-10431; Flavor Orange Givaudan 74388-74; Flavor Orange No. 7679; Flavor Orange P-5614; Flavor Orange Pfw-730016u; Flavor Orange Pineapple Fv-43; Flavor Orange Wonf 608352; Flavor Orbit Serene 20340; Flavor Peach 10457; Flavor Peach 13503584; Flavor Peach 23070; Flavor Peach 302789; Flavor Peach 57695; Flavor Peach Mint Fritzsche 106109; Flavor Peach Pineapple Fmc 14258; Flavor Peppermint 104; Flavor Peppermint 131989; Flavor Peppermint 501500; Flavor Peppermint 517; Flavor Peppermint 894.115; Flavor Peppermint 894.143; Flavor Peppermint Art F-10012; Flavor Peppermint Extract Fn-2356; Flavor Peppermint F94249; Flavor Peppermint K373; Flavor Peppermint Pfc 9927; Flavor Peppermint Seelock 34907; Flavor Peppermint Sn583865; Flavor Peppermint Stick Fmc 16170; Flavor Peppermint Tak-022173; Flavor Peppermint Wl-6167; Flavor Peppermint, Natural Spraylene; Flavor Perlarom Strawberry; Flavor Pharmaceutical 182608; Flavor Pharmasweet 10772900; Flavor Pineapple 182661; Flavor Pineapple 501085; Flavor Pineapple N-2566; Flavor Pineapple N-2766; Flavor Pineapple-Coconut; Flavor Prosweet 694; Flavor Punch 610962u; Flavor Punch Wl-7126; Flavor Raspberry 1840; Flavor Raspberry 21028d; Flavor Raspberry 262085; Flavor Raspberry 28106; Flavor Raspberry 50776; Flavor Raspberry 65934; Flavor Raspberry 8456; Flavor Raspberry 954; Flavor Raspberry 954k (Bk77); Flavor Raspberry 998; Flavor Raspberry A 11693; Flavor Raspberry Arome Pfc-9908; Flavor Raspberry Cream Pfc-9950; Flavor Raspberry D9599; Flavor Raspberry Dy-04447; Flavor Raspberry F-1784; Flavor Raspberry F-1840; Flavor Raspberry F-6887-S; Flavor Raspberry Pfc-8407; Flavor Raspberry Polak 5000064; Flavor Refrachessment Fd-8027d; Flavor Rhodia Pharmaceutical No. Rf 451; Flavor Rob Nv-23027; Flavor Root Beer 180339; Flavor Strawberry 052311 Ap0551; Flavor Strawberry 11545; Flavor Strawberry 133.5655; Flavor Strawberry 14953; Flavor Strawberry 17.36.8509; Flavor Strawberry 17c56217; Flavor Strawberry 52.311ap; Flavor Strawberry 5210(Fd&D); Flavor Strawberry 52312/A; Flavor Strawberry 52312/Ap0551; Flavor Strawberry 55058; Flavor Strawberry 5951; Flavor Strawberry 9843; Flavor Strawberry Banana 24020; Flavor Strawberry Cream 11407-33; Flavor Strawberry Cream Phl-131991; Flavor Strawberry Dy-04359; Flavor Strawberry F-5665; Flavor Strawberry F-5930-A; Flavor Strawberry Fn-13819; Flavor Strawberry Guarana 586.997/Apo5.51; Flavor Strawberry Microseal; Flavor Strawberry Pfc-9626; Flavor Strawberry Phs-132962; Flavor Strawberry Trusil Windsor 2373031; Flavor Strawberry Wd Fo-1022; Flavor Strawberry Wl-16650; Flavor Sweet 24052; Flavor Sweet 604978; Flavor Sweet Tone 28837; Flavor Sweet-Am 918.005; Flavor Sweetness Enhancer 5401b; Flavor Tangerine Fritzsche 51465; Flavor Tetrarome; Flavor Tm 313298; Flavor Tpf 135; Flavor Tpf 143; Flavor Tropical Blend Fv-50; Flavor Tropical Fruit Punch 1591; Flavor Tropical Fruit Punch N&A 50432; Flavor Tutti Frutti 0002028; Flavor Tutti Frutti 24093fm; Flavor Tutti Frutti 501.103/A; Flavor Tutti Frutti 51.880/Ap05.51; Flavor Tutti Frutti P-5400; Flavor Tutti Frutti Wl-18481; Flavor Vanilla 20.4573.5p Pha; Flavor *Vanilla* 323453; Flavor *Vanilla* 33869; Flavor *Vanilla* 501441 Ap2004; Flavor *Vanilla* C7984; Flavor *Vanilla* F-6257; Flavor *Vanilla* Orange; Flavor *Vanilla* P-1160; Flavor *Vanilla* Pfc-8541; Flavor *Vanilla* Pfc-9772; Flavor Veralock Bubble Gum; Flavor Wild Cherry 29653; Flavor Wild Cherry 695047u; Flavor Wild Cherry Givaudan F-1813; Flavor Wild Cherry K-321; Flavor Wild Cherry Nv-101-1489; Flavor Wild Cherry Pfc-14783; Flavor Wild Cherry Wl-1093; Flavor Wintergreen Pfc-8421; Flavor Yellow Plum Lemon 39k 020; Florasynth; Flour; Fluorescein; Fluorochlorohydrocarbons; Formaldehyde; Fosveset; Fragrance 3949-5; Fragrance 520a; Fragrance 6.007; Fragrance 91-122; Fragrance 9128-Y; Fragrance 93498g; Fragrance Balsam Pine; Fragrance Balsam Pine No. 5124; Fragrance Bouquet 10328; Fragrance Chemoderm 6401-B; Fragrance Chemoderm 6411; Fragrance Cream; Fragrance Cream No. 73457; Fragrance Cs-28197; Fragrance Felton 066m; Fragrance Firmenich 47373; Fragrance Givaudan Ess 9090/1c; Fragrance H-6540; Fragrance Herbal 10396; Fragrance Nj-1085; Fragrance P O F1-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Fructose; Fumaric Acid; Fumaryl Diketopiperazine; Gadolinium Oxide; Galactose; Gamma Cyclodextrin; Gelatin; Gelatin 200 Bloom; Gelatin Capsule, Hard; Gelatin Type A, Pork; Gelatin, Crosslinked; Gelfoam Sponge; Gellan Gum (Low Acyl); Gelucire 33/01; Gelva 737; Gentisic Acid; Gentisic Acid Ethanolamide; Gentisic Acid Ethanolamine; Ginger; Gluceptate Sodium; Gluceptate Sodium Dihydrate; Gluconolactone; Glucuronic Acid; Glutamic Acid Hydrochloride; Glutamic Acid, Dl-; Glutathione; Glycerin; Glycerin Polymer Solution I-137; Glycerin Polymer Solution Im-137; Glycerol Ester Of Hydrogenated Rosin; Glyceryl 1-Stearate; Glyceryl Behenate/Eicosadioate; Glyceryl Caprylate; Glyceryl Dibehenate; Glyceryl Distearate; Glyceryl Isostearate; Glyceryl Laurate; Glyceryl Monostearate; Glyceryl Oleate; Glyceryl Oleate/Propylene Glycol; Glyceryl Palmitate; Glyceryl Palmitostearate; Glyceryl Ricinoleate; Glyceryl Stearate—Laureth-23; Glyceryl Stearate Se; Glyceryl Stearate/Peg Stearate; Glyceryl Stearate/Peg-100 Stearate; Glyceryl Stearate/Peg-40 Stearate; Glyceryl Stearate-Stearamidoethyl Diethylamine; Glyceryl Trioleate; *Glycine; Glycine* Hydrochloride; Glycol Distearate; Glycol Stearate; Glycyrrhizin; Green Starch Blend; Guanidine Hydrochloride; Guar Gum; Guinea Green B; Gum Base, Chewing; Hair Conditioner (18n195-1m); Heptane; Hetastarch; Hexane; Hexylene Glycol; Hexylresorcinol; High Density Polyethylene; High Fructose Corn Syrup; Histidine; Hornstedtia *Costata* Seed; Human Albumin Microspheres; Hyaluronate Sodium; Hydrocarbon; Hydrocarbon Gel, Plasticized; Hydrochloric Acid; Hydrocortisone; Hydrogel Polymer; Hydrogen Peroxide; Hydrogenated Castor Oil; Hydrogenated Coconut Oil; Hydrogenated Cottonseed Oil; Hydrogenated Palm Oil; Hydrogenated Palm/Palm Kernel Oil Peg-6 Esters; Hydrogenated Polybutene 635-690; Hydrogenated Soybean Lecithin; Hydrogenated Soybean Oil; Hydrogenated Starch Hydrolysate; Hydrogenated Tallow Acid; Hydrolyzed Soy Protein (Enzymatic; 2000 Mw); Hydroxyethyl Cellulose; Hydroxyethyl Cellulose (140 Mpa·S At 5%); Hydroxyethyl Cellulose (5000 Mpa·S At 1%); Hydroxyethylpiperazine Ethane Sulfonic Acid; Hydroxymethyl Cellulose; Hydroxyoctacosanyl Hydroxystearate; Hydroxyprogesterone Caproate; Hydroxypropyl .Beta.-Cyclodextrin; Hydroxypropyl .Gamma.-Cyclodextrin; Hydroxypropyl Cellulose (Type H); Hydroxypropyl Cellulose (Type L); Hydroxypropyl Cellulose, Low Substituted; Hypromellose 2208 (100 Mpa·S); Hypromellose 2208 (100000 Mpa·S); Hypromellose 2208 (15000 Mpa·S); Hypromellose 2208 (3 Mpa·S); Hypromellose 2208 (4000 Mpa·S); Hypromellose 2208 (60000 Mpa·S); Hypromellose 2906 (4000 Mpa·S); Hypromellose 2910 (15 Mpa·S); Hypromellose 2910 (15000 Mpa·S); Hypromellose 2910 (3 Mpa·S); Hypromellose 2910 (4000 Mpa·S); Hypromellose 2910 (5 Mpa·S); Hypromellose 2910 (50 Mpa·S); Hypromellose 2910 (6 Mpa·S); Hypromellose Acetate Succinate; Hypromellose Acetate Succinate 06081224 (3 Mm2/S); Hypromellose Phthalate; Hypromellose Phthalate (24% Phthalate, 55 Cst); Hypromellose Phthalate (31% Phthalate, 40 Cst); Hypromelloses; Hystrene; Icodextrin; Imidurea; Indigotindisulfonate Sodium; Ink Black 2271; Ink Black A-10464; Ink Black A-10527; Ink Black Fge-1386; Ink Black Gg-606; Ink Black S-1-8100-Hv; Ink Black Sw-9007; Ink Black Sw-9008; Ink Black Sw-9009; Ink Black Sw-9010; Ink Blue And Yellow Imprint Gg-823; Ink Blue Black A-10463; Ink Blue Black A-9371; Ink Blue S-1-10551; Ink Blue S-1-4118; Ink Blue Tek Print Sb-6029; Ink Blue Tekprint Sb-6008; Ink Blue Videojet V496-D; Ink Dark Yellow And Yellow Imprint Gg-824; Ink Edible Black; Ink Edible Blue; Ink Edible Brown; Ink Edible Gray; Ink Edible Orange; Ink Edible Pink; Ink Edible Red; Ink Edible Red A-8032; Ink Edible White; Ink Fine Black 2202c; Ink Fine Black 2212; Ink Flexographic Pink; Ink Green A-10454; Ink Green A-10629; Ink Orange And Yellow Imprint Gg-822; Ink Pink Imprinting Sb-1003; Ink Purple Tekprint Sb-7007; Ink Red 5-1-9034; Ink Red A-8032; Ink Red And Aqua Imprinting Gg-827; Ink Red And Caramel Imprinting Gg-825; Ink Red Imprinting Gg-826; Ink S-1-7085; Ink Thinner; Ink White A-8154; Ink White S-1-7075; Ink White Sb-0007p; Ink White Sw-0012; Ink White Tek Print Sb-007p; Ink/Polyethylene Terephthalate/Aluminum/Polyethylene/Sodium Polymethacrylate/Ethylene Vinylacetate Copolymer; Invert Sugar; Invert Syrup, Medium; Iobenguane; Iodine; Iodoxamic Acid; Iofetamine Hydrochloride; Iron Oxide Beige; Isobutane; Isobutyl Alcohol; Isoceteth-20; Isoleucine; Isomalt; Isooctyl Acrylate; Isooctyl Acrylate/Acrylamide/Vinyl Acetate Copolymer, Kollidon Va 64 Polymer; Isopropyl Alcohol; Isopropyl Isostearate; Isopropyl Myristate; Isopropyl Myristate—Myristyl Alcohol; Isopropyl Palmitate; Isopropyl Stearate; Isostearic Acid; Isostearyl Alcohol; Jelene; Kaolin; Karaya Gum; Karion 83 (D-Sorbitol Content 19-25%); Kathon Cg; Kathon Cg Ii; Lactic Acid, Dl-; Lactic Acid, L-; Lactic Acid, Unspecified Form; Lactitol Monohydrate; Lactobionic Acid; Lactoferrin, Bovine; Lactose Monohydrate; Lactose Monohydrate—Cellulose, Microcrystalline; Lactose, Unspecified Form; Laneth; Lanolin; Lanolin Alcohol—Mineral Oil; Lanolin Alcohols; Lanolin Cholesterols; Lanolin Nonionic Derivatives; Lanolin, Ethoxylated; Lauralkonium Chloride; Lauramine Oxide; Laurdimonium Hydrolyzed Animal Collagen; Laureth Sulfate; Laureth-2; Laureth-23; Laureth-4; Lauric Diethanolamide; Lauric/Myristic Diethanololamide; Lauroyl Polyoxylglycerides; Lauroyl Sarcosine; Lauryl Lactate; Lauryl Sulfate; *Lavandula Angustifolia* Flowering Top; Lecithin; Lecithin Unbleached; Lecithin, Soybean; Lemon Oil; Leucine; Levomenthol; Levulinic Acid; Lidofenin; Light Green Cf Yellowish; Light Mineral Oil; Ligroin; Lime (Calcium Oxide); Lime Oil; Limonene, (+/−)-; Linoleoyl Macrogolglycerides; Lipocol Sc-15; Liquefied Petroleum Gas; Locust Bean Gum; Lubritab; Ludipress; Lysine; Lysine Acetate; Lysine Monohydrate; Magnesium Acetate; Magnesium Aluminum Silicate; Magnesium Aluminum Silicate Type Iia; Magnesium Aspartate; Magnesium Carbonate; Magnesium Chloride; Magnesium Citrate; Magnesium Hydroxide; Magnesium Nitrate; Magnesium Oxide; Magnesium Phosphate, Tribasic, Pentahydrate; Magnesium Silicate; Magnesium Stearate; Magnesium Sulfate Anhydrous; Magnesium Sulfate, Unspecified Form; Magnesium Tartrate; Magnesium Trisilicate; Maleic Acid; Malic Acid; Malic Acid, L-; Maltitol; Maltodextrin; Maltol; Maltose; Maltose Anhydrous; Mandarin Oil; Mannitol; Mannose, D-; Maprofix; Mebrofenin; Medical Antifoam Emulsion C; Medical Antiform A-F Emulsion; Medium-Chain Triglycerides; Medronate Disodium; Medronic Acid; Meglumine; Melojel; Menthol, Unspecified Form; Metacresol; Metanil Yellow; Metaphosphoric Acid; Methacrylic Acid; Methacrylic Acid—Ethyl Acrylate Copolymer (1:1) Type A; Methacrylic Acid—Methyl Methacrylate Copolymer (1:1); Methacrylic Acid—Methyl Methacrylate Copolymer (1:2); Methacrylic Acid Copolymer; Methanesulfonic Acid; Methionine; Methoxy Peg-16; Methyl Acrylate—Methyl Methacrylate; Methyl Alcohol; Methyl Chloride; Methyl Ethyl Ketone; Methyl Gluceth-10; Methyl Gluceth-20; Methyl Glucose Sesquistearate; Methyl Hydroxyethyl Cellulose; Methyl Laurate; Methyl Pyrrolidone; Methyl Salicylate; Methyl Stearate; Methylated Spirits; Methylboronic Acid; Methylcellulose (15 Mpa·S); Methylcellulose (1500 Mpa·S); Methylcellulose (400 Mpa·S); Methylcellulose (4000 Mpa·S); Methylcelluloses; Methylchloroisothiazolinone; Methylene Blue; Methylene Chloride; Methylisothiazolinone; Methylparaben; Methylparaben Sodium; Methylphenidate; Microcrystalline Wax; Milk Protein Concentrate; Mineral Oil; Miripirium Chloride; Misoprostol; Mistron Spray Talc; Modified Corn Starch (1-Octenyl Succinic Anhydride); Mono And Diglyceride; Monoethanolamine; Monoglyceride Citrate; Monoglycerides; Monosodium Citrate; Monosodium Glutamate; Monostearyl Citrate; Monothioglycerol; Montan Wax; Multisterol Extract; Muscatel Wine; Myristic Acid; Myristyl Alcohol; Myristyl Lactate; Myvacet Type 5-00; N-(Carbonyl-Methoxypolyethylene Glycol 2000)-1,2-Distearoyl-Sn-Glycero-3-Phosphoethanolamine; N-(Carbonyl-Methoxypolyethylene Glycol 2000)-Distearoyl-Glycerophosphoethanolamine, Sodium Salt; N,N-Dimethylacetamide; Naphtha; Naphthol Blue Black; Neohesperidin Dihydrochalone; Neotame; Neutral Oil; Niacinamide; Nioxime; Nipasept; Nipastat; Nitric Acid; Nitrogen; Nonoxynol Iodine; Nonoxynol-15; Nonoxynol-9; Non-Pareil Seeds; Non-Pareil Seeds Blue; Non-Pareil Seeds Orange; Non-Pareil Seeds White; Norethindrone; Norflurane; Nutmeg Oil; Oatmeal; Octadecene-1/Maleic Acid Copolymer; Octanoic Acid; Octisalate; Octoxynol-1; Octoxynol-40; Octoxynol-9; Octreotide; Octyldodecanol; Octylphenol Polymethylene; Oil Cream Soda; Oil Orange Ss; Oil, Hydrogenated; Oleic Acid; Oleth-10/Oleth-5; Oleth-2; Oleth-20; Oleyl Alcohol; Oleyl Oleate; Oleyl Polyethylene Glycol Glyceride; Olive Oil; Opacoat Na2123; Opacoat Na2203; Opacoat Na4108 Blue; Opacoat Na4711 Lavender; Opacoat Na7013 Clear; Opacode A-10450 Black; Opacode A-10509 Black; Opacode Ns-78-10013-N; Opacode Ns-78-17502 Gray; Opacode Ns-78-17821 Wb Black; Opacode Ns-78-8000 Black; Opacode Ns-78-8001; Opacode Nsp-78-17734 Black; Opacode S-1-13001 Orange; Opacode S-1-15034-Fd Red; Opacode S-1-15038 Red; Opacode S-1-16507; Opacode S-1-1666 Red; Opacode S-1-1666-M Red; Opacode S-1-1681 Red; Opacode S-1-17706 Black; Opacode S-1-17711 Black; Opacode S-1-17734 Black; Opacode S-1-17749 Black; Opacode S-1-17762 Black; Opacode S-1-17797 Black; Opacode S-1-17822 Black; Opacode S-1-17823 Black; Opacode S-1-18025 White; Opacode S-1-26514 Brown; Opacode S-1-27794 Black; Opacode S-1-3110 Green; Opacode S-1-3171 Green; Opacode S-1-4124 Blue; Opacode S-1-4157; Opacode S-1-4159 Black; Opacode S-1-4160 Blue; Opacode S-1-4172 Blue; Opacode S-1-4172m Blue; Opacode S-1-4362; Opacode S-1-7020;

Opacode S-1-7077; Opacode S-1-7078; Opacode S-1-7085 White; Opacode S-1-7090 White; Opacode S-1-800hv Black; Opacode S-1-8025 Black; Opacode S-1-8081 Black; Opacode S-1-8090 Black; Opacode S-1-8092 Black; Opacode S-1-8093 Black; Opacode S-1-8094 Black; Opacode S-1-8095; Opacode S-1-8100-Hv Black; Opacode S-1-8105 Black; Opacode S-1-8106 Black; Opacode S-1-8109 Black; Opacode S-1-8110 Black; Opacode S-1-8114 Black; Opacode S-1-8115 Black; Opacode S-1-8152hv Black; Opacode S-1-8814 Black; Opacode S-1-8815 Black; Opacode S-1-9009 Brown; Opacode S-1-9032; Opacode S-1-9037 Brown; Opacode S-1-9048c; Opacode S-1-9460hv Brown; Opacode S-19-7014 White; Opacode S-8-20931; Opacode Sb-4028 Green; Opacode Wb Ns-78-10521 Blue; Opacode Wb Ns-78-17715 Black; Opacode Wb Ns-78-18001 White; Opacode Wb Nsp-78-18022 White; Opadry 00a28646; Opadry 00b53815 Orange; Opadry 00b57513 Grey; Opadry 00f44042 Red; Opadry 02a82904 Yellow; Opadry 02b14941 Pink; Opadry 02b22429 Yellow; Opadry 02b32413 Yellow; Opadry 02b58839 White; Opadry 02b94016 Pink; Opadry 02f34337 Pink; Opadry 02f54181 Pink; Opadry 02g22555 Yellow; Opadry 02g24523 Pink; Opadry 02g26637 Brown; Opadry 02g28619 White; Opadry 02g59011 Clear; Opadry 02-H-22703 Yellow; Opadry 03a 58900 White; Opadry 03a14309 Pink; Opadry 03b11434 Green; Opadry 03b12878 Yellow; Opadry 03b12896 Yellow; Opadry 03b12914 Yellow; Opadry 03b14424 Pink; Opadry 03b14436 Pink; Opadry 03b14899 Pink; Opadry 03b16083 Maroon; Opadry 03b17426 Beige; Opadry 03b17495 Beige; Opadry 03b17618 Gray; Opadry 03b20024 Purple; Opadry 03b20556 Blue; Opadry 03b21517 Green; Opadry 03b22426 Yellow; Opadry 03b23523 Orange; Opadry 03b24562 Peach; Opadry 03b28796 White; Opadry 03b32034 Yellow; Opadry 03b34239 Pink; Opadry 03b34399 Pink; Opadry 03b50899 Blue; Opadry 03b510003 Green; Opadry 03b53850 Orange; Opadry 03b54138 Pink; Opadry 03b54180 Pink; Opadry 03b54504 Pink; Opadry 03b54573 Pink; Opadry 03b54588 Pink; Opadry 03b54955 Pink; Opadry 03b56518 Brown; Opadry 03b56982 Brown; Opadry 03b57310 Brown; Opadry 03b57520 Grey; Opadry 03b57631 Grey; Opadry 03b58902 White; Opadry 03b58930 White; Opadry 03b58965 White; Opadry 03b68903 White; Opadry 03b80829 Blue; Opadry 03b80969 Blue; Opadry 03b82316 Yellow; Opadry 03b82419 Yellow; Opadry 03b82836 Yellow; Opadry 03b82849 Yellow; Opadry 03b82943 Yellow; Opadry 03b84681 Pink; Opadry 03b84755 Pink; Opadry 03b86585 Brown; Opadry 03b86625 Brown; Opadry 03b86636 Brown; Opadry 03b86737 Brown; Opadry 03b86811 Brown; Opadry 03b86891 Brown; Opadry 03b86892 Brown; Opadry 03c34219 Pink; Opadry 03f12920 Yellow; Opadry 03f12967 Yellow; Opadry 03f13325 Orange; Opadry 03f14895 Pink; Opadry 03f42192 Yellow; Opadry 03f43159 Brown; Opadry 03f51681 Green; Opadry 03f540000 Pink; Opadry 03f54568 Pink; Opadry 03f565001 Brown; Opadry 03f57311 Brown; Opadry 03f58741 White; Opadry 03f58991 White; Opadry 03f59016 Clear; Opadry 03f82329 Yellow; Opadry 03f82604 Yellow; Opadry 03f82726 Yellow; Opadry 03f82788 Yellow; Opadry 03f84641 Pink; Opadry 03f84782 Pink; Opadry 03f84793 Pink; Opadry 03f86762 Brown; Opadry 03f86776 Brown; Opadry 03f86845 Brown; Opadry 03f86990 Brown; Opadry 03g24389 Pink; Opadry 03g82464 Yellow; Opadry 03g82490 Yellow; Opadry 03j18312 White; Opadry 03k14881 Pink; Opadry 03k29121 Clear; Opadry 03k50891 Blue; Opadry 03k51211 Green; Opadry 03k52543 Yellow; Opadry 03k54121 Pink; Opadry 03k80846 Blue; Opadry 04e28779 White; Opadry 04f50603 Blue; Opadry 04f50702 Blue; Opadry 04f51279 Green; Opadry 04f52565 Yellow; Opadry 04f53544 Orange; Opadry 04f58804 White; Opadry 05b10446 Purple; Opadry 05b10457 Purple; Opadry 05b11552 Green; Opadry 05b 11781 Green; Opadry 05b12337 Yellow; Opadry 05b15325 Red; Opadry 05b17055 Tan; Opadry 06f32500 Yellow; Opadry 06f34520 Pink; Opadry 06f34521 Orange; Opadry 06f34522 Pink; Opadry 06f34523 Pink; Opadry 12b58900 White; Opadry 12f20984 Blue; Opadry 12f21129 Green; Opadry 12f22609 Yellow; Opadry 12j18255 White; Opadry 13b50159 Purple; Opadry 13b50780 Blue; Opadry 13b51260 Green; Opadry 13b52329 Yellow; Opadry 13b58802 White; Opadry 13b58894 White; Opadry 13b80922 Blue; Opadry 13b82555 Yellow; Opadry 13f51381 Green; Opadry 13f52194 Yellow; Opadry 13f52195 Yellow; Opadry 13f54198 Pink; Opadry 13f58866 White; Opadry 13h52750 Yellow; Opadry 13h52754 Yellow; Opadry 13h54756 Pink; Opadry 13h54757 Pink; Opadry 13k52177 Yellow; Opadry 13m530001 Orange; Opadry 13m565001 Brown; Opadry 13m86920 Brown; Opadry 15b110003 Green; Opadry 15b11947 Green; Opadry 15b13335 Orange; Opadry 15b20780 Blue; Opadry 15b21340 Green; Opadry 15b22275 Yellow; Opadry 15b24473 Pink; Opadry 15b24879 Pink; Opadry 15b28665 White; Opadry 15b50612 Blue; Opadry 15b52000 Yellow; Opadry 15b52070 Yellow; Opadry 15b53449 Orange; Opadry 15b58810 White; Opadry 15b86703 Brown; Opadry 15b91211 Green; Opadry 15b92484 Yellow; Opadry 15b96558 Brown; Opadry 16b38982 White; Opadry 16b5900 Yellow; Opadry 20014832 Pink; Opadry 20a28569 White; Opadry 20a52229 Yellow; Opadry 20a52560 Yellow; Opadry 20a52900 Yellow; Opadry 20a54211 Pink; Opadry 20a54239 Pink; Opadry 20a54614 Pink; Opadry 20a54616 Pink; Opadry 20a54900 Pink; Opadry 20a54901 Pink; Opadry 20a56500 Brown; Opadry 20a56694 Brown; Opadry 20a56788 Brown; Opadry 20a58806 White; Opadry 20a58916 White; Opadry 20a59015 Clear; Opadry 20a91487 Green; Opadry 20a99171 Blue; Opadry 20a99172 Blue; Opadry 20b11521 Green; Opadry 20b17583 Gray; Opadry 20b50135 Purple; Opadry 20b50184 Purple; Opadry 20b97160 Beige; Opadry 20c15347 Red; Opadry 20h52619 Yellow; Opadry 20h58983 White; Opadry 21k84964 Pink; Opadry 31f20963 Blue; Opadry 31f32870 Yellow; Opadry 32f540014 Pink; Opadry 32k14834 Pink; Opadry 32k23123 Orange; Opadry 33g12976 Yellow; Opadry 33g25171 Brick Red; Opadry 40114278 Pink; Opadry 80w 12319 Yellow; Opadry 80w22657 Amb Yellow; Opadry 80w-93032 Amb Orange; Opadry 85f14999 Pink; Opadry 85f19250 Clear; Opadry 85f21445 Green; Opadry 85f21446 Green; Opadry 85f21450 Green; Opadry 85g689183 White; Opadry 85g93096 Orange; Opadry Amb 80w52110 Yellow; Opadry Amb 80w62680 Yellow; Opadry Amb 80w62681 Yellow; Opadry Amb 80w64837 Pink; Opadry Amb 80w68912 White; Opadry Amb Oy-B-28920 White; Opadry I 03b22409 Yellow; Opadry I 03b23197 Orange; Opadry I 03b24658 Pink; Opadry Ii 03b10903 Blue; Opadry Ii 30f84515 Pink; Opadry Ii 31f22088 Yellow; Opadry Ii 31f23111 Orange; Opadry Ii 31f24128 Pink; Opadry Ii 31f24239 Pink; Opadry Ii 31f27625 Gray; Opadry Ii 31f32090 Yellow; Opadry Ii 31f58914 White; Opadry Ii 31k34575 Pink; Opadry Ii 31k34581 Pink; Opadry Ii 31k52633 Yellow; Opadry Ii 31k84972 Pink; Opadry Ii 32b10817 Blue; Opadry Ii 32f28553 White; Opadry Ii 32f505001 Blue; Opadry Ii 32f540002 Pink; Opadry Ii 32f540012 Pink; Opadry Ii 32f58900 White; Opadry Ii 32f84835 Pink; Opadry Ii 32k10054 Purple; Opadry Ii 32k12160 Yellow; Opadry Ii 32k12884 Yellow; Opadry Ii 32k12942 Yellow; Opadry Ii 32k12968 Yellow; Opadry Ii 32k13357 Orange; Opadry Ii 32k13699 Orange; Opadry Ii 32k14826 Pink; Opadry Ii 32k 14827 Pink; Opadry Ii 32k14833 Pink; Opadry Ii 32k15649 Red; Opadry Ii 32k16706 Brown; Opadry Ii 32k17089 Tan; Opadry Ii 32k17573 Gray; Opadry Ii 33f28627 White; Opadry Ii 33g10148 Purple; Opadry Ii 33g10907 Blue; Opadry Ii 33g11635 Green; Opadry Ii 33g11938 Green; Opadry Ii 33g28435 White; Opadry Ii 33g28707 White; Opadry Ii 33g32605 Yellow; Opadry Ii 33g34594 Pink; Opadry Ii 33g92112 Yellow; Opadry Ii 39b18529 White; Opadry Ii 40 L14235 Pink; Opadry Ii 40 L17589 Gray; Opadry Ii 40014876 Pink; Opadry Ii 40b12994 Beige; Opadry Ii 40b97172 Yellow; Opadry Ii 40c10881 Blue; Opadry Ii 40c13396 Orange; Opadry Ii 40c18303 White; Opadry Ii 40110412 Purple; Opadry Ii 40110884 Blue; Opadry Ii 40111438 Green; Opadry Ii 40111588 Green; Opadry Ii 40112917 Yellow; Opadry Ii 40112979 Yellow; Opadry Ii 40113950 Orange; Opadry Ii 40114190 Pink; Opadry Ii 40114336 Pink; Opadry Ii 40114836 Pink; Opadry Ii 40117427 Beige; Opadry Ii 40117587 Gray; Opadry Ii 40192058 Yellow; Opadry Ii 40193159 Orange; Opadry Ii 40o93122 Orange; Opadry Ii 45f22481 Yellow; Opadry Ii 45f24512 Yellow; Opadry Ii 49b10882 Blue; Opadry Ii 49b13460 Orange; Opadry Ii 49b16716 Brown; Opadry Ii 57u92682 Yellow; Opadry Ii 57u97337 Tan; Opadry Ii 57u97508 Gray; Opadry Ii 85f10129 Purple; Opadry Ii 85f10245 Purple; Opadry Ii 85f10447 Purple; Opadry Ii 85f10919 Blue; Opadry Ii 85f 1881 Green; Opadry Ii 85f12345 Yellow; Opadry Ii 85f12372 Yellow; Opadry Ii 85f12375 Yellow; Opadry Ii 85f13751 Orange; Opadry Ii 85f13980 Orange; Opadry Ii 85f140024 Pink; Opadry Ii 85f14452 Pink; Opadry Ii 85f16876 Brown; Opadry Ii 85f18378 White; Opadry Ii 85f18422 White; Opadry Ii 85f18442 White; Opadry Ii 85f22055 Yellow; Opadry Ii 85f22075 Yellow; Opadry Ii 85f22079 Yellow; Opadry Ii 85f23470 Pink; Opadry Ii 85f23499 Orange; Opadry Ii 85f23976 Orange; Opadry Ii 85f24033 Pink; Opadry Ii 85f24035 Pink; Opadry Ii 85f24307 Pink; Opadry Ii 85f28751 White; Opadry Ii 85f32121 Yellow; Opadry Ii 85f32157 Yellow; Opadry Ii 85f32547 Yellow; Opadry Ii 85f32782 Yellow; Opadry Ii 85f34610 Pink; Opadry Ii 85f62534 Yellow; Opadry Ii 85f64712 Pink; Opadry Ii 85f64732 Pink; Opadry Ii 85f66775 Brown; Opadry Ii 85f66815 Brown; Opadry Ii 85f90093 Purple; Opadry Ii 85f91135 Green; Opadry Ii 85f91136 Green; Opadry Ii 85f91137 Green; Opadry Ii 85f91238 Green; Opadry Ii 85f92008 Yellow; Opadry Ii 85f92204 Yellow; Opadry Ii 85f92621 Yellow; Opadry Ii 85f92716 Yellow; Opadry Ii 85f93042 Orange; Opadry Ii 85f93314 Orange; Opadry Ii 85f94172 Pink; Opadry Ii 85f94552 Pink; Opadry Ii 85f97458 Beige; Opadry Ii 85f97531 Gray; Opadry Ii 85f97533 Gray; Opadry Ii 85f99126 Blue; Opadry Ii 85g20583 Blue; Opadry Ii 85g56434 Maroon; Opadry Ii 85g56867 Brown; Opadry Ii 85g57680 Grey; Opadry Ii 85g62591 Yellow; Opadry Ii Oy-L-22903; Opadry Ii Oy-L-23028 Orange; Opadry Ii Oy-L-24802 Pink; Opadry Ii Oy-L-24803 Pink; Opadry Ii Oy-L-24808; Opadry Ii Oy-L-28900 White; Opadry Ii Oy-L-32920; Opadry Ii Pink 85g94027; Opadry Ii Pink 85g94065; Opadry Ii Red 85g94101; Opadry Ii Y-19-19054 Clear; Opadry Ii Y-19-7483 Clear; Opadry Ii Y-22-10274 Lavender; Opadry Ii Y-22-10508 Blue; Opadry Ii Y-22-10519 Blue; Opadry Ii Y-22-10538 Blue; Opadry Ii Y-22-10702 Blue; Opadry Ii Y-22-10764 Blue; Opadry Ii Y-22-11184 Green; Opadry Ii Y-22-11210 Green; Opadry Ii Y-22-11251 Green; Opadry Ii Y-22-12098 Yellow; Opadry Ii Y-22-12553 Yellow; Opadry Ii Y-22-12664 Yellow; Opadry Ii Y-22-12718 Yellow; Opadry Ii Y-22-12720 Pale Yellow; Opadry Ii Y-22-12780 Yellow; Opadry Ii Y-22-13034 Orange; Opadry Ii Y-22-13061 Orange; Opadry Ii Y-22-13083 Orange; Opadry Ii Y-22-13089 Orange; Opadry Ii Y-22-13167 Orange; Opadry Ii Y-22-13526 Orange; Opadry Ii Y-22-13577 Flesh; Opadry Ii Y-22-13603 Orange; Opadry Ii Y-22-13613 Orange; Opadry Ii Y-22-13663 Orange; Opadry Ii Y-22-14001 Pink; Opadry Ii Y-22-14701 Pink; Opadry Ii Y-22-15061; Opadry Ii Y-22-16562 Brown; Opadry Ii Y-22-16577 Brown; Opadry Ii Y-22-17025 Beige; Opadry Ii Y-22-17165 Beige; Opadry Ii Y-22-17221 Beige; Opadry Ii Y-22-17279 Beige; Opadry Ii Y-22-17515 Gray; Opadry Ii Y-22-18238 White; Opadry Ii Y-22-7719 White; Opadry Ii Y-30-10671a Blue; Opadry Ii Y-30-10701 Blue; Opadry Ii Y-30-12705 Yellow; Opadry Ii Y-30-12736a Yellow; Opadry Ii Y-30-12737a Yellow; Opadry Ii Y-30-12842a Yellow; Opadry Ii Y-30-12863a Yellow; Opadry Ii Y-30-13091 Orange; Opadry Ii Y-30-13242a Orange; Opadry Ii Y-30-13616 Orange; Opadry Ii Y-30-13642a Orange; Opadry Ii Y-30-14700a Pink; Opadry Ii Y-30-14758 Pink; Opadry Ii Y-30-17295a Tan; Opadry Ii Y-30-17296a Beige; Opadry Ii Y-30-17340a Beige; Opadry Ii Y-30-17528 Gray; Opadry Ii Y-30-18037 White; Opadry Ii Ys-1-12524a; Opadry Ii Ys-1-19025a Clear; Opadry Ii Ys-1-7006 Clear; Opadry Ii Ys-22-13571 Orange; Opadry Ii Ys-22-17227a Beige; Opadry Ii Ys-22-18096 White; Opadry Ii Ys-30-12788a Yellow; Opadry Ii Ys-30-13641a Orange; Opadry Ii Ys-30-14743a Pink; Opadry Ii Ys-30-14777a Pink; Opadry Ii Ys-30-17265a Beige; Opadry Ii Ys-30-17271a Beige; Opadry Ii Ys-30-18105 White; Opadry O2b24864 Pink; Opadry Os-F-32867 Yellow; Opadry Oy-22959 Yellow; Opadry Oy-23050 Orange; Opadry Oy-27202 Tan; Opadry Oy-27301 Butterscotch; Opadry Oy-3736 Butterscotch; Opadry Oy-38924 White; Opadry Oy-52945 Yellow; Opadry Oy-54937 Pink; Opadry Oy-58900 White; Opadry Oy-7240 Clear; Opadry Oy-7300 White; Opadry Oy-8764h Orange; Opadry Oy-B-28920 White; Opadry Oy-B-32830; Opadry Oy-Gm-28900; Opadry Oy-L-27204 Tan; Opadry Oy-L-27205 Beige; Opadry Oy-L-28906; Opadry Oy-L-34836 Pink; Opadry Oy-Ls-20921 Blue; Opadry Oy-Ls-23016 Orange; Opadry Oy-Ls-23018 Orange; Opadry Oy-Ls-28908 White; Opadry Oy-Ls-28914 White; Opadry Oy-Ls-33111 Orange; Opadry Oy-Ls-37200 Buff; Opadry Oy-Ls-58900 White; Opadry Oy-S-1387 Pink; Opadry Oy-S-20007 Purple; Opadry Oy-S-20900 Blue; Opadry Oy-S-20901 Blue; Opadry Oy-S-21001 Green; Opadry Oy-S-21027 Green; Opadry Oy-S-22802 Yellow; Opadry Oy-S-22815 Yellow; Opadry Oy-S-22907 Yellow; Opadry Oy-S-23049 Orange; Opadry Oy-S-24900 Pink; Opadry Oy-S-24972 Pink; Opadry Oy-S-26529 Red; Opadry Oy-S-26530 Red; Opadry Oy-S-28833 White; Opadry Oy-S-28849 White; Opadry Oy-S-28876 White; Opadry Oy-S-28924 White; Opadry Oy-S-29019 Clear; Opadry Oy-S-30013 Purple; Opadry Oy-S-30913 Blue; Opadry Oy-S-30953 Blue; Opadry Oy-S-32921 Yellow; Opadry Oy-S-32986 Yellow; Opadry Oy-S-33016 Orange; Opadry Oy-S-34800 Pink; Opadry Oy-S-34817 Pink; Opadry Oy-S-34923 Pink; Opadry Oy-S-34995 Pink; Opadry Oy-S-38928; Opadry Oy-S-38944 White; Opadry Oy-S-52902 Yellow; Opadry Oy-S-53010 Orange; Opadry Oy-S-54902 Pink; Opadry Oy-S-54904 Pink; Opadry Oy-S-6937 Pink; Opadry Oy-S-7322 White; Opadry Oy-S-7399 White; Opadry Oy-S-9476 Brown; Opadry Oy-S-9603 White; Opadry Oy-Sr-34907; Opadry S-1-1666 Red; Opadry Y-1-1518 Pink; Opadry Y-1-17272a Beige; Opadry Y-1-17517 Gray; Opadry Y-1-2102 Yellow; Opadry Y-1-

2132 Yellow; Opadry Y-1-2516 Orange; Opadry Y-1-2553 Orange; Opadry Y-1-2605 Beige; Opadry Y-1-3211 Green; Opadry Y-1-4205 Blue; Opadry Y-1-4234 Blue; Opadry Y-1-7000 White; Opadry Y-1-7000b White; Opadry Y-1-7000h White; Opadry Y-1-7006 Blue; Opadry Y-1-7503 Gray; Opadry Y-22-10501 Blue; Opadry Y-22-12721 Light Yellow; Opadry Y-22-12751 Yellow; Opadry Y-22-13558 Orange; Opadry Y-22-14525 Pink; Opadry Y-22-15008 Red; Opadry Y-22-15119 Red; Opadry Y-22-18238 White; Opadry Y-30-13168a Orange; Opadry Y-30-14565 Pink; Opadry Y-30-17267 Beige; Opadry Y-33g-27241 Beige; Opadry Y-5-10272a Lavender; Opadry Y-5-10300 Lavender; Opadry Y-5-10670 Blue; Opadry Y-5-12539 Yellow; Opadry Y-5-12544a Yellow; Opadry Y-5-12584 Yellow; Opadry Y-5-13512 Orange; Opadry Y-5-13513 Orange; Opadry Y-5-14530a Pink; Opadry Y-5-1727 Red; Opadry Y-5-2028 Yellow; Opadry Y-5-2042 Yellow; Opadry Y-5-2086 Yellow; Opadry Y-5-2312 Yellow; Opadry Y-5-2328 Orange; Opadry Y-5-2371 Orange; Opadry Y-5-2394 Orange; Opadry Y-5-2450 Orange; Opadry Y-5-2644 Beige; Opadry Y-5-2646 Beige; Opadry Y-5-3140 Green; Opadry Y-5-3171 Green; Opadry Y-5-3193 Green; Opadry Y-5-3296 Green; Opadry Y-5-4129 Blue; Opadry Y-5-4270 Blue; Opadry Y-5-4287 Blue; Opadry Y-5-4295 Blue; Opadry Y-5-6233 Light Orange; Opadry Y-5-6301 Yellow; Opadry Y-5-6308; Opadry Y-5-7058 White; Opadry Y-5-7068 White; Opadry Y-5-7072 White; Opadry Y-5-7524 Grey; Opadry Y-5-8050 Black; Opadry Y-5-9006 Brown; Opadry Y-5-9020 Brown; Opadry Yellow; Opadry Yps-7-2127; Opadry Ys-1-003 White; Opadry Ys-1-10010 Purple; Opadry Ys-1-10291 Lavender; Opadry Ys-1-10523a Blue; Opadry Ys-1-10525 Blue; Opadry Ys-1-10533a; Opadry Ys-1-10542a Blue; Opadry Ys-1-10547a Blue; Opadry Ys-1-10563 Blue; Opadry Ys-1-10613a Blue; Opadry Ys-1-10618; Opadry Ys-1-10629; Opadry Ys-1-10654a Blue; Opadry Ys-1-10682 Blue; Opadry Ys-1-10690a Blue; Opadry Ys-1-10699 Blue; Opadry Ys-1-10745 Blue; Opadry Ys-1-10748a Light Blue; Opadry Ys-1-10755 Blue; Opadry Ys-1-10783a Blue; Opadry Ys-1-11000 Pink; Opadry Ys-1-11051 Green; Opadry Ys-1-11060 Green; Opadry Ys-1-1107 Green; Opadry Ys-1-11075a Green; Opadry Ys-1-11113 Green; Opadry Ys-1-11171 Green; Opadry Ys-1-11234 Green; Opadry Ys-1-11305 Green; Opadry Ys-1-11369 Green; Opadry Ys-1-1246 Pink; Opadry Ys-1-1252 Pink; Opadry Ys-1-12524a Yellow; Opadry Ys-1-12525a Yellow; Opadry Ys-1-12526a Yellow; Opadry Ys-1-12529 Yellow; Opadry Ys-1-12541 Yellow; Opadry Ys-1-1256-A Yellow; Opadry Ys-1-12573 Yellow; Opadry Ys-1-12581 Yellow; Opadry Ys-1-1262 Pink; Opadry Ys-1-12625 Yellow; Opadry Ys-1-12702a Yellow; Opadry Ys-1-12726a Yellow; Opadry Ys-1-12732 Yellow; Opadry Ys-1-1277 Pink; Opadry Ys-1-12789 Yellow; Opadry Ys-1-12826 Yellow; Opadry Ys-1-1283 Pink; Opadry Ys-1-12844 Yellow; Opadry Ys-1-12847 Yellow; Opadry Ys-1-1298 Pink; Opadry Ys-1-13013 Peach; Opadry Ys-1-13065a Orange; Opadry Ys-1-13119 Orange; Opadry Ys-1-13121 Yellow; Opadry Ys-1-13148a Orange; Opadry Ys-1-13214 Orange; Opadry Ys-1-13269 Orange; Opadry Ys-1-13271 Orange; Opadry Ys-1-13555 Orange; Opadry Ys-1-13591a Orange; Opadry Ys-1-13664a Orange; Opadry Ys-1-13673a Orange; Opadry Ys-1-13675a Orange; Opadry Ys-1-14012 Pink; Opadry Ys-1-14129 Pink; Opadry Ys-1-14130 Pink; Opadry Ys-1-14142 Pink; Opadry Ys-1-1418 Pink; Opadry Ys-1-1441g; Opadry Ys-1-1448g Pink; Opadry Ys-1-14518a Pink; Opadry Ys-1-14519a Pink; Opadry Ys-1-14532 Pink; Opadry Ys-1-1454 Pink; Opadry Ys-1-14555a Pink; Opadry Ys-1-14559 Pink; Opadry Ys-1-1456g Pink; Opadry Ys-1-14587a Pink; Opadry Ys-1-14593a Pink; Opadry Ys-1-14595 Pink; Opadry Ys-1-14608a; Opadry Ys-1-14643a Pink; Opadry Ys-1-14725 Pink; Opadry Ys-1-14756a Pink; Opadry Ys-1-14779a Pink; Opadry Ys-1-15050 Red; Opadry Ys-1-1510 Pink; Opadry Ys-1-1528 Pink; Opadry Ys-1-1543 Pink; Opadry Ys-1-15585a Red; Opadry Ys-1-16002 Maroon; Opadry Ys-1-16518a Brown; Opadry Ys-1-17169a; Opadry Ys-1-17180a Beige; Opadry Ys-1-17181a Beige; Opadry Ys-1-17192a; Opadry Ys-1-17209 Beige; Opadry Ys-1-17220; Opadry Ys-1-17222a Tan; Opadry Ys-1-17235a Peach; Opadry Ys-1-1724 Red; Opadry Ys-1-17274a Beige; Opadry Ys-1-17277a Beige; Opadry Ys-1-17307a Butterscotch; Opadry Ys-1-17505a Gray; Opadry Ys-1-17506a Gray; Opadry Ys-1-1751g Red; Opadry Ys-1-1755 Gray; Opadry Ys-1-18005 White; Opadry Ys-1-18022 White; Opadry Ys-1-18027 White; Opadry Ys-1-18027a White; Opadry Ys-1-18028 White; Opadry Ys-1-18097a White; Opadry Ys-1-1811 Red; Opadry Ys-1-18111 White; Opadry Ys-1-18130a White; Opadry Ys-1-1814 Red; Opadry Ys-1-18177a White; Opadry Ys-1-18202a White; Opadry Ys-1-18229 White; Opadry Ys-1-1846 Red; Opadry Ys-1-1847 Red; Opadry Ys-1-1891 Red; Opadry Ys-1-19025-A Clear; Opadry Ys-1-2007 Yellow; Opadry Ys-1-2013 Yellow; Opadry Ys-1-2053 White; Opadry Ys-1-2053 Yellow; Opadry Ys-1-2063 Yellow; Opadry Ys-1-2074 Yellow; Opadry Ys-1-2083 Yellow; Opadry Ys-1-2115 Yellow; Opadry Ys-1-2122 Yellow; Opadry Ys-1-2134 Yellow; Opadry Ys-1-2135 Yellow; Opadry Ys-1-2136 Yellow; Opadry Ys-1-2141 Yellow; Opadry Ys-1-2152 Yellow; Opadry Ys-1-2167 Yellow; Opadry Ys-1-2181 Yellow; Opadry Ys-1-2184 Gold; Opadry Ys-1-2186 Yellow; Opadry Ys-1-2192 Yellow; Opadry Ys-1-2305 Orange; Opadry Ys-1-2308 Dark Orange; Opadry Ys-1-2344 Yellow; Opadry Ys-1-2383 Orange; Opadry Ys-1-2398 Orange; Opadry Ys-1-2449 Orange; Opadry Ys-1-2455 Red; Opadry Ys-1-2465; Opadry Ys-1-2487 Orange; Opadry Ys-1-2522 Orange; Opadry Ys-1-2526 Orange; Opadry Ys-1-2527 Orange; Opadry Ys-1-2534; Opadry Ys-1-2546 Orange; Opadry Ys-1-2548 Orange; Opadry Ys-1-2549 Orange; Opadry Ys-1-2558 Orange; Opadry Ys-1-2563 Orange; Opadry Ys-1-2564; Opadry Ys-1-2578 Orange; Opadry Ys-1-2596 Orange; Opadry Ys-1-2604 Beige; Opadry Ys-1-2612 Beige; Opadry Ys-1-2619; Opadry Ys-1-2621 Rust; Opadry Ys-1-2623 Brown; Opadry Ys-1-12630 Yellow; Opadry Ys-1-2635 Tan; Opadry Ys-1-2660 Salmon; Opadry Ys-1-2665 Beige; Opadry Ys-1-2669 Rust; Opadry Ys-1-2671 Beige; Opadry Ys-1-3105 Green; Opadry Ys-1-3130 Green; Opadry Ys-1-3134 Green; Opadry Ys-1-3146 Green; Opadry Ys-1-3147; Opadry Ys-1-3166 Green; Opadry Ys-1-3256 Green; Opadry Ys-1-3288 Green; Opadry Ys-1-4014 Blue; Opadry Ys-1-4018 Blue; Opadry Ys-1-4112 Blue; Opadry Ys-1-4137 Blue; Opadry Ys-1-4215; Opadry Ys-1-4216; Opadry Ys-1-4221 Blue; Opadry Ys-1-4228 Blue; Opadry Ys-1-4229 Blue; Opadry Ys-1-4234 Blue; Opadry Ys-1-4235 Blue; Opadry Ys-1-4236 Blue; Opadry Ys-1-4240 Blue; Opadry Ys-1-4241 Blue; Opadry Ys-1-4245 Blue; Opadry Ys-1-4249 Blue; Opadry Ys-1-4251 Blue; Opadry Ys-1-4254; Opadry Ys-1-4255; Opadry Ys-1-4256 Blue; Opadry Ys-1-4282 Blue; Opadry Ys-1-4298 Blue; Opadry Ys-14644 Pink; Opadry Ys-1-4700 Purple; Opadry Ys-1-4710; Opadry Ys-1-4739 Lavender; Opadry Ys-1-4812 Lavender; Opadry Ys-1-4845 Purple; Opadry Ys-1-6275 Orange; Opadry Ys-1-6300; Opadry Ys-1-6312 Yellow; Opadry Ys-1-6318 Yellow; Opadry Ys-1-6320 Yellow; Opadry Ys-1-6357 Yellow; Opadry Ys-1-6370g Yellow; Opadry Ys-1-6378g Yellow; Opadry Ys-1-6381 Yellow; Opadry Ys-1-6382g Yellow; Opadry Ys-1-7000e White;

Opadry Ys-1-7002 White; Opadry Ys-1-7003 White; Opadry Ys-1-7003h White; Opadry Ys-1-7006 Clear; Opadry Ys-1-7022 Off-White; Opadry Ys-1-7027 White; Opadry Ys-1-7040 White; Opadry Ys-1-7052 White; Opadry Ys-1-7059 White; Opadry Ys-1-7060 White; Opadry Ys-1-7079 White; Opadry Ys-1-7086 White; Opadry Y-S-17191 Brown; Opadry Ys-1-7444g White; Opadry Ys-1-7449 White; Opadry Ys-1-7472 Clear; Opadry Ys-1-7507 Grey; Opadry Ys-1-7552 Grey; Opadry Ys-1-7700 White; Opadry Ys-1-7706 Clear; Opadry Ys-1-7706g White; Opadry Ys-1-7724 White; Opadry Ys-1-8325 Beige; Opadry Ys-1-8343g Beige; Opadry Ys-1-8345g Beige; Opadry Ys-1-8608 Orange; Opadry Ys-1-8619 Orange; Opadry Ys-1-89193 Clear; Opadry Ys-1-9011 Brown; Opadry Ys-1-9012 Brown; Opadry Ys-1r-1418 Pink; Opadry Ys-1r-7006 Clear; Opadry Ys-2-10657 Blue; Opadry Ys-2-19071a Clear; Opadry Ys-2-19114a Clear; Opadry Ys-22-16576 Brown; Opadry Ys-22-18119 White; Opadry Ys-2-7013 Clear; Opadry Ys-2-7063 White; Opadry Ys-3-7011 Clear; Opadry Ys-3-7031 Clear; Opadry Ys-3-7413 Clear; Opadry Ys-5-12575 Yellow; Opadry Ys-5-12576 Yellow; Opadry Ys-5-1260 Pink; Opadry Ys-5-1296 Pink; Opadry Ys-5-17266 Tan; Opadry Ys-5-18011 White; Opadry Ys-5-18068 White; Opadry Ys-5-18074 White; Opadry Ys-5-19010 Clear; Opadry Ys-5-2085 Yellow; Opadry Ys-5-2370 Orange; Opadry Ys-5-3116 Green; Opadry Ys-5-4277 Blue; Opadry Ys-5-4278 Blue; Opadry Ys-5-7017; Opadry Ys-5-7042 Clear; Opadry Ys-5-7068; Opadry Ys-5-7099 White; Opaglos 2 97w19206 Clear; Opaglos 6000 White; Opaglos Gs 2-0300; Opaglos Gs 2-0310; Opaglos Ii 97w90646 Blue; Opaglos S 0750; Opalux As 1406 Pink; Opalux As 1459 Pink; Opalux As 1589 Pink; Opalux As 2006 Yellow; Opalux As 2007 Yellow; Opalux As 2052 Yellow; Opalux As 2062 Yellow; Opalux As 2086 Chartreuse; Opalux As 2094; Opalux As 2167 Yellow; Opalux As 2236; Opalux As 2269 Yellow; Opalux As 2324 Orange; Opalux As 2336 Orange; Opalux As 2395 Peach; Opalux As 2413; Opalux As 2433 Orange; Opalux As 2490 Coral; Opalux As 2498 Orange; Opalux As 2553 Orange; Opalux As 2612; Opalux As 2613 Tan; Opalux As 2620-B Tan; Opalux As 2676 Salmon Jasper Red; Opalux As 2754; Opalux As 2768; Opalux As 2787 Butterscotch; Opalux As 3140 Green; Opalux As 3287; Opalux As 3288 Green; Opalux As 3308 Green; Opalux As 3348-C Green; Opalux As 3376; Opalux As 3378-A Green; Opalux As 3381; Opalux As 3389 Green; Opalux As 3391 Green; Opalux As 3942 Maroon; Opalux As 4025; Opalux As 4151 Blue; Opalux As 4188 Blue; Opalux As 4193 Blue; Opalux As 4258 Blue; Opalux As 4270 Blue; Opalux As 4800 Lavender; Opalux As 4854 Lavender; Opalux As 4855 Purple; Opalux As 4891; Opalux As 5005-A Red; Opalux As 5034 Red; Opalux As 5107; Opalux As 5162 Green; Opalux As 5178 Green; Opalux As 5203 Green; Opalux As 5212 Green; Opalux As 7000-B; Opalux As 7000-P White; Opalux As 7001; Opalux As 7535 Gray; Opalux As 8010-A Black; Opalux As 8050-L Black; Opalux As 9010 Brown; Opalux As 9050 Brown; Opalux As-1475 Pink; Opalux As-9030 Brown; Opalux Blue; Opalux Green; Opaque Blue 100; Opaque Blue 147; Opaque Blue 605; Opaque Brown 85 Bfj; Opaque Green 1664; Opaque Green 97; Opaque Green/Flesh; Opaque Maroon 6 Dar; Opaque Pink 0439; Opaque White 001; Opaque White 002; Opaque White 535; Opaque White 536; Opaque White 538; Opaque White 8; Opaspray 3-1700; Opaspray 3-1810; Opaspray 3-1820; Opaspray 3-1830; Opaspray Im-176; Opaspray K-1-1230 Pink; Opaspray K-1-1243; Opaspray K-1-1254; Opaspray K-1-1279; Opaspray K-1-1289 Pink; Opaspray K-1-14016 Pink; Opaspray K-1-1413 Pink; Opaspray K-1-1414 Pink; Opaspray K-1-1432; Opaspray K-1-1437; Opaspray K-1-1455 Pink; Opaspray K-1-1526 Pink; Opaspray K-1-1563 Pink; Opaspray K-1-1573 Lavender; Opaspray K-1-1574; Opaspray K-1-1584; Opaspray K-1-1719 Red; Opaspray K-1-2004 Yellow; Opaspray K-1-2013 Yellow; Opaspray K-1-2043 Yellow; Opaspray K-1-2182 Yellow; Opaspray K-1-2186 Yellow; Opaspray K-1-2216-A Yellow; Opaspray K-1-2227 Yellow; Opaspray K-1-2228 Yellow; Opaspray K-1-2239; Opaspray K-1-2240 Yellow; Opaspray K-1-2256 Yellow; Opaspray K-1-2275 Yellow; Opaspray K-1-2300 Peach; Opaspray K-1-2301 Peach; Opaspray K-1-2303 Orange; Opaspray K-1-2304 Orange; Opaspray K-1-2314 Orange; Opaspray K-1-2327 Orange; Opaspray K-1-2330 Orange; Opaspray K-1-2335 Orange; Opaspray K-1-2406 Orange; Opaspray K-1-2410 Orange; Opaspray K-1-2417 Orange; Opaspray K-1-2430; Opaspray K-1-2441 Orange; Opaspray K-1-2471 Orange; Opaspray K-1-2473; Opaspray K-1-2492; Opaspray K-1-2531; Opaspray K-1-2533 Orange; Opaspray K-1-2554; Opaspray K-1-2568 Orange; Opaspray K-1-2570 Orange; Opaspray K-1-2588 Orange; Opaspray K-1-2614 Beige; Opaspray K-1-2621 Brown; Opaspray K-1-2626 Orange; Opaspray K-1-2656 Beige; Opaspray K-1-2670 Tan; Opaspray K-1-2674 Beige; Opaspray K-1-2711; Opaspray K-1-2723 Butterscotch; Opaspray K-1-2837; Opaspray K-1-3000; Opaspray K-1-3142 Green; Opaspray K-1-3144 Green; Opaspray K-1-3147; Opaspray K-1-3148 Green; Opaspray K-1-3156; Opaspray K-1-3173 Green; Opaspray K-1-3178 Green; Opaspray K-1-3197 Green; Opaspray K-1-3202 Green; Opaspray K-1-3209 Green; Opaspray K-1-3220 Green; Opaspray K-1-3227; Opaspray K-1-3300-A Green; Opaspray K-1-3300-C Green; Opaspray K-1-3843; Opaspray K-1-4108 Blue; Opaspray K-1-4119; Opaspray K-1-4122 Blue; Opaspray K-1-4136 Blue; Opaspray K-1-4205 Blue; Opaspray K-1-4210-A; Opaspray K-1-4213 Blue; Opaspray K-1-4214; Opaspray K-1-4227; Opaspray K-1-4234 Blue; Opaspray K-1-4235 Blue; Opaspray K-1-4728; Opaspray K-1-4731 Purple; Opaspray K-1-4743 Lavender; Opaspray K-1-4786; Opaspray K-1-7000 White; Opaspray K-1-70008 White; Opaspray K-1-7000b; Opaspray K-1-7076; Opaspray K-1-9027 Brown; Opaspray K-1-9039-L Brown; Opaspray K-1-9060 Red; Opaspray K-1-9080 Brown; Opaspray K-1-9112 Brown, Opaspray L-2113; Opaspray L-3305 Green, Opaspray L-3306 Green; Opaspray L-7000 White; Opaspray M-1-2042; Opaspray M-1-3459 B Orange, Opaspray M-1-4395b Blue; Opaspray M-1-7111-B; Opaspray M-1-711b White; Opaspray M-1-7120 White; Opaspray M-1-8429 Yellow; Opaspray Wd-1270 Pink; Opatint Ad-22901 Yellow; Opatint Ad-25000 Red; Opatint Dd-14000 Pink; Opatint Dd-18000 White; Orange Juice; Orange Juice, Synthetic; Orange Oil; Orange Oil Terpeneless; Orange Peel; Orvus K Liquid; Oxidronate Disodium; Palm Kernel Oil; Palm Oil—Soybean Oil, Hydrogenated; Palmitamine Oxide; Palmitic Acid; Parabens; Paraffin; Parfum Creme 45/3; Parmacoat 606; Pd Base-1000; Peanut Oil; Pectin; Peg 6-32 Stearate/Glycol Stearate; Peg Vegetable Oil; Peg/Ppg-18/18 Dimethicone; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-20 Methyl Glucose Sesquistearate; Peg-20 Sorbitan Isostearate; Peg-20 Stearate; Peg-22 Methyl Ether/Dodecyl Glycol Copolymer; Peg-25 Propylene Glycol Stearate; Peg-4 Dilaurate; Peg-4 Laurate; Peg-40 Castor Oil; Peg-40 Sorbitan Diisostearate; Peg-45/Dodecyl Glycol Copolymer; Peg-5 Oleate; Peg-50 Stearate; Peg-54 Hydrogenated Castor Oil;

Peg-6 Isostearate; Peg-60 Hydrogenated Castor Oil; Peg-7 Methyl Ether; Peg-75 Lanolin; Peg-8 Caprylic/Capric Glycerides; Peg-8 Laurate; Peg-8 Stearate; Pegoxol 7 Stearate; Pentadecalactone; Pentaerythritol Cocoate; Pentasodium Pentetate; Pentetate Calcium Trisodium; Pentetic Acid; Peppermint Oil; Perflutren; Perfume 25677; Perfume B-8412; Perfume Bouquet; Perfume E-1991; Perfume Gd 5604; Perfume Tana 90/42 Scba; Perfume W-1952-1; Petrolatum; Petroleum Distillates; Pharmaburst B1; Pharmaburst B2; Pharmaburst C1; Phenol; Phenonip; Phenoxyethanol; Phenylalanine; Phenylethyl Alcohol; Phenylmercuric Acetate; Phenylmercuric Nitrate; Phosphate Ion; Phospholipid; Phosphoric Acid; Pigment Blend 86620 Brown; Pigment Blend Pb-2145 Red; Pigment Blend Pb-2289 Yellow; Pigment Blend Pb-2389 Off-White, Pigment Blend Pb-2417 Pink; Pigment Blend Pb-2418 Black; Pigment Blend Pb-24899 Ih; Pine Needle Oil (*Pinus Sylvestris*); Pineapple; Piperazine; Piperazine Hexahydrate; Placebo; Plasacryl; Plastibase-50w; Pluweet; Polacrilin; Polacrilin Potassium; Polidronium Chloride; Polish Wax 7625 P 100; Polishing Solution Im-182; Poloxamer; Poloxamer 70; Poloxamer 124; Poloxamer 181; Poloxamer 182; Poloxamer 188; Poloxamer 237; Poloxamer 331; Poloxamer 338; Poloxamer 407; Poly(Bis (P-Carboxyphenoxy)Propane Anhydride): Sebacic Acid; Poly(Dimethylsiloxane/Methylvinylsiloxane/Methylhydrogensiloxane) Dimethylvinyl Or Dimethylhydroxy Or Trimethyl Endblocked; Poly(Dl-Lactic-Co-Glycolic Acid), (50:50; 12000 Mw); Poly(Dl-Lactic-Co-Glycolic Acid), (75:25; 20000 Mw); Poly(Dl-Lactic-Co-Glycolic Acid), Ethyl Ester Terminated, (50:50; 12000 Mw); Poly(Methyl Acrylate-Co-Methyl Methacrylate-Co-Methacrylic Acid 7:3:1; 280000 Mw); Polyacrylic Acid (250000 Mw); Polybutene (1400 Mw); Polycarbophil; Polydextrose; Polydextrose K; Polyester; Polyester Polyamine Copolymer; Polyester Rayon; Polyester/Ethylene-Vinyl Acetate; Polyethylene Glycol 1000; Polyethylene Glycol 1450; Polyethylene Glycol 1500; Polyethylene Glycol 200; Polyethylene Glycol 20000; Polyethylene Glycol 300; Polyethylene Glycol 3000; Polyethylene Glycol 3350; Polyethylene Glycol 3500; Polyethylene Glycol 400; Polyethylene Glycol 4000; Polyethylene Glycol 4500; Polyethylene Glycol 540; Polyethylene Glycol 600; Polyethylene Glycol 6000; Polyethylene Glycol 7000; Polyethylene Glycol 800; Polyethylene Glycol 8000; Polyethylene Glycol 900; Polyethylene Glycols; Polyethylene High Density Containing Ferric Oxide Black (<1%); Polyethylene Low Density Containing Barium Sulfate (20-24%); Polyethylene Oxide 1000000; Polyethylene Oxide 200000; Polyethylene Oxide 2000000; Polyethylene Oxide 600000; Polyethylene Oxide 7000000; Polyethylene Oxide 900000; Polyethylene T; Polyethylene Terephthalates; Polygalacturonic Acid; Polyglactin; Polyglyceryl-10 Oleate; Polyglyceryl-10 Tetralinoleate; Polyglyceryl-3 Oleate; Polyglyceryl-4 Oleate; Polyhydroxyethyl Methacrylate; Polyisobutylene; Polyisobutylene (1100000 Mw); Polyisobutylene (2300 Mw); Polyisobutylene (35000 Mw); Polyisobutylene (55000 Mw); Polyisobutylene (800000 Mw); Polyisobutylene Low Molecular Weight; Polyisobutylene Medium Molecular Weight; Polyisobutylene/Polybutene Adhesive; Polylactide; Polyols; Polyoxyethylene—Polyoxypropylene 1800; Polyoxyethylene Alcohols; Polyoxyethylene Fatty Acid Esters; Polyoxyethylene Propylene; Polyoxyl 20 Cetostearyl Ether; Polyoxyl 35 Castor Oil; Polyoxyl 40 Hydrogenated Castor Oil; Polyoxyl 40 Stearate; Polyoxyl 6 And Polyoxyl 32 Palmitostearate; Polyoxyl Distearate; Polyoxyl Glyceryl Stearate; Polyoxyl Lanolin; Polyoxyl Palmitate; Polyoxyl Stearate; Polyoxylethylene Isononylphenyl Ester; Polypropylene; Polypropylene Glycol; Polyquaternium-10; Polyquaternium-7 (70/30 Acrylamide/Dadmac; 1600000 Mw); Polysaccharides; Polysaccharides Soy; Polysiloxane; Polysorbate 20; Polysorbate 40; Polysorbate 60; Polysorbate 65; Polysorbate 80; Polysorbate 85; Polystyrene Sulfonic Acid; Polyurethane; Polyvinyl Acetate; Polyvinyl Acetate Phthalate; Polyvinyl Alcohol; Polyvinyl Alcohol Graft Polyethylene Glycol Copolymer (3:1; 45000 Mw); Polyvinyl Chloride; Polyvinyl Chloride-Polyvinyl Acetate Copolymer; Polyvinylacetal; Polyvinylpyridine; Polyvinylpyrrolidone Ethylcellulose; Ponceau 3r; Ponceau Xylidine; Poppy Seed Oil; Potassium; Potassium Acetate; Potassium Alum; Potassium Bicarbonate; Potassium Bisulfite; Potassium Bitartrate; Potassium Carbonate; Potassium Chloride; Potassium Citrate; Potassium Citrate Anhydrous; Potassium Hydroxide; Potassium Metabisulfite; Potassium Metaphosphate; Potassium Phosphate, Dibasic; Potassium Phosphate, Monobasic; Potassium Soap; Potassium Sorbate; Povidone Acrylate Copolymer; Povidone Hydrogel; Povidone K12; Povidone K17; Povidone K25; Povidone K26/28; Povidone K29/32; Povidone K30; Povidone K90; Povidone/Eicosene Copolymer; Povidones; Powdered Cellulose; Ppg-11 Stearyl Ether; Ppg-12/Smdi Copolymer; Ppg-15 Stearyl Ether; Ppg-20 Methyl Glucose Ether Distearate; Ppg-26 Oleate; Pramoxine Hydrochloride; Primajel; Primary Taste Modifier No. 29275; Product Wat; Proline; Promulgen D; Promulgen G; Propane; Propenyl Guaethol; Propyl Gallate; Propylene Carbonate; Propylene Glycol; Propylene Glycol—Lecithin, Propylene Glycol Alginate; Propylene Glycol Diacetate; Propylene Glycol Dicaprylate; Propylene Glycol Laurates; Propylene Glycol Monolaurate; Propylene Glycol Monopalmitostearate, Propylene Glycol Monostearate; Propylene Glycol Ricinoleate; Propylene Glycol/Diazolidinyl Urea/Methylparaben/Propylparben; Propylparaben; Propylparaben Sodium; Prosolv; Prosolv 50; Prosolv 90; Prosolv Hd 90; Prosolv Smcc 50; Prosolv Smcc 90; Prosweet; Prosweet 604; Prosweet K; Protamine Sulfate; Protein Hydrolysate; Pvm/Ma Copolymer; Quaternium-15; Quaternium-15 Cis-Form; Quaternium-52; Ra-2397; Ra-3011; Raspberry; Raspberry Juice; Rhodamine B; Riboflavin; Rosin; Saccharin; Saccharin Calcium; Saccharin Sodium; Saccharin Sodium Anhydrous; Safflower Oil; Scandium; Sd Alcohol 3a; Sd Alcohol 3a Anhydrous; Sd Alcohol 40, Sd Alcohol 40-2, Sd Alcohol 40b; Sepifilm Lp-761 Blanc; Sepineo P 600; Sepisperse Ap 3527; Serine; Sesame Oil; Shea Butter; Shellac; Shellac P.V.P. Solution No. 4; Silastic Brand Medical Grade Tubing; Silastic Medical Adhesive, Silicone Type A; Silicon; Silicon Dioxide; Silicone; Silicone Emulsion; Silicone/Polyester Film Strip; Simethicone; Simethicone C; Simethicone Emulsion; Sipon Ls 20np; Soap; Sodium 1,2-Ethanedisulfonate; Sodium 2-Naphthalenesulfonate; Sodium Acetate; Sodium Acetate Anhydrous; Sodium Alginate; Sodium Alkyl Sulfate; Sodium Aluminium Silicate; Sodium Ascorbate; Sodium Benzoate; Sodium Bicarbonate; Sodium Bisulfate; Sodium Bisulfate Acetone; Sodium Bisulfite; Sodium Bitartrate; Sodium Borate; Sodium Carbonate; Sodium Carbonate Decahydrate; Sodium Carbonate Monohydrate; Sodium Carboxymethyl .Beta.-Glucan (Ds 0.65-0.85); Sodium Caseinate; Sodium Cellulose; Sodium Cetostearyl Sulfate; Sodium Chlorate; Sodium Chloride; Sodium Chlorite; Sodium Cholesteryl Sulfate; Sodium Citrate; Sodium Citrate, Unspecified Form; Sodium Cocoyl Sarcosinate; Sodium Cyclamate; Sodium Desoxycholate; Sodium Dithionite; Sodium Dodecylbenzenesulfonate; Sodium Ethylparaben; Sodium Formaldehyde Sulfoxylate; Sodium Gluconate; Sodium Hydroxide; Sodium Hypochlorite; Sodium Iodide; Sodium Lactate; Sodium Lactate, L-; Sodium Laureth-2 Sulfate; Sodium Laureth-3 Sulfate; Sodium Laureth-5 Sulfate; Sodium Lauroyl Sarcosinate; Sodium Lauryl Sulfate; Sodium Lauryl Sulfoacetate; Sodium Metabisulfite; Sodium Nitrate; Sodium Oleate; Sodium Phosphate; Sodium Phosphate Dihydrate; Sodium Phosphate P-32; Sodium Phosphate, Dibasic; Sodium Phosphate, Dibasic Dihydrate; Sodium Phosphate, Dibasic Dodecahydrate; Sodium Phosphate, Dibasic, Anhydrous; Sodium Phosphate, Dibasic, Dodecahydrate; Sodium Phosphate, Dibasic, Heptahydrate; Sodium Phosphate, Monobasic, Anhydrous; Sodium Phosphate, Monobasic, Dihydrate; Sodium Phosphate, Monobasic, Monohydrate; Sodium Phosphate, Monobasic, Unspecified Form; Sodium Phosphate, Tribasic; Sodium Phosphate, Tribasic, Anhydrous; Sodium Phosphate, Tribasic, Monohydrate; Sodium Phosphite; Sodium Polyacrylate; Sodium Polyacrylate (2500000 Mw); Sodium Polymetaphosphate; Sodium Polystyrene Sulfonate; Sodium Propionate; Sodium Pyrophosphate; Sodium Pyrrolidone Carboxylate; Sodium Starch Glycolate Type A Corn; Sodium Starch Glycolate Type A Potato; Sodium Starch Glycolate Type B Potato; Sodium Stearate; Sodium Stearyl Fumarate; Sodium Succinate Hexahydrate; Sodium Sulfate; Sodium Sulfate Anhydrous; Sodium Sulfite; Sodium Sulfosuccinated Undecyclenic Monoalkylolamide; Sodium Tartrate; Sodium Thioglycolate; Sodium Thiomalate; Sodium Thiosulfate; Sodium Thiosulfate Anhydrous; Sodium Trimetaphosphate; Sodium Tripolyphosphate, Unspecified Form; Sodium Xylenesulfonate; Solvent Red 49; Somay 44; Sorbic Acid; Sorbitan; Sorbitan Isostearate; Sorbitan Monolaurate; Sorbitan Monooleate; Sorbitan Monopalmitate; Sorbitan Monostearate; Sorbitan Sesquioleate; Sorbitan Trioleate; Sorbitan Tristearate; Sorbitol; Sorbitol Special Polyol Solution; Sorbitol-Glycerin Blend; Soybean; Soybean Oil; Spearmint; Spearmint Oil; Spectrablend Csl-15764 (Blue); Spermaceti; Squalane; Stannous 2-Ethylhexanoate; Stannous Chloride; Stannous Chloride Anhydrous; Stannous Fluoride; Stannous Tartrate; Star Anise; Starch; Starch 7150; Starch 825; Starch 826; Starch, Corn; Starch, Modified; Starch, Potato; Starch, Pregelatinized; Starch, Rice; Starch, Tapioca; Starch, Wheat; Stearalkonium Chloride; Stearalkonium Hectorite/Propylene Carbonate; Stearamidoethyl Diethylamine; Stearates; Steareth-10; Steareth-100; Steareth-2; Steareth-20; Steareth-21; Steareth-40; Stearic Acid; Stearic Diethanolamide; Stear-O-Wet C; Stear-O-Wet M; Stearoxytrimethylsilane; Stearoyl Polyoxylglycerides; Steartrimonium Hydrolyzed Animal Collagen; Stearyl Alcohol; Strawberry; Styrene/Isoprene/Styrene Block Copolymer; Succimer; Succinic Acid; Sucralose; Sucrose; Sucrose Laurate; Sucrose Palmitate; Sucrose Polyesters; Sucrose Stearate; Sucrose Stearate/Sucrose Distearate; Sugar Liquid Type No. 0; Sugar/Starch Insert Granules; Sulfacetamide Sodium; Sulfur Dioxide; Sulfuric Acid; Sulfurous Acid; Surelease E-719010 Clear; Surelease E-7-7050; Surfactol Qs; Synchron Oral Carrier; Synchron Oral Carrier Base Kf, Synchron Oral Carrier Vehicle Type Em; Synthetic Iron Oxides; Tagatose; Talc; Talc 127; Talc Triturate; Tall Oil; Tallow Glycerides; Tartaric Acid; Tartaric Acid, Dl-; Tegacid; Tenox; Tenox-2; Terpene Resin; Tert-Butyl Alcohol; Tert-Butyl Hydroperoxide; Tert-Butylhydroquinone; Tetrachloroethylene; Tetrakis(2-Methoxyisobutylisocyanide)Copper(I) Tetrafluoroborate; Tetrapropyl Orthosilicate; Tetrofosmin; Thimerosal; Threonine; Thymol; Timing Solution Clear N-7; Tin; Titanium Dioxide; Tocopherol; Tocophersolan; Tolterodine Tartrate; Tolu Balsam; Tragacanth; Trehalose; Triacetin; Tribasic Calcium Phosphate; Tribehenin; Tricaprylin; Triceteareth-4 Phosphate; Trichloroethane; Trichloroethylene; Trichloromonofluoromethane; Trideceth-10; Triethanolamine Lauryl Sulfate; Triethyl Citrate; Trifluoroacetic Acid; Triglyceride, Synthetic; Trihydroxystearin; Trilaneth-4 Phosphate; Trilaureth-4 Phosphate; Trimethylsilyl Treated Dimethiconol/Trimethylsiloxysilicate Crosspolymer (35/65 W/W; 50000000 Pa·S); Trimethylsilyl Treated Dimethiconol/Trimethylsiloxysilicate Crosspolymer (40/60 W/W; 5000000 Pa·S); Trimethylsilyl Treated Dimethiconol/Trimethylsiloxysilicate Crosspolymer (45/55 W/W; 100000 Pa·S); Trimyristin; Trisodium Citrate Dihydrate; Trisodium Hedta; Tristearin; Triton 720; Trolamine; Tromantadine; Tromethamine; Tryptophan; Turpentine Oil; Tyloxapol; Ty-Med Filler, Blue; Tyrosine; Undecylenic Acid; Union 76 Amsco-Res 6038; Urea; Urethane; Ursodiol; Valine; *Vanilla*; Vanillin; Vegetable Oil; Vegetable Oil Glyceride, Hydrogenated; Vegetable Oil, Hydrogenated; Vegetable Shortening; Velvetine Black Powder; *Verbascum Densiflorum* Leaf; Versetamide; Vinyl Acetate—Crotonic Acid Copolymer; Viscose/Cotton; Water; Wax; Wax Blend; Wax, Emulsifying; Wax, Vegetable; Wecobee Fs; Wheat; Wheat Gluten; White Wax; Xanthan Gum; Xylitol; Xylitol 300; Yellow Ob; Yellow Wax; Zein; Zinc; Zinc Acetate; Zinc Carbonate; Zinc Chloride; Zinc Oxide; Zinc Stearate; Zinc Sulfate Monohydrate; and Zinc Sulfate, Unspecified Form.

In some embodiments, the cooling compounds and combinations thereof are further combined with one or more silicone compounds, terpenes, abrasives, and/or surfactants. Such compounds are known in the art and are useful in the production of, for example, cosmetic and topical compositions (See U.S. Patent App. Pub. No. 2013/0202543, incorporated herein by reference in its entirety). Representative silicone compounds include but are not limited to: Acefylline Methylsilanol Mannuronate, Acetylmethionyl Methylsilanol Elastinate Acrylates/Behenyl, Acrylate/Dimethicone Methacrylate Copolymer, Acrylates/Behenyl Methacrylate/Dimethicone Methacrylate Copolymer, Acrylates/Bis-Hydroxypropyl Dimethicone Crosspolymer, Acrylates/Dimethicone Copolymer, Acrylates/Dimethicone Methacrylate/Ethylhexyl Acrylate Copolymer, Acrylates/Dimethiconol Acrylate Copolymer, Acrylates/Ethylhexyl Acrylate/Dimethicone Methacrylate Copolymer, Acrylates/Octylacrylamide/Diphenyl Amodimethicone Copolymer, Acrylates/Polytrimethylsiloxymethacrylate Copolymer, Acrylates/Propyl Trimethicone Methacrylate Copolymer, Acrylates/Stearyl Acrylate/Dimethicone Methacrylate Copolymer, Acrylates/Tridecyl Acrylate/Triethoxysilylpropyl Methacrylate/Dimethicone Methacrylate Copolymer, Acrylates/Trifluoropropylmethacrylate/Polytrimethyl Siloxymethacrylate Copolymer, Amino Bispropyl Dimethicone, Aminoethylaminopropyl Dimethicone, Aminopropyl Dimethicone, Aminopropyl Phenyl Trimethicone, Aminopropyl Triethoxysilane, Ammonium Dimethicone PEG-7 Sulfate, Amodimethicone, Amodimethicone Hydroxystearate, Amodimethicone/Silsesquioxane Copolymer, Ascorbyl Carboxydecyl Trisiloxane, Ascorbyl Methylsilanol Pectinate, Behenoxy Dimethicone, Behentrimonium Dimethicone PEG-8 Phthalate, Behenyl Dimethicone, Bisamino PEG/PPG-41/3 Aminoethyl PG-Propyl Dimethicone, Bis-Aminopropyl/Ethoxy Aminopropyl Dimethicone, Bis(Butylbenzoate) Diaminotriazine Aminopropyltrisiloxane, Bis-Butyldimethicone Polyglyceryl-3, Bis-Butyloxyamodimethicone/PEG-60 Copolymer, Bis($C_{13-15}$ Alkoxy) Hydroxybutamidoamodimethicone, Bis ($C_{13-15}$ Alkoxy) PG-Amodimethicone, Bis-($C_{1-8}$ Alkyl Lauroyl Lysine Decylcarboxamide) Dimethicone, Bis-Cetyl Cetyl Dimethicone, Bis-Cetyl/PEG-8 Cetyl PEG-8 Dimethicone, Bis-Diphenylethyl Disiloxane, Bis-Ethyl Ethyl Methicone, Bis-Gluconamidoethylaminopropyl Dimethicone, Bis-Hydrogen Dimethicone, Bis-Hydroxyethoxypropyl Dimethicone Bis-Hydroxylauryl, Dimethicone/IPDI Copolymer, Bis-Hydroxy/Methoxy Amodimethicone, Bis-Hydroxypropyl Dimethicone Behenate, Bis-Hydroxypropyl Dimethicone/SMDI Copolymer, Bis-Isobutyl PEG-14/Amodimethicone Copolymer, Bis-Isobutyl PEG-15/Amodimethicone Copolymer, Bis-Isobutyl PEG/PPG-20/35/Amodimethicone Copolymer, Bis-Isobutyl PEG/PPG-10/7/Dimethicone Copolymer, Bis-Isobutyl PEG-24/PPG-7/Dimethicone Copolymer, Bis-PEG-1 Dimethicone, Bis-PEG-4 Dimethicone, Bis-PEG-8 Dimethicone, Bis-PEG-12 Dimethicone, Bis-PEG-20 Dimethicone, Bis-PEG-12 Dimethicone Beeswax, Bis-PEG-12 Dimethicone Candelillate, Bis-PEG-15 Dimethicone/IPDI Copolymer, Bis-PEG-15 Methyl Ether Dimethicone, Bis-PEG-18 Methyl Ether Dimethyl Silane, Bis-PEG/PPG-14/14 Dimethicone, Bis-PEG/PPG-15/5 Dimethicone, Bis-PEG/PPG-18/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Bisphenylhexamethicone, Bis-Phenylpropyl Dimethicone, Bispolyethylene Dimethicone, Bis-(Polyglyceryl-3 Oxyphenylpropyl) Dimethicone, Bis-(Polyglyceryl-7 Oxyphenylpropyl) Dimethicone, Bis-PPG-15 Dimethicone/IPDI Copolymer, Bis(PPG-7 Undeceneth-21) Dimethicone, Bis-Stearyl Dimethicone, Bis-Trimethoxysilylethyl Tetramethyldisiloxyethyl Dimethicone, Bis-Vinyldimethicone, Bis-Vinyl Dimethicone/Dimethicone Copolymer, Borage Seed Oil PEG-7 Dimethicone Esters, Butyl Acrylate/C6-14 Perfluoroalkylethyl Acrylate/Mercaptopropyl Dimethicone Copolymer, Butyl Acrylate/Hydroxypropyl Dimethicone Acrylate Copolymer, Butyl Dimethicone Acrylate/Cyclohexylmethacrylate/Ethylhexyl Acrylate Copolymer, Butyldimethicone Methacrylate/Methyl Methacrylate Crosspolymer, t-Butyl Dimethyl Silyl Grape Seed Extract, Butyl Polydimethylsiloxyl Ethylene/Propylene/Vinylnorbornene Copolymer, C6-8 Alkyl C3-6 Alkyl Glucoside Dimethicone, C20-24 Alkyl Dimethicone, C24-28 Alkyl Dimethicone, C26-28 Alkyl Dimethicone, C30-45 Alkyl Dimethicone, C30-60 Alkyl Dimethicone, C32 Alkyl Dimethicone, C30-45 Alkyl Dimethicone/Polycyclohexene Oxide Crosspolymer, C26-28 Alkyldimethylsilyl Polypropylsilsesquioxane, C30-45 Alkyldimethylsilyl Polypropylsilsesquioxane, C20-24 Alkyl Methicone, C24-28 Alkyl Methicone, C26-28 Alkyl Methicone, C30-45 Alkyl Methicone, C20-28 Alkyl Perfluorodecylethoxy Dimethicone, C26-54 Alkyl Tetradecyl Dimethicone, Capryl Dimethicone, Caprylyl Dimethicone Ethoxy Glucoside, Caprylyl Methicone, Caprylyl Trimethicone, Carboxydecyl Trisiloxane, Castor Oil Bis-Hydroxypropyl Dimethicone Esters Cerotyl Dimethicone, Cetearyl Dimethicone Crosspolymer, Cetearyl Dimethicone/Vinyl Dimethicone Crosspolymer, Cetearyl Methicone, Cetrimonium Carboxydecyl PEG-8 Dimethicone, Cetrimonium Dimethicone PEG-7 Phthalate, Cetyl Behenyl Dimethicone, Cetyl Dimethicone, Cetyl Dimethicone/Bis-Vinyldimethicone Crosspolymer, Cetyl Hexacosyl Dimethicone, Cetyloxy Dimethicone, Cetyl PEG-8 Dimethicone, Cetyl PEG/PPG-15/15 Butyl Ether Dimethicone, Cetyl PEG/PPG-7/3 Dimethicone, Cetyl PEG/PPG-10/1 Dimethicone, Cetyl Triethylmonium Dimethicone PEG-8 Phthalate, Cetyl Triethylmonium Dimethicone PEG-8 Succinate, Copper Acetyl Tyrosinate Methylsilanol, Copper PCA Methylsilanol, C4-14 Perfluoroalkylethoxy Dimethicone, Cycloethoxymethicone, Cycloheptasiloxane, Cyclohexasiloxane, Cyclomethicone, Cyclopentasiloxane, Cyclophenylmethicone, Cyclotetrasiloxane, Cyclovinylmethicone, Cystine Bis-PG-Propyl Silanetriol, DEA PG-Propyl PEG/PPG-18/21 Dimethicone, Diisostearoyl Trimethylolpropane Siloxy Silicate, Dilauroyl Trimethylolpropane Siloxy Silicate, Dilinoleamidopropyl Dimethylamine Dimethicone PEG-7 Phosphate, Dimethicone, Dimethicone Crosspolymer, Dimethicone Crosspolymer-3, Dimethicone/Divinyldimethicone/Silsesquioxane Crosspolymer, Dimethicone Ethoxy Glucoside, Dimethicone Hydroxypropyl Trimonium Chloride, Dimethicone/Mercaptopropyl Methicone Copolymer, Dimethicone PEG-15 Acetate Dimethicone PEG-8 Adipate, Dimethicone PEG-7 Avocadoate, Dimethicone PEG-8 Avocadoate, Dimethicone PEG-8 Beeswax, Dimethicone PEG-8 Benzoate, Dimethicone PEG-8 Borageate, Dimethicone PEG-7 Cocoate, Dimethicone/PEG-10 Crosspolymer, Dimethicone/PEG-10/15 Crosspolymer, Dimethicone/PEG-15 Crosspolymer, Dimethicone PEG-7 Isostearate, Dimethicone PEG-8 Isostearate, Dimethicone PEG-7 Lactate, Dimethicone PEG-8 Lanolate, Dimethicone PEG-8 Laurate, Dimethicone PEG-8 Meadowfoamate, Dimethicone PEG-7 Octyldodecyl Citrate, Dimethicone PEG-7 Olivate, Dimethicone PEG-8 Olivate, Dimethicone PEG-7 Phosphate, Dimethicone PEG-8 Phosphate, Dimethicone PEG-10 Phosphate, Dimethicone PEG-7 Phthalate, Dimethicone PEG-8 Phthalate, Dimethicone PEG-8 Polyacrylate, Dimethicone PEG/PPG-20/23 Benzoate, Dimethicone PEG/PPG-7/4 Phosphate, Dimethicone PEG/PPG-12/4 Phosphate, Dimethicone PEG-7 Succinate, Dimethicone PEG-8 Succinate, Dimethicone PEG-7 Sulfate, Dimethicone PEG-7 Undecylenate, Dimethicone PG-Diethylmonium Chloride, Dimethicone/Phenyl Vinyl Dimethicone Crosspolymer, Dimethicone/Polyglycerin-3 Crosspolymer, Dimethicone/PPG-20 Crosspolymer, Dimethicone Propylethylenediamine Behenate, Dimethicone Propyl PG-Betaine, Dimethicone/Silsesquioxane Copolymer, Dimethicone Silylate, Dimethicone/Vinyl Dimethicone Crosspolymer, DimethiconeNinyltrimethylsiloxysilicate Crosspolymer, Dimethiconol, Dimethiconol Arginine, Dimethiconol Beeswax, Dimethiconol Behenate, Dimethiconol Borageate, Dimethiconol Candelillate, Dimethiconol Carnaubate, Dimethiconol Cysteine, Dimethiconol Dhupa Butterate, Dimethiconol Fluoroalcohol Dilinoleic Acid, Dimethiconol Hydroxystearate, Dimethiconol Illipe Butterate, Dimethiconol/IPDI Copolymer, Dimethiconol Isostearate, Dimethiconol Kokum Butterate, Dimethiconol Lactate, Dimethiconol Meadowfoamate, Dimethiconol Methionine, Dimethiconol/Methylsilanol/Silicate Crosspolymer, Dimethiconol Mohwa Butterate, Dimethiconol Panthenol, Dimethiconol Sal Butterate, Dimethiconol/Silica Crosspolymer, Dimethiconol/Silsesquioxane Copolymer, Dimethiconol Stearate, Dimethiconol/Stearyl, Methicone/Phenyl Trimethicone Copolymer, Dimethoxysilyl Ethylenediaminopropyl Dimethicone, Dimethylaminopropylamido PCA Dimethicone, Dimethyl Oxobenzo Dioxasilane, Dimethylsilanol Hyaluronate, Dioleyl Tocopheryl Methylsilanol, Diphenyl Amodimethicone, Diphenyl Dimethicone, Diphenyl Dimethicone Crosspolymer Diphenyl Dimethicone/Vinyl Diphenyl Dimethicone/Silsesquioxane Crosspolymer, Diphenylethyl Benzyloxy Dilsiloxane, Diphenylisopropyl Dimethicone, Diphenylsiloxy Phenyl/Propyl Trimethicone, Diphenylsiloxy Phenyl Trimethicone Disiloxane, Disodium Amodimethicone Disuccinamide, Disodium PEG-12 Dimethicone Sulfosuccinate, Disodium PEG-8 Lauryl Dimethicone Sulfosuccinate, Divinyldimethicone/Dimethicone Copolymer, Divinyldimethicone/Dimethicone Crosspolymer, Drometrizole Trisiloxane, Ethylhexyl Acrylate/VP/Dimethicone Methacrylate Copolymer, Ethyl Methicone, Ethyl Trisiloxane, Fluoro C2-8 Alkyldimethicone, Gluconamidopropyl Aminopropyl Dimethicone, 4-(2-Beta-Glucopyranosiloxy) Propoxy-2-Hydroxybenzophenone, Glyceryl Undecyl Dimethicone, Glycidoxy Dimethicone, Hexadecyl Methicone, Hexyl Dimethicone, Hexyl Methicone, Hexyltrimethoxysilane, Hydrogen Dimethicone, Hydrogen Dimethicone/Octyl Silsesquioxane Copolymer, Hydrolyzed Collagen PG-Propyl Dimethiconol, Hydrolyzed Collagen PG-Propyl Methylsilanediol, Hydrolyzed Collagen PG-Propyl Silanetriol, Hydrolyzed Keratin PG-Propyl Methylsilanediol, Hydrolyzed Sesame Protein PG-Propyl Methylsilanediol, Hydrolyzed Silk PG-Propyl Methylsilanediol, Hydrolyzed Silk PG-Propyl Methylsilanediol Crosspolymer, Hydrolyzed Soy Protein/Dimethicone PEG-7 Acetate, Hydrolyzed Soy Protein PG-Propyl Methylsilanediol, Hydrolyzed Vegetable Protein PG-Propyl Silanetriol, Hydrolyzed Wheat Protein/Cystine Bis-PG-Propyl Silanetriol Copolymer, Hydrolyzed Wheat Protein/Dimethicone PEG-7 Acetate, Hydrolyzed Wheat Protein/Dimethicone PEG-7 Phosphate Copolymer, Hydrolyzed Wheat Protein PG-Propyl Methylsilanediol, Hydrolyzed Wheat Protein PG-Propyl Silanetriol, Hydroxyethyl Acetomonium PG-Dimethicone, Hydroxypropyldimethicone, Hydroxypropyl Dimethicone Behenate, Hydroxypropyl Dimethicone Isostearate, Hydroxypropyl Dimethicone Stearate, Isobutylmethacrylate/Bis-Hydroxypropyl Dimethicone Acrylate Copolymer, Isobutylmethacrylate/Trifluoroethylmethacrylate/Bis-Hydroxypropyl Dimethicone Acrylate Copolymer, Isopentyl Trimethoxycinnamate Trisiloxane, Isopolyglyceryl-3 Dimethicone, Isopolyglyceryl-3 Dimethiconol, Isopropyl Titanium Triisostearate/Triethoxysilylethyl, Polydimethylsiloxyethyl Dimethicone Crosspolymer, Isostearyl Carboxydecyl PEG-8 Dimethicone, Lactoyl Methylsilanol Elastinate, Lauryl Dimethicone, Lauryl Dimethicone PEG-15 Crosspolymer, Lauryl Dimethicone PEG-10 Phosphate, Lauryl Dimethicone/Polyglycerin-3 Crosspolymer, Lauryl Methicone, Lauryl PEG-8 Dimethicone, Lauryl PEG-10 Methyl Ether Dimethicone, Lauryl PEG-9 Polydimethylsiloxyethyl Dimethicone, Lauryl PEG/PPG-18/18 Methicone, Lauryl Phenylisopropyl Methicone, Lauryl Phenylpropyl Methicone, Lauryl Polydimethylsiloxyethyl Dimethicone/Bis-Vinyldimethicone Crosspolymer, Lauryl Polyglyceryl-3 Polydimethylsiloxyethyl Dimethicone, Lauryl Trimethicone, Linoleamidopropyl PG-Dimonium Chloride Phosphate Dimethicone, Methacryloyl Propyltrimethoxysilane, Methicone, Methoxy Amodimethicone/Silsesquioxane Copolymer, Methoxycinnamidopropyl Polysilsesquioxane, Methoxycinnamoylpropyl Silsesquioxane Silicate, Methoxy PEG-13 Ethyl Polysilsesquioxane, Methoxy PEG/PPG-7/3 Aminopropyl Dimethicone, Methoxy PEG/PPG-25/4 Dimethicone, Methoxy PEG-10 Propyltrimethoxysilane, Methyleugenyl PEG-8 Dimethicone, Methylpolysiloxane Emulsion, Methylsilanol Acetylmethionate, Methylsilanol Acetyltyrosine, Methylsilanol Ascorbate, Methylsilanol Carboxymethyl Theophylline, Methylsilanol Carboxymethyl Theophylline Alginate, Methylsilanol Elastinate, Methylsilanol Glycyrrhizinate, Methylsilanol Hydroxyproline, Methylsilanol Hydroxyproline Aspartate, Methylsilanol Mannuronate, Methylsilanol PCA, Methylsilanol PEG-7 Glyceryl Cocoate, Methylsilanol/Silicate Crosspolymer, Methylsilanol Spirulinate, Methylsilanol Tri-PEG-8 Glyceryl Cocoate, Methyl Trimethicone, Methyltrimethoxysilane, Myristylamidopropyl Dimethylamine Dimethicone PEG-7 Phosphate, Myristyl Methicone, Myristyl Trisiloxane, Nylon-611/Dimethicone Copolymer, PCA Dimethicone, PEG-7 Amodimethicone, PEG-8 Amodimethicone, PEG-8 Cetyl Dimethicone, PEG-3 Dimethicone, PEG-6 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG-10 Dimethicone Crosspolymer, PEG-12 Dimethicone Crosspolymer, PEG-8 Dimethicone Dimer Dilinoleate, PEG-8 Dimethicone/Dimer Dilinoleic Acid Copolymer, PEG-10 Dimethicone/Vinyl Dimethicone Crosspolymer, PEG-8 Distearmonium Chloride PG-Dimethicone, PEG-10/Lauryl Dimethicone Crosspolymer, PEG-15/Lauryl Dimethicone Crosspolymer, PEG-15/Lauryl Polydimethylsiloxyethyl Dimethicone Crosspolymer, PEG-8 Methicone, PEG-6 Methicone Acetate, PEG-6 Methyl Ether Dimethicone, PEG-7 Methyl Ether Dimethicone, PEG-8 Methyl Ether Dimethicone, PEG-9 Methyl Ether Dimethicone, PEG-10 Methyl Ether Dimethicone, PEG-11 Methyl Ether Dimethicone, PEG-32 Methyl Ether Dimethicone, PEG-8 Methyl Ether Triethoxysilane, PEG-10 Nonafluorohexyl Dimethicone Copolymer, PEG-4 PEG-12 Dimethicone, PEG-8 PG-Coco-Glucoside Dimethicone, PEG-9 Polydimethylsiloxyethyl Dimethicone, PEG/PPG-20/22 Butyl Ether Dimethicone, PEG/PPG-22/22 Butyl Ether Dimethicone, PEG/PPG-23/23 Butyl Ether Dimethicone, PEG/PPG-24/18 Butyl Ether Dimethicone, PEG/PPG-27/9 Butyl Ether Dimethicone, PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6 Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, PEG/PPG-30/10 Dimethicone, PEG/PPG-25/25 Dimethicone/Acrylates Copolymer, PEG/PPG-20/22 Methyl Ether Dimethicone, PEG/PPG-24/24 Methyl Ether Glycidoxy Dimethicone, PEG/PPG-10/3 Oleyl Ether Dimethicone, PEG/PPG-5/3 Trisiloxane, PEG-4 Trifluoropropyl Dimethicone Copolymer, PEG-8 Trifluoropropyl Dimethicone Copolymer, PEG-10 Trifluoropropyl Dimethicone Copolymer, PEG-8 Trisiloxane, Perfluorocaprylyl riethoxysilylethyl Methicone, Perfluorononyl Dimethicone, Perfluorononyl Dimethicone/Methicone/Amodimethicone Crosspolymer, Perfluorononylethyl Carboxydecyl Behenyl Dimethicone, Perfluorononylethyl Carboxydecyl Hexacosyl Dimethicone, Perfluorononylethyl Carboxydecyl Lauryl/Behenyl Dimethicone, Perfluorononylethyl Carboxydecyl Lauryl Dimethicone, Perfluorononylethyl Carboxydecyl PEG-8 Dimethicone, Perfluorononylethyl Carboxydecyl PEG-10 Dimethicone, Perfluorononylethyl Dimethicone/Methicone Copolymer, Perfluorononylethyl PEG-8 Dimethicone, Perfluorononylethyl Stearyl Dimethicone, Perfluorooctylethyl/Diphenyl Dimethicone Copolymer, Perfluorooctylethyl Triethoxysilane, Perfluorooctylethyl Trimethoxysilane, Perfluorooctylethyl Trisiloxane, Perfluorooctyl Triethoxysilane, PG-Amodimethicone, Phenethyl Dimethicone, Phenethyl Disiloxane, Phenyl Dimethicone, Phenylisopropyl Dimethicone, Phenyl Methicone, Phenyl Methiconol, Phenylpropyldimethylsiloxysilicate, Phenylpropyl Ethyl Methicone, Phenyl Propyl Trimethicone, Phenyl Propyl Trimethicone/Diphenylmethicone, Phenyl Trimethicone, Platinum Divinyldisiloxane, Polyacrylate-6, Polydiethylsiloxane, Polydimethylsiloxyethyl Dimethicone/Bis-Vinyldimethicone Crosspolymer, Polydimethylsiloxyethyl Dimethicone/

Methicone Copolymer, Polydimethylsiloxy PEG/PPG-24/19 Butyl Ether Silsesquioxane, Polydimethylsiloxy PPG-13 Butyl Ether Silsesquioxane, Polyglyceryl-3 Disiloxane Dimethicone, Polyglyceryl-3/Lauryl Polydimethylsiloxyethyl Dimethicone Crosspolymer, Polyglyceryl-3 Polydimethylsiloxyethyl Dimethicone, Poly(Glycol Adipate)/Bis-Hydroxyethoxypropyl Dimethicone Copolymer, Polymethylsilsesquioxane, Polymethylsilsesquioxane/Trimethylsiloxysilicate, Polyphenylsilsesquioxane, Polypropylsilsesquioxane, Polysilicone-1, Polysilicone-2, Polysilicone-3, Polysilicone-4, Polysilicone-5, Polysilicone-6, Polysilicone-7, Polysilicone-8, Polysilicone-9, Polysilicone-10, Polysilicone-11, Polysilicone-12, Polysilicone-13, Polysilicone-14, Polysilicone-15, Polysilicone-16, Polysilicone-17, Polysilicone-18, Polysilicone-19, Polysilicone-20, Polysilicone-21, Polysilicone-18 Cetyl Phosphate, Polysilicone-1 Crosspolymer, Polysilicone-18 Stearate, Polyurethane-10, Potassium Dimethicone PEG-7 Panthenyl Phosphate, Potassium Dimethicone PEG-7 Phosphate, PPG-12 Butyl Ether Dimethicone, PPG-2 Dimethicone, PPG-12 Dimethicone, PPG-27 Dimethicone, PPG-4 Oleth-10 Dimethicone, Propoxytetramethyl Piperidinyl Dimethicone, Propyl Trimethicone, Quaternium-80, Retinoxytrimethylsilane, Silanediol Salicylate, Silanetriol, Silanetriol Arginate, Silanetriol Glutamate, Silanetriol Lysinate, Silanetriol Melaninate, Silanetriol Trehalose Ether, Silica, Silica Dimethicone Silylate, Silica Dimethyl Silylate, Silica Silylate, Silicon Carbide, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Silicone Quaternium-22, Silicone Quaternium-24, Silicone Quaternium-25, Siloxanetriol Alginate, Siloxanetriol Phytate, Simethicone, Sodium Carboxydecyl PEG-8 Dimethicone, Sodium Dimethicone PEG-7 Acetyl Methyltaurate, Sodium Hyaluronate Dimethylsilanol, Sodium Lactate Methylsilanol, Sodium Mannuronate Methylsilanol, Sodium PCA Methylsilanol, Sodium PG-Propyldimethicone Thiosulfate Copolymer, Sodium PG-Propyl Thiosulfate Dimethicone, Sodium Propoxyhydroxypropyl Thiosulfate Silica, Sorbityl Silanediol, Soy Triethoxysilylpropyldimonium Chloride, Stearalkonium Dimethicone PEG-8 Phthalate, Stearamidopropyl Dimethicone, Steardimonium Hydroxypropyl Panthenyl PEG-7 Dimethicone Phosphate Chloride, Steardimonium Hydroxypropyl PEG-7 Dimethicone Phosphate Chloride, Stearoxy Dimethicone, Stearoxymethicone/Dimethicone Copolymer, Stearoxytrimethylsilane, Stearyl Aminopropyl Methicone, Stearyl Dimethicone, Stearyl/Lauryl Methacrylate Crosspolymer, Stearyl Methicone, Stearyl Triethoxysilanek, Stearyl Trimethicone, Styrene/Acrylates/Dimethicone Acrylate Crosspolymer, Styrene/Acrylates/Dimethicone Copolymer, TEA-Dimethicone PEG-7 Phosphate, Tetrabutoxypropyl Trisiloxane, Tetramethyl Hexaphenyl Tetrasiloxane, Tetramethyl Tetraphenyl Trisiloxane, Tocopheryloxypropyl Trisiloxane, Trideceth-9 PG-Amodimethicone, Triethoxycaprylylsilane, Triethoxysilylethyl Dimethicone/Methicone Copolymer, Triethoxysilylethyl Polydimethylsiloxyethyl Dimethicone, Triethoxysilylethyl Polydimethylsiloxyethyl Hexyl Dimethicone. Triethoxysilylpropylcarbamoyl Ethoxypropyl Butyl Dimethicone, Trifluoromethyl $C_{1-4}$ Alkyl Dimethicone, Trifluoropropyl Cyclopentasiloxane, Trifluoropropyl Cyclotetrasiloxane, Trifluoropropyl Dimethicone, Trifluoropropyl Dimethicone/PEG-10 Crosspolymer, Trifluoropropyl Dimethicone/Trifluoropropyl Divinyldimethicone Crosspolymer, Trifluoropropyl Dimethicone/Vinyl Trifluoropropyl, Dimethicone/Silsesquioxane Crosspolymer, Trifluoropropyl Dimethiconol, Trifluoropropyldimethyl/trimethylsiloxysilicate, Trifluoropropyl Methicone, Trimethoxycaprylylsilane, Trimethoxysilyl Dimethicone, Trimethyl Pentaphenyl Trisiloxane, Trimethylsiloxyamodimethicone, Trimethylsiloxyphenyl Dimethicone, Trimethylsiloxysilicate, Trimethylsiloxysilicate/Dimethicone Crosspolymer, Trimethylsiloxysilicate/Dimethiconol Crosspolymer, Trimethylsiloxysilylcarbamoyl Pullulan, Trimethylsilyl Hydrolyzed Conchiolin Protein PG-Propyl Methylsilanediol Crosspolymer, Trimethylsilyl Hydrolyzed Silk PG-Propyl Methylsilanediol Crosspolymer, Trimethylsilyl Hydrolyzed Wheat Protein PG-Propyl Methylsilanediol Crosspolymer, Trimethylsilyl Pullulan, Trimethylsilyl Trimethylsiloxy Glycolate, Trimethylsilyl Trimethylsiloxy Lactate, Trimethylsilyl Trimethylsiloxy Salicylate, Triphenyl Trimethicone, Trisiloxane, Tris-Tributoxysiloxymethylsilane, Undecylcrylene Dimethicone, Vinyl Dimethicone, Vinyl Dimethicone/Lauryl Dimethicone Crosspolymer, Vinyl Dimethicone/Methicone Silsesquioxane Crosspolymer, Vinyldimethyl/Trimethylsiloxysilicate Stearyl Dimethicone Crosspolymer, VP/Dimethiconylacrylate/Polycarbamyl/Polyglycol Ester, Zinc Carboxydecyl Trisiloxane and Zinc Dimethicone PEG-8 Succinate.

Representative terpenes suitable for the preparation of cosmetic or topical compositions are known in the art and include but are not limited to: Acyclic terpene alcohols such as for example citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof; Acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal; Cyclic terpene alcohols such as for example menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates; cyclic terpene aldehydes and ketones such as for example menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4-a-methanonaphthalen-8(5-H)-one; nootkatone; dihydronootkatone; alpha-sinensal; beta-sinensal and acetylated cedarwood oil, carvone, cineol, alpha-terpineol and limonene, and methyl cedryl ketone.

Representative abrasives suitable for the preparation of cosmetic or topical compositions are known in the art and include, but are not limited to *Actinidia Chinensis* (Kiwi) Seed, *Adansonia Digitata* Seed Powder, Agave Americana Leaf Powder, Alumina, Aluminum Iron Silicates, Aluminum Silicate, Amethyst Powder, Ammonium Acryloyldimethyltaurate/Laureth-7 Methacrylate Copolymer, Amorphophallus Konjac Root Powder, *Ampelopsis Japonica* Root Powder, *Angelica Archangelica* Seed Powder, *Angelica Dahurica* Root Powder, *Angelica Dahurica* Seed Powder, *Arachis Hypogaea* (Peanut) Flour, *Argania Spinosa* Shell Powder, *Artemisia Carvifolia* Powder, *Astragalus Membranaceus* Root Powder, *Astrocaryum Murumuru* Seed Powder, *Atractyloides Macrocephala* Root/Stalk Powder, Attapulgite, *Avena Sativa* (Oat) Bran, *Avena Sativa* (Oat) Kernel Flour, *Avena Sativa* (Oat) Kernel Meal, *Bambusa Arundinacea* Juice, *Bambusa Arundinacea* Stem Powder, *Bertholletia Excelsa* Seed Powder, *Bletilla Striata* Root/Stalk Powder, 1,4-Butandiol/Succinic Acid/Adipic Acid/HDI Copolymer, *Butyrospermum Parkii* (Shea) Nut Shell Powder, Calcium Carbonate, Calcium Phosphate, Calcium Pyrophosphate, Calcium Sulfate, Calcium Sulfate Hydrate, *Cannabis Sativa* Seedcake, *Carapa Guaianensis* Seed Powder, *Carya Illinoensis* (Pecan) Shell Powder, *Castanea Crenata* (Chestnut) Shell Powder, Chalk, Charcoal Powder, *Chenopodium Quinoa* Seed, Chitin, *Chlorophora Tinctoria* Wood Extract, *Chondrus Crispus* Powder, *Cicer Arietinum* Seed Powder, *Citrullus Lanatus* (Watermelon) Seed Powder, *Citrus Nobilis* (Mandarin Orange) Peel Powder, *Citrus Tangerina* (Tangerine) Peel, *Cnidium Monnieri* Seed Powder, *Cocos Nucifera* (Coconut) Fruit, *Cocos Nucifera* (Coconut) Shell Powder, *Codonopsis Pilosula* Root Powder, *Coffea Arabica* (Coffee) Seed Powder, *Coffea Robusta* Seed Powder, Colloidal Oatmeal, Conchiolin Powder, *Coptis Chinensis* Root/Stalk Powder, Coral Powder, *Corylus Avellana* (Hazel) Seed Powder, *Corylus Avellana* (Hazel) Shell Powder, *Cymbopogon Flexuosus* Leaf Powder, Diamond Powder, Diatomaceous Earth, Dicalcium Phosphate, Dicalcium Phosphate Dihydrate, Dipentaerythrityl Hexaisostearate, Dolomite, Egg Shell Powder, Eijitsu, Elguea Clay, Emerald, Empetrum *Nigrum* Flower/Fruit/Leaf Extract, *Eucalyptus Globulus* Leaf Powder, *Euterpe Oleracea* Pulp Powder, *Ficus Carica* (Fig) Seed, *Foeniculum Vulgare* (Fennel) Seed, *Fragaria Vesca* (Strawberry) Seed, Fuller's Earth, *Garcinia Mangostana* Peel Powder, Garnet Powder, *Glycine Soja* (Soybean) Flour, *Glycine Soja* (Soybean) Seed Powder, Hakka, *Helianthus Annuus* (Sunflower) Seed, *Helianthus Annuus* (Sunflower) Seedcake, *Helianthus Annuus* (Sunflower) Seed Flour, *Hibiscus Sabdariffa* Flower Powder, *Hippophae Rhamnoides* Husk Powder. *Hippophae Rhamnoides* Seed Powder, Honey Powder, *Hordeum Distichon* (Barley) Seed Flour, *Hordeum Vulgare* Powder, *Hordeum Vulgare* Seed Flour, Hydrated Silica, Hydroxyapatite, Ilite, *Ipomoea* Seed Powder, *Isatis Tinctoria* Root Powder, *Juglans Mandshurica* (Walnut) Shell Powder, *Juglans Regia* (Walnut) Shell Powder, *Juniperus Oxycedrus* Wood Powder, Kaolin, *Kochia Scoparia* Fruit Powder, Kurumi Kaku, Lauryl Acrylate/VA Crosspolymer, *Leonurus Artemisia* Powder, *Linum Usitatissimum* (Linseed) Seed Flour, *Litchi Chinensis* Seed Powder, *Lithothamnium Calcarum* Powder, *Lithothamnium Corallioides* Powder, Loess, *Luffa Cylindrica* Fruit, *Luffa Cylindrica* Fruit Powder, *Lygodium Japonicum* Spore, *Macadamia Integrifolia* Shell Powder, *Macadamia Ternifolia* Shell Powder, Magnesium Potassium Fluorosilicate, Magnesium Sodium Fluorosilicate, Magnesium Trisilicate, *Magnolia Denudata* Bud Powder, *Mangifera Indica* (Mango) Seed, Marble Powder, *Matricaria Maritima* Powder, *Matteuccia Struthiopteris* Bud Powder, *Mauritia Flexuosa* Pulp Powder, *Melaleuca Alternifolia* (Tea Tree) Leaf, *Melaleuca Alternifolia* (Tea Tree) Leaf Powder, Microcrystalline Cellulose, Montmorillonite, Moring a Oleifera Fruit Powder, Moroccan Lava Clay, Mother of Pearl, Mudstone Powder, Myristyl Betaine, Nacre Powder, *Nelumbo Nucifera* Flower Powder, *Nelumbo Nucifera* Seed Powder, *Nigella Damascena* Seed Powder, *Oenothera Biennis* (Evening Primrose) Seed, *Olea Europaea* (Olive) Fruit, *Olea Europaea* (Olive) Husk Powder, *Olea Europaea* (Olive) Leaf Powder, *Olea Europaea* (Olive) Seed, *Olea Europaea* (Olive) Seed Powder, *Oryza Sativa* (Rice) Bran, *Oryza Sativa* (Rice) Germ Powder, Ostrea Shell Extract, Ostrea Shell Powder, Oubaku, Ovum Powder, Oyster Shell Powder, *Paeonia Lactiflora* Root Powder, *Paeonia Officinalis* Flower Powder, *Papaver Somniferum* Seed, *Passiflora Edulis* Seed Powder, Pegmatite, Perlite, *Persea Gratissima* (Avocado) Fruit Powder, *Persea Gratissima* (Avocado) Seed, *Phaseolus Angularis* Seed, *Phaseolus Radiatus* Seed Starch, *Pistacia Vera* Shell Powder, *Plantago Psyllium* Husk, *Plantago Psyllium* Husk Powder, Platinum Powder, Polyethylene, Polylactic Acid, *Poria Cocos* Powder, *Porphyra Umbilicalis* Powder, Potassium Undecylenoyl Glutamate, *Prunus Amygdalus Dulcis* (Sweet Almond) Seedcoat Powder, *Prunus Amygdalus Dulcis* (Sweet Almond) Seed Meal, *Prunus Amygdalus Dulcis* (Sweet Almond) Shell Powder, *Prunus Armeniaca* (Apricot) Seed Powder, *Prunus Avium* (Sweet Chemy) Seed Powder, *Prunus Avium* (Sweet Chemy) Shell Powder, *Prunus Cerasus* (Bitter Chemy) Shell Powder, *Prunus Mume* Fruit, *Prunus Persica* (Peach) Flower Powder, *Prunus Persica* (Peach) Seed Powder, Pumice, *Punica Granatum* Seed, *Punica Granatum* Seed Powder, Quartz, Quartz Powder, *Quassia Amara* Wood Powder, *Rosa Canina* Seed, *Rosa Canina* Seed Powder, *Rosa Centifolia* Flower Powder, *Rosa Rugosa* Bud Powder, *Rubus Idaeus* (Raspberry) Seed, *Rubus Idaeus* (Raspberry) Seed Powder, Salt Mine Mud, *Salvia Hispanica* Seed, *Salvia Hispanica* Seed Powder, Sand, *Sanguisorba Officinalis* Root/Stalk Powder, *Schinziophyton Rautanenii* Kernel Powder, *Sclerocarya Birrea* Seed Powder, *Scutellaria Baicalensis* Root Powder, Sea Salt, *Secale Cereale* (Rye) Seed Flour, Silica, Sillimanite, *Smilax Lanceaefolia* Root/Stalk Powder, Sodium Bicarbonate, Sodium Calcium Boron Phosphate, Sodium Hydroxypropyl Starch Phosphate, Sodium Magnesium Fluorosilicate, Sodium Silicoaluminate, Solum Diatomeae, *Sophora Flavescens* Root Powder, *Stemona Sessifolia* Root Powder, *Symphytum Officinale* Leaf Powder, Synthetic Ruby, Synthetic Ruby Powder, *Syring a Oblata* Bark/Leaf Powder, Talc, *Theobroma Cacao* (Cocoa) Husk, *Theobroma Cacao* (Cocoa) Seed Powder, *Theobroma Cacao* (Cocoa) Shell Powder, *Theobroma Grandiflorum* Seed Powder, Tin Oxide, Titanium Oxynitride, Topaz, Touki, *Tribulus Terrestris* Fruit Powder, Tricalcium Phosphate, *Trichosanthes Kirilowii* Fruit Powder, *Triticum Vulgare* (Wheat) Bran, *Triticum Vulgare* (Wheat) Germ Powder, *Triticum Vulgare* (Wheat) Kernel Flour, *Triticum Vulgare* (Wheat) Starch, *Vaccinium Angustifolium* (Blueberry) Seed, *Vaccinium Macrocarpon* (Cranberry) Seed, *Vaccinium Macrocarpon* (Cranberry) Seed Powder, *Vanilla Planifolia* Seed Powder, *Vanilla Tahitensis* Seed, *Viola Prionantha* Powder, *Virola Sebifera* Seed Powder, *Vitis Vinifera* (Grape) Seed Powder, Volcanic Ash, Volcanic Rock, Wood Powder, Yokuinin, *Zea Mays* (Corn) Cob Meal, *Zea Mays* (Corn) Cob Powder, *Zea Mays* (Corn) Kernel Meal, *Zea Mays* (Corn) Seed Flour, *Zea Mays* (Corn) Starch and Zirconium Silicate.

Representative surfactants suitable for the preparation of cosmetic or topical compositions are known in the art and include, but are not limited to Almond amidopropylamine Oxide, Almond amidopropyl Betaine, Aminopropyl Laurylglutamine, Ammonium $C_{12-15}$ Alkyl Sulfate, Ammonium $C_{12-16}$ Alkyl Sulfate, Ammonium Capryleth Sulfate, Ammonium Cocomonoglyceride Sulfate, Ammonium Coco-Sulfate, Ammonium Cocoyl Isethionate, Ammonium Cocoyl Sarcosinate, Ammonium $C_{12-15}$ Pareth Sulfate, Ammonium $C_{9-10}$ Perfluoroalkylsulfonate, Ammonium Dinonyl Sulfosuccinate, Ammonium Dodecylbenzenesulfonate, Ammonium Isostearate, Ammonium Laureth-6 Carboxylate, Ammonium Laureth-8 Carboxylate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauroyl Sarcosinate, Ammonium Lauryl Sulfate, Ammonium Lauryl Sulfosuccinate, Ammonium Myreth Sulfate, Ammonium Myristyl Sulfate, Ammonium Nonoxynol-4 Sulfate, Ammonium Nonoxynol-30 Sulfate, Ammonium Oleate, Ammonium Palm Kernel Sulfate, Ammonium Stearate, Ammonium Tallate, AMPD-Isostearoyl Hydrolyzed Collagen, AMPD-Rosin Hydrolyzed Collagen, AMP-Isostearoyl Hydrolyzed Collagen, AMP-Isostearoyl Hydrolyzed Keratin, AMP-Isostearoyl Hydrolyzed Soy Protein, AMP-Isostearoyl Hydrolyzed Wheat Protein, Apricotamidopropyl Betaine, Arachidic Acid, Arginine Hexyldecyl Phosphate, Avocadamidopropyl Betaine, Avocado Oil Glycereth-8 Esters, Babassu Acid, Babassuamidopropylamine Oxide, Babassuamidopropyl Betaine, Beeswax Acid, Behenamidopropyl Betaine, Behenamine Oxide, Beheneth-25, Beheneth-30, Behenic Acid, Behenyl Betaine, Bis-Butyldimethicone Polyglyceryl-3, Butoxynol-5 Carboxylic Acid, Butoxynol-19 Carboxylic Acid, Butyldimoniumhydroxypropyl Butylglucosides Chloride, Butyldimoniumhydroxypropyl Laurylglucosides Chloride, Butyl Glucoside, Butylglucoside Caprate, Butylglucosides Hydroxypropyltrimonium Chloride, Butyloctanoic Acid, $C_{18-36}$ Acid, $C_{20-40}$ Acid, $C_{30-50}$ Acid, $C_{16-22}$ Acid Amide MEA, Calcium Dodecylbenzenesulfonate, Calcium Lauroyl Taurate, $C_{9-16}$ Alkane/Cycloalkane, $C_{10-14}$ Alkyl Benzenesulfonic Acid, $C_{12-14}$ Alkyl Diaminoethylglycine HCL, $C_{9-15}$ Alkyl Phosphate, *Candida Bombicola*/Glucose/Methyl Rapeseedate Ferment, Canolamidopropyl Betaine, Capric Acid, Caproic Acid, Caproyl Ethyl Glucoside, Capryl/Capramidopropyl Betaine, Capryleth-4 Carboxylic Acid, Capryleth-6 Carboxylic Acid, Capryleth-9 Carboxylic Acid, Caprylic Acid, Caprylol Collagen Amino Acids, Caprylol *Glycine*, Caprylol Hydrolyzed Collagen, Caprylol Hydrolyzed Keratin, Caprylol Keratin Amino Acids, Caprylol Silk Amino Acids, Caprylyl/Capryl Glucoside, Caprylyl/Capryl Wheat Bran/Straw Glycosides, Caprylyl Glucoside, Caprylyl Glyceryl Ether, Caprylyl Pyrrolidone, Carnitine, Ceteareth-20, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, Ceteareth-25 Carboxylic Acid, Ceteareth-2 Phosphate, Ceteareth-4 Phosphate, Ceteareth-5 Phosphate, Ceteareth-10 Phosphate, Ceteth-20, Ceteth-23, Ceteth-24, Ceteth-25, Ceteth-30, Ceteth-40, Ceteth-45, Ceteth-150, Ceteth-8 Phosphate, Ceteth-10 Phosphate, Ceteth-20 Phosphate, Cetoleth-22, Cetoleth-24, Cetoleth-25, Cetoleth-30, Cetyl Betaine, *Chrysanthemum Sinense* Flower Extract, $C_{12-14}$ Hydroxyalkyl Hydroxyethyl Beta-Alanine, $C_{12-14}$ Hydroxyalkyl Hydroxyethyl Sarcosine, Cocamidoethyl Betaine, Cocamidopropylamine Oxide, Cocamidopropyl Betainamide MEA Chloride, Cocamidopropyl Betaine, Cocamidopropyl Hydroxysultaine, Cocamine Oxide, Cocaminobutyric Acid, Cocaminopropionic Acid, Coceth-7 Carboxylic Acid, Coceth-4 Glucoside, Cocoamphodipropionic Acid, Cocobetainamido Amphopropionate, Coco-Betaine, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Coco-Glucoside, Cocoglucosides Hydroxypropyltrimonium Chloride, Coco-Hydroxysultaine, Coco-Morpholine Oxide, Coconut Acid, Coconut Oil Glycereth-8 Esters, Coco/Oleamidopropyl Betaine, Coco-Sultaine, Coco/Sunfloweramidopropyl Betaine, Cocoylcholine Methosulfate, Cocoyl Glutamic Acid, Cocoyl Hydrolyzed Collagen, Cocoyl Hydrolyzed Keratin, Cocoyl Hydrolyzed Oat Protein, Cocoyl Hydrolyzed Rice Protein, Cocoyl Hydrolyzed Silk, Cocoyl Hydrolyzed Soy Protein, Cocoyl Hydrolyzed Wheat Protein, Cocoyl Sarcosine, Corn Acid, Cottonseed Acid, Cottonseed Oil Glycereth-8 Esters, $C_{10-16}$ Pareth-1, $C_{10-16}$ Pareth-2, $C_{11-13}$ Pareth-6, $C_{11-13}$ Pareth-9, $C_{11-13}$ Pareth-10, $C_{11-15}$ Pareth-30, $C_{11-15}$ Pareth-40, $C_{12-13}$ Pareth-1, $C_{12-13}$ Pareth-23, $C_{12-14}$ Pareth-5, $C_{12-14}$ Pareth-9, $C_{13-15}$ Pareth-21, $C_{14-15}$ Pareth-8, $C_{20-22}$ Pareth-30, $C_{20-40}$ Pareth-40, $C_{20-40}$ Pareth-95, $C_{22-24}$ Pareth-33, $C_{30-50}$ Pareth-40, $C_{9-11}$ Pareth-6 Carboxylic Acid, $C_{9-11}$ Pareth-8 Carboxylic Acid, $C_{11-15}$ Pareth-7 Carboxylic Acid, $C_{12-13}$ Pareth-5 Carboxylic Acid, $C_{12-13}$ Pareth-7 Carboxylic Acid, $C_{12-13}$ Pareth-8 Carboxylic Acid, $C_{12-13}$ Pareth-12 Carboxylic Acid, $C_{12-15}$ Pareth-7 Carboxylic Acid, $C_{12-15}$ Pareth-8 Carboxylic Acid, $C_{12-15}$ Pareth-12 Carboxylic Acid, $C_{14-15}$ Pareth-8 Carboxylic Acid, $C_{6-10}$ Pareth-4 Phosphate, $C_{12-13}$ Pareth-2 Phosphate, $C_{12-13}$ Pareth-10 Phosphate, $C_{12-15}$ Pareth-6 Phosphate, $C_{12-15}$ Pareth-8 Phosphate, $C_{12-15}$ Pareth-10 Phosphate, $C_{12-16}$ Pareth-6 Phosphate, $C_{4-18}$ Perfluoroalkylethyl Thiohydroxypropyltrimonium Chloride, Cupuassuamidopropyl Betaine, DEA-$C_{12-13}$ Alkyl Sulfate, DEA-$C_{12-15}$ Alkyl Sulfate, DEA-Ceteareth-2 Phosphate, DEA-Cetyl Sulfate, DEA-Cocoamphodipropionate, DEA-$C_{12-13}$ Pareth-3 Sulfate, DEA-Cyclocarboxypropyloleate, DEA-Dodecylbenzenesulfonate, DEA-Isostearate, DEA-Laureth Sulfate, DEA-Lauryl Sulfate, DEA-Linoleate, DEA-Methyl Myristate Sulfonate, DEA-Myreth Sulfate, DEA-Myristate, DEA-Myristyl Sulfate, DEA-Oleth-5 Phosphate, DEA-Oleth-20 Phosphate, DEA PG-Oleate, Deceth-7 Carboxylic Acid, Deceth-7 Glucoside, Deceth-9 Phosphate, Decylamine Oxide, Decyl Betaine, Decyl Glucoside, Decyltetradeceth-30, Decyltetradecylamine Oxide, Diammonium Lauramido-MEA Sulfosuccinate, Diammonium Lauryl Sulfosuccinate, Diammonium Oleamido PEG-2 Sulfosuccinate, Dibutoxymethane, Di-$C_{12-15}$ Pareth-2 Phosphate, Di-$C_{12-15}$ Pareth-4 Phosphate, Di-$C_{12-15}$ Pareth-6 Phosphate, Di-$C_{12-15}$ Pareth-8 Phosphate, Di-$C_{12-15}$ Pareth-10 Phosphate, Didodecyl Butanetetracarboxylate, Diethylamine Laureth Sulfate, Diethylhexyl Sodium Sulfosuccinate, Dihydroxyethyl $C_{8-10}$ Alkoxypropylamine Oxide, Dihydroxyethyl $C_{9-11}$ Alkoxypropylamine Oxide, Dihydroxyethyl $C_{12-15}$ Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Dimethicone PEG-7 Phosphate, Dimethicone PEG-10 Phosphate, Dimethicone PEG/PPG-7/4 Phosphate, Dimethicone PEG/PPG-12/4 Phosphate, Dimethicone/Polyglycerin-3 Crosspolymer, Dimethicone Propyl PG-Betaine, Dimyristyl Phosphate, Dioleoylamidoethyl Hydroxyethylmonium Methosulfate, DIPA-Hydrogenated Cocoate, DIPA-Lanolate, DIPA-Myristate, Dipotassium Capryloyl Glutamate, Dipotassium Lauryl Sulfosuccinate, Dipotassium Undecylenoyl Glutamate, Disodium Babassuamido MEA-Sulfosuccinate, Disodium Caproamphodiacetate, Disodium Caproamphodipropionate, Disodium Capryloamphodiacetate, Disodium Capryloamphodipropionate, Disodium Capryloyl Glutamate, Disodium Cetearyl Sulfosuccinate, Disodium Cetyl Phenyl Ether Disulfonate, Disodium Cetyl Sulfosuccinate, Disodium Cocamido MEA-Sulfosuccinate, Disodium Cocamido MIPA PEG-4 Sulfosuccinate, Disodium Cocamido MIPA-Sulfosuccinate, Disodium Cocamido PEG-3 Sulfosuccinate, Disodium Coceth-3 Sulfosuccinate, Disodium Cocoamphocarboxyethylhydroxypropylsulfonate, Disodium Cocoamphodiacetate, Disodium Cocoamphodipropionate, Disodium Coco-Glucoside Sulfosuccinate, Disodium Coco-Sulfosuccinate, Disodium Cocoyl Butyl Gluceth-10 Sulfosuccinate, Disodium Cocoyl Glutamate, Disodium $C_{12-14}$ Pareth-1 Sulfosuccinate, Disodium $C_{12-14}$ Pareth-2 Sulfosuccinate, Disodium $C_{12-15}$ Pareth Sulfosuccinate, Disodium $C_{12-14}$ Sec-Pareth-3 Sulfosuccinate, Disodium $C_{12-14}$ Sec-Pareth-5 Sulfosuccinate, Disodium $C_{12-14}$ Sec-Pareth-7 Sulfosuccinate, Disodium $C_{12-14}$ Sec-Pareth-9 Sulfosuccinate, Disodium $C_{12-14}$ Sec-Pareth-12 Sulfosuccinate, Disodium Deceth-5 Sulfosuccinate, Disodium Deceth-6 Sulfosuccinate, Disodium Decyl Phenyl Ether Disulfonate, Disodium Dihydroxyethyl Sulfosuccinylundecylenate, Disodium Ethylene Dicocamide PEG-15 Disulfate, Disodium Hydrogenated Cottonseed Glyceride Sulfosuccinate, Disodium Hydrogenated Tallow Glutamate, Disodium Hydroxydecyl Sorbitol Citrate, Disodium Isodecyl Sulfosuccinate, Disodium Isostearamido MEA-Sulfosuccinate, Disodium Isostearamido MIPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido MIPA Glycol Sulfosuccinate, Disodium Lauramido PEG-2 Sulfosuccinate, Disodium Lauramido PEG-5 Sulfosuccinate, Disodium Laureth-5 Carboxyamphodiacetate, Disodium Laureth-7 Citrate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauriminobishydroxypropylsulfonate, Disodium Lauriminodiacetate, Disodium Lauriminodipropionate, Disodium Lauriminodipropionate Tocopheryl Phosphates, Disodium Lauroamphodiacetate, Disodium Lauroamphodipropionate, Disodium N-Lauroyl Aspartate, Disodium Lauroyl Glutamate, Disodium Lauryl Phenyl Ether Disulfonate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Phosphate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-12 Dimethicone Sulfosuccinate, Disodium PEG-8 Palm Glycerides Sulfosuccinate, Disodium PPG-2-Isodeceth-7 Carboxyamphodiacetate, Disodium Ricinoleamido MEA-Sulfosuccinate, Disodium Sitostereth-14 Sulfosuccinate, Disodium Soyamphodiacetate, Disodium Stearamido MEA-Sulfosuccinate, Disodium Steariminodipropionate, Disodium Stearoamphodiacetate, Disodium Stearoyl Glutamate, Disodium Stearyl Sulfosuccinate, Disodium Stearyl Sulfosuccinate, Disodium 2-Sulfolaurate, Disodium 2-Sulfopalmitate, Disodium Tallamido MEA-Sulfosuccinate, Disodium Tallowamido MEA-Sulfosuccinate, Disodium Tallowamphodiacetate, Disodium Tallowiminodipropionate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Undecylenoyl Glutamate, Disodium Wheat Germamido MEA-Sulfosuccinate, Disodium Wheat Germamido PEG-2 Sulfosuccinate, Disodium Wheatgermamphodiacetate, Di-TEA-Cocamide Diacetate, Di-TEA-Oleamido PEG-2 Sulfosuccinate, Di-TEA-Palmitoyl Aspartate, Ditridecyl Sodium Sulfosuccinate, Dodecylbenzene Sulfonic Acid, Erucamidopropyl Hydroxysultaine, Ethylhexeth-3 Carboxylic Acid, Ethyl PEG-15 Cocamine Sulfate, Glyceryl Capryl Ether, Hexyldecanoic Acid, Hydrogenated Coconut Acid, Hydrogenated Laneth-25, Hydrogenated Menhaden Acid, Hydrogenated Palm Acid, Hydrogenated Palm Kernel Amine Oxide, Hydrogenated Tallow Acid, Hydrogenated Tallowamine Oxide, Hydrogenated Tallow Betaine, Hydrogenated Talloweth-25, Hydrogenated Tallowoyl Glutamic Acid, Hydrolyzed *Candida Bombicola* Extract, Hydroxyceteth-60, Hydroxyethyl Acetomonium PG-Dimethicone, Hydroxyethylbutylamine Laureth Sulfate, Hydroxyethyl Carboxymethyl Cocamidopropylamine, Hydroxyethyl Hydroxypropyl $C_{12-15}$ Alkoxypropylamine Oxide, Hydroxylauryl/Hydroxymyristyl Betaine, Hydroxystearic Acid, Hydroxysuccinimidyl $C_{10-40}$ Isoalkyl Acidate, Hydroxysuccinimidyl $C_{21-22}$ Isoalkyl Acidate, Hydroxysultaines, IPDI/PEG-15 Soyamine Oxide Copolymer, IPDI/PEG-15 Soyethonium Ethosulfate Copolymer, IPDI/PEG-15 Soy Glycinate Copolymer, Isoceteth-30, Isolaureth-4 Phosphate, Isopolyglyceryl-3 Dimethicone, Isopolyglyceryl-3 Dimethiconol, Isopropanolamine Lanolate, Isopropylamine Dodecylbenzenesulfonate, Isostearamidopropylamine Oxide, Isostearamidopropyl Betaine, Isostearamidopropyl Morpholine Oxide, Isosteareth-8, Isosteareth-16, Isosteareth-22, Isosteareth-25, Isosteareth-50, Isostearic Acid, Isostearoyl Hydrolyzed Collagen, Jojoba Oil PEG-150 Esters, Jojoba Wax PEG-80 Esters, Jojoba Wax PEG-120 Esters, Laneth-20, Laneth-25, Laneth-40, Laneth-50, Laneth-60, Laneth-75, Lanolin Acid, Lauramidopropylamine Oxide, Lauramidopropyl Betaine, Lauramidopropyl Hydroxysultaine, Lauramine Oxide, Lauraminopropionic Acid, Laurdimoniumhydroxypropyl Decylglucosides Chloride, Laurdimoniumhydroxypropyl Laurylglucosides Chloride, Laureth-16, Laureth-20, Laureth-21, Laureth-23, Laureth-25, Laureth-30, Laureth-38, Laureth-40, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Laureth-6 Citrate, Laureth-7 Citrate, Laureth-1 Phosphate, Laureth-2 Phosphate, Laureth-3 Phosphate, Laureth-4 Phosphate, Laureth-7 Phosphate, Laureth-8 Phosphate, Laureth-7 Tartrate, Lauric Acid, Laurimino Bispropanediol, Lauriminodipropionic Acid, Lauroamphodipropionic Acid, Lauroyl Beta-Alanine, Lauroyl Collagen Amino Acids, Lauroyl Ethyltrimonium Methosulfate, Lauroyl Hydrolyzed Collagen, Lauroyl Hydrolyzed Elastin, Lauroyl Methyl Glucamide, Lauroyl Sarcosine, Lauroyl Silk Amino Acids, Lauryl Betaine, Lauryl Dimethicone/Polyglycerin-3 Crosspolymer, Lauryldimoniumhydroxypropyl Cocoglucosides Chloride, Lauryl Glucoside, Laurylglucosides Hydroxypropyltrimonium Chloride, Lauryl Glycol Hydroxypropyl Ether, Lauryl Hydroxysultaine, Lauryl Malamide, Lauryl Methylglucamide, Lauryl/Myristyl Glycol Hydroxypropyl Ether, Lauryl/Myristyl Wheat Bran/Straw Glycosides, Lauryl Polyglyceryl-3 Polydimethylsiloxyethyl Dimethicone, Lauryl Pyrrolidone, Lauryl Sultaine, Linoleic Acid, Linolenic Acid, Linseed Acid, Lysine Cocoate, *Macadamia* Seed Oil Glycereth-8 Esters, Magnesium Coceth Sulfate, Magnesium Coco-Sulfate, Magnesium Isododecylbenzenesulfonate, Magnesium Laureth-11 Carboxylate, Magnesium Laureth Sulfate, Magnesium Laureth-5 Sulfate, Magnesium Laureth-8 Sulfate, Magnesium Laureth-16 Sulfate, Magnesium Laureth-3 Sulfosuccinate, Magnesium Lauryl Hydroxypropyl Sulfonate, Magnesium Lauryl Sulfate, Magnesium Methyl Cocoyl Taurate, Magnesium Myreth Sulfate, Magnesium Oleth Sulfate, Magnesium/TEA-Coco-Sulfate, Manicouagan Clay, MEA-Cocoate, MEA-Laureth-6 Carboxylate, MEA-Laureth Sulfate, MEA-Lauryl Sulfate, MEA PPG-6 Laureth-7 Carboxylate, MEA-PPG-8-Steareth-7 Carboxylate, MEA-Undecylenate, Meroxapol 108, Meroxapol 174, Meroxapol 178, Meroxapol 254, Meroxapol 255, Meroxapol 258, Meroxapol 314, Methoxy PEG-450 Amidoglutaroyl Succinimide, Methoxy PEG-450 Amido Hydroxysuccinimidyl Succinamate, Methoxy PEG-450 Maleimide, Methyl Morpholine Oxide, Milkamidopropyl Amine Oxide, Milkamidopropyl Betaine, Minkamidopropylamine Oxide, Minkamidopropyl Betaine, MIPA $C_{12-15}$ Pareth Sulfate, MIPA-Dodecylbenzenesulfonate, MIPA-Laureth Sulfate, MIPA-Lauryl Sulfate, Mixed Isopropanolamines Lanolate, Mixed Isopropanolamines Lauryl Sulfate, Mixed Isopropanolamines Myristate, Morpholine Oleate, Morpholine Stearate, Myreth-3 Carboxylic Acid, Myreth-5 Carboxylic Acid, Myristalkonium Chloride, Myristamidopropylamine Oxide, Myristamidopropyl Betaine, Myristamidopropyl Dimethylamine Phosphate, Myristamidopropyl Hydroxysultaine, Myristamidopropyl PG-Dimonium Chloride Phosphate, Myristamine Oxide, Myristaminopropionic Acid, Myristic Acid, Myristoyl Ethyltrimonium Methosulfate, Myristoyl Glutamic Acid, Myristoyl Hydrolyzed Collagen, Myristoyl Sarcosine, Myristyl Betaine, Myristyl/Cetyl Amine Oxide, Myristyldimoniumhydroxypropyl Cocoglucosides Chloride, Myristyl Glucoside, Myristyl Phosphate, Nonoxynol-20, Nonoxynol-23, Nonoxynol-25, Nonoxynol-30, Nonoxynol-35, Nonoxynol-40, Nonoxynol-44, Nonoxynol-50, Nonoxynol-100, Nonoxynol-120, Nonoxynol-5 Carboxylic Acid, Nonoxynol-8 Carboxylic Acid, Nonoxynol-10 Carboxylic Acid, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-30, Nonyl Nonoxynol-49, Nonyl Nonoxynol-100, Nonyl Nonoxynol-150, Nonyl Nonoxynol-7 Phosphate, Nonyl Nonoxynol-8 Phosphate, Nonyl Nonoxynol-9 Phosphate, Nonyl Nonoxynol-10 Phosphate, Nonyl Nonoxynol-11 Phosphate, Nonyl Nonoxynol-15 Phosphate, Nonyl Nonoxynol-24 Phosphate, Oatamidopropyl Betaine, Octoxynol-16, Octoxynol-25, Octoxynol-30, Octoxynol-33, Octoxynol-40, Octoxynol-70, Octoxynol-20 Carboxylic Acid, Octyldodeceth-20, Octyldodeceth-25, Octyldodeceth-30, Oleamidopropylamine Oxide, Oleamidopropyl Betaine, Oleamidopropyl Hydroxysultaine, Oleamine Oxide, Oleic Acid, Oleoyl Hydrolyzed Collagen, Oleoyl Sarcosine, Oleth-20, Oleth-23, Oleth-24, Oleth-25, Oleth-30, Oleth-35, Oleth-40, Oleth-44, Oleth-50, Oleth-3 Carboxylic Acid, Oleth-6 Carboxylic Acid, Oleth-10 Carboxylic Acid, Oleyl Betaine, Olivamidopropylamine Oxide, Olivamidopropyl Betaine, Olive Acid, Olivoyl Hydrolyzed Wheat Protein, Ophiopogon Extract Stearate, Ozonized Oleth-10, Ozonized PEG-10 Oleate. Ozonized PEG-14 Oleate, Ozonized Polysorbate 80, Palm Acid, Palmamidopropyl Betaine, Palmeth-2 Phosphate, Palmitamidopropylamine Oxide, Palmitamidopropyl Betaine, Palmitamine Oxide, Palmitic Acid, Palmitoyl Collagen Amino Acids, Palmitoyl *Glycine*, Palmitoyl Hydrolyzed Collagen, Palmitoyl Hydrolyzed Milk Protein, Palmitoyl Hydrolyzed Wheat Protein, Palmitoyl Keratin Amino Acids, Palmitoyl Oligopeptide, Palmitoyl Silk Amino Acids, Palm Kernel Acid, Palm Kernelamidopropyl Betaine, Peach Kernel Oil Glycereth-8 Esters, Peanut Acid, PEG-10 Castor Oil, PEG-40 Castor Oil, PEG-44 Castor Oil, PEG-50 Castor Oil, PEG-54 Castor Oil, PEG-55 Castor Oil, PEG-60 Castor Oil, PEG-80 Castor Oil, PEG-100 Castor Oil, PEG-200 Castor Oil, PEG-11 Cocamide. PEG-6 Cocamide Phosphate. PEG-4 Cocamine, PEG-8 Cocamine, PEG-12 Cocamine, PEG-150 Dibehenate, PEG-90 Diisostearate, PEG-75 Dilaurate, PEG-150 Dilaurate, PEG-75 Dioleate, PEG-150 Dioleate, PEG-75 Distearate, PEG-120 Distearate, PEG-150 Distearate, PEG-175 Distearate, PEG-190 Distearate, PEG-250 Distearate, PEG-30 Glyceryl Cocoate, PEG-40 Glyceryl Cocoate, PEG-78 Glyceryl Cocoate, PEG-80 Glyceryl Cocoate, PEG-30 Glyceryl Isostearate, PEG-40 Glyceryl Isostearate, PEG-50 Glyceryl Isostearate, PEG-60 Glyceryl Isostearate, PEG-90 Glyceryl Isostearate, PEG-23 Glyceryl Laurate, PEG-30 Glyceryl Laurate, PEG-25 Glyceryl Oleate, PEG-30 Glyceryl Oleate, PEG-30 Glyceryl Soyate, PEG-25 Glyceryl Stearate, PEG-30 Glyceryl Stearate, PEG-40 Glyceryl Stearate, PEG-120 Glyceryl Stearate, PEG-200 Glyceryl Stearate, PEG-28 Glyceryl Tallowate, PEG-80 Glyceryl Tallowate, PEG-82 Glyceryl Tallowate, PEG-130 Glyceryl Tallowate, PEG-200 Glyceryl Tallowate, PEG-45 Hydrogenated Castor Oil, PEG-50 Hydrogenated Castor Oil, PEG-54 Hydrogenated Castor Oil, PEG-55 Hydrogenated Castor Oil, PEG-60 Hydrogenated Castor Oil, PEG-80 Hydrogenated Castor Oil, PEG-100 Hydrogenated Castor Oil, PEG-200 Hydrogenated Castor Oil, PEG-30 Hydrogenated Lanolin, PEG-70 Hydrogenated Lanolin, PEG-50 Hydrogenated Palmamide, PEG-2 Isostearate, PEG-3 Isostearate, PEG-4 Isostearate, PEG-6 Isostearate, PEG-8 Isostearate, PEG-10 Isostearate, PEG-12 Isostearate, PEG-20 Isostearate, PEG-30 Isostearate, PEG-40 Isostearate, PEG-26 Jojoba Acid, PEG-40 Jojoba Acid, PEG-15 Jojoba Alcohol, PEG-26 Jojoba Alcohol, PEG-40 Jojoba Alcohol, PEG-35 Lanolin, PEG-40 Lanolin, PEG-50 Lanolin, PEG-55 Lanolin, PEG-60 Lanolin, PEG-70 Lanolin, PEG-75 Lanolin, PEG-85 Lanolin, PEG-100 Lanolin, PEG-150 Lanolin, PEG-75 Lanolin Oil, PEG-2 Lauramide, PEG-3 Lauramine Oxide, PEG-20 Laurate, PEG-32 Laurate, PEG-75 Laurate, PEG-150 Laurate, PEG-70 Mango Glycerides, PEG-20 Mannitan Laurate, PEG-8 Methyl Ether Dimethicone, PEG-120 Methyl Glucose Dioleate, PEG-80 Methyl Glucose Laurate, PEG-120 Methyl Glucose Trioleate, PEG-4 Montanate, PEG-30 Oleamine, PEG-20 Oleate, PEG-23 Oleate, PEG-32 Oleate, PEG-36 Oleate, PEG-75 Oleate, PEG-150 Oleate, PEG-20 Palmitate, PEG-150 Polyglyceryl-2 Tristearate, PEG/PPG-28/21 Acetate Dimethicone, PEG/PPG-24/18 Butyl Ether Dimethicone, PEG/PPG-3/17 Copolymer, PEG/PPG-5/35 Copolymer, PEG/PPG-8/55 Copolymer, PEG/PPG-10/30 Copolymer, PEG/PPG-10/65 Copolymer, PEG/PPG-12/35 Copolymer, PEG/PPG-16/17 Copolymer, PEG/PPG-20/9 Copolymer, PEG/PPG-20/20 Copolymer, PEG/PPG-20/60 Copolymer, PEG/PPG-20/65 Copolymer, PEG/PPG-22/25 Copolymer, PEG/PPG-28/30 Copolymer, PEG/PPG-30-35 Copolymer, PEG/PPG-30/55 Copolymer, PEG/PPG-35/40 Copolymer, PEG/PPG-50/40 Copolymer, PEG/PPG-150/35 Copolymer, PEG/PPG-160/30 Copolymer, PEG/PPG-190/60 Copolymer, PEG/PPG-200/40 Copolymer, PEG/PPG-300/55 Copolymer, PEG/PPG-20/22 Methyl Ether Dimethicone, PEG-26-PPG-30 Phosphate, PEG/PPG-4/2 Propylheptyl Ether, PEG/PPG-6/2 Propylheptyl Ether, PEG-7/PPG-2 Propylheptyl Ether, PEG/PPG-8/2 Propylheptyl Ether, PEG/PPG-10/2 Propylheptyl Ether, PEG/PPG-14/2 Propylheptyl Ether, PEG/PPG-40/2 Propylheptyl Ether, PEG/PPG-10/2 Ricinoleate, PEG/PPG-32/3 Ricinoleate, PEG-55 Propylene Glycol Oleate, PEG-25 Propylene Glycol Stearate, PEG-75 Propylene Glycol Stearate, PEG-120 Propylene Glycol Stearate, PEG-5 Rapeseed Sterol, PEG-10 Rapeseed Sterol, PEG-40 Ricinoleamide, PEG-75 Shea Butter Glycerides, PEG-75 Shorea Butter Glycerides, PEG-20 Sorbitan Cocoate, PEG-20 Sorbitan Isostearate, PEG-40 Sorbitan Lanolate, PEG-75 Sorbitan Lanolate, PEG-10 Sorbitan Laurate, PEG-40 Sorbitan Laurate, PEG-44 Sorbitan Laurate, PEG-75 Sorbitan Laurate, PEG-80 Sorbitan Laurate, PEG-20 Sorbitan Oleate, PEG-80 Sorbitan Palmitate, PEG-40 Sorbitan Stearate, PEG-60 Sorbitan Stearate, PEG-160 Sorbitan Triisostearate, PEG-40 Soy Sterol, PEG-2 Stearamide Carboxylic Acid, PEG-9 Stearamide Carboxylic Acid, PEG-20 Stearate, PEG-23 Stearate, PEG-25 Stearate, PEG-30 Stearate, PEG-32 Stearate, PEG-35 Stearate, PEG-36 Stearate, PEG-40 Stearate, PEG-45 Stearate, PEG-50 Stearate, PEG-55 Stearate, PEG-75 Stearate, PEG-90 Stearate, PEG-100 Stearate, PEG-120 Stearate, PEG-150 Stearate, PEG-45 Stearate Phosphate, PEG-20 Tallate, PEG-50 Tallow Amide, PEG-2 Tallowamide DEA, PEG-20 Tallowate, PEG-66 Trihydroxystearin, PEG-200 Trihydroxystearin, PEG-60 Tsubakiate Glycerides. Pelargonic Acid, Pentadoxynol-200, Pheneth-6 Phosphate, Poloxamer 105, Poloxamer 108, Poloxamer 182, Poloxamer 183, Poloxamer 184, Poloxamer 188, Poloxamer 217, Poloxamer 234, Poloxamer 235, Poloxamer 237, Poloxamer 238, Poloxamer 288, Poloxamer 334, Poloxamer 335, Poloxamer 338, Poloxamine 908, Poloxamine 1508, Polydimethylsiloxy PEG/PPG-24/19 Butyl Ether Silsesquioxane, Polydimethylsiloxy PPG-13 Butyl Ether Silsesquioxane, Polyglyceryl-6 Caprate, Polyglyceryl-10 Dilaurate, Polyglyceryl-20 Heptacaprylate, Polyglyceryl-20 Hexacaprylate, Polyglyceryl-2 Lauryl Ether, Polyglyceryl-10 Lauryl Ether, Polyglyceryl-20 Octaisononanoate, Polyglyceryl-6 Pentacaprylate, Polyglyceryl-10 Pentacaprylate, Polyglyceryl-3 Polydimethylsiloxyethyl Dimethicone, Polyglyceryl-6 Tetracaprylate, Polyglyceryl-10 Tetralaurate, Polyglyceryl-6 Tricaprylate, Polyglyceryl-10 Trilaurate, Polyquaternium-77, Polyquaternium-78, Polyquaternium-79, Polyquaternium-80, Polyquaternium-81, Polyquaternium-82, *Pomaderris Kumerahou* Flower/Leaf Extract, *Poria Cocos* Extract, Potassium Abietoyl Hydrolyzed Collagen, Potassium Babassuate, Potassium Behenate, Potassium $C_{9\text{-}15}$ Alkyl Phosphate, Potassium $C_{11\text{-}15}$ Alkyl Phosphate, Potassium $C_{12\text{-}13}$ Alkyl Phosphate, Potassium $C_{12\text{-}14}$ Alkyl Phosphate, Potassium Caprate, Potassium Capryloyl Glutamate, Potassium Capryloyl Hydrolyzed Rice Protein, Potassium Castorate, Potassium Cocoate, Potassium Cocoyl Glutamate, Potassium Cocoyl Glycinate, Potassium Cocoyl Hydrolyzed Casein, Potassium Cocoyl Hydrolyzed Collagen, Potassium Cocoyl Hydrolyzed Corn Protein, Potassium Cocoyl Hydrolyzed Keratin, Potassium Cocoyl Hydrolyzed Oat Protein, Potassium Cocoyl Hydrolyzed Potato Protein, Potassium Cocoyl Hydrolyzed Rice Bran Protein, Potassium Cocoyl Hydrolyzed Rice Protein, Potassium Cocoyl Hydrolyzed Silk, Potassium Cocoyl Hydrolyzed Soy Protein, Potassium Cocoyl Hydrolyzed Wheat Protein, Potassium Cocoyl Hydrolyzed Yeast Protein, Potassium Cocoyl PCA, Potassium Cocoyl Sarcosinate, Potassium Cocoyl Taurate, Potassium Cornate, Potassium Cyclocarboxypropyloleate, Potassium Dihydroxyethyl Cocamine Oxide Phosphate, Potassium Dimethicone PEG-7 Phosphate, Potassium Dodecylbenzenesulfonate, Potassium Hempseedate, Potassium Hydrogenated Cocoate, Potassium Hydrogenated Palmate, Potassium Hydrogenated Tallowate, Potassium Hydroxystearate, Potassium Isostearate, Potassium Lanolate, Potassium Laurate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Laureth Phosphate, Potassium Lauroyl Collagen Amino Acids, Potassium Lauroyl Glutamate, Potassium Lauroyl Hydrolyzed Collagen, Potassium Lauroyl Hydrolyzed Pea Protein, Potassium Lauroyl Hydrolyzed Soy Protein, Potassium Lauroyl PCA, Potassium Lauroyl Pea Amino Acids, Potassium Lauroyl Sarcosinate, Potassium Lauroyl Silk Amino Acids, Potassium Lauroyl Wheat Amino Acids, Potassium Lauryl Phosphate, Potassium Lauryl Sulfate, Potassium Linoleate, Potassium Metaphosphate, Potassium Methyl Cocoyl Taurate, Potassium Myristate, Potassium Myristoyl Glutamate, Potassium Myristoyl Hydrolyzed Collagen, Potassium Octoxynol-12 Phosphate, Potassium Oleate, Potassium Oleoyl Hydrolyzed Collagen, Potassium Olivate, Potassium Olivoyl Hydrolyzed Oat Protein, Potassium Olivoyl Hydrolyzed Wheat Protein, Potassium Olivoyl/Lauroyl Wheat Amino Acids, Potassium Olivoyl PCA, Potassium Palmate, Potassium Palmitate, Potassium Palmitoyl Hydrolyzed Corn Protein, Potassium Palmitoyl Hydrolyzed Oat Protein, Potassium Palmitoyl Hydrolyzed Rice Protein, Potassium Palmitoyl Hydrolyzed Sweet Almond Protein, Potassium Palmitoyl Hydrolyzed Wheat Protein, Potassium Palm Kernelate, Potassium Peanutate, Potassium Rapeseedate, Potassium Ricinoleate, Potassium Safflowerate, Potassium Soyate, Potassium Stearate, Potassium Stearoyl Hydrolyzed Collagen, Potassium Tallate, Potassium Tallowate, Potassium Taurate, Potassium Taurine Laurate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, Potassium Trideceth-6 Phosphate, Potassium Trideceth-7 Phosphate, Potassium Tsubakiate, Potassium Undecylenate, Potassium Undecylenoyl Hydrolyzed Collagen, Potassium Undecylenoyl Hydrolyzed Rice Protein, PPG-30-Buteth-30, PPG-36-Buteth-36, PPG-38-Buteth-37, PPG-30-Capryleth-4 Phosphate, PPG-10 Cetyl Ether Phosphate, PPG-2 C9-11 Pareth-8, PPG-1-Deceth-5, PPG-3-Deceth-2 Carboxylic Acid, PPG-30 Ethylhexeth-4 Phosphate, PPG-20-Glycereth-30, PPG-2 Hydroxyethyl Coco/Isostearamide, PPG-2-Isodeceth-8, PPG-2-Isodeceth-10, PPG-2-Isodeceth-18, PPG-2-Isodeceth-25, PPG-4-Isodeceth-10, Propyltrimonium Hydrolyzed Collagen, Quaternium-24, Quaternium-52, Quaternium-87, Rapeseed Acid, Rice Bran Acid, Rice Oil Glycereth-8 Esters, Ricinoleamidopropyl Betaine, Ricinoleic Acid, Ricinoleth-40, Safflower Acid, *Sapindus Oahuensis* Fruit Extract, *Saponaria Officinalis* Root Powder, Saponins, Sekken-K, Sekken-Na/K, Sekken Soji, Sekken Soji-K, Sesame Oil Glycereth-8 Esters, Sesamidopropylamine Oxide, Sesamidopropyl Betaine, Shea Butteramidopropyl Betaine, Shea Butter Glycereth-8 Esters, Sodium Arachidate, Sodium Arganampohoacetate, Sodium *Astrocaryum Murumuruate*, Sodium Avocadoate, Sodium Babassuamphoacetate, Sodium Babassuate, Sodium Babassu Sulfate, Sodium Behenate, Sodium Bisglycol Ricinosulfosuccinate, Sodium Bis-Hydroxyethylglycinate Coco-Glucosides Crosspolymer, Sodium Bis-Hydroxyethylglycinate Lauryl-Glucosides Crosspolymer, Sodium Borageamidopropyl PG-Dimonium Chloride Phosphate, Sodium Butoxynol-12 Sulfate, Sodium Butylglucosides Hydroxypropyl Phosphate, Sodium $C_{13\text{-}17}$ Alkane Sulfonate, Sodium $C_{14\text{-}18}$ Alkane Sulfonate, Sodium $C_{12\text{-}15}$ Alkoxypropyl Iminodipropionate, Sodium $C_{10\text{-}16}$ Alkyl Sulfate, Sodium $C_{11\text{-}15}$ Alkyl Sulfate, Sodium $C_{12-13}$ Alkyl Sulfate, Sodium $C_{12-15}$ Alkyl Sulfate, Sodium $C_{12-18}$ Alkyl Sulfate, Sodium $C_{16-20}$ Alkyl Sulfate, Sodium $C_{9-22}$ Alkyl Sec Sulfonate, Sodium $C_{14-17}$ Alkyl Sec Sulfonate, Sodium Caprate, Sodium Caproamphoacetate, Sodium Caproamphohydroxypropylsulfonate, Sodium Caproamphopropionate, Sodium Caproyl Methyltaurate, Sodium Caprylate, Sodium Capryleth-2 Carboxylate, Sodium Capryleth-9 Carboxylate, Sodium Capryloamphoacetate, Sodium Capryloamphohydroxypropylsulfonate, Sodium Capryloamphopropionate, Sodium Capryloyl Glutamate, Sodium Capryloyl Hydrolyzed Wheat Protein, Sodium Caprylyl PG-Sulfonate, Sodium Caprylyl Sulfonate, Sodium Castorate, Sodium Ceteareth-13 Carboxylate, Sodium Cetearyl Sulfate, Sodium Ceteth-13 Carboxylate, Sodium Cetyl Sulfate, Sodium Cocamidopropyl PG-Dimonium Chloride Phosphate, Sodium Cocaminopropionate, Sodium Coceth Sulfate, Sodium Coceth-30 Sulfate, Sodium Cocoabutteramphoacetate, Sodium Cocoa Butterate, Sodium Cocoamphoacetate, Sodium Cocoamphohydroxypropylsulfonate, Sodium Cocoamphopropionate, Sodium Cocoate, Sodium Coco/Babassu/Andiroba Sulfate, Sodium Coco/Babassu Sulfate, Sodium Cocoglucosides Hydroxypropyl Phosphate, Sodium Cocoglucosides Hydroxypropylsulfonate, Sodium Coco-Glucoside Tartrate, Sodium Cocoglyceryl Ether Sulfonate, Sodium Coco/Hydrogenated Tallow Sulfate, Sodium Cocoiminodiacetate, Sodium Cocomonoglyceride Sulfate, Sodium Cocomonoglyceride Sulfonate, Sodium Coco PG-Dimonium Chloride Phosphate, Sodium Coco-Sulfate, Sodium Coco Sulfoacetate, Sodium Cocoyl Alaninate, Sodium Cocoyl Amino Acids, Sodium Cocoyl Collagen Amino Acids, Sodium Cocoyl Glutamate, Sodium Cocoyl Glutaminate, Sodium Cocoyl Glycinate, Sodium Cocoyl/Hydrogenated Tallow Glutamate, Sodium Cocoyl Hydrolyzed Collagen, Sodium Cocoyl Hydrolyzed Keratin, Sodium Cocoyl Hydrolyzed Rice Protein, Sodium Cocoyl Hydrolyzed Silk, Sodium Cocoyl Hydrolyzed Soy Protein, Sodium Cocoyl Hydrolyzed Sweet Almond Protein, Sodium Cocoyl Hydrolyzed Wheat Protein, Sodium Cocoyl Hydrolyzed Wheat Protein Glutamate, Sodium Cocoyl Isethionate, Sodium Cocoyl Methylaminopropionate, Sodium Cocoyl Oat Amino Acids, Sodium Cocoyl/Palmoyl/Sunfloweroyl Glutamate, Sodium Cocoyl Proline, Sodium Cocoyl Sarcosinate, Sodium Cocoyl Taurate, Sodium Cocoyl Threoninate, Sodium Cocoyl Wheat Amino Acids, Sodium $C_{12-14}$ Olefin Sulfonate, Sodium $C_{14-16}$ Olefin Sulfonate, Sodium $C_{14-18}$ Olefin Sulfonate, Sodium $C_{16-18}$ Olefin Sulfonate, Sodium Cornamphopropionate, Sodium Cottonseedamphoacetate, Sodium $C_{13-15}$ Pareth-8 Butyl Phosphate, Sodium $C_{9-11}$ Pareth-6 Carboxylate, Sodium $C_{11-15}$ Pareth-7 Carboxylate, Sodium $C_{12-13}$ Pareth-5 Carboxylate, Sodium $C_{12-13}$ Pareth-8 Carboxylate, Sodium $C_{12-13}$ Pareth-12 Carboxylate, Sodium $C_{12-15}$ Pareth-6 Carboxylate, Sodium $C_{12-15}$ Pareth-7 Carboxylate, Sodium $C_{12-15}$ Pareth-8 Carboxylate, Sodium $C_{14-15}$ Pareth-8 Carboxylate, Sodium $C_{12-14}$ Sec-Pareth-8 Carboxylate, Sodium $Cl_{4-15}$ Pareth-PG Sulfonate, Sodium $C_{12-13}$ Pareth-2 Phosphate, Sodium $C_{13-15}$ Pareth-8 Phosphate, Sodium $C_{9-15}$ Pareth-3 Sulfate, Sodium $C_{10-15}$ Pareth Sulfate, Sodium $C_{10-16}$ Pareth-2 Sulfate, Sodium $C_{12-13}$ Pareth Sulfate, Sodium $C_{12-15}$ Pareth Sulfate, Sodium $C_{12-15}$ Pareth-3 Sulfate, Sodium $C_{13-15}$ Pareth-3 Sulfate, Sodium $C_{12-14}$ Sec-Pareth-3 Sulfate, Sodium $C_{12-15}$ Pareth-3 Sulfonate, Sodium $C_{12-15}$ Pareth-7 Sulfonate, Sodium $C_{12-15}$ Pareth-15 Sulfonate, Sodium Deceth-2 Carboxylate, Sodium Deceth Sulfate, Sodium Decylbenzenesulfonate, Sodium Decylglucosides Hydroxypropyl Phosphate, Sodium Decylglucosides Hydroxypropylsulfonate, Sodium Dilaureth-7 Citrate, Sodium Dilaureth-10 Phosphate, Sodium Dilinoleamidopropyl PG-Dimonium Chloride Phosphate, Sodium Dilinoleate, Sodium Dioleth-8 Phosphate, Sodium Dodecylbenzenesulfonate, Sodium Ethyl 2-Sulfolaurate, Sodium Glyceryl Oleate Phosphate, Sodium Grapeseedamidopropyl PG-Dimonium Chloride Phosphate, Sodium Grapeseedamphoacetate, Sodium Grapeseedate, Sodium Hempseedamphoacetate, Sodium Hexeth-4 Carboxylate, Sodium Hydrogenated Cocoate, Sodium Hydrogenated Cocoyl Methyl Isethionate, Sodium Hydrogenated Palmate, Sodium Hydrogenated Tallowate, Sodium Hydrogenated Tallowoyl Glutamate, Sodium Hydroxylauryldimonium Ethyl Phosphate, Sodium Hydroxypropyl Palm Kernelate Sulfonate, Sodium Hydroxypropylphosphate Decylglucoside Crosspolymer, Sodium Hydroxypropylphosphate Laurylglucoside Crosspolymer, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer, Sodium Hydroxystearate, Sodium Isostearate, Sodium Isosteareth-6 Carboxylate, Sodium Isosteareth-11 Carboxylate, Sodium Isostearoamphoacetate, Sodium Isostearoamphopropionate, Sodium N-Isostearoyl Methyltaurate, Sodium Laneth Sulfate, Sodium Lanolate, Sodium Lardate, Sodium Lauramido Diacetate, Sodium Lauraminopropionate, Sodium Laurate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Laureth-7 Tartrate, Sodium Lauriminodipropionate, Sodium Lauroamphoacetate, Sodium Lauroamphohydroxypropylsulfonate, Sodium Lauroampho PG-Acetate Phosphate, Sodium Lauroamphopropionate, Sodium Lauroyl Aspartate, Sodium Lauroyl Collagen Amino Acids, Sodium Lauroyl *Glycine* Propionate, Sodium Lauroyl Hydrolyzed Collagen, Sodium Lauroyl Hydrolyzed Silk, Sodium Lauroyl Hydroxypropyl Sulfonate, Sodium Lauroyl Isethionate, Sodium Lauroyl Methylaminopropionate, Sodium Lauroyl Methyl Isethionate, Sodium Lauroyl Millet Amino Acids, Sodium Lauroyl/Myristoyl Aspartate, Sodium Lauroyl Oat Amino Acids, Sodium Lauroyl Sarcosinate, Sodium Lauroyl Silk Amino Acids, Sodium Lauroyl Taurate, Sodium Lauroyl Wheat Amino Acids, Sodium Lauryl Diethylenediaminoglycinate, Sodium Lauryl Glucose Carboxylate, Sodium Laurylglucosides Hydroxypropyl Phosphate, Sodium Laurylglucosides Hydroxypropylsulfonate, Sodium Lauryl Glycol Carboxylate, Sodium Lauryl Hydroxyacetamide Sulfate, Sodium Lauryl Phosphate, Sodium Lauryl Sulfate, Sodium Lauryl Sulfoacetate, Sodium Linoleate, Sodium Macadamiaseedate, Sodium Mangoamphoacetate, Sodium Mangoseedate, Sodium/MEA Laureth-2 Sulfosuccinate, Sodium Methoxy PPG-2 Acetate, Sodium Methyl Cocoyl Taurate, Sodium Methyl Lauroyl Taurate, Sodium Methyl Myristoyl Taurate, Sodium Methyl Oleoyl Taurate, Sodium Methyl Palmitoyl Taurate, Sodium Methyl Stearoyl Taurate, Sodium Methyl 2-Sulfolaurate, Sodium Methyl 2-Sulfopalmitate, Sodium Methyltaurate Isopalmitamide, Sodium Methyltaurine Cocoyl Methyltaurate, Sodium Myreth Sulfate, Sodium Myristate, Sodium Myristoamphoacetate, Sodium Myristoyl Glutamate, Sodium Myristoyl Hydrolyzed Collagen, Sodium Myristoyl Isethionate, Sodium Myristoyl Sarcosinate, Sodium Myristyl Sulfate, Sodium Nonoxynol-6 Phosphate, Sodium Nonoxynol-9 Phosphate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Ethane Sulfonate, Sodium Octoxynol-2 Sulfate, Sodium Octoxynol-6 Sulfate, Sodium Octoxynol-9 Sulfate, Sodium Oleate, Sodium Oleoamphoacetate, Sodium Oleoamphohydroxypropylsulfonate, Sodium Oleoamphopropionate, Sodium Oleoyl Hydrolyzed Collagen, Sodium Oleoyl Isethionate, Sodium Oleth Sulfate, Sodium Oleyl Methyl Isethionate, Sodium Oleyl Sulfate, Sodium Olivamphoacetate, Sodium Olivate, Sodium Olivoyl Glutamate, Sodium Palmamphoacetate, Sodium Palmate, Sodium Palm Glyceride Sulfonate, Sodium Palmitate, Sodium Palmitoyl Hydrolyzed Collagen, Sodium Palmitoyl Hydrolyzed Wheat Protein, Sodium Palmitoyl Sarcosinate, Sodium Palm Kernelate, Sodium Palm Kerneloyl Isethionate, Sodium Palmoyl Glutamate, Sodium *Passiflora Edulis* Seedate, Sodium Peanutamphoacetate, Sodium Peanutate, Sodium PEG-6 Cocamide Carboxylate, Sodium PEG-8 Cocamide Carboxylate, Sodium PEG-4 Cocamide Sulfate, Sodium PEG-3 Lauramide Carboxylate, Sodium PEG-4 Lauramide Carboxylate, Sodium PEG-8 Palm Glycerides Carboxylate, Sodium Pentaerythrityl Hydroxypropyl Iminodiacetate Dendrimer, Sodium Propoxy PPG-2 Acetate, Sodium Rapeseedate, Sodium Ricebranamphoacetate, Sodium Ricinoleate, Sodium Ricinoleoamphoacetate, Sodium Rose Hipsamphoacetate, Sodium Rosinate, Sodium Safflowerate, Sodium Saffloweroyl Hydrolyzed Soy Protein, Sodium Sesameseedate, Sodium Sesamphoacetate, Sodium Sheabutteramphoacetate, Sodium Soyate, Sodium Soy Hydrolyzed Collagen, Sodium Stearate, Sodium Stearoamphoacetate, Sodium Stearoamphohydroxypropylsulfonate, Sodium Stearoamphopropionate, Sodium Stearoyl Casein, Sodium Stearoyl Glutamate, Sodium Stearoyl Hyaluronate, Sodium Stearoyl Hydrolyzed Collagen, Sodium Stearoyl Hydrolyzed Corn Protein, Sodium Stearoyl Hydrolyzed Silk, Sodium Stearoyl Hydrolyzed Soy Protein, Sodium Stearoyl Hydrolyzed Wheat Protein, Sodium Stearoyl Lactalbumin, Sodium Stearoyl Methyl Isethionate, Sodium Stearoyl Oat Protein, Sodium Stearoyl Pea Protein, Sodium Stearoyl Soy Protein, Sodium Stearyl Dimethyl *Glycine*, Sodium Stearyl Sulfate, Sodium Sunflowerseedamphoacetate, Sodium Surfactin, Sodium Sweetalmondamphoacetate, Sodium Sweet Almondate, Sodium Tallamphopropionate, Sodium Tallate, Sodium Tallowamphoacetate, Sodium Tallowate, Sodium Tallow Sulfate, Sodium Tamanuseedate, Sodium Taurate, Sodium Taurine Cocoyl Methyltaurate, Sodium Taurine Laurate, Sodium/TEA-Lauroyl Collagen Amino Acids, Sodium/TEA-Lauroyl Hydrolyzed Collagen, Sodium/TEA-Lauroyl Hydrolyzed Keratin, Sodium/TEA-Lauroyl Keratin Amino Acids, Sodium/TEA-Undecylenoyl Collagen Amino Acids, Sodium/TEA-Undecylenoyl Hydrolyzed Collagen. Sodium/TEA-Undecylenoyl Hydrolyzed Corn Protein, Sodium/TEA-Undecylenoyl Hydrolyzed Soy Protein, Sodium/TEA-Undecylenoyl Hydrolyzed Wheat Protein, Sodium *Theobroma Grandiflorum* Seedate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Trideceth Sulfate, Sodium Tridecylbenzenesulfonate, Sodium Tridecyl Sulfate, Sodium Trimethylolpropane Hydroxypropyl Iminodiacetate Dendrimer, Sodium Undeceth-5 Carboxylate, Sodium Undecylenate, Sodium Undecylenoamphoacetate, Sodium Undecylenoamphopropionate, Sodium Undecylenoyl Glutamate, Sodium Wheat Germamphoacetate, Sorbeth-160 Tristearate, Soy Acid, Soyamidopropylamine Oxide, Soyamidopropyl Betaine, Soybean Oil Glycereth-8 Esters, Stearamidopropylamine Oxide, Stearamidopropyl Betaine, Stearamine Oxide, Steareth-15, Steareth-16, Steareth-20, Steareth-21, Steareth-25, Steareth-27, Steareth-30, Steareth-40, Steareth-50, Steareth-80, Steareth-100, Steareth-2 Phosphate, Steareth-3 Phosphate, Stearic Acid, Stearoxypropyltrimonium Chloride, Stearoyl Glutamic Acid, Stearoyl Sarcosine, Stearyl Betaine. Stearyldimoniumhydroxypropyl Butylglucosides Chloride, Stearyldimoniumhydroxypropyl Decylglucosides Chloride, Stearyldimoniumhydroxypropyl Laurylglucosides Chloride, Sulfated Castor Oil, Sulfated Coconut Oil, Sulfated Glyceryl Oleate, Sulfated Olive Oil, Sulfated Peanut Oil, Sunfloweramide MEA, Sunflower Seed Acid, Sunflowerseedamidopropyl Hydroxyethyldimonium Chloride, Sunflower Seed Oil Glycereth-8 Esters, Tall Oil Acid, Tallow Acid, Tallowamidopropylamine Oxide, Tallowamidopropyl Betaine, Tallowamidopropyl Hydroxysultaine, Tallowamine Oxide, Tallow Betaine. Tallow Dihydroxyethyl Betaine, Tallowoyl Ethyl Glucoside, TEA-Abietoyl Hydrolyzed Collagen, TEA-$C_{12-14}$ Alkyl Phosphate, TEA-$C_{10-15}$ Alkyl Sulfate, TEA-$C_{11-15}$ Alkyl Sulfate, TEA-$C_{12-13}$ Alkyl Sulfate, TEA-$C_{12-14}$ Alkyl Sulfate, TEA-$C_{12-15}$ Alkyl Sulfate, TEA $C_{14-17}$ Alkyl Sec Sulfonate, TEA-Canolate, TEA-Cocamide Diacetate, TEA-Cocoate, TEA-Coco-Sulfate, TEA-Cocoyl Alaninate, TEA-Cocoyl Glutamate, TEA-Cocoyl Glutaminate, TEA-Cocoyl Glycinate, TEA-Cocoyl Hydrolyzed Collagen, TEA-Cocoyl Hydrolyzed Soy Protein, TEA-Cocoyl Sarcosinate, TEA-Dimethicone PEG-7 Phosphate, TEA-Dodecylbenzenesulfonate, TEA-Hydrogenated Cocoate. TEA-Hydrogenated Tallowoyl Glutamate, TEA-Isostearate, TEA-Isostearoyl Hydrolyzed Collagen, TEA-Lauraminopropionate, TEA-Laurate. TEA-Laurate/Myristate, TEA-Laureth Sulfate, TEA-Lauroyl Collagen Amino Acids, TEA-Lauroyl Glutamate, TEA-Lauroyl Hydrolyzed Collagen, TEA-Lauroyl Keratin Amino Acids, TEA-Lauroyl Methylaminopropionate, TEA-Lauroyl/Myristoyl Aspartate, TEA-Lauroyl Sarcosinate, TEA-Lauryl Phosphate, TEA-Lauryl Sulfate, TEA-Myristaminopropionate, TEA-Myristate, TEA-Myristoyl Hydrolyzed Collagen, TEA-Oleate, TEA-Oleoyl Hydrolyzed Collagen, TEA-Oleoyl Sarcosinate, TEA-Oleyl Sulfate, TEA-Palmitate, TEA-Palm Kernel Sarcosinate, TEA-PEG-3 Cocamide Sulfate. TEA-Rosinate, TEA-Stearate, TEA-Tallate, TEA-Tridecylbenzenesulfonate, TEA-Undecylenate, TEA-Undecylenoyl Hydrolyzed Collagen, Tetramethyl Decynediol, Tetrasodium Dicarboxyethyl Stearyl Sulfosuccinamate, TIPA-Laureth Sulfate, TIPA-Lauryl Sulfate, TIPA-Myristate, TIPA-Stearate, Tocopheryl Phosphate, Trehalose Undecylenoate, Tri-$C_{12-15}$ Pareth-2 Phosphate, Tri-$C_{12-15}$ Pareth-6 Phosphate, Tri-$C_{12-15}$ Pareth-8 Phosphate, Tri-$C_{12-15}$ Pareth-10 Phosphate, Trideceth-20, Trideceth-50, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid, Trideceth-10 Phosphate, Tridecylbenzenesulfonic Acid, Trilaureth-9 Citrate, Trimethylolpropane Hydroxypropyl Bis-Hydroxyethylamine Dendrimer, Trisodium Lauroampho PG-Acetate Chloride Phosphate, Undecanoic Acid, Undeceth-5 Carboxylic Acid, Undecylenamidopropylamine Oxide, Undecylenamidopropyl Betaine, Undecylenic Acid, Undecylenoyl Collagen Amino Acids, Undecylenoyl *Glycine*, Undecylenoyl Hydrolyzed Collagen, Undecylenoyl Wheat Amino Acids, Undecyl Glucoside, Wheat Germ Acid, Wheat Germamidopropylamine Oxide, Wheat Germamidopropyl Betaine, *Yucca Schidigera* Leaf/Root/Stem Extract, *Yucca Schidigera* Stem Extract, Zinc Coceth Sulfatea and Zinc Coco-Sulfate.

Pharmaceutical and Topical Preparations

In some embodiments, the composition further comprises an active pharmaceutical ingredient. In some further embodiments, the active pharmaceutical ingredient is a compound with cooling effect. In some other embodiments, the active pharmaceutical ingredient is not a cooling compound.

In some embodiments, the cooling compounds and combinations thereof are present in a topical composition. Such a topical composition can be in the form of a solid, semi-solid, plaster, solution, suspension, lotion, cream, foam, gel, paste, poultice, emulsion, or a combination thereof.

In some embodiments, a method of treating insect bites, insect stings, allergenic effects, burns, scrapes, cuts, abrasions, psoriasis, dandruff, pruritus, itching, nasal complaints, sore throats, upper respiratory ailments, acne, athlete's foot, or skin irritation as result of contact with poison ivy, poison oak, or poison sumac is provided comprising applying the a composition disclosed herein to a subject in need thereof.

In some embodiments, the topical composition can be selected from a poultice for the treatment of burns, a topical cough suppressant, an anti-itch cream, an antibiotic ointment, an after-sun gel, or an after-sun lotion.

In some embodiments, the topical composition can be a personal care product selected from the group consisting of shaving products, deodorants, odorants, insect repellants, facial care products, body care products, cosmetics, soap products, and lip products.

In some embodiments, the topical composition can be selected from the group consisting of a shaving cream, a shaving lotion, and after-shave lotion, a roll-on deodorant, a spray deodorant, an air freshener, a room deodorizer, a perfume, a cologne, a hand-soap, a facial soap, a lipstick, a lip balm, a lip gloss, a body lotion, and a shower gel.

In some embodiments, a method for enhancing the massage therapy treatment is provided comprising applying a topical composition disclosed herein to a subject in need thereof. In some embodiments, the topical composition can be an aphrodisiac.

Compounds 101-105, or salts, solvates, and combinations thereof, can be used as modulators, e.g., agonists, of the TRPM8 receptor in personal products for modulating, e.g., inducing, chemesthetic sensations, particularly the cold, cool, or tingling sensations. These compounds are also important to the flavorings and fragrance industry because they can increase or induce/generate a cooling or cold sensation which is often associated with freshness and cleanliness. As modulators of the TRPM8 receptor, the above-disclosed compounds also have repellent effect on insects, therapeutic effect in antitumor treatments (e.g., an influencing of prostate tumors), activity in the treatment of inflammatory pain/hyperalgesia, and efficacy (as TRPM8 antagonists) in the treatment of bladder syndrome or overactive bladder.

In one embodiment, the composition comprises a chemesthetic sensation modulating amount of the one of Compounds 101-105. In another embodiment, the composition comprises a chemesthetic sensation inducing amount of a combination of one or more cooling compounds as described herein. In some other embodiments, the composition further comprises an inactive pharmaceutical ingredient, active pharmaceutical ingredient, perfume, fragrance, odorant, flavorant, or food additive. In some embodiments, the chemesthetic sensation is a cold or cooling sensation. In one embodiment of the composition, the cooling compound is in a concentration ranging from about 0.0001 ppm to 100,000 ppm. In another embodiment of the composition, the cooling compound is in a concentration ranging from about 0.001 ppm to 10,000 ppm. In another embodiment of the composition, the cooling compound is in a concentration ranging from about 0.01 ppm to 1,000 ppm. In another embodiment of the composition, the cooling compound is in a concentration ranging from about 0.1 ppm to 500 ppm. In another embodiment of the composition, the cooling compound is in a concentration ranging from about 1 ppm to 500 ppm. In another embodiment of the composition, the cooling compound is in a concentration ranging from about 10 ppm to 500 ppm. In another embodiment of the composition, the cooling compound is in a concentration ranging from about 1 ppm to 400 ppm.

The topical compositions described herein may comprise one or more cooling compounds. The topical composition can be a "pharmaceutical composition" or a composition intended for "personal care." By "pharmaceutical composition", it is meant a composition which is used to treat the symptoms and/or root causes of a disease or ailment. In one embodiment, the pharmaceutical composition comprises one or more compounds of the present invention and at least one pharmaceutically acceptable carrier. The pharmaceutical composition category includes both the prescription medications and the over-the-counter medications. The present compound may or may not be the therapeutically active ingredient in the pharmaceutical composition. In general, over the counter (OTC) product and oral hygiene product generally refer to product for household and/or personal use which may be sold without a prescription and/or without a visit to a medical professional. Examples of the OTC products include, but are not limited to topical analgesics and/or anesthetic; cough, cold and allergy remedies; antihistamines and/or allergy remedies; and combinations thereof. Topical analgesics and/or anesthetics include any topical creams/ointments/gels used to alleviate superficial or deep-seated aches and pains, e.g. muscle pain; teething gel; toothpaste; sports creams; patches with analgesic ingredient; and combinations thereof. In some embodiments, the pharmaceutical composition is hemorrhoid product. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. In some embodiments, the topical pharmaceutical composition can be a sinus relief product or a nasal spray. Examples of oral hygiene product include, but are not limited to mouth cleaning strips, toothpaste, toothbrushes, mouthwashes/dental rinses, denture care, mouth fresheners, breath freshening sprays, breath freshening drops, breath freshening concentrates, chewing gum, mouth moisturizers, at-home teeth whiteners and dental floss. The topical pharmaceutical composition can further be in the form of a first aid product. For example, the topical pharmaceutical composition can be applied as an ointment or on a bandage, band aid, or in a spray. In some embodiments, the pharmaceutical can nausea relief products. For example, the composition can be a topical nausea relief product or a sea band. In some embodiments, the pharmaceutical composition can be an ingestible composition. For example, the composition can be an ingestible nausea relief composition, an antacid, or a heartburn relief composition.

In some embodiments, the topical pharmaceutical composition can be a composition for the treatment and alleviation of pain in a subject. Topical compositions for providing such pain relief can comprise a combination of one or more of the cooling compounds as disclosed herein. The topical composition for the relief of pain can further comprise an additional active ingredient. In some embodiments the additional active ingredient can be an anti-inflammatory agent. Topical compositions comprising a cooling agent and applied in the relief of pain are well known in the art. For example, several such compositions are described in U.S. 2011/0135627 and U.S. Pat. No. 8,105,624, which are incorporated herein by reference in their entirety.

In some embodiments, the topical pharmaceutical composition can be applied in the treatment of allergenic effects. In some embodiments a topical composition comprising one or more cooling compounds as disclosed herein can further comprise an antibacterial agent, an anti-inflammatory agent, and or a corticosteroid. Exemplary topical compositions used in the treatment of allergenic effects and comprising menthol and/or camphor as a cooling agent are described in U.S. 2010/0104547, which is incorporated herein by reference in its entirety. In some embodiments, the topical composition can be used in the treatment of insect bites or insect stings. In some embodiments, the topical composition can be used in the treatment of psoriasis or eczema. In some embodiments, the topical composition can be a nasal decongestant.

Representative anti-inflammatories suitable for combination with one or more of the cooling agents described herein are known in the art and include, but are not limited to, Aspirin, Choline, and, magnesium, salicylates, Choline, salicylate, Celecoxib, Diclofenac, potassium, Diclofenac sodium, Diclofenac sodium with misoprostol, Diflunisal, Etodolac, Fenoprofen calcium, Flurbiprofen, Ibuprofen, Indomethacin, Ketoprofen, Magnesium, salicylate, Meclofenamate sodium, Mefenamic acid, Meloxicam), Nabumeton), Naproxen, Naproxen sodium, Oxaprozin, Piroxicam, Rofecoxib, Salsalate, Sodium salicylate, Sulindac, Tolmetin sodium, and Valdecoxib.

Representative antibiotics suitable for combination with one or more of the cooling agents described herein are known in the art and include, but are not limited to: Amikacin, Gentamicin, Kanamycin, Neomycin, Netilmicin, Tobramycin, Paromomycin, Streptomycin, Spectinomycin, Geldanamycin, Herbimycin, Rifaximin, Loracarbef, Ertapenem, Doripenem, Imipenem/Cilastatin, Meropenem, Cefadroxil, Cefazolin, Cefalotin/Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Dalbavancin, Oritavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G. Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole(Co-trimoxazole) (TMP-SMX), Sulfonamidochrysoidine, Demeclocycline, Doxycycline, Minocycline, Oxytetracycline, Tetracycline, Clofazimine, Dapsone, Capreomycin, Cycloserine, Ethambutol(Bs), Ethionamide, Isoniazid, Pyrazinamide, Rifampicin/Rifampin, Rifabutin, Rifapentine, Streptomycin, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, and Trimethoprim. In some preferred embodiments, the compositions described herein further comprise an antibiotic selected from the list of neomycin, erythromycin, mupirocin, polymyxin B, Bacitracin, and Oxacillin.

Representative corticosteroids suitable for combination with one or more of the cooling agents described herein are known in the art and include, but are not limited to: Betamethasone dipropionate, Clobetasol propionate, Fluocinonide, Flurandrenolide, Halobetasol propionate, Amcinonide, Betamethasone dipropionate, Desoximetasone, Diflorasone diacetate, Halocinonide, Triamcinolone, Betamethasone valerate, Fluticasone propionate, Mometasone furoate, Triamcinolone acetonide, Clocortolone pivalate, Fluocinolone acetonide, Hydrocortisone valerate, Desonide, Fluticasone proprionate, Hydrocortisone butyrate, Hydrocortisone probutate, Prednicarbate, Aclometasone dipropionate, Hydrocortisone (base), Hydrocortisone acetate/*Aloe vera*, and Hydrocortisone acetate/urea.

In some embodiments, the topical pharmaceutical composition disclosed herein can be an anti-dandruff or an anti-itch composition. The anti-dandruff and/or anti-itch composition can take several forms including, but not limited to, shampoos, soaps, ointments, eye drops and creams. The anti-dandruff composition may further comprise an anti-dandruff agent such as zinc salt of 1-hydroxy-2-pyridine thione, allantoin, cholesterol, coal tar, grape seed extract, tea tree oil, hexachlorophene, neem oil, lanolin, p-dimethoxybezene, petrolatum, pine tar, resorcinol, salicylic acid, pyroctane olamine, undecylenic acid, sodium shale oil sulfonate, bay laurel extract, bee balm extract, burdock root extract, colloidal sulfur, ammonium salts of low molecular weight huminates, cetyldimethylbenzylammonium bromide, piroctone olamine, hexachlorophene, miconazole, ketoconazole, or selenium sulfide. The anti-itch composition may further comprise an anti-itch agent such as beta-methasone valerate. Exemplary anti-itch and anti-dandruff topical compositions comprising a cooling agent are described in U.S. 2003/0161802, which is incorporated herein by reference in its entirety. Such antipruritic agents include but are not limited to, chamomile, *eucalyptus*, camphor, talc, hydrocortisone, betamethasone valerate, fluocinolone acetonide, hydrocortisone valerate, triamcinolone acetonide, betamethasone dipropionate, halcinonide, clobetasol propionate and halobetasol propionate. The weight percent of anti-itch agent found in a cream or soap is optionally from about 0.02% to about 3.0%. In some further embodiments, the weight percent of anti-itch agent found in a cream or soap is optionally from about 0.002% to about 12.0%. Exemplary topical compositions in the form of eye drops comprising a cooling agent are described in EP 2014333 A1, which is incorporated herein by reference in its entirety. While ophthalmic preparations may include any of the ingredients disclosed above as inert ingredients in pharmaceutical formulations, preferred ophthalmic preparations will include, in addition to a cooling agent as disclosed herein, a buffer, a tonicity modifier, and a preservative.

In some embodiments, the topical pharmaceutical composition disclosed herein can be an antibacterial or an antimicrobial composition. The topical antibacterial and or antimicrobial composition disclosed herein may further comprise an antibiotic, antifungal, or anti-viral agent. For example, the topical formulation may comprise one or more of Compounds 101-105 and a quaternary ammonium compound such as benzethonium chloride. Exemplary antibacterial and antimicrobial topical compositions comprising menthyl lactate as a cooling agent are described in U.S. Pat. No. 8,951,582, which is incorporated herein by reference in its entirety. In some embodiments, the antimicrobial composition can be applied in the treatment of athlete's foot.

Antifungal drugs suitable for incorporation into the compositions disclosed herein are known in the art and include, but are not limited to: amphotericin b, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, abafungin, amorolfin, butenafine, naftifine, terbinafine, echinocandins, anidulafungin, caspofungin, micafungin, benzoic acid, ciclopirox/ciclopirox olamine, flucytosine or 5-fluorocytosine, griseofulvin, haloprogin tolnaftate, undecylenic acid, crystal violet, and balsam of peru.

Antiviral drugs suitable for incorporation into the compositions disclosed herein are known in the art and include, but are not limited to: abacavir, aciclovir, acyclovir, adefovir, amantadine, amprenavir, ampligen, arbidol, atazanavir, balavir, cidofovir, combivir dolutegravir, darunavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, ganciclovir, ibacitabine, imunovir, idoxuridine, imiquimod, indinavir, inosine, integrase inhibitor, interferon type iii, interferon type ii, interferon type i, interferon, lamivudine, lopinavir, loviride, maraviroc, moroxydine, methisazone, nelfinavir, nevirapine, nexavir, nucleoside analogues, novir, oseltamivir (tamiflu), peg-interferon alfa-2a, penciclovir, peramivir, pleconaril, podophyllotoxin, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, valaciclovir (valtrex), valganciclovir, vicriviroc, vidarabine, viramidine, zalcitabine, zanamivir (relenza), and zidovudine.

In some embodiments, a topical pharmaceutical composition as disclosed herein can be a composition for treatment of skin irritation as a result of contact with poison ivy, poison oak, or poison sumac. For example, the topical pharmaceutical composition can be a composition for removing urushiol, the primary irritant contracted from poison ivy, poison oak, or poison sumac. In some embodiments, the one or more of Compounds 101-105 provide a soothing effect to a subject having contracted poison ivy, poison oak, or poison sumac. Exemplary topical compositions for such treatment comprising one or more cooling agents are described in U.S. Pat. No. 7,858,570, which is incorporated herein by reference in its entirety.

In some embodiments, a topical pharmaceutical composition as disclosed herein can be a composition for the treatment of upper respiratory ailments. VapoRub®, sold by Vicks Corporation, is an example of a topical formulation for the treatment of upper respiratory ailments, including the common cold, cough, and bronchitis, the active ingredients of which are menthol and camphor. One of skill in the art, would recognize that one of Compounds 101-105 would likewise be suitable in a topical composition for such treatment. Other exemplary topical compositions which have employed cooling agents in the treatment of upper respiratory ailments are described in U.S. Pat. No. 6,196,348 and WO 200205802 A1, which are incorporated herein by reference in their entirety.

In some embodiments, a topical pharmaceutical composition as disclosed herein can be a composition for the treatment of acne. Cooling agents such as camphor, menthol, and menthyl lactate have been commonly used to aid in the treatment of acne. One of skill in the art would immediately recognize that each of Compounds 101-105 would be suitable for use as a cooling agent in the treatment of acne.

In some embodiments, a topical composition as disclosed herein can be a composition for the treatment of burns, cuts, scrapes, and abrasions. In some embodiments, the topical composition is used to treat sunburns. For example, the topical composition disclosed herein can be a sun-tanning product, a sunscreen product, an after-sun lotion, an ointment, a salve, a balm, and the like.

As used herein, a "personal care composition" refers to a composition to be directly applied to the skin, mucosa, hair, nails or other surface area of the body. Examples of personal care composition include, but are not limited to, an oral care composition, such as toothpaste, chewing gum, breath refresher, dentifrices, and mouthwashes; a skincare or haircare composition, such as sunscreen cream, sunburn lotions, shaving cream, plasters, shampoos, conditioners, face cleaners, facial washes, soaps, bath oils or bath foam, antiperspirants, and deodorant; a cosmetic composition, such as moisturizer, lip balms, cosmetic balms, foundation, etc.; an insect repellent composition; or an insecticide composition.

In some embodiments, the compositions disclosed herein further comprise the combination of a cooling agent and a fragrance. In further embodiments, the compositions disclosed herein further comprise one or more of Compounds 101-105 in combination with a fragrance. The combination of cooling agents with fragrances is known in the art, see for example, U.S. Pat. Nos. 9,222,055 and 9,220,805, incorporated by reference herein in their entireties. Formulation of personal care products with fragrance components is also known in the art, see, for example, *Formulating Detergents and Personal Care Products A guide to Products Development* by L Ho Tan Tai, ISBN 1-893997-10-3 published by the AOCS Press, and *Harry's Cosmeticology* published by CHS Press 8.sup.th Edn. 2000 ISBN 0820603724, incorporated by reference herein in their entireties. Fragrance components suitable for incorporation into the compositions disclosed herein are known in the art and include, but are not limited to: Acetoin, Ambergris, Ambrein, Ambroxide, Aroma compound, *Artemisia pallens*, Balm of Gilead, Balsam of Peru, Bdellium, Benzoin resin, Benzyl acetate, Benzyl alcohol, Benzyl benzoate, Benzyl cinnamate, Benzylacetone, Bisabolol, Bourgeonal, Calone, Camphene, Camphor, Cashmeran, *Cedrus*, Chavicol, Cinnamyl alcohol, Citral, Citronellol, Civet (perfumery), Civetone, Copaiba, Cyclopentadecanolide, Cyclopentanone, *Cyperus articulatus*, Damascenone, Damascone, Deer musk, Diethyl malonate, Estragole, Ethyl benzoate, Ethyl maltol, Ethyl methylphenylglycidate, Ethyl salicylate, Eugenol, *Evernia prunastri*, Farnesene, Farnesol, Filbertone, Fixative (perfumery), Fragrance oil, Geraniol, Geranyl acetate, Gourmand (fragrance), Grapefruit mercaptan, Heptyl acetate, Herbal distillate, Hexyl cinnamaldehyde, Hydroxymethylpentylcyclohexenecarboxaldehyde, Hyraceum, Ionone, Irone, Iso E Super, Isobornyl cyclohexanol, Isovanillin, Labdanum, Menthone, Methyl benzoate, Methyl butyrate, Muscone, Musk xylene, Myrcene, *Nardostachys jatamansi*, Nerol, Nerolidol, Ocimene, Opopanax, Patchouli, Patchoulol, *Pelargonium graveolens*, Perillaldehyde, Phellandrene, Phenethyl alcohol, Beta-Pinene, *Polianthes tuberosa*, Pomarose, Pulegone, Raspberry ketone, Safrole, Sandalore, Sandalwood, A-Santalol, B-Santalol, Skatole, Spikenard, *Styrax* balsam, Synthetic musk, Tetramethyl acetyloctahydronaphthalenes, Thujone, Tincture of benzoin, Tolu balsam, *Valeriana celtica*, Vanillin, Ortho-Vanillin, A-Vetivone, Anethole, Aroma lamp, *Artemisia pallens*, *Backhousia citriodora*, Benzoin resin, Bergamot essential oil, Black pepper, Cajeput oil, Calophyllum inophyllum seed oil, *Cananga odorata*, *Cannabis* flower essential oil, Carrot seed oil, Cedar oil, Citron, Citronella oil, Oil of clove, Copaiba, *Cymbopogon martinii*, *Cyperus scariosus*, Dill oil, *Eucalyptus* oil, Fragrance oil, Herbal distillate, *Hydnocarpus wightiana* seed oil, Juniper berry, Lavender oil, Lemon oil, Monoi oil, Mustard oil, Myrrh, Myrtol standardized, Neroli, Nutmeg oil, Oil of guaiac, Olbas Oil, Orange oil, Orris oil, Palmarosa Oil, Patchouli, *Pelargonium graveolens*, Petitgrain, Pine oil, Rose oil, Rosewood oil, Sage oil, *Salvia sclarea*, Sandalwood oil, *Santalum album*, *Santalum spicatum*, Sfumatura, Spearmint, *Styrax* balsam, Tea tree oil, Wintergreen, Yarrow oil, Herbal distillate, Orange flower water, Rose water, alpha-hexylcinnamaldehyde, 2-phenoxyethylisobutyrate, dihydromyrcenol (2,6-dimethyl-7-octen-2-ol), methyl dihydrojasmonate, 4,6,6,7,8,8-hexamethyl-1,3,4,6,7,8-hexahydrocyclopenta[g]benzopyran, tetrahydrolinalool (3,7-dimethyloctan-3-ol), ethyllinalool, benzylsalicylate, 2-methyl-3-(4-tert-butyl-phenyl)propanal, cinnamon alcohol, 4,7-methano-3a,4,5,6,7,7a-hexahydro-5-indenyl acetate and/or 4,7-methano-3a,4,5,6,7,7a-hexahydro-6-indenyl acetate, citronellol, linalyl acetate, styrolyl acetate(l-phenylethyl acetate), octahydro-2,3,8,8-tetramethyl-2-acetonaphthone and/or 2-acetyl-1,2,3,4,6,7,8-octahydro-2,3,8,8-tetramethylnaphthalene, hexylsalicylate, 4-tert.-butylcyclohexyl acetate, 2-tert.-butylcyclohexyl acetate, alpha-ionone (4-(2,2,6-trimethyl-2-cyclohexen-1-yl)-3-buten-2-one), coumarin, terpinyl acetate, 4-(4-hydroxy-4-methylpentyl)-3-cyclohexene carboxaldehyde, alpha-amyl cinnamon aldehyde, (E)- and/or (Z)-3-methyl-cyclopentadec-5-enone, 15-pentadec-11-enolide and/or 15-pentadec-12-enolide, 15-cyclopentadecanolide, 1-(5,6,7,8-tetrahydro-3,5,5,6,8,8-hexamethyl-2-naphthalenyl)ethanone, 2-isobutyl-4-methyltetrahydro-2H-pyran-4-ol, 2-ethyl-4-(2,2,3-trimethyl-3-cyclopenten-1-yl)-2-buten-1-ol, menthol, anethole, geraniol, nerol, linalool, citronellol, linalyl acetate, 2-phenylethyl alcohol, 2,2-dimethyl-3-(3-methylphenyl)-propanol, rose oxide (4-methyl-2-(2-methyl-1-propenyl)tetrahydropyran), allyl heptanoate, 4-methylacetophenone, (4aR,5R,7aS,9R)-octahydro-2,2,5,8,8,9a-hexamethyl-4H-4a,9-methanoazuleno(-5,6-d)-1,3-dioxol), 1-(2,2,6-trimethylcyclohexyl)hexan-3-ol, 2,4,6-trimethyl-4-phenyl-1,3-dioxan, benzylacetone, methyl cinnamate, 3a,6,6,9a-tetramethyldodecahydronaphtho[2,1-b]furan, Ambrettolide Cyclohexadecen-7-olide Celestolide (IFF) 4-Acetyl-6-tert-butyl-1,1-dimethylindane Dihydroambrettolide Cyclohexadecanolide Ethylene brassylate cyclo-1,13-ethylenedioxy-tridecan-1,13-dione Exaltolide (F) Cyclopentadecanolide Exaltone (F) Cyclopentadecanone Habanolide (F) 1-oxa-5(6)-cyclohexadecen-16-one Galaxolide (IFF) 1,3,4,6,7,8-hexahydro-4,6,6,7,8.8-hexamethylcyclopenta-2-benzopyran Moskene (GIV) 1,1,3,3,5-Pentamethyl-4,6-dinitroindane Musk ambrette 2,4-dinitro-3-methyl-6-tert-butylanisole Musk Ketone 4-tert-butyl-3,5-dinitro-2,6-dimethylacetophenone Musk MC4 (SA) Ethylene 1,12-dodecanedioate Musk R1 (Q) 11-Oxahexadecanolide Musk tibetine 2-tert-butyl-1,3-dinitrol-4,5,6-trinitrobenzene Musk xylol 1-tert-butyl-3,5-dimethyl-2,4,6-trinitrobenzene Phantolide (PFW) 5-Acetyl-1,1,2,3,3,6-hexamethylindane Tonalid (PFW) 1,1,2,4,4,7-Hexamethyl-6-acetyl-1,2,3,4-tetrahydronaphthalene Traseolide 6-acetyl-1-isopropyl-2,3,3,5-tetramethylindane Versalide (PFW) 1,1,4,4-tetramethyl-6-acetyl-7-ethyl-1,2,3,4-tetrahydronaphthalene, allyl hexanoate, n-amyl acetate, isoamyl acetate, n-amyl propionate, anisic alcohol, anisic aldehyde, benzaldehyde, benzyl alcohol, benzyl acetate, butyl acetate, cinnamic alcohol, cinnamic aldehyde, citral, citronellol, coumarin, decalactone gamma, ethyl 2-methylbutyrate, ethyl butyrate, ethyl caproate, ethyl caprylate, ethyl heptanoate, ethyl lactate, ethyl propionate, eugenol, geraniol, heliotropine, trans-2-hexenal, cis-3-hexenol, cis-3-hexenyl acetate, cis-3-hexenyl propionate, hexyl acetate, isobutyl acetate, limonene, linalool, L-manthol, methyl benzoate, methyl salicylate, methyl anthranilate, octalactone gamma, 2-phenylethyl acetate, 2-phenylethylalcohol, 1-terpinen-4-ol, alpha-terpineol, vanillin, 3-hydroxy-2-methyl-4-pyrone, Amyl salicylate, benzyl salicylate, beta-caryophyllene, cedrol, cedryl acetate, cedryl formate, cyclohexyl salicylate, gamma-dodecalactone, ethyl undecylenate, geranyl anthranilate, alpha-irone, phenyl ethyl benzoate, phenylethyl phenyl acetate, 5-acetyl-1,1,2,3,3,6-hexamethyl indane, cyclopentadecanolide, d-limonene, cis-p-t-butylcyclohexyl acetate, amyl cinnamic aldehyde, linalyl benzoate, Benzaldehyde, benzyl acetate, laevocarvone, geraniol, cis-jasmone, beta-phenylethyl alcohol, alpha-terpineol, delta-nonalactone, dihydromyrcenol, delta-undecalactone, amyl cinnamate, benzophenone, alpha-irone, nerol, 2-methoxynaphthalene, musk ketone, musk tibetine, myristicin, 6-phenyl heptanol-2, 1-phenyl hexanol, alpha-santalol, iso-eugenol, linalyl acetate, eugenol, amyl salicylate, benzyl salicylate, beta-caryophyllene, cedrol, cedryl acetate, cedryl formate, cyclohexyl salicylate, gamma-dodecalactone, ethyl undecylenate, geranyl anthranilate, beta-phenylethyl benzoate, beta-phenylethyl phenyl acetate, 5-acetyl-1,1,2,3,3,6-hexamethyl indane, cyclopentadecanolide, d-limonene, cis-p-t-butylcyclohexyl acetate, amyl cinnamic aldehyde, and linalyl benzoate.

In some embodiments, the topical composition disclosed herein can be a fragrance product. As used herein, the term "fragrance product" or "odorant" relates to a product which provides an enhanced aroma. Examples of fragrance products include, but are not limited to, air fresheners, room deodorizers, nebulizers, fragrance wicks, scented candles, heated waxes, scent-impregnated membranes, scent-impregnated polymer or ceramic granules, perfume, eau de perfume, eau de toilet, and eau de cologne. In other embodiments the topical composition can be an antiperspirant or deodorant.

Preferred fragrance components for shampoos, skin care products, and personal care products include: allyl hexanoate, n-amyl acetate, isoamyl acetate, n-amyl propionate, anisic alcohol, anisic aldehyde, benzaldehyde, benzyl alcohol, benzyl acetate, butyl acetate, cinnamic alcohol, cinnamic aldehyde, citral, citronellol, coumarin, decalactone gamma, ethyl 2-methylbutyrate, ethyl butyrate, ethyl caproate, ethyl caprylate, ethyl heptanoate, ethyl lactate, ethyl propionate, eugenol, geraniol, heliotropine, trans-2-hexenal, cis-3-hexenol, cis-3-hexenyl acetate, cis-3-hexenyl propionate, hexyl acetate, isobutyl acetate, limonene, linalool, L-manthol, methyl benzoate, methyl salicylate, methyl anthranilate, octalactone gamma, 2-phenylethyl acetate, 2-phenylethylalcohol, 1-terpinen-4-ol, alpha-terpineol, vanillin, 3-hydroxy-2-methyl-4-pyrone, Amyl salicylate, benzyl salicylate, beta-caryophyllene, cedrol, cedryl acetate, cedryl formate, cyclohexyl salicylate, gamma-dodecalactone, ethyl undecylenate, geranyl anthranilate, alpha-irone, phenyl ethyl benzoate, phenylethyl phenyl acetate, 5-acetyl-1,1,2,3,3,6-hexamethyl indane, cyclopentadecanolide, d-limonene, cis-p-t-butylcyclohexyl acetate, amyl cinnamic aldehyde, linalyl benzoate, Benzaldehyde, benzyl acetate, laevocarvone, geraniol, cis-jasmone, beta-phenylethyl alcohol, alpha-terpineol, delta-nonalactone, dihydromyrcenol, delta-undecalactone, amyl cinnamate, benzophenone, alpha-irone, nerol, 2-methoxynaphthalene, musk ketone, musk tibetine, myristicin. 6-phenyl heptanol-2, 1-phenyl hexanol, alpha-santalol, iso-eugenol, linalyl acetate, eugenol, amyl salicylate, benzyl salicylate, beta-caryophyllene, cedrol, cedryl acetate, cedryl formate, cyclohexyl salicylate, gamma-dodecalactone, ethyl undecylenate, geranyl anthranilate, beta-phenylethyl benzoate, beta-phenylethyl phenyl acetate, 5-acetyl-1,1,2,3,3,6-hexamethyl indane, cyclopentadecanolide, d-limonene, cis-p-t-butylcyclohexyl acetate, amyl cinnamic aldehyde, and linalyl benzoate.

Preferred fragrance components for deodorants include: alpha-hexylcinnamaldehyde, 2-phenoxyethylisobutyrate, dihydromyrcenol (2,6-dimethyl-7-octen-2-ol), methyl dihydrojasmonate, 4,6,6,7,8,8-hexamethyl-1,3,4,6,7,8-hexahydrocyclopenta[g]benzopyran, tetrahydrolinalool (3,7-dimethyloctan-3-ol), ethyllinalool, benzylsalicylate, 2-methyl-3-(4-tert-butyl-phenyl)propanal, cinnamon alcohol, 4,7-methano-3a,4,5,6,7,7a-hexahydro-5-indenyl acetate and/or 4,7-methano-3a,4,5,6,7,7a-hexahydro-6-indenyl acetate, citronellol, linalyl acetate, styrolyl acetate(1-phenylethyl acetate), octahydro-2,3,8,8-tetramethyl-2-acetonaphthone and/or 2-acetyl-1,2,3,4,6,7,8-octahydro-2,3,8,8-tetramethyl-naphthalene, hexylsalicylate, 4-tert.-butylcyclohexyl acetate, 2-tert.-butylcyclohexyl acetate, alpha-ionone (4-(2,2,6-trimethyl-2-cyclohexen-1-yl)-3-buten-2-one), coumarin, terpinyl acetate, 4-(4-hydroxy-4-methylpentyl)-3-cyclohexene carboxaldehyde, alpha-amyl cinnamon aldehyde, (E)- and/or (Z)-3-methylcyclopentadec-5-enone, 15-pentadec-11-enolide and/or 15-pentadec-12-enolide, 15-cyclopentadecanolide, 1-(5,6,7,8-tetrahydro-3,5,5,6,8,8-hexamethyl-2-naphthalenyl)ethanone, 2-isobutyl-4-methyltetrahydro-2H-pyran-4-ol, 2-ethyl-4-(2,2,3-trimethyl-3-cyclopenten-1-yl)-2-buten-1-ol, menthol, anethole, geraniol, nerol, linalool, citronellol, linalyl acetate, 2-phenylethyl alcohol, 2,2-dimethyl-3-(3-methylphenyl)-propanol, rose oxide (4-methyl-2-(2-methyl-1-propenyl)tetrahydropyran), allyl heptanoate, 4-methylacetophenone, (4aR,5R,7aS,9R)-octahydro-2,2,5,8,8,9a-hexamethyl-4H-4a,9-methanoazuleno(-5,6-d)-1,3-dioxol), 1-(2,2,6-trimethylcyclohexyl)hexan-3-ol, 2,4,6-trimethyl-4-phenyl-1,3-dioxan, benzylacetone, methyl cinnamate, 3a,6,6,9a-tetramethyldodecahydronaphtho[2,1-b]furan, Ambrettolide, Cyclohexadecen-7-olide, Celestolide (IFF), 4-Acetyl-6-tert-butyl-1,1-, dimethylindane, Dihydroambrettolide, Cyclohexadecanolide, Ethylene, brassylate, cyclo-1,13-ethylenedioxy-tridecan-, 1,13-dione, Exaltolide (F), Cyclopentadecanolide, Exaltone (F), Cyclopentadecanone, Habanolide (F), 1-oxa-5(6)-cyclohexadecen-16-one, Galaxolide (IFF), 1,3,4,6,7,8-hexahydro-4,6,6,7,8.8-, hexamethylcyclopenta-2-benzopyran, Moskene (GIV), 1,1,3,3,5-Pentamethyl-4,6-, dinitroindane, Musk, ambrette, 2,4-dinitro-3-methyl-6-tert-, butylanisole, Musk, Ketone, 4-tert-butyl-3,5-dinitro-2,6-, dimethylacetophenone, Musk, MC4 (SA), Ethylene, 1,12-dodecanedioate, Musk, R1 (Q), 11-Oxahexadecanolide, Musk, tibetine, 2-tert-butyl-1,3-dinitrol-4,5,6-, trinitrobenzene, Musk, xylol, 1-tert-butyl-3,5-dimethyl-2,4,6-, trinitrobenzene, Phantolide (PFW), 5-Acetyl-1,1,2,3,3,6-, hexamethylindane, Tonalid (PFW), 1,1,2,4,4,7-Hexamethyl-6-acetyl-1,2,3,4-tetrahydronaphthalene, Traseolide, 6-acetyl-1-isopropyl-2,3,3,5, tetramethylindane, Versalide (PFW), and 1,1,4,4-tetramethyl-6-acetyl-7-ethyl-1,2,3,4-tetrahydronaphthalene.

Preferred fragrance components for perfume compositions include: Acetoin, Ambergris, Ambrein, Ambroxide, Aroma compound, *Artemisia pallens*, Balm of Gilead, Balsam of Peru, Bdellium, Benzoin resin, Benzyl acetate, Benzyl alcohol, Benzyl benzoate, Benzyl cinnamate, Benzylacetone, Bisabolol, Bourgeonal, Calone, Camphene, Camphor, Cashmeran, Castoreum, *Cedrus*, Chavicol, Cinnamyl alcohol, Citral, Citronellol, Civet (perfumery), Civetone, Copaiba, Cyclopentadecanolide, Cyclopentanone, *Cyperus articulatus*, Damascenone, Damascone, Deer musk, Diethyl malonate, Estragole, Ethyl benzoate, Ethyl maltol, Ethyl methylphenylglycidate, Ethyl salicylate, Eugenol, *Evernia prunastri*, Farnesene, Farnesol, Filbertone, Fixative (perfumery), Fragrance oil, Geraniol, Geranyl acetate, Gourmand (fragrance), Grapefruit mercaptan, Heptyl acetate, Herbal distillate, Hexyl cinnamaldehyde, Hydroxymethylpentylcyclohexenecarboxaldehyde, Hyraceum, Ionone, Irone, Iso E Super, Isobornyl cyclohexanol, Isovanillin, Labdanum, Menthone, Methyl benzoate, Methyl butyrate, Muscone, Musk xylene, Myrcene, *Nardostachys jatamansi*, Nerol, Nerolidol, Ocimene, Opopanax, Patchouli, Patchoulol, *Pelargonium graveolens*, Perillaldehyde, Phellandrene, Phenethyl alcohol, Beta-Pinene, *Polianthes tuberosa*, Pomarose, Pulegone, Raspberry ketone, Safrole, Sandalore, Sandalwood, A-Santalol, B-Santalol, Skatole, Spikenard, *Styrax* balsam, Synthetic musk, Tetramethyl acetyloctahydronaphthalenes, Thujone, Tincture of benzoin. Tolu balsam, *Valeriana celtica*, Vanillin, Ortho-Vanillin, A-Vetivone, Anethole, Aroma lamp, *Artemisia pallens, Backhousia citriodora*, Benzoin resin, Bergamot essential oil, Black pepper, Cajeput oil, Calophyllum inophyllum seed oil, *Cananga odorata, Cannabis* flower essential oil, Carrot seed oil, Cedar oil, Citron, Citronella oil, Oil of clove, Copaiba, *Cymbopogon* martinii, *Cyperus scariosus*, Dill oil, *Eucalyptus* oil, Fragrance oil, Herbal distillate, *Hydnocarpus wightiana* seed oil, Juniper berry, Lavender oil, Lemon oil, Monoi oil, Mustard oil, Myrrh, Myrtol standardized, Neroli, Nutmeg oil, Oil of guaiac, Olbas Oil, Orange oil, Orris oil, Palmarosa Oil, Patchouli, *Pelargonium graveolens*, Petitgrain, Pine oil, Rose oil, Rosewood oil, Sage oil, *Salvia sclarea*, Sandalwood oil, *Santalum* album, *Santalum spicatum*, Sfumatura, Spearmint, *Styrax* balsam, Tea tree oil, Wintergreen, Yarrow oil, Herbal distillate, Orange flower water, and Rose water.

In some embodiments, a topical composition as disclosed herein can be a skincare product. Examples of skincare products include, but are not limited to face washing creams, scar smoothing products, skin irritation soothing products (oils, sprays, salves, lotions, ointments, or gels), facial cleansing wipes, body cleansing wipes, anti-aging facial and/or eye creams, pore cleansing strips, pore cleansing oils, pore cleansing ointments, hair removal products (wax, wax strips, roll-ons, creams, gels, lotions, etc.), varnishing creams, cleansing creams, cold creams, massage creams, milky lotions, skin toning lotion, cosmetic solution, packs, makeup remover, and the like; as makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like.

In some embodiments, a topical composition as disclosed herein can be a hair care product, Examples of hair care products include, but are not limited to hair care cosmetics, pomades, brillantine, setting lotions, hair sticks, hair solids, hair oils, hair treatments, hair creams, hair tonics, hair liquids, hair sprays, mousse, hair gel, bandlin, hair restorers, hair dyes, and the like; further examples include shampoos, permanent wave lotions, medicated shampoos, rinses, hair conditioners, hair treatments, hair packs, and the like.

In some embodiments, a topical composition as disclosed herein can be a body care or bathing composition. For example, the topical composition can be a shaving cream, a shaving gel, a shaving lotion, an after-shave lotion, an after-shave gel, a medicated soap, sanitizing gel, a hand sanitizer, sanitizing wipes, cool nasal tissues (tissues that have lotion on them), sports cooling towels, cooling fabrics, sport shirts, eye pillows, sheets, cooling pillows, hats, diapers, adult diapers, potty-training pants and pull-ups, talcum powder, baby powder, slimming gels, a bath soap, a face soap, a hand soap, exfoliating washes, hand scrub, foot scrub, shower mists, shower sprays, a body washing soap, a body washing gel, a bath salt, a bath tablet, a bath foam, a bubble-bath concentrate, a bath oil, a bath perfume, a bath capsule, a milk bath, a bath gel, or a bath cube.

In some embodiments, a topical composition as disclosed herein can be a composition used as an insect repellant. JP 11171703 A, which is incorporated herein by reference in its entirety, describes a pest repellant which contains menthol.

In some embodiments, a topical composition as disclosed herein can be a composition for the enhancement of massage therapy treatment. For example, the topical composition can be in the form of a massage oil, massage cream, massage lotion, or massage gel that comprises one or more of Compounds 101-105.

In some embodiments a topical composition as disclosed herein is an aphrodisiac composition comprising one or more of Compounds 101-105. By "aphrodisiac" is meant a composition that improves the sexual desire, sexual sensation, or sexual satisfaction of a subject. Examples of topical aphrodisiac compositions in the form of a cream, lotion, or gel and comprising menthol or peppermint oil have been previously reported in WO 03/047610, which is incorporated herein by reference in its entirety.

In some embodiments, the chemestetic effect of the compounds disclosed herein can be enhanced through the combination of one or more of the presently disclosed compounds with one or more natural or synthetic cooling agents. Through such a combination, a synergistic effect can be achieved whereby the chemestetic effect of the combination is greater than the sum of chemestetic effects of each individual agent used in the combination. A person of ordinary skill in the art would understand that the topical compositions described herein can comprise any of the compounds disclosed herein alone or in combination.

In some preferred embodiments, one or more of the compounds disclosed herein can be combined with one or more compounds selected from peppermint oil, menthol, menthone, eucalyptol, borneol, camphor, 4-terpinol, Freskomenthe (2-(1-methylpropyl)-cyclohexanone), neomenthol, isomenthol, neoisomenthol, monomethyl succinate, dimethyl succinate, ormenthyl acetate, methyl acetate, menthol ethylene glycol carbonate (marketed as Frescolat® MGC), menthol propylene clycol carbonate (marketed as Frescolat® MPC), menthone glycerol ketal (marketed as Frescolat® MGA), menthyl lactate (marketed as Frescolat® ML), 3-(1-Menthoxy) propane-1,2-diol (MPD), 3-(1-menthoxy)-2-methylpropane-1,2-diol, 3-(1-metnhoxy)ethanol (Coolact® 5), 3-(1-menthoxy)propan-1-ol, 3-(1-metnhoxy)butan-1-ol, isopulegol (Coolact® P), Questice® (menthyl pyrrolidin-2-one 5-carboxylate), WS-3 (N-ethyl-p-menthane-3-carboxamide), WS-23 (2-isopropyl-N,2,3-trimethylbutyramide), WS-14 [N-([ethoxycarbonyl]methyl)-p-menthane-3-carboxamide], WS-5 [ethyl 3-(p-menthane-3-carboxamido)acetate], N,N-dimethyl menthyl succinamide, N-(2-ethoxyethyl)-2-isopropyl-2,3-dimethylbutanamide, N-(1-isopropyl-1,2-dimethylpropyl)-1,3-benzodioxole-5-carboxamide, N-benzo[1,3]dioxol-5-yl-3-p-menthanecarboxamide, N-benzooxazol-4-yl-3-p-menthanecarboxamide, HASE-1 (1R,4S,5R)—N-(2-ethoxyethyl)-2-isopropyl-5-methylcyclohexane-1-carboxamide), N—(R)-2-oxotetrahydrofuran-3-y 1-(1R,2S,5R)-p-menthane-3-carboxamide (D-HSL), L-phenylephrine p-menthane carboxamide (CPS-195), WS-12 (1R,2S,5R)—N-(4-Methoxyphenyl)-p-menthanecarboxamide, WS-27 (N-Ethyl-2,2-diisopropylbutanamide), N-Cyclopropyl-5-methyl-2-isopropylcyclohexanecarboxamide, WS-116 (N-(1,1-Dimethyl-2-hydroxyethyl)-2,2-diethylbutanamide), Evercool™ 190 (G-190, (1R,2S,5R)—N-(2-(pyridin-2-yl)ethyl)menthylcarboxamide), Ultracool 7 (menthyl acetoacetate), Evercool™ 180 ((1R,2S,5R)—N-(4-(cyanomethyl)phenyl)menthylcarboxamide), menthyl glutarate, PMD 38 (Coolact® 38, trans-p-menthane-3,8-diol), Freshone® (menthone (S)-lactic acid ketal, (−)-Cubebol ((1R,4S,5R,6R,7S,10R)-7-isopropyl-4,10-dimethyl-tricyclo[4.4.0.0(1,5)]decan-4-ol), N-(2-Hydroxyethyl)-2,3-dimethyl-2-isopropylbutanamide, Di-(−)-menthyl glutarate, (1R,2S,5R)—N-(4-(carbamoylmethyl)phenyl)-menthylcarboxamide, (1R,2S,5R)-2-[2-(2-isopropyl-5-methyl-cyclohexyloxy)ethoxy]-ethanol, (1R,2R,4R)-1-(2-Hydroxy-4-methylcyclohexyl) ethanone, 2-(p-tolyloxy)-N-(1H-pyrazol-5-yl)-N-((thiophen-2-yl)methyl)acetamide, N-(1,1-Dimethyl-2-hydroxyethyl)2,2-diethylbutanamide, 2,2,5,6,6-pentamethyl-2,3,6,6a-tetrahydropentalen-3a(1H)-ol, 5-(2-hydroxy-2-methylpropyl)-3,4,4-trimethylcyclopent-2-en-1-one, Icilin (AG-3-5, 1-[2-hydroxyphenyl]-4-[2-nitrophenyl-]-1,2,3,6-tetrahydropyrimidine-2-one), and compounds with the structures given in Table 3.

TABLE 3

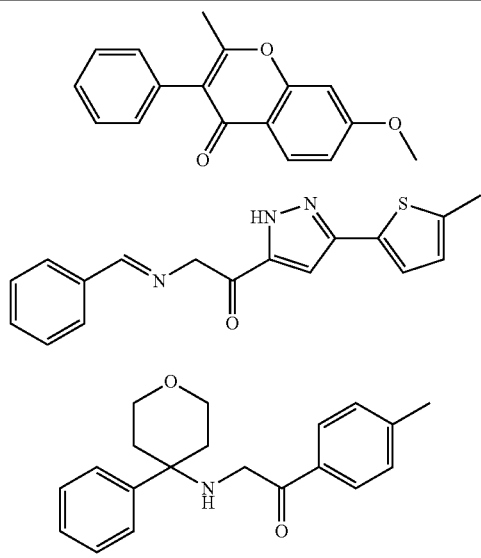

TABLE 3-continued

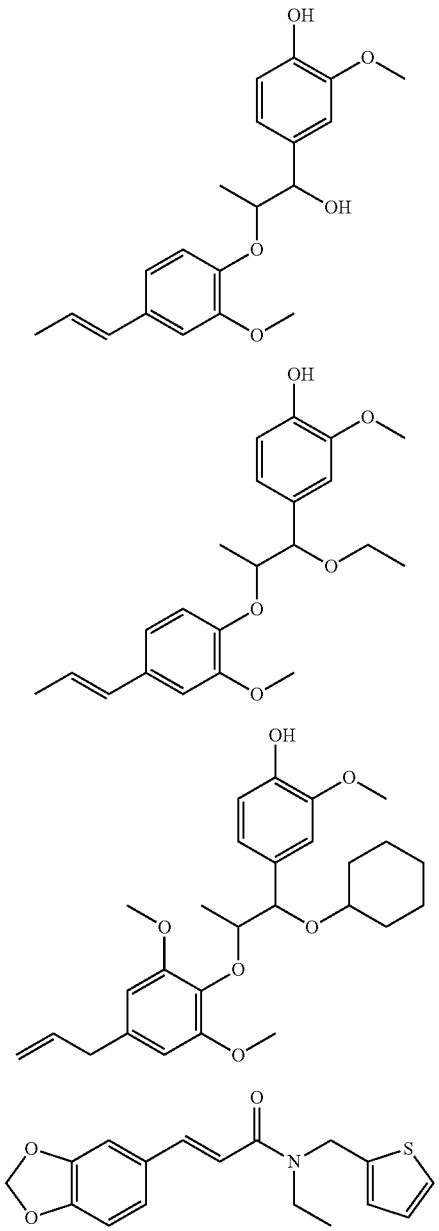

It is further known in the art that cooling compounds can create or enhance a warming effect when combined with a warming compound. Some such combinations are disclosed in U.S. Patent App. Pub. No. 2002/0142015, and further in U.S. Patent App. Pub. No. 2015/0104498 which are incorporated by reference herein in their entireties. Suitable warming compounds for combination with the present cooling compounds include but are not limited to: vanillyl ethyl ether, vanillyl propyl ether, capsaicin, gingerol, vanillyl butyl ether, vanillyl butyl ether acetate, 4-(1-menthoxymethyl)-2-phenyl-1,3-dioxolan, 4-(1-menthoxymethyl)-2-(3', 4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3-dioxolan, 4-(1-menthoxymethyl)-2-(3',4'-methylenedioxy-phenyl)-1,3-dioxolan, 4-(1-menthoxymethyl)-2-(3'-methoxy-4'-hydroxyphenyl)-1,3-dioxolan, red pepper oil, red pepper oleoresin, ginger oleoresin, nonylic acid vanillyl amide, jamboo oleoresin, *Zanthoxylum piperitum* extract, sanshool I, sanshool II, sanshoamide, black pepper extract, chavicine, pipeline, szechuan pepper, szechuan pepper extract, and spilanthole.

It is known in the art that warming agents can function as incapacitants (see, for example, U.S. Pat. No. 5,821,450). In some embodiments, the enhanced warming composition comprising the combinations disclosed herein can function as an incapacitant. Additionally, it is known in the art that cooling compounds can themselves cause eye or other irritation (for example, see Leffingwell, J. C., "Cooler than Menthol," available at http://leffingwell.com/cooler_than_menthol.htm (last accessed Jan. 1, 2016)). Therefore, one of ordinary skill in the art would readily appreciate that Compounds 101-105, and the compositions disclosed herein, could be incorporated into an incapacitant even in the absence of a warming agent.

In one embodiment, the composition disclosed herein comprises i) compounds as disclosed and described herein, individually or in combination; ii) a carrier; and iii) optionally at least one adjuvant. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The term "adjuvant" denotes an additive which supplements, stabilizes, maintains, or enhances the intended function or effectiveness of the active ingredient, such as the compound of the present invention. In one embodiment, the at least one adjuvant comprises one or more topically acceptable materials that may be used to preserve or alter the properties of the topical composition disclosed herein. These materials include, but are not limited to, materials having anti-acne, anti-ageing, anti-wrinkle, antifungal, anti-inflammatory, antimicrobial, antioxidant, antiperspirant, antidandruff, anti-dermatitis, antipruritic, anti-emetic, anti-dry skin, anti-psoriatic, anti-seborrhea, anti-asthmatic, astringents, bronchodilators, biocides, chemical exfoliants, cleansers, colorants, corticosteroids, deodorants, depigmenting, depilating, emollients, epilating, analgesics, hair conditioners, hormones, humectants, light-interacting, luster-imparting, make-up removers, pH adjusters, powders, rheological modifiers, shine-imparting, skin bleaching, skin conditioning, skin protecting, tanning, UV screening vitamins, and/or wound-healing properties.

In one embodiment, a topical formulation disclosed herein can be in a form selected from the group consisting of liquid, including solution and suspension, solid, foamy material, emulsion, paste, gel, cream, and a combination thereof, such as a liquid containing a certain amount of solid contents. In one embodiment, the flavoring concentrate formulation is in form of a liquid including aqueous-based and nonaqueous-based.

In some embodiments, the topical composition is an ophthalmic composition. A liquid composition, which is formulated for topical ophthalmic use, is formulated such that it can be administered topically to the eye. The comfort may be maximized as much as possible, although sometimes formulation considerations (e.g. compound stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, biologically acceptable preservatives, stabilizers and surfactants.

Preservatives that may be used in the topical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

Topical formulations may generally be comprised of a pharmaceutical carrier, co-solvent, emulsifier, penetration enhancer, preservative system, and emollient.

In some embodiments, a topical composition as disclosed herein may comprise an aqueous component. For example, the composition can be a cream, lotion, ointment, conditioning shampoo, moisturizing hand soap, etc. In some embodiments, the topical composition disclosed herein can comprise about 35% (w/w) to about 90% (w/w), about 40% (w/w) to about 85% (w/w), about 45% (w/w) to about 80% (w/w), about 50% (w/w) to about 75% (w/w), about 55% (w/w) to about 70% (w/w), about 60% (w/w) to about 65% (w/w), or about 62% (w/w) of water. In some embodiments, the topical composition disclosed herein can comprise at least 50% (w/w), 55% (w/w), 60% (w/w), 65% (w/w), 70% (w/w), 75% (w/w), 80% (w/w), or 85% (w/w) of water. In some embodiments, the topical composition disclosed herein can comprise up to 50% (w/w), 55% (w/w), 60% (w/w), 65% (w/w), 70% (w/w), 75% (w/w), 80% (w/w), or 85% (w/w) of water. In some embodiments, the topical composition disclosed herein can comprise 50% (w/w), 55% (w/w), 60% (w/w), 65% (w/w), 70% (w/w), 75% (w/w), 80% (w/w), or 85% (w/w) of water or a range defined by any two of the preceding values.

Some embodiments provide a topical composition including skin penetration enhancers.

Examples of suitable skin penetration enhancers include alcohols, fatty acids, fatty acid esters, polyols, sulphoxides, glyceryl monooleate, lauryl lactate, Dodecyl-2-(N,N-dimethyl)-amino propionate (DDAIP), N-(4-bromobenzoyl)-S,S-dimethyliminosulfurane, NexACT enhancers, 2-nonyl-1,3-dioxolane (SEPA®), 1-dodecylazacycloheptan-2-one (Azone®), pyrrolidones, essential oil, terpenes, terpenoids, oxazolidinones, urea and the like.

Further suitable skin penetration enhancers are known in the art and include, but are not limited to, monoglycerides, polyglycosylated glycerides, glyceryl monoethyl ether, polysorbates, beta-cyclodextrin, cyclopentadecalactone, alkyl-2-(N,N-disubstituted amino)-alkanoate ester, 2-(n-nonyl)-1,3-dioxolane, isopropyl myristate, terpinol, menthol, cineol, monoolein, sodium oleate, oleyl oleate, laurylcapram, bisabolol, capsaicin, and *capsicum*. Other examples of suitable skin penetration enhancers and a description of their mechanism of action may be found in Goodman and Barry, "Percutaneous Absorption," in Mechanisms-Methodology-Drug Delivery, 2nd Edition, Bronaugh and Maibach, eds., 1989, pp. 567-593, Marcel Dekker, Inc., NY, which is incorporated herein by reference in its entirety.

In some embodiments, the skin penetration enhancer can be selected from the group consisting of n-octanol, D-limonene, oleic acid, cineol, isopropyl myristate, monooleate, monoolein, sodium oleate, oleyl oleate, laurylcapram, sodium lauryl sulfate, bisabolol, lauric acid, myristic acid, isopropyl palmitate, diisopropyl adipate, dimethyl isosorbide, propylene glycol, butylene glycol, polyethylene glycol, dipropylene glycol, ethoxydiglycol, and pentylene glycol or combinations thereof. In a typical embodiment, the skin penetration enhancer can be selected from the group consisting of oleic acid, laurocapram, sodium lauryl sulphate, bisabolol, lauric acid, myristic acid, isopropyl myristate, isopropyl palmitate, diisopropyl adipate, dimethyl isosorbide, propylene glycol, butylene glycol, polyethylene glycol, dipropylene glycol, ethoxydiglycol, and pentylene glycol, or combinations thereof.

Examples of suitable fatty acids include, but are not limited to, valeric acid, heptanoic acid, pelagonic acid, caproic acid, capric acid, lauric acid, myristic acid, stearic acid, oleic acid, and caprylic acid; and branched fatty acids, such as isovaleric acid, neopentanoic acid, neoheptanoic acid, neononanoic acid, trimethyl hexanoic acid, neodecanoic acid, and isostearic acid.

Examples of suitable fatty acid esters include but are not limited to, isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate; and diisopropyl adipate and dimethyl isosorbide.

In some embodiments, skin penetration can be achieved by formulating the compositions disclosed herein into a nanoparticle or nanoemulsion. Such particles and emulsions are known in the art and include but are not limited to, polylactic acid particles, polylactic/glycolic acid nanoparticles, polystyrene nanoparticles, silicon dioxide nanoparticles, metallic nanoparticles, water-in-oil emulsions, oil-in-water emulsions, polymer nanoparticles and emulsions, and block copolymer nanoparticles and emulsions.

In some embodiments, the topical composition disclosed herein can comprise at least 5% (w/w), 6% (w/w), 7% (w/w), 8% (w/w), 9% (w/w), 10% (w/w), 11% (w/w), or 12% (w/w) of a skin penetration enhancer. In some embodiments, the topical composition disclosed herein can comprise 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 21% (w/w), 22% (w/w), 23% (w/w), 24% (w/w), 25% (w/w), 26% (w/w), 27% (w/w), 28% (w/w), 29%0 (w/w), or 30% (w/w)) of a skin penetration enhancer or a range defined by any two of the preceding values. In a typical embodiment, the skin penetration enhancer can be ethoxydiglycol.

In some embodiments, the composition can include an emollient. In some embodiments, the emollient can be alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof. In some embodiments, the emollient can be selected from the group consisting of cetyl palmitate, stearyl palmitate, cetyl stearate, isopropyl laurate, isopropyl myristate, isopropyl palmitate, or combinations thereof. In some embodiments, the emollient can be selected from the group consisting of octyldodecanol, lauryl, myristyl, cetyl, stearyl, and behenyl alcohol, or combinations thereof. In some embodiments, the emollient can be selected from the group consisting of eucalyptol, ceteraryl glucoside, dimethyl isosorbic polyglyceryl-3 cetyl ether, polyglyceryl-3 decyltetradecanol, propylene glycol and myristyl ether, or combinations thereof.

In some embodiments, a topical composition disclosed herein can comprise at least 1% (w/w), 2% (w/w), 3% (w/w), 4% (w/w), 5% (w/w), 6% (w/w), 7% (w/w), 8% (w/w), 9% (w/w), 10% (w/w), 11% (w/w), or 12% (w/w) of an emollient. In some embodiments, the topical composition disclosed herein can comprise 1% (w/w), 2% (w/w), 3% (w/w), 4% (w/w), 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 21% (w/w), 22% (w/w), 23% (w/w), 24% (w/w), 25% (w/w), 26% (w/w), 27% (w/w), 28% (w/w), 29% (w/w), or 30% (w/w)) of an emollient or a range defined by any two of the preceding values.

In some embodiments, a topical composition as disclosed herein can comprise natural fats and oils. In some embodiments, the natural fats and oils can be selected from the group consisting of *citrus* oil, olive oil, avocado oil, apricot oil, babassu oil, borage oil, *camellia* oil, canola oil, castor oil, coconut oil, corn oil, cottonseed oil, emu oil, evening primrose oil, hydrogenated cottonseed oil, hydrogenated palm kernel oil, maleated soybean oil, meadowfoam oil, palm kernel oil, peanut oil, rapeseed oil, grapeseed oil, safflower oil, sphingolipids, seed almond oil, tall oil, lauric acid, palmitic acid, stearic acid, linoleic acid, stearyl alcohol, lauryl alcohol, myristyl alcohol, behenyl alcohol, rose hip oil, *calendula* oil, chamomile oil, *eucalyptus* oil, juniper oil, sandlewood oil, tea tree oil, sunflower oil, and soybean oil, or combinations thereof.

In some embodiments, a topical composition disclosed herein can comprise at least 5% (w/w), 6% (w/w), 7% (w/w), 8% (w/w), 9% (w/w), 10% (w/w), 11% (w/w), or 12% (w/w) of a vegetable oil. In some embodiments, the topical composition disclosed herein can comprise 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 21% (w/w), 22% (w/w), 23% (w/w), 24% (w/w), 25% (w/w), 26% (w/w), 27% (w/w), 28% (w/w), 29% (w/w), or 30% (w/w)) of a vegetable oil or a range defined by any two of the preceding values. In a typical embodiment, the topical composition disclosed herein can comprise coconut oil.

In some embodiments, a topical composition as disclosed herein may optionally further comprise ingredients to relieve irritation, such as anti-itch agents. In some embodiments, the anti-itch agents may be present in the topical composition disclosed herein in an amount of from about 0.1% to about 33% (w/w), more typically, from about 0.5% to about 5% (w/w). Examples of suitable anti-itch agents are listed below, as well as the preferred concentration for each agent, given in percent by weight of the composition: lauromacrogols, benzocaine (about 5% to about 20%), butamben picrate (about 1%), dibucaine (about 0.25% to about 1%), dibucaine hydrochloric acid (0.25% to about 1%), dimethisoquin hydrochloric acid (about 0.3% to about 0.5%), dyclonine hydrochloric acid (about 0.5% to about 1%), lidocaine (about 0.5% to about 5%), lidocaine hydrochloric acid (about 0.5% to about 5%), pramoxine hydrochloric acid (about 0.5% to about 1%), tetracaine (about 1% to about 2%), tetracaine hydrochloric acid (about 1% to about 2%), benzyl alcohol (about 10% to about 33%), camphor (about 0.1% to about 3%), juniper tar (about 1% to about 5%), menthol (about 0.1% to about 1%), phenol (about 0.5% to about 1.5%), phenolate sodium (about 0.5% to about 1.5%), resorcinol (about 0.5% to about 3%), diphenhydramine hydrochloric acid (about 1% to about 2%), tripelennamine hydrochloric acid (about 0.5% to about 2%), hydrocortisone (about 0.1% to about 5%, preferably about 0.5% to about 2.5%), and combinations thereof. In some embodiments, the topical composition disclosed herein may optionally also comprise cosmetic anti-itch ingredients such as, for example, Symcalmin® (Symrise GmbH & Co., Holzminden, Germany).

In some embodiments, the compositions may include adjunct components conventionally found in pharmaceutical compositions in their art-established fashion and at their art-established levels. For example, the compositions may comprise additional compatible pharmaceutically active materials for combination therapy, such as antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, and combinations thereof.

In some embodiments, the compositions may include colorants, deodorants, fragrances, perfumes, emulsifiers, anti-foaming agents, lubricants, natural moisturizing agents, skin conditioning agents, skin protectants and skin benefit agents (e.g., *aloe vera* and laponite), solvents, solubilizing agents, suspending agents, wetting agents, humectants, preservatives, propellants, dyes and/or pigments, and combinations thereof. In some embodiments, the compositions may have a particularly pleasant fragrance. In some embodiments, the compositions may have a particularly pleasant texture. In some embodiments, the compositions may have a particularly pleasant soothing effect.

In some embodiments, the compositions may include excipients conventionally found in topical compositions.

In some embodiments, the excipients can include a viscosity-adjusting agent. In some embodiments, the viscosity adjusting agents can be selected from the group consisting of long chain alcohols, cellulose ethers, gums, magnesium aluminum silicate, silica, microcrystalline wax, beeswax, paraffin, and cetyl palmitate, homopolymers, and copolymers. In some embodiments, the long chain alcohols can be cetyl alcohol, stearyl alcohol, or cetearyl alcohol. In some embodiments, the cellulose ethers can be hydroxypropylmethylcellulose, hydroxyethylcellulose, hydroxypropylcellulose, or carboxymethylcellulose. In some embodiments, the gum can be xanthan gum or *sclerotium* gum. In a particular embodiment, the viscosity adjusting agents can include xanthan gum. In another embodiment, the viscosity adjusting agents is xanthan gum. In another embodiment, the viscosity adjusting agent is a polyalkylene oxide such as polyethylene glycol. In other embodiments, the viscosity adjusting agent is pullulan. In other embodiments, the viscosity adjusting agent is a polyvinyl halide, such as polyvinyl chloride.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a viscosity adjusting agent. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a viscosity adjusting agent or a range defined by any two of the preceding values.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of xanthan gum. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of xanthan gum or a range defined by any two of the preceding values.

In some embodiments, the excipients can include a topical pharmaceutical and cosmetically-acceptable emollient. As used herein, "emollients" refer to materials used for the prevention or relief of dryness, as well as for the protection of the skin. Sagarin, Cosmetics, Science and Technology, 2nd Edition, Vol. 1, pp. 32-43 (1972), which is incorporated herein by reference in its entirety, contains numerous examples of suitable materials for use as emollients. Examples of classes of useful emollients include, but are not limited to, hydrocarbon oils and waxes such as mineral oil, petrolatum, paraffin, ceresin, ozokerite, microcrystalline wax, polyethylene, and perhydrosqualene; silicone oil, such as dimethyl polysiloxanes, methylphenyl polysiloxanes, and water-soluble and alcohol-soluble silicone glycol copolymers. Other suitable emollients include triglyceride esters such as vegetable and animal fats and oils including castor oil, safflower oil, cotton seed oil, corn oil, olive oil, cod liver oil, almond oil, avocado oil, palm oil, sesame oil, and soybean oil; acetoglyceride esters, such as acetylated monoglycerides; ethoxylated glycerides, such as ethoxylated glycerylmonostearate; alkyl esters of fatty acids including methyl, isopropyl, and butyl esters of fatty acids, alkyl esters including hexyl laurate, isohexyl laurate, iso-hexyl palmitate, isopropyl palmitate, decyl oleate, isodecyl oleate, hexadecyl stearate, decyl stearate, isopropyl isostearate, diisopropyl adipate, dissohexyl adipate, di-hexyldecyl adipate, di-isopropyl sebacate, lauryl lactate, myristyl lactate, and cetyl lactate; and alkenyl esters of fatty acids such as oleyl myristate, oleyl stearate, and oleyl oleate. Other suitable classes of emollients include fatty acids such as pelargonic, lauric, myristic, palmitic, stearic, isostearic, hydroxystearic, oleic, linoleic, ricinoleic, arachidic, behenic, and erucic acids; fatty alcohols such as lauryl, myristyl, cetyl, hexadecyl, stearyl, isostearyl, hydroxystearyl, oleyl, ricinoleyl, behenyl, and erucyl alcohols, as well as 2-octyl dodecanol; fatty alcohol ethers; ethoxylated fatty alcohols; ether-esters such as fatty acid esters of ethoxylated fatty alcohols; lanolin and derivatives including lanolin oil, lanolin wax, lanolin alcohols, lanolin fatty acids, isopropyllanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysis of lanolin, ethoxylated hydrogenated lanolin, ethoxylated sorbitol lanolin, and liquid and semisolid lanolin absorption bases are illustrative of emollients derived from lanolin; polyhydric alcohols and polyether derivatives such as propylene glycol, dipropylene glycol, polypropylene glycols, polyoxyethylene polyoxypropylene glycols, polyoxypropylene polyoxyethylene glycols, glycerol, sorbitol, ethoxylated sorbitol, hydroxypropylsorbitol, polyethylene glycols, methoxy polyethylene glycols, polyalkylene glycols and derivatives, hexylene glycol(2-methyl-2,4-pentanediol), 1,3-butylene glycol, 1,2,6-hexanetriol, 2-ethyl,3-hexanediol, and polyoxypropylene derivatives of trimethylolpropane; polydydric alcohol esters such as ethylene glycol mono- and di-fatty acid esters, diethylene glycol mono- and di-fatty acid esters, polyethylene glycol, mono- and di-fatty acid esters, propylene glycol mono- and di-fatty esters, polypropylene glycol monooleate, polypropylene glycol monostearate, ethoxylatedpropylene glycol monostearate, glyceryl mono- and di-fatty acid esters, polyglycerol poly-fatty acid esters, ethoxylated glyceryl monostearate, 1,3-butylene glycolmonostearate, 1,3-butylene glycol distearate, polyoxyethylene polyol fatty acid ester, sorbitan fatty acid esters, and polyoxyethylene sorbitan fatty acid esters; wax esters such as beeswax, spermaceti, myristyl myristate and stearyl stearate; beeswax derivatives, e.g., polyoxyethylene sorbitol beeswax; vegetable waxes including carnauba and candelilla waxes; and phospholipids, such as lecithin and derivatives;

sterols including, for example, cholesterol and cholesterol fatty acid esters; amides such as fatty acid amides, ethoxylated fatty acid amides and solid fatty acid alkanolamides. In some embodiments, the emollient can be selected from the group consisting of glycerol, hexanetriol, butanetriol, lactic acid, urea, pyrrolidone carboxylic acid, amino acids, guanidine, diglycerol and triglycerol. In a typical embodiment, the emollient can include glycerol.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5% (w/w), 2.6% (w/w), 2.7% (w/w), 2.8% (w/w), 2.9% (w/w), 3.0% (w/w), 3.1% (w/w), 3.2% (w/w), 3.3% (w/w), 3.4% (w/w), 3.5% (w/w), 3.6% (w/w), 3.7% (w/w), 3.8% (w/w), 3.9% (w/w), or 4.0% (w/w) of an emollient. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5% (w/w), 2.6% (w/w), 2.7% (w/w), 2.8% (w/w), 2.9% (w/w), 3.0% (w/w), 3.1% (w/w), 3.2% (w/w), 3.3% (w/w), 3.4% (w/w), 3.5% (w/w), 3.6% (w/w), 3.7% (w/w), 3.8% (w/w), 3.9% (w/w), 4% (w/w), 5% (w/w), 6% (w/w), 7% (w/w), 8% (w/w), 9% (w/w), 10% (w/w), 20% (w/w) or 30% (w/w) of an emollient or a range defined by any two of the preceding values.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5% (w/w), 2.6% (w/w), 2.7% (w/w), 2.8% (w/w), 2.9% (w/w), 3.0% (w/w), 3.1% (w/w), 3.2% (w/w), 3.3% (w/w), 3.4% (w/w), 3.5% (w/w), 3.6% (w/w), 3.7% (w/w), 3.8% (w/w), 3.9% (w/w), or 4.0% (w/w) of glycerol. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5% (w/w), 2.6% (w/w), 2.7% (w/w), 2.8% (w/w), 2.9% (w/w), 3.0% (w/w), 3.1% (w/w), 3.2% (w/w), 3.3% (w/w), 3.4% (w/w), 3.5% (w/w), 3.6% (w/w), 3.7% (w/w), 3.8% (w/w), 3.9% (w/w), 4% (w/w), 5% (w/w), 6% (w/w), 7% (w/w), 8% (w/w), 9% (w/w), 10% (w/w), 20% (w/w) or 30% (w/w) of glycerol or a range defined by any two of the preceding values.

In some embodiments, the excipients can include fatty acid triglycerides, namely the triglycerol esters of saturated and/or unsaturated, branched and/or unbranched alkanecarboxylic acids having a chain length of from 6 to 24 carbon atoms, in particular 6-10 carbon atoms. In a particular embodiment, the ester oil can be caprylic/capric triglyceride.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a fatty acid triglyceride. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a fatty acid triglyceride or a range defined by any two of the preceding values.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of caprylic/capric triglyceride. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of caprylic/capric triglyceride or a range defined by any two of the preceding values.

In some embodiments, the excipients can include fatty acid triglycerides, namely the triglycerol esters of saturated and/or unsaturated, branched and/or unbranched alkanecarboxylic acids having a chain length of from 6 to 24 carbon atoms, in particular 6-10 carbon atoms. In a particular embodiment, the fatty acid triglyceride can be caprylic/capric triglyceride.

In some embodiments, the excipients can include fatty acid diglycerides, namely the diglycerol esters of saturated and/or unsaturated, branched and/or unbranched alkanecarboxylic acids having a chain length of from 6 to 24 carbon atoms, in particular 6-10 carbon atoms.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a fatty acid diglyceride. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a fatty acid diglyceride or a range defined by any two of the preceding values.

In some embodiments, the excipients can include fatty acid monoglycerides, namely the monoglycerol esters of saturated and/or unsaturated, branched and/or unbranched alkanecarboxylic acids having a chain length of from 6 to 24 carbon atoms, in particular 6-10 carbon atoms.

In some embodiments, a topical composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a fatty acid monoglyceride. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a fatty acid monoglyceride or a range defined by any two of the preceding values.

In some embodiments, the excipients can include an emulsifier. Suitable emulsifiers are disclosed in, for example, in McCutcheon's Detergents and Emulsifiers, North American Edition, pp. 317-324 (1986), and the ICI Handbook, pp. 1673-1686, which are incorporated herein by reference in their entirety. In some embodiments, the emulsifier can include glycerol monostearate. In some embodiments, the emulsifier can include polyoxyl stearate. In some embodiments, the emulsifier can include glycerol monostearate and polyoxyl stearate. In some embodiments, the emulsifier can include PEG-6 Stearate and Glycol stearate and PEG-32 stearate. In some embodiments, the emulsifier can include glycerol monostearate, PEG-6 Stearate, Glycol stearate and PEG-32 stearate.

In some embodiments, the compositions disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 2% (w/w), 3% (w/w), 4% (w/w), 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 30% (w/w), or 40% (w/w) of an emulsifier. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 2% (w/w), 3% (w/w), 4% (w/w), 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 30% (w/w), or 40% (w/w) of an emulsifier or a range defined by any two of the preceding values. In some embodiments, the emulsifier can include one or more components, two or more components or three or more components.

In some embodiments, the composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 2% (w/w), 3% (w/w), 4% (w/w), 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 30% (w/w), or 40% (w/w) of an emulsifier including glycerol monostearate, PEG-6 Stearate, Glycol stearate and PEG-32 stearate. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 2% (w/w), 3% (w/w), 4% (w/w), 5% (w/w), 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 30% (w/w), or 40% (w/w) of an emulsifier including glycerol monostearate, PEG-6 Stearate, Glycol stearate and PEG-32 stearate or a range defined by any two of the preceding values. In some embodiments, the can be a mixture of glycerol monostearate, PEG-6 Stearate, Glycol stearate and PEG-32 stearate.

In some embodiments, the excipients can include preservatives. In some embodiments, the preservatives can be selected from the group consisting of benzyl alcohol, methyl paraben, propyl paraben, DMDM hydantoin, methylchloroisothiaoline, methylisothiazolinone, imidazolidinyl urea phenoxyethanol, sodium benzoate and benzoic acid. In some embodiments, the preservatives can include phenoxyethanol, propyl paraben, and methyl paraben. In some embodiments, the preservatives can include benzalkonium chloride and/or poly(hexamethylenebiguanide) hydrochloride (PHMB).

In some embodiments, the composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a preservative. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a preservative or a range defined by any two of the preceding values. In some embodiments, the preservative can include one or more components, two or more components or three or more components.

In some embodiments, the composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a preservative including phenoxyethanol, propyl paraben, and methyl paraben. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a preservative including phenoxyethanol, propyl paraben, and methyl paraben or a range defined by any two of the preceding values.

In some embodiments, the composition may include colorants, deodorants, fragrances, perfumes, anti-foaming agents, lubricants, natural moisturizing agents, skin conditioning agents, skin protectants, skin benefit agents, solvents, solubilizing agents, suspending agents, wetting agents, humectants, propellants, dyes, pigments, and combinations thereof.

In some embodiments, the composition may include additional components added to enhance the odor, texture or color of the composition. For example, fragrances may be added to enhance odor. For example, emulsifiers or inert spheres may be added to enhance texture. For example, colorants may be added to enhance color.

In some embodiments, the composition may be applied to a body portion, such as a hand, foot, knee, elbow, and the like to treat pain and/or inflammation of the body portion. The composition may be applied by any suitable means, such as rubbing, spraying, rolling, wiping, and the like, and massaged into the body portion to be treated.

In some embodiments, the compounds as disclosed and described herein and/or topical compositions thereof can be used in combination therapy with at least one other agent. In some embodiments, a compound as disclosed and described herein and/or topical composition thereof is administered concurrently with the administration of another agent, which may be part of the same topical composition as the compound of the present invention or a different composition. In other embodiments, a topical composition of the present invention is administered prior or subsequent to administration of another agent.

In some embodiments the compositions described herein are incorporated into a patch or film for transdermal drug delivery. In some embodiments, such patches further comprise a porous or resorbable film, an active pharmaceutical agent, and optionally a transdermal carrier or penetration enhancer. Exemplary transdermal carriers include dimethylsulfoxide; 1-dodecylazacycloheptan-2-one or laurocapran; dimethylacetamide; dimethylformamide; lauric acid; myristic acid; capric acid; caprylic acid; oleic acid; diethylene glycol; tetraethylene glycol; terpenes; essential oils of *eucalyptus, chenopodium* and ylang-ylang; dimethyl isosorbide; Oxazolidinones such as 4-decyloxazolidin-2-one; 2-pyrrolidone; N-methyl-2-pyrrolidone; urea; EDTA; Sodium Glycolate; polysorbates; sodium deoxycholate; polyethylene glycol; PLA/PLGA nanoparticles; polymer nanoparticles; block-copolymer nanoparticles, especially those comprising Pluronic®-type polyethylene oxide-block-polypropylene oxide copolymers; porous silica nanoparticles; metallic nanoparticles, especially those comprising gold, palladium, and iron; metal oxide nanoparticles, especially those comprising $TiO_2$ and $Al_2O_3$; short chain alcohols such as ethanol, propanol, and butanol; and oils such as mineral oil and coconut oil. In some embodiments the compositions described herein are incorporated into an adhesive for a transdermal patch. In some further embodiments, the compositions described herein are incorporated into a resorbable film. In some embodiments, the active pharmaceutical agent is contained within a separate reservoir layer. In some embodiments, the transdermal patch consists of a single layer. In some embodiments, the transdermal patch is constructed in multiple layers.

Food Additives and Foodstuffs

In some embodiments, the compositions disclosed herein comprise a combination of one or more of Compounds 101-105 with one or more food additives. Representative food additives that are well known in the art include, but are not limited to, those declared to the U.S. Food and Drug Administration (See U.S. FDA list of Everything Added to Food in the U.S. (EAFUS), available at http://www.accessdata.fda.gov/scripts/fcn/fcnNavigation.cfm?rpt-eafusListing, last accessed Nov. 16, 2015). Such food additives include: Gum *Acacia* (*Acacia* Senegal (L.) Willd.), Acai Berry Extract, Acesulfame Potassium, Acetal, Acetaldehyde, Acetaldehyde, Butyl Phenethyl Acetal, Acetaldehyde Di-Cis-3-Hexenyl Acetal, Acetaldehyde Diisoamyl Acetal, Acetaldehyde Di-Isobutylacetal, Acetaldehyde Ethyl Cis-3-Hexenyl Acetal, Acetaldehyde Ethyl Isobutyl Acetal, (+/−)-Acetaldehyde Ethyl Isopropyl Acetal, Acetaldehyde Hexyl Isoamyl Acetal, Acetaldehyde 1,3-Octanediol Acetal, Acetaldehyde Phenethyl Propyl Acetal, Acetamide, Acetanisole, Acetic Acid, Acetic Anhydride, Acetoin, Acetoin Propyleneglycol Ketal, Alpha-Acetolactate Decarboxylase Enzyme Preparation From *Bacillus Subtilis* Recombinant, Acetolein, Acetone, Acetone Peroxides, Acetophenone, Acetostearin, 6-Acetoxydihydrotheaspirane, 4-Acetoxy-2,5-Dimethyl-3(2h)-Furanone, (+/−)-1-Acetoxy-1-Ethoxyethane, 4-(P-Acetoxyphenyl)-2-Butanone, 5-Acetyl-2,3-Dihydro-1,4-Thiazine, 2-Acetyl-3,5-Dimethylfuran, 3-Acetyl-2,5-Dimethylfuran, 4-Acetyl-2,5-Dimethyl-3(2h)-Furanone, 2-Acetyl-3, 5(Or 6)-Dimethylpyrazine, Mixture Of Isomers, 2-Acetyl-3-Ethylpyrazine, 4-Acetyl-2-Isopropenylpyridine, 2-Acetyl-4-Isopropenylpyridine, 2-Acetyl-4-Isopropylpyridine, 3-Acetylmercaptohexyl Acetate, N-Acetyl-L-Methionine, Acetyl Methyl Carbinyl Acetate, 2-Acetyl-5-Methylfuran, 2-Acetyl-3-Methylpyrazine, 4-Acetyl-2-Methylpyrimidine, 2-Acetyl-5-Methylthiophene, Acetylpyrazine, 2-Acetylpyridine, 3-Acetylpyridine, 2-Acetyl-1-Pyrroline, 4-Acetyl-6-Tert-Butyl-1,1-Dimethylindane, 2-Acetylthiazole, 2-Acetyl-2-Thiazoline, 3-(Acetylthio)-2-Methylfuran, Aconitic Acid, Acrolein, 3-(2-Furyl) Acrolein, Acrylamide-Acrylic Acid Resin, Acrylamide-Sodium Acrylate Resin, Acrylic Acid-2-Acrylamido-2-Methyl Propane Sulfonic Acid Copolymer, Activated Carbon, Adipic Acid, Adipic Anhydride, Advantame, Agar (*Gelidium* Spp.), Alpha-Bisabolol, Dl-Alanine, L-Alanine, Beta-Alanine, L-Alanyl-L-Glutamine, Albumin, Alcohol, Denatured Formula 23a, Alcohol Sda-3a, Alfalfa, Extract (*Medicago Sativa* L.), Alfalfa, Herb And Seed (*Medicago Sativa* L.), Algae, Brown, Extract (*Macrocystis* And *Laminaria* Spp.), Algae, Red (*Porphyra* Spp. And *Gloiopeltis Furcata* And *Rhodymenia Palmata* (L.)), Algae, Red, Extract (*Porphyra* Spp. And *Gloiopeltis Furcata* And *Rhodymenia Palmata* (L.)), Alginate, Ammonium, Alginate, Calcium, Alginate, Potassium, Alginate, Sodium, Alginate, Sodium Calcium, Alginic Acid, Alkanet Root, Extract (*Alkanna Tinctoria* Tausch), Alkanolamide Of Coconut Oil Fatty Acids And Diethanolamine, Alkylene Oxide Adducts Of Alkyl Alcohols/Phosphate Esters Of Same, (Mixture), N-Alkyl($C_8$-$C_{18}$ From Coconut Oil) Amine Acetate, Alpha-Alkyl-Omega-Hydroxy-Poly(Oxyethylene), Allspice (*Pimenta Officinalis* Lindl.), Allspice, Oil (*Pimenta Officinalis* Lindl.), Allspice, Oleoresin (*Pimenta Officinalis* Lindl.), Allyl Alpha-Ionone, Allyl Anthranilate, Allyl Butyrate, Allyl Cinnamate, Allyl Crotonate, Allyl Cyclohexaneacetate, Allyl Cyclohexanebutyrate, Allyl Cyclohexanehexanoate, Allyl Cyclohexanepropionate, Allyl Cyclohexanevalerate, S-Allyl-L-Cysteine, 4-Allyl-2,6-Dimethoxyphenol, Allyl Disulfide, Allyl 2-Ethylbutyrate, Allyl 2-Furoate, Allyl Heptanoate, Allyl Hexanoate, Allyl Hexenoate, Allyl Isothiocyanate, Allyl Isovalerate, Allyl Mercaptan, Allyl Methyl Disulfide, Allyl Methyl Trisulfide, Allyl Nonanoate, Allyl Octanoate, 4-Allylphenol, Allyl Phenoxyacetate, Allyl Phenylacetate, Allyl Propionate, Allyl Propyl Disulfide, Allyl Sorbate, Allyl Sulfide, Allyl Thiohexanoate, Allyl Thiopropionate, Allyl Tiglate, Allyl 10-Undecenoate, Allyl Valerate, Almond, Bitter, Oil (Ffpa) (*Prunus* Spp.), *Aloe*, Extract (*Aloe* Spp.), Alpha-Amylcinnamyl Isovalerate, Alpha-Ethyl Benzyl Butyrate, Alpha-Hydro-Omega-Hydroxy Poly(Oxyethylene) Poly(Oxypropylene) Poly(Oxyethylene) (15 Mole Minimum) Blocked Copolymer, Low Erucic Acid Rapeseed Oil Polymers. Alpha-Isobutylphenethyl Alcohol, Alpha-Methylbenzyl Butyrate, Alpha-Methylbenzyl Isobutyrate, Alpha-Tocopherol Acid Succinate, *Althea* Flowers (*Althea Officinalis* L.), *Althea* Root (*Althea Officinalis* L.), Alum (Double Sulfate Of Al And Nh4, K, Or Na), Aluminum Ammonium Sulfate, Aluminum Calcium Silicate, Aluminum Caprate, Aluminum Caprylate, Aluminum Hydroxide, Aluminum Laurate, Aluminum Myristate, Aluminum Nicotinate, Aluminum Oleate, Aluminum Palmitate, Aluminum Potassium Sulfate, Aluminum Salts Of Fatty Acids, Aluminum Sodium Sulfate, Aluminum Stearate, Aluminum Sulfate, Ambergris, Tincture, Ambrette, Absolute, Oil (*Hibiscus Abelmoschus* L.), Ambrette Seed (*Hibiscus Abelmoschus* L.), Ambrette Seed, Oil (*Hibiscus Abelmoschus* L.), Ambrette, Tincture (*Hibiscus Abelmoschus* L.), 1-Amino-2-Propanol, 2'-Aminoacetophenone, P-Aminobenzoic Acid, 4-Aminobutyric Acid, Dl-(3-Amino-3-Carboxypropyl)Dimethylsulfonium Chloride, 4-Amino-5,6-Dimethylthieno[2,3-D]Pyrimidin-2(1h)-One, 4-Amino-5,6-Dimethylthieno[2,3-D]Pyrimidin-2(1 h)-One Hydrochloride, 3-[(4-Amino-2,2-Dioxido-1h-2,1,3-Benzothiadiazin-5-Yl)Oxy]-2,2-Dimethyl-N-Propylpropanamide, Aminoglycoside 3'-Phosphotransferase Ii, Aminopeptidase From *Lactococcus Lactis*, Amino Tri(Methylene Phosphonic Acid), Sodium Salt, Ammonia (Also Includes Ammonium Chloride), Ammonium Acetate. Ammonium Bicarbonate, Ammonium Carbonate, Ammonium Caseinate, Ammonium Chloride, Ammonium Citrate, Dibasic, Ammonium Gluconate, Ammonium Hydroxide, Ammonium Isovalerate, Ammonium Pectinate, Ammonium Persulfate, Ammonium Phosphate, Dibasic, Ammonium Phosphate, Monobasic, Ammonium Sulfate, Ammonium Sulfide, Ammonium Sulfite, Amyl Alcohol, Alpha-Amylase Enzyme Preparation From

*Bacillus Stearothermophilus*, Amylase From *Aspergillus Flavus*, Amylase From *Aspergillus Niger*, Amylase From *Aspergillus Oryzae*, Amylase From *Bacillus Subtilis*, Amyl Butyrate, Alpha-Amylcinnamaldehyde, Alpha-Amylcinnamaldehyde Dimethyl Acetal, Alpha-Amylcinnamyl Acetate, Alpha-Amylcinnamyl Alcohol, Alpha-Amylcinnamyl Formate, Amyl Decanoate, Amyl Formate, Amyl 2-Furoate, Amyl Heptanoate, Amyl Hexanoate, Amyl Isothiocyanate, Amyl Methyl Disulfide, Amyl Octanoate, Amyloglucosidase From *Rhizopus Niveus*, 2-Amyl-5 Or 6-Keto-1,4-Dioxane, Amyl Salicylate, *Amyris* (*Amyris Balsamifera* L.), *Amyris*, Oil (*Amyris Balsamifera* L.), (2,4)- And (3,5)- And (3,6)-Dimethyl-3-Cyclohexenylcarbaldehyde, Trans-Anethole, *Angelica* (*Angelica* Spp.), Beta-Angelicalactone, *Angelica* Root (*Angelica* Spp.), *Angelica* Root Extract (*Angelica Archangelica* L.), *Angelica* Root Oil (*Angelica Archangelica* L.), *Angelica* Seed (*Angelica* Spp.), *Angelica* Seed Extract (*Angelica Archangelica* L.), *Angelica* Seed Oil (*Angelica Archangelica* L.), *Angelica* Stem Oil (*Angelica Archangelica* L.), Angola Weed (*Roccella Fuciformis* Ach.), Angostura (*Galipea Offincinalis* Hancock), Angostura Extract (*Galipea Officinalis* Hancock), Anisaldehyde Propyleneglycol Acetal, Anise (*Pimpinella Anisum* L.), Anise Oil (*Pimpinella Anisum* L.), Anise, Star (*Illicium Verum* Hook, F.), Star Anise Oil (*Illicium Verum* Hook, F.), Anisic Acid, Anisole, Anisyl Acetate, Anisyl Alcohol, Anisyl Butyrate, Anisyl Formate, Anisyl Phenylacetate, Anisyl Propionate, Annatto, Extract (*Bixa Orellana* L.), Annatto. Seed (*Bixa Orellana* L.), Anoxomer, Sulfonated Anthracite Coal, Beta-Apo-8'-Carotenal, Apple Essence, Apricot Kernel Oil (*Prunus Armeniaca* L.), Arabinogalactan, L-Arabinose, L-Arginine, *Arnica* Flowers (*Arnica* Spp.), Arrowroot Starch, *Artemisia* (*Artemisia* Spp.), *Artemisia* Extract, *Artemisia* Oil, Artichoke Leaves (*Cynara Scolymus* L.), Asafetida Fluid Extract (*Ferula Assafoetida* L.), Asafetida Gum (*Ferula Assafoetida* L.), Asafetida Oil (*Ferula Assafoetida* L.), Ascorbic Acid, Ascorbyl Palmitate, Ascorbyl Stearate, L-Asparagine, Asparagus, Seed And Root, Extract, Aspartame, L-Aspartic Acid, *Aspergillus Niger* For Fermentation Production Of Citric Acid, Astaxanthin, Azodicarbonamide, Bacterial Catalase From *Micrococcus Lysodeikticus*, Bakers Yeast Extract, Baker's Yeast Glycan, Baker's Yeast Protein, Balm (*Melissa Officinalis* L.), Balm Leaves (*Melissa Officinalis* L.), Balm Leaves Extract (*Melissa Officinalis* L.), Balm Oil (*Melissa Officinalis* L.), Balsam Fir Needles And Twigs (*Abies Balsamea* (L.) Mill.), Balsam Fir Oil (*Abies Balsamea* (L.) Mill.), Balsam Fir Oleoresin (*Abies Balsamea* (L.) Mill.), Peru Balsam (*Myroxylon Pereirae* Klotzsch), Peru Balsam, Oil (*Myroxylon Pereirae* Klotzsch), Basil (*Ocimum Basilicum* L.), Basil Bush (*Ocimum Minimum* L.), Basil Extract (*Ocimum Basilicum* L.), Basil Oil (*Ocimum Basilicum* L.), Basil Oleoresin (*Ocimum Basilicum* L.), Bay (*Laurus Nobilis* L.), Sweet Bay Leaves Extract (*Laurus Nobilis* L.), Sweet Bay Leaves Oil (*Laurus Nobilis* L.), Bay Leaves, West Indian, Extract (*Pimenta Acris* Kostel), Bay Leaves, West Indian, Oil (*Pimenta Racemosa* (Mill.) J. W. Moore), Bay Leaves, West Indian, Oleoresin (*Pimenta Acris* Kostel), Beechwood, Creosote (*Fagus* Spp.), Beeswax, Bleached Beeswax, Bentonite, Benzaldehyde, Benzaldehyde Dimethyl Acetal, Benzaldehyde Glyceryl Acetal, Benzaldehyde Propylene Glycol Acetal, Benzene, Benzenethiol, 2-Benzofurancarboxaldehyde, Benzoic Acid, Benzoin, Benzoin, Resin (*Styrax* Spp.), Benzophenone, Benzothiazole, N-Benzoylanthranilic Acid, Benzoyl Peroxide, Benzyl Acetate, Benzyl Acetoacetate, Benzyl Alcohol, Benzyl Benzoate, Benzyl Butyl Ether, Benzyl Butyrate, Benzyl Cinnamate, Benzyl 2,3-Dimethylcrotonate, Benzyl Disulfide, Benzyl Ethyl Ether, Benzyl Formate, 3-Benzyl-4-Heptanone, Benzyl Hexanoate, Benzyl Isobutyrate, Benzyl Isothiocyanate, Benzyl Isovalerate, Benzyl Levulinate, Benzyl Mercaptan, Benzyl Methoxyethyl Acetal, Benzyl Trans-2-Methyl-2-Butenoate, Benzyl Methyl Sulfide, Benzyl Nonanoate, Benzyl Phenylacetate, Benzyl Propionate, Benzyl Salicylate, Bergamot, Oil (*Citrus Aurantium* L. Subsp. *Bergamia Wright* Et Am.), Betaine, Biotin. Biphenyl, Birch, Sweet, Oil (*Betula Lenta* L.), Birch Tar. Oil (*Betula Pendula* Roth And Related *Betula* Spp.), Bisabolene, Bis(2,5-Dimethyl-3-Furyl) Disulfide, Bis(2-Methyl-3-Furyl) Disulfide, Bis(1-Mercaptopropyl)Sulfide, Bis-(Methylthio)Methane, Bis(2-Methylphenyl) Disulfide, Bis (2-Methyl-3-Furyl) Tetrasulfide, Blackberry Bark, Extract (*Rubus*, Spp. Of Section Eubatus), Blackberry Fruit Extract, Bois De Rose, Oil (Aniba Rosaeodora Ducke), *Boldus* Leaves (*Peumus Boldus* Mol.), Bonito, Dried, Borax, Boric Acid, Borneol, L-Bornyl Acetate, Bornyl Acetate, Bornyl Butyrate, Bornyl Formate, Bornyl Isovalerate, Bornyl Valerate, *Boronia*, Absolute (*Boronia Megastigma* Nees), Bouillon, Vegetable, Smoke, Beta-Bourbonene, Bromelain, Brominated Vegetable Oil, *Bryonia* Root (*Bryonia* Spp.), Buchu Leaves (*Barosma Betulina* And *Crenulata*), Buchu Leaves Extract, Buchu Leaves, Oil (*Barosma* Spp.), Buckbean Leaves (*Menyanthes Trifoliata* L.), Buckbean Leaves, Extract (*Menyanthes Trifoliata* L.), Butadiene-Styrene Rubber, 4-(Methylthio)Butanal, Butanal Dibenzyl Thioacetal, N-Butane, 1,3-Butanedithiol, 1,2-Butanedithiol, 2,3-Butanedithiol, I-Butanethiol, 2-Butanol, 2-Butanone, Butan-3-One-2-Y1 Butanoate, (E)-2-Butenoic Acid, 4-(2-Butenylidene)-3,5,5-Trimethylcyclohex-2-En-1-One, 3-Butenyl Isothiocyanate, 1-Buten-1-Y1 Methyl Sulfide, Butter Acids, Butter Esters, Butter Fat, Enzyme-Modified, With Added Butyric Acid, Butter Starter Distillate, Butyl Acetate, Butyl Acetoacetate, Butyl Alcohol, Butylamine, Sec-Butylamine, Butyl Anthranilate, Butylated Hydroxyanisole, Butylated Hydroxytoluene, 2-Butyl-2-Butenal, Butyl Butyrate, Butyl Butyryllactate, Alpha-Butylcinnamaldehyde, Butyl Cinnamate, Butyl 2-Decenoate, 1,3-Butylene Glycol, Butyl Ethyl Disulfide, Butyl Ethyl Malonate, Butyl Formate, 2-Butylfuran, Butyl Heptanoate, Butyl Hexanoate, Butyl P-Hydroxybenzoate, Alpha-Butyl-Omega-Hydroxypoly(Oxyethylene) Poly(Oxypropylene), 3-Butylidenephthalide, Butyl Isobutyrate. 2-Butylisothiocyanate, Butyl Isothiocyanate, Butyl Isovalerate, Butyl Lactate, Butyl Laurate, Butyl Levulinate, N-Butyl 2-Methylbutyrate, Butyl Beta-(Methylthio) Acrylate, Butyl Beta-Naphthyl Ether, Butyl Oleate Sulfate, 2-Butyl-5 Or 6-Keto-1,4-Dioxane, Butyl Phenylacetate, 3-N-Butylphthalide, Butyl Propionate, Butyl Salicylate, Butyl Stearate, Butyl Sulfide, Butyl 10-Undecenoate, Butyl Valerate, Butyraldehyde, Butyramide, Butyric Acid, 2-Butyrylfuran, Cadinene, Caffeine, Cajeput, Oil (*Melaleuca Leucadendron* L.), Calcium Acetate, Calcium Ascorbate, Calcium Benzoate, Calcium Bromate, Calcium Caprate, Calcium Caprylate, Calcium Carbonate, Calcium Caseinate, Calcium Chloride, Calcium Citrate, Calcium Diglutamate, Calcium Fumarate, Calcium Gluconate, Calcium Glycerophosphate, Calcium Hexametaphosphate, Calcium Hydroxide, Calcium Hypophosphite, Calcium Iodate, Calcium Lactate, Calcium Lactobionate, Calcium Laurate, Calcium Lignosulfonate, Calcium Myristate, Calcium Oleate, Calcium Oxide, Calcium Palmitate, Calcium Pantothenate, Calcium Pantothenate, Calcium Chloride Double Salt, Calcium Peroxide, Calcium Phosphate, Dibasic, Calcium Phosphate, Monobasic, Calcium Phosphate, Tribasic, Calcium Phytate, Calcium Propionate, Calcium Pyrophosphate, Calcium Salts Of Fatty Acids, Calcium Silicate, Calcium Sorbate, Calcium Stearate, Calcium Stearoyl-2-Lactylate, Calcium Sulfate, Calumba Root (*Jatrorrhiza Palmata* (Lam.) Miers), Calumba Root, Extract (*Jatrorrhiza Palmata* (Lam.) Miers), Camphene, Campholene Acetate, Alpha-Campholenic Alcohol, D-Camphor, Camphor, Japanese, White, Oil (*Cinnamomum Camphora* (L.) Nees Et Eberm.), Camphor Oil, Formosan Ho-Sho, Leaves (*Cinnamomum Camphora*), *Cananga*, Oil (*Cananga Odorata* Hook. F. And Thoms.), Candelilla Wax (Wax From Stems And Branches Of *Euphorbia Cerifera*), Candida Guilliermondii, Candida Lipolytica, Canthaxanthin, Capers (*Capparis Spinosa* L.), Caprolactam, *Capsicum* (*Capsicum* Spp.), *Capsicum* Extract (*Capsicum* Spp.), *Capsicum*, Oleoresin (*Capsicum* Spp.), Caramel, Caraway (*Carum Carvi* L.), Caraway, Black (*Nigella Sativa* L.), Caraway, Oil (*Carum Carvi* L.), Carbohydrase And Cellulase From *Aspergillus Niger*, Carbohydrase And Protease, Mixture, From *Bacillus Subtilis*, Carbohydrase From *Aspergillus Oryzae*, Carbohydrase From *Bacillus Amyloliquefaciens*, Carbohydrase From *Bacillus Licheniformis*, Carbohydrase From *Bacillus Subtilis*, Carbohydrase From *Rhizopus Oryzae*, Carbohydrase From *Saccharomyces* Spp., Carbohydrase/Proteinase Preparation, *Bacillus Licheniformis*, Carbon Dioxide, Carboxymethyl Cellulose, Carboxymethyl Cellulose, Sodium Salt, Carboxymethyl Hydroxyethyl Cellulose, Cardamom (*Elletaria Cardamomum* (L.) Maton), Cardamom Oleoresin, Cardamom Seed, Oil (*Elletaria Cardamomum* (L.) Maton), 3-Carene, Carmine (*Coccus Cacti* L.), Carnauba Wax (*Copernicia Cerifera* (Arruda) Mart.), L-Carnitine, Carob Bean, Extract (*Ceratonia Siliqua* L.), Beta-Carotene, Carrageenan, Carrageenan, Ammonium Salt Of, Carrageenan, Ammonium Salt Of, With Polysorbate 80, Carrageenan And Salts Of Carrageenan, Carrageenan, Calcium Salt Of, Carrageenan, Calcium Salt Of, With Polysorbate 80, Carrageenan, Potassium Salt Of, Carrageenan, Potassium Salt Of, With Polysorbate 80, Carrageenan Salts With Polysorbate 80, Carrageenan, Sodium Salt Of, Carrageenan, Sodium Salt Of, With Polysorbate 80, Carrageenan With Polysorbate 80, Carrot (*Daucus Carota* L.), Carrot, Dehydrated, Carrot, Extract, Carrot, Oil (*Daucus Carota* L.), Carvacrol, Carvacryl Ethyl Ether, Carveol, 4-Carvomenthenol, Carvomenthol, Carvone, Cis-Carvone Oxide, Carvyl Acetate, Carvyl Palmitate, Carvyl Propionate, Beta-Caryophyllene, Beta-Caryophyllene Alcohol, Caryophyllene Alcohol, Beta-Caryophyllene Alcohol Acetate, Caryophyllene Alcohol Acetate, Beta-Caryophyllene Oxide, Cascara, Bitterless, Extract (*Rhamnus Purshiana* Dc.), Cascarilla Bark, Extract (*Croton* Spp.), Cascarilla Bark, Oil (*Croton* Spp.), Casein, Cassia Buds (*Cinnamomum Cassia* Blume), Cassie, Absolute (*Acacia Farnesiana* (L.) Willd.), Castoreum, Extract (Castor Spp.), Castoreum, Liquid (Castor Spp.), Castor Oil (*Ricinus Communis* L.), Catalase From *Aspergillus Niger*, Catalase From Bovine Liver, Catalase From *Penicillium Notatum*, Catechu, Black, Extract (*Acacia Catechu* Willd.), Catechu, Black, Powder (*Acacia Catechu* Willd.), Cedar Leaf Oil (*Thuja Occidentalis* L.), Cedarwood Oil Alcohols, Cedarwood Oil Terpenes, (+)-Cedrol, Cedryl Acetate, Celery Seed (*Apium Graveolens* L.), Celery Seed, Extract (*Apium Graveolens* L.), Celery Seed, Extract Solid (*Apium Graveolens* L.), Celery Seed, Oil (*Apium Graveolens* L.), Celery Seed, Oleoresin, Cellulase From *Trichoderma Longibrachiatum*, Cellulose Acetate, Cellulose, Diethylaminoethyl, Cellulose, Methyl, Cellulose, Methyl Ethyl, Cellulose, Microcrystalline, Cellulose Triacetate, Centaury (*Centaurium Umbellatum* Gilib.), Cereal Solids, Hydrolyzed, Cetyl Alcohol, Chamomile Flower (*Matricaria Chamomilla* L.), Chamomile Flower (*Anthemis Nobilis* L.), Chamomile Flower, Hungarian, Oil (*Matricaria Chamomilla* L.), Chamomile Flower, Oil (*Anthemis Nobilis* L.), Chamomile Flower, Roman, Extract (*Anthemis Nobilis* L.), Char Smoke Flavor, Cherry Bark, Wild, Extract (*Prunus Serotina* Ehrh.), Cherry-Laurel Leaves (*Prunus Laurocerasus* L.), Cherry Laurel, Oil (*Prunus Laurocerasus* L.) (Ffpa), Cherry-Laurel Water (*Prunus Laurocerasus* L.), Cherry Pits, Extract (*Prunus* Spp.), Chervil (*Anthriscus Cerefolium* (L.) Hoffm.), Chervil, Extract (*Anthriscus Cerefolium* L.), Chestnut Leaves (*Castanea Dentata* (Marsh.) Borkh.), Chestnut Leaves, Extract (*Castanea Dentata* (Marsh.) Borkh.), Chestnut Leaves, Extract Solid (*Castanea Dentata* (Marsh.) Borkh.), Chicle (*Manilkara Zapotilla Gilly* And *M. Chicle Gilly*), Chicle, Venezuelan (*Manilkara Williamsii* Standley And Related Spp.), Chicory, Extract (*Cichorium Intybus* L.), Chilte (*Cnidoscolus* (Also Known As *Jatropha*) Spp.), Chiquibul (*Manilkara Zapotilla Gilly*), Chirata (*Swertia Chirata* Buch.-Ham.), Chirata, Extract (*Swertia Chirata* Buch.-Ham.), Chives (*Allium Schoenoprasum* L.), Chlorine, Chlorine Dioxide, Chlorine Solution, Aqueous, Chloroform, Chloromethyl Methyl Ether, Chloropentafluoroethane, Chlorophyll, Cholic Acid, Choline Bitartrate, Choline Chloride, Choline Chloride(Also Includes Choline), *Chrysanthemum* Extract, Chymosin Preparation, *Aspergillus Niger* Var. *Awamori*, Chymosin Preparation, *Escherichia Coli* K-12, Chymosin Preparation, *Kluyveromyces Marxianus* Var. *Lactis*, Cinchona Bark, Red (*Cinchona Succirubra* Pav. Or Its Hybrids), Cinchona Bark, Red, Extract (*Cinchona Succirubra* Pav. Or Its Hybrids), Cinchona Bark, Yellow (*Cinchona* Spp.), Cinchona Bark, Yellow, Extract (*Cinchona* Spp.), *Cinchona*, Extract (*Cinchona* Spp.), 1,4-Cineole, Cinnamaldehyde, Cinnamaldehyde Ethylene Glycol Acetal, Cinnamaldehyde Propyleneglycol Acetal, Cinnamic Acid, Cinnamon (*Cinnamomum* Spp.), Cinnamon Bark, Extract (*Cinnamomum* Spp.), Cinnamon Bark, Oil (*Cinnamomum* Spp.), Cinnamon Bark Oleoresin, Ceylon, Chinese, Or Saigon (*Cinnamomum* Spp.), Cinnamon Leaf, Oil (*Cinnamomum* Spp.), Cinnamon Leaf Oil, Rectified, Cinnamyl Acetate, Cinnamyl Alcohol, Cinnamyl Benzoate, Cinnamyl Butyrate, Cinnamyl Cinnamate, Cinnamyl Formate, Cinnamyl Isobutyrate, Cinnamyl Isovalerate, Cinnamyl Phenylacetate, Cinnamyl Propionate, Cis- And Trans-Ethyl 2,4-Dimethyl-1,3-Dioxolane-2-Acetate, Cis- And Trans-5-Ethyl-4-Methyl-2-(2-Butyl)-Thiazoline, Cis And Trans-5-Ethyl-4-Methyl-2-(2-Methylpropyl)-Thiazoline, Cis- And Trans-2-Isobutyl-4-Methyl-1,3-Dioxolane, Cis- And Trans-2-Isopropyl-4-Methyl-1,3-Dioxolane, Cis- And Trans-L-Mercapto-P-Menthan-3-One, (+−)-Cis- And Trans-2-Methyl-2-(4-Methyl-3-Pentenyl) Cyclopropanecarbaldehyde, (+/−)Cis- And Trans-2-Pentyl-4-Propyl-1,3-Oxathiane, Cis-4-Decenol, Cis-4-Heptenal, Cis-3-Hexenoic Acid, Cis-3-Hexen-1-Ol, Cis-3-Hexen-1-Yl Acetate, Cis-3-Hexenyl Acetoacetate, Cis-3-Hexenyl Butyrate, Cis-3-Hexenyl Cis-3-Hexenoate, Cis-3-Hexenyl Formate, Cis-3-Hexenyl Hexanoate, Cis-5-Isopropenyl-Cis-2-Methylcyclopentan-1-Carboxaldehyde, Cis-3-Nonen-1-Ol, Cis-9-Octadecenyl Acetate, Cis-5-Octenoic Acid, Cis-4-Octenol, Cis-2-Octenol, Citral, Citral Diethyl Acetal, Citral Dimethyl Acetal, Citral Glyceryl Acetal, Citral Propylene Glycol Acetal, Citric Acid, Citric And Fatty Acid Esters Of Glycerol, Citronellal, Citronella, Oil (*Cymbopogon* Nardus Rendle), Dl-Citronellol, Citronelloxyacetaldehyde, Citronellyl Acetate, Citronellyl Anthranilate, Citronellyl Butyrate, Citronellyl Formate, Citronellyl Isobutyrate, Citronellyl Phenylacetate, Citronellyl Propionate, Citronellyl Trans-2-Methyl-2-Butenoate, Citronellyl Valerate, *Citrus* Peels, Extract (*Citrus* Spp.), *Citrus* Red No. 2, Civet, Absolute (Viverra Civetta Schreber And Viverra Zibetha Schreber), Clary (*Salvia Sclarea* L.), Clary Sage, Absolute, Clary, Oil (*Salvia Sclarea* L.), Clary Sage, Concrete, Clay, Attapulgite, Clove Bud, Extract (*Eugenia* Spp.), Clove Bud, Oil (*Eugenia* Spp.), Clove Bud, Oleoresin (*Eugenia* Spp.), Clove Leaf, Oil (*Eugenia* Spp.), Clover (*Trifolium* Spp.), Clover, Extract (*Trifolium* Spp.), Clover Herb Distillate, Clover, Oil (*Trifolium* Spp.), Clover Tops, Red. Extract Solid (*Trifolium Pratense* L.), Cloves (*Eugenia* Spp.), Clove Stem, Oil (*Eugenia* Spp.), Coca Leaf, Extract (Decocainized) (Erythroxylon Coca Lam.), Cochineal Extract (*Coccus Cacti* L.), Cocoa Butter Substitute From Coconut Oil, Palm Kernel Oil Or Both Oils, Cocoa Butter Substitute From Palm Oil, Cocoa Butter Substitute Primarily From High-Oleic Safflower Or Sunflower Oil, Cocoa Extract, Cocoa With Dioctyl Sodium Sulfosuccinate, Coconut Oil, Coconut Oil, Refined, Coffee Concentrate, Pure, Coffee Extract (*Coffea* Spp.), Coffee Extract, Solid, Cognac, Green, Oil, Cognac, White, Oil, Collagen, Combustion Product Gas, Copaiba (South American Spp. Of *Copaifera* L.), Copaiba, Oil (South American Spp. Of *Copaifera* L.), Copals, Manila, Copper Gluconate, Copper Sulfate, Coriander (*Coriandrum Sativum* L.), Coriander Leaf Oil (*Coriandrum Sativum* L.), Coriander, Oil (*Coriandrum Sativum* L.), Cork, Oak (*Quercus* Spp.), Corn Endosperm Oil, Corn Gluten, Corn Mint Oil, Corn Silk, Corn Silk Extract (*Zea Mays* L.), Corn Silk, Oil (*Zea Mays* L.), Cornstarch, Cornstarch, Waxy, Corn Steep Liquor, Corn Syrup, Costmary (*Chrysanthemum Balsamita* L.), Costus Root, Oil (*Saussurea Lappa* Clarke), Cottonseed Flour, Defatted, Cottonseed Flour, Partially Defatted, Cooked, Cottonseed Flour, Partially Defatted, Cooked, Toasted, Cottonseed Kernels, Glandless, Raw, Cottonseed Kernels, Glandless, Roasted, Coumarone-Indene Resins, M-Cresol, P-Cresol, O-Cresol, Crown Gum, Cubeb (*Piper Cubeba* L. F.), Cubeb, Oil (*Piper Cubeba* L. F.), Cubebol, Cumin (*Cuminum Cyminum* L.), Cuminaldehyde, Cumin, Oil (*Cuminum Cyminum* L.), Cuprous Iodide, Curdlan, Currant Buds, Black, Absolute (*Ribes Nigrum* L.), Currant Juice, Black, Currant Leaves, Black (*Ribes Nigrum* L.), Beta-Cyclodextrin, Cycloheptadeca-9-En-1-One, Cyclohexane, Cyclohexaneacetic Acid, Cyclohexanecarboxylic Acid, Cyclohexaneethyl Acetate, Cyclohexanone, Cyclohexanone Diethyl Ketal, 2-Cyclohexenone, Cyclohexyl Acetate, Cyclohexylamine, Cyclohexyl Anthranilate, Cyclohexyl Butyrate, Cyclohexyl Cinnamate, Cyclohexyl Formate, Cyclohexyl Isovalerate, Cyclohexylmethyl Pyrazine, Cyclohexyl Propionate, Cycloionone, Cyclopentanethiol, Cyclopentanone, 2-Cyclopentylcyclopentanone, Cyclopropanecarboxylic Acid (2-Isopropyl-5-Methyl-Cyclohexyl)-Amide, N-Cyclopropyl-5-Methyl-2-Isopropylcyclohexanecarboxamide, N-Cyclopropyl-Trans-2-Cis-6-Nonadienamide, Cyclotene Butyrate, Cyclotene Propionate, P-Cymene, L-Cysteine, L-Cysteine Monohydrochloride, Dl-Cystine, L-Cystine, Daidai Peel Oil, Damar Gum (Shorea Dipterocarpaceae), Alpha-Damascone, Delta-Damascone, Trans-Alpha-Damascone, Damiana Leaves (*Turnera Diffusa* Willd.), Dandelion, Fluid Extract (*Taraxacum* Spp.), Dandelion Root, Extract Solid (*Taraxacum* Spp.), Davana Oil (*Artemesia Pallens* Wall.), 2-Trans,4-Trans-Decadienal, (E,E)-2,4-Decadien-1-Ol, Delta-Decalactone, Gamma-Decalactone, *Decalepis Hamiltonii* Extract, Decanal, Decanal Dimethyl Acetal, Decanal Propyleneglycol Acetal, Decanoic Acid, 1-Decanol, 3-Decanol, 3-Decanone, 2-Decanone, 2-Trans-4-Trans-7-Cis-Decatrienal, 9-Decenal, 2-Decenal, 4-Decenal, 4-Decenoic Acid, (E)-2-Decenoic Acid, 9-Decenoic Acid, 6-Decenoic Acid, 5-Decenoic Acid, 1-Decen-3-Ol, 8-Decen-5-Olide, 9-Decen-5-Olide, 7-Decen-4-Olide, 9-Decen-2-One, 3-Decen-2-One, 6-[5(6)-Decenoyloxy]Decanoic Acid, 4-Decenyl Acetate, Cis-, Decyl Acetate, Decyl Butyrate, 2-Decylfuran, Decyl Propionate, Deertongue Solid Extract, Dehydrated Beets, Dehydroacetic Acid, Dehydrodihydroionol, Dehydrodihydroionone, Dehydromenthofurolactone, Dehydronootkatone, 8,9-Dehydrotheaspirone, Desoxycholic Acid, Dextrans (Avg M W Less Than 100,000), Dextrin, Dextrose, Diacetyl, Di-N-Alkyl $C_8$-$C_{18}$ From Coconut Oil Dimethyl Ammonium Chloride, Diallyl Polysulfides, Diallyl Trisulfide, Diamyl Ketone, Diastase From *Aspergillus Oryzae*, Diatomaceous Earth, Dibenzyl Ether, 2,2-Dibromo-3-Nitrilopropionamide, 4,4-Dibutyl-Gamma-Butyrolactone, Dibutyl Sebacate, Dichlorodifluoromethane, Dicyclohexyl Disulfide, Diethanolamide Condensate From Soybean Oil Fatty Acids ($C_{16}$-$C_{18}$), Diethanolamide Condensate From Stripped Coconut Oil Fatty Acids($C_{10}$-$C_{18}$), Diethylaminoethanol, Diethyl Disulfide, Diethylene Glycol Distearate, Diethylenetriamine, Diethylenetriamine Crosslinked With Epichlorohydrin, Diethyl Malate, Diethyl Malonate, 3,5-Diethyl-2-Methylpyrazine, 2,5-Diethyl-3-Methylpyrazine, 2,3-Diethyl-5-Methylpyrazine, 2,3-Diethylpyrazine, Diethyl Sebacate, Diethyl Succinate, Diethyl Sulfide, Diethyl Tartrate, 2,5-Diethyltetrahydrofuran, Diethyl Trisulfide, (+/-)-Cis- And Trans-3,5-Diethyl-1,2,4-Trithiolane, Difurfuryl Ether, 2,4-Difurfurylfuran, Di-2-Furylmethane, Digeranyl Ether, Dihydro-Alpha-Ionone, Dihydrocarveol, Cis-Dihydrocarvone, Dihydrocarvyl Acetate, Dihydrocoumarin, 6,7-Dihydro-2,3-Dimethyl-5h-Cyclopentapyrazine, 4,5-Dihydro-2,5-Dimethyl-4-Oxo-3-Furanyl Butyrate, (+/-)-Dihydrofarnesol, Dihydrogalangal Acetate, Dihydro-Beta-Ionol, Dihydro-Beta-Ionone, 3,6-Dihydro-4-Methyl-2(2-Methylpropen-1-Yl)-2h-Pyran, 5,7-Dihydro-2-Methylthieno(3,4-D)Pyrimidine, (+/-)-Dihydromintlactone, Dihydronootkatone, (+/-)-Cis- And Trans-1,2-Dihydroperillaldehyde, 4,5-Dihydro-3(2h)Thiophenone, Dihydro-2,4,6-Trimethyl-4h-1,3,5-Dithiazine, Dihydro-2,4,6-Tris(2-Methylpropyl)-4h-1,3,5-Dithiazine, Dihydroxyacetone (Dimer), Dihydroxyacetone (Monomer), Dihydroxyacetophenone, 2,4-Dihydroxybenzoic Acid, 3,4-Dihydroxybenzoic Acid, 2,5-Dihydroxy-1,4-Dithiane, 5,7-Dihydroxy-2-(3-Hydroxy-4-Methxy-Phenyl)-Chroman-4-One, 3',7-Dihydroxy-4'-Methoxyflavan, Diisoamyl Disulfide, Diisoamyl Trisulfide, Diisobutyl Adipate, Diisobutyl Ketone, Diisopentyl Thiomalate, Diisopropyl Adipate, Diisopropyl Disulfide, Diisopropyl Trisulfide, Dilauryl Thiodipropionate, Dill (*Anethum Graveolens* L.), Dill, Oil (*Anethum Graveolens* L.), Dill Seed, Indian (*Anethum* Spp.), Dill Seed Oil(*Anethum Sowa* Roxb.), Dimenthyl Glutarate, Dimercaptomethane, M-Dimethoxybenzene, P-Dimethoxybenzene, 1,2-Dimethoxybenzene, N1-(2,4-Dimethoxybenzyl)-N2-(2-(Pyridin-2-yl) Ethyl)Oxalamide, 1,1-Dimethoxyethane, 1,1-Dimethoxy-Trans-2-Hexene, 2,6-Dimethoxyphenol, N-[2-(3,4-Dimethoxyphenyl)Ethyl]-3,4-Dimethoxycinnamic Acid Amide, 3,4-Dimethoxy-1-Vinylbenzene, 3,6-Dimethyl-2,3,3a,4,5,7a-Hexahydrobenzofuran, 2,4-Dimethylacetophenone, 1,4-Dimethyl-4-Acetyl-1-Cyclohexene, 2,4-Dimethyl-5-Acetylthiazole, Dimethyl Adipate, Dimethylamine, Dimethylamine-Epichlorohydrin Copolymer, 2,4-Dimethylanisole, 2,4-Dimethylbenzaldehyde, 2,3-Dimethylbenzofuran, P,Alpha-Dimethylbenzyl Alcohol. Dimethylbenzyl Carbinyl Crotonate, Dimethylbenzyl Carbinyl Hexanoate, Alpha,Alpha-Dimethylbenzyl Isobutyrate, 3,5-Dimethyl-1, 2-Cyclopentadione, 3,4-Dimethyl-1,2-Cyclopentadione, (+/-)-Trans- And Cis-5-(2,2-Dimethylcyclopropyl)-3-Methyl-2-Pentenal, Dimethyl Dialkyl Ammonium Chloride, Dimethyl Dicarbonate, 2(3),5-Dimethyl-6,7-Dihydro-5h-Cyclopentapyrazine, 2,5-Dimethyl-2,5-Dihydroxy-1,4-Dithiane, 2,4-Dimethyl-1,3-Dioxolane, Dimethylethanolamine, 2,5-Dimethyl-4-Ethoxy-3(2h)-Furanone, 2,5-Dimethyl-4-Ethyloxazole, 4-(1,1-Dimethylethyl)Phenol, 4,5-Dimethyl-2-Ethyl-3-Thiazoline, 2,5-Dimethylfuran, 2,5-Dimethyl-3(2h)-Furanone, 2,5-Dimethyl-3-Furanthiol, 2,5-Dimethyl-3-Furanthiol Acetate, 2,6-Dimethyl-4-Heptanol, 2,6-Dimethyl-3-((2-Methyl-3-Furyl)Thio)-4-Heptanone, 2,6-Dimethyl-5-Heptenal, 2,6-Dimethyl-5-Heptenal Propyleneglycol Acetal, 2,6-Dimethyl-6-Hepten-1-Ol, 4,5-Dimethyl-3-Hydroxy-2,5-Dihydrofuran-2-One, 3,6-Dimethyl-2-Isobutylpyrazine, 3,5-Dimethyl-2-Isobutylpyrazine, 4,5-Dimethyl-2-Isobutylthiazole, 4,5-Dimethyl-2-Isobutyl-3-Thiazoline, 3-(1-((3,5-Dimethylisoxazol-4-Yl)Methyl)-1h-Pyrazol-4-Yl)-1-(3-Hydroxybenzyl)-5,5-Dimethylimidazolidine-2,4-Dione, 3-(1-((3,5-Dimethylisoxazol-4-Yl)Methyl)-1h-Pyrazol-4-Yl)-1-(3-Hydroxybenzyl) Imidazolidine-2,4-Dione, (+/−)-N,N-Dimethyl Menthyl Succinamide, 2,5-Dimethyl-3-Mercaptotetrahydrofuran, 2,5-Dimethyl-4-Methoxy-3(2h)-Furanone, 2,6-Dimethyl-10-Methylene-2,6,11-Dodecatrienal, 3,9-Dimethyl-6-(1-Methylethyl)-1,4-Dioxaspiro[4.5] Decan-2-One, 2,2-Dimethyl-5-(1-Methylpropen-1-Yl) Tetrahydrofuran, (+/−)-Trans- And Cis-4,8-Dimethyl-3,7-Nonadien-2-Ol, 4,8-Dimethyl-3,7-Nonadien-2-One, Cis-, 4,8-Dimethyl-3,7-Nonadien-2-One, 4,8-Dimethyl-3,7-Nonadien-2-One, Trans-, (+/−)-Trans- And Cis-4,8-Dimethyl-3,7-Nonadien-2-Yl Acetate, 2,4-Dimethyl-4-Nonanol, (E)-2-(3,7-Dimethyl-2,6-Octadienyl)Cyclopentanone, N-3,7-Dimethyl-2,6-Octadienylcyclopropylcarboxamide, 2-Trans-3,7-Dimethylocta-2,6-Dienyl 2-Ethylbutanoate, 2,6-Dimethyloctanal, 3,7-Dimethyloctanal, 3,7-Dimethyl-1-Octanol, (E)-3,7-Dimethyl-1,5,7-Octatrien-3-Ol, 3,7-Dimethyl-6-Octenoic Acid, 2,4-Dimethyl-3-Oxazoline, 2,4-Dimethyl-2-Pentenoic Acid, Alpha,Alpha-Dimethylphenethyl Acetate, Alpha,Alpha-Dimethylphenethyl Alcohol, N,N-Dimethylphenethylamine, Alpha,Alpha-Dimethylphenethyl Butyrate, Alpha,Alpha-Dimethylphenethyl Formate, Dimethylpolysiloxane, 2,5-Dimethylpyrazine, 2,6-Dimethylpyrazine, 2,3-Dimethylpyrazine, 2,6-Dimethylpyridine, 2,4-Dimethylpyridine, 2,5-Dimethylpyrrole, P,Alpha-Dimethylstyrene, Dimethyl Succinate, Dimethyl Sulfoxide, 2,5-Dimethylthiazole, 4,5-Dimethylthiazole, 2-(2-Butyl)-4,5-Dimethyl-3-Thiazoline, 2,5-Dimethyl-3-Thioisovalerylfuran, 3,4-Dimethylthiophene, 2,6-Dimethylthiophenol, Dimethyl Trisulfide, 3,5-Dimethyl-1,2,4-Trithiolane, 2,4-Dimethyl-5-Vinylthiazole, Dioctyl Adipate, Dioctyl Sodium Sulfosuccinate, Diphenyl Ether, 1,3-Diphenyl-2-Propanone, Dipotassium Phosphate, 1,1-Dipropoxyethane, Dipropyl Adipate, Dipropyl Trisulfide, Di-Sec-Butyl Disulfide, Disodium Citrate, Disodium Cyanodithioimidocarbonate, Disodium Ethylenebisdithiocarbamate, Disodium Guanylate, Disodium Inosinate, Disodium Succinate, Di-(Butan-3-One-1-Yl) Sulfide, 2,5-Dithiahexane, 1,4-Dithiane, 2,8-Dithianon-4-En-4-Carboxaldehyde, 2,2'-(Dithiodimethylene) Difuran, Dittany Of Crete (*Origanum Dictamnus* L.), Dittany (*Fraxinella*) Roots (*Dictamnus Albus* L.), Divanillin, Dl-Camphor, D-Limonen-10-Ol, Dl-Isoleucine, Dl-Isomenthone, Dl-Valine, Epsilon-Dodecalactone, Gamma-Dodecalactone, Delta-Dodecalactone, Dodecanal Dimethyl Acetal, (Z)-4-Dodecenal, 2-Dodecenal, 11-Dodecenoic Acid, 9-Dodecen-5-Olide, Dodecyl Butyrate, Dodecyl Gallate, Dodecyl Isobutyrate, Dodecyl Lactate, N-Dodecylmercaptan, Alpha-(P-Dodecylphenyl)-Omega-Hydroxypoly(Oxyethylene), Dodecyl Propionate, Dog Grass, Extract (*Agropyron Repens* (L.) Beauv.), D-8-P-Menthene-1,2-Epoxide, Dragon's Blood, Extract (*Daemonorops* Spp. Or Other Botanical Sources), Dried Algae Meal, Edta, Calcium Disodium, Edta, Disodium, Edta, Disodium Iron, Edta, Tetrasodium, (2e,6e,8e)-N-(2-Methylpropyl)-2,6,8-Decatrienamide, Egg White Lysozyme, Elder Flowers (*Sambucus Canadensis* L. Or *Sambucus Nigra* L.), Elder Flowers, Extract (*Sambucus Canadensis* L. Or *Sambucus Nigra* L.), Elder Tree Leaves (*Sambucus Nigra* L.), Elecampane Root, Extract (*Inula Helenium* L.), Elecampane Root, Oil (*Inula Helenium* L.), Elemi, Gum, Elemi, Oil (*Canarium* Spp.), Enzyme-Modified Fats, Enzymes, Bacterial, Enzymes, Proteolytic, Epichlorohydrin Crosslinked With Ammonia, (+/−)-2,8-Epithio-Cis-P-Menthane, 2,3-Epoxydecanal, 4,5-Epoxy-(E)-2-Decenal, 2,3-Epoxyheptanal, 2,3-Epoxyoctanal, Epoxyxophorone, Epsilon-Decalactone, *Erigeron*, Oil (*Erigeron Canadensis* L.), (?)-Eriodictyol, Erythorbic Acid, Esterase-Lipase From *Mucor Miehei*, Estragole, 1,2-Ethanedithiol, Ethane-1,1-Dithiol, Ethanesulfonic Acid, 2-(1-(Difluoro-((Trifluoroethenyl)Oxy)Methyl)-1,2,2,2-Tetrafluoroethoxy)-1,1,2,2-Tetrafluoro-, Polymer With Tetrafluoroethane, Ethanethiol, P-Ethoxybenzaldehyde, N-[(Ethoxycarbonyl)Methyl)-P-Menthane-3-Carboxamide, 2-Ethoxy-3-Ethylpyrazine, 2-Ethoxy-3-Isopropylpyrazine, 1-Ethoxy-3-Methyl-2-Butene. O-(Ethoxymethyl)Phenol, Ethoxyquin, 2-Ethoxythiazole, (+−)-Ethyl 3-Hydroxy-2-Methylbutyrate, Ethyl Abietate, Ethyl (P-Tolyloxy)Acetate, Ethyl Acetate, Ethyl 2-(Methylthio)Acetate, Ethyl Acetoacetate, Ethyl Acetoacetate Ethyleneglycol Ketal, (+/−)-Ethyl 3-Acetoxy-2-Methylbutyrate, Ethyl 5-Acetoxyoctanoate, S-Ethyl 2-Acetylaminoethanethioate, Ethyl Alpha-Acetylcinnamate, Ethyl 2-Acetylhexanoate, Ethyl 2-Acetyloctanoate, Ethyl 2-Acetyl-3-Phenylpropionate, 1-Ethyl-2-Acetylpyrrole, Ethyl 4-(Acetylthio)Butyrate, Ethyl Aconitate (Mixed Esters), Ethyl Acrylate, Ethyl Alcohol, Ethylamine, Ethyl P-Anisate, Ethyl Anthranilate, 4-Ethylbenzaldehyde, Ethyl Benzoate, Ethyl Benzoylacetate, Ethyl Brassylate, 2-Ethylbutyl Acetate, 2-Ethylbutyraldehyde, Ethyl Butyrate, Ethyl 3-(Methylthio)Butyrate, 2-Ethylbutyric Acid, Ethyl Cellulose, Ethyl Cinnamate, Ethyl Crotonate, Ethyl Cyclohexanecarboxylate, Ethyl Cyclohexanepropionate, Ethyl Trans-2,Cis-4-Decadienoate, Ethyl Decanoate, Ethyl 2,4,7-Decatrienoate, Ethyl Trans-2-Decenoate, Ethyl Trans-4-Decenoate, Ethyl 4,5-Dihydro-2,5-Dimethyl-4-Oxo-3-Furancarboxylate, 2-Ethyl-2,5-Dihydro-4-Methylthiazole, 4-Ethyl-2,6-Dimethoxyphenol, 2(4)-Ethyl-4(2),6-Dimethyldihydro-1,3,5-Dithiazine (Mixture Of Isomers), 2-Ethyl-4,5-Dimethyloxazole, 3-Ethyl-2,6-Dimethylpyrazine, 5-Ethyl-2,3-Dimethylpyrazine, Ethyl 2,4-Dioxohexanoate, Ethylenediamine, Ethylenediaminetetraacetic Acid Disodium Salt, Ethylene Dichloride, Ethylene Glycol Distearate, Ethylene Glycol Monobutyl Ether, Ethylene Glycol Monoethyl Ether, Ethylene Glycol Monophenyl Ether, Ethylene Oxide, Ethylene Oxide Polymer, Ethylene Oxide Polymer, Alkyl Adduct, Ethylene Oxide Polymer, Alkyl Adduct, Phosphate Ester, Ethylene Oxide/Propylene Oxide Copolymer (Avg M W 9,760-13,200), Ethylene Oxide/Propylene Oxide Copolymer (Min Avg M W 1,900), Ethylene Oxide/Propylene Oxide Copolymer (Avg M W 14,000), Ethylene Oxide/Propylene Oxide Copolymer, Ethylene Oxide/Propylene Oxide Copolymer (Avg M W 3,500-4,125), Ethylene Oxide/Propylene Oxide Copolymer, Alkyl Adduct, Ethylene Oxide/Propylene Oxide Copolymer, Alkyl Adduct, Phosphate Ester, Ethyl Esters Of Fatty Acids (Edible), Ethyl N-Ethylanthranilate, Ethyl 2-Ethylbutyrate, Ethyl 2-Ethylhexanoate, Ethyl Alpha-Ethyl-Beta-Methyl-Beta-Phenylglycidate, Ethyl 2-Ethyl-3-Phenylpropanoate, Ethyl 3-(Ethylthio)Butyrate, Ethyl Formate, 2-Ethylfuran, Ethyl 2-Furanpropionate, Ethyl Furfuryl Ether, Ethyl 3-(Furfurylthio) Propionate, Ethyl 3-(2-Furyl)Acrylate, 4-Ethylguaiacol, Ethyl Heptanoate, 2-Ethyl-2-Heptenal, Ethyl 4-Heptenoate, Cis-, 2-Ethylhexanethiol, Ethyl Hexanoate, 2-Ethyl-1-Hexanol, 2-Ethyl-2-Hexenal, Ethyl Cis-3-Hexenoate, Ethyl 5-Hexenoate, Ethyl 3-Hexenoate, Ethyl 2-Hexenoate, 2-Ethylhexyl Benzoate, 2-Ethylhexyl 3-Mercaptopropionate, 1-Ethylhexyl Tiglate, Ethyl 3-Hydroxybutyrate, 3-Ethyl-2-Hydroxy-2-Cyclopenten-1-One, Ethyl 5-Hydroxydecanoate, Ethyl 2-Hydroxyethyl Sulfide, Ethyl 3-Hydroxyhexanoate, (+/−)-Ethyl 2-Hydroxy-2-Methylbutyrate, 3-Ethyl-2-Hydroxy-4-Methylcyclopent-2-En-1-One, 5-Ethyl-2-Hydroxy-3-Methylcyclopent-2-En-1-One, 5-Ethyl-3-Hydroxy-4-Methyl-2(5h)-Furanone, 2-Ethyl-4-Hydroxy-5-Methyl-3(2h)-Furanone, (+/−)-Ethyl 2-Hydroxy-3-Methylvalerate, Ethyl 3-Hydroxyoctanoate, Ethyl 5-Hydroxyoctanoate, Ethyl 2-Hydroxy-3-Phenylpropionate, Ethyl Isobutyrate, N-Ethyl-2-Isopropyl-5-Methylcyclohexane Carboxamide, Ethyl Isothiocyanate, Ethyl Isovalerate, Ethyl Lactate, Ethyl Laurate, Ethyl Levulinate, Ethyl Levulinate Propyleneglycol Ketal, Ethyl Linalyl Ether, Ethyl Maltol, Ethyl Maltol Isobutyrate, Ethyl 3-Mercaptobutyrate, (+−)-Ethyl 3-Mercapto-2-Methylbutanoate, Ethyl 2-Mercapto-2-Methylpropionate, Ethyl 3-Mercaptopropionate, Ethyl 2-Mercaptopropionate, Ethyl N-Methylanthranilate, Ethyl 2-Methylbutyrate, Ethyl Methyl Disulfide, Ethyl 2-Methyl-3,4-Pentadienoate, Ethyl 4-Methylpentanoate, Ethyl 3-Methylpentanoate, Ethyl 2-Methylpentanoate, Ethyl 2-Methyl-3-Pentenoate, Ethyl 2-Methyl-4-Pentenoate, 3-Ethyl-2-Methylpyrazine, 2-Ethyl-6-Methylpyrazine, 2-Ethyl-5-Methylpyrazine, 5-Ethyl-2-Methylpyridine, 5-Ethyl-2-Methylthiazole, 2-Ethyl-4-Methylthiazole, Ethyl 4-(Methylthio) Butyrate, Ethyl 3-(Methylthio)-Cis-2-Propenoate, Ethyl 3-(Methylthio)-2-Propenoate, Ethyl 3-Methylthiopropionate, 2-Ethyl-3-Methylthiopyrazine, Ethyl 3-(Methylthio)-Trans-2-Propenoate, Ethyl 5-(Methylthio) Valerate, Ethyl Methyl-P-Tolylglycidate, 2-Ethyl-(3 Or 5 Or 6)-Mop(85%) And 2-Methyl-(3 Or 5 Or 6)-Mop(13%), Ethyl Myristate, Ethyl Nitrite, N-Ethyl Trans-2-Cis-6-Nonadienamide, Ethyl Nonanoate, Ethyl 2-Nonynoate, Ethyl Octadecanoate, Ethyl Cis-4,7-Octadienoate, (+/−)-4-Ethyloctanal, Ethyl Octanoate, 4-Ethyloctanoic Acid, Ethyl Cis-4-Octenoate, Ethyl 3-Octenoate, Ethyl Trans-2-Octenoate, Ethyl Oleate, 2-Ethyl-3,(5 Or 6)-Dimethylpyrazine, Ethyl 5-Oxodecanoate, Ethyl 3-Oxohexanoate, Ethyl Palmitate, Ethyl 4-Pentenoate, P-Ethylphenol, Ethyl Phenylacetate, Ethyl 4-Phenylbutyrate, Ethyl 3-Phenylglycidate, Ethyl 3-Phenylpropionate, Ethyl Propionate, Ethyl 2-(Methyldithio)Propionate, Ethyl Propyl Disulfide, Ethyl Propyl Trisulfide, 2-Ethylpyrazine, 3-Ethylpyridine, 1-Ethyl-2-Pyrrolecarboxaldehyde, Ethyl Pyruvate, Ethyl Salicylate, Ethyl Sorbate, Ethyl Thioacetate, (+/−)-3-(Ethylthio)Butanol, 2-Ethylthiophenol, Ethyl Tiglate, Ethyl Trans-2-Hexenoate, Ethyl Trans-2-Methyl-2-Pentenoate, 2-Ethyl-1,3,3-Trimethyl-2-Norbornanol, Ethyl Undecanoate, Ethyl 10-Undecenoate, Ethyl Valerate, Ethyl Vanillin, Ethyl Vanillin Beta-D-Glucopyranoside, Ethyl Vanillin Isobutyrate, Ethyl Vanillin Propylene Glycol Acetal, Eucalyptol, *Eucalyptus*, Oil (*Eucalyptus Globulus* Labille), Eugenol, Eugenyl Acetate, Eugenyl Benzoate, Eugenyl Formate, Eugenyl Isovalerate, Eugenyl Methyl Ether, (2e,6z,8e)-N-(2-Methylpropyl)-2,6,8-Decatrienamide, Farnesal, Farnesene, Farnesol, Fatty Acids. Fatty Alcohols, Synthetic, Fd&C Blue No. 2, Fd&C Blue No. 1, Fd&C Blue No. 2, Aluminum Lake, Fd&C Blue No. 1, Aluminum Lake, Fd&C Blue No. 2, Calcium Lake, Fd&C Blue No. 1, Calcium Lake, Fd&C Green No. 3, Fd&C Green No. 3, Aluminum Lake, Fd&C Green No. 3, Calcium Lake, Fd&C Red No. 40, Fd&C Red No. 3, Fd&C Red No. 40, Aluminum Lake, Fd&C Red No. 3, Fd&C Red No. 40, Calcium Lake, Fd&C Red No. 3, Fd&C Yellow No. 6, Fd&C Yellow No. 5, Fd&C Yellow No. 5, Aluminum Lake, Fd&C Yellow No. 6, Aluminum Lake, Fd&C Yellow No. 5, Calcium Lake, Fd&C Yellow No. 6, Calcium Lake, D-Fenchone, Fenchyl Alcohol, Fennel, Common (*Foeniculum Vulgare* Mill.), Fennel, Sweet (*Foeniculum Vulgare* Mill. Var. Dulce (D.C.) Alef.), Fennel, Sweet, Oil (*Foeniculum Vulgare* Mill. Var. Dulce (D.C.) Alef.), Fenugreek (*Trigonella Foenum-Graecum* L.), Fenugreek, Extract (*Trigonella Foenum-Graecum* L.), Fenugreek, Oleoresin (*Trigonella Foenum-Graecum* L.), Ferric Ammonium Citrate, Brown, Ferric Chloride, Ferric Citrate, Ferric Oxide, Ferric Peptonate, Ferric Phosphate, Ferric Pyrophosphate, Ferric Sodium Pyrophosphate, Ferric Sulfate, Ferrocyanide Salts, Ferrous Ascorbate, Ferrous Carbonate, Ferrous Citrate, Ferrous Fumarate, Ferrous Gluconate, Ferrous L-Lactate, Ferrous Lactate, Ferrous Peptonate, Ferrous Sulfate, Ficin, Fir (Pine) Needles And Twigs (*Abies Sibirica* Ledeb.), Fir Needles And Twigs, Oil (*Abies* Spp.), Fish Oil (Hydrogenated), Fish Protein Concentrate, Whole, Fish Protein Isolate, Folic Acid, Formaldehyde, Formic Acid, 2-Formyl-6,6-Dimethylbicyclo(3.1.1)Hept-2-Ene, 4-Formyl-2-Methoxyphenyl 2-Hydroxypropanoate, Fruit Juice, Fullers Earth, Fumaric Acid, Fungal Hemicellulase, Fungal Pectinase, 2-Furanmethanethiol Formate, 4-((Furanmethyl) Thio)-2-Pentanone, Furcelleran, Furcelleran, Ammonium Salt Of, Furcelleran And Salts Of Furcelleran, Furcelleran, Calcium Salt Of, Furcelleran, Potassium Salt Of, Furcelleran, Sodium Salt Of, Furfural, Furfural Propyleneglycol Acetal, Furfuryl Acetate, Furfuryl Alcohol, Furfuryl Butyrate, Furfuryl Decanoate, Furfuryl Formate, 2-Furfurylidenebutyraldehyde, Furfuryl Isopropyl Sulfide, Furfuryl Mercaptan, Furfuryl 3-Methylbutanoate, Furfuryl Methyl Ether, Furfuryl 2-Methyl-3-Furyl Disulfide, Furfuryl Methyl Sulfide, Alpha-Furfuryl Octanoate, Alpha-Furfuryl Pentanoate, Furfuryl Propionate, Furfuryl Propyl Disulfide, N-Furfurylpyrrole, Furfuryl Thioacetate, 1-(2-Furfurylthio)Propanone, Furfuryl Thiopropionate, 3-(2-Furoylthio)-2,5-Dimethylfuran, 1-(2-Furyl)-1,3-Butanedione, 1-(2-Furyl) Butan-3-One, 4-(2-Furyl)-3-Buten-2-One, 2-Furyl Methyl Ketone, Fusel Oil, Refined, Alpha-Galactosidase From Morteirella Vinaceae Raffinoseutilizer, *Galanga*, Greater (*Alpinia Galanga* Willd), Galangal Root (*Alpinia* Spp.), Galangal Root, Extract (*Alpinia* Spp.), Galangal Root, Oil (*Alpinia* Spp.), *Galbanum*, Oil (*Ferula* Spp.), *Galbanum*, Resin (*Ferula* Spp.), Gambir (*Uncaria Gambir* Roxb.), *Gardenia Gummifera* Distillate, Garlic, Garlic Extract, Garlic Oil (*Allium Sativum* L.), Dehydrated Garlic, Garlic Powder, Gelatin, Gellan Gum, Genet Absolute (*Spartium Junceum* L.), Genet Extract (*Spartium Junceum* L.), Gentian Root Extract (*Gentiana Lutea* L.), Gentian, Stemless (*Gentiana Acaulis* L.), Geranic Acid, Geraniol, Geranium (*Pelargonium* Spp.), Geranium, East Indian, Extract (*Cymbopogon Martini* Stapf.), Geranium, East Indian, Oil (*Cymbopogon Martini* Stapf.), Geranium Extract (*Pelargonium* Spp.), Geranium, Oil (*Pelargonium* Spp.), Geranium, Rose, Oil (*Pelargonium Graveolens* L'her.), Geranyl Acetate, Geranyl Acetoacetate, Geranyl Acetone, Geranyl Benzoate, Geranyl Butyrate, Geranyl Formate, Geranyl Hexanoate, Geranyl Isobutyrate, Geranyl Isovalerate, Geranyl 2-Methylbutyrate, Geranyl Phenylacetate, Geranyl Propionate, Geranyl Tiglate, Geranyl Valerate, Germander, *Chamaedrys* (*Teucrium Chamaedrys* L.), Germander, *Chamaedrys*, Extract (*Teucrium Chamaedrys* L.), Germander, *Chamaedrys*, Extract Solid (*Teucrium Chamaedrys* L.), Germander, Golden (*Teucrium Polium* L.), Ghatti, Gum (*Anogeissus Latifolia* Wall.), Gibberellic Acid & Potassium Gibberellate, Ginger (*Zingiber Officinale* Rosc.), Ginger, Extract (*Zingiber Officinale* Rosc.), Ginger, Oil (*Zingiber Officinale* Rosc.), Ginger, Oleoresin (*Zingiber Officinale* Rosc.), D-Gluconic Acid, Glucono-Delta Lactone, N-Gluconyl Ethanolamine, N-Gluconyl Ethanolamine Phosphate, Glucose Isomerase From *Bacillus Coagulans*, Glucose Isomerase From Immobilized *Arthrobacter Globiformis*, Glucose Isomerase From *Streptomyces Olivaceus*, Glucose Isomerase From *Streptomyces Olivochromogenes*, Glucose Isomerase From *Streptomyces Rubiginosus*, Glucose Oxidase Catalase Preparation, Glucose Oxidase From *Aspergillus Niger*, Glucose Oxidase From *Penicillium Notatum*, Glucose Pentaacetate, Glucosidase From *Aspergillus Flavus*, Glucosidase From *Aspergillus Niger*, Glucosidase From *Aspergillus Oryzae*, L-Glutamic Acid, Glutamic Acid Hydrochloride, L-Glutamine, Gamma-Glutamyl-Valyl-*Glycine*, Glutaraldehyde, Gluten, Gum, Glycerin, Glycerin, Synthetic, Glycerol Tributyrate, Glyceryl Behenate, Glyceryl 5-Hydroxydecanoate, Glyceryl 5-Hydroxydodecanoate, Glyceryl-Lacto Esters Of Fatty Acids, Glyceryl Lactooleate, Glyceryl Lactopalmitate, Glyceryl Monooleate, Glyceryl Monostearate, Glyceryl Palmitostearate, Glyceryl Tribenzoate, Glyceryl Tripropanoate, Glyceryl Tristearate, *Glycine*, Glycocholic Acid, Glycyrrhizin, Ammoniated (*Glycyrrhiza* Spp.), Grains Of Paradise (*Aframomum Melegueta* (Rosc.) K. Schum.), Grape Color Extract, Grape Essence, Natural, Grapefruit Essence, Natural, Grapefruit, Extract, Grapefruit, Juice, Grapefruit, Oil (*Citrus Paradisi* Macf.), Grapefruit Oil, Conc., Grapefruit, Oil, Terpeneless (*Citrus Paradisi*), Grape Seed Extract, Grape Skin Extract, Ground Limestone, Guaiac Gum (*Guaiacum* Spp.), Guaiac Gum, Extract (*Guaiacum* Spp.), Guaiacol, Guaiacol Butyrate, Guaiacol Propionate, Guaiac Wood, Extract (*Guaiacum* Spp.), Guaiac Wood, Oil (*Guaiacum* Spp.), Guaiacyl Acetate, Guaiacyl Isobutyrate, Guaiacyl Phenylacetate, Guaiene, Guaiol Acetate, Guarana, Gum (Paullinia Cupana Hbk), Guarana Seed, Extract, Guar, Gum (*Cyamopsis Tetragonolobus* (L.)), Guava (*Psidium* Spp.), Guava Extract, Gum Arabic, Hydrogen Octenylbutane Dioate, Gutta Hang Kang (Palaquium Leiocarpum Boerl. And P. Oblongifolium Burck.), Haematococcus Algae Meal, Haw Bark, Black, Extract (*Viburnum Prunifolium* L.), *Heliopsis Longipes* Extract, Helium, Hemlock (*Tsuga* Spp.), Hemlock Needles And Twigs, Oil (*Tsuga* Spp.), 2,4-Heptadienal, Trans-2-Trans-4-Heptadien-1-ol, Gamma-Heptalactone, Heptanal, Heptanal Dimethyl Acetal, Heptanal Glyceryl Acetal (Mixed 1,2 And 1,3 Acetals), Heptanal Propyleneglycol Acetal, 2,3-Heptanedione, 2-Heptanethiol, Heptane-1-Thiol, Heptanoic Acid, 2-Heptanol, 3-Heptanol, 2-Heptanone, 3-Heptanone, 4-Heptanone, N-(Heptan-4-Yl)Benzo[D][1,3]Dioxole-5-Carboxamide, 2-Heptenal, 4-Heptenal Diethyl Acetal, (E)-2-Heptenoic Acid, (+/−)-1-Hepten-3-Ol, (Z)-4-Hepten-1-Ol, 3-Hepten-2-One, 2-Hepten-4-One, Hept-Trans-2-En-1-Y1 Acetate, Hept-2-En-1-Yl Isovalerate, Trans-3-Heptenyl 2-Methylpropanoate, 3-Heptyl Acetate, Heptyl Acetate, Heptyl Alcohol, Heptyl Butyrate. 2-Heptyl Butyrate, Heptyl Cinnamate, Cis- And Trans-2-Heptylcyclopropanecarboxylic Acid, 3-Heptyldihydro-5-Methyl-2(3h)-Furanone, Heptyl Formate, 2-Heptylfuran, Heptyl Heptanoate, Heptyl Isobutyrate, Heptyl Octanoate, Heptylparaben, Hesperidin, Delta-Hexadecalactone, Omega-6-Hexadecenlactone, Hexadecyl Lactate, Trans, Trans-2,4-Hexadienal, 2,4-Hexadien-1-ol, 2,4-Hexadienyl Acetate, 2,4-Hexadienyl Butyrate, 2,4-Hexadienyl Isobutyrate, 2,4-Hexadienyl Propionate, Delta-Hexalactone, Gamma-Hexalactone, Hexanal, Hexanal Butane-2,3-Diol Acetal, Hexanal Dihexyl Acetal, Hexanal Hexyl Isoamyl Acetal, Hexanal Octane-1,3-Diol Acetal, Hexane, 2,3-Hexanedione, 3,4-Hexanedione, 1,6-Hexanedithiol, 1-Hexanethiol, Hexanoic Acid, 3-Hexanol, 3-Hexanone, Cis-3-Hexenal, Trans-4-Hexenal, 3-Hexenal, Cis-4-Hexenal, Trans-3-Hexenal, 2-Hexenal, (+/−)-Trans- And Cis-2-Hexenal Glyceryl Acetal, (E)-2-Hexenal Diethyl Acetal, 4-Hexene-3-One, (Z)-3-Hexenyl (E)-2-Hexenoate, Trans-2-Hexenoic Acid, 3-Hexenoic Acid, 1-Hexen-3-Ol, 2-Hexen-1-ol, 4-Hexen-1-Ol, 5-Hexenol, (Z)-2-Hexen-1-O, (Z)-3-Hexenyl Anthranilate, Cis-3-Hexenyl Benzoate, (E)-2-Hexenyl Butyrate, 3-Hexenyl Crotonate, Cis-, (E)-2-Hexenyl Formate, 2-Hexenyl Hexanoate, Trans-, (Z)-3-Hexenyl Isobutyrate, 5-Hexenyl Isothiocyanate, (E)-2-Hexenyl Isovalerate, 3-Hexenyl Isovalerate, Cis-3-Hexenyl Lactate, 3-Hexenyl 2-Methylbutyrate, 2-Hexenyl Octanoate, 3-Hexenyl Phenylacetate, (E)-2-Hexenyl Propionate, Cis-3 & Trans-2-Hexenyl Propionate, (Z)-3-Hexenyl Propionate, (Z)-3-Hexenyl Pyruvate, (Z)-3-Hexenyl Valerate, (E)-2-Hexenyl Valerate, Hexyl Acetate, 2-Hexyl-4-Acetoxytetrahydrofuran, Hexyl Alcohol, Hexylamine, Hexyl Benzoate, N-Hexyl 2-Butenoate, Hexyl Butyrate, Alpha-Hexylcinnamaldehyde, Hexyl Decanoate, 2-Hexyl-4,5-Dimethyl-1,3-Dioxolane, Hexyl Formate, Hexyl 2-Furoate, Hexyl Heptanoate, Hexyl Hexanoate, Hexyl Trans-2-Hexenoate, 2-Hexylidene Cyclopentanone, 2-Hexylidenehexanal, Hexyl Isobutyrate, Hexyl Isothiocyanate, Hexyl Isovalerate, 2-Hexyl-5 Or 6-Keto-1,4-Dioxane, Hexyl 3-Mercaptobutanoate, Hexyl 2-Methylbutyrate, Hexyl 2-Methyl-3(Or 4)-Pentenoate, Hexyl Nonanoate, Hexyl Octanoate, Hexyl Phenylacetate, Hexyl Propionate, 2-Hexylthiophene, Hickory Bark, Extract (*Carya* Spp.), Hickory Smoke Dist., High Fructose Corn Syrup, L-Histidine, (−)-Homoeriodictyol, Sodium Salt, Honeysuckle Extract, Hops, Extract (*Humulus Lupulus* L.), Hops Extract, Modified, Hops, Extract Solid (*Humulus Lupulus* L.), Hops, Oil (*Humulus Lupulus* L.), Horehound Extract (*Marrubium Vulgare* L.), Horehound (*Marrubium Vulgare* L.), Horehound Solid, Extract, Horsemint Leaves, Extract (*Monarda* Spp.), Horseradish (*Armoracia* Lapathifolia Gilib.), Horseradish Oil, Hyacinth, Absolute (*Hyacinthus Orientalis* L.), Hyacinth Flowers (*Hyacinthus Orientalis* L.), Hydratropic Aldehyde Propylene Glycol Acetal, Hydrazine, Hydrochloric Acid, Hydrogen Peroxide, Hydrogen Sulfide, Hydroquinone Monoethyl Ether, Hydroxyacetone, 4-Hydroxyacetophenone, 2-Hydroxyacetophenone, 4-Hydroxybenzaldehyde, 4-Hydroxybenzoic Acid, 3-Hydroxybenzoic Acid, 4-Hydroxybenzyl Alcohol, 4-Hydroxybutanoic Acid Lactone, 1-Hydroxy-2-Butanone, 4-Hydroxy-2-Butenoic Acid Gamma-Lactone, 6-Hydroxycarvone, Hydroxycitronellal, Hydroxycitronellal Diethyl Acetal, Hydroxycitronellal Dimethyl Acetal, Hydroxycitronellal Propyleneglycol Acetal, Hydroxycitronellol, 2-Hydroxy-2-Cyclohexen-1-One, 5-Hydroxy-2,4-Decadienoic Acid Delta-Lactone, 5-Hydroxy-2-Decenoic Acid Delta-Lactone, 5-Hydroxy-7-Decenoic Acid Delta-Lactone, 6-Hydroxydihydrotheaspirane, 4-Hydroxy-3,5-Dimethoxybenzaldehyde, 4-Hydroxy-2,5-Dimethyl-3(2h)-Furanone, 4-Hydroxy-2,3-Dimethyl-2,4-Nonadienoic Acid Gamma Lactone, 6-Hydroxy-3,7-Dimethyloctanoic Acid Lactone, (Z)-4-Hydroxy-6-Dodecenoic Acid Lactone, 5-Hydroxy-2-Dodecenoic Acid Lactone, 1-Hydroxyethylidene-1, 1-Diphosphonic Acid, 4-Hydroxy-4-(3-Hydroxy-1-Butenyl)-3,5,5-Trimethyl-2-Cyclohexen-1-One, Hydroxy(4-Hydroxy-3-Methoxyphenyl)Acetic Acid, 1-(2-Hydroxy-4-Isobutoxyphenyl)-3-(Pyridin-2-Yl)Propan-1-One, Hydroxylated Lecithin, 2-Hydroxy-4-Methoxybenzaldehyde, N-(4-Hydroxy-3-Methoxybenzyl)-8-Methyl-6-Nonenamide, 1-(4-Hydroxy-3-Methoxyphenyl)Decan-3-One, 1-(2-Hydroxy-4-Methoxyphenyl)-3-(Pyridin-2-Yl)Propan-1-One, 2-Hydroxy-5-Methylacetophenone, 2-Hydroxy-4-Methylbenzaldehyde, 2-(2-Hydroxy-4-Methyl-3-Cyclohexenyl)Propionic Acid Gamma-Lactone, 4-Hydroxy-4-Methyl-7-Cis-Decanoic Acid Gamma Lactone, 2-Hydroxymethyl-6,6-Dimethylbicyclo(3.1.1)Hept-2-Enyl Formate, 4-Hydroxymethyl-2,6-Di-Tertbutylphenol, 10-Hydroxymethylene-2-Pinene, 4-Hydroxy-5-Methyl-3(2h)-Furanone, 3-(Hydroxymethyl)-2-Heptanone, 5-Hydroxy-4-Methylhexanoic Acid Delta-Lactone, 3-Hydroxy-5-Methyl-2-Hexanone, 2-Hydroxy-5-Methyl-3-Hexanone, 4-Hydroxy-4-Methyl-5-Hexenoic Acid Gamma Lactone, (?)-3-Hydroxy-3-Methyl-2,4-Nonanedione, 4-Hydroxy-3-Methyloctanoic Acid Lactone, 1-Hydroxy-4-Methyl-2-Pentanone, 1-(3-Hydroxy-5-Methyl-2-Thienyl)Ethanone, Hydroxynonanoic Acid, Delta-Lactone, 3-Hydroxy-2-Octanone, 5-Hydroxy-4-Octanone, 3-Hydroxy-2-Oxopropionic Acid, 3-Hydroxy-2-Pentanone, 4-Hydroxy-3-Pentenoic Acid Lactone, 4-(P-Hydroxyphenyl)-2-Butanone, 3-Hydroxy-4-Phenylbutan-2-One, 2-(2-Hydroxyphenyl) Cyclopropanecarboxylic Acid Delta Lactone, 1-(2-Hydroxyphenyl)-3-(Pyridin-4-Yl)Propan-1-One, (+/−)-2-Hydroxypiperitone, L-Hydroxyproline, Hydroxypropyl Cellulose, Hydroxypropyl Methylcellulose, 2-Hydroxy-3,5,5-Trimethyl-2-Cyclohexenone, 5-Hydroxyundecanoic Acid Lactone, 5-Hydroxy-8-Undecenoic Acid Delta-Lactone, Hyssop, Extract (*Hyssopus Officinalis* L.), Hyssop (*Hyssopus Officinalis* L.), Hyssop, Oil (*Hyssopus Officinalis* L.), Iceland Moss (*Cetraria Islandica* Ach.), Immortelle, Absolute (*Helichrysum Angustifolium* Dc), Immortelle, Extract (*Helichrysum Angustifolium* Dc.), Imperatoria (*Peucedanum Ostruthium* (L.) Koch (*Imperatoria Ostruthium* L.)), Indole, Inositol, Insoluble Glucose Isomerase Enzyme Preparations, Invertase From *Saccharomyces Cerevisiae*, Invert Sugar, Invert Sugar Syrup, Alpha-Ionene, Ion Exchange Membranes, Ion Exchange Resin, Beta-Ionol, Alpha-Ionol, Beta-Ionone, Gamma-Ionone, Alpha-Ionone, Beta-Ionone Epoxide, Beta-Ionyl Acetate, Iron Ammonium Citrate, Iron Caprylate, Iron-Choline Citrate Complex, Iron Citrate, Alpha-Irone, Iron, Elemental, Iron Linoleate, Iron Naphthenate, Iron Oxide, Iron Peptonate, Iron Polyvinylpyrrolidone, Iron Tallate, Isoambrettolide, Isoamyl Acetate, Isoamyl Acetoacetate, Isoamyl Alcohol, Isoamyl Benzoate, Isoamyl Butyrate, Isoamyl Cinnamate, Isoamyl Formate, Isoamyl 4-(2-Furan)Butyrate, Isoamyl 3-(2-Furan)Propionate, Isoamyl Hexanoate, Isoamyl Isobutyrate, Isoamyl Isothiocyanate, Isoamyl Isovalerate, Isoamyl Laurate, Isoamyl Levulinate, Isoamyl 2-Methylbutyrate, Isoamyl Nonanoate, Isoamyl Octanoate, Isoamyl Phenethyl Ether, Isoamyl Phenylacetate, Isoamyl Propionate, Isoamyl Pyruvate, Isoamyl Salicylate, Isoborneol, Isobornyl Acetate, Isobornyl Formate, Isobornyl Isobutyrate, Isobornyl Isovalerate, Isobornyl 2-Methylbutyrate, Isobornyl Propionate, Isobutane, Isobutyl Acetate, Isobutyl Acetoacetate, Isobutyl Alcohol, Isobutylamine, Isobutyl Angelate, Isobutyl Anthranilate, Isobutyl Benzoate, Isobutyl 2-Butenoate, Isobutyl Butyrate. Isobutyl Cinnamate, N-Isobutyldeca-Trans-2-Trans-4-Dienamide, 2(4)-Isobutyl-4(2),6-Dimethyldihydro-4h-1,3,5-Dithiazine, 2-Isobutyl-4,5-Dimethyloxazole, Isobutylene-Isoprene Copolymer, Isobutyl Formate, Isobutyl 2-Furanpropionate, Isobutyl Heptanoate, Isobutyl Hexanoate, Isobutyl Isobutyrate, Isobutyl Isothiocyanate, 2-Isobutyl-3-Methoxypyrazine, Isobutyl N-Methylanthranilate, 2-Isobutyl-3-Methylpyrazine, (+/−)-Isobutyl 3-Methylthiobutyrate, Isobutyl Phenylacetate, Isobutyl Propionate, Isobutyl Salicylate, 2-Isobutylthiazole, Isobutyl 10-Undecenoate, Isobutyraldehyde, Isobutyric Acid, Isocyclocitral, Isoeugenol, Isoeugenyl Acetate, Isoeugenyl Benzyl Ether, Isoeugenyl Ethyl Ether, Isoeugenyl Formate, Isoeugenyl Methyl Ether, Isoeugenyl Phenylacetate, Isojasmone, L-Isoleucine, Alpha-Isomethylionone, Beta-Isomethylionone, Alpha-Isomethylionyl Acetate, Isoparaffinic Petroleum Hydrocarbons, Synthetic, Isopentylamine, Isopentylideneisopentylamine, Isophorone, Isopropenyl Acetate, 5-Isopropenyl-2-Methyl-2-Vinyltetrahydrofuran, 3-Isopropenyl-6-Oxoheptanoic Acid, 3-Isopropenylpentanedioic Acid, Isopropenylpyrazine, Isopropyl Acetate, P-Isopropylacetophenone, Isopropyl Alcohol, Isopropylamine, Isopropyl Benzoate, P-Isopropylbenzyl Alcohol, Isopropyl Butyrate, Isopropyl Cinnamate, Isopropyl Citrate, Isopropyl-2-Cyclohexenone, 5-Isopropyl-2,6-Diethyl-2-Methyltetrahydro-2h-Pyran, 2(4)-Isopropyl-4(2),6-Dimethyldihydro-4h-1,3,5-Dithiazine, Isopropyl Formate, Isopropyl Hexanoate, Isopropylideneglyceryl 5-Hydroxydecanoate, Isopropyl Isobutyrate, Isopropyl Isothiocyanate, Isopropyl Isovalerate, S-Isopropyl 3-Methylbut-2-Enethioate, Isopropyl 2-Methylbutyrate, 2-Isopropyl-5-Methyl-2-Hexenal, (+/−)-[R-(E)]-5-Isopropyl-8-Methylnona-6,8-Dien-2-One, 2-Isopropyl-4-Methylthiazole, Isopropyl Myristate, Isopropyl Palmitate. 2-Isopropylphenol. P-Isopropylphenylacetaldehyde, Isopropyl Phenylacetate, 3-(P-Isopropylphenyl)Propionaldehyde, Isopropyl Propionate, 2-Isopropylpyrazine, Isopropyl Tiglate, 2-Isopropyl-N,2,3-Trimethylbutyramide, Isopulegol, Isopulegone, Isopulegyl Acetate, Isoquercitrin, Enzymatically Modified, Isoquinoline, Isovaleraldehyde Diethyl Acetal, Isovaleraldehyde Glyceryl Acetal, Isovaleric Acid, Iva (*Achillea Moschata* Jacq.), Iva, Extract (*Achillea Moschata* Jacq.), Jambu Oleoresin, Japan Wax, Jasmine, Absolute (*Jasminum* Spp.), Jasmine, Concrete (*Jasminum* Spp.), Jasmine, Oil (*Jasminum Grandiflorum* L.), Jasmine, Spiritus (*Jasminum Grandiflorum* L.), Jasmone, Cis-, Jelutong (*Dyera Costulata* Hook, F. And D. Lowii Hook, F.), Juniper (Berries) (*Juniperus Communis* L.), Juniper, Extract (*Juniperus Communis* L.), Juniper Oil (*Juniperus Communis* L.), Karaya, Gum (*Sterculia Urens* Roxb.), Kelp, 2-Keto-4-Butanethiol, Alpha-Ketobutyric Acid, Kola Nut, Extract (Cola *Acuminata* Schott Et Endl.), Labdanum, Absolute (*Cistus* Spp.), Labdanum, Oil (*Cistus* Spp.), Labdanum, Oleoresin (*Cistus* Spp.), Lactalbumin, Lactalbumin Phosphate, Lactase From *Saccharomyces Fragilis*, Lactase From *Saccharomyces* (*Kluyveromyces*) *Lactis*, Lactase Preparation, *Candida Pseudotropicalis*, Lactic Acid, Lactose, Lactose, Hydrolyzed, N-Lactoyl Ethanolamine, N-Lactoyl Ethanolamine Phosphate, Lactylated Fatty Acid Esters Of Glycerol And Propylene Glycol, Lactylic Esters Of Fatty Acids, Lanolin, Lard, Lard Oil, Laurel Berries (*Laurus Nobilis* L.), Lauric Acid, Lauric Aldehyde, Lauroyl Diethanolamide, Lauryl Acetate, Lauryl Alcohol, Lavandin Absolute, Lavandin, Concrete, Lavandin, Oil, Lavender, Absolute (*Lavandula Officinalis* Chaix), Lavender, Concrete (*Lavandula Officinalis* Chaix), Lavender (*Lavandula Officinalis* Chaix), Lavender, Oil (*Lavandula Officinalis* Chaix), Lavender, Spike (*Lavandula Latifolia* Bill.), Lavender, Spike, Oil (*Lavandula* Spp.), Leche Caspi (*Couma Macrocarpa* Barb. Rodr.), Leche De Vaca (Brosimum Utile (H.B.K.) Pittier, And *Poulsenia* Spp.), Lecithin, Lecithin, Benzoyl Peroxide Modified, Lecithin, Enzyme-Modified, Lecithin, Hydrogen Peroxide Modified, Lecithin (Vegetable), Leek Oil, Lemon Essence, Lemon, Extract (*Citrus Limon* (L.) Burm. F.), Lemon Grass, Oil (*Cymbopogon Citratus* Dc. And *Cymbopogon Flexuosusstapf*), Lemon, Juice, Lemon, Oil (*Citrus Limon* (L.) Burm. F.), Lemon, Oil, Terpeneless (*Citrus Limon* (L.) Burm. F.), Lemon Peel Extract, Lemon Peel Granules, Lemon Terpenes, Lemon-*Verbena* (*Lippia Citriodora* Hbk.), Lemon *Verbena*, Oil (*Lippia Citriodora*), Lepidine, L-Leucine, Levulinic Acid, Levulose, L-Fenchone, Licorice Extract (*Glycyrrhiza* Spp.), Licorice Extract Powder (*Glycyrrhiza* Spp.), Licorice (*Glycyrrhiza* Spp.), Lignin, Lignin Sodium Sulfonate, Lignosulfonic Acid, Lime, Essence, Lime, Juice, Lime Juice, Dehydrated, Lime Oil, Distilled, Lime Oil, Expressed, Lime, Oil, Terpeneless (*Citrus Aurantifolia* (Christman) Swingle), L-Limonene, D-Limonene, Dl-Limonene, Linaloe Wood, Oil (*Bursera Delpechiana Poiss*. And Other *Bursera* Spp.), Linalool, Linalool Oxide, Linalool Oxide Pyranoid, Linalyl Acetate, Linalyl Anthranilate, Linalyl Benzoate, Linalyl Butyrate, Linalyl Cinnamate, Linalyl Formate, Linalyl Hexanoate, Linalyl Isobutyrate, Linalyl Isovalerate, Linalyl Octanoate, Linalyl Phenylacetate, Linalyl Propionate, Linden Flowers, Extract (*Tilia* Spp.), Linden Flowers (*Tilia Glabra* Vent.), Linden Leaves (*Tillia* Spp.), Linoleic Acid, Lipase, Lipase From Animal Tissue, Lipase From *Aspergillus Niger*, Lipase From *Aspergillus Oryzae*, Lipase From *Rhizopus Niveus, Listeria*-Specific Bacteriophage Preparation, *Litsea Cubeba* Berry Oil, L-Menthyl Butyrate, Locust (Carob) Bean Gum, Lovage, Extract (*Levisticum Officinale* Koch), Lovage (*Levisticum Officinale* Koch), Lovage, Oil (*Levisticum Officinale* Koch), L-8-P-Menthene-1,2-Epoxide, Lungmoss (*Sticta Pulmonacea* Ach.), Luo Han Fruit Concentrate, Lupulin (*Humulus Lupulus* L.), L-Lysine, Mace (*Myristica Fragrans* Houtt.), Mace. Oil (*Myristica Fragrans* Houtt.), Mace, Oleoresin (*Myristica Fragrans* Houtt.), Magnesium Caprate, Magnesium Caprylate, Magnesium Carbonate, Magnesium Chloride, Magnesium Fumarate, Magnesium Gluconate, Magnesium Glycerophosphate, Magnesium Hydroxide, Magnesium Laurate, Magnesium Myristate, Magnesium Oleate, Magnesium Oxide, Magnesium Palmitate, Magnesium Phosphate, Dibasic, Magnesium Phosphate, Tribasic, Magnesium Salts Of Fatty Acids, Magnesium Silicate, Magnesium Stearate, Magnesium Sulfate, Magnolol, Maidenhair Fern (Adiantum *Capillus-Veneris* L.), L-Malic Acid, Malic Acid, Malt, Maltodextrin, Maltol, Maltol Propionate, Maltose, Malt Syrup (Malt Extract), Maltyl Isobutyrate, Mandarin, Oil (*Citrus Reticulata* Blanco), Manganese Chloride, Manganese Citrate, Manganese Gluconate, Manganese Glycerophosphate, Manganese Hypophosphite, Manganese Sulfate, Manganous Oxide, Mannitol, Marigold, Pot (*Calendula Officinalis* L.), Marjoram, Oleoresin (*Marjorana Hortensis* Moench (*Origanum Majorana* L.)), Marjoram, Pot (*Majorana Onites* (L.) Benth. (*Origanum Vulgare* L.)), Marjoram Seed (*Majorana Hortensis* Moench (*Origanum Majorana* L.)), Marjoram, Sweet (*Majorana Hortensis* Moench (*Origanum Majorana* L.)), Marjoram, Sweet, Oil (*Majorana Hortensis* Moench (*Origanum Majorana* L.)), *Massaranduba Balata* (*Manilkara Huberi* (Ducke) Chevalier), *Massaranduba Balata*, Solvent-Free Resin Extract, *Massaranduba* Chocolate (*Manilkara Solimoesensis Gilly*), *Massoia* Bark Oil, Mastic Gum, Mate, Absolute (*Ilex Paraguariensis* St. Hil.), Mate, Leaves, Menadiol Sodium Diphosphate, Menhaden Oil, Menhaden Oil, Hydrogenated, Menhaden Oil, Partially Hydrogenated, D-2,8-P-Menthadien-1-Ol, Menthadienol, P-*Mentha*-1,8-Dien-7-Ol, Cis- And Trans-P-1(7),8-Menthadien-2-Yl Acetate, P-Menthan-2-One, P-*Mentha*-8-Thiol-3-One, P-Menth-1-Ene-9-Al, 8-P-Menthene-1,2-Diol, 1-P-Menthene-8-Thiol, P-Menth-1-En-3-Ol, P-Menth-3-En-1-Ol, 1-P-Menthen-9-Yl Acetate, Menthol, Menthone, Menthone 1,2-Glycerol Ketal, L-Menthone 1,2-Glycerol Ketal, Menthone-8-Thioacetate, 2-(L-Menthoxy)Ethanol, 3-(L-Menthoxy)-2-Methylpropane-1,2-Diol, 3-L-Menthoxypropane-1,2-Diol, Menthyl Acetate, L-Menthyl Acetoacetate, L-Menthyl Ethylene Glycol Carbonate, Menthyl Formate, L-Menthyl (R,S)-3-Hydroxybutyrate, Menthyl Isovalerate, L-Menthyl Lactate, 1-Menthyl Methyl Ether, 2-[2-(P-Menthyloxy)Ethoxy]Ethanol, Menthyl Propionate, Menthyl Propylene Glycol Carbonate, L-Menthyl 1,2-Propylene Glycol Carbonate, Menthyl Pyrrolidonecarboxylate, Menthyl Valerate. 2-Mercaptoanisole, 2-Mercapto-3-Butanol, 3-Mercapto-2-Butanone, (+/−)-3-Mercapto-1-Butyl Acetate, 2-Mercaptoethanol, 3-Mercaptoheptyl Acetate, 3-Mercaptohexanal, 3-Mercaptohexanol, 3-Mercaptohexyl Acetate, 3-Mercaptohexyl Butyrate, 3-Mercaptohexyl Hexanoate, 4-Mercapto-3-Methyl-2-Butanol, 3-Mercapto-2-Methyl-1-Butanol, 3-Mercapto-3-Methyl-1-Butanol, 3-Mercapto-3-Methyl-1-Butyl Acetate, 3-Mercapto-3-Methylbutyl Formate, 3-Mercapto-3-Methylbutyl Isovalerate, 4-Mercapto-4-Methyl-2-Hexanone, 3-Mercapto-2-Methylpentanal, 3-Mercapto-2-Methyl-1-Pentanol, (+/−)-4-Mercapto-4-Methyl-2-Pentanol, 2-Mercapto-2-Methyl-1-Pentanol, 4-Mercapto-4-Methyl-2-Pentanone, 2-Mercaptomethylpyrazine, 3-Mercapto-2-Pentanone, 4-Mercapto-2-Pentanone, 2,3 Or 10-Mercaptopinane, 1-Mercapto-2-Propanone, 2-Mercaptopropionic Acid, 3-Mercaptopropionic Acid, Mesquite Wood Extract, Methacrylic Acid-Divinylbenzene Copolymer, Methional Diethyl Acetal, L-Methionine, Dl-Methionine, Methionyl Butyrate, L-Methionylglycine, 2-Methoxyacetophenone, P-Methoxy-Alpha-Methylcinnamaldehyde, O-Methoxybenzaldehyde, P-Methoxybenzaldehyde, 4-Methoxybenzoic Acid, 3-Methoxybenzoic Acid, 2-Methoxybenzoic Acid, P-Methoxycinnamaldehyde, O-Methoxycinnamaldehyde, Trans- And Cis-1-Methoxy-1-Decene, (S1)-Methoxy-3-Heptanethiol, 2-Methoxy-(3 Or 5 Or 6)-Isopropylpyrazine, N1-(2-Methoxy-4-Methylbenzyl)-N2-(2-(5-Methylpyridin-2-Yl)Ethyl)Oxalamide, N1-(2-Methoxy-4-Methylbenzyl)-N2-(2-(Pyridin-2-Yl) Ethyl)Oxalamide, 4-Methoxy-2-Methyl-2-Butanethiol, 2-Methoxy-4-Methylphenol, (2 Or 5 Or 6)-Methoxy-3-Methylpyrazine (Mixture Of Isomers), 4-(P-Methoxyphenyl)-2-Butanone, 1-(P-Methoxyphenyl)-1-Penten-3-One, 2-Methoxy-6-(2-Propenyl)Phenol, 2-Methoxy-4-Propylphenol, 2-Methoxy-3-(1-Methylpropyl)Pyrazine, Methoxypyrazine, 2-Methoxypyridine, 6-Methoxyquinoline, 2-Methoxy-4-Vinylphenol, Methyl Methacrylate, Methyl Acetate, 4'-Methylacetophenone, 2-Methylacetophenone, Methyl 1-Acetoxycyclohexyl Ketone, (+/−)-Methyl 5-Acetoxyhexanoate, Methyl 3-Acetoxy-2-Methylbutyrate, Methyl 3-Acetoxyoctanoate, Methyl N-Acetylanthranilate, 1-Methyl-2-Acetylpyrrole, 2-Methyl-3-(2-Furyl)Acrolein, Methyl Acrylate, Methyl Acrylate-Divinylbenzene, Completely Hydrolyzed, Copolymer, Methyl Acrylate-Dvb-Acrylonitrile, Completely Hydrolyzed, Terpolymer, Methyl Acrylate-Dvb(3.5%), Copolymer, Aminolyzed With Dmapa, Methyl Acrylate-Dvb(2%), Copolymer, Aminolyzed With Dmapa, Methyl Acrylate—Dvb-(Deg-Divinyl Ether), Aminolyzed And Quarternized, Terpolymer, Methyl Acrylate-Dvb-(Deg-Divinyl Ether), Aminolyzed, Terpolymer, Methyl Alcohol, 2-Methylallyl Butyrate, Methyl-Alpha-Ionone, Methyl Anisate, P-Methylanisole, O-Methylanisole, Methyl Anthranilate, Methylated Silica, 4-Methylbenzaldehyde Propyleneglycol Acetal, Methyl Benzoate, 2-Methylbenzofuran, S-Methyl Benzothioate, 2-Methyl-4,5-Benzoxazole, Alpha-Methylbenzyl Acetate, Methylbenzyl Acetate (Mixed O-, M-, P-), Alpha-Methylbenzyl Alcohol, 4-Methylbenzyl Alcohol, Methyl Benzyl Disulfide, Alpha-Methylbenzyl Formate, Alpha-Methylbenzyl Propionate, 4-Methylbiphenyl, 3-Methylbutanethiol, 3-Methyl-2-Butanethiol, 2-Methyl-1-Butanethiol, 3-Methyl-2-Butanol, 2-Methyl-1-Butanol, 2-Methyl-2-Butenal, 3-Methyl-2-Butenal, (Z)-3-Hexenyl(E)-2-Methyl-2-Butenoate, Trans-2-Methyl-2-Butenoic Acid, 2-Methylbut-2-En-1-Ol, 3-Methyl-2-Buten-1-Ol, 2-Methyl-3-Buten-2-Ol, 3-Methyl-3-Buten-2-One, 3-Methyl-3-Butenyl Acetate, 2-Methylbutyl Acetate, 2-Methylbutylamine, 2-Methylbutyl Isovalerate, 2-Methylbutyl 3-Methyl-2-Butenoate, 2-Methylbutyl 2-Methylbutyrate, 3-Methylbutyraldehyde, 2-Methylbutyraldehyde, Methyl Butyrate, 2-Methylbutyric Acid, Alpha-Methylcinnamaldehyde, P-Methylcinnamaldehyde, Methyl Cinnamate, 4-Methyl-Cis-2-Pentene, 6-Methylcoumarin, 3-Methylcrotonic Acid, 2-Methyl-1,3-Cyclohexadiene, 1-Methyl-2,3-Cyclohexadione, Methyl Cyclohexanecarboxylate, 4-Methylcyclohexanone, 3-Methylcyclohexanone, 2-Methylcyclohexanone, 3-Methyl-2-Cyclohexen-1-One, N-(2-Methylcyclohexyl)-2,3,4,5,6-Pentafluorobenzamide, 3-Methyl-1-Cyclopentadecanone, Methylcyclopentenolone, 1-Methyl-1-Cyclopenten-3-One, Methyl(E)-2-(Z)-4-Decadienoate, 3-Methyl-Gamma-Decalactone, Gamma-Methyldecalactone, Methyl 2-Decenoate, Methyl-Delta-Ionone, 5h-5-Methyl-6,7-Dihydrocyclopenta(B)Pyrazine, 2-Methyl-4,5-Dihydrofuran-3-Thiol, Methyl Dihydrojasmonate, 4-Methyl-2,6-Dimethoxyphenol, Methyl N,N-Dimethylanthranilate, Methyl 3,7-Dimethyl-6-Octenoate, Methyl Disulfide, 2-Methyl-1,3-Dithiolane, 1-(Methyldithio)-2-Propanone, Methylene Chloride, 4-(3,4-Methylenedioxyphenyl)-2-Butanone, 3-(3,4-Methylenedioxyphenyl)-2-Methylpropanal, Methyl Esters Of Fatty Acids (Edible), 2-Methyl-(3 Or 5 Or 6)-Ethoxypyrazine, Methyl Ethyl Sulfide, Methyl Ethyl Trisulfide, Methyl N-Formylanthranilate, 2-Methylfuran, 2-Methyl-3-(Methylthio)Furan, 2-Methyl-5-(Methylthio)Furan, 5-Methyl-3(2h)-Furanone, 2-Methyl-3-Furanthiol, Methyl Furfuracrylate, 5-Methylfurfural, 5-Methylfurfuryl Alcohol, Methyl Furfuryl Disulfide, 5-Methylfurfurylmercaptan, Methyl 3-(Furfurylthio)Propionate, Methyl 2-Furoate, 3-(5-Methyl-2-Furyl)-Butanal, 2-Methyl-3-Furyl 2-Methyl-3-Tetrahydrofuryl Disulfide, 2-Methyl-3-Furyl Methylthiomethyl Disulfide, 3-(5-Methyl-2-Furyl)Prop-2-Enal, 3-[(2-Methyl-3-Furyl)Thio]Butanal, (+/−)-3-[(2-Methyl-3-Furyl)Thio]-2-Butanone, 3-((2-Methyl-3-Furyl)Thio)-4-Heptanone, Methyl Glucoside-Coconut Oil Ester, 6-Methyl-3,5-Heptadien-2-One, 6-Methylheptanal, Methyl Heptanoate, 2-Methylheptanoic Acid, 2-Methyl-3-Heptanone, 6-Methyl-5-Hepten-2-Ol, 5-Methyl-2-Hepten-4-One, 6-Methyl-3-Hepten-2-One, Trans-, 6-Methyl-5-Hepten-2-One, 6-Methyl-5-Hepten-2-One Propyleneglycol Acetal, 6-Methyl-5-Hepten-2-Y1 Acetate, 3-Methylhexanal, 5-Methyl-2,3-Hexanedione, S-Methyl Hexanethioate, Methyl Hexanoate, 2-Methylhexanoic Acid, 5-Methylhexanoic Acid, Methyl 3-Hexenoate, Methyl Cis-3-Hexenoate, Methyl 2-Hexenoate, 5-Methyl-5-Hexen-2-One, 5-Methyl-3-Hexen-2-One, 5-Methylhexyl Acetate, Methyl Hexyl Ether, 1-Methyl-1h-Pyrrole-2-Carboxaldehyde, Methyl P-Hydroxybenzoate, Methyl 3-Hydroxybutyrate, Methyl 3-Hydroxyhexanoate, Methyl 2-Hydroxy-4-Methylpentanoate, Alpha-Methyl-Beta-Hydroxypropyl Alpha-Methyl-Beta-Mercaptopropyl Sulfide, Methyl-Beta-Ionone, Methyl Isobutanethioate, Methyl Isobutyl Ketone, Methyl Isobutyrate, Methyl Isopentyl Disulfide, 2-Methyl-5-Isopropylpyrazine, Methyl Isothiocyanate, Methyl Isovalerate, Methyl Jasmonate, Methyl Laurate, Methyl Levulinate, Methyl Linoleate (48%) Methyl Linolenate (52%) Mixture, Methyl Mercaptan, Methyl 3-Mercaptobutanoate, Methyl O-Methoxybenzoate, 1-Methyl-3-Methoxy-4-Isopropylbenzene, 2-Methyl-5-Methoxythiazole, Methyl N-Methylanthranilate, S-Methyl 3-Methylbutanethioate, Methyl 3-Methyl-1-Butenyl Disulfide, 3-Methyl-2(3-Methylbut-2-En-1-Yl)Furan, Methyl 2-Methylbutyrate, Methyl 2-Methyl-3-Furyl Disulfide, S-Methyl 4-Methylpentanethioate, Methyl 2-Methylpentanoate, Methyl 2-Methylphenyl Disulfide, Methyl (Methylthio)Acetate, Methyl 3-(Methylthio)Butanoate, 2-Methyl-1-Methylthio-2-Butene, Methyl 4-(Methylthio)Butyrate, Methyl 2-Methylthiobutyrate, Methyl (Methylthio)Methyl Disulfide, 4-Methyl-2-(Methylthiomethyl)-2-Hexenal, 5-Methyl-2-(Methylthiomethyl)-2-Hexenal, 4-Methyl-2-(Methylthiomethyl)-2-Pentenal, Methyl 3-Methylthiopropionate, Methyl 4-Methylvalerate, Methyl Myristate, 1-Methylnaphthalene, Methyl Beta-Naphthyl Ketone, Methyl Nicotinate, 3-Methyl-2,4-Nonanedione, Methyl Nonanoate, 4-Methylnonanoic Acid, Methyl 2-Nonenoate, Methyl 3-Nonenoate, Methyl 2-Nonynoate, 2-Methyloctanal, (+/−)-6-Methyloctanal. Methyl Octanoate, 4-Methyloctanoic Acid, 2-Methyl-2-Octenal, Methyl 2-Octenoate, Methyl Cis-4-Octenoate, Methyl Trans-2-Octenoate, Methyl Cis-5-Octenoate, (E)-7-Methyl-3-Octen-2-One, Methyl Octyl Sulfide, Methyl 2-Octynoate, 2-Methyl-3 Or 5 Or 6-(Furfurylthio)Pyrazine (Mixture Of Isomers), 3-Methyl-2-Oxobutanoic Acid, Methyl 2-Oxo-3-Methylpentanoate, 3-Methyl-2-Oxopentanoic Acid, 4-Methyl-2-Oxopentanoic Acid, 2-Methylpentanal, 4-Methyl-2,3-Pentanedione, 4-Methylpentanoic Acid, 3-Methylpentanoic Acid, 3-Methyl-1-Pentanol, 4-(Methylthio)-4-Methyl-2-Pentanone, 2-Methyl-2-Pentenal, 4-Methyl-2-Pentenal, Methyl 4-Pentenoate, 2-Methyl-4-Pentenoic Acid, 4-Methylpent-2-Enoic Acid, 2-Methyl-3-Pentenoic Acid. 2-Methyl-2-Pentenoic Acid, 1-(4-Methoxyphenyl)-4-Methyl-1-Penten-3-One, 4-Methyl-3-Penten-2-One, 4-Methyl-4-Penten-2-One, 4-Methyl-2-Pentyl-1,3-Dioxolane, 4-Methylpentyl Isovalerate, Beta-Methylphenethyl Alcohol, Alpha-Methylphenethyl Butyrate, Methyl Phenethyl Ether, Methyl Phenylacetate, 2-Methyl-4-Phenyl-2-Butanol, 3-Methyl-4-Phenyl-3-Butene-2-One, 2-Methyl-4-Phenyl-2-Butyl Acetate, 2-Methyl-4-Phenyl-2-Butyl Isobutyrate, 2-Methyl-4-Phenylbutyraldehyde, 3-Methyl-2-Phenylbutyraldehyde, Methyl 4-Phenylbutyrate, Methyl Phenyl Disulfide, Methyl Beta-Phenylglycidate, 3-Methyl-3-Phenyl Glycidic Acid Ethyl Ester, 5-Methyl-2-Phenyl-2-Hexenal, 4-Methyl-1-Phenyl-2-Pentanone, 4-Methyl-2-Phenyl-2-Pentenal, Methyl 3-Phenylpropionate. Methyl Phenyl Sulfide, 2-Methylpiperidine, Methylpolysilicone, 2-Methyl-2-(Methyldithio)Propanal, S-Methyl Propanethioate, 2-Methyl-1-Propanethiol, Methyl Propenyl Disulfide, Methyl 1-Propenyl Sulfide, 2-Methyl-3-(P-Isopropylphenyl) Propionaldehyde, Methyl Propionate, 3-Methyl-5-Propyl-2-Cyclohexen-1-One, Methyl Propyl Disulfide, 2-Methylpropyl-3-Methylbutyrate, (?)-4-Methyl-2-Propyl-1,3-Oxathiane, 2-Methyl-4-Propyl-1,3-Oxathiane, 2-(2-Methylpropyl)Pyridine, 2-(1-Methylpropyl)Thiazole, Methyl Propyl Trisulfide, Methyl-(3 Or 5 Or 6)-(Methylthio) Pyrazine (Mixture Of Isomers), 2-Methylpyrazine, Methyl 2-Pyrrolyl Ketone, 6-Methylquinoline, 5-Methylquinoxaline, Methyl Salicylate, Methyl Sorbate, Methyl Sulfide, Methyl P-Tert-Butylphenylacetate, 2-Methyltetrahydrofuran-3-One, 2-Methyl-3-Tetrahydrofuranthiol, (?)-2-Methyltetrahydrofuran-3-Thiol Acetate, 7-Methyl-4,4a,5,6-Tetrahydro-2(3h)-Naphthalenone, 2-Methyltetrahydrothiophen-3-One, 4-Methylthiazole, 4-Methyl-5-Thiazoleethanol, 4-Methyl-5-Thiazoleethanol Acetate, 4-Methyl-3-Thiazoline, 2-(4-Methyl-5-Thiazolyl)Ethyl Butanoate, 2-(4-Methyl-5-Thiazolyl)Ethyl Decanoate, 2-(4-Methyl-5-Thiazolyl)Ethyl Formate, 2-(4-Methyl-5-Thiazolyl)Ethyl Hexanoate, 2-(4-Methyl-5-Thiazolyl)Ethyl Isobutyrate, 2-(4-Methyl-5-Thiazolyl)Ethyl Octanoate, 2-(4-Methyl-5-Thiazolyl)Ethyl Propionate, 2-Methylthioacetaldehyde, S-Methyl Thioacetate, 2-Methyl-3-Thioacetoxy-4,5-Dihydrofuran, Methylthio 2-(Acetyloxy)Propionate, 3-(Methylthio)Butanal, 4-(Methylthio)Butanol, 1-(Methylthio)-2-Butanone, 4-(Methylthio)-2-Butanone, 3-(Methylthio)-2-Butanone, 4-(Methylthio)Butyl Isothiocyanate, Methyl Thiobutyrate, 1-(3-(Methylthio)-Butyryl)-2,6,6-Trimethylcyclohexene, 2-(Methylthio)Ethanol, 2-(Methylthio)Ethyl Acetate, Methyl 2-Thiofuroate, (+/−)-3-(Methylthio)Heptanal, 3-(Methylthio)-1-Hexanol, 3-Methylthiohexenal, 3-(Methylthio)Hexyl Acetate, 6-(Methylthio)Hexyl Isothiocyanate, 2-((Methylthio)Methyl)-2-Butenal, Methylthiomethyl Butyrate, Methylthiomethyl Hexanoate, Methylthiomethylmercaptan, 2-(Methylthiomethyl)-3-Phenylpropenal, 3-(Methylthio)Methylthiophene, 1-(Methylthio)-3-Octanone, 4-(Methylthio)-2-Oxobutanoic Acid, 4-(Methylthio)-2-Pentanone, 5-(Methylthio)Pentyl Isothiocyanate, 5-Methyl-2-Thiophenecarboxaldehyde, O-(Methylthio)Phenol, 1-Methylthio-2-Propanone, Methylthio 2-(Propionyloxy)Propionate, 3-(Methylthio)Propyl Acetate, 3-(Methylthio)Propylamine, 3-(Methylthio)Propyl Hexanoate, 3-Methylthiopropyl Isothiocyanate, 3-(Methylthio)Propyl Mercaptoacetate. 2-Methyl-3-Tolylpropionaldehyde (Mixed O-, M-, P-), 12-Methyltridecanal, 3-Methyl-1,2,4-Trithiane, 2-Methylundecanal, Methyl 9-Undecenoate, Methyl 10-Undecenoate, Methyl 2-Undecynoate, Methyl Valerate, 2-Methylvaleric Acid, 2-Methyl-5-Vinylpyrazine, (+/−)-2-(5-Methyl-5-Vinyltetrahydrofuran-2-Yl)Propionaldehyde, 4-Methyl-5-Vinylthiazole, Michelia Alba, Extract, Microparticulated Protein Product, Milk, Skim Milk, Nonfat Milk, Reduced-Fat Milk, Milk Clotting Enzyme, *Aspergillus Oryzae* Recombinant, Milk Clotting Enzyme From *Bacillus Cereus* (Frankland And Frankland), Milk Clotting Enzyme From *Endothia Parasitica*, Milk Clotting Enzyme From *Mucor Miehei* Cooney Et Emerson, Milk Clotting Enzyme From *Mucor Pusillus* L., Milk Powder, Whole, Enzyme-Modified, *Mimosa*, Absolute (*Acacia Decurrens* Willd. Var. *Dealbata*), *Mimosa* Concrete (*Acacia Decurrens* Willd. Var. *Dealbata*), Mineral Oil, White, Mintlactone, Mixture Of 3,6-Diethyl-1,2,4,5-Tetrathiane And 3,5-Diethyl-1,2,4-Trithiolane, Mixture Of Methyl Cyclohexadiene And Methylene Cyclohexene, Mixture Of Butyl Propyl Disulfide And Propyl And Butyl Disulfide, Molasses, Concentrate, Molasses, Extract (*Saccharum Officinarum* L.), Molasses (*Saccharum Officinarum* L.), Molecular Sieve Resins, Monoammonium Glutamate, Mono- And Diglycerides, Mono- And Diglycerides, Acetic Acid Esters And Sodium And Calcium Salts, Mono- And Diglycerides, Acetyltartaric Acid Esters And Sodium And Calcium Salts, Mono- And Diglycerides, Citric Acid Esters And Sodium And Calcium Salts, Mono- And Diglycerides, Diacetyltartaric Acid Esters, Mono- And Diglycerides, Ethoxylated, Mono- And Diglycerides, Lactic Acid Esters And Sodium And Calcium Salts, Mono- And Diglycerides, Monosodium Phosphate Derivatives, Mono- And Diglycerides, Sodium Sulfoacetate Derivatives, Mono-, Di-, And Triglycerides, Monoethanolamine, Monoglyceride Citrate, Monoglycerides, Acetylated, Monoisopropyl Citrate, Monomenthyl Glutarate, L-, Monomenthyl Succinate, Monopotassium Glutamate, Monosodium Glutamate, Montan Wax Fatty Acids, Oxidatively Refined, Polyhydric Alcohol Diesters, Morpholine, Morpholine, Fatty Acid Salts, Mountain Maple (*Acer Spicatum* Lam.), Mountain Maple Bark (*Acer Spicatum* Lam.), Mountain Maple, Extract Solid (*Acer Spicatum* Lam.), Mullein Flowers (*Verbascum* Spp.), Mushroom Oil, Distilled, Musk Ambrette, Musk, Ketone, Musk Tonquin (*Moschus Moschiferus* L.), Mustard, Brown (*Brassica* Spp.), Mustard, Brown, Extract (*Brassica* Spp.), Mustard Flour, Mustard Oil, Mustard, Oriental, Mustard, Yellow (*Brassica* Spp.), Mustard, Yellow, Extract (*Brassica* Spp.), Beta-Myrcene, Myrcenyl Methyl Ether, Myricitrin, Myristaldehyde, Myristic Acid, Myristyl Alcohol, Myrrh, Extract, Myrrh, Gum (*Commiphora* Spp.), Myrrh, Oil (*Commiphora* Spp.), Myrtenol, Myrtenyl Acetate, Myrtle Leaves (*Myrtus Communis* L.), Myrtle, Oil (*Myrtus Communis* L.), Naphtha, 2-Naphthalenthiol, Beta-Naphthyl Anthranilate, Beta-Naphthyl Ethyl Ether, Beta-Naphthyl Isobutyl Ether, Beta-Naphthyl Methyl Ether, Naringin Dihydrochalcone, Naringin, Extract (*Citrus Paradisi* Macf), Natamycin, Natural Gas, N-(1,1-Dimethyl-2-Hydroxyethyl)-2,2-Diethylbutanamide, Neohesperidin Dihydrochalcone, D-Neomenthol, Neotame, Nerol, Neroli, Bigarade Oil (*Citrus Aurantium* L.), Nerolidol, Nerolidol Oxide, Neryl Acetate, Neryl Butyrate, Neryl Formate, Neryl Isobutyrate, Neryl Isovalerate, Neryl Propionate, N-Ethyl-2,2-Diisopropylbutanamide, N-(2-Hydroxyethyl)-2,3-Dimethyl-2-Isopropylbutanamide, Niacin, Niacinamide, Nickel, Nicotinamide-Ascorbic Acid Complex, *Niger* Gutta (*Ficus Platyphylla* Del.), Nisin Preparation, Nispero, Nitrates, Sodium & Potassium, Nitrites, Sodium & Potassium, Nitrogen, Nitrogen Oxides, Nitrosyl Chloride, Nitrous Oxide, (+/−)-N-Lactoyltyramine, 2,4-Nonadienal, 2-Trans-6-Trans-Nonadienal, 2,6-Nonadienal Diethyl Acetal, 2,4-Nonadien-1-Ol, (E)-3-(Z)-6-Nonadien-1-O1, (Z)(Z)-3,6-Nonadien-1-Ol, 2,6-Nonadien-1-Ol, (E,Z)-2,6-Nonadien-1-Ol Acetate, (E,Z)-3,6-Nonadien-1-Ol Acetate, Cis,Cis-3,6-Nonadienyl Acetate, Gamma-Nonalactone, Nonanal, Nonanal Dimethyl Acetal, Nonanal Propyleneglycol Acetal, 1,3-Nonanediol Acetate (Mixed Esters), 1,4-Nonanediol Diacetate, 1,9-Nonanedithiol, Nonanoic Acid, 2-Nonanol, 4-((2-Methyl-3-Furyl) Thio)-5-Nonanone, 2-Nonanone, 3-Nonanone, 2-Nonanone Propyleneglycol Acetal, 3-Nonanon-1-Ol, 3-Nonanon-1-Yl Acetate, Nonanoyl 4-Hydroxy-3-Methoxybenzylamide, Nona-2,4,6-Trienal, Cis-6-Nonenal, 2-Nonenal, 1-Nonene, (E)-2-Nonenoic Acid, 2-Nonenoic Acid Gamma-Lactone, Cis-6-Nonen-1-Ol, Trans-2-Nonen-1-Ol, Cis-2-Nonen-1-Ol, 3-Nonen-2-One, 8-Nonen-2-One, 5-Nonen-Trans-2-One, Cis-6-Nonenyl Acetate, Cis-3-Nonenyl Acetate, 3-Nonyl Acetate, Nonyl Acetate, Nonyl Alcohol, Nonyl Isovalerate, Nonyl Octanoate, Nootkatone, N—P-Benzeneacetonitrilementhanecarboxamide, N-(2-(Pyridin-2-Yl) Ethyl)-3-P-Menthanecarboxamide, Nutmeg (*Myristica Fragrans* Houtt.), Nutmeg, Oil (*Myristica Fragrans* Houtt.), Nutmeg Oleoresin, Oak Chips, White, Extract (*Quercus Alba* L.), Oak Moss, Absolute (*Evernia* Spp.), Oak Moss, Concrete (*Evernia Prunasti* Spp.), Oak Wood, English (*Quercus Robur* L.), Oat Gum, Ocimene, 9,12-Octadecadienoic Acid (48%) And 9,12,15-Octadecatrienoic Acid (52%), Delta-Octadecalactone, Gamma-Octadecalactone, 9-Octadecenal, Octadecylamine, 2-Trans-6-Trans-Octadienal, Trans,Trans-2,4-Octadienal, (E,E)-2,4-Octadien-1-Ol, 3,5-Octadien-2-One, Trans, Trans-, 1,5-Octadien-3-One, Octafluorocyclobutane, Octahydro-4,8a-Dimethyl-4a(2h)-Naphthol, Octahydrocoumarin, Delta-Octalactone, Gamma-Octalactone, Octanal, Octanal Dimethyl Acetal, Octanal Propyleneglycol Acetal, 4,5-Octanedione, 2,3-Octanedione, 1,8-Octanedithiol, Octanoic Acid, 3-Octanol, 2-Octanol, 1-Octanol, 2-Octanone, 3-Octanone, 3-(Hydroxymethyl)-2-Octanone, 6-Octenal, 2-Octenal, Cis-5-Octenal, 1-Octene, 3-Octenoic Acid, (E)-2-Octenoic Acid, (E)-2-Octen-1-O1, Cis-3-Octen-1-Ol, 1-Octen-3-Ol, (E)-2-Octen-4-01, Cis-5-Octen-1-Ol, Trans-3-Octen-2-Ol, 3-Octen-2-One, 2-Octen- 4-One, 1-Octen-3-One, 4-Octen-3-One, Z-5-Octenyl Acetate, 1-Octen-3-Yl Acetate, Trans-2-Octen-1-Yl Acetate, Trans-2-Octen-1-Yl Butanoate, 1-Octen-3-Yl Butyrate, (E)-2-(2-Octenyl)Cyclopentanone, Cis-3-Octenyl Propionate, (Z)-5-Octenyl Propionate, 1-Octenyl Succinic Anhydride, 3-Octyl Acetate, Octyl Acetate, Octyl Alcohol, Synthetic, Octyl Butyrate, 3-Octyl Butyrate, Octyl Formate, 3-Octyl Formate, Octyl 2-Furoate, Octyl Gallate, Octyl Heptanoate, Octyl Isobutyrate, Octyl Isovalerate. Octyl 2-Methylbutyrate. Octyl Octanoate, Octyl Phenylacetate, Octyl Propionate, (?)-6-Octyltetrahydro-2h-Pyran-2-One, O-Ethyl S-(2-Furylmethyl)Thiocarbonate, Oiticica Oil, Oleic Acid, Oleic Acid, From Tall Oil Fatty Acids, Olestra, Oleyl Alcohol, Olibanum, Absolute (*Boswellia* Spp.), Olibanum, Gum, Resin (*Boswellia* Spp.), Olibanum, Oil (*Boswellia* Spp.), Olibanum, Resinoid (*Boswellia* Spp.), Onion, Oil (*Allium Cepa* L.), Opopanax, Gum, Opopanax, Non-Specific, Opopanax, Oil, Opopanax Tincture, Orange B, Orange Essence, Natural, Orange Essence Oil, Natural, Orange, Extract, Orange Flowers, Absolute (*Citrus Aurantium* L.), Orange Flowers, Bitter (*Citrus Aurantium* L), Orange, Juice, Orange Leaf, Absolute (*Citrus Aurantium* L.), Orange, Oil, Distilled (*Citrus Sinensis* (L.) Osbeck), Orange, Oil, Terpeneless (*Citrus Sinensis* (L.) Osbeck), Orange Peel, Orange Peel, Bitter, Extract (*Citrus Aurantium* L.), Orange Peel, Bitter, Oil (*Citrus Aurantium* L.), Orange Peel, Sweet, Extract (*Citrus Sinensis* (L.) Osbeck), Orange Peel, Sweet, Oil (*Citrus Sinensis* (L.) Osbeck), Orange Peel, Sweet, Oil, Terpeneless (*Citrus Sinensis* (L.) Osbeck), Oregano, European (*Origanum* Spp.), Oregano (*Lippia* Spp., Usually L. *Graveolens* Hbk), Oregano (Other Genera Including *Coleus*, Lantana And Hyptis), *Origanum* Oil Extractive) (*Thymus-Capitatus Hoff*. Et Link), Orin Lactone, L-Ornithine Monochlorohydrate/Ornithine, Orris, Concrete, Liquid, Oil (*Iris Florentina* L.), Orris Root, Extract (*Iris Florentina* L.), *Osmanthus* Absolute, Ox Bile Extract, Oxirane (Chloromethyl)-, Polymer With Ammonia, Reaction Product With Chloromethane, 3-Oxobutanal, Dimethyl Acetal, 5-Oxodecanoic Acid, 3-Oxodecanoic Acid Glyceride, 5-Oxododecanoic Acid, 3-Oxododecanoic Acid Glyceride, 2-Oxo-3-Ethyl-4-Butanolide, 3-Oxohexadecanoic Acid Glyceride, 3-Oxohexanoic Acid Diglyceride, 5-Oxooctanoic Acid, 3-Oxooctanoic Acid Glyceride, 2-Oxopentanedioic Acid, 2-Oxo-3-Phenylpropionic Acid, 3-Oxotetradecanoic Acid Glyceride, 2-Oxothiolane, Oxystearin, Ozone, Palmitic Acid, Pancreatin, Pansy (*Viola Tricolor* L.), D-Pantothenamide, D-Pantothenyl Alcohol, Papain (*Carica Papaya* L.), Paprika (*Capsicum Annuum* L.), Paprika Oleoresin (*Capsicum Annuum* L.), Paraffin And Succinic Derivatives, Synthetic, Paraffin Wax, Paraldehyde, Cheese, Cheddar Cheese, Cheese Powder, Parmesan Cheese, Reggiano Cheese, Parsley, Oil (*Petroselinum* Spp.), Parsley, Oleoresin (*Petroselinum* Spp.), Parsley (*Petroselinum* Spp.), Passion Flower Extract, Passion Flower (*Passiflora Incarnata* L.), Patchouly, Oil (*Pogostemon* Spp.), Peach Kernel, Extract (*Prunus Persica* Sieb Et Zucc.), Peach Leaves, Extract (*Prunus Persica* (L.) Batsch), Peach Leaves (*Prunus Persica* (L.) Batsch), Peanut Oil, Peanut Stearine (*Arachis Hypogaea* L.), Pecan Shell Flour, Pectin, Pectin, Amidated, Pectinase From *Aspergillus Niger*, Pectinase From *Bacillus Subtilis*, Pectin, Modified, Peg Fatty Acid Esters And Mono-, Di-, And Triglycerides Mixture, Pendare (*Couma Macrocarpa* Barb. Rodr. & *Couma Utilis* (Mart.) Muell. Arg.), Penicillinase From *Bacillus Subtilis, Penicillium Roqueforti*, Pennyroyal, Oil, American (*Hedeoma Pulegiodes* (L.)), Pennyroyal, Oil, European (*Mentha Pulegium* L.), Omega-Pentadecalactone, Pentadecanoic Acid, 2-Pentadecanone, 2,4-Pentadienal, 2,3-Pentanedione, 3-Pentanethiol, 2-Pentanethiol, 1-Pentanethiol, 2-Pentanol, 2-Pentanone, 2-Pentanoylfuran, 2-Pentenal, 4-Pentenal, 2-Pentenoic Acid, 4-Pentenoic Acid, 1-Penten-3-Ol, 2-Penten-1-Ol, 3-Penten-2-One, 1-Penten-3-One, 4-Pentenyl Acetate, Pent-2-Enyl Hexanoate, 4-Pentenyl Isothiocyanate, 2-Pentenyl-4-Propyl-1,3-Oxathiane (Mixture Of Isomers), 2-Pentyl Acetate, Pentylamine, 2-Pentyl-1-Buten-3-One, 2-Pentyl Butyrate, 2-Pentylfuran, Pentyl 2-Furyl Ketone, 5-Pentyl-3h-Furan-2-One, 2-Pentyl-3-Methyl-2-Cyclopenten-1-One, 2-Pentyl 2-Methylpentanoate, 2-Pentylpyridine, 2-Pentylthiazole, 2-Pentylthiophene, Pepper, Black, Oil (*Piper Nigrum* L.), Pepper, Black, Oleoresin (*Piper Nigrum* L.), Pepper, Black (*Piper Nigrum* L.), Pepper, Cayenne, Peppermint Leaves (*Mentha Piperita* L.), Peppermint, Oil (*Mentha Piperita* L.), Peppermint Plant, Pepper, Red, Pepper, White, Oil (*Piper Nigrum* L.), Pepper, White, Oleoresin (*Piper Nigrum* L.), Pepper, White (*Piper Nigrum* L.), Pepsin, Peptones, Peracetic Acid, Perillaldehyde, Perillaldehyde Propyleneglycol Acetal, *Perilla* Leaf Oil, Perillo, Perillyl Acetate, Periodic Acid, Petitgrain, Lemon, Oil (*Citrus Limon* (L.) Burm. F.), Petitgrain, Mandarin, Oil (*Citrus Reticulata* Blanco Var. Mandarin), Petitgrain, Oil (*Citrus Aurantium* L.), Petrolatum, Petroleum Hydrocarbons, Odorless, Light, Petroleum Naphtha, Petroleum Wax, Petroleum Wax, Synthetic, Phaffia Yeast, Alpha-Phellandrene, Phenethyl Acetate, Phenethyl Alcohol, Phenethylamine, Phenethyl Anthranilate, Phenethyl Benzoate, Phenethyl Butyrate, Phenethyl Cinnamate, Phenethyl Decanoate, Phenethyl Formate, Phenethyl 2-Furoate, Phenethyl Hexanoate, Phenethyl Isobutyrate, Phenethyl Isothiocyanate, Phenethyl Isovalerate, Phenethyl 2-Methylbutyrate, Phenethyl Octanoate, Phenethyl Phenylacetate, Phenethyl Propionate, Phenethyl Salicylate, Phenethyl Senecioate, Phenethyl Tiglate, Phenol, Phenol-Formaldehyde, Cross-Linked, Tetraethylenepentamine Activated, Phenol-Formaldehyde, Cross-Linked, Triethylenetetramine Activated, Phenol-Formaldehyde, Cross-Linked, Triethylenetetramine & Tetraethylenepentamine Activated, Phenol-Formaldehyde, Sulfite-Modified, Cross-Linked. Phenoxyacetic Acid, 2-Phenoxyethyl Isobutyrate, 2-Phenoxyethyl Propionate, Phenylacetaldehyde, Phenylacetaldehyde 2,3-Butylene Glycol Acetal, Phenylacetaldehyde Diethyl Acetal, Phenylacetaldehyde Diisobutyl Acetal, Phenylacetaldehyde Dimethyl Acetal, Phenylacetaldehyde Glyceryl Acetal, Phenylacetaldehyde Propyleneglycol Acetal, Phenyl Acetate, Phenylacetic Acid, Dl-Phenylalanine, L-Phenylalanine, 4-Phenyl-2-Butanol, 2-Phenyl-2-Butenal, 4-Phenyl-3-Buten-2-Ol, 4-Phenyl-3-Buten-2-One, 4-Phenyl-2-Butyl Acetate, Phenyl Butyrate, 2-Phenyl-3-Carbethoxy Furan, Phenyl Disulfide, (+/−)-1-Phenylethylmercaptan, Phenylethyl Mercaptan, (+/−)-2-Phenyl-4-Methyl-2-Hexenal, 1-Phenyl-3-Methyl-3-Pentanol, 1-Phenyl-3 Or 5-Propylpyrazole, 5-Phenylpentanol, 2-Phenyl-4-Pentenal, 3-Phenyl-4-Pentenal, O-Phenylphenol, 1-Phenyl-1,2-Propanedione, 3-Phenyl-1-Propanol, 1-Phenyl-1-Propanol, 2-Phenyl-3-(2-Furyl)-Prop-2-Enal, 3-Phenylpropionaldehyde, 2-Phenylpropionaldehyde, 2-Phenylpropionaldehyde Dimethyl Acetal, 3-Phenylpropionic Acid, 3-Phenylpropyl Acetate, 2-Phenylpropyl Butyrate, 3-Phenylpropyl Cinnamate, 3-Phenylpropyl Formate, 3-Phenylpropyl Hexanoate, 2-Phenylpropyl Isobutyrate, 3-Phenylpropyl Isobutyrate, 3-Phenylpropyl Isovalerate, 3-Phenylpropyl Propionate, 2-(3-Phenylpropyl) Pyridine, 2-(3-Phenylpropyl)Tetrahydrofuran, Phenyl Salicylate, Phosphoric Acid, Phosphorus Oxychloride, Phthalide, Phytol, Phytyl Acetate, *Pimenta* Leaf, Oil (*Pimenta Officinalis* Lindl.), 3-Pinanone, Pine Bark, White, Extract Solid (*Pinus Strobus* L.), Pine Bark, White, Oil (*Pinus Strobus* L.), Pine Bark, White (*Pinus Strobus* L.), Alpha-Pinene, Beta-Pinene, Pine Needle, Dwarf, Oil (*Pinus Mugo* Turra Var. *Pumilio* (Haenke) Zenari), Pine, Scotch, Oil (*Pinus Sylvestris* L.), Pine Tar, Oil (*Pinus* Spp.), Pine, White, Oil (*Pinus* Spp.), Pinocarveol, Pinocarvyl Isobutyrate, Piperazine, Piperazine Dihydrochloride, Piperidine, Piperine, Piperitenone, Piperitenone Oxide, L-Piperitone, D-Piperitone, *Piper Longum* Distillate, Piperonal, Piperonal Propyleneglycol Acetal, Piperonyl Acetate, Piperonyl Isobutyrate, Pipsissewa Leaves, Extract (*Chimaphila Umbellata* Nutt.), 1,3-P-Menthadien-7-Al, P-Menthane-3,8-Diol, P-Menthan-7-Ol, P-Menth-1-En-9-Ol, Polyacrylamide, Polyacrylamide Resin, Modified, Poly(Acrylic Acid-Co-Hypophosphite), Sodium Salt, Polyacrylic Acid, Sodium Salt, Poly(Alkyl($C_{16-22}$)Acrylate), Polydextrose, Poly(Divinylbenzene-Co-Ethylstyrene), Poly(Divinylbenzene-Co-Trimethyl(Vinylbenzyl)Ammonium Chloride), Polyethylene (M W 2,000-21,000), Polyethylene Glycol (M W 200-9,500), Polyethylene Glycol (400) Dioleate, Polyethylene, Oxidized, Polyethylenimine Reaction Product W/1,2-Dichloroethane, Polyglycerol Esters Of Fatty Acids, Polyglyceryl Phthalate Ester Of Coconut Oil Fatty Acids, Polyisobutylene (Min M W 37,000), Polylimonene, Polymaleic Acid, Polymaleic Acid, Sodium Salt, Poly(Maleic Anhydride), Sodium Salt, Polyoxyethylene (600) Dioleate, Polyoxyethylene Dioleate, Polyoxyethylene (600) Monoricinoleate, Polyoxyethylene 40 Monostearate, Polypropylene Glycol (M W 1,200-3,000), Polysorbate 20, Polysorbate 60, Polysorbate 65, Polysorbate 80, Polystyrene, Cross-Linked, Chloromethylated, Then Aminated With Trimethylamine, Dimethylamine, Diethylenetriamine, Or Triethanolamine, Polyvinyl Acetate, Polyvinyl Alcohol, Polyvinyl Polypyrrolidone, Polyvinylpyrrolidone, Pomegranate Bark, Extract (*Punica Granatum* L.), Poplar Buds (*Populus* Spp.), Poppy Seed (*Papaver Somniferum* L.), Potassium Acetate, Potassium Acid Pyrophosphate, Potassium Acid Tartrate, Potassium Benzoate, Potassium Bicarbonate, Potassium Bisulfite, Potassium Borate, Potassium Bromate, Potassium Bromide, Potassium Caprate, Potassium Caprylate, Potassium Carbonate, Potassium Caseinate, Potassium Chloride, Potassium Citrate, 2-(1'-Ethoxy)Ethoxypropanoate, Potassium Fumarate, Potassium Gibberellate, Potassium Gluconate, Potassium Glycerophosphate, Potassium Hydroxide, Potassium Hypophosphate, Potassium Hypophosphite, Potassium Iodate, Potassium Iodide, Potassium Lactate, Potassium Laurate, Potassium Metabisulfite, Potassium N-Methyldithiocarbamate, Potassium Myristate, Potassium Nitrate, Potassium Nitrite, Potassium Oleate, Potassium Palmitate, Potassium Pectinate, Potassium Permanganate, Potassium Persulfate, Potassium Phosphate, Monobasic, Potassium Phosphate, Tribasic, Potassium Polymetaphosphate, Potassium Pyrophosphate, Potassium Salts Of Fatty Acids, Potassium Sorbate, Potassium Stearate, Potassium Sulfate, Potassium Sulfite, Potassium Tripolyphosphate, Potato Starch, Prenyl Acetate, Prenyl Benzoate, Prenyl Caproate, Prenyl Formate, Prenyl Isobutyrate, Prenyl Thioacetate, Prenylthiol, Prickly Ash Bark Extract (*Xanthoxylum* Spp.), Prickly Ash Bark, Oil, L-Proline, 1,2-(Di(1'-Ethoxy)Ethoxy)Propane, Propane, 1,3-Propanedithiol, 1,2-Propanedithiol, 1,1-Propanedithiol, 2-Propanethiol, 3-(Methylthio)Propanol, (2-Furyl)-2-Propanone, 1-(P-Methoxyphenyl)-2-Propanone, Di-(1-Propenyl)-Sulfide (Mixture Of Isomers), 4-Propenyl-2,6-Dimethoxyphenol, Propenylguaethol, (Z)-4-Propenylphenol, 4-(2-Propenyl)Phenyl-Beta-D-Glucopyranoside, Propenyl Propyl Disulfide, Propionaldehyde, 3-(Methylthio) Propionaldehyde, Propionic Acid, 2-(4-Methyl-2-Hydroxyphenyl)Propionic Acid-Gamma-Lactone, 2-Propionylpyrrole, 2-Propionylpyrroline, 2-Propionylthiazole, 2-Propionyl-2-Thiazoline, Propiophenone, Propyl Acetate, Propyl Alcohol, Propylamine, P-Propylanisole, Propyl Benzoate, Propyl Butyrate, Propyl Cinnamate, Propyl 2,4-Decadienoate, 4-Propyl-2,6-Dimethoxyphenol, 2-Propyl-4,5-Dimethyloxazole, Propyl Disulfide, Propylene Chlorohydrin, Propylene Glycol, Propylene Glycol Alginate, Propyleneglycol Diacetate, Propylene Glycol Dibenzoate, Propyleneglycol Dibutyrate, Propyleneglycol Dihexanoate, Propyleneglycol Di-2-Methylbutyrate, Propyleneglycol Dioctanoate, Propyleneglycol Dipropionate, Propylene Glycol Mono- And Diesters Of Fats And Fatty Acids, Propyleneglycol Monobutyrate, Propyleneglycol Monohexanoate, Propyleneglycol Mono-2-Methylbutyrate, Propylene Glycol Stearate, Propylene Oxide, Propyl Formate, Propyl 2-Furanacrylate, Propyl 2-Furoate, Propyl Gallate, Propyl Heptanoate, Propyl Hexanoate, Propyl P-Hydroxybenzoate, 3-Propylidenephthalide, Propyl Isobutyrate, Propyl Isovalerate, Propyl Levulinate, Propyl Mercaptan, Propyl 2-Mercaptopropionate, Propyl 2-Methyl-3-Furyl Disulfide, Alpha-Propylphenethyl Alcohol, P-Propylphenol, O-Propylphenol, Propyl Phenylacetate, Propyl Propane Thiosulfonate, Propyl Propionate, 2-Propylpyrazine, 2-Propylpyridine, Propyl Pyruvate, Propyl Sorbate, Propyl 4-Tert-Butylphenylacetate, Propyl Thioacetate, Protease From *Aspergillus Flavus*, Protease From *Aspergillus Niger*, Protease From *Aspergillus Oryzae*, Protease From *Bacillus Amyloliquefaciens*, Protease From *Bacillus Licheniformis*, Protease From *Bacillus Subtilis*, Protein, Animal, Hydrolyzed, Protein Hydrolysate, Unspecified, Protein, Milk, Hydrolyzed, Protein, Vegetable, Hydrolyzed, Pseudoionone, *Psyllium* Seed Husk, Pulegone, Pulp, Pyrazine, Pyrazine Ethanethiol, Pyrazinyl Methyl Sulfide, 3-(2-Methylpropyl)Pyridine, Pyridine, 2-Pyridinemethanethiol, Pyridoxine, Pyridoxine Hydrochloride, Pyroligneous Acid, Pyroligneous Acid, Extract, Pyrrole, Pyrrolidine, Pyrrolidino-[1,2e]-4h-2,4-Dimethyl-1,3,5-Dithiazine, 1-Pyrroline, Pyruvaldehyde, Pyruvic Acid, *Quassia*, Extract (*Picrasma Excelsa* (Sw.) Planch Or *Quassia Amara* L.), Quaternary Ammonium Chloride Combination, Quebracho Bark Extract, *Quillaia* Extract (*Quillaja Saponaria* Molina), *Quillaia* (*Quillaja Saponaria* Molina), Quince Seed, Extract (*Cydonia* Spp.), Quinine Bisulfate, Quinine Hydrochloride, Quinine Sulfate, Quinoline, Rapeseed Oil, Hydrogenated, Rapeseed Oil, Hydrogenated, Superglycerinated, Rapeseed Oil, Low Erucic Acid, Rapeseed Oil, Low Erucic Acid, Partially Hydrogenated, Rebaudioside C, Rebaudioside A, Rennet, Resin, From Formaldehyde, Acetone, And Tetraethylenepentamine, Resorcinol, L-Rhamnose, Rhatany, Extract (*Krameria* Spp.), Rhodinol, Rhodinyl Acetate, Rhodinyl Butyrate, Rhodinyl Formate, Rhodinyl Isobutyrate, Rhodinyl Isovalerate, Rhodinyl Phenylacetate, Rhodinyl Propionate, Rhubarb, Garden Root (*Rheum Rhaponticum* L.), Rhubarb Root (*Rheum* Spp.), Riboflavin, Riboflavin 5'-Phosphate, Riboflavin 5'-Phosphate, Sodium, D-Ribose, Rice Bran Wax, Rice, Milled, Rice Starch, (R)-(-)-1-Octen-3-Ol, Rose, Absolute (*Rosa* Spp.), Rose, Bud (*Rosa* Spp.), Rose Flowers (*Rosa* Spp.), Rose Hips, Extract (*Rosa* Spp.), Rose Leaves (*Rosa* Spp.), Roselle (*Hibiscus Sabdariffa* L.), Rosemary, Extract (*Rosmarinus Officinalis* L.), Rosemary, Oil (*Rosemarinus Officinalis* L.), Rosemary, Oleoresin, Rosemary (*Rosemarinus Officinalis* L.), Rose, Oil (*Rosa* Spp.), Rose Water, Stronger (*Rosa Centifolia* L.), Rosidinha (*Micropholis* (Also Known As Sideroxylon) Spp.), Rosin, Adduct With Fumaric Acid, Pentaerythritol Ester, Rosin, Glycerol Ester, Rosin, Gum, Glycerol Ester, Rosin, Gum Or Wood, Partially Hydrogenated, Glycerol Ester, Rosin, Gum Or Wood, Partially Hydrogenated, Pentaerythritol Ester, Rosin, Gum Or Wood, Pentaerythritol Ester, Rosin, Limed, Rosin, Methyl Ester, Partially Hydrogenated, Rosin, Partially Dimerized, Calcium Salt, Rosin, Partially Dimerized, Glycerol Ester, Rosin, Partially Hydrogenated, Rosin (*Pinus* Spp.) And Rosin Derivatives, Rosin, Polymerized, Glycerol Ester, Rosin, Tall Oil, Glycerol Ester, Rosin, Wood, Rosin, Wood, Glycerol Ester, Rosin, Wood, Maleic Anhyd. Mod., Pentaerythritol Ester, Acid #176-186, Rosin, Wood, Maleic Anhyd. Mod., Pentaerythritol Ester, Acid #134-145, (1r,2s,5r)-N-(4-Methoxyphenyl)-5-Methyl-2-(1-Methylethyl)Cyclohexanecarboxamide, Rubber, Natural-Smoked Sheet And Latex Solids (*Hevea Brasiliensis*), Rue, Oil (*Ruta Graveolens* L.), Rue (*Ruta Graveolens* L.), Rum, Rum Ether, Rutin, Saccharin, Saccharin, Ammonium Salt, Saccharin, Calcium Salt, Saccharin, Sodium Salt, Saffron (*Crocus Sativus* L.), Saffron, Extract (*Crocus Sativus* L.), Safrole-Free Extract Of *Sassafras*, Sage, Greek (*Salvia Triloba* L.), Sage, Oil (*Salvia Officinalis* L.), Sage, Oleoresin (*Salvia Officinalis* L.), Sage (*Salvia Officinalis* L.), Sage, Spanish, Oil (*Salvia Lavandulaefolia* Vahl.), Salicylaldehyde, Salicylic Acid, Salts Of Fatty Acids, Sandalwood, Red (*Pterocarpus Santalinus* L.F.), Sandalwood, White (*Santalum Album* L.), Sandalwood, Yellow, Oil (*Santalum Album* L.), Sandarac (*Tetraclinis Articulata* (Vahl.) Mast.), Santalol, Beta, Santalol, Alpha, Santalol (Alpha And Beta), Santalyl Acetate, Santalyl Phenylacetate, Sarcodactylis Oil, Sarsaparilla, Extract (*Smilax* Spp.), Sassafras Bark, Extract (Safrole-Free) (*Sassafras Albidum* (Nutt.) Nees), Sassafras Leaves (Safrole-Free) (*Sassafras Albidum* (Nutt.) Nees), Sausage Casing (Hcl And Cellulose Fibers), Savory, Summer, Oil (*Satureja Hortensis* L.), Savory, Summer, Oleoresin (*Satureja Hortensis* L.), Savory, Summer (*Satureja Hortensis* L.), Savory, Winter, Oil (*Satureja Montana* L.), Savory, Winter, Oleoresin (*Satureja Montana* L.), Savory, Winter (*Satureja Montana* L.), *Schinus Molle*, Oil (*Schinus Molle* L.), (–)-Sclareol, Sclareolide, Scotch Spearmint Oil, *Mentha Cardiaca* L., 2-Sec-Butylcyclohexanone, Sec-Butyl Ethyl Ether, *Senna*, Alexandria (*Cassia Acutifolia* Delile), L-Serine, *Serpentaria* (*Aristolochia Serpentaria* L.), Sesame (*Sesamum Indicum* L.), Sheanut Oil, Shellac, Purified, Shellac Wax, Silica Aerogel, Silicon Dioxide, Silver Fir, Needles And Twigs, Oil (*Abies Alba* Mill.), Silver-Silver Dragees, *Simaruba* Bark (*Simaruba Amara* Aubl.), Skatole, Sloe Berries, Extract (*Prunus Spinosa* L.), Sloe Berries, Extract Solid (*Prunus Spinosa* L.), Sloe Berries (*Prunus Spinosa* L.), Snakeroot, Canadian, Oil (*Asarum Canadense* L.), Sodium Acetate, Sodium Acid Pyrophosphate, Sodium N-Alkylbenzenesulfonate, Sodium Aluminate, Sodium Aluminum Phosphate, Acidic Or Basic, Sodium Aluminum Silicate, Sodium Ascorbate, Sodium Benzoate, Sodium Bicarbonate, Sodium Bisulfite, Sodium Borate, Sodium Borohydride, Sodium Calcium Aluminosilicate, Hydrated, Sodium Caprate, Sodium Caprylate, Sodium Carbonate, Sodium Caseinate, Sodium Chloride, Sodium Chlorite, Sodium Copper Chlorophyllin, Sodium Decylbenzenesulfonate, Sodium Dehydroacetate, Sodium Diacetate, Sodium Dimethyldithiocarbamate, Sodium Dodecylbenzenesulfonate, Sodium Erythorbate, Sodium 2-Ethylhexyl Sulfate, Sodium Ferricitropyrophosphate, Sodium Ferritripolyphosphate, Sodium Fluoride, Sodium Formate, Sodium Fumarate, Sodium Glucoheptonate, Sodium Gluconate, Sodium Hexametaphosphate, Sodium Humate, Sodium Hydrosulfite, Sodium Hydroxide, Sodium Hypochlorite, Sodium Hypophosphite, Sodium Lactate, Sodium Laurate, Sodium Lauryl Sulfate, Sodium 3-Mercaptooxopropionate, Sodium Metabisulfite, Sodium Metaphosphate, Sodium Metasilicate, Sodium (4-Methoxybenzoyloxy)Acetate, Sodium 3-Methoxy-4-Hydroxycinnamate, Sodium 2-(4-Methoxyphenoxy)Propanoate, Sodium Methyl Sulfate, Sodium Mono- And Dimethyl Naphthalene Sulfonates, Sodium Myristate, Sodium Nitrate, Sodium Nitrite, Sodium Oleate, Sodium Palmitate, Sodium Pantothenate, Sodium Pectinate, Sodium Phosphate, Dibasic, Sodium Phosphate, Monobasic, Sodium Phosphate, Tribasic, Sodium Polymethacrylate, Sodium Potassium Tartrate, Sodium Propionate, Sodium Pyrophosphate, Sodium Salts Of Fatty Acids, Sodium Sesquicarbonate, Sodium Silicate, Sodium Sorbate, Sodium Stearate, Sodium Stearoyl-2-Lactylate, Sodium Stearyl Fumarate, Sodium Sulfate, Sodium Sulfide, Sodium Sulfite, Sodium Tartrate, Sodium Taurocholate, Sodium Thiosulfate, Sodium Tripolyphosphate, Sodium Zinc Metasilicate, Sorbic Acid, Sorbitan Monooleate, Sorbitan Monostearate, D-Sorbitol, Sorbose, Soya Bean Oil Fatty Acids, Hydroxylated, Soya Fatty Acid Amine, Ethoxylated, Soybean Oil, Epoxidized, Soybean Oil, Hydrogenated, Soy Protein Concentrate, Enzyme Activated. Soy Protein, Isolate, Spearmint, Extract (*Mentha Spicata* L.), Spearmint (*Mentha Spicata* L.), Spearmint, Oil (*Mentha Spicata* L.), Sperm Oil, Sperm Oil, Hydrogenated, Spikenard Extract, Spiro(2,4-Dithia-1-Methyl-8-Oxabicyclo(3.3.0)Octane-3,3'-(1'-Oxa-2'-Methyl) Cyclopentane), Spruce Needles And Twigs, Extract (*Picea* Spp.), Spruce Needles And Twigs, Oil (*Picea* Spp.), (2s,5r)-N-[4-(2-Amino-2-Oxoethyl)Phenyl]-5-Methyl-2-(Propan-2-Yl)Cyclohexanecarboxamide, Stannic Chloride, Stannous Chloride, Starch, Acid Modified, Starch, Alpha-Amylase Modified, Starch, Bleached, Starch, Food, Modified, Starch, Food, Modified: Acetylated Distarch Adipate, Starch, Food, Modified: Acetylated Distarch Glycerol, Starch, Food, Modified: Acetylated Distarch Oxypropanol, Starch, Food, Modified: Acetylated Distarch Phosphate, Starch, Food, Modified: Beta-Amylase Modified Starch, Starch, Food, Modified: Beta-Amylase Sodium Starch Octenylsuccinate, Starch, Food, Modified: Distarch Glycerol, Starch, Food, Modified: Distarch Oxypropanol, Starch, Food, Modified: Distarch Phosphate (From Phosphorus Oxychloride), Starch, Food, Modified: Distarch Phosphate (From Sodium Trimetaphosphate), Starch, Food, Modified: Glucoamylase Modified Starch, Starch, Food, Modified: Hydroxypropyl Distarch Glycerol, Starch, Food, Modified: Hydroxypropyl Distarch Phosphate, Starch, Food, Modified: Hydroxypropyl Starch, Starch, Food, Modified: Isoamylase Modified Starch, Starch, Food, Modified: Oxidized Hydroxypropyl Starch, Starch, Food, Modified: Oxidized Starches, Starch, Food, Modified: Phosphated Distarch Phosphate, Starch, Food, Modified: Pullulanase Modified Starch, Starch, Food, Modified: Starch Acetate, Starch, Food, Modified: Starch Aluminum Octenyl Succinate, Starch, Food, Modified: Starch Phosphate, Starch, Food, Modified: Starch Sodium Octenyl Succinate, Starch, Food, Modified: Starch Sodium Succinate, Starch, Food, Modified: Succinyl Distarch Glycerol, Starch, Pregelatinized, Starch, Unmodified. Stearic Acid, Stearyl Alcohol, Stearyl Alcohol, Plus Beeswax, Stearyl Citrate, Stearyl Monoglyceridyl Citrate, S-(Tetrahydro-2,5-Dimethyl-3-Furanyl) Ethanethioate, St. Johnswort Leaves, Flowers And Caulis (*Hypericum Perforatuml.*), Storax Extract (*Liquidambar* Spp.), Storax (*Liquidambar* Spp.), Storax Oil, Styrene, Styrene-Divinylbenzene-Acrylonitrile, Sulfonated Terpolymer, Styrene-Divinylbenzene Copolymer, Chloromethylated, Aminated, Oxidized, Styrene-Divinylbenzene-Methyl Acrylate, Sulfonated Terpolymer, Styrene, Divinylbenzene, Sulfonated Copolymer, Styrene-Dvb-Acrylonitrile-Methyl Acrylate, Sulfonated Tetrapolymer, Succinic Acid, Succinic Anhydride, Succinylated Gelatin, Succinylated Monoglycerides, Succistearin, Sucralose, Sucrose, Sucrose Acetate Isobutyrate, Sucrose Fatty Acid Esters, Sucrose Liquid, Sucrose Monopalmitate, Sucrose Octaacetate, Sucrose Oligoesters, Sugar Beet Juice Extract, Sugar Beet Extract Flavor Base, Sulfamic Acid, Sulfites, Strong Alkali, Sulfiting Agents, Sulfopropyl Cellulose, Sulfur Dioxide, Sulfuric Acid, Sulfurous Acid, Sweet Blackberry Leaves Extract, *Tagetes* Meal & Extract, *Tagetes*, Oil (*Tagetes* Spp.), Talc, Tallow Alcohol, Hydrogenated, Tallow, Beef, Tallow Flakes, Tallow, Hydrogenated, Tallow, Hydrogenated, Oxidized Or Sulfated, Tamarind Extract (*Tamarindus Indica* L.), Tamarinds, Tangerine, Essence, Tangerine, Extract (*Citrus Reticulata* Blanco), Tangerine, Oil (*Citrus Reticulata* Blanco), Tannic Acid, Tansy, Oil (*Tanacetum Vulgara* L.), Tansy (*Tanacetum Vulgara* L.), Tapioca Starch, Tarragon (*Artemisia Dracunculus* L.), Tarragon Extract (*Artemisia Dracunculus* L.), Tarragon Oil (*Artemisia Dracunculus* L.), Tartaric Acid, L, Taurine, Taurocholic Acid, Tea Extract (*Thea Sinensis* L.), Tea Tree Oil (*Melaleuca Alternifolia*), Terpene Resin, Terpene Resins, Natural, Terpene Resins, Synthetic, Alpha-Terpinene, Gamma-Terpinene, Alpha-Terpineol, Beta-Terpineol, Terpinolene, Terpinyl Acetate, Alpha-Terpinyl Anthranilate, Terpinyl Butyrate, Terpinyl Cinnamate, Terpinyl Formate, Terpinyl Isobutyrate, Terpinyl Isovalerate, Terpinyl Propionate, Tert-Butylhydroquinone, 2-Tert-Pentylcyclohexyl Acetate, Delta-Tetradecalactone, (Z)-8-Tetradecenal, Tetradec-2-Enal, 9-Tetradecen-5-Olide, Tetraethylenepentamine Crosslinked With Epichlorohydrin, 1,1'-(Tetrahydro-6a-Hydroxy-2,3a,5-Trimethylfuro[2,3-D]-1,3-Dioxole-2,5-Diyl)Bis-Ethanone, 1,2,5,6-Tetrahydrocuminic Acid, 4,5,6,7-Tetrahydro-3,6-Dimethylbenzofuran, Tetrahydrofurfuryl Acetate, Tetrahydrofurfuryl Alcohol, Tetrahydrofurfuryl Butyrate, Tetrahydrofurfuryl Cinnamate, 2-Tetrahydrofurfuryl 2-Mercaptopropionate. Tetrahydrofurfuryl Propionate, Tetrahydrolinalool, Tetrahydro-4-Methyl-2-(2-Methylpropen-1-Yl)Pyran, Tetrahydro-Pseudo-Ionone, 5,6,7,8-Tetrahydroquinoxaline, 2,2,6,7-Tetramethylbicyclo[4.3.0]Nona-4,9(1)-Dien-8-Ol, 2,2,6,7-Tetramethylbicyclo[4.3.0]Nona-4,9(1)-Dien-8-One, Alpha-(P-(1,1,3,3-Tetramethylbutyl)Phenyl)-Omega-Hydroxypoly Oxyethylene)(1 Mol), Alpha-{P-(1,1,3,3-Tetramethylbutyl)Phenyl}-Omega-Hydroxypoly(Oxyethylene), Alpha-(P-(1,1,3,3-Tetramethylbutyl)Phenyl)-Omega-Hydroxypoly(Oxyethylene)(Greater Than 1 Mol), Tetramethyl Ethylcyclohexenone (Mixture Of Isomers), (+/−)-2,6,10,10-Tetramethyl-1-Oxaspiro[4,5]Deca-2,6-Dien-8-One, 1,5,5,9-Tetramethyl-13-Oxatricyclo(8.3.0.0(4,9))Tridecane, 2,3,5,6-Tetramethylpyrazine, Thaumatin, Thaumatin B, Recombinant, Theaspirane, Theobromine, Thiamine, Thiamine Hydrochloride, Thiamine Mononitrate, Thiazole, 2-Thienyl Disulfide, 1-(2-Thienyl)Ethanethiol, 2-Thienyl Mercaptan, 2-Thienylmethanol, Thioacetic Acid, 2,2'-(Thiodimethylene)-Difuran, Thiodipropionic Acid, Thiogeraniol, Thistle, Blessed (*Cnicus Benedictus* L.), Thistle, Blessed, Extract (*Cnicus Benedictus* L.), Thistle, Blessed, Extract Solid (*Cnicus Benedictus* L.), Thistle, Blessed, Oil (*Cnicus Benedictus* L.), L-Threonine, 4-Thujanol, Thujyl Alcohol, Thyme, Extract, Thyme Oil (*Thymus Vulgaris* L. And *T. Zygis* Var. *Gracilis Boiss.*), Thyme Oleoresin, Thyme (*Thymus Serpyllum* L.), Thyme (*Thymus Vulgaris* L.), Thyme, Wild Or Creeping, Extract (*Thymus Serpyllum* L.), Thymol, Titanium Dioxide, Alpha-Tocopherol Acetate, Tocopherols, Tolualdehyde Glyceryl Acetal (Mixed O-, M-, P-), Tolualdehydes (Mixed O-, M-, P-), Tolu Balsam Extract (*Myroxylon* Spp.), Tolu Balsam Gum (*Myroxylon* Spp.), O-Toluenethiol, P-Tolylacetaldehyde, O-Tolyl Acetate, P-Tolyl Acetate, 4-(P-Tolyl)-2-Butanone, O-Tolyl Isobutyrate, P-Tolyl Isobutyrate, P-Tolyl Laurate, P-Tolyl 3-Methylbutyrate. P-Tolyl Octanoate, P-Tolyl Phenylacetate, 2-(P-Tolyl)-Propionaldehyde, O-Tolyl Salicylate, Tomato Lycopene, Tragacanth, Gum (*Astragalus* Spp.), (+/−)-Trans- And Cis-2-Hexenal Propylene Glycol Acetal, 2-Trans-6-Cis-Dodecadienal, 2-Trans-6-Cis-Nonadienal, O-Trans-Coumaric Acid, Trans-2-Decenol, Trans-3-Heptenyl Acetate, Trans-3-Hexenol, Trans-3-Hexenyl Acetate, Trans-2-Hexen-1-Yl Acetate, Trans-2-Hexenyl 2-Methylbutyrate, Trans-4-Nonenal, Trans-3-Nonen-1-ol, Trans-2-Nonen-4-One, Trans-2-Nonenyl Acetate, Trans-4-Octenoic Acid, 2-(Trans-2-Pentenyl)Cyclopentanone, Trans-4-Tert-Butylcyclohexanol, Trans,Trans-2,4-Dodecadienal, Trans-2-Trans-4-Nonadiene, Trans-2-Tridecenol, Trefoil, Sweet (*Melilotus Coerulea*), Trehalose, Dihydrate, Triacetin (Glycerol Triacetate), Tributyl Acetylcitrate, Trichloroethylene, Tridecanal, Tridecanoic Acid, 2-Tridecanone, 2-Trans,4-Cis,7-Cis-Tridecatrienal, 2-Tridecenal, Tridodecyl Amine, Triethanolamine, Triethylamine, Triethyl Citrate, Triethylenetetramine Cross-Linked With Epichlorohydrin, Trifluoromethane Sulfonic Acid, 2,4,5-Trihydroxybutyrophenone, (Trihydroxy-Phenyl)-Propan-1-One, Trilobatin, Trimethylamine, Trimethylamine Oxide, 2,6,6-Trimethyl-1 And 2-Cyclohexen-1-Carboxaldehyde, P,Alpha,Alpha-Trimethylbenzyl Alcohol, 4-(2,6,6-Trimethylcyclohexa-1,3-Dienyl)But-2-En-4-One, 2,6,6-Trimethylcyclohexa-1,3-Dienyl Methanal, 3,3,5-Trimethylcyclohexanol, 2,2,6-Trimethylcyclohexanone, 2,6,6-Trimethyl-1-Cyclohexen-1-Acetaldehyde, 2,6,6-Trimethylcyclohex-2-Ene-1,4-Dione, 4-(2,6,6-Trimethylcyclohex-1-Enyl)But-2-En-4-One, 3,3,5-Trimethylcyclohexyl Acetate, 2,2,3-Trimethylcyclopent-3-En-1-Yl Acetaldehyde, 4-(2,2,3-Trimethylcyclopentyl)Butanoic Acid, 3,7,11-Trimethyldodeca-2,6,10-Trienyl Acetate, 3,5,5-Trimethylhexanal, 3,5,5-Trimethyl-1-Hexanol, 2,6,6-Trimethyl-2-Hydroxycyclohexanone, (2,6,6-Trimethyl-2-Hydroxycyclohexylidene)Acetic Acid Gamma-Lactone. 2,3,3-Trimethylindanone, Trans- And Cis-2,4,8-Trimethyl-3,7-Nona-Dien-2-Ol, (+/−)-2,4,8-Trimethyl-7-Nonen-2-Ol, 1,3,3-Trimethyl-2-Norbornanyl Acetate, 2,2,4-Trimethyl-1,3-Oxacyclopentane, Trimethyloxazole, 2,4,5-Trimethyl-Delta-3-Oxazoline, 2,6,10-Trimethyl-2,6,10-Pentadecatrien-14-One, 2,3,4-Trimethyl-3-Pentanol, 2,4,6-Trimethylphenol, 2,3,6-Trimethylphenol, 2,3,5-Trimethylpyrazine, 2,4,5-Trimethylthiazole, 2,2,6-Trimethyl-6-Vinyltetrahydropyran, Tripropylamine, 1,2,3-Tris((1'-Ethoxy)Ethoxy)-Propane, Trisodium Citrate, Trisodium Nitrilotriacetate, 2,4,6-Trithiaheptane, Trithioacetone, Trypsin From Animal Tissue, L-Tryptophan, Tuberose Lactone, Tuberose, Oil (*Polianthes Tuberosa* L.), Tunu (*Castilla Fallax* Cook), Turmeric (*Curcuma Longa* L.), Turmeric Extract (*Curcuma Longa* L.), Turmeric Oleoresin (*Curcuma Longa* L.), Turpentine, Turpentine, Gum (*Pinus* Spp.), Turpentine, Rectified, Turpentine, Steam Distilled (*Pinus* Spp.), Tyramine, L-Tyrosine, L-Tyrosine Ethyl Ester Hydrochloride, Ultramarine Blue, 2,4-Undecadienal, 2,5-Undecadienal, 2,3-Undecadione, Gamma-Undecalactone, Undecanal, Undecanal Propyleneglycol Acetal, Undecanoic Acid, 2-Undecanol, 2-Undecanone, 1,3,5,7-Undecatetraene, 1,3,5-Undecatriene, 9-Undecenal, 10-Undecenal, 2-Undecenal, (E)-4-Undecenal, 10-Undecenoic Acid, 2-Undecen-1-Ol, Undecen-1-Ol, 2-Undecen-1-Ol, 10-Undecen-2-One, 10-Undecen-1-Yl Acetate, Undecyl Alcohol, N-Undecylbenzenesulfonic Acid, Urea, Urease Enzyme Preparation (*Lactobacillus Fermentum*), Valencene, Valeraldehyde, Valeraldehyde Dibutyl Acetal, Valeraldehyde Propyleneglycol Acetal, Valerian Root, Extract (*Valeriana Officinalis* L.), Valerian Root, Oil (*Valeriana Officinalis* L.), Valeric Acid, Gamma-Valerolactone, L-Valine, *Vanilla*, Absolute (*Vanilla* Spp.), *Vanilla*, Extract (*Vanilla* Spp.), *Vanilla*, Oleoresin (*Vanilla* Spp.), *Vanilla* (*Vanilla* Spp.), Vanillic Acid, Vanillin, Vanillin Acetate, Vanillin 1,2-Butylene Glycol Acetal, Vanillin Isobutyrate, Vanillin 3-(L-Menthoxy)Propane-1,2-Diol Acetal, Vanillin Propylene Glycol Acetal, Vanillyl Alcohol, Vanillyl Butyl Ether, Vanillyl Ethyl Ether, Vanillylidene Acetone, Vegetable Gum, Other Than Those Cfr Listed, Vegetable Juice, Veratraldehyde, Verbenol, Verbenone, *Veronica* (*Veronica Officinalis* L.), Vervain, European (*Verbena Officinalis* L.), Vetiver, Oil (Vetiveria Zizanioides Stapf), Vetiverol, Vetiver (Vetiveria Zizaniodes Stapf), Vetiveryl Acetate, Vinyl Acetate, O-Vinylanisole, Vinyl Chloride-Vinylidene Chloride Copolymer, P-Vinylphenol, Violet Leaves Absolute (*Viola Odorata* L.), Violet, Swiss (*Viola Calcarata* L.), Vitamin D-2, Vitamin D-3, Vitamin B-12, Vitamin A, Vitamin A Acetate, Vitamin B Complex And Syrup, Vitamin D, Vitamin K, Vitamin A Palmitate, Walnut Hull, Extract (*Juglans* Spp.), Walnut Leaves, Extract (*Juglans* Spp.), Wheat Gluten, Wheat Starch, Whey, Whey, Delactosed, Whey, Demineralized, Whey, Partially Diminieralized And Partially Delactosed, Whey Protein Concentrate, Whey Powder, Wintergreen, Extract (*Gaultheria Procumbens* L.), Wintergreen, Oil (*Gaultheria Procumbens* L.), Woodruff, Sweet (*Asperula Odorata* L.), Wort, Xanthan Gum, Xanthophyll, 2,6-Xylenol, 2,5-Xylenol, 3,4-Xylenol, Xylitol, D-Xylose, Yarrow, Herb (*Achillea Millefolium* L.), Yarrow, Oil (*Achillea Millefolium* L.), Yeast Autolysate, Yeast, Dried Irradiated, Yeast Extract Autolyzed, Yeast-Malt Sprout Extract, Yeasts, Dried Yeasts, Yellow Prussiate Of Soda, Yerba Santa, Fluid Extract (*Eriodictyon Californicum* (Hook And Am) Torr), Ylang-Ylang, Oil (*Cananga Odorata* Hook. F. And Thomas), *Yucca*, Joshua-Tree (*Yucca Brevifolia* Engelm.), *Yucca*, Mohave, Extract (*Yucca* Spp.), Yuzunone, Zedoary Bark, Extract (*Curcuma Zedoaria* (Berg.) Rosc.), Zedoary (*Curcuma Zedoaria* (Berg.) Rosc.), Zein Powder, Zinc Acetate, Zinc Carbonate, Zinc Chloride, Zinc Dithionite, Zinc Gluconate, Zinc Methionine Sulfate, Zinc Oxide, Zinc Stearate, Zinc Sulfate, and Zingerone.

Food additives may also include, without limitation, vanillin, ethyl vanillin. 2-hydroxy-4-methoxybenzaldehyde, ethyl vanillin isobutyrate (=3 ethoxy-4-isobutyryloxybenzaldehyde), Furaneol® (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and its derivatives (e.g. ethyl maltol), coumarin and its derivatives, gamma-lactones (e.g. gamma-undecalactone, gamma-nonalactone), delta-lactones (e.g. 4-methyl delta-lactone, *massoia* lactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenylglycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, and phenylacetaldehyde and mixtures thereof; (a2) carbohydrates selected from the group consisting of saccharose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrins and mixtures thereof and plant formulations containing one or a plurality of the cited carbohydrates, preferably in a proportion of at least 5 wt %, preferably at least 15 wt %, whereby the carbohydrates can also be present as a naturally occurring or synthetically produced mixture, in this arrangement particularly as honey, invert sugar syrup or highly enriched fructose syrup from maize starch, and the physiologically acceptable salts of these carbohydrates, particularly sodium, potassium, calcium or ammonium salts; (a3) sugar alcohols, preferably naturally occurring sugar alcohols selected from the group consisting of glycerine, erythritol, threitol, arabitol, ribitol, xylitol, sorbitol, mannitol, maltitol, isomalt, dulcitol, lactitol and mixtures thereof, and the physiologically acceptable salts of these sugar alcohols, particularly sodium, potassium, calcium or ammonium salts; (a4) naturally occurring sweeteners, preferably selected from the group consisting of (a4-1) miraculin, monellin, mabinlin, thaumatin, curculin, brazzein, pentaidin, D-phenylalanine, D-tryptophan, and extracts or fractions obtained from natural sources containing these amino acids and/or proteins and mixtures thereof, and the physiologically acceptable salts of these amino acids and/or proteins, particularly the sodium, potassium, calcium or ammonium salts; (a4-2)neohesperidin dihydrochalcone, naringin dihydrochalcone, stevioside, steviolbioside, rebaudiosides, particularly rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1 baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin-3-acetate, perillartine, telosmoside A.sub.15, periandrin I-V, pterocaryosides, cyclocaryosides, mukuroziosides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanine, chlorogenic acid, albiziasaponin, telosmosides, gaudichaudioside, mogrosides, mogroside V, hernandulcins, monatin, phyllodulcin, glycyrrhetinic acid, and derivatives thereof and mixtures thereof, particularly its glycosides such as glycyrrhizin, and the physiologically acceptable salts of these compounds, particularly the sodium, potassium, calcium or ammonium salts; (a4-3) extracts or enriched fractions of extracts, selected from the group consisting of Thaumatococcus extracts (katemfe bush), extracts of *Stevia* ssp. (particularly *Stevia rebaudiana*), swingle extracts (*Momordica* or *Siratia grosvenorii*, Luo-Han-Guo), extracts of *Glycerrhyzia* ssp. (particularly *Glycerrhyzia glabra*), extracts of *Rubus* ssp. (particularly *Rubus suavissimus*), citrus extracts, and extracts of *Lippia dulcis* and mixtures thereof, and mixtures of any of (a4-1) to (a4-3); (a5) synthetically sweet-tasting substances, preferably selected from the group consisting of magap, sodium cyclamate or other physiologically acceptable salts of cyclamic acid, acesulfame K or other physiologically acceptable salts, neohesperidin dihydrochalcone, naringin dihydrochalcone, saccharin, saccharin-sodium salt, aspartame, superaspartame, neotame, alitame, advantame, perillartine, sucralose, lugduname, carrelame, sucrononate, and sucrooctate.

Flavorants

In some embodiments, the composition comprises a combination of one or more of Compounds 101-105 with one or more flavorants. Representative flavorants include but are not limited to, those compounds identified as such by the Flavor and Extract Manufacturers Association (FEMA; see the FEMA Flavor Ingredient Library, accessible at http://www.femaflavor.org/flavor, last accessed Nov. 16, 2015). Such flavorants include: Acacia Gum (*Acacia* Senegal (L.) Willd.), Acetal, Acetaldehyde, Propyl Phenethyl Acetal, Acetanisole, Acetic Acid, (Tri-)Acetin, Acetoin, Acetophenone, Aconitic Acid, Adipic Acid, Agar (*Gelidium* Spp.), Alfalfa Extract (*Medicago Sativa* L.), Algin (*Laminaria* Spp. And Other Kelps), Alginates, Sodium, Calcium, And Ammonium, Allspice (*Pimenta Officinalis* Lindl.), Allspice Oil (*Pimenta Officinalis* Lindl.), Allspice Oleoresin (*Pimenta Officinalis* Lindl.), Allyl Anthranilate, Allyl Butyrate, Allyl Cinnamate, Allyl Cyclohexaneacetate, Allyl Cyclohexanebutyrate, Allyl Cyclohexanehexanoate, Allyl Cyclohexanepropionate, Allyl Cyclohexanevalerate, Allyl Disulfide, Allyl 2-Ethylbutyrate, Allyl 2-Furoate, Allyl Heptanoate, Allyl Hexanoate, Allyl Alpha-Ionone, Allyl Isothiocyanate, Allyl Mercaptan, Allyl Nonanoate, Allyl Octanoate, Allyl Phenoxyacetate, Allyl Phenylacetate, Allyl Propionate, Allyl Sorbate, Allyl Sulfide, Allyl Tiglate, Allyl 10-Undecenoate, Allyl Isovalerate, Almond Oil, Bitter (Ffpa) (*Prunus* Spp.), *Aloe* Extract (*Aloe* Spp.), *Althea* Root (*Althea Officinalis* L.), Ambergris Tincture, Ambrette Absolute Oil (*Hibiscus Abelmoschus* L.), Ambrette Seed Oil (*Hibiscus Abelmoschus* L.), Ambrette Tincture (*Hibiscus Abelmoschus* L.), Ammonium Sulfide, Ammonium Isovalerate, Isoamyl Acetate, Amyl Alcohol, Isoamyl Alcohol, Isoamyl Benzoate, Amyl Butyrate, Isoamyl Butyrate, Alpha-Amylcinnamaldehyde, Alpha-Amylcinnamaldehyde Dimethyl Acetal, Isoamyl Cinnamate, Alpha-Amylcinnamyl Acetate, Alpha-Amylcinnamyl Alcohol, Alpha-Amylcinnamyl Formate, Alpha-Amylcinnamyl Isovalerate, Amyl Formate, Isoamyl Formate, Isoamyl 4(2-Furan)Butyrate, Isoamyl 3(2-Furan)Propionate, Amyl 2-Furoate, Amyl Heptanoate, Amyl Hexanoate. Isoamyl Hexanoate. 2-Amyl-5 Or 6-Keto-1,4-Dioxane, Isoamyl Laurate, Isoamyl Nonanoate, Amyl Octanoate, Isoamyl Octanoate, Isoamyl Phenylacetate, Isoamyl Propionate, Isoamyl Pyruvate, Isoamyl Salicylate, Isoamyl Isovalerate, Trans-Anethole, *Angelica* Root Extract (*Angelica Archangelica* L.), *Angelica* Root Oil (*Angelica Archangelica* L.), *Angelica* Seed Extract (*Angelica Archangelica* L.), *Angelica* Seed Oil (*Angelica Archangelica* L.), *Angelica* Stem Oil (*Angelica Archangelica* L.), Angostura Extract (*Galipea Offincinalis* Hancock), Anise (*Pimpinella Anisum* L.), Anise Oil (*Pimpinella Anisum* L.), Anise, Star (*Illicium Verum* Hook, F.), Anise, Star, Oil (*Illicium Verum* Hook, F.), Anisole, P-Anisyl Acetate, Anisyl Alcohol, Anisyl Butyrate, Anisyl Formate, Anisyl Propionate, Annatto Extract (*Bixa Orellana* L.), Annatto Seed (*Bixa Orellana* L.), Apricot Kernel Oil (*Prunus Armeniaca* L.), Asafetida Fluid Extract (*Ferula Assafoetida* L.), Asafetida Gum (*Ferula Assafoetida* L.), *Asafoetida* Oil (*Ferula Asafoetida* L.), Ascorbic Acid, Ash Bark, Prickly, Extract (*Xanthoxylum* Spp.), Balm (*Melissa Officinalis* L.), Balm Leaves Extract (*Melissa Officinalis* L.), Balm Oil (*Melissa Officinalis* L.), Balsam Fir Oil (*Abies Balsamea* (L.) Mill.), Balsam Fir Oleoresin (*Abies Balsamea* (L.) Mill.), Balsam, Peru (*Myroxylon Pereirae* Klotzsch), Balsam Oil, Peru (*Myroxylon Pereirae* Klotzsch), Basil (*Ocimum Basilicum* L.), Basil Oil (*Ocimum Basilicum* L.), Basil Oleoresin (*Ocimum Basilicum* L.), Bay Leaves, West Indian, Extract (*Pimenta Acris* Kostel), Bay Leaves, West Indian, Oil (*Pimenta Acris* Kostel), Bay Leaves, West Indian, Oleoresin (*Pimenta Acris* Kostel), Bay, Sweet (*Laurus Nobilis* L.), Bay Oil, Sweet (*Laurus Nobilis* L.), Beeswax, White (*Apis Mellifera* L.), Benzaldehyde, Benzaldehyde Dimethyl Acetal, Benzaldehyde Glyceryl Acetal, Benzaldehyde Propylene Glycol Acetal, Benzoic Acid, Benzoin, Benzoin Resinoid, Benzophenone, Benzyl Acetate, Benzyl Acetoacetate, Benzyl Alcohol, Benzyl Benzoate, Benzyl Butyl Ether, Benzyl Butyrate, Benzyl Isobutyrate, Benzyl Cinnamate, Benzyl 2,3-Dimethylcrotonate, Benzyl Ethyl Ether, Benzyl Formate, 3-Benzyl-4-Heptanone, Benzyl Mercaptan, Benzyl Methoxyethyl Acetal, Benzyl Phenylacetate, Benzyl Propionate, Benzyl Salicylate, Benzyl Isovalerate, Bergamot Oil, Birch, Sweet, Oil (*Betula Lenta* L.), Blackberry Bark Extract (*Rubus*, Spp. Of Section Eubatus), Bois De Rose Oil, Borneol, Isoborneol, Bornyl Acetate, Isobornyl Acetate, Bornyl Formate, Isobornyl Formate, Isobornyl Propionate, Bornyl Valerate, Bornyl Isovalerate (Endo-), Isobornyl Isovalerate, *Boronia* Absolute (*Boronia Megastigma* Nees), Buchu Leaves Oil (*Barosma* Spp.), 2-Butanone, Butter Acids, Butter Esters, Butter Starter Distillate, Butyl Acetate, Isobutyl Acetate, Butyl Acetoacetate, Isobutyl Acetoacetate, Butyl Alcohol, Isobutyl Alcohol, Isobutyl Angelate, Butyl Anthranilate, Isobutyl Anthranilate, Butylated Hydroxyanisole, Butylated Hydroxytoluene, Isobutyl Benzoate, Butyl Butyrate, Isobutyl Butyrate, Butyl Isobutyrate, Isobutyl Isobutyrate, Butyl Butyryllactate, Alpha-Butylcinnamaldehyde, Butyl Cinnamate, Isobutyl Cinnamate, Butyl 2-Decenoate, Butyl Ethyl Malonate, Butyl Formate, Isobutyl Formate, Isobutyl 3-(2-Furan)Propionate, Butyl Heptanoate, Isobutyl Heptanoate, Butyl Hexanoate, Isobutyl Hexanoate, Butyl P-Hydroxy Benzoate, 2-Butyl-5- Or 6-Keto-1,4-Dioxane, Butyl Lactate, Butyl Laurate, Butyl Levulinate, Alpha-Isobutylphenethyl Alcohol, Butyl Phenylacetate, Isobutyl Phenylacetate, Butyl Propionate, Isobutyl Propionate, Isobutyl Salicylate, Butyl Stearate, Butyl Sulfide, Butyl 10-Undecenoate, Butyl Valerate, Butyl Isovalerate, Butyraldehyde, Isobutyraldehyde, Butyric Acid, Isobutyric Acid, (Tri-)Butyrin, Caffeine, Cajeput Oil (*Melaleuca Leucadendron* L.), Calcium Acetate, Camphene, D-Camphor, Camphor, Japanese, White, Oil (*Cinnamomum Camphora* (L.) Nees Et Eberm.), *Cananga* Oil, *Capsicum* Extract (*Capsicum* Spp.), *Capsicum* Oleoresin (*Capsicum* Spp.), Caramel Color, Caraway (*Carum Carvi* L.), Caraway, Black (*Nigella Sativa* L.), Caraway Oil, Carboxymethylcellulose, Cardamom (*Elettaria Cardamomum* (L.) Maton), Cardamom Seed Oil (*Elettaria Cardamomum* (L.) Maton), Carmine (*Coccus Cacti* L.), Carob Bean Extract (*Ceratonia Siliqua* L.), Carrot Oil, Carvacrol, Carvacryl Ethyl Ether, Carveol, 4-Carvomenthenol, Carvone, Carvyl Acetate, Carvyl Propionate, Beta-Caryophyllene, Cascara Bitterless Extract (*Rhamnus Purshiana* Dc.), Cascarilla Bark Extract (*Croton* Spp.), Cascarilla Bark Oil (*Croton* Spp.), *Cassia* (*Cinnamomum Cassia* Blume), *Cassia* Bark Extract (*Cinnamomum Cassia* Blume), *Cassia* Bark Oil, *Cassia* Buds (*Cinnamomum Cassia* Blume), Cassie Absolute (*Acacia Farnesiana* (L.) Willd.), Castoreum Oil, Castoreum, Liquid (*Castor* Spp.), Castor Oil (*Ricinus Communis* L.), Catechu Extract (*Acacia Catechu* Willd.), Catechu Powder (*Acacia Catechu* Willd.), Cayenne (*Capsicum Annuum* L. Var. *Longum Sendt*), Cedar Leaf Oil (*Thuja Occidentalis* L.), Celery Seed (*Apium Graveolens* L.), Celery Seed Extract (*Apium Graveolens* L.), Celery Seed Extract Solid (*Apium Graveolens* L.), Celery Seed Oil, Chamomile Flower, English, Oil (*Anthemis Nobilis* L.), Chamomile Flower, Hungarian, Oil (*Matricaria Chamomilla* L.), Chamomile Flower, Roman, Extract (*Anthemis Nobilis* L.), Chamomile Flower, Roman, Oil (*Anthemis Nobilis* L.), Cherry Bark, Wild, Extract (*Prunus Serotina* Ehrh.), Cherry Laurel Oil (Ffpa) (*Prunus Laurocerasus* L.), Cherry Pits Extract (*Prunus* Spp.), Chervil (*Anthriscus Cerefolium* (L.) Hoffm.), Chicory Extract (*Cichorium Intybus* L.), *Cinchona* Bark Red (*Cinchona Succirubra* Pav. Or Its Hybrids), *Cinchona* Bark Red Extract (*Cinchona Succirubra* Pav. Or Its Hybrids), *Cinchona* Bark Yellow (*Cinchona* Spp.), *Cinchona* Bark Yellow Extract (*Cinchona* Spp.), *Cinchona* Extract (*Cinchona* Spp.), Cinnamaldehyde, Cinnamaldehyde Ethylene Glycol Acetal, Cinnamic Acid, Cinnamon (*Cinnamomum* Spp.), Cinnamon Bark Extract (*Cinnamomum* Spp.), Cinnamon Bark Oil, Cinnamon Leaf Oil, Cinnamyl Acetate, Cinnamyl Alcohol, Cinnamyl Butyrate, Cinnamyl Isobutyrate, Cinnamyl Cinnamate, Cinnamyl Formate, Cinnamyl Phenylacetate, Cinnamyl Propionate, Cinnamyl Isovalerate, Citral, Citral Diethyl Acetal, Citral Dimethyl Acetal, Citric Acid, Citronellal, Citronella Oil, Dl-Citronellol, Citronelloxyacetaldehyde, Citronellyl Acetate, Citronellyl Butyrate, Citronellyl Isobutyrate, Citronellyl Formate, Citronellyl Phenylacetate, Citronellyl Propionate, Citronellyl Valerate, *Citrus* Peels Extract (*Citrus* Spp.), Civet Absolute (Viverra Civetta Schreber And Viverra Zibetha Schreber). Clary (*Salvia Sclarea* L.), Clary Oil (*Salvia Sclarea* L.), Clove Bud Extract (*Eugenia* Spp.), Clove Bud Oil (*Eugenia* Spp.), Clove Bud Oleoresin (*Eugenia* Spp.), Clove Leaf Oil, Madagascar, Clover Tops Red Extract Solid (*Trifolium Pratense* L.), Cloves (*Eugenia* Spp.), Clove Stem, Oil (*Eugenia* Spp.), Coca Leaf Extract (Decocainized) (Erythroxylon Coca Lam.), Cognac Oil, Green, Cognac Oil, White, Coriander (*Coriandrum Sativum* L.), Coriander Oil (*Coriandrum Sativum* L.), Corn Silk (*Zea Mays* L.), Costus Root Oil (*Saussurea Lappa* Clarke), P-Cresol, Cubebs (*Piper Cubeba* L. F.), Cubeb Oil (*Piper Cubeba* L. F.), Cumin (*Cuminum Cyminum* L.), Cuminaldehyde, Cumin Black (*Nigella Sativa* L.), Cumin Oil, Curacao Peel Extract (*Citrus Aurantium* L.), Curacao Peel Oil (*Citrus Aurantium* L.), Currant Buds Black Absolute (*Ribes Nigrum* L.), Cyclohexaneacetic Acid, Cyclohexaneethyl Acetate, Cyclohexyl Acetate, Cyclohexyl Anthranilate, Cyclohexyl Butyrate, Cyclohexyl Cinnamate, Cyclohexyl Formate, Cyclohexyl Propionate, Cyclohexyl Isovalerate, P-Cymene, Dandelion Fluid Extract (*Taraxacum* Spp.), Dandelion Root Extract Solid (*Taraxacum* Spp.), Davana Oil (*Artemisia Pallens* Wall.), Gamma-Decalactone, Delta-Decalactone, Decanal, Decanal Dimethyl Acetal, Decanoic Acid, 1-Decanol, 2-Decenal, Decyl Acetate, Decyl Butyrate, Decyl Propionate, Diacetyl, Dibenzyl Ether, 4,4-Dibutyl-Gamma-Butyrolactone, Dibutyl Sebacate, Diethyl Malate, Diethyl Malonate, Diethyl Sebacate, Diethyl Succinate, Diethyl Tartrate, Dihydrocarveol (Isomer Unspecified), Dihydrocarvyl Acetate, Dihydrocoumarin, Dill (*Anethum Graveolens* L.), Dill Oil (*Anethum Graveolens* L.), Dill Seed Indian (*Anethum* Spp.), M-Dimethoxybenzene, P-Dimethoxybenzene, 2,4-Dimethylacetophenone, Alpha,Alpha-Dimethylbenzyl Isobutyrate, 2,6-Dimethyl-5-Heptenal, 2,6-Dimethyloctanal, 3,7-Dimethyl-1-Octanol, Alpha,Alpha-Dimethylphenethyl Acetate, Alpha,Alpha-Dimethylphenethyl Alcohol, Alpha,Alpha-Dimethylphenethyl Butyrate, Alpha,Alpha-Dimethylphenethyl Formate, Dimethyl Succinate, 1,3-Diphenyl-2-Propanone, Disodium Phosphate, Dittany Of Crete (*Origanum Dictamnus* L.), Gamma-Dodecalactone, Delta-Dodecalactone, 2-Dodecenal, Doggrass Extract (*Agropyron Repens* (L.) Beauv.), Dragon's Blood Extract (*Daemonorops* Spp. Or Other Botanical Sources), Dulse (*Rhodymenia Palmata* (L.) Grev.), Elder Flowers (*Sambucus Canadensis* L. Or *Sambucus Nigra* L.), Elemi Gum (*Canarium* Spp.), Elemi Oil (*Canarium* Spp.), *Erigeron* Oil (*Erigeron Candensis* L.), Erythrobic Acid, Estragole, Estragon Oil (*Artemisia Dracunculus* L.), P-Ethoxybenzaldehyde, Ethyl Acetate, Ethyl Acetoacetate, Ethyl 2-Acetyl-3-Phenylpropionate, Ethyl Aconitate (Mixed Esters), Ethyl Acrylate, Ethyl Alcohol, Ethyl P-Anisate, Ethyl Anthranilate, Ethyl Benzoate, Ethyl Benzoylacetate, Alpha-Ethylbenzyl Butyrate, 2-Ethylbutyl Acetate, 2-Ethylbutyraldehyde, Ethyl Butyrate, Ethyl Isobutyrate, 2-Ethylbutyric Acid, Ethyl Cinnamate, Ethyl Cyclohexanepropionate, Ethyl Decanoate, Ethyl Formate, Ethyl 3(2-Furyl)Propanoate, 4-Ethylguaiacol, Ethyl Heptanoate, 2-Ethyl-2-Heptenal, Ethyl Hexanoate, Ethyl Lactate, Ethyl Laurate, Ethyl Levulinate, Ethyl 2-Methylbutyrate, Ethyl Methylphenylglycidate, Ethyl Myristate, Ethyl Nitrite, Ethyl Nonanoate, Ethyl 2-Nonynoate, Ethyl Octanoate, Ethyl Oleate, Ethyl Palmitate, Ethyl Phenylacetate, Ethyl 4-Phenylbutyrate, Ethyl 3-Phenylglycidate, Ethyl 3-Phenylpropionate, Ethyl Propionate, Ethyl Pyruvate, Ethyl Salicylate, Ethyl Sorbate, Ethyl Tiglate, Ethyl 10-Undecenoate, Ethyl Valerate, Ethyl Isovalerate, Ethyl Vanillin, Eucalyptol, *Eucalyptus* Oil (*Eucalyptus Globulus* Labille), Eugenol, Isoeugenol, Eugenyl Acetate, Isoeugenyl Acetate, Eugenyl Benzoate, Isoeugenyl Ethyl Ether, Eugenyl Formate, Isoeugenyl Formate, Eugenyl Methyl Ether, Isoeugenyl Methyl Ether, Isoeugenyl Phenylacetate, Farnesol, D-Fenchone, Fenchyl Alcohol, Fennel, Common (*Foeniculum Vulgare* Mill.), Fennel, Sweet (*Foeniculum Vulgare* Mill. Var Dulce (D.C.), Fennel Oil, Sweet (*Foeniculum Vulgare* Mill. Var. Dulce Dc.), Fenugreek (*Trigonella Foenum-Graecum* L.), Fenugreek Extract (*Trigonella Foenum-Graecum* L.), Fenugreek Oleoresin (*Trigonella Foenumgraecum* L.), Formic Acid, Fumaric Acid, Furfural, Furfuryl Acetate, Furfuryl Alcohol, 2-Furfurylidene Butyraldehyde, Furfuryl Mercaptan, 3-(2-Furyl)Acrolein, 4-(2-Furyl)-3-Buten-2-One, (2-Furyl)-2-Propanone, Fusel Oil, Refined, Galangal Root (*Alpinia* Spp.), Galangal Root Extract (*Alpinia* Spp.), Galangal Root Oil (*Alpinia* Spp.), *Galbanum* Oil (*Ferula* Spp.), *Galbanum* Resin (*Ferula* Spp.), Garlic Oil (*Allium Sativum* L.), Genet Absolute (*Spartium Junceum* L.), Genet Extract (*Spartium Junceum* L.), Gentian Root Extract (*Gentiana Lutea* L.), Geraniol, Elemi Gum (*Canarium* Spp.), Elemi Oil (*Canarium* Spp.), *Erigeron* Oil (*Erigeron Candensis* L.), Erythrobic Acid, Estragole, Estragon Oil (*Artemisia Dracunculus* L.), P-Ethoxybenzaldehyde, Ethyl Acetate, Ethyl Acetoacetate, Ethyl 2-Acetyl-3-Phenylpropionate, Ethyl Aconitate (Mixed Esters), Ethyl Acrylate, Ethyl Alcohol, Ethyl P-Anisate, Ethyl Anthranilate, Ethyl Benzoate, Ethyl Benzoylacetate, Alpha-Ethylbenzyl Butyrate, 2-Ethylbutyl Acetate, 2-Ethylbutyraldehyde, Ethyl Butyrate, Ethyl Isobutyrate, 2-Ethylbutyric Acid, Ethyl Cinnamate, Ethyl Cyclohexanepropionate, Ethyl Decanoate, Ethyl Formate, Ethyl 3(2-Furyl)Propanoate, 4-Ethylguaiacol, Ethyl Heptanoate, 2-Ethyl-2-Heptenal, Ethyl Hexanoate, Ethyl Lactate, Ethyl Laurate, Ethyl Levulinate, Ethyl 2-Methylbutyrate, Ethyl Methylphenylglycidate, Ethyl Myristate, Ethyl Nitrite, Ethyl Nonanoate, Ethyl 2-Nonynoate, Ethyl Octanoate, Ethyl Oleate, Ethyl Palmitate, Ethyl Phenylacetate, Ethyl 4-Phenylbutyrate, Ethyl 3-Phenylglycidate, Ethyl 3-Phenylpropionate, Ethyl Propionate, Ethyl Pyruvate, Ethyl Salicylate, Ethyl Sorbate, Ethyl Tiglate, Ethyl 10-Undecenoate, Ethyl Valerate, Ethyl Isovalerate, Ethyl Vanillin, Eucalyptol, *Eucalyptus* Oil (*Eucalyptus Globulus* Labille), Eugenol, Isoeugenol, Eugenyl Acetate, Isoeugenyl Acetate, Eugenyl Benzoate, Isoeugenyl Ethyl Ether, Eugenyl Formate, Isoeugenyl Formate, Eugenyl Methyl Ether, Isoeugenyl Methyl Ether, Isoeugenyl Phenylacetate, Farnesol, D-Fenchone, Fenchyl Alcohol, Fennel, Common (*Foeniculum Vulgare* Mill.), Fennel, Sweet (*Foeniculum Vulgare* Mill. Var Dulce (D.C.), Fennel Oil, Sweet (*Foeniculum Vulgare* Mill. Var. Dulce Dc.), Fenugreek (*Trigonella Foenum-Graecum* L.), Fenugreek Extract (*Trigonella Foenum-Graecum* L.), Fenugreek Oleoresin (*Trigonella Foenumgraecum* L.), Formic Acid, Fumaric Acid, Furfural, Furfuryl Acetate, Furfuryl Alcohol, 2-Furfurylidene Butyraldehyde, Furfuryl Mercaptan, 3-(2-Furyl)Acrolein, 4-(2-Furyl)-3-Buten-2-One, (2-Furyl)-2-Propanone, Fusel Oil, Refined, Galangal Root (*Alpinia* Spp.), Galangal Root Extract (*Alpinia* Spp.), Galangal Root Oil (*Alpinia* Spp.), *Galbanum* Oil (*Ferula* Spp.), *Galbanum* Resin (*Ferula* Spp.), Garlic Oil (*Allium Sativum* L.), Genet Absolute (*Spartium Junceum* L.), Genet Extract (*Spartium Junceum* L.), Gentian Root Extract (*Gentiana Lutea* L.), Geraniol, Labdanum Absolute (*Cistus* Spp.), Labdanum Oil (*Cistus* Spp.), Labdanum Oleoresin (*Cistus* Spp.), Lactic Acid, Laurel Berries (*Laurus Nobilis* L.), Laurel Leaves Extract (*Laurus Nobilis* L.), Lauric Acid, Lauric Aldehyde, Lauryl Acetate, Lauryl Alcohol, Lavandin Oil (*Lavandula Hybrida*), Lavender (*Lavandula Officinalis* Chaix), Lavender Absolute (*Lavandula Officinalis* Chaix), Lavender Concrete (*Lavandula Officinalis* Chaix), Lavender Oil (*Lavandula Officinalis* Chaix), Lemon Extract (*Citrus Limon* (L.) Burm. F.), Lemongrass Oil, Lemon Oil, Lemon Oil Terpeneless (*Citrus Limon* (L.) Burm. F.), Levulinic Acid, Licorice Extract (*Glycyrrhiza* Spp.), Licorice Extract Powder (*Glycyrrhiza Glabra* L.), Licorice Root (*Glycyrrhiza Glabra* L.), Lime Oil, Lime Oil, Terpeneless (*Citrus* Aurantifolia (Christman) Swingle), D-Limonene, Linaloe Wood Oil (*Bursera Delpechiana Poiss*. And Other *Bursera* Spp.), Linalool, Linalyl Acetate, Linalyl Anthranilate, Linalyl Benzoate, Linalyl Butyrate, Linalyl Isobutyrate, Linalyl Cinnamate, Linalyl Formate, Linalyl Hexanoate, Linalyl Octanoate, Linalyl Propionate, Linalyl Isovalerate, Linden Flowers (*Tilia Glabra* Vent.), Locust Gum (*Ceratonia Siliqua* L.), Lovage (*Levisticum Officinale* Koch), Lovage Extract (*Levisticum Officinale* Koch), Lovage Oil (*Levisticum Officinale* Koch), Mace (*Myristica Fragrans* Houtt.), Mace Oil (*Myristica Fragrans* Houtt.), Mace Oleoresin (*Myristica Fragrans* Houtt.), L-Malic Acid, Maltol, Mandarin Oil, Expressed, Marigold, Pot (*Calendula Officinalis* L.), Marjoram Oleoresin (*Majorana Hortensis* Moench-*Origanum Majorana* L.), Marjoram, Pot (*Origanum Vulgare* L.), Marjoram Seed (*Majorana Hortensis* Moench-*Origanum Majorana* L.), Marjoram, Sweet (*Majorana Hortensis* Moench-*Origanum Majorana* L.), Marjoram Oil, Sweet (*Origanum Majorana*), P-*Mentha*-1,8-Dien-7-Ol, Menthol Racemic, (+)-Neoisomenthol, Menthone, Menthyl Acetate (Isomer Unspecified), Menthyl Isovalerate, P-Methoxybenzaldehyde, 2-Methoxy-4-Methylphenol, 4-(P-Methoxyphenyl)-2-Butanone, 1-(P-Methoxyphenyl)-1-Penten-3-One, 1-(P-Methoxyphenyl)-2-Propanone, 2-Methoxy-4-Vinylphenol, Methyl Acetate, 4'-Methylacetophenone, 2-Methylallyl Butyrate, Methyl Anisate, O-Methylanisole, P-Methylanisole, Methyl Anthranilate, Methyl Benzoate, Alpha-Methylbenzyl Acetate, Alpha-Methylbenzyl Alcohol, Alpha-Methylbenzyl Butyrate, Alpha-Methylbenzyl Isobutyrate, Alpha-Methylbenzyl Formate, Alpha-Methylbenzyl Propionate, Methyl P-Tert-Butylphenylacetate, 2-Methylbutyraldehyde, 3-Methylbutyraldehyde, Methyl Butyrate, Methyl Isobutyrate, 2-Methylbutyric Acid, Methyl Cellulose, Alpha-Methylcinnamaldehyde, Methyl Cinnamate, 6-Methylcoumarin, Methylcyclopentenolone, 4-(3,4-Methylenedioxyphenyl)-2-Butanone, 5-Methylfurfural, Methyl 2-Furoate, 2-Methyl-3(2-Furyl)Acrolein, Methyl Heptanoate, 2-Methylheptanoic Acid, 6-Methyl-5-Hepten-2-One, Methyl Hexanoate, Methyl 2-Hexenoate, Methyl P-Hydroxybenzoate, Methyl-Alpha-Ionone, Methyl-Beta-Ionone, Methyl-Delta-Ionone, Alpha-Iso-Methylionone, Methyl Laurate. Methyl Mercaptan, Methyl O-Methoxybenzoate, Methyl N-Methylanthranilate, Methyl 2-Methylbutyrate, Methyl 3-Methylthiopropionate, Methyl 4-Methylvalerate, Methyl Myristate, Methyl Beta-Naphthyl Ketone, Methyl Nonanoate, Methyl 2-Nonenoate, Methyl 2-Nonynoate, 2-Methyloctanal, Methyl Octanoate, Methyl 2-Octynoate, 4-Methyl-2,3-Pentanedione, 4-Methyl-2-Pentanone, Beta-Methylphenethyl Alcohol, Methyl Phenylacetate, 3-Methyl-4-Phenyl-3-Butene-2-One, 2-Methyl-4-Phenyl-2-Butyl Acetate, 2-Methyl-4-Phenyl-2-Butyl Isobutyrate, 2-Methyl-4-Phenylbutyraldehyde, 3-Methyl-2-Phenylbutyraldehyde, Methyl 4-Phenylbutyrate, 4-Methyl-1-Phenyl-2-Pentanone, Methyl 3-Phenylpropionate, Methyl Propionate, 2-Methyl-3-(P-Isopropylphenyl)Propionaldehyde, 6-Methylquinoline, Methyl Salicylate, Methyl Sulfide, 3-(Methylthio)Propionaldehyde, 2-Methyl-3-Tolylpropionaldehyde, 2-Methylundecanal, Methyl 9-Undecenoate, Methyl 2-Undecynoate, Methyl Valerate, Methyl Isovalerate, 2-Methylvaleric Acid, *Mimosa* Absolute (*Acacia Decurrens* Willd. Var. *Dealbata*), Monosodium Glutamate, Mountain Maple Extract Solid (*Acer Spicatum* Lam.), Musk Tonquin (*Moschus Moschiferus* L.), Mustard, Brown (*Brassica* Spp.), Mustard, Yellow (*Brassica* Spp.), Myrcene, Myristaldehyde, Myristic Acid, Myrrh Gum (*Commiphora* Spp.), Myrrh Oil (*Commiphora* Spp.), Beta-Naphthyl Anthranilate, Beta-Naphthyl Ethyl Ether, Naringen Extract (*Citrus Paradisi* Macf.), Nerol, Neroli Bigarde Oil (*Citrus Aurantium* L.), Nerolidol (Isomer Unspecified), Neryl Acetate, Neryl Butyrate, Neryl Isobutyrate, Neryl Formate, Neryl Propionate, Neryl Isovalerate, Nitrous Oxide, 2,6-Nonadien-1-Ol, Gamma-Nonalactone, Nonanal, 1,3-Nonanediol Acetate (Mixed Esters), Nonanoic Acid, 2-Nonanone, Nonanoyl 4-Hydroxy-3-Methoxybenzylamide, Nonyl Acetate, Nonyl Alcohol, Nonyl Octanoate, Nonyl Isovalerate, Nutmeg (*Myristica Fragrans* Houtt.), Nutmeg Oil, Oak Chips Extract (*Quercus Alba* L.), Oakmoss Absolute (*Evernia* Spp.), Gamma-Octalactone, Octanal, Octanal Dimethyl Acetal, Octanoic Acid, 1-Octanol, 2-Octanol, 2-Octanone, 3-Octanone, 3-(Hydroxymethyl)-2-Heptanone, 1-Octen-3-ol, Octyl Acetate, Octyl Butyrate, Octyl Isobutyrate, Octyl Formate, Octyl Heptanoate, Octyl Octanoate, Octyl Phenylacetate, Octyl Propionate, Octyl Isovalerate, Oleic Acid, Olibanum Oil (*Boswellia* Spp.), Onion Oil (*Allium Cepa* L.), Onion Flakes, Onion Powder, onion Extract, Orange Blossoms Absolute, Orange Flowers (*Citrus Aurantium* L.), Orange Leaf Absolute (*Citrus Aurantium* L.), Orange Oil Distilled (*Citrus Sinensis* (L.) Osbeck), Orange Oil Terpeneless (*Citrus Sinensis* (L.) Osbeck), Orange Peel Oil, Bitter (*Citrus Aurantium* L.), Orange Peel, Sweet, Extract (*Citrus Sinensis* L. Osbeck), Orange Peel Oil, Sweet (*Citrus Sinensis* (L.) Osbeck), Orange Peel, Sweet, Oil, Terpeneless (*Citrus Sinensis* L. Osbeck), Oregano (*Lippia* Spp.), *Origanum* Oil (Extractive) (*Thymus Capitatus* L. Hoffmanns & Link), Orris Concrete Liquid Oil (*Iris Florentina* L.), Orris Root Extract (*Iris Florentina* L.), Palmarosa Oil (*Cymbopogon Martini* (Roxb.) Stapf), Palmitic Acid, Paprika (*Capsicum Annuum* L.), Paprika Oleoresin (*Capsicum Annuum* L.), Parsley (*Petroselinum Crispum* (Miller) Nyman-P. *Sativum* Hoffm.), Parsley Oil, Parsley Oleoresin (*Petroselinum* Spp.), Parsnip (*Pastinaca Sativa*), Parsnip, Dehydrated, Parsnip Extract, Patchouly Oil, Pennyroyal Oil (*Mentha Pulegium* L.), Omega-Pentadecalactone, 2,3-Pentanedione, 2-Pentanone, 4-Pentenoic Acid, Pepper, Black (*Piper Nigrum* L.), Pepper, Black, Oil (*Piper*

Nigrum L.), Pepper, Black, Oleoresin (*Piper Nigrum* L.), Pepperment Leaves (*Mentha Piperita* L.), Peppermint Oil, Pepper (*Capsicum Frutescens* L. (*Capsicum Annuum* L.)), Pepper, Red (*Capsicum Frutescens* L. (*Capsicum Annuum* L.)), Pepper, Green (*Capsicum Frutescens* L. (*Capsicum Annuum* L.)), Pepper, Orange (*Capsicum Frutescens* L. (*Capsicum Annuum* L.)), Pepper, Yellow (*Capsicum Frutescens* L. (*Capsicum Annuum* L.)), Pepper, White (*Piper Nigrum* L.), Pepper, White, Oil (*Piper Nigrum* L.), Pepper, White. Oleoresin (*Piper Nigrum* L.), Petitgrain, Lemon, Oil (*Citrus Limon* L. Burm. F), Petitgrain Mandarin Oil (*Citrus Reticulata* Blanco Var. Mandarin), Petitgrain Paraguay Oil, Alpha-Phellandrene, Phenethyl Acetate, Phenethyl Alcohol, Phenylethyl Anthranilate, Phenethyl Benzoate, Phenethyl Butyrate, Phenethyl Isobutyrate, Phenethyl Cinnamate, Phenethyl Formate, Phenethyl 2-Furoate, Phenethyl Phenylacetate, Phenethyl Propionate, Phenethyl Salicylate, Phenethyl Senecioate, Phenethyl Tiglate, Phenethyl Isovalerate, Phenoxyacetic Acid, 2-Phenoxyethyl Isobutyrate, Phenylacetaldehyde, Phenylacetaldehyde 2,3-Butylene Glycol Acetal, Phenylacetaldehyde Dimethyl Acetal, Phenylacetaldehyde Glyceryl Acetal, Phenylacetic Acid, 4-Phenyl-2-Butanol, 4-Phenyl-3-Buten-2-Ol, 4-Phenyl-3-Buten-2-One, 4-Phenyl-2-Butyl Acetate, 1-Phenyl-3-Methyl-3-Pentanol, 1-Phenyl-1-Propanol, 3-Phenyl-1-Propanol, 2-Phenylpropionaldehyde, 3-Phenylpropionaldehyde, 2-Phenylpropionaldehyde Dimethyl Acetal, 3-Phenylpropionic Acid, 3-Phenylpropyl Acetate, 2-Phenylpropyl Butyrate, 2-Phenylpropyl Isobutyrate, 3-Phenylpropyl Isobutyrate, 3-Phenylpropyl Cinnamate, 3-Phenylpropyl Formate, 3-Phenylpropyl Hexanoate, 3-Phenylpropyl Propionate, 2-(3-Phenylpropyl)Tetrahydrofuran, 3-Phenylpropyl Isovalerate, Phosphoric Acid, *Pimenta* Leaf Oil, Alpha-Pinene, Beta-Pinene, Pine Needle, Dwarf, Oil (*Pinus Mugo* Turra Var. *Pumilio* (Haenke) Zenari), Pine Needle Oil (*Abies* Spp.), Pine Scotch Oil (*Pinus Sylvestris* L.), Pine Tar Oil (*Pinus Palustris* Mill. And Other *Pinus* Spp.), Piperidine, Piperine, D-Piperitone, Piperonal, Piperonyl Acetate, Piperonyl Isobutyrate, Pipsissewa Leaves Extract (*Chimaphila Umbellata* Nutt.), Polysorbate 20, Polysorbate 60, Polysorbate 80, Pomegranate Bark Extract (*Punica Granatum* L.), Poppy Seed (*Papaver Somniferum* L.), Potassium Acetate, Potassium Sorbate, Propenylguaethol, Propionaldehyde, Propionic Acid, Propyl Acetate, Isopropyl Acetate, P-Isopropylacetophenone, Propyl Alcohol, Isopropyl Alcohol, P-Propylanisole, Propyl Benzoate. Isopropyl Benzoate, P-Isopropylbenzyl Alcohol, Propyl Butyrate, Isopropyl Butyrate, Propyl Isobutyrate, Isopropyl Isobutyrate, Propyl Cinnamate, Isopropyl Cinnamate, Propylene Glycol, Propylene Glycol Alginate, Propylene Glycol Stearate, Propyl Formate, Isopropyl Formate, Propyl 2-Furanacrylate, Propyl 2-Furoate, Propyl Gallate, Propyl Heptanoate, Propyl Hexanoate, Isopropyl Hexanoate, Propyl P-Hydroxybenzoate, 3-Propylidenephthalide, Alpha-Propylphenethyl Alcohol, P-Isopropyl Phenylacetaldehyde, Propyl Phenylacetate, Isopropyl Phenylacetate, 3-(P-Isopropylphenyl)Propionaldehyde, Propyl Propionate, Isopropyl Propionate, Propyl Isovalerate, Isopropyl Isovalerate, Isopulegol, Pulegone, Isopulegone, Isopulegyl Acetate, Pyridine, Pyroligneous Acid, Pyroligneous Acid, Extract, Pyruvaldehyde, Pyruvic Acid, *Quassia* Extract (*Picrasma Excelsa* (Sw.) Planch.-*Quassia Amara* L.), Quebracho Bark Extract, *Quillaia* (*Quillaja Saponaria* Molina), Quince Seed Extract (*Cydonia* Spp.), Quinine Bisulfate, Quinine Hydrochloride, Quinine Sulfate, Isoquinoline, Rhatany Extract (*Krameria* Spp.), Rhodinol, Rhodinyl Acetate, Rhodinyl Butyrate, Rhodinyl Isobutyrate, Rhodinyl Formate, Rhodinyl Phenylacetate, Rhodinyl Propionate, Rhodinyl Isovalerate, Rose Absolute (*Rosa* Spp.), Rose Oil (*Rosa Damascena* Mill.), Rose Hips Extract (*Rosa* Spp.), Rosemary (*Rosemarinus Officinalis* L.), Rosemary Oil (*Rosemarinus Officinalis* L.), Rose Water, Stronger (*Rosa Centifolia* L.), Rue (*Ruta Graveolens* L.), Rue Oil (*Ruta Graveolens* L.), Rum Ether, Saccharine, Sodium Salt, Saffron (*Crocus Sativus* L.), Saffron Extract (*Crocus Sativus* L.), Sage (*Salvia Officinalis* L.), Sage Oil (*Salvia Officinalis* L.), Sage Oleoresin (*Salvia Officinalis* L.), Sage Oil, Spanish (*Salvia* Lavandulaefolia Vahl.), Salicylaldehyde, Sandalwood Yellow Oil (*Santalum Album* L.), Santalol (Alpha And Beta), Santalyl Acetate, Santalyl Phenylacetate, Sarsaparilla Extract (*Smilax* Spp.), *Sassafras* Bark Extract (Safrol-Free) (*Sassafras Albidum* (Nutt.) Nees), *Sassafras* Leaves (Safrol-Free) (*Sassafras Albidum* (Nutt.) Nees), Savory, Summer (*Satureja Hortensis* L.), Savory Summer Oil (*Satureja Hortensis* L.), Savory, Summer, Oleoresin (*Satureja Hortensis* L.), Savory, Winter (*Satureja Montana* L.), Savory Winter Oil (*Satureja Montana* L.), Savory, Winter, Oleoresin (*Satureja Montana* L.), *Schinus Molle* Oil (*Schinus Molle* L.), Skatole, Sloe Berries (*Prunus Spinosa* L.), Sloe Berries Extract (*Prunus Spinosa* L.), Sloe Berries Extract Solid (*Prunus Spinosa* L.), Snakeroot Oil, Canadian (*Asarum Canadense* L.), Sodium Acetate, Sodium Benzoate, Sodium Citrate, Sodium Hexametaphosphate, Sorbitan Monostearate, D-Sorbitol, Sour Cream, Sour Cream Solids. Spearmint (*Mentha Spicata* L.), Spearmint Extract (*Mentha Spicata* L.), Spearmint Oil (*Mentha Spicata* L.), Spike Lavender Oil (*Lavandula* Spp.), Spruce Oil (*Tsuga* And *Picea* Spp.), Stearic Acid, Storax (*Liquidambar* Spp.), *Styrax* Extract(*Liquidambar* Spp.), Sucrose Octaacetate, Sulfur Dioxide, *Tagetes* Oil (*Tagetes Erecta* L.; T. Patula L.; Or T. Glandulifera Schrank), Tangerine Oil (*Citrus Reticulata* Blanco), Tannic Acid (*Quercus* Spp.), Tarragon (*Artemisia Dracunculus* L.), Tartaric Acid (D-, L-, Dl-, Meso-), Alpha-Terpineol, Terpinolene, Terpinyl Acetate (Isomer Mixture), Beta-Terpinyl Anthranilate, Terpinyl Butyrate, Terpinyl Isobutyrate, Terpinyl Cinnamate, Terpinyl Formate, Terpinyl Propionate, Terpinyl Isovalerate, Tetrahydrofurfuryl Acetate, Tetrahydrofurfuryl Alcohol, Tetrahydrofurfuryl Butyrate, Tetrahydrofurfuryl Propionate, 3,4,5,6-Tetrahydropseudoionone, Tetrahydrolinalool, Tetramethyl Ethylcyclohexenone (Mixture Of Isomers), 2-Thienyl Mercaptan, Thyme (*Thymus Vulgaris* L.), Thyme Oil (*Thymus Vulgaris* L.), Thyme, White, Oil (*Thymus Vulgaris* L.), Thymol, Tolualdehyde Glyceryl Acetal (Mixed O-, M-, P-), Tolualdehydes (Mixed O,M,P), Tolu, Balsam, Extract (*Myroxylon* Spp.), Tolu, Balsam, Gum (*Myroxylon* Spp.), P-Tolylacetaldehyde, O-Tolyl Acetate, P-Tolyl Acetate, 4-(P-Tolyl)-2-Butanone, P-Tolyl Isobutyrate, P-Tolyl Laurate, P-Tolyl Phenylacetate, P-Tolyl Phenylacetate, 2-(P-Tolyl)Propionaldehyde, Tragacanth Gum (*Astragalus* Spp.), Tributyl Acetylcitrate, Tricalcium Phosphate, 2-Tridecenal, Triethyl Citrate, Tuberose Oil (*Polianthes Tuberosa* L.), Turmeric (*Curcuma Longa* L.), Turmeric Extract (*Curcuma Longa* L.), Turmeric Oleoresin (*Curcuma Longa* L.), Turpentine Gum (*Pinus* Spp.), Turpentine, Steam Distilled (*Pinus* Spp.), 2,3-Undecadione, Gamma-Undecalactone, Undecanal, 2-Undecanone, 9-Undecenal, 10-Undecenal, 10-Undecen-1-Yl Acetate, Undecyl Alcohol, Valeraldehyde, Valerian Root Extract (*Valeriana Officinalis* L.), Valerian Root Oil (*Valeriana Officinalis* L.), Valeric Acid, Isovaleric Acid, Gamma-Valerolactone, *Vanilla* (*Vanilla* Spp.), *Vanilla* Extract (*Vanilla* Spp.), *Vanilla* Oleoresin (*Vanilla* Spp.), Vanillin, Vanillin Acetate, Veratraldehyde, Violet Leaves Absolute (*Viola Odorata* L.), Walnut Hull Extract (*Juglans* Spp.), Wintergreen Extract (*Gaultheria Procum-* bens L.), Wintergreen Oil (*Gaultheria Procumbens* L.), Wormwood (*Artemisia Absinthium* L.), Wormwood Extract (*Artemisia Absinthium* L.), Wormwood Oil (*Artemisia Absinthium* L.), Yarrow Herb (*Achillea Millefolium* L.), Yerba Santa Fluid Extract (*Eriodictyon Californicum* (Hook And Am) Torr, Ylang Ylang Oil (*Cananga Odorata* Hook. F. And Thomas), *Yucca* Joshua Tree (*Yucca Brevifolia* Engelm.), *Yucca* Mohave Extract (*Yucca* Spp.), Zedoary (*Curcuma Zedoaria* (Berg.) Rosc.), Zedoary Bark Extract (*Curcuma Zedoaria* (Berg.) Rosc.), Zingerone, Acetaldehyde Butyl Phenethyl Acetal, Acetylpyrazine, Allyl Methyl Disulfide, 2-Benzofurancarboxaldehyde, Biphenyl, Butylamine, Sec-Butyl Ethyl Ether, 2-Isobutyl-3-Methoxypyrazine, 2-Isobutyl-3-Methylpyrazine, 2-Isobutylthiazole, 2-Trans,4-Trans-Decadienal, 2,3-Diethylpyrazine, 2,6-Dimethoxyphenol, 3,4-Dimethoxy-1-Vinylbenzene, P-Alpha-Dimethylbenzyl Alcohol, 2,6-Dimethyl-4-Heptanol, 2,6-Dimethyl-10O-Methylene-2,6,11-Dodecatrienal, 3,7-Dimethyl-6-Octenoic Acid, 2,4-Dimethyl-2-Pentenoic Acid, P,Alpha-Dimethylstyrene, 2,4-Dimethyl-5-Vinylthiazole, 2,2'-(Dithiodimethylene)-Difuran, 1-Ethyl-2-Acetylpyrrole, Ethyl Trans-2,Cis-4-Decadienoate, 2-Ethyl-3,(5 Or 6)-Dimethylpyrazine, 3-Ethyl-2,6-Dimethylpyrazine, 2-Ethyl-1-Hexanol, 2-Ethyl-2-Hydroxy-2-Cyclopenten-1-One, 5-Ethyl-3-Hydroxy-4-Methyl-2(5h)-Furanone, 2-Ethyl-5-Methylpyrazine, 2-Ethyl-3-Methylpyrazine, P-Ethylphenol, Ethyl (P-Tolyloxy)Acetate, 2-Furanmethanethiol Formate, Furfuryl Methyl Ether, Furfuryl Methyl Sulfide, Furfuryl Isopropyl Sulfide, Furfuryl Thioacetate, 2-Furyl Methyl Ketone, (2e,4e)-Heptadienal, Trans-2-Heptenal, Nootkatone, Delta-Hexalactone, 3,4-Hexanedione, Trans-2-Hexenoic Acid, 3-Hexenoic Acid, Cis-3-Hexen-1-Yl Acetate, Hexyl Isobutyrate. 1-Hydroxy-2-Butanone, 4-Hydroxy-2,5-Dimethyl-3(2h)-Furanone, Gamma-Ionone, P-Menthan-2-One, P-*Mentha*-8-Thiol-3-One, P-Menth-1-Ene-9-Al, P-Menth-1-En-3-Ol, 2-Mercaptopropionic Acid, O-Methoxycinnamaldehyde, P-Methoxy-Alpha-Methylcinnamaldehyde, 2,5 Or 6-Methoxy-3-Methylpyrazine (Mixture Of Isomers), 1-Methyl-2-Acetylpyrrole, Methylated Silica, 4-Methylbiphenyl, 3-Methylcrotonic Acid, 2-Methyl-3-Furanthiol, 2-Methyl-3-,5 Or 6-(Furfurylthio)Pyrazine (Mixture Of Isomers), 5-Methyl-2,3-Hexanedione, 2-Methylhexanoic Acid, 2-Methyl-5-Methoxythiazole, 1-Methylnaphthalene, 2-Methyl-2-Pentenal, 2-Methyl-2-Pentenoic Acid, 3-Methyl-2-(2-Pentenyl)-2-Cyclopenten-1-One, Alpha-Methylphenethyl Butyrate, Methyl Phenethyl Ether, 5-Methyl-2-Phenyl-2-Hexenal, 4-Methyl-2-Phenyl-2-Pentenal, Methyl Propyl Disulfide, Methyl 2-Pyrrolyl Ketone, 5-Methylquinoxaline, 4-Methyl-5-Thiazoleethanol, 4-Methyl-5-Thiazoleethanol Acetate, 2-Methylthioacetaldehyde, 1-(Methylthio)-2-Butanone, (Methylthio)Methylpyrazine (Mixture Of Isomers), 5-Methyl-2-Thiophenecarboxaldehyde, O-(Methylthio)-Phenol, 2-Methyl-5-Vinylpyrazine (Re-Gras), 2,4-Nonadienal, 2-Nonenal, Delta-Octalactone, 2-Octenal, Paraffin Wax, 2,4-Pentadienal, 2-Pentenal, Isopentylamine, Phenethylamine, Phenethyl Hexanoate, Phenethyl Octanoate, Phenol, 2-Phenyl-2-Butenal, Phenyl Disulfide, 1-Phenyl-1,2-Propanedione, Propenyl Propyl Disulfide, Propyl Disulfide, Isopropyl Tiglate, Pyrazine Ethanethiol, Pyrazinyl Methyl Sulfide, 2-Pyridinemethanethiol, 4,5,6,7-Tetrahydro-3,6-Dimethylbenzofuran, Tetrahydro-4-Methyl-2-(2-Methylpropen-1-Yl)Pyran, 2,3,5,6-Tetramethylpyrazine, 2,2'-(Thiodimethylene)-Difuran, 4-Thujanol, O-Toluenethiol, Trimethylamine, P-Alpha,Alpha-Trimethylbenzyl Alcohol, 1-(2,6,6-Trimethyl-1-Cyclohexen-1-Yl)-2-Buten-1-One, 2,3,5-Trimethylpyrazine, Undecanoic Acid. 2-Undecanol, 10-Undecenoic Acid, 2,6-Xylenol, 2-Acetyl-3-Ethylpyrazine. 2-Acetylpyridine, Beta-Alanine, Allyl Methyl Trisulfide, Arabinogalactan, L-Arabinose, Benzothiazole, Bis(2-Methyl-3-Furyl) Disulfide, Bis(2-Methyl-3-Furyl) Tetrasulfide, 2-Sec-Butylcyclohexanone, Cyclopentanethiol, L-Cysteine, 4-Decenal, Diallyl Trisulfide, 4,5-Dihydro-3(2h)Thiophenone, 2,4-Dimethyl-5-Acetylthiazole, 3,4-Dimethyl-1,2-Cyclopentadione, 3,5-Dimethyl-1,2-Cyclopentadione, Spiro(2,4-Dithia-1-Methyl-8-Oxabicyclo(3.3.0)Octane-3,3'-(1'-Oxa-2'-Methyl)-Cyclopentane), 2,3-Dimethylpyrazine, 2,5-Dimethylpyrazine, 2,6-Dimethylpyrazine, 4,5-Dimethylthiazole, Dimethyl Trisulfide, Dipropyl Trisulfide, Disodium Succinate, Ethyl 2,4-Dioxohexanoate, Ethyl 2-Mercaptopropionate, 2-Ethyl(Or Methyl)-(3,5 And 6)-Methoxypyrazine, 2-Ethylpyrazine, Ethyl Thioacetate, Furfuryl 3-Methylbutanoate, N-Furfurylpyrrole, L-Glutamic Acid, Glyceryl Tripropanoate, *Glycine,* 2-Heptanol, 4-Heptenal, 3-Hexanone, 4-Hydroxybutanoic Acid Lactone, 3-(Hydroxymethyl)-2-Octanone, 4-Hydroxy-3-Pentenoic Acid Lactone, 5-Hydroxyundecanoic Acid Lactone, D,L-Isoleucine, Isopropenylpyrazine, L-Leucine, 3-Mercapto-2-Butanone, 2-Mercaptomethylpyrazine, 3-Mercapto-2-Pentanone, D,L-Methionine, Methoxypyrazine, 2-Methyl-1-Butanethiol, 3-Methyl-2-Butanethiol, 1-Methyl-2,3-Cyclohexadione, 5h-5-Methyl-6,7-Dihydrocyclopenta(B) Pyrazine, 3-(5-Methyl-2-Furyl)-Butanal, Methyl Propyl Trisulfide, 2-Methylpyrazine, Methyl Thiobutyrate, Methyl 2-Thiofuroate, 3-Methylthiopropyl Isothiocyanate, 4-Methyl-5-Vinylthiazole, 2-Naphthalenthiol, 2-Nonanol, 2-Pentanol, 2-Pentylfuran, 3-Phenyl-4-Pentenal, L-Proline, Tetrahydrofurfuryl Cinnamate, 5,6,7,8-Tetrahydroquinoxaline, Thiamine Hydrochloride, 2-Thienyl Disulfide, 3,5,5-Trimethyl-1-Hexanol, 2,4,5-Trimethylthiazole, Acetone, 2-Acetyl-3,5(And 6)-Dimethylpyrazine, 2-Acetylthiazole, Allyl Thiopropionate, Benzyl Trans-2-Methyl-2-Butenoate, Bisabolene, Butan-3-One-2-Y1 Butanoate, 3-Butylidenephthalide, 3-N-Butylphthalide, Di(Butan-3-One-1-Yl) Sulfide, 2,3-Diethyl-5-Methylpyrazine, Difurfuryl Ether, 5,7-Dihydro-2-Methylthieno(3,4-D)Pyrimidine, 3,7-Dimethylocta-2,6-Dienyl 2-Ethylbutanoate, 2-Ethoxythiazole, Ethyl 2-Ethyl-3-Phenylpropanoate, Ethyl 3-Hexenoate, Ethyl 3-Methylthiopropionate, Ethyl Cis-4-Octenoate, 2-Ethylthiophenol, Furfuryl Propionate, Furfuryl Thiopropionate, Heptanoic Acid, 4-Heptenal Diethyl Acetal, 3-Heptyldihydro-5-Methyl-2(3h)-Furanone, 3-Hexanol, 4-Hexene-3-One, Cis-3-Hexenyl Formate, N-Hexyl 2-Butenoate, 6-Hydroxy-3,7-Dimethyloctanoic Acid Lactone, Hydroxynonanoic Acid, Delta-Lactone, 2-Keto-4-Butanethiol, 2-Methoxy-3(5 And 6)-Isopropylpyrazine, 2-Methylbutyl 2-Methylbutyrate, 3-Methyl-2-Cyclohexen-1-One, Methyl 3,7-Dimethyl-6-Octenoate, Methyl Furfuryl Disulfide, 6-Methyl-3,5-Heptadien-2-One, Methyl 3-Hexenoate, 5-Methyl-5-Hexen-2-One, 2-Methyl-5-(Methylthio)Furan, Methyl Cis-4-Octenoate, 4-Methyl-3-Penten-2-One, 2-Methylpropyl 3-Methylbutyrate, 2-(2-Methylpropyl)Pyridine, 3-(2-Methylpropyl)Pyridine, 2-(1-Methylpropyl)Thiazole, 2-Methyltetrahydrofuran-3-One, 3-(Methylthio)Butanal, 4-(Methylthio)-2-Butanone, 4-(Methylthio)-4-Methyl-2-Pentanone, Nona-2-Trans-6-Cis-Dienal, 2,6-Nonadienal Diethyl Acetal, Trans-2-Nonen-1-Ol, 9,12-Octadecadienoic Acid (48%) And 9,12,15-Octadecatrienoic Acid (52%), 3-Oxobutanal Dimethyl Acetal, 1-Penten-3-One, 2-Pentylpyridine, Phenylacetaldehyde Diisobutyl Acetal, Propyl Thioacetate, Pyrrole, P-Tolyl 3-Methylbutyrate, 2-Tridecanone, 2,6,6-Trimethylcyclohexa-1,3-Dienyl Methanal, 1,3,3-Trimethyl-2-Norbornanyl Acetate, 3-Acetyl-2,5-Dimethylfuran, 2-Butyl-2-Butenal, N-Butyl 2-Methylbutyrate, 3-Ethylpyridine, 2-Formyl-6,6-Dimethylbicyclo(3.1.1) Hept-2-Ene, Alpha-Furfuryl Octanoate, Alpha-Furfuryl Pentanoate, Glyceryl Tribenzoate, 2-Hepten-4-One, 3-Hepten-2-One, 2-Heptylfuran, Cis-3-Hexenyl Butyrate. Cis-3-Hexenyl Hexanoate, Capsaicin, 2-Hydroxymethyl-6,6-Dimethylbicyclo(3.1.1)Hept-2-Enyl Formate, 2-Isopropyl-5-Methyl-2-Hexenal, 2-Methyl-2-Butenal, Methyl Dihydrojasmonate, 5-Methyl-3-Hexen-2-One, Methyl Jasmonate, Methyl Linoleate (48%) Methyl Linolenate (52%) Mixture, Methyl 4-(Methylthio)Butyrate, 2-Methylpentanal, 4-(Methylthio)Butanal, 3-(Methylthio)Propanol, 3-Octen-2-One, 3-Penten-2-One, Pentyl 2-Furyl Ketone, Propylene Glycol Dibenzoate, 1-(2,6,6-Trimethylcyclohexa-1,3-Dienyl)-2-Buten-1-One, 2,6,6-Trimethylcyclohex-2-Ene-1,4-Dione, 2,4-Undecadienal, 2-Undecenal, 3-Acetylpyridine, Cycloheptadeca-9-En-1-One, 1,1-Dimethoxyethane, 2,4-Dimethylbenzaldehyde, Ethyl 3-Hydroxybutyrate, Trans, Trans-2,4-Hexadienal, 4-Hexen-1-ol, Isobutyl 2-Butenoate, 2-Methoxy-3-(1-Methylpropyl)Pyrazine, 3-Methyl-1-Cyclopentadecanone, 1-Methyl-1-Cyclopenten-3-One, 1-Methyl-3-Methoxy-4-Isopropylbenzene, 3-Methylpentanoic Acid, 3-(Methylthio)-1-Hexanol, Myrtenol, 3-Nonanone, 2,2,4-Trimethyl-1,3-Oxacyclopentane, 2,6,10-Trimethyl-2,6,10-Pentadecatrien-14-One, Valencene, D,L-Valine, Dl-(3-Amino-3-Carboxypropyl)Dimethylsulfonium Chloride, Dehydrodihydroionol, Dehydrodihydroionone, Dicyclohexyl Disulfide, 1,4-Dimethyl-4-Acetyl-1-Cyclohexene, 2,5-Dimethyl-2,5-Dihydroxy-1,4-Dithiane, 2,5-Dimethyl-3-Furanthiol, Dodecyl Isobutyrate, 3-Ethyl-2-Hydroxy-4-Methylcyclopent-2-En-1-One, 5-Ethyl-2-Hydroxy-3-Methylcyclopent-2-En-1-One, N-Ethyl-2-Isopropyl-5-Methylcyclohexane Carboxamide, Ethyl 2-Methyl-3-Pentenoate, Hexyl Phenylacetate, 2-Hydroxy-2-Cyclohexen-1-One, 2-Hydroxy-3,5,5-Trimethyl-2-Cyclohexenone, D,L-Isomenthone, 2-Isopropylphenol, Maltyl Isobutyrate, 4-Methylpentanoic Acid, 2-Methyl-3-Pentenoic Acid, Cis-6-Nonen-1-Ol, 2-Trans-6-Trans-Octadienal, Cis-3-Octen-1-Ol, 2-Phenyl-3-Carbethoxy Furan, Propiophenone, 1,5,5,9-Tetramethyl-13-Oxatricyclo(8.3.0.0 (4,9))Tridecane, Thiogeraniol, 2,2,6-Trimethylcyclohexanone, 2,6,6-Trimethyl-1-Cyclohexen-1-Acetaldehyde, Trithioacetone, Bis(2,5-Dimethyl-3-Furyl) Disulfide, 2,3-Butanedithiol, 1-Butanethiol, Candelilla Wax (Wax From Stems And Branches Of *Euphorbia Cerifera*), O-Cresol, S-(2,5-Dimethyl-3-Furyl)Thio-2-Furoate, 2,5-Dimethyl-3-Thioisovalerylfuran, 2,8-Dithianon-4-En-4-Carboxaldehyde, 1,2-Ethanedithiol, O-(Ethoxymethyl)Phenol, Ethyl Trans-2-Butenoate, Ethyl Maltol, Ethyl 2-Methylpentanoate, Ethyl 2-Methyl-4-Pentenoate, Ethyl Octadecanoate, 2-Ethyl-1,3,3-Trimethyl-2-Norbornanol, Ethyl Undecanoate, Trans-3-Heptenyl Acetate, Trans-3-Heptenyl 2-Methylpropanoate, 1,6-Hexanedithiol, Cis-4-Hexenal, 3-Hexenyl 2-Methylbutanoate, 3-Hexenyl 3-Methylbutanoate, Hexyl 2-Methylbutanoate, Hexyl Isovalerate, Linalyl Phenylacetate, 2-Mercapto-3-Butanol, 2,3 Or 10-Mercaptopinane, Methyl Benzyl Disulfide, 3-Methylbutyl 2-Methylbutanoate, 2-Methylbutyl 3-Methylbutanoate, 3-Methylbutyl 2-Methylpropanoate, Methyl 3-Hydroxyhexanoate, Alpha-Methyl-Beta-Hydroxypropyl Alpha-Methyl-Beta-Mercaptopropyl Sulfide, 4-Methyl-2-Pentenal, 2-Methyl-4-Pentenoic Acid, 2-Methyltetrahydrothiophen-3-One, 1,9-Nonanedithiol, 1,8-Octanedithiol, 1-Octen-3-One, Trans-2-Octen-1-Yl Acetate, Trans-2-Octen-1-Y Butanoate. Octyl 2-Furoate, 2-Phenyl-2-Pentenal, 1,2-Propanedithiol, Propanethiol, O-Propylphenol, Pyrrolidine, 3,5,5-Trimethylhexanal, 2,4,5-Trimethyl-Delta-3-Oxazoline, 2-Acetoxy-3-Butanone, 1,2-Butanedithiol, 1,3-Butanedithiol, M-Cresol, Cyclohexanecarboxylic Acid, 3-Decen-2-One, Diallyl Polysulfides, 1,2-Di((1'-Ethoxy)Ethoxy)Propane, 2,3-Dimethylbenzofuran, Dimethyl Disulfide, 2,6-Dimethyl-4-Heptanone, 2,6-Dimethyl-3-((2-Methyl-3-Furyl)Thio)-4-Heptanone, 3,7-Dimethyl-1,3,6-Octatriene, 2,6-Dimethylpyridine, 3,5-Dimethyl-1,2,4-Trithiolane, 6,10-Dimethyl-5,9-Undecadien-2-One, Ethylene Brassylate, Ethyl Cyclohexanecarboxylate, Ethyl 3-Hydroxyhexanoate, 5-Ethyl-2-Methylpyridine, 3-Heptanol, 2-Hydroxyacetophenone, 6-Hydroxydihydrotheaspirane, 3-Hydroxy-2-Pentanone, Isoamyl Acetoacetate, Isojasmone, Isophorone, 5-Isopropyl-2-Methylpyrazine, 2-Isopropyl-4-Methylthiazole, Isopropyl Myristate, P-*Mentha*-1,8-Dien-7-Al, P-*Mentha*-1,3-Diene, P-*Mentha*-1,4-Diene, P-*Mentha*-1,4(8)-Dien-3-One, P-*Mentha*-1,8-Dien-7-Yl Acetate, P-Menthan-2-Ol, P-Menth-3-En-1-Ol, P-Menth-8-En-1-Ol, P-Menth-8-En-2-One, 1-P-Menthen-9-Yl Acetate, P-Methoxycinnamaldehyde, Methyl Cyclohexanecarboxylate, 2-Methyl-3,5 Or 6-Ethoxypyrazine, 3-((2-Methyl-3-Furyl)Thio)-4-Heptanone, 4-((2-Methyl-3-Furyl)Thio)-5-Nonanone, 5-Methylhexanoic Acid, Methyl 2-Methyl-3-Furyl Disulfide, 4-Methylnonanoic Acid, 4-Methyloctanoic Acid, Methyl 1-Propenyl Disulfide, 3-Methyl-5-Propyl-2-Cyclohexen-1-One, 2-Methyl-4-Propyl-1,3-Oxathiane, 1,4-Nonanediol Diacetate, Cis-6-Nonenal, 3-Octanol, 1-Octen-3-Yl Acetate, 3-Octyl Acetate, 1-Penten-3-Ol, L-Phenylalanine, 2-Phenyl-3-(2-Furyl)Prop-2-Enal, 2(10)-Pinen-3-Ol, 1,3-Propanedithiol, Resorcinol, Delta-Tetradecalactone, Theobromine, (2,2,3-Trimethylcyclopent-3-En-1-Yl)Acetaldehyde, 1,2,3-Tris((1'-Ethoxy)Ethoxy)Propane, Verbenol, 2,5-Xylenol, 3,4-Xylenol, Benzyl Methyl Sulfide, 2-Methoxy-4-Propylphenol, 2-Methyl-Trans-2-Butenoic Acid, 4-(Methylthio)Butanol, 2-(Methylthio)Methyl-2-Butenal, 3-Octen-2-Ol, 2-Octen-4-One, Octyl 2-Methylbutyrate, 3-Decanol, D-Xylose, Propyl 2-Methyl-3-Furyl Disulfide, 1-Hexen-3-Ol, 2-Acetyl-5-Methylfuran, Epsilon-Dodecalactone, 2-Propionylthiazole, I-Octen-3-Yl Butyrate, Epsilon-Decalactone, 2-Propionylpyrrole, Thiazole, Benzenethiol, Benzyl Disulfide, 5-Phenylpentanol, 2-(2-Butyl)-4,5-Dimethyl-3-Thiazoline, 4,5-Dimethyl-2-Ethyl-3-Thiazoline, 4,5-Dimethyl-2-Isobutyl-3-Thiazoline, Delta-1-(2, 6,6-Trimethyl-3-Cyclohexen-1-Yl)-2-Buten-1-One, 2-Ethyl-4-Hydroxy-5-Methyl-3(2h)-Furanone, Alpha-Ionol, Beta-Ionol, Dihydro-Beta-Ionone, Dihydro-Beta-Ionol, Dihydro-Alpha-Ionone, 2-Methyl-4-Phenyl-2-Butanol, 4-Methyl-2-Pentyl-1,3-Dioxolan, Cyclohexylmethyl Pyrazine, Phenylethyl 2-Methylbutyrate, 3-Hexenyl Phenylacetate, 4,5-Dimethyl-3-Hydroxy-2,5-Dihydrofuran-2-One, 4-Hydroxy-5-Methyl-3(2h)-Furanone, 2-Methyl-3-Thioacetoxy-4,5-Dihydrofuran, 2-Trans-6-Cis-Dodecadienal, 2-Trans-4-Cis-7-Cis-Tridecatrienal, 2,6,6-Trimethyl-1&2-Cyclohexen-1-Carboxaldehyde, P-Methylcinnamaldehyde, Ethyl Trans-2-Decenoate, Ethyl Trans-4-Decenoate, Ethyl Trans-2-Octenoate, 2-Methylbutyl Acetate, Cis-5-Isopropenyl-Cis-2-Methylcyclopentan-1-Carboxaldehyde, 3-Methyl-2-Butenal, 3-Methyl-2-Buten-1-Ol, Propyl 2,4-Decadienoate, P-Propylphenol, Butyl Salicylate, 6-Acetoxydihydrotheaspirane, 4-(P-Acetoxyphenyl)-2-Butanone, 4-Acetyl-6-T-Butyl-1,1-Dimethylindan, 4-Acetyl-2-Methylpyrimidine, 4-Allyl-2,6-Dimethoxyphenol, L-Aspartic Acid, Campholene Acetate, 1,4-Cineole, Alpha-1-(2,6,6-Trimethyl-2-Cyclohexen-1-Yl)-2-Buten-1-One, 9-Decenoic Acid, Nerol Oxide, Dihydroxyacetophenone, 2,6-Dimethyl-6-Hepten-1-Ol, 2,5-Dimethyl-4-Methoxy-3(2h)-Furanone, 2,2-Dimethyl-5-(1-Methylpropen-1-Yl)Tetrahydrofuran, 2,6-Dimethylthiophenol, Diphenyl Ether, Disodium 5-Guanylate, Disodium 5-Inosinate, Trans,Trans-2,4-Dodecadienal, 4-Ethyl-2,6-Dimethoxyphenol, 2-Ethyl-4,5-Dimethyloxazole, 2-Ethylfuran, Ethyl 3-(Furfurylthio)Propionate, Ethyl Trans-2-Hexenoate, 1-Ethylhexyl Tiglate, Ethyl 3-Mercaptopropionate, Ethyl 2-Methyl-3,4-Pentadienoate, Ethyl 3-Methylpentanoate, 2-Ethyl-4-Methylthiazole, Ethyl 4-(Methylthio)Butyrate, Ethyl Cis-4,7-Octadienoate, Ethyl 3-Oxohexanoate, L-Glutamine, Glyceryl 5-Hydroxydecanoate, Glyceryl 5-Hydroxydodecanoate, Guaiacyl Acetate, Cis-3-Hexenyl Benzoate, Cis-3-Hexenyl Cis-3-Hexenoate, Cis-3-Hexenyl Lactate, Hexyl Benzoate, Hexyl Trans-2-Hexenoate, Hexyl 2-Methyl-3&4-Pentenoate, L-Histidine, Hydroquinone Monoethyl Ether, 5-Hydroxy-2,4-Decadienoic Acid Delta-Lactone, 2-Hydroxy-4-Methylbenzaldehyde, Isoeugenyl Benzyl Ether, Isopropyl 2-Methylbutyrate, 1-P-Menthene-8-Thiol, Methyl 1-Acetoxycyclohexyl Ketone, Methylbenzyl Acetate (Mixed O,M,P), 3-Methyl-2-Butanol, 4-Methyl-2,6-Dimethoxyphenol, 2-Methyl-1,3-Dithiolane, Methyl 2-Hydroxy-4-Methylpentanoate, Methyl 2-Methylpentanoate, Methyl 2-Methylthiobutyrate, Methyl Nicotinate, Methyl 3-Nonenoate, 2-Methyl-2-Octenal, Methyl Trans-2-Octenoate, Methyl 2-Oxo-3-Methylpentanoate, Methyl Sorbate, 7-Methyl-4,4a,5,6-Tetrahydro-2(3h)-Naphthalenone, 4-Methylthiazole, 2-(Methylthioethyl)-3-Phenylpropenal, 3-Methyl-1,2,4-Trithiane, Beta-Naphthyl Isobutyl Ether, Cis-2-Nonen-1-Ol, Trans,Trans-2,4-Octadienal, Cis-5-Octen-1-Ol, 2-Oxobutyric Acid, 2-Pentadecanone, 2-Pentyl-1-Buten-3-One, D,L-Phenylalanine, 1-Phenyl-3 Or 5-Propylpyrazole, 4-Propenyl-2,6-Dimethoxyphenol, 4-Propyl-2,6-Dimethoxyphenol, L-Rhamnose, 1,2,5,6-Tetrahydrocuminic Acid, Thaumatin, P-Tolyl Octanoate, O-Tolyl Salicylate, 2,2,6-Trimethyl-6-Vinyltetrahydropyran, L-Tyrosine, Vanillyl Alcohol, Vanillylidene Acetone, P-Vinylphenol, Anisyl Phenylacetate, Alpha-Campholenic Alcohol, 5- And 6-Decenoic Acid, 2,5-Diethyltetrahydrofuran, 5-Hydroxy-2-Decenoic Acid Delta-Lactone, 5-Hydroxy-7-Decenoic Acid Delta-Lactone, Linalool Oxide, *Massoia* Bark Oil (*Cryptocarya Massoio*), L-Menthyl Lactate, Cis-5-Octenal, *Osmanthus* Absolute (*Osmanthus Fragrans* Lour.), 2-(3-Phenylpropyl)Pyridine, Potassium 2-(1'-Ethoxy)Ethoxypropanoate, O-Tolyl Isobutyrate, Vanillin Isobutyrate, Dehydromenthofurolactone, 4-Ethylbenzaldehyde, Ethyl Methyl-P-Tolylglycidate, 5-Hydroxy-8-Undecenoic Acid Delta-Lactone, 5-Isopropenyl-2-Methyl-2-Vinyltetrahydrofuran, 1-(4-Methoxyphenyl)-4-Methyl-1-Penten-3-One, 5-Methyl-2-Hepten-4-One, 3-Methyl-1-Pentanol, 3-Methyl-2-(N-Pentanyl)-2-Cyclopenten-1-One, Mintlactone, Myrtenyl Acetate, 2-Trans-6-Trans-Nonadienal, 3-Oxodecanoic Acid Glyceride, 3-Oxododecanoic Acid Glyceride, 3-Oxohexadecanoic Acid Glyceride, 3-Oxohexanoic Acid Glyceride, 3-Oxooctanoic Acid Glyceride, 3-Oxotetradecanoic Acid Glyceride, Sodium 2-(4-Methoxyphenoxy)Propanoate, Theaspirane, Acetaldehyde Ethyl Cis-3-Hexenyl Acetal, Dihydronootkatone, 1-Ethoxy-3-Methyl-2-Butene, (Z)-3 & (E)-2-Hexenyl Propionate, Hydrogen Sulfide, 1,4-Dodec-6-Enolactone, 2 Or 4-Isobutyl-(4 Or 2),6-Dimethyldihydro-4h-1,3,5-Dithiazine, 2 Or 4-Isopropyl-(4 Or 2),6-Dimethyldihydro-4h-1,3,5-Dithiazine, Jambu Oleoresin, 3-L-Menthoxypropane-1,2-Diol, 4-Methoxy-2-Methyl-2-Butanethiol, Gamma-Methyldecalactone, 2-Methyl-3-Tetrahydrofuranthiol, Methylthio 2-(Acetyloxy)Propionate, 3-(Methylthio)Hexyl Acetate, Methylthio-2-(Propionyloxy)Propionate, Octahydrocoumarin, 2-Pentanethiol, D-Ribose, Sclareolide, 1,3,5-Undecatriene, Vanillyl Butyl Ether, 4-Acetoxy-2,5-Dimethyl-3(2h)Furanone, 2,4-Dihydroxybenzoic Acid, 1,2-Dimethoxybenzene, 4-Ethyloctanoic Acid, Ethyl Vanillin Beta-D-Glucopyranoside, 5-Hydroxy-2-Dodecenoic Acid Lactone, 4-Hydroxy-3-Methyloctanoic Acid Lactone, 2-Isopropyl-N,2,3-Trimethylbutyramide, L-Menthol Ethylene Glycol Carbonate, L-Menthol 1- And 2-Propylene Glycol Carbonate, L-Menthone 1,2-Glycerol Ketal, D,L-Menthone 1,2-Glycerol Ketal, Cis- And Trans-Menthone-8-Thioetate, Mono-Menthyl Succinate, Neohesperidin Dihydrochalcone, Sodium 3-Methoxy-4-Hydroxycinnamate, Taurine, Thaumatin B—Recombinant, Vanillyl Ethyl Ether, 3-Acetylmercaptohexyl Acetate, 2-Acetyl-2-Thiazoline, Dl-Alanine, L-Arginine, 1-Buten-1-Y1 Methyl Sulfide, Delta-3-Carene, Cycloionone, Daidai Peel Oil, 1-Decen-3-Ol, Diethyl Sulfide, 2,5-Dihydroxy-1,4-Dithiane, Diisopropyl Disulfide, 2,4-Dimethylanisole, 2-(3,7-Dimethyl-2,6-Octadienyl)Cyclopentanone, (E,R)-3,7-Dimethyl-1,5,7-Octatrien-3-Ol, 1,4-Dithiane, Ethyl 2,4,7-Decatrienoate, 2-Ethylhexanethiol, Ethyl 2-(Methyldithio)Propionate, Ethyl 2-(Methylthio)Acetate, Ethyl 3-(Methylthio)Butyrate, Ethyl Vanillin Isobutyrate, Ethyl Vanillin Propylene Glycol Acetal, Alpha-Farnesene, 4-[(2-Furanmethyl)Thio]-2-Pentanone, (Z)-4-Hepten-1-Ol, 1-Hexanethiol, 3-Hydroxy-2-Oxopropionic Acid, Beta-Ionyl Acetate, Alpha-Isomethylionyl Acetate, *Litsea Cubeba* Oil, L-Lysine, Cis- And Trans-P-1(7),8-Menthadien-2-Yl Acetate, 3-(L-Menthoxy)-2-Methylpropane-1,2-Diol, 3-Mercaptohexanol, 3-Mercaptohexyl Acetate, 3-Mercaptohexyl Butyrate, 3-Mercaptohexyl Hexanoate, 3-Mercapto-3-Methyl-1-Butanol, 3-Mercapto-3-Methylbutyl Formate, 1-Mercapto-2-Propanone, S-Methyl Benzothioate, 3-Methylbutanethiol, Methyl (E)-2-(Z)-4-Decadienoate, Methyl Ethyl Sulfide, Methyl Ethyl Trisulfide, S-Methyl Hexanethioate, 2-(4-Methyl-2-Hydroxyphenyl)Propionic Acid-Gamma-Lactone, S-Methyl 3-Methylbutanethioate, Methyl 3-Methyl-1-Butenyl Disulfide, 2-Methyl-2-(Methyldithio)Propanal, S-Methyl 4-Methylpentanethioate, (E)-7-Methyl-3-Octen-2-One, 3-Methyl-2-Oxobutanoic Acid, 3-Methyl-2-Oxopentanoic Acid, 4-Methyl-2-Oxopentanoic Acid, Methyl Phenyl Disulfide, Methyl Phenyl Sulfide, 2-Methyl-1-Propanethiol, Methylsulfinylmethane, S-Methyl Thioacetate, 3-Methylthiohexanal, Bis-(Methylthio)Methane, Methylthiomethyl Butyrate, Methylthiomethyl Hexanoate, 4-(Methylthio)-2-Oxobutanoic Acid, 1-Methylthio-2-Propanone, 3-(Methylthio)Propyl Acetate, (E)-3-(Z)-6-Nonadien-1-ol, (Z)(Z)-3,6-Nonadien-1-Ol, 8-Ocimenyl Acetate, (E)-2-Octen-1-Ol, (E)-2-Octen-4-Ol, (E)-2-(2-Octenyl)Cyclopentanone, (Z)-5-Octenyl Propionate, 2-Oxopentanedioic Acid, 2-Oxo-3-Phenylpropionic Acid, 2-Pentyl Butyrate, Phenylethyl Mercaptan, Prenyl Thioacetate, Prenylthiol, 2-Propanethiol, 1-Pyrroline, Sarcodactylis Oil, Sodium Diacetate, Sodium 3-Mercaptooxopropionate, Tea Tree Oil, 2,3,4-Trimethyl-3-Pentanol, Vanillin 3-(L-Menthoxy)Propane-1,2-Diol Acetal, Vanillin Propylene Glycol Acetal, 2-Aminoacetophenone, Bornyl Butyrate, (E)-2-Butenoic Acid, Cyclohexanone, Cyclopentanone, 2,4-Decadien-1-Ol, 9-Decenal, 2-Decenoic Acid, 4-Decenoic Acid, 2,5-Diethyl-3-Methylpyrazine, 3,5-Diethyl-2-Methylpyrazine, 6,7-Dihydro-2,3-Dimethyl-5h-Cyclopentapyrazine, P-Tert-Butylphenol, 2-Ethyl-6-Methylpyrazine, (E)-2-Heptenoic Acid, 2,4-Hexadienoic Acid, (E,E)-, 2,4-Hexadien-1-Ol, 3-Hexenal, (Z)-2-Hexen-1-Ol, Cis-3-Hexenyl Anthranilate, Trans-2-Hexenyl Butyrate, (E)-2-Hexenyl Formate, 3-Hexenyl 2-Hexenoate, Cis-3-Hexenyl Isobutyrate, Trans-2-Hexenyl Isovalerate, Cis-3-Hexenyl Tiglate, Trans-2-Hexenyl Propionate, Cis-3-Hexenyl Propionate, 3-Hexenyl 2-Oxopropionate, Trans-2-Hexenyl Pentanoate, Cis-3-Hexenyl Valerate, 5-(Cis-3-Hexenyl)Dihydro-5-Methyl-2(3h)Furanone, 4-Isopropyl-2-Cyclohexenone, 2-Isopropylpyrazine, 2-Methyl-3-(1-Oxopropoxy)-4h-Pyran-4-One, Mesquite Wood Extract, 2-Methoxybenzoic Acid, 3-Methoxybenzoic Acid, 4-Methoxybenzoic Acid, 2-Methylcyclohexanone, 3-Methylcyclohexanone, 4-Methylcyclohexanone, 2-Methyl-3-(Methylthio)Furan, Michelia Alba Oil, 2,4-Nonadien-1-Ol, (E,Z)-2,6-Nonadien-1-Ol Acetate, (E,Z)-3,6-Nonadien-1-Ol Acetate, (E)-2-Nonenoic Acid, 3-Nonen-2-One, (E,E)-2,4-Octadien-1-Ol, (E)-2-Octenoic Acid, Phenyl Acetate, 2-Phenylphenol, Phenyl Salicylate, Propylpyrazine, 3,5,5-Trimethylcyclohexanol, 2,3,6-Trimethylphenol, 2-Acetyl-3-Methylpyrazine, 1-Amino-2-Propanol, 3-Decanone, Cis-4-Decenyl Acetate, Diisopropyl Trisulfide, (E) & (Z)-4,8-Dimethyl-3,7-Nonadien-2-One, 2,5-Dimethyl-3-Oxo-(2h)-Fur-4-Yl Butyrate Cis And Trans-2,5-Dimethyltetrahydrofuran-3-Thiol, Cis And Trans-2,5-Dimethyltetrahydro-3-Furyl Thioacetate, Ethanethioic Acid, S-(2-Methyl-3-Furanyl) Ester, Ethyl 4-(Acetylthio)Butyrate, Ethyl Cis-4-Heptenoate, Ethyl 5-Hexenoate, (+/−)-Ethyl 3-Mercaptobutyrate, Ethyl 5-(Methylthio)Valerate, Furfuryl Propyl Disulfide, (+/−)-Heptan-3-Yl Acetate, (+/−)-Heptan-2-Yl Butyrate, (Z)-3-Hexenyl (E)-2-Butenoate, (E)-2-Hexenyl Hexanoate, 4-Hydroxybenzaldehyde, 2-Hydroxybenzoic Acid, 4-Hydroxybenzoic Acid, 4-Hydroxybenzyl Alcohol, 4-Hydroxy-3-Methoxybenzoic Acid, 3(2)-Hydroxy-5-Methyl-2(3)-Hexanone, Isopentylidene Isopentylamine, Isoprenyl Acetate, D,L-Menthol(+/−)-Propylene Glycol Carbonate, Erythro And Threo-3-Mercapto-2-Methylbutan-1-Ol, 3-Mercapto-2-Methylpentanal, (+/−)-2-Mercapto-2-Methylpentan-1-Ol, 3-Mercapto-2-Methylpentan-1-ol (Racemic), 4-Mercapto-4-Methyl-2-Pentanone, (+/−)-2-Methyl-1-Butanol, (+/−)-3-Methyl-Gamma-Decalactone, 2-Methylheptan-3-One, (E)-6-Methyl-3-Hepten-2-One, Methyl 2-Methyl-2-Propenoate, Methyl (Methylthio)Acetate, 2-(Methylthio)Ethanol, 12-Methyltridecanal, L-Monomenthyl Glutarate. (+/−)-Nonan-3-Yl Acetate, (E,E)-3,5-Octadien-2-One, (+/−)-Octan-3-Yl Formate, Paraldehyde, 4-Pentenyl Acetate, 2-Pentyl Acetate, *Perilla* Leaf Oil, Phenethyl Isothiocyanate, Pyrazine, Sodium 4-Methoxybenzoyloxyacetate, 2,4,6-Triisobutyl-5,6-Dihydro-4h-1,3,5-Dithiazine, 2,4,6-Trimethyldihydro-4h-1,3,5-Dithiazine, 3,7,11-Trimethyl-2,6,10-Dodecatrienal, (+/−)-(2,6,6-Trimethyl-2-Hydroxycyclohexylidene)Acetic Acid Gamma-Lactone, Trithiahexane-2,3,5, 6-Undecanone, Vanillin Erythro And Threo-Butan-2,3-Diol Acetal, Acetaldehyde Diisoamyl Acetal, Amyl Methyl Disulfide, Benzyl Hexanoate, Butyl Ethyl Disulfide, Beta-Cyclodextrin, Diethyl Trisulfide, (+/−)-3,5-Diethyl-1,2,4-Trithiolane, (+/−)-Dihydrofarnesol, Dihydromintlactone, Dihydroxyacetone, 2,5-Dimethyl-3-Furanthiol Acetate, 2,5-Dimethylthiazole, (Z)-4-Dodecenal, 4,5-Epoxy-(E)-2-Decenal, Ethyl 3-Acetoxy-2-Methyl Butyrate, S-Ethyl 2-Acetylamino Ethanethioate, Ethyl Methyl Disulfide, Ethyl Propyl Disulfide, Ethyl Propyl Trisulfide, O-Ethyl S-(2-Furylmethyl)Thiocarbonate, Geranyl Tiglate, Grape Seed Extract, Trans-4-Hexenal, (E)-2-Hexenal Diethyl Acetal, 2-Hexyl-4,5-Dimethyl-1,3-Dioxolane, 4-Hydroxy-3,5,-Dimethoxy Benzaldehyde, 4-Hydroxy-2,3-Dimethyl-2,4-Nonadienoic Acid Gamma Lactone, 4-Hydroxy-4-Methyl-5-Hexenoic Acid Gamma Lactone, 3-Hydroxy-4-Phenylbutan-2-One, P-Menthane-3,8-Diol, L-Menthyl Methylether, Methyl 5-Acetoxyhexanoate. 3-[(2-Methyl-3-Furyl)Thio]-2-Butanone, 3-Methyl-2,4-Nonanedione, (+/−)-2-(5-Methyl-5-Vinyl-Tetrahydrofuran-2-Yl)Propionaldehyde, 9-Octadecenal, 2,3-Octanedione, (+/−)-1-Phenylethylmercaptan, 4-Propenylphenol, 2-Propionylpyrroline, 2-Propionyl-2-Thiazoline, 2-Propylpyridine, (Z)-8-Tetradecenal, Tuberose Lactone, 2-Undecen-1-O, (+/−)-1-Acetoxy-1-Ethoxyethane, 4-Acetyl-2,5-Dimethyl-3(2h)-Furanone, 2-Acetyl-3,5-Dimethylfuran, Allyl Crotonate, Allyl Propyl Disulfide, Allyl Valerate, 4-Allylphenol, Allyl Thiohexanoate, O-Anisaldehyde, N-Benzoylanthranilic Acid, Thujyl Alcohol, L-Bornyl Acetate, 2-Butylfuran, Butyl Isothiocyanate, 2-Butyrylfuran, Carvone-5,6-Oxide, Beta-Caryophyllene Oxide, Citronellyl Anthranilate, N-Cyclopropyl-Trans-2-Cis-6-Nonadienamide, Trans-Alpha-Damascone, 2,4,7-Decatrienal, 2-Decylfuran, Dehydronootkatone, Diacetyl Tartaric Acid Esters Of Mono- And Diglycerides, Diethyl Disulfide, Mixture Of 3,6-Diethyl-1,2,4,5-Tetrathiane And 3,5-Diethyl-1,2,4-Trithiolane, 2,4-Difurfurylfuran, Diisopentyl Thiomalate, Dimercaptomethane, 1,1-Dimethoxy-Trans-2-Hexene, 2,4-Dimethyl-1,3-Dioxolane, 3,5- And 3,6-Dimethyl-2-Isobutylpyrazine, 2,5-Dimethyl-3(2h)-Furanone, (+/−)-Trans- And Cis-4,8-Dimethyl-3,7-Nonadien-2-Ol, (+/−)-Trans- And Cis-4,8-Dimethyl-3,7-Nonadien-2-Yl Acetate, 2,5-Dimethyl-4-Ethoxy-3(2h)-Furanone, (+/−)-Trans- And Cis-5-(2,2-Dimethylcyclopropyl)-3-Methyl-2-Pentenal, 2,5-Dimethylfuran, Divanillin, (+/−)-2,8-Epithio-Cis-P-Menthane, Epoxyoxophorone, Tomato Lycopene, Tomato Powder, Dehydrated Tomato, Tomato Extract, Tomato Juice, Tomato, Ethane-1,1-Dithiol, Ethyl Cis-3-Hexenoate, N-Ethyl Trans-2-Cis-6-Nonadienamide, Ethyl Furfuryl Ether, Ethyl N-Ethylanthranilate, Ethyl N-Methylanthranilate, (+/−)-4-Ethyloctanal, Eugenyl Isovalerate, Furfuryl 2-Methyl-3-Furyl Disulfide, 1-(2-Furyl)Butan-3-One, Geranic Acid, Geranyl 2-Methylbutyrate, Geranyl Valerate, Glyceryl-Lacto Esters Of Fatty Acids, Hept-Trans-2-En-1-Yl Acetate, Hept-2-En-1-Yl Isovalerate, Trans-2-Trans-4-Heptadien-1-Ol, 2-Heptanethiol, (+/−)-1-Hepten-3-Ol, Cis- And Trans-2-Heptylcyclopropanecarboxylic Acid, 2,4-Hexadienyl Propionate, 2,4-Hexadienyl Acetate, 2,4-Hexadienyl Butyrate, 2,4-Hexadienyl Isobutyrate, 2-Hexenyl Octanoate, Hexyl 3-Mercaptobutanoate, 2-Hexylthiophene, 4-Hydroxy-2-Butenoic Acid Gamma-Lactone, 3-Hydroxy-2-Octanone, 2-(2-Hydroxy-4-Methyl-3-Cyclohexenyl)Propionic Acid Gamma-Lactone, 5-Hydroxy-4-Methylhexanoic Acid Delta-Lactone, 1-(3-Hydroxy-5-Methyl-2-Thienyl)Ethanone, (+/−)-2-Hydroxypiperitone, Beta-Ionone Epoxide, Isoambrettolide, Isobornyl Isobutyrate, Isobornyl 2-Methylbutyrate, N-Isobutyldeca-Trans-2-Trans-4-Dienamide, Isobutyl N-Methylanthranilate, (+/−)-Isobutyl 3-Methylthiobutyrate, Beta-Isomethylionone, Isopropenyl Acetate, Lactylated Fatty Acid Esters Of Glycerol And Propylene Glycol, 2-(L-Menthoxy)Ethanol, Menthyl Pyrrolidone Carboxylate, Menthyl Valerate, 4-Mercapto-2-Pentanone, (+/−)-4-Mercapto-4-Methyl-2-Pentanol, 2-Mercaptoanisole, Methionyl Butyrate, Trans- And Cis-1-Methoxy-1-Decene, (S1)-Methoxy-3-Heptanethiol, 2-Methoxyacetophenone, Methyl Cis-3-Hexenoate, Methyl Cis-5-Octenoate, Methyl 3-(Methylthio)Butanoate, Methyl 3-Mercaptobutanoate, Methyl Isopentyl Disulfide, Methyl N,N-Dimethylanthranilate, Methyl N-Acetylanthranilate, Methyl N-Formylanthranilate, S-Methyl Propanethioate, 2-Methyl-1-Methylthio-2-Butene, 3-Methyl-2(3-Methylbut-2-En-1-Yl)Furan, 3-(5-Methyl-2-Furyl)Prop-2-Enal, 5-Methyl-3(2h)-Furanone, 6-Methyl-5-Hepten-2-Yl Acetate, 2-Methylbut-2-En-1-Ol, 2-Methylfuran, 4-Methylpent-2-Enoic Acid, 3-(Methylthio)-2-Butanone, 4-(Methylthio)-2-Pentanone, (+/−)-3-(Methylthio)Heptanal, 3-(Methylthio)Methylthiophene, Methylthiomethylmercaptan, Mono- And Diglycerides Of Fatty Acids, Nona-2,4,6-Trienal, 2-Nonenoic Acid Gamma-Lactone, Cis-3-Octenyl Propionate, L-Ornithine Monochlorohydrate/Ornithine, Pent-2-Enyl Hexanoate, 2-Pentanoylfuran, 2-Pentenoic Acid, (+/−)-2-Phenyl-4-Methyl-2-Hexenal, Phthalide, Phytol, Phytyl Acetate, 3-Pinanone, Piperitenone Oxide, L-Piperitone, Polyglycerol Esters Of Fatty Acids, Prenyl Acetate, Prenyl Benzoate, Prenyl Caproate, Prenyl Formate, Prenyl Isobutyrate, Propyl 2-Mercaptopropionate, Propylene Glycol Mono- And Diesters Of Fatty Acids, Tetradec-2-Enal, Thioacetic Acid, Trans- And Cis-2,4,8-Trimethyl-3,7-Nonadien-2-O1, (+/−)-2,4,8-Trimethyl-7-Nonen-2-Ol, 3,7,11-Trimethyldodeca-2,6,10-Trienyl Acetate, 2,4,6-Trithiaheptane, Tyramine, Verbenone, Vetiverol, Vetiveryl Acetate, Cornmint Oil, *Mentha Arvensis* L., *Heliopsis Longipes* Extract, Scotch Spearmint Oil, *Mentha Cardiaca* L., Natural Hickory Smoke Flavor, Betaine, Adenosine Monophosphate; Monosodium, Or Disodium Adenylate, Isoquercitrin, Enzymatically Modified, Glycerol Ester Of Rosin, Gum Arabic, Hydrogen Octenylbutane Dioate, (−)-Homoeriodictyol, Sodium Salt, Sugar Beet Juice Extract, (+/−)-N,N-Dimethyl Menthyl Succinamide, N1-(2-Methoxy-4-Methylbenzyl)-N2-(2-(Pyridin-2-Yl)Ethyl)Oxalamide, N-(Heptan-4-Yl)Benzo[D][1,3]Dioxole-5-Carboxamide, N1-(2,4-Dimethoxybenzyl)-N2-(2-(Pyridin-2-Yl)Ethyl)Oxalamide, N1-(2-Methoxy-4-Methylbenzyl)-N2-(2-(5-Methylpyridin-2-Y1)Ethyl) Oxalamide, 1,6-Hexalactam, Ethylamine, Propylamine, Isopropylamine, Isobutylamine, Sec-Butylamine, 2-Methylbutylamine, Pentylamine, Hexylamine, 2-Methylpiperidine, Trimethylamine Oxide, Triethylamine, Tripropylamine, N,N-Dimethylphenethylamine, 2-Acetyl-1-Pyrroline, Piperazine, Butyramide, Methyl 10-Undecenoate, N-Gluconyl Ethanolamine, N-Gluconyl Ethanolamine Phosphate, N-Lactoyl Ethanolamine, N-Lactoyl Ethanolamine Phosphate, Ethanethiol, Heptane-1-Thiol, S-Isopropyl 3-Methylbut-2-Enethioate, 3-Methylhexanal, 4-Pentenal, Propyl Propane Thiosulfonate, Alpha-Ionene, *Gardenia Gummifera* Distillate, *Piper Longum* Distillate, N-3,7-Dimethyl-2,6-Octadienylcyclopropylcarboxamide, (+/−)-Ethyl 2-Hydroxy-2-Methylbutyrate, (+/−)-Ethyl 2-Hydroxy-3-Methylvalerate, 2-(2-Hydroxyphenyl) Cyclopropanecarboxylic Acid Delta Lactone, 2-Decanone, (+/−)-Trans- And Cis-2-Hexenal Propylene Glycol Acetal, (+/−)-Trans- And Cis-2-Hexenal Glyceryl Acetal, Trans-2-Hexenyl 2-Methylbutyrate, 2-(4-Methyl-5-Thiazolyl)Ethyl Formate, 2-(4-Methyl-5-Thiazolyl)Ethyl Propionate, 2-(4-Methyl-5-Thiazolyl)Ethyl Butanoate, 2-(4-Methyl-5-Thiazolyl)Ethyl Isobutyrate, 2-(4-Methyl-5-Thiazolyl)Ethyl Hexanoate, 2-(4-Methyl-5-Thiazolyl)Ethyl Octanoate, 2-(4-Methyl-5-Thiazolyl)Ethyl Decanoate, (+/−)-3-(Ethylthio)Butanol, *Decalepis Hamiltonii* Extract, 2-(Trans-2-Pentenyl)Cyclopentanone, 3,9-Dimethyl-6-(1-Methylethyl)-1,4-Dioxaspiro[4.5]Decan-2-One, Cis- And Trans-2-Isobutyl-4-Methyl-1,3-Dioxolane, Cis- And Trans-2-Isopropyl-4-Methyl-1,3-Dioxolane, 4-Aminobutyric Acid, 3-Mercaptoheptyl Acetate, Ethyl Trans-2-Methyl-2-Pentenoate, Methyl Hexyl Ether, Trans-2-Trans-4-Nonadiene, 1-Octene, Cis- And Trans-Ethyl 2,4-Dimethyl-1,3-Dioxolane-2-Acetate, Citronellyl Trans-2-Methyl-2-Butenoate, 5-Acetyl-2,3-Dihydro-1,4-Thiazine, Bis(1-Mercaptopropyl)Sulfide, 2,5-Dithiahexane, Pseudoionone, Cis- And Trans-L-Mercapto-P-Menthan-3-One, Trans-2-Nonen-4-One, Trans-4-Nonenal, 1,1'-(Tetrahydro-6a-Hydroxy-2,3a,5-Trimethylfuro[2,3-D]-1,3-Dioxole-2,5-Diyl)Bis-Ethanone. Trans-2-Decenol, Cis-2-Pentenol, 2-Methylbutyl 3-Methyl-2-Butenoate, Citric And Fatty Acid Esters Of Glycerol, L-Menthyl (R,S)-3-Hydroxybutyrate, N-[(Ethoxycarbonyl)Methyl)-P-Menthane-3-Carboxamide, N-[2-(3,4-Dimethoxyphenyl)Ethyl]-3,4-Dimethoxycinnamic Acid Amide, Mixture Of Methyl Cyclohexadiene And Methylene Cyclohexene, (+/−)-Cis- And Trans-1,2-Dihydroperillaldehyde, 5,7-Dihydroxy-2-(3-Hydroxy-4-Methoxyphenyl)Chroman-4-One, Phenethyl Decanoate, 3,6-Dimethyl-2,3,3a,4,5,7a-Hexahydrobenzofuran, 2-Methylacetophenone, 1-Ethyl-2-Pyrrolecarboxaldehyde, Cis- And Trans-5-Ethyl-2,5-Dihydro-4-Methyl-2-(1-Methylpropyl)-Thiazole, Cis And Trans-5-Ethyl-4-Methyl-2-(2-Methylpropyl)-Thiazoline, 2-Methyl-3-Furyl Methylthiomethyl Disulfide, Pyrrolidino-[1,2e]-4h-2,4-Dimethyl-1,3,5-Dithiazine, S-Allyl-L-Cysteine, 5-Pentyl-3h-Furan-2-One, 3-Mercapto-3-Methyl-1-Butyl Acetate, (+/−)-3-Mercapto-1-Butyl Acetate, 5-Nonen-Trans-2-One, L-Menthyl Acetoacetate, 4-Octen-3-One, 2,4,6-Trimethylphenol, 4-Hydroxyacetophenone, (+/−)-[R-(E)]-5-Isopropyl-8-Methylnona-6,8-Dien-2-One, 1-Methyl-1h-Pyrrole-2-Carboxaldehyde, 1-Pentanethiol, Pentadecanoic Acid, Tridecanal, Tridecanoic Acid. Hexyl Heptanoate, Dodecyl Propionate, Hexyl Nonanoate, Dodecyl Butyrate, Heptyl Heptanoate, Hexyl Decanoate, Ethyl 4-Methylpentanoate, Ethyl 2-Ethylbutyrate, Ethyl 2-Ethylhexanoate, 5-Methylhexyl Acetate, 4-Methylpentyl Isovalerate, 3,7-Dimethyloctanal, Cis-4-Decenol, Cis-5-Octenoic Acid, 5-Hexenol, 3-Isopropenylpentanedioic Acid, Methyl 4-Pentenoate, Cis-4-Octenol, 11-Dodecenoic Acid, Trans-3-Hexenol, Trans-4-Octenoic Acid, Isobutyl 10-Undecenoate, Cis-9-Octadecenyl Acetate, Ethyl 4-Pentenoate, Ethyl 3-Octenoate, 3-Octenoic Acid, Cis-9-Octadecenol, Decanal Propyleneglycol Acetal, Acetaldehyde Hexyl Isoamyl Acetal, Dodecanal Dimethyl Acetal, Nonanal Dimethyl Acetal, Heptanal Propyleneglycol Acetal, Hexanal Hexyl Isoamyl Acetal, Hexanal Dihexyl Acetal, Isovaleraldehyde Diethyl Acetal, Valeraldehyde Propyleneglycol Acetal, Nonanal Propyleneglycol Acetal, Undecanal Propyleneglycol Acetal, Valeraldehyde Dibutyl Acetal, Acetaldehyde 1,3-Octanediol Acetal, Hexanal Octane-1,3-Diol Acetal, Isovaleraldehyde Glyceryl Acetal, Acetaldehyde Di-Cis-3-Hexenyl Acetal, 2,6-Dimethyl-5-Heptenal Propyleneglycol Acetal, Octanal Propyleneglycol Acetal, Hexanal Butane-2,3-Diol Acetal, Pecan Shell Flour, Di-(1-Propenyl)-Sulfide (Mixture Of Isomers), 2-Pentylthiophene, 5-Ethyl-2-Methylthiazole, 2,4-Dimethylpyridine, 3-(4-Hydroxyphenyl)-1-(2,4,6-Trihydroxyphenyl)Propan-1-One, (+/−)-Ethyl 3-Hydroxy-2-Methylbutyrate, (+/−)-Ethyl 3-Mercapto-2-Methylbutanoate, (+/−)-Cis- And Trans-2-Methyl-2-(4-Methyl-3-Pentenyl)Cyclopropanecarbaldehyde, Trimethyloxazole, 2,5-Dimethyl-4-Ethyloxazole, 2-Propyl-4,5-Dimethyloxazole, 2-Isobutyl-4,5-Dimethyloxazole, 2-Methyl-4,5-Benzoxazole, 2-Nonanone Propyleneglycol Acetal, 6-Methyl-5-Hepten-2-One Propyleneglycol Acetal, 2-Pentyl 2-Methylpentanoate, 3-Octyl Butyrate, Dimethylbenzyl Carbinyl Crotonate, Dimethylbenzyl Carbinyl Hexanoate, 1,5-Octadien-3-One, 10-Undecen-2-One, 2,4-Dimethyl-4-Nonanol, 8-Nonen-2-One, 8-P-Menthene-, 2-Diol, Caryophyllene Alcohol, D-2,8-P-Menthadien-1-O1, Cis-3-Nonen-1-Ol, Trans-3-Hexenyl Acetate, 4-(Methylthio)Butyl Isothiocyanate, 6-(Methylthio)Hexyl Isothiocyanate, 5-(Methylthio)Pentyl Isothiocyanate, Amyl Isothiocyanate, 3-Butenyl Isothiocyanate, 2-Butylisothiocyanate, Ethyl Isothiocyanate, 5-Hexenyl Isothiocyanate, Hexyl Isothiocyanate, Isoamyl Isothiocyanate, Isobutyl Isothiocyanate, Isopropyl Isothiocyanate, Methyl Isothiocyanate, 4-Pentenyl Isothiocyanate, Benzyl Isothiocyanate, 2,4-Dimethyl-3-Oxazoline, 3,4-Dihydroxybenzoic Acid, 3-Hydroxybenzoic Acid, (+/−)-Acetaldehyde Ethyl Isopropyl Acetal, (+/−)-6-Methyloctanal, 5-Ethyl-2,3-Dimethylpyrazine, 2-Hydroxy-4-Methoxybenzaldehyde, 3-(Methylthio) Propyl Hexanoate, Sodium Lauryl Sulfate, Beta-Angelicalactone, 7-Decen-4-Olide, 9-Decen-5-Olide, 8-Decen-5-Olide, 6-[5(6)-Decenoyloxy]Decanoic Acid, Ethyl 5-Acetoxyoctanoate, Ethyl 5-Hydroxydecanoate, 9-Dodecen-5-Olide, Gamma-Octadecalactone, Delta-Octadecalactone, 9-Tetradecen-5-Olide, Orin Lactone, Methyl 3-Hydroxybutyrate, Methyl 3-Acetoxy-2-Methylbutyrate, Ethyl 2-Acetylhexanoate, Ethyl 3-Hydroxyoctanoate, Methyl 3-Acetoxyoctanoate, 5-Oxooctanoic Acid, 5-Oxodecanoic Acid, Ethyl 5-Oxodecanoate, 5-Oxododecanoic Acid, Ethyl 2-Acetyloctanoate, 2-Oxo-3-Ethyl-4-Butanolide, 3-Isopropenyl-6-Oxoheptanoic Acid, Hydroxyacetone, 1-Hydroxy-4-Methyl-2-Pentanone, Propyleneglycol Diacetate, Propyleneglycol Dipropionate, Propyleneglycol Dibutyrate, Propyleneglycol Mono-2-Methylbutyrate, Propyleneglycol Di-2-Methylbutyrate, Propyleneglycol Monohexanoate, Propyleneglycol Dihexanoate, Propyleneglycol Dioctanoate, Dimethyl Adipate, Dipropyl Adipate, Diisopropyl Adipate, Diisobutyl Adipate, Dioctyl Adipate, Ethyl Acetoacetate Ethyleneglycol Ketal, Methyl Levulinate, Ethyl Levulinate Propyleneglycol Ketal, Propyl Levulinate, Isoamyl Levulinate, Dodecyl Lactate, Hexadecyl Lactate, Propyl Pyruvate, Hydroxycitronellal Propyleneglycol Acetal, Citral Glyceryl Acetal, Mushroom Oil, Distilled, Propyleneglycol Monobutyrate, Cis-3-Hexenyl Acetoacetate, 2-Methoxy-6-(2-Propenyl)Phenol, Myricitrin, (R)-(−)-1-Octen-3-Ol, Cis-3-Hexenoic Acid, Ammonia (Also Includes Ammonium Chloride), Naringin Dihydrochalcone, N—P—Benzeneacetonitrilementhanecarboxamide, Cubebol, 6-Methylheptanal, (+/−)-Cis- And Trans-2-Pentyl-4-Propyl-1,3-Oxathiane, Choline Chloride (Also Includes Choline), 3-[(2-Methyl-3-Furyl)Thio]Butanal, (−)-Sclareol, (+)-Cedrol, D-Limonen-10-Ol, (2,4)- And (3,5)- And (3,6)-Dimethyl-3-Cyclohexenylcarbaldehyde, 1,3-P-Menthadien-7-Al, P-Menthan-7-Ol, P-Menth-1-En-9-Ol, Menthyl Formate, Menthyl Propionate, Cyclotene Propionate, 3,3,5-Trimethylcyclohexyl Acetate, Dl-Camphor, 2-Cyclopentylcyclopentanone, Carvyl Palmitate, Cyclohexanone Diethyl Ketal, 2-Cyclohexenone, 8,9-Dehydrotheaspirone, L-Fenchone, Ethylenediaminetetraacetic Acid Disodium Salt, 2,2,6,7-Tetramethylbicyclo[4.3.0]Nona-4,9(1)-Dien-8-Ol, 2,2,6,7-Tetramethylbicyclo[4.3.0]Nona-4,9(1)-Dien-8-One, 6-Hydroxycarvone, L-Menthyl Butyrate, Pinocarvyl Isobutyrate, 2-Pentenyl-4-Propyl-1,3-Oxathiane (Mixture Of Isomers), Acetaldehyde Di-Isobutylacetal, Acetaldehyde Ethyl Isobutyl Acetal, 4-(2,2,3-Trimethylcyclopentyl)Butanoic Acid, Perillaldehyde Propyleneglycol Acetal, 2,6,6-Trimethyl-2-Hydroxycyclohexanone, Acetoin Propyleneglycol Ketal, 4,5-Octanedione, Ethyl Maltol Isobutyrate, 2-Tetrahydrofurfuryl 2-Mercaptopropionate, Nerolidol Oxide, Furfural Propyleneglycol Acetal, Methyl 3-(Furfurylthio)Propionate, Furfuryl Decanoate, Di-2-Furylmethane, (E)-Ethyl 3-(2-Furyl)Acrylate, Furfuryl Formate, 2-Methylbenzofuran, 5-Methylfurfuryl Alcohol, 2-Methyl-3-Furyl 2-Methyl-3-Tetrahydrofuryl Disulfide, Ethyl 2,5-Dimethyl-3-Oxo-4(2h)-Furyl Carbonate, Acai Berry Extract, 4-(2-Propenyl)Phenyl-Beta-D-Glucopyranoside, N-(2-(Pyridin-2-Yl)Ethyl)-3-P-Menthanecarboxamide, (+/−)-N-Lactoyl Tyramine, Cis,Cis-3,6-Nonadienyl Acetate. Trans-2-Nonenyl Acetate, Cis-3-Nonenyl Acetate, Cis-6-Nonenyl Acetate, Dihydrogalangal Acetate, 2,3,3-Trimethylindanone, N-Ethyl-2,2-Diisopropylbutanamide, Cyclopropanecarboxylic Acid (2-Isopropyl-5-Methylcyclohexyl)Amide, Magnolol, 2-(Methylthio)Ethyl Acetate, 3-(Methylthio)Propyl Mercaptoacetate, Ethyl 2-Hydroxyethyl Sulfide, Ethyl 3-(Methylthio)-Cis-2-Propenoate, Ethyl 3-(Methylthio)-Trans-2-Propenoate, Ethyl 3-(Methylthio)-2-Propenoate, 4-Methyl-2-(Methylthiomethyl)-2-Hexenal, 5-Methyl-2-(Methylthiomethyl)-2-Hexenal, 4-Methyl-2-(Methylthiomethyl)-2-Pentenal, 1-(3-(Methylthio)-Butyryl)-2,6,6-Trimethylcyclohexene, 2-Oxothiolane, Butyl Beta-(Methylthio) Acrylate, Ethyl 3-(Ethylthio)Butyrate, Methyl Octyl Sulfide, Methyl 1-Propenyl Sulfide, Diisoamyl Disulfide, Bis(2-Methylphenyl) Disulfide, Mixture Of Butyl Propyl Disulfide And Propyl And Butyl Disulfide, Di-Sec-Butyl Disulfide, Methyl 2-Methylphenyl Disulfide, Diisoamyl Trisulfide, Dodecanethiol, 2-Hydroxyethanethiol, 4-Mercapto-4-Methyl-2-Hexanone, 3-Mercapto-3-Methylbutyl Isovalerate, 3-Mercaptohexanal, Methyl Isobutanethioate, 3-Mercaptopropionic Acid, 2-Ethylhexyl 3-Mercaptopropionate, Butanal Dibenzyl Thioacetal, Methional Diethyl Acetal, Ethyl Linalyl Ether, Myrcenyl Methyl Ether, Linalool Oxide Pyranoid, 2-Hydroxy-5-Methylacetophenone, 2-Phenylpropanal Propyleneglycol Acetal, Cinnamaldehyde Propyleneglycol Acetal, Ethyl Alpha-Acetylcinnamate, Ethyl 2-Hydroxy-3-Phenylpropionate, 3-(3,4-Methylenedioxyphenyl)-2-Methylpropanal, Trehalose, Dihydrate, Rebaudioside A, N-(2-Hydroxyethyl)-2,3-Dimethyl-2-Isopropylbutanamide, N-(1,1-Dimethyl-2-Hydroxyethyl)-2,2-Diethylbutanamide, Dimenthyl Glutarate, Trans-3-Nonen-1-Ol, 4-Formyl-2-Methoxyphenyl 2-Hydroxypropanoate, Guaiacol Butyrate, Guaiacol Isobutyrate. Guaiacol Propionate, Ethyl 5-Hydroxyoctanoate, Isopropylideneglyceryl 5-Hydroxydecanoate, 2-Ethyl-2-Hexenal, Ethyl 2-Hexenoate, Propyl Sorbate, Cis-2-Octenol, 2-Hexylidenehexanal, Trans-2-Tridecenol, 2-Phenoxyethyl Propionate, Propyl 4-Tert-Butylphenylacetate, 2-Phenoxyethanol, Phenyl Butyrate, Piperonal Propyleneglycol Acetal, Benzyl Levulinate, 4-Methylbenzyl Alcohol, Phenylacetaldehyde Diethyl Acetal, Benzyl Nonanoate, Anisaldehyde Propyleneglycol Acetal, 4-Methylbenzaldehyde Propyleneglycol Acetal, Phenylacetaldehyde Propyleneglycol Acetal, 2-Ethylhexyl Benzoate, 2-Ethyl-3-Methylthiopyrazine, 2-Ethoxy-3-Isopropylpyrazine, 2-Ethoxy-3-Ethylpyrazine, Butyl Beta-Naphthyl Ether, Isoamyl Phenethyl Ether, 2-Acetyl-4-Isopropenylpyridine, 4-Acetyl-2-Isopropenylpyridine, 2-Acetyl-4-Isopropylpyridine, 2-Methoxypyridine, 6-Methoxyquinoline, 2-Pentylthiazole, 2-Thienylmethanol, 2-Acetyl-5-Methylthiophene, 4-Methyl-3-Thiazoline, 3,4-Dimethylthiophene, 1-(2-Thienyl)Ethanethiol, 4,5-Dimethyl-2-Isobutylthiazole, Cyclotene Butyrate, 3-(Methylthio)Propylamine, 4-Methyl-Cis-2-Pentene, 1-Nonene, 1,3,5,7-Undecatetraene, Ethyl Alpha-Ethyl-Beta-Methyl-Beta-Phenylglycidate, Methyl Beta-Phenylglycidate, D-8-P-Menthene-1,2-Epoxide, L-8-P-Menthene-1,2-Epoxide, 2,3-Epoxyoctanal, 2,3-Epoxyheptanal, 2,3-Epoxydecanal, Hydroxy(4-Hydroxy-3-Methoxyphenyl)Acetic Acid, 4-Hydroxy-4-(3-Hydroxy-1-Butenyl)-3,5,5-Trimethyl-2-Cyclohexen-1-One, (+/−)-2,6,10,10-Tetramethyl-1-Oxaspiro[4,5]Deca-2,6-Dien-8-One, 4-(2-Butenylidene)-3,5,5-Trimethylcyclohex-2-En-1-One, Digeranyl Ether, 1-(4-Hydroxy-3-Methoxyphenyl)Decan-3-One, Alpha-Bisabolol, 2(4)-Ethyl-4(2),6-Dimethyldihydro-1,3,5-Dithiazine (Mixture Of Isomers), (2e,6e/Z,8e)-N-(2-Methylpropyl)-2,6,8-Decatrienamide, 4-Amino-5,6-Dimethylthieno[2,3-D]Pyrimidin-2(1h)One And 4-Amino-5,6-Dimethylthieno[2,3-D]Pyrimidin-2(1h)One Hydrochloride, 1,1-Propanedithiol, Z-5-Octenyl Acetate, (E)-4-Undecenal, Delta-Hexadecalactone, Trilobatin, L-Isoleucine, 1-(2-Furfurylthio)-Propanone. (+/−)-4-Methyl-2-Propyl-1,3-Oxathiane, N-(2-Methylcyclohexyl)-2,3,4,5,6-Pentafluorobenzamide, Arachidonic Acid Enriched Oil, 5-Isopropyl-2,6-Diethyl-2-Methyltetrahydro-2h-Pyran, (1r, 2s,5r)-N-(4-Methoxyphenyl)-5-Methyl-2-(1-Methylethyl) Cyclohexanecarboxamide, Octahydro-4,8a-Dimethyl-4a (2h)-Naphthol, 2-Methyl-4,5-Dihydrofuran-3-Thiol, (2s,5r)-N-[4-(2-Amino-2-Oxoethyl)Phenyl]-5-Methyl-2-(Propan-2-Yl)Cyclohexanecarboxamide, (+/−)-6-Octyltetrahydro-2h-Pyran-2-One, (+/−)-2-Methyltetrahydrofuran-3-Thiol Acetate, (+/−)-3-Hydroxy-3-Methyl-2,4-Nonanedione, 1,1-Dipropoxyethane, *Chrysanthemum* Extract, Honeysuckle Extract, Yuzunone, L-Methionyiglycine, N-Cyclopropyl-5-Methyl-2-Isopropylcyclohexanecarboxamide, 3-Pentanethiol, 2-Ethyl-2,5-Dihydro-4-Methylthiazole, 1-(Methyldithio)-2-Propanone, 5-Methylfurfurylmercaptan, 4-Mercapto-3-Methyl-2-Butanol, Ferrous L-Lactate, O-Trans-Coumaric Acid, 3-[(4-Amino-2,2-Dioxido-1h-2,1,3-Benzothiadiazin-5-Yl)Oxy]-2,2-Dimethyl-N-Propylpropanamide, 2(3),5-Dimethyl-6,7-Dihydro-5h-Cyclopentapyrazine, Cinnamyl Benzoate, Beta-Naphthyl Methyl Ether, Rosemary Oleoresin, 9-Decen-2-One, 1-(Methylthio)-3-Octanone, 3',7-Dihydroxy-4'-Methoxyflavan, Glutamyl-Valyl-*Glycine*, L-Threonine, Luo Han Fruit Concentrate, L-Alanyl-L-Glutamine, Sucrose Monopalmitate, Ethyl 2-Mercapto-2-Methylpropionate, 2-(3,4-Dihydroxyphenyl)-5,7-Dihydroxy-4-Chromanon, N—[N-[3-(3-Hydroxy-4-Methoxyphenyl)Propyl]-L-Alpha-Aspartyl]-L-Phenylalanine 1-Methylester, Monohydrate, Sweet Blackberry Leaves Extract, 2-[(2-(P-Menthyloxy)Ethoxy]Ethanol, Succinic Acid, Rebaudioside C, 1-(2-Hydroxyphenyl)-3-(Pyridin-4-Yl)Propan-1-One, 1-(2-Hydroxy-4-Isobutoxyphenyl)-3-(Pyridin-2-Yl)Propan-1-One, 1-(2-Hydroxy-4-Methoxyphenyl)-3-(Pyridin-2-Yl)Propan-1-One, Trans-4-Tert-Butylcyclohexanol, 3-(1-((3,5-Dimethylisoxazol-4-Yl)Methyl)-1h-Pyrazol-4-Yl)-1-(3-Hydroxybenzyl) Imidazolidine-2,4-Dione, 3-(1-((3,5-Dimethylisoxazol-4-Yl)Methyl)-1h-Pyrazol-4-Yl)-1-(3-Hydroxybenzyl)-5,5-Dimethylimidazolidine-2,4-Dione, Clover Herb Distillate, Glucosyl Steviol Glycosides, Dl-Isomenthol, O-Ethyl S-1-Methoxyhexan-3-Yl Carbonothioate, Cassyrane, 1,5-Octadien-3-Ol, (+/−)-2-Mercaptoheptan-4-Ol, 3-(Methylthio) Decanal, (4z,7z)-Trideca-4,7-Dienal, *Persicaria Odorata* Oil, Amacha Leaves Extract, Glutamyl-2-Aminobutyric Acid, Glutamyl-Norvalyl-*Glycine*, Glutamyl-Norvaline, N1-(2,3-Dimethoxybenzyl)-N2-(2-(Pyridin-2-Yl)Ethyl) Oxalamide, 1-(2-Hydroxy-4-Methylcyclohexyl)Ethanone, Mexican Lime Oil, Expressed, Persian Lime Oil, Expressed, (+/−)-6-Methoxy-2,6-Dimethylheptanal, 3,5-Undecadien-2-One, (+/−)-2,5-Undecadien-1-Ol, Triethyithialdine, 4-Methylpentyl 4-Methylvalerate, Cis-3-Hexenyl Salicylate, (R)—N-(1-Methoxy-4-Methylpentan-2-Yl)-3,4-Dimethylbenzamide, N-Acetyl Glutamate, 1,3-Propanediol, Szechuan Pepper Extract, *Tasmannia Lanceolata* Extract, *Mentha Longifolia* Oil, Mangosteen Distillate, Ethyl 3-(2-Hydroxyphenyl)Propanoate, 1-Cyclopropanemethyl-4-Methoxybenzene, Prenyl Thioisobutyrate, Prenyl Thioisovalerate, (−)-Matairesinol, Stevioside, 1-(2,4-Dihydroxyphenyl)-3-(3-Hydroxy-4-Methoxyphenyl) Propan-1-One, Ethyl 5-Formyloxydecanoate, 3-[3-(2-Isopropyl-5-Methyl-Cyclohexyl)Ureido]Butyric Acid Ethyl Ester, 2-Isopropyl-4-Methyl-3-Thiazoline, 2,6,10-Trimethyl-9-Undecenal, 5-Mercapto-5-Methyl-3-Hexanone, Meyer Lemon Oil, Cold Pressed, *Citrus×Meyeri*, Steviol Glycoside Extract, *Stevia Rebaudiana*, Rebaudioside A 60%, Steviol Glycoside Extract, *Stevia Rebaudiana*, Rebaudioside A 80%, (E)-N-[2-(1,3-Benzodioxol-5-Yl)Ethyl]-3-(3,4-Dimethoxyphenyl)Prop-2-Enamide, 4-Amino-5-(3-(Isopropylamino)-2,2-Dimethyl-3-Oxopropoxy)-2-Methylquinoline-3-Carboxylic Acid, 3-Methyl-5-(2,2,3-Trimethylcyclopent-3-En-1-Yl)Pent-4-En-2-Ol, (1-Methyl-2-(1,2,2-Trimethylbicyclo[3.1.0]Hex-3-Ylmethyl) Cyclopropyl)Methanol, Erospicata Oil, *Mentha Spicata*, Curly Mint Oil, *Mentha Spicata* Var. *Crispa*, (+/−)-2-Mercapto-5-Methylheptan-4-One, Caryophylla-3(4),8-Dien-5-Ol, L-Cysteine Methyl Ester Hydrochloride, 2(3)-Hexanethiol, Mixture Of 1-Vinyl-3-Cyclohexenecarbaldehyde And 4-Vinyl-1-Cyclohexenecarbaldehyde, (+/−)-4-Hydroxy-6-Methyl-2-Heptanone, 2-Octyl-2-Dodecenal, 2-Hexyl-2-Decenal, Trans-6-Octenal, (E)-3-Benzo[,3]Dioxol-5-Yl-N,N-Diphenyl-2-Propenamide, 2,6-Dimethyl-5-Heptenol, (+/−)-Bicyclo[2.2.1]Hept-5-Ene-2-Carboxylic Acid, Ethyl Ester, 3-(Acetylthio)Hexanal, (+/−)-3-Mercapto-1-Pentanol, (3r,3s)-3-[[(4-Amino-2,2-Dioxido-1h-2,1,3-Benzothiadiazin-5-Yl)Oxy]Methyl]-N-Cyclopentyl-2-Oxo-3-Piperidinecarboxamide, (+/−)-1-Cyclohexylethanol, (+/−)-8-Methyldecanal, Steviol Glycoside Extract, *Stevia Rebaudiana*, Rebaudioside C 30%, (+/−)-Naringenin, 2-(((3-(2,3-Dimethoxyphenyl)-1h-1,2,4-Triazol-5-Yl)Thio) Methyl)Pyridine, (2r)-3',5-Dihydroxy-4'-Methoxyflavanone, Glucosylated *Rubus Suavissimus* Extract, 20-30% Glucosylated Rubusoside Glycosides, Olive Fruit Extract, (S)-1-(3-(((4-Amino-2,2-Dioxido-1h-Benzo[C][1,2,6]Thiadiazin-5-Yl)Oxy)Methyl)Piperidin-1-Yl)-3-Methylbutan-1-One, 8-Methylnonanal, Mixture Of Ricinoleic Acid, Linoleic Acid, And Oleic Acid, Steviol Glycoside Extract, *Stevia Rebaudiana*, Rebaudioside A 22%, Steviol Glycoside Extract, *Stevia Rebaudiana*, Rebaudioside C 22%, Pinocarvyl Acetate, N-Ethyl-5-Methyl-2-(1-Methylethenyl) Cyclohexanecarboxamide, 2-(4-Methylphenoxy)-N-(1h-Pyrazol-3-Yl)-N-(Thiophen-2-Ylmethyl)Acetamide, Ethyl 2-(4-Hydroxy-3-Methoxy-Phenyl)Acetate, Ginger Mint Oil (*Mentha×Gracilis*), Palmitoylated Green Tea Extract Catechins, 2-(5-Isopropyl-2-Methyltetrahydrothiophen-2-Yl) Ethanol, Glucosylated *Rubus Suavissimus* Extract, 60% Glucosylated Rubusoside Glycosides, Sandalwood Austrocaledonicum Oil, and Sugar Cane Distillate.

In some embodiments, the combination of the cooling compounds with the flavorants described above has a synergistic effect. For example, the combination may further enhance the cooling properties of the composition or enhance the flavor properties of the flavorant.

Sweeteners

In some embodiments, the composition comprises a combination of one or more of Compounds 101-105 and one or more sweeteners, sweet flavorants, or sweet taste enhancers. Representative sweeteners, sweet flavorants, or sweet taste enhancers include but are not limited to: natural or synthetic carbohydrates or carbohydrate analogues, monosaccharides, disaccharides, oligosaccharides, and polysaccharides, rare sugars, sugars in either of the D- or L-conformations, sucrose, fructose, glucose, L-arabinose, L-fucose, L-glucose, L-ribose, D-arabino-hexulose, psicose, altrose, arabinose, turanose, abequose, allose, abrusoside A, aldotriose, threose, xylose, xylulose, xylo-oligosaccharide (such as xylotriose and xylobiose), lyxose, polydextrose, oligofructose, fucose, galacto-oligosaccharide, galactosamine, galactose, gentio-oligosaccharide (such as gentiobiose, gentiotriose, and gentiotetraose), dextrose, cellobiose, D-leucrose, D-psicose, D-ribose, D-tagatose, trehalose (mycose), neotrehalose, isotrehalose, raffinose, idose, tagatose, melibiose, mannan-oligosaccharide, rhamnose, ribose, ribulose, malto-oligosaccharide (such as maltotriose, maltotetraose, maltopentaose, maltohexaose, and maltoheptaose), maltose, sucrose acetate isobutyrate, dextrose, erythrose, erythrulose, deoxyribose, gulose, ketotriose, lactose, lactulose, kestose, nystose, mannose, sucralose, palatinose, polydextrose, sorbose, sugaridextrose (blended sugar), talose, sweetener compositions comprising one or more natural or synthetic carbohydrate, corn syrup, high fructose corn syrup, high maltose corn syrup, glucose syrup, sucralose syrup, hydrogenated glucose syrup (HGS), hydrogenated starch hydrolyzate (HSH), other syrups or sweetener concentrates derived from natural fruit and vegetable sources, semi-synthetic "sugar alcohol" sweeteners, polyols, erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, sugar alcohols, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green *stevia* powder, *stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet *stevia*-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrva virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, golden sugar, yellow sugar, golden syrup, granulated sugar, *gynostemma*, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falernum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), *vanilla* sugar, volemitol, birch syrup, aspartame-acesulfame, assugrin, chemically or enzymatically modified natural high potency sweeteners, glycosylated natural high potency sweeteners, glucosyl-derivatives containing 1-50 glycosidic residues, galactosyl-derivatives containing 1-50 glycosidic residues, fructosyl-derivatives containing 1-50 glycosidic residues, Theasaponin E1, Acesulfame K, Alitame, Aspartame, CH 401, Dulcin, Erythritol, Guanidine Sweetener, Isomalt, Isomaltosylfructoside, Isoraffinose, NC 174, Neotame, Perillartine, Phenylacetylglycyl-L-Lysine, Saccharin, SC 45647, sodium Cyclamate, Sorbitol, Sucralose, Sucrononic Acid, Suosan, Superaspartame, Methyl alpha-L-arabinoside, Methyl beta-L-arabinoside, Methyl beta-D-Glucoside, Methyl a-D-mannoside, Methyl beta-L-xylopyranoside, Methyl alpha-D-xyloside, Methyl alpha-D-Glucoside 2,3-Di-threonine, Methyl alpha-D-Glucoside 2,3-Di-isoleucine, Protocatechuic Acid, Cynarin, Glycyphyllin, Rebaudioside C, Abrusoside A, Abrusoside B, Abrusoside C, Abrusoside D, Abrusoside E, Apioglycyrrhizin, Araboglycyrrhizin, Baiyunoside, Brazzein, Bryodulcoside, Carnosifloside V, Carnosifloside VI, D. cumminsii, Cyclocarioside A, Cyclocarioside I, Dulcoside A, Fluorene-4-alpha, 6-dicarboxylic acid, 4-beta,10-alpha-dimethyl-1,2,3,4,5,10-hexahydor-Gaudichaudioside A, Glycyrrhizic Acid, Hernandulcin, Hernandulcin, 4beta-hydroxy-Hesperitin-7-Glucoside Dihydrochalcone, Huangqioside E, Huangqioside E, 3-Hydroxyphloridzin, Kaempferol, 2,3-Dihydro-6-Methoxy 3-O-Acetate, Mabinlin Maltosyl-Alpha-(1,6)-Neohesperidin Dihydrochalcone, Mogroside IIE, Mogroside III, Mogroside IIIE, Mogroside IV, Mogroside V, 11-Oxo Mogroside V, Monatin, Monellin, Monoammonium Glycyrrhizinate (Mag), Mukurozioside lib, Naringin Dihydrochalcone, Neoastilbin, Neohesperidin Dihydrochalcone (NH-DHC), Neomogroside, Osladin, Pentadin, Periandrin I, Periandrin II, Periandrin III, Periandrin IV, Periandrin V, Phlomisoside I, Phlorizin, Phyllodulcin, Polypodoside A, Potassium magnesium calcium glycyrrhizin, Pterocaryosides A, Pterocaryosides B, Quercetin, 2,3-Dihydro-3-O-Acetate, Quercetin, 2,3-Dihydro-6-Methoxy-Quercetin, 2,3-Dihydro-6-Methoxy-3-O-Acetate, Rebaudioside A, Rebaudioside B, Rubusoside, Scandenoside R6, Siamenoside I, Sodium glycyrrhizinate, Steviolbioside, Stevioside, Stevioside, alpha-Glycosyl Suavioside A, Suavioside B, Suavioside G, Suavioside H, Suavioside I, Suavioside J, Thaumatin, Triammonium Glycyrrhizinate (TAG), Trilobatin Selligueain A, Haematoxylin, Maltitol, Mannitol, Methyl alpha-D-Glucoside 2,3-Di-aspartic acid, Benzoic Acid, 2-(4-Dimethylaminobenzoyl)-Benzoic Acid, 2-Hydroxy-4-aminomethyl-Benzoic Acid, 2-(3-Hydroxy-4-Methoxybenzoyl)-Methyl beta-D-fructoside, Methyl alpha-D-galactoside, Methyl beta-D-galactoside, Curculin, Strogin 1, Strogin 2, Strogin 4, Miraculin, Phenylacetic Acid, 3,4-Dimethoxy-Aminobenzoic Acid, 3-Anisic Acid, Benzyl alcoho, 3-Amino-4-n-propoxyl, 3,4-Caffeic Acid, Cinnamic Acid, Dihydroxycinnamic Acid, 2,4-Ferulic Acid, Hydrolyzed Guar Gum, Hydroxyaminobenzoic Acid, 2,4-Nigeroolisaccharides, Sugarcane Bagasse Extract, Dihydroxybenzoic Acid, 2,3-Dihydroxybenzoic Acid, 2,4-Coumaric Acid, p-Dihydroxybenzoic Acid, 3,5-Hydroxybenzoic Acid, 3-Gurmarin, Gymnemasaponin III, Gymnemasaponin IV, Gymnemasaponin V, Gymnemic Acid I, Gymnemic Acid II, Gymnemic Acid III, Gymnemic Acid IV, Hodulcin, Jujubasaponin II, Jujubasaponin III, Propionic Acid, (−)-2-(4-Methoxyphenoxy)-Ziziphin, Ethyl Maltol, Maltol, Butanoic Acid, 2-Oxo-3-Methyl-Alanine, N-(1-Methyl-4-oxo-2-imidazolin-2-yl) Creatinine, Abrusoside E, monomethyl ester, Lactitol, Periandrinic acd I, monoglucuronide, Periandrinic acid II, monoglycuronide, Xylitol, Tagatose, d-Benzoyloxyacetic acid, 4-Methoxy Huduloside I, 4-Nitrophenyl a-D-galactoside, 4-Nitrophenyl alpha-D-glucoside, 4-Nitrophenyl beta-D-glucoside, 4-Nitrophenyl alpha-D-mannopyranoside, Urea, (N-(4-cyanophenyl)-N'-((sodiosulfo)methyl)-Chloramphenicol, Chlorogenic Acid, Methyl alpha-D-Glucoside, Methyl alpha-D-Glucoside 2,3-Di-alanine, Methyl alpha-D-Glucoside 2,3-Di-glycine, Methyl alpha-D-Glucoside 2,3-Di-proline, Methyl alpha-D-Glucoside 2,3-Di-valine, Aniline, 2-Butoxy-5-Nitro-Aniline, 2-Ethoxy-5-Nitro-Aniline, 2-Methoxy-5-Nitro-Aniline, 3-Nitro-(+)-Baiyunol-beta-D-gluccoside-alpha-D-glucoside, Aniline, 1,3-Hydroxy-4-methoxybenzylAniline, 2-Propxy-5-Nitro-(P4000)Benzo-1,4-dioxane 2-(3-Hydroxy-4-Methoxyphenyl)-Benzoe-1,3-dioxan-4-one 2-(3-Hydroxy-4-methoxyphenyl)-Benzoic Acid, 2-Benzoyl-4-Methoxy-Benzoic Acid, 2-(4-Methoxybenzoyl)-Benzo-1,3 (4H)-xathiane, 2-(3-Hydroxy-4-Methoxyphenyl)-Benzo-1, 4-xathiane 3-(3-Hydroxy-4-methoxyphenyl)-Butanoic acid, 4-[3,5-dihydroxy-4[3-(3-hydroxy-4-methoxyphenyl)-1-oxopropyl]phenoxy]-2-hydroxy-monosodium salt, Butanoic acid, 4-[3,5-dihydroxy-4-[3-(3-hydroxy-4-methoxyphenyl)-1-oxopropyl]phenoxy]-3-oxo-monosodium salt, Cyclohexadiene-1,4 1-Carboxaldehyde-4-(Methoxymethyl)-, (E)oxime Ethylbenzene, beta-(1,3-Hydroxy-4-methoxybenzyl)-Hespertin Dihydrochalcone, 3'-Carboxy-Hespertin Dihydrochalcone, 3'-Formyl-Isocoumarin, 3,4-Dihydro-3-(3-Hydroxy-4-methoxy)-Perillartine, 8,9-epoxy-Phenyl 3-Hydroxy-4-methoxybenzyl Ether, Phosphonic acid, [3-[3, 5-dihydroxy-4-[3-(3-hydroxy-4-methoxyphenyl)-1-oxopropyl]phenoxy]propyl]monopotassium salt, Stevioside analogue, Sulfamic acid, [2-[3,5-dihydroxy-4-[3-(3-hydroxy-4-methoxyphenyl)-1-oxopropyl]phenoxy]ethyl]-monopotassium salt, Urea, and N-(4-cyanophenyl)-N'-(2-carboxyethyl)-L-Theanine.

In some embodiments, the combination of one or more cooling compounds as described herein with one or more of the sweeteners described above has a synergistic effect. For example, the combination may further enhance the cooling character of the composition or enhance the flavor or other properties of the sweetener.

Bitterants

In some embodiments, the composition comprises a combination of one or more Compounds 101-105 and one or more bitterants, bitter flavor compounds, or bitterness-enhancing compounds. Representative bitterants, bitter flavor compounds, and bitterness-enhancing compounds include but are not limited to: Acteoside, Adhumulone, Adlupulone, Aesculetin, Aesculin, L-Alanine, L-alanyl-L-alanyl-L-Alanine, L-alanyl-L-isoleucyl-Alanine L-, L-valyl-L-valyl-Amarogentin, Amaropanin Amaroswerin, Amygdalin, Angustifoline, Antiacetylhumulone, Antiisohumulone, Arginine, L-Arginyl Leucine, Arginyl Leucy Leucine, Arginyl Proline, Asaronaldehyde, Aspartyl Aspartic acid, Asparasaponin I, Atropine, Benzyl beta-D-arabinoside, Benzyl beta-L-arabinoside, Benzyl beta-D-fructoside, Benzyl beta-D-galactoside, Benzyl alpha-D-glucoside, Benzyl beta-D-glucoside, Benzyl alpha-D-mannoside, Bitter Peptides, Bitter Peptides from Soy Proteins, Butyl alpha-D-glucoside, Butyl beta-D-glucoside, Caffeine, Carnosifloside II, Carnosifloside III, Carnosifloside IV, Catechin, Epicatechin, Epicatechin gallate, Chaconine, alpha-Chaconine, beta2-Chloramphenicol, Cholic Acid, Cichoriin, Cohumulone, Colupulone, Cryptochlorogenic Acid, gamma-lactone, Cucurbitacin B, Cucurbitacin D, Cyclo Alanine-glycine, Cyclo Alanine-phenylanaline, Cyclo Alanine-valine, Cyclo (L-arginylglycyl-L-prolyl-L-prolyl-L-phenylalanyl-L-isoleucyl-L-valyl), Cyclo Asparagine-phenylalanine, Cyclo Glycine-phenylalanine, Cycloheximide Cyclo Lucine-Tryptophan, Cyclopent(b)azepin-8(1H)-one, 7-Methyl-2,3,6,7-Tetrahydro-Cyclopent(b)azepin-8(1H)-one, 2,3,6,7-tetrahydro-7-hydroxy-7-methyl-Cyclopent-2-en-1-one, 2,5-dihydroxy-5-methyl-3-(1-piperidinyl)-Cyclopent-2-en-1-one, 2,5-dihydroxy-5-methyl-3-(1-pyrrolidinyl) Cyclopent-2-en-1-one, 2,3-di-1-pyrrolidinyl-Cyclopent-2-en-1-one, 5-hydroxy-5-methyl-2,3-di-1-piperidinyl-Cyclopent-2-en-1-one, 5-hydroxy-5-methyl-2,3-di-1-pyrrolidinyl-Cyclopent-2-en-1-one, 5-methyl-2,3-di-1-pyrrolidinyl-Cyclopent-2-en-1-one, 5-methylene-2,3-di-1-pyrrolidinyl-Cyclopent-2-en-1-one, 3-methyl-2-(1-pyrrolidinyl)-Cyclo Phenylalanine-aspartic acid, Cyclo Proline-alanine, Cyclo Proline-asparagine, Cyclo Proline-glycine, Cyclo Proline-isolucine, Cyclo Proline-leucine, Cyclo Proline-methionine, Cyclo Proline-phenylalanine, Cyclo Proline-proline, Cyclo Proline-valine, Cyclo Valine-phenylalanine, Cynaratriol, Cynaropicrin, Cynaropicrin, Daidzein, Daidzin Denatonium benzoate, Denatonium saccharide, Dhurrin, Dihydroxybenzoic Acid, 2,3-Dihydroxybenzoic Acid, 2,4-Ethyl b-L-arabinoside, Ethyl alpha-D-Glucoside, Ethyl beta-D-Glucoside, Eustomoroside, Eustomoside, Gallic Acid, Epigallocatechin, Epigallocatechin gallate, Gaudichaudioside F, Gelidoside, Genistein, Genistin, Gentiopicroside, Gentistic Acid, Gentomoside, Geshoidin, 6'-O-beta-D-Glucosylgentiopicroside, ucozaluzanin C, Glutamyl Aspartic Acid, Glutamyl Glutamic Acid. Glycyl Leucine, Goitrin, Gramine, Grosshemin, Haematoxylin Tetramethyl Ether Helicin, Heptadeca-16-ene, 1-Acetoxy-2,4-Dihydroxy-Heptadeca-16-ene, 1,2, 4-Trihydroxy-Histidine, L-Hulupone, Humulinone, Humulone, Hydroxybenzoic Acid, 4-Hymenoside A, Hymenoside B, Hymenoside C, Hymenoside D, Hymenoside E, Hymenoside F, Isohumulone, cis-Isohumulone, trans-Isoleucine, L-Isolupanine, Isosparteine, beta-Isosparteine, 10,17-Dioxo-beta-Isosparteine, 10-oxo-beta-Lactucin, L-Leucine, L-alanyl-L-alanyl-L-Leucine, N—[(R2R)-6-amino-2-[(4S)-2,5-dioxo-4-(phenylmethyl)-1-imidazolidinyl]-1-oxohexyl]-L-leucyl-L-methionyl-N-methyl-L-phenylalanyl-, (4-1)-lactam, L-Leucine, glycyl-L-alanyl-Leucine, L-L-Leucine, N—(N2-L-leucyl-L-glytaminyl)-L-Leucine, N—(N-L-leucyl-L-a-glutamyl)-L-Leucine, N—[N2-[N2-[N-(1-L-leucyl-L-prolyl)-L-phenylalanyl]-L-asparaginyl]-L-gluta-minyl]-L-Leucine, N—[N2-[N—[N-(1-L-leucyl-L-prolyl)-L-phenylalanyl]-L-seryl]-L-glutaminyl]-L-Leucine, L-leucyl-L-valyl-Leucy Leucine, Leucyl Phenylalanine, Limonin, Limoninmonolactone, Linamarin, Lotaustralin, Lupine, Lupanine, 13-Hydroxy-Lupanine, 7-hydroxy-Lupinine, Epilupinine Lupoxes B, Lupoxes C, Lupulone, Luputrione, Mellein, 6-Methoxy-Methionine, L-Methyl alpha-L-arabinoside, Methyl beta-L-arabinoside, Methyl beta-D-Glucoside, Methyl alpha-D-Glucoside 2,3-Di-isoleucine, Methyl alpha-D-Glucoside 2,3-Di-leucine, Methyl alpha-D-Glucoside 2,3-Di-L-phenylalanine, Methyl alpha-D-Glucoside 2,3-Di-threonine, Methyl alpha-D-Glucoside 2,3-Di-tyrosine, Methyl a-D-mannoside, Methyl beta-L-xylopyranoside, Methyl alpha-D-xyloside, Naringin, Neochlorogenic Acid, gamma-Lactone, Neohesperidin, Nuezhenide, Oleonuezhenide, Oleuropein, Olivieroside A, Olivieroside B, Olivieroside C, Perrottetin H, Phenylalanine, L-Phenyl alpha-D-galactoside, Phenyl alpha-D-glucoside, Phenyl beta-D-glucoside, Phenylthiourea, Phlomisoside II, Piperidine-2-carboxylic acid, 4-[(2-carboxy-2-hydroxyethyl(thio]-Piperidinecarboxylic acid-2, 4-[(2-carboxy-2-hydroxyethyl)thio]-Prehumulone, Prelupulone, Propyl beta-D-fructoside, Propyl alpha-D-glucoside, Propyl beta-D-glucoside, Protocatechuic Acid, Prunasin, Pulcherrimine, Quinidine, Quinine, Quinolizinium-7-olate, Ranitidine, Rebaudioside C, Salicin, Salidroside, Scabraside, Scandenoside R5, Sclareolide, Scopolin, Septemfidoside, Seryl Lysyl Glycyl Leucine, Sinapine, Solanine, alpha-Sparteine, Sparteine, 17-oxo-Stevisalioside A, Strychnine, Suavioside C1, Suavioside D2, Suavioside F, Sucrose Octaacetate, Sweroside, Swertiamarin, Swertiapunimarin, Taxiphyllin, TFI (Furostan, beta-D-galactopyranoside), Theaflavin, Theaflavin Gallate A, Theaflavin Gallate B, Tomatidine, Tomatine, alpha-Tricyclodehydroisohumulone, Trifloroside, Trihydroxybenzoic Acid, 2,4, 6-Tryptophan, L-Uracil, 6-propyl-2-thio-L-Valine, L-arginylglycyl-L-prolyl-L-prolyl-L-phenylalanyl-L-isoleucyl-(BPIa)Valine, L-Yohimbine, extract of wild cucumber, Denatonium, denatonium benzoate, and denatonium saccharide.

In some embodiments, the combination of one or more of Compounds 101-105 with one or more of the bitterants described above has a synergistic effect. For example, the combination may further enhance the cooling character of the composition or enhance the properties of the bitterant.

Sour Flavorants

In some embodiments, the composition comprises a combination of one or more of Compounds 101-105 and one or more acids or sour flavorants. Representative sour flavorants include but are not limited to: ascorbic acid, benzoic acid, gallic acid, glucuronic acid, adipic acid, glutaric acid, malonic acid, succinic acid, malic acid, acetic acid, lactic acid, citric acid, tartaric acid, fumaraic acid, phosphoric acid, pyrophosphoric acid, tannic acid, vinegar, lemon juice, lime juice, acidic fruit juices, and acidic fruit extracts.

In some embodiments, the combination of the one or more of Compounds 101-105 with one or more of the sour flavorants described above has a synergistic effect. For example, the combination may further enhance the cooling character of the composition or enhance the properties of the sour flavorant.

Salty Flavorants

In some embodiments, the composition comprises a combination of one or more of Compounds 101-105 and one or more salts or salt flavor enhancers. Representative salts or salt flavor enhancers include but are not limited to: mineral salts, sodium chloride, potassium chloride, magnesium chloride, ammonium chloride, sodium gluconate, sodium phosphates, glycine, L-alanine, L-valine, L-leucine, L-isoleucine, L-phenylalanine, L-tyrosine, L-glutamine, L-glutamic acid, L-asparagine, L-aspartic acid, L-serine, L-threonine, L-cysteine, L-methionine, L-proline, L-lysine, L-arginine, L-tryptophan, L-histidine, L-pyrolysine, L-pyroglutamine, L-4-trans-hydroxyproline, L-3-cis-hydroxyproline, L-homoserine, L-homocysteine, L-cystine, L-ornithine and L-citrulline, L-glutamine, L-glutamic acid, L-asparagine, L-aspartic acid, L-valine, L-arginine and L-lysine.

In some embodiments, the combination of the one or more of Compounds 101-105 with one or more of the salty flavorants described above has a synergistic effect. For example, the combination may further enhance the cooling character of the composition or enhance the properties of the salty flavorant. In some embodiments, the combination imparts a synergistic salt flavor.

Umami Flavorants

In some embodiments, the composition comprises a combination of one or more of Compounds 101-105 with one or more umami flavor compounds or umami flavor enhancing compounds. Representative umami flavor compounds or umami flavor enhancing compounds include but are not limited to the compounds identified in U.S. Patent Application Publications 2005/0084506A1, U.S. 2009/0111834A1, U.S. 2012/0201763A1, U.S. 2015/0093339A1, U.S. 2006/0263411A1, U.S. 2012/0226047A1, and 2009/0220662A1. Additional representative umami flavor compounds or umami flavor enhancing compounds include but are not limited to: hydrolyzed soy protein, hydrolyzed corn protein, hydrolyzed wheat protein, anchovy, anchovy paste, fish sauce, yeast extract, nutritional yeast, hydrolyzed yeast extract, mushrooms, mushroom powder, dehydrated mushrooms, mushroom extract, kombucha, hydrolyzed vegetable protein, oyster sauce, soy sauce, soy extract, tamari, miso powder, miso paste, parmesan cheese, parmesan cheese solids, kombu powder, kombu, dehydrated kombu, kombu paste, nori, nori powder, nori paste, seaweed, dehydrated seaweed, seaweed powder, seaweed extract, tomato, dehydrated tomato, tomato powder, tomato extract, vegetable powder, vegetable extract, whey powder, whey solids, whey, collagen, gelatin, textured vegetable protein, sodium caseinate, calcium caseinate, magnesium caseinate, potassium caseinate, glyoxylic acid, 3-methyl-2-oxo-butanoic acid, 3-methyl-2-oxo-pentanoic acid, 4-methyl-2-oxo-pentanoic acid, 3-hydroxy-2-oxo-propanoic acid, oxalacetic acid, 2-oxo-glutaric acid, 2-oxo-3-phenyl-propanoic acid, 3-(4-hydroxyphenyl)-2-oxo-propanoic acid, 2-oxo-1H-indole-3-propanoic acid, 2-oxo-1H-imidazole-4-propanoic acid, 4-methylthio-2-oxo-butanoic acid, 3-mercapto-2-oxo-propanoic acid, 3-hydroxy-2-oxo-butanoic acid, 6-amino-2-oxo-hexanoic and 5-guanidino-2-oxo-pentanoic acid, 2-amino-butanoic acid, .alpha.-alanine, glycine, norvaline, valine, aspartic acid, norleucine, leucine, isoleucine, serine, threonine, glutamic acid, phenylalanine, tyrosine, cysteine, methionine, lysine, tryptophane, histidine, arginine, asparagine, glutamine, cystine, citrulline, theanine, .gamma.-methylene-glutamic acid, isoeugenol, 2-propylphenol, p-vinylguaiacol, 2-acetylpyrazine, 2-ethyl-3,5-dimethylpyrazine, 2,3,5-trimethylpyrazine, 2,3-diethyl-5-methylpyrazine, 3-ethyl-2-methylpyrazine, dimethyl sulfide, dimethyl disulfide, dimethyl trisulfide, methylpropyl disulfide, 2-methylthiophenol, methional (3-methylthiopropanal), 2-octenal, 2,4-nonadienal, 2,4-decadienal, 2,4-undecadienal, 2-methoxybenzaldchyde, 2,4-dodecadienal, decenal, methyl 2-furanecarboxylate, 2-ethyl-4-hydroxy-3-methyl 5(2H)-furanone, 2,6-dimethylbenzenethiol 2-nonen-1-ol, 10-undecenoic acid, undecanoic acid, isodecanoic acid and isononanoic acid, 2-oxo-butanoic acid, oxalacetic acid, 3-methyl-2-oxo-butanoic acid, 3-methyl-2-oxo-pentanoic acid, 2-oxo-glutaric and 3-mercapto-2-oxo-propanoic acid, NaCl, KCl, MSG, guanosine monophosphate (GMP), inosin monophospahte (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxyphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2, 4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide, glutamic acid, glutamate, monosodium glutamate, monopotassium glutamate, monoammonium glutamate, calcium diglutamate, magnesium diglutamate, L-asparagine or a salt thereof, 5'-ribonucleotides or their salts, calcium 5'-ribonucleotides, disodium 5'-ribonucleotides, dipotassium 5'-ribonucleotides, inosinic acid, guanylic acid, adenosinic acid, inosinates, guanylates, and adenylates, guanosine 5'-monophosphate, inosine 5'-monophosphate, 5'-adenylate, disodium guanylate, disodium inosinate, disodium adenylate; dipotassium guanylate, dipotassium inosinate, dipotassium adenylate, calcium guanylate, calcium inosinate, calcium adenylate, maltol, ethyl maltol, glycine, L-leucine, autolyzed or hydrolyzed proteins (e.g. autolyzed yeast, hydrolyzed yeast, hydrolyzed vegetable proteins), Koji-Aji (Ajinomoto Food Ingredients), fermented wheat gluten, Glutathione. Glutamyl Glutamic Acid, (Z)-6-Dodecen-4-olide, Inosinic acid, Dodec-Z6-en-4-olide, Glutamic Acid, L-Aconitic Acid, N-(1-deoxy-fructos-1-yl) glutamate, hydrolyzed vegetable protein, Methyl alpha-D-Glucoside, 2,3-Di-lysine, Methyl alpha-D-Glucoside 2,3-Di-ornithine, L-Asparagine, L-a-glutamyl-L-a-glutamyl-L-Glutamic acid, L-a-aspartyl-L-a-glutamyl-Glutamyl valine, Wheat gluten hydrolyzate, Aspartic acid L-, L-a-aspartyl-L-a-aspartyl-L-a-aspartyl-Docosahexaenoic acid, and (4Z,7Z,10Z,13Z,16Z,19Z)-L-Theanine, allyl cysteine, propenyl cysteine, S-(.alpha., .beta.-dicarboxyethyl) .gamma.-L-glutamyl-L-cysteinyl-glycine, S-(.alpha., .beta.-dicarboxyethyl) cysteine, 3-(carboxymethoxy)-alanine, S-carboxymethyl-glutathione (glutaramic acid), S-carboxymethyl-cysteinyl-glycine, (S-carboxymethyl)-lysyl-cysteine, S-dicarboxymethyl-glutathione, S-carboxymethyl-cysteine, S-(1,2-dicarboxyethyl)-glutathione, and S-(1,2-dicarboxyethyl)-cysteine, N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, N-acetyl AMP, N-formyl AMP, N-propanoyl AMP, N-butanoyl AMP, N-pentanoyl AMP, N-hexanoyl AMP, N-heptanoyl AMP, N-octanoyl AMP, N-oxalyl AMP, N-succinyl AMP, N-glutaryl AMP, N-fumaryl AMP, N-maleyl AMP, N-adipyl AMP, N-citryl AMP, N-galloyl AMP, N-oxalacetyl-AMP, N-feruloyl AMP, N-pyruvyl AMP, N-benzoyl AMP, N-vanilloyl AMP, N-anthranoyl AMP, N-caffeoyl AMP, N-cinnamoyl AMP, N-acetyl CMP, N-formyl CMP, N-propanoyl CMP, N-butanoyl CMP, N-pentanoyl CMP, N-hexanoyl CMP, N-heptanoyl CMP, N-octanoyl CMP, N-oxalyl CMP, N-succinyl CMP, N-glutaryl CMP, N-fumaryl CMP, N-maleyl CMP, N-adipyl CMP, N-citryl CMP, N-galloyl CMP. N-oxalacetyl-CMP, N-feruloyl CMP, N-pyruvyl CMP, N-benzoyl CMP, N-vanilloyl CMP, N-anthranoyl CMP, N-caffeoyl CMP, N-cinnamoyl CMP, N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, flavor modifiers created by maillard reactions, S-(.alpha., .beta.-dicarboxyethyl) .gamma.-L-glutamyl-L-cysteinyl-glycine, S-(.alpha., .beta.-dicarboxyethyl) cysteine, 3-(carboxymethoxy)-alanine, S-carboxymethyl-glutathione (glutaramic acid), S-carboxymethyl-cysteinyl-glycine, (S-carboxymethyl)-lysyl-cysteine, S-dicarboxymethyl-glutathione, S-carboxymethyl-cysteine, S-(1,2-dicarboxyethyl)-glutathione, and S-(1,2-dicarboxyethyl)-cysteine, Gamma-L-glutamyl-L-cysteinyl-glycine or γ-Glu-Cys-Gly, Rubemamine, rubemamide, rubescenamine, Rubescenamide, zanthosine, zanthosinamide, dioxamide, dioxamine, zanthomamine, and zanthomamide.

Umami flavor compounds or umami flavor enhancing compounds may also include peptides with the sequence Lys-Ile-His-Pro-Phe, Gly-Pro-Phe-Pro-Ile, or Lys-Lys-Tyr-Lys-Val-Pro-Gln, Glu-Glu-Leu, Glu(Glu-Leu), Leu-Glu-Glu, Glu-Asp-Phe, Glu-Glu-Ile, Asp-Glu-Leu and Glu-Leu-Glu. And their N-lactoyl derivatives, Lys-Gly-Asp-Glu-Glu-Ser-Leu-Ala, Ser-Leu-Ala-Lys-Gly-Asp-Glu-Glu, Ser-Leu-Ala-Asp-Glu-Glu-Lys-Gly, Lys-Gly-Ser-Leu-Ala,-Asp-Glu-Glu, Lys-Gly-Asp-Glu-Glu, Glu-Glu-Asp-Gly-Lys, or Asp-Glu-Glu (See Nakata et al., Biosci. Biotechnol. Biochem. (1995) 59(4):689-93).

In some embodiments, the combination of one or more of Compounds 101-105 with one or more umami flavor compounds or umami flavor enhancing compounds described above has a synergistic effect. For example, the combination may further enhance the cooling character or the umami flavor of the composition.

Plant or Animal Products

In some embodiments, the composition comprises one or more of Compounds 101-105 and one or more plant or animal products. Representative plant or animal products include but are not limited to: zedoary bark extract (*curcuma zedoaria* (berg.) rosc.), zedoary (*curcuma zedoaria* (berg.) rosc.), alfalfa extract (*medicago sativa* l.), alfalfa herb and seed (*medicago sativa* l.), algae brown extract (*macrocystis* and *laminaria* spp.), algae red (*porphyra* spp. and *gloiopeltis furcata* and *rhodymenia palmata* (l.)), algae red extract (*porphyra* spp. and *gloiopeltis furcata* and *rhodymenia*, alkanet root extract (*alkanna tinctoria* tausch), allspice (*pimenta officinalis* lindl.), allspice, oil (*pimenta officinalis* lindl.), allspice, oleoresin (*pimenta officinalis* lindl.), almond, bitter, oil (ffpa) (*prunus* spp.), aloe, extract (*aloe* spp.), ambrette, absolute, oil (*hibiscus abelmoschus* l.), ambrette seed (*hibiscus abelmoschus* l.), ambrette seed, oil (*hibiscus abelmoschus* l.), ambrette, tincture (*hibiscus abelmoschus* l.), amyris (*amyris balsamifera* l.), amyris, oil (*amyris balsamifera* l.), angelica root (*angelica* spp.), angelica root, extract (*angelica archangelica* l.), angelica root, oil (*angelica archangelica* l.), angelica seed (*angelica* spp.), angelica seed, extract (*angelica archangelica* l.), angelica seed, oil (*angelica archangelica* l.), angelica stem, oil (*angelica archangelica* l.), angola weed (*roccella fuciformis* ach.), angostura (*galipea offincinalis* hancock), angostura, extract (*galipea officinalis* hancock), anisaldehyde propyleneglycol acetal, anise (*pimpinella anisum* l.), anise, oil (*pimpinella anisum* l.), anise, star (*illicium verum* hook, f.), anise, star, oil (*illicium verum* hook, f.), annatto, extract (*bixa orellana* l.), annatto, seed (*bixa orellana* l.), apple essence, natural, apricot kernel, oil (*prunus armeniaca* l.), arnica flowers (*arnica* spp.), arrowroot starch, *artemisia* (*artemisia* spp.), *artemisia* extract, *artemisia* oil, artichoke leaves (*cynara scolymus* l.), asafetida, fluid extract (*ferula assafoetida* l.), asafetida, gum (*ferula assafoetida* l.), asafetida, oil (*ferula assafoetida* l.), asparagus, seed and root, extract, bakers yeast extract, baker's yeast glycan, baker's yeast protein, balm (*melissa officinalis* l.), balm leaves (*melissa officinalis* l.), balm leaves, extract (*melissa officinalis* l.), balm, oil (*melissa officinalis* l.), fir, balsam, needles and twigs (*abies balsamea* (l.) mill.), balsam fir, oil (*abies balsamea* (l.) mill.), balsam fir, oleoresin (*abies balsamea* (l.) mill.), balsam, peru (*myroxylon pereirae* klotzsch), balsam, peru, oil (*myroxylon pereirae* klotzsch), basil (*ocimum basilicum* l.), basil bush (*ocimum minimum* l.), basil, extract (*ocimum basilicum* l.), basil, oil (*ocimum basilicum* l.), basil, oleoresin (*ocimum basilicum* l.), bay (*laurus nobilis* l.), bay leaves, sweet, extract (*laurus nobilis* l.), bay leaves, sweet, oil (*laurus nobilis* l.), bay leaves, west indian, extract (*pimenta acris* kostel), bay leaves, west indian, oil (*pimenta racemosa* (mill.) j. w. moore), bay leaves, west indian, oleoresin (*pimenta acris* kostel), beechwood, creosote (*fagus* spp.), benzoin, resin (*styrax* spp.), bergamot, oil (*citrus aurantium* l. subsp. *bergamia wright* et arn), birch, sweet, oil (*betula lenta* l.), birch tar, oil (*betula pendula* roth and related *betula* spp.), blackberry bark, extract (*rubus*, spp. of section eubatus), blackberry fruit extract, bois de rose, oil (*aniba rosaeodora* ducke), *boldus* leaves (*peumus boldus* mol.), bonito, dried, *boronia*, absolute (*boronia megastigma* nees), bouillon, vegetable, smoke, *bryonia* root (*bryonia* spp.), buchu leaves (*barosma betulina* and *crenulata*), buchu leaves extract, buchu leaves, oil (*barosma* spp.), buckbean leaves (*menyanthes trifoliata* l.), buckbean leaves, extract (*menyanthes trifoliata* l.), cajeput, oil (*melaleuca leucadendron* l.), calumba root (*jatrorrhiza palmata* (lam.) miers), calumba root, extract (*jatrorrhiza palmata* (lam.) miers), d-camphor, camphor, japanese, white, oil (*cinnamomum camphora* (l.) nees et eberm.), camphor oil, formosan ho-sho, leaves (*cinnamomum camphora*), cananga, oil (*cananga odorata* hook. f. and thoms.), candelilla wax (wax from stems and branches of *euphorbia* cerifera), capers (*capparis spinosa* l.), capsicum (*capsicum* spp.), capsicum extract (*capsicum* spp.), capsicum, oleoresin (*capsicum* spp.), caramel, caraway (*carum carvi* l.), caraway, black (*nigella sativa* l.), caraway, oil (*carum carvi* l.), cardamom (*elletaria cardamomum* (l.) maton), cardamom oleoresin, cardamom seed, oil (*elletaria cardamomum* (l.) maton), carob bean, extract (*ceratonia siliqua* l.), cascara, bitterless, extract (*rhamnus purshiana* dc.), cascarilla bark, extract (*croton* spp.), cascarilla bark, oil (*croton* spp.), casein, *cassia* buds (*cinnamomum cassia* blume), cassie, absolute (*acacia farnesiana* (l.) *willd.*), castoreum, extract (castor spp.), castoreum, liquid (castor spp.), castor oil (*ricinus communis* l.), *catechu*, black, extract (*acacia catechu willd.*), *catechu*, black, powder (*acacia catechu willd.*), cedar leaf, oil (*thuja occidentalis* i.), cedarwood oil alcohols, cedarwood oil terpenes, celery seed (*apium graveolens* l.), celery seed, extract (*apium graveolens* l.), celery seed, extract solid (*apium graveolens* l.), celery seed, oil (*apium graveolens* l.), celery seed, centaury (*centaurium umbellatum* gilib.), cereal solids, hydrolyzed, chamomile flower (*matricaria chamomilla* l.), chamomile flower (*anthemis nobilis* l.), chamomile flower, hungarian, oil (*matricaria chamomilla* l.), chamomile flower, oil (*anthemis nobilis* l.), chamomile flower, roman, extract (*anthemis nobilis* l.), char smoke flavor, cherry bark, wild, extract (*prunus serotina* ehrh.), cherry-laurel leaves (*prunus laurocerasus* l.), cherry laurel, oil (*prunus laurocerasus* l.) (ffpa), cherry-laurel water (*prunus laurocerasus* l.), cherry pits, extract (*prunus* spp.), chervil (*anthriscus cerefolium* (l.) hoffm.), chervil, extract (*anthriscus cerefolium* l.), chestnut leaves (*castanea dentata* (marsh.) borkh.), chestnut leaves, extract (*castanea dentata* (marsh.) borkh.), chestnut leaves, extract solid (*castanea dentata* (marsh.) borkh.), chicory, extract (*cichorium intybus* l.), chilte (*cnidoscolus* (also known as *jatropha*) spp.), chiquibul (*manilkara zapotilla gilly*), chirata (*swertia chirata* buch.-ham.), chirata, extract (*swertia chirata* buch.-ham.), chives (*allium schoenoprasum* l.), cinchona bark, red (*cinchona succirubra* pav. or its hybrids), cinchona bark, red, extract (*cinchona succirubra* pav. or its hybrids), cinchona bark, yellow (*cinchona* spp.), cinchona bark, yellow, extract (*cinchona* spp.), *cinchona*, extract (*cinchona* spp.), cinnamon (*cinnamomum* spp.), cinnamon bark, extract (*cinnamomum* spp.), cinnamon bark, oil (*cinnamomum* spp.), cinnamon bark oleoresin, ceylon, chinese, or saigon (*cinnamomum* spp.), cinnamon leaf, oil (*cinnamomum* spp.), cinnamon leaf oil, rectified, citronella, oil (*cymbopogon* nardus rendle), citrus peels, extract (*citrus* spp.), clary (*salvia sclarea* l.), clary sage, absolute, clary, oil (*salvia sclarea* l.), clary sage, clove bud, extract (*eugenia* spp.), clove bud, oil (*eugenia* spp.), clove bud, oleoresin (*eugenia* spp.), clove leaf, oil (*eugenia* spp.), clover (*trifolium* spp.), clover, extract (*trifolium* spp.), clover herb distillate, clover, oil (*trifolium* spp.), clover tops, red, extract solid (*trifolium pratense* l.), cloves (*eugenia* spp.), clove stem, oil (*eugenia* spp.), coca leaf, extract (decocainized) (erythroxylon coca lam.), cocoa extract, cocoa with dioctyl sodium sulfosuccinate, refined, coffee concentrate, pure, coffee extract (*coffea* spp.), coffee extract, solid, cognac, green, oil, cognac, white, oil, copaiba (south american spp. of *copaifera* l.), copaiba, oil (south american spp. of *copaifera* l.), coriander (*coriandrum sativum* l.), coriander leaf oil (*coriandrum sativum* l.), coriander, oil (*coriandrum sativum* l.), cork, oak (*quercus* spp.), corn silk extract (*zea mays* l.), corn silk, oil(*zea mays* l.), costmary (*chrysanthemum balsamita* l.), costus root, oil (*saussurea lappa* clarke), cottonseed flour, defatted, cottonseed flour, partially defatted, cooked, cottonseed flour, partially defatted, cooked, toasted, cottonseed kernels, glandless, raw, cottonseed kernels, glandless, roasted, cubeb (*piper cubeba* l. f.), cubeb, oil (*piper cubeba* l. f.), cubebol, cumin (*cuminum cyminum* l.), cumin, oil (*cuminum cyminum* l.), currant buds, black, absolute (*ribes nigrum* l.), currant juice, black, currant leaves, black (*ribes nigrum* l.), daidai peel oil, damiana leaves (*turnera diffusa willd.*), dandelion, fluid extract (*taraxacum* spp.), dandelion root, extract solid (*taraxacum* spp.), davana oil (*artemesia pallens* wall.), dehydrated beets, dill (*anethum graveolens* l.), dill, oil (*anethum graveolens* l.), dill seed, indian (*anethum* spp.), dill seed oil(*anethum sowa* roxb.), dittany of crete (*origanum dictamnus* l.), dittany (*fraxinella*) roots (*dictamnus albus* l.), dog grass, extract (*agropyron repens* (l.) beauv.), dragon's blood, extract (*daemonorops* spp. or other botanical sources), dried algae meal, elder flowers (*sambucus canadensis* l. or *sambucus nigra* l.), elder flowers, extract (*sambucus canadensis* l. or *sambucus nigra* l.), elder tree leaves (*sambucus nigra* l.), elecampane root, extract (*inula helenium* l.), elecampane root, oil (*inula helenium* l.), elemi, gum, elemi, oil (*canarium* spp.), erigeron, oil (*erigeron canadensis* l.), eucalyptol, eucalyptus, oil (*eucalyptus globulus* labille), eugenol, fennel, common (*foeniculum vulgare* mill.), fennel, sweet (*foeniculum vulgare* mill. var. dulce (d.c.) alef.), fennel, sweet, oil (*foeniculum vulgare* mill. var. dulce (d.c.) alef.), fenugreek (*trigonella foenum-graecum* l.), fenugreek, extract (*trigonella foenum-graecum* l.), fenugreek, oleoresin (*trigonella foenum-graecum* l.), fir (pine) needles and twigs (*abies sibirica* ledeb.), fir needles and twigs, oil (*abies* spp.), fish oil (hydrogenated), fish protein concentrate, whole, fish protein isolate, fruit juice, *galanga*, greater (*alpinia galanga willd*), galangal root (*alpinia* spp.), galangal root, extract (*alpinia* spp.), galangal root, oil (*alpinia* spp.), *galbanum*, oil (*ferula* spp.), *galbanum*, resin (*ferula* spp.), gambir (*uncaria gambir* roxb.), *gardenia gummifera* distillate, garlic, garlic extract, garlic, oil (*allium sativum* l.), gelatin, genet, absolute (*spartium junceum* l.), genet, extract (*spartium junceum* l.), gentian root, extract (*gentiana lutea* l.), gentian, stemless (*gentiana acaulis* l.), geranium (*pelargonium* spp.), geranium, east indian, extract (*cymbopogon martini* stapf.), geranium, east indian, oil (*cymbopogon martini* stapf), geranium extract (*pelargonium* spp.), geranium, oil (*pelargonium* spp.), geranium, rose, oil (*pelargonium graveolens* l'her.), germander, *chamaedrys* (*teucrium chamaedrys* l.), germander, *chamaedrys*, extract (*teucrium chamaedrys* l.), germander, *chamaedrys*, extract solid (*teucrium chamaedrys* l.), germander, golden (*teucrium polium* l.), ghatti, gum (*anogeissus latifolia* wall.), ginger (*zingiber officinale* rosc.), ginger, extract (*zingiber officinale* rosc.), ginger, oil (*zingiber officinale* rosc.), ginger, oleoresin (*zingiber officinale* rosc.), glycyrrhizin, ammoniated (*glycyrrhiza* spp.), grains of paradise (*aframomum melegueta* (rosc.) k. schum.), grape color extract, grape essence, natural, grapefruit essence, natural, grapefruit, extract, grapefruit, juice, grapefruit, oil (*citrus paradisi* macf.), grapefruit oil, conc, grapefruit, oil, terpeneless (*citrus paradisi*), grape seed extract, grape skin extract, ground limestone, guaiac gum (*guaiacum* spp.), guaiac gum, extract (*guaiacum* spp.), guaiac wood, extract (*guaiacum* spp.), guaiac wood, oil (*guaiacum* spp.), guarana, gum (paullinia cupana hbk), guarana seed, extract, guava (*psidium* spp.), guava extract, gum arabic, gutta hang kang (palaquium leiocarpum boerl. and p. oblongifolium burck.), haematococcus algae meal, haw bark, black, extract (*viburnum prunifolium* l.), heliopsis *longipes* extract, hemlock (*tsuga* spp.), hemlock needles and twigs, oil (*tsuga* spp.), hickory bark, extract (*carya* spp.), hickory smoke dist., honeysuckle extract, hops, extract (*humulus lupulus* l.), hops extract, modified, hops, extract solid (*humulus lupulus* l.), hops, oil (*humulus lupulus* l.), horehound extract (*marrubium vulgare* l.), horehound (*marrubium vulgare* l.), horehound solid, extract, horsemint leaves, extract (*monarda* spp.), horseradish (*armoracia* lapathifolia gilib.), horseradish oil, hyacinth, absolute (*hyacinthus orientalis* l.), hyacinth flowers (*hyacinthus orientalis* l.), hyssop, extract (*hyssopus officinalis* l.), hyssop (*hyssopus officinalis* l.), hyssop, oil (*hyssopus officinalis* l.), iceland moss (*cetraria islandica* ach.), immortelle, absolute (*helichrysum angustifolium* dc), immortelle, extract (*helichrysum angustifolium* dc.), imperatoria (*peucedanum ostruthium* (l.) koch (*imperatoria ostruthium* l.)), iva (*achillea moschata* jacq.), iva, extract (*achillea moschata* jacq.), jambu oleoresin, japan wax, jasmine, absolute (*jasminum* spp.), jasmine, concrete (*jasminum* spp.), jasmine, oil (*jasminum grandiflorum* l.), jasmine, spiritus (*jasminum grandiflorum* l.), jelutong (*dyera costulata* hook, f. and d. lowii hook, f.), juniper (berries) (*juniperus communis* l.), juniper, extract (*juniperus communis* l.), juniper oil (*juniperus communis* l.), karaya, gum (*sterculia urens* roxb.), kelp, kola nut, extract (cola *acuminata* schott et endl.), labdanum, absolute (*cistus* spp.), labdanum, oil (*cistus* spp.), labdanum, oleoresin (*cistus* spp.), laurel berries (*laurus nobilis* l.), lavandin absolute, lavandin, concrete, lavandin, oil, lavender, absolute (*lavandula officinalis* chaix), lavender, concrete (*lavandula officinalis* chaix), lavender (*lavandula officinalis* chaix), lavender, oil (*lavandula officinalis* chaix), lavender, spike (*lavandula latifolia* bill.), lavender, spike, oil (*lavandula* spp.), leche caspi (*couma macrocarpa* barb. rodr.), leche de vaca (brosimum utile (h.b.k.) pittier, and *poulsenia* spp.), leek oil, lemon essence, lemon, extract (*citrus limon* (l.) burm. f), lemon grass, oil (*cymbopogon citratus* dc. and *cymbopogon* flexuosusstapf), lemon, juice, lemon, oil (*citrus limon* (l.) burm. f.), lemon, oil, terpeneless (*citrus limon* (l.) burm. f.), lemon peel extract, lemon peel granules, lemon terpenes, lemon-*verbena* (*lippia citriodora* hbk.), lemon *verbena*, oil (*lippia citriodora*), licorice extract (*glycyrrhiza* spp.), licorice extract powder (*glycyrrhiza* spp.), licorice (*glycyrrhiza* spp.), lime, essence, lime, juice, lime juice, dehydrated, lime oil, distilled, lime oil, expressed, lime, oil, terpeneless (*citrus aurantifolia* (christman) swingle), linaloe wood, oil (*bursera* delpechiana poiss. and other *bursera* spp.), linden flowers, extract (*tilia* spp.), linden flowers (*tilia glabra* vent.), linden leaves (*tillia* spp.), *litsea cubeba* berry oil, locust (carob) bean gum, lovage, extract (*levisticum officinale* koch), lovage (*levisticum officinale* koch), lovage, oil (*levisticum officinale* koch), luo han fruit concentrate, lupulin (*humulus lupulus* l.), mace (*myristica fragrans* houtt.), mace, oil (*myristica fragrans* houtt.), mace, oleoresin (*myristica fragrans* houtt.), maidenhair fern (*adiantum capillus-veneris* l.), malt syrup (malt extract), mandarin, oil (*citrus reticulata* blanco), marigold, pot (*calendula officinalis* l.), marjoram, oleoresin (*marjorana hortensis* moench (*origanum majorana* l.)), marjoram, pot (*majorana onites* (l.) benth. (*origanum vulgare* l.)), marjoram seed (*majorana hortensis* moench (*origanum majorana* l.)), marjoram, sweet (*majorana hortensis* moench (*origanum majorana* l.)), marjoram, sweet, oil (*majorana hortensis* moench (*origanum majorana* l.)), *massaranduba balata* (*manilkara huberi* (ducke) chevalier), *massaranduba balata*, solvent-free resin extract, *massaranduba* chocolate (*manilkara solimoesensis gilly*), *massoia* bark oil, mastic gum, mate, absolute (*ilex paraguariensis* st. hil.), mate, leaves, menhaden oil, menhaden oil, hydrogenated, menhaden oil, partially hydrogenated, menthol, mesquite wood extract, milk powder, whole, enzyme-modified, *mimosa*, absolute (*acacia decurrens* willd. var. *dealbata*), *mimosa* concrete (*acacia decurrens* willd. var. *dealbata*), mineral oil, white, molasses, concentrate, molasses, extract (*saccharum officinarum* l.), molasses (*saccharum officinarum* l.), mountain maple (*acer spicatum* lam.), mountain maple bark (*acer spicatum* lam.), mountain maple, extract solid (*acer spicatum* lam.), mullein flowers (*verbascum* spp.), mushroom oil, distilled, musk ambrette, musk, ketone, musk tonquin (*moschus moschiferus* l.), mustard, brown (*brassica* spp.), mustard, brown, extract (*brassica* spp.), mustard flour, mustard oil, mustard, oriental, mustard, yellow (*brassica* spp.), mustard, yellow, extract (*brassica* spp.), myrrh, extract, myrrh, gum (*commiphora* spp.), myrrh, oil (*commiphora* spp.), myrtle leaves (*myrtus communis* l.), myrtle, oil (*myrtus communis* l.), naringin, extract (*citrus paradisi* macf.), nisin preparation, nutmeg (*myristica fragrans* houtt.), nutmeg, oil (*myristica fragrans* houtt.), white, extract (*quercus alba* l.), oak moss, absolute (*evernia* spp.), oak moss, concrete (*evernia prunasti* spp.), oak wood, english (*quercus robur* l.), oat gum, oiticica oil, oleic acid, oleic acid, from tall oil fatty acids, olestra, oleyl alcohol, olibanum, absolute (*boswellia* spp.), olibanum, gum, resin (*boswellia* spp.), olibanum, oil (*boswellia* spp.), olibanum, resinoid (*boswellia* spp.), onion, oil (*allium cepa* l.), opopanax, gum, opopanax, non-specific, opopanax, oil, opopanax tincture, orange b, orange essence, natural, orange essence oil, natural, orange, extract, orange flowers, absolute (*citrus aurantium* l.), orange flowers, bitter (*citrus aurantium* l), orange, juice, orange leaf, absolute (*citrus aurantium* l.), orange, oil, distilled (*citrus sinensis* (l.) osbeck), orange, oil, terpeneless (*citrus sinensis* (l.) osbeck), orange peel, orange peel, bitter, extract (*citrus aurantium* l.), orange peel, bitter, oil (*citrus aurantium* l.), orange peel, sweet, extract (*citrus sinensis* (l.) osbeck), orange peel, sweet, oil (*citrus sinensis* (l.) osbeck), orange peel, sweet, oil, terpeneless (*citrus sinensis* (l.) osbeck), oregano, european (*origanum* spp.), oregano (*lippia* spp., usually l. *graveolens* hbk), oregano (other genera including *coleus*, lantana and hyptis), *origanum* oil (extractive)(*thymus capitatus* hoff. et link), orin lactone, l-ornithine monochlorohydrate/ornithine, orris, concrete, liquid, oil (*iris florentina* l.), orris root, extract (*iris florentina* l.), osmanthus absolute, ox bile extract, pansy (*viola tricolor* l.), papain (*carica papaya* l.), paprika (*capsicum annuum* l.), paprika oleoresin (*capsicum annuum* l.), parsley, oil (*petroselinum* spp.), parsley, oleoresin (*petroselinum* spp.), parsley (*petroselinum* spp.), passion flower extract, passion flower (*passiflora incarnata* l.), patchouly, oil (*pogostemon* spp.), peach kernel, extract(*prunus persica* sieb et zucc.), peach leaves, extract (*prunus persica* (l.) batsch), peach leaves (*prunus persica* (l.) batsch), peanut oil, peanut stearine (*arachis hypogaea* l.), pecan shell flour, pennyroyal, oil, american (*hedeoma pulegiodes* (l.)), pennyroyal, oil, european (*mentha pulegium* l.), pepper, black, oil (*piper nigrum* l.), pepper, black, oleoresin (*piper nigrum* l.), pepper, black (*piper nigrum* l.), pepper, cayenne, peppermint leaves (*mentha piperita* l.), peppermint, oil (*mentha piperita* l.), peppermint plant, pepper, red, pepper, white, oil (*piper nigrum* l.), pepper, white, oleoresin (*piper nigrum* l.), pepper, white (*piper nigrum* l.), perilla leaf oil, petitgrain, lemon, oil (*citrus limon* (l.) burm. f.), petitgrain, mandarin, oil (*citrus reticulata* blanco var. mandarin), petitgrain, oil (*citrus aurantium* l.), pimenta leaf, oil (*pimenta officinalis* lindl.), 3-pinanone, pine bark, white, extract solid (*pinus strobus* l.), pine bark, white, oil (*pinus strobus* l.), pine bark, white (*pinus strobus* l.), pine needle, dwarf, oil (*pinus mugo* turra var. *pumilio* (haenke) zenari), pine, scotch, oil (*pinus sylvestris* l.), pine tar, oil (*pinus* spp.), pine, white, oil (*pinus* spp.), pomegranate bark, extract (*punica granatum* l.), poplar buds (*populus* spp.), poppy seed (*papaver somniferum* l.), prickly ash bark extract (*xanthoxylum* spp.), prickly ash bark, oil, protein, animal, hydrolyzed, protein hydrolysate, unspecified, protein, milk, hydrolyzed, protein, vegetable, hydrolyzed, pulegone, extract (*picrasma excelsa* (sw.) planch or *quassia amara* l.), quebracho bark extract, *quillaia* extract (*quillaja saponaria* molina), *quillaia* (*quillaja saponaria* molina), quince seed, extract (*cydonia* spp.), rhatany, extract (*krameria* spp.), rhubarb, garden root (*rheum rhaponticum* l.), rhubarb root (*rheum* spp.), rose, absolute (*rosa* spp.), rose, bud (*rosa* spp.), rose flowers (*rosa* spp.), rose hips, extract (*rosa* spp.), rose leaves (*rosa* spp.), roselle (*hibiscus sabdariffa* l.), rosemary, extract (*rosmarinus officinalis* l.), rosemary, oil (*rosemarinus officinalis* l.), rosemary, oleoresin, rosemary (*rosemarinus officinalis* l.), rose, oil (*rosa* spp.), rose water, stronger (*rosa centifolia* l.), rosidinha (*micropholis* (also known as sideroxylon) spp.), rosin, glycerol ester, rosin, gum, glycerol ester, rosin, gum or wood, partially hydrogenated, glycerol ester, rosin, gum or wood, partially hydrogenated, pentaerythritol ester, rosin, gum or wood, pentaerythritol ester, rosin, limed, rosin, methyl ester, partially hydrogenated, rosin, partially dimerized, calcium salt, rosin, partially dimerized, glycerol ester, rosin, partially hydrogenated, rosin (*pinus* spp.) and rosin derivatives, rosin, polymerized, glycerol ester, rosin, tall oil, glycerol ester, rosin, wood, rosin, wood, glycerol ester, rosin, wood, oil (*ruta graveolens* l.), rue (*ruta graveolens* l.), rum, saffron (*crocus sativus* l.), saffron, extract (*crocus sativus* l.), safrole-free extract of *sassafras*, safrole-prohibited, sage, greek (*salvia triloba* l.), sage, oil (*salvia officinalis* l.), sage, oleoresin (*salvia officinalis* l.), sage (*salvia officinalis* l.), sage, spanish, oil (*salvia* lavandulaefolia vahl.), sandalwood, red (*pterocarpus santalinus* l.f.), sandalwood, white (*santalum album* l.), sandalwood, yellow, oil (*santalum album* l.), sandarac (*tetraclinis articulata* (vahl.) mast.), sarcodactylis oil, sarsaparilla, extract (*smilax* spp.), *sassafras* bark, extract (safrole-free) (*sassafras albidum* (nutt.) nees), *sassafras* leaves (safrole-free) (*sassafras albidum* (nutt.) nees), sausage casing (hcl and cellulose fibers), savory, summer, oil (*satureja hortensis* l.), savory, summer, oleoresin (*satureja hortensis* l.), savory, summer (*satureja hortensis* l.), savory, winter, oil (*satureja montana* l.), savory, winter, oleoresin (*satureja montana* l.), savory, winter (*satureja montana* l.), schinus molle, oil (*schinus molle* l.), scotch spearmint oil, *senna*, alexandria (*cassia acutifolia* delile), serpentaria (*aristolochia serpentaria* l.), sesame (*sesamum indicum* l.), silver fir, needles and twigs, oil (*abies alba* mill.), silver-silver dragees, simaruba bark (*simaruba amara* aubl.), sloe berries, extract (*prunus spinosa* l.), sloe berries, extract solid (*prunus spinosa* l.), sloe berries (*prunus spinosa* l.), snakeroot, canadian, oil (*asarum canadense* l.), soya bean oil fatty acids, hydroxylated, soya fatty acid amine, ethoxylated, soybean oil, epoxidized, soybean oil, hydrogenated, soy protein concentrate, enzyme activated, soy protein, isolate, spearmint, extract (*mentha spicata* l.), spearmint (*mentha spicata* l.), spearmint, oil (*mentha spicata* l.), spikenard extract, spruce needles and twigs, extract (*picea* spp.), spruce needles and twigs, oil (*picea* spp.), st. johnswort leaves, flowers and caulis (*hypericum perforatum* l.), storax extract (*liquidambar* spp.), storax (*liquidambar* spp.), storax oil, sugar beet juice extract, sugar beet extract flavor base, sweet blackberry leaves extract, *tagetes* meal & extract, *tagetes*, oil (*tagetes* spp.), tallow alcohol, hydrogenated, tallow, beef, tallow flakes, tallow, hydrogenated, tallow, hydrogenated, oxidized or sulfated, tamarind extract (*tamarindus indica* l.), tamarinds, tangerine, essence, tangerine, extract (*citrus reticulata* blanco), tangerine, oil (*citrus reticulata* blanco), tannic acid, tansy, oil (*tanacetum vulgara* l.), tansy (*tanacetum vulgara* l.), tarragon (*artemisia dracunculus* l.), tarragon extract (*artemisia dracunculus* l.), tarragon oil (*artemisia dracunculus* l.), tea extract (*thea sinensis* l.), tea tree oil (*melaleuca alternifolia*), blessed (*cnicus benedictus* l.), thistle, blessed, extract (*cnicus benedictus* l.), thistle, blessed, extract solid (*cnicus benedictus* l.), thistle, blessed, oil (*cnicus benedictus* l.), thyme, extract, thyme oil (*thymus vulgaris* l. and *t. zygis* var. *gracilis boiss.*), thyme oleoresin, thyme (*thymus serpyllum* l.), thyme (*thymus vulgaris* l.), thyme, wild or creeping, extract (*thymus serpyllum* l.), thymol, balsam, extract (*myroxylon* spp.), tolu, balsam, gum (*myroxylon* spp.), tragacanth, gum (*astragalus* spp.), trefoil, sweet (*melilotus coerulea*), triacetin (glycerol triacetate), oil (*polianthes tuberosa* l.), tunu (*castilla fallax* cook), turmeric (*curcuma longa* l.), turmeric, extract (*curcuma longa* l.), turmeric, oleoresin (*curcuma longa* l.), valerian root, extract (*valeriana officinalis* l.), valerian root, oil (*valeriana officinalis* l.), vanilla, absolute (*vanilla* spp.), vanilla, extract (*vanilla* spp.), vanilla, oleoresin (*vanilla* spp.), vanilla (*vanilla* spp.), vegetable juice, veronica (*veronica officinalis* l.), vervain, european (*verbena officinalis* l.), vetiver, oil (vetiveria zizanioides stapf), vetiverol, vetiver (vetiveria zizaniodes stapf), violet leaves absolute (*viola odorata* l.), violet, swiss (*viola calcarata* l.), walnut hull, extract (*juglans* spp.), walnut leaves, extract (*juglans* spp.), wheat gluten, whey, whey, delactosed, whey, demineralized, whey, partially demineralized and partially delactosed, whey protein concentrate, wintergreen, extract (*gaultheria procumbens* l.), wintergreen, oil (*gaultheria procumbens* l.), woodruff, sweet (*asperula odorata* l.), wort, yarrow, herb (*achillea millefolium* l.), yarrow, oil (*achillea millefolium* l.), yeast autolysate, yeast, dried irradiated, yeast extract autolyzed, yeast-malt sprout extract, yeasts, yeasts, dried, yerba santa, fluid extract (*eriodictyon californicum* (hook and arn) torr), ylang-ylang, oil (*cananga odorata* hook. f. and thomas), yucca, joshua-tree (*yucca brevifolia* engelm.), yucca, mohave, extract (*yucca* spp.), and acai berry extract In some preferred embodiments, the composition comprises a combination of one or more of Compounds 101-105 and one or more plant or animal products where the plant or animal product is a culinary herb or spice. Representative culinary herbs and spices include but are not limited to: carrot, dehydrated carrot, carrot extract, parsnip, dehydrated parsnip, parsnip extract, onion, dehydrated onion, onion powder, onion flakes, onion extract, garlic, dehydrated garlic, garlic flakes, garlic powder, garlic extract, buttermilk, buttermilk powder, buttermilk solids, whey, whey powder, whey solids, milk, reduced fat milk, milk powder, milk solids, cream, cheese, cheese powder, cheese solids, cheese cultures, annatto, turmeric, sodium caseinate, milk protein, enzymatic digest of milk protein, tomato, tomato paste, tomato powder, tomato sauce, tomato extract, dehydrated tomato, sour cream, sour cream solids, caramel color, soy flour, chives, dehydrated chives, chive powder, ajwain, carom seeds (*trachyspermum ammi*), akudjura (*solanum centrale*), alkanet (*alkanna tinctoria*), for red color, alligator pepper, mbongo spice (*mbongochobi*), hepper pepper (*aframomum danielli, a. citratum, a. exscapum*), allspice (*pimenta dioica*), angelica (*angelica archangelica*), anise (*pimpinella anisum*), anise hyssop (*agastache foeniculum*), aniseed myrtle (*syzygium anisatum*), annatto (*bixa orellana*), apple mint (*mentha suaveolens, mentha×rotundifolia* and *mentha×villosa*), artemisia (*artemisia* spp.), asafoetida (*ferula assafoetida*), asarabacca (*asarum europaeum*), avens (*geum urbanum*), avocado leaf (*persea americana*), barberry (*berberis vulgaris* and other *berberis* spp.), basil, sweet (*ocimum basilicum*), basil, holy (*ocimum tenuiflorum*), basil, lemon (*ocimum×citriodorum*), basil, thai (*O. basilicum* var. *thyrsiflora*), bay leaf (*laurus nobilis*), bay leaf, indian, tejpat, malabathrum, bee balm (*monarda didyma*), boldo (*peumus boldus*), borage (*borago officinalis*), blue fenugreek, blue melilot (*trigonella caerulea*), caper (*capparis spinosa*), caraway (*carum carvi*), cardamom (*elettaria cardamomum*), cardamom, black (*amomum subulatum, amomum costatum*), cassia (*cinnamomum aromaticum*), catnip (*nepeta cataria*), cayenne pepper (*capsicum annuum*), celery leaf (*apiumi graveolens*), celery seed (*apiumi graveolens*), chervil (*anthriscus cerefolium*), chicory (*cichorium intybus*), chili pepper (*capsicum* spp.), cicely, sweet cicely (*myrrhis odorata*), cilantro, coriander greens, coriander herb (*coriandrum sativum*), cinnamon, indonesian (*cinnamomum burmannii, cassia vera*), cinnamon, saigon or vietnamese (*cinnamomum loureiroi*), cinnamon, true or ceylon (*cinnamomum verum, c. zeylanicum*), cinnamon, white (*canella winterana*), cinnamon myrtle (*backhousia myrtifolia*), clary, clary sage (*salvia sclarea*), clove (*syzygium aromaticum*), coriander seed (*coriandrum sativum*), coriander, vietnamese (*persicaria odorata*), costmary (*tanacetum balsamita*), cubeb pepper (*piper cubeba*), cudweed (*gnaphalium* spp.), culantro, culangot, long coriander (*eryngium foetidum*), cumin (*cuminum cyminum*), curry leaf (*murraya koenigii*), curry plant (*helichrysum italicum*), dill herb or weed (*anethum graveolens*), dill seed (*anethum graveolens*), elderflower (*sambucus* spp.), epazote (*dysphania ambrosioides*), fennel (*foeniculum vulgare*), fenugreek (*trigonella foenum-graecum*), file powder, gumbo file (*sassafras albidum*), fingerroot, krachai, temu kuntji (*boesenbergia rotunda*), galangal, greater (*alpinia galanga*), galangal, lesser (*alpinia officinarum*), galingale (*cyperus* spp.), garlic chives (*allium tuberosum*), ginger (*zingiber officinale*), ginger, torch, bunga siantan (*etlingera elatior*), golpar, persian hogweed (*heracleum persicum*), grains of paradise (*aframomum melegueta*), grains of selim, kani pepper (*xylopia aethiopica*), horseradish (*armoracia rusticana*), houttuynia *cordata* (vietnam), huacatay, mexican marigold, mint marigold (*tagetes minuta*), hyssop (*hyssopus officinalis*), indonesian bay leaf, daun salam (*syzygium polyanthum*), jasmine flowers (*jasminum* spp.), jiaogulan (*gynostemma pentaphyllum*), jimbu (*allium hypsistum*), juniper berry (*juniperus communis*), kaffir lime leaves, makrud lime leaves (*citrus hystrix*), kala zeera (or kala jira), black cumin (*bunium persicum*), kawakawa seeds (*macropiper excelsum*), keluak, kluwak, kepayang (*pangium edule*), kencur, galangal, kentjur (*kaempferia galanga*), kinh gioi, vietnamese balm (*elsholtzia ciliata*), kokam seed (garcinia indica), korarima, ethiopian cardamom, false cardamom (*aframomum corrorima*), koseret leaves (*lippia adoensis*), lavender (*lavandula* spp.), lemon balm (*melissa officinalis*), lemon ironbark (*eucalyptus staigeriana*), lemon myrtle (*backhousia citriodora*), lemon verbena (*lippia citriodora*), lemongrass (*cymbopogon citratus, c. flexuosus*, and other *cymbopogon* spp.), leptotes bicolor, lesser calamint (*calamintha nepeta*), nipitella, nepitella, licorice, liquorice (*glycyrrhiza glabra*), lime flower, linden flower (*tilia* spp.), lovage (*levisticum officinale*), mace (*myristica fragrans*), mahleb, st. lucie cherry (*prunus mahaleb*), marjoram (*origanum majorana*), mastic (*pistacia lentiscus*), mint (*mentha* spp.), 25 species, hundreds of varieties, mountain horopito (*pseudowintera colorata*), 'pepper-plant', musk mallow, abelmosk (*abelmoschus moschatus*), mustard, black, mustard plant, mustard seed (*brassica nigra*), mustard, brown, mustard plant, mustard seed (*brassica juncea*), mustard, white, mustard plant, mustard seed (*sinapis alba*), mustard, yellow (*brassica hirta*=*sinapis alba*), nigella, kalonji, black caraway, black onion seed (*nigella sativa*), njangsa, djansang (*ricinodendron heudelotii*), nutmeg (*myristica fragrans*), olida (*eucalyptus olida*), oregano (*origanum vulgare, o. heracleoticum*, and other species), oregano, cuban (*plectranthus amboinicus*), orris root (*iris germanica, i. florentina, i. pallida*), pandan flower, kewra (*pandanus odoratissimus*), pandan leaf, screwpine (*pandanus amaryllifolius*), paprika (*capsicum annuum*), paracress (*spilanthes acmella, soleracea*), parsley (*petroselinum crispum*), pepper, black, white, and green (*piper nigrum*), pepper, brazilian, or pink pepper (*schinus terebinthifolius*), pepper, dorrigo (*tasmannia stipitata*), pepper, long (*piper longum*), pepper, mountain, cornish pepper leaf (*tasmannia lanceolata*), peppermint (*mentha piperata*), peppermint gum leaf (*eucalyptus dives*), perilla, shiso (*perilla* spp.), peruvian pepper (*schinus molle*), quassia (*quassia amara*), rice paddy herb (*limnophila aromatica*), rosemary (*rosmarinus officinalis*), rue (*ruta graveolens*), safflower (*carthamus tinctorius*), saffron (*crocus sativus*), trade and use of saffron, sage (*salvia officinalis*), saigon cinnamon (*cinnamomum loureiroi*), salad burnet (*sanguisorba minor*), salep (*orchis mascula*), sassafras (*sassafras albidum*), savory, summer (*satureja hortensis*), savory, winter (*satureja montana*), shiso (*perilla frutescens*), silphium, silphion, laser, laserpicium, lasarpicium, sorrel (*rumex acetosa*), sorrel, sheep (*rumex acetosella*), spearmint (*mentha spicata*), spikenard (*nardostachys grandiflora* or *N. jatamansi*), star anise (*illicium verum*), sumac (*rhus coriaria*), sweet woodruff (*galium odoratum*), szechuan pepper, sichuan pepper (*zanthoxylum piperitum*), tarragon (*artemisia dracunculus*), thyme (*thymus vulgaris*), thyme, lemon (*thymus×citriodorus*), turmeric (*curcuma longa*), vanilla (*vanilla planifolia*), voatsiperifery (*piper borbonense*), wasabi (*wasabia japonica*), water-pepper, smartweed (*polygonum hydropiper*), watercress (*rorippa nasturtium-aquatica*), wattleseed, wild thyme (*thymus serpyllum*), willow herb (epilobium *parviflorum*), wintergreen (*gaultheria procumbens*), wood avens, herb bennet (*geum urbanum*), woodruff (*galium odoratum*), wormwood, absinthe (*artemisia *absinthium*), yerba buena, yarrow (*achillea millefolium*), za'atar (herbs from the genera *origanum*, calamintha, *thymus*, and *satureja*), zedoary (*curcuma zedoaria*), herb mixes, curry, tandoor masala, garam masala, chaat masala, tikka masala, masala dosa, paan masala, biryani masala, berbere, jerk seasonings, and spice rubs.

In some embodiments, the combination of one or more of Compounds 101-105 with the plant or animal products described above has a synergistic effect. For example, the combination may further enhance the cooling character of the composition or enhance the properties of the plant or animal product.

Fats, Oils, and Emulsions

In some preferred embodiments, the composition comprises one or more of Compounds 101-105 and one or more fats, oils, or emulsions. Representative fats, oils, and emulsions include but are not limited to: corn oil, peanut oil, soybean oil, palm oil, cottonseed oil, coconut oil, canola oil, rapeseed oil, olive oil, safflower oil, sunflower oil, sesame oil, almond oil, beech nut oil, brazil nut oil, cashew oil, linseed oil, flaxseed oil, hazelnut oil, mongongo nut oil, pecan oil, pine nut oil, pistachio oil, walnut oil, grapeseed oil, grapefruit seed oil, lemon oil, orange oil, mineral oil, petrolatum, cucumber oil, bitter gourd oil, bottle gourd oil, buffalo gourd oil, butternut squash oil, squash oil, pumpkinseed oil, watermelon seed oil, hemp oil, castor oil, butter, lard, margarine, cocoa butter, butterfat, whale oil, sperm oil, fish oil, cod liver oil, shark liver oil, krill oil, shrimp oil, codfish oil, salmon oil, herring oil, anchovy oil, smelt oil, candlefish oil, sprat oil, sardine oil, mackerel oil, tilefish oil, tuna (Thunnus) oil, swordfish oil, macadamia oil, acai oil, blackcurrant seed oil, borage seed oil, evening primrose oil, amaranth oil, wheat oil, wheat germ oil, apricot oil, argan oil, artichoke oil, avocado oil, babassu oil, ben oil, tallow nut oil, borneo tallow nut oil, carob pod oil, carob oil, coriander seed oil, false flax oil, kapok seed oil, lallemantia oil, meadowfoam seed oil, mustard oil, okra seed oil, *perilla* seed oil, pequi oil, prune kernel oil, *quinoa* oil, ramtil oil, rice bran oil, rice oil, barley oil, barley seed oil, tea oil, tea tree oil, thistle oil, *jatropha* oil, cork tree oil, apple seed oil, balanos oil, bladderpod oil, brucea *javanica* oil, burdock oil, candlenut oil, carrot seed oil, chaulmoogra oil, *crambe* oil, *cuphea* oil, jojoba oil, mango oil, palm kernel oil, mowrah butter, neem oil, orange oil, rosehip seed oil, sea buckthorn oil, shea butter, snowball seed oil, tall oil, tamanu oil, tonka bean oil, chicken fat, schmaltz, beef fat, lamb fat, animal fat, tallowate, tallow, beef tallow, bacon fat, ham fat, suet, milk fat, olestra, stearic acid, lauric acid, linoleic acid, palmitic acid, palmitoleic acid, myristic acid, goose fat, duck fat, drippings from roasting, mayonnaise, and oil-in water or water-in oil emulsions.

In some embodiments, the combination of one or more of Compounds 101-105 with the fats, oils, or emulsions described above has a synergistic effect. For example, the combination may further enhance the cooling character of the composition or enhance the properties of the fat, oil, or emulsion.

Food or Beverage Products

In some embodiments, a composition incorporating one or more of Compounds 101-105 or a cooling composition as described herein may be included in food or beverage products or formulations. Examples of food and beverage products or formulations include, but are not limited to any foodstuff or item intended for ingestion, including any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to Bloody Mary, beer, cider/perry, FABs, wine, whiskey, flavored whiskey, rum, flavored rum, and other spirits. The soft drinks include, but are not limited to carbonates, such as colas and non-cola carbonates; fruit juice, such as juice, nectars, juice drinks and fruit flavored drinks; bottled water, which includes sparkling water, spring water, purified/table water, and vitamin water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee, tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips, crisps, flavored chips, flavored crisps, extruded snacks, tortilla/corn chips, flavored corn/tortilla chips, popcorn, flavored popcorn, pretzels, flavored pretzels, nuts, flavored nuts, and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; marinated or seasoned fresh meats, and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chilled Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for ingestible compositions, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, fresh sausages, smoked sausages, bacon, ham, smoked meats, frankfurters, luncheon meats, cold cuts, prepared deli meats, smoked fish/seafood, marinated fresh meat, flavor-treated fresh meat, broth-injected fresh meat, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof.

Some embodiments provide medicaments, supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products including one or more of Compounds 101-105 or a cooling composition as described herein.

In some embodiments, one or more of Compounds 101-105 or a cooling composition as described herein may be provided in a concentrate formulation, e.g., suitable for subsequent processing to produce a ready-to-use (i.e., ready-to-serve) product. By a "cooling concentrate formulation," it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal.

In some embodiments the compositions described herein are included in a pet food, animal treat, or animal feed. In other embodiments, the compositions are applied to a veterinary medicament. In other embodiments, the compositions are applied to an animal oral health care product.

Home, Personal Care, and Pet Care Products

It is known in the art that it is sometimes beneficial to incorporate a cooling agent into a wider variety of home, personal care, and pet care products. For example, U.S. Patent App. Pub. Nos. 2015/0094365 and 2011/0081393, incorporated herein by reference in their entireties, disclose the combination of cooling agents with packaging materials, textiles, home products, and personal care products. Methods of incorporating cooling agents into home, personal, and pet care products are known in the art and include but are not limited to direct suspension or dissolution, surface application; covalent attachment, and the use of agent reservoirs, including core-shell nanoparticles (see, for example, U.S. Patent App. Pub. No. 2005/0176598, incorporated herein by reference in its entirety). Therefore, in some embodiments, one or more of Compounds 101-105 or the cooling compositions described herein are combined with an ingredient known to be useful in the production of home, personal care, and pet care products. Such ingredients suitable for incorporation into the present compositions are known in the art (see, for example, The U.S. Department of Health and Human Services Household Products Database, http://householdproducts.nlm.nih.gov/ (last accessed Dec. 31, 2015)) and include but are not limited to, (+)-R-2-(2-methyl-4-chlorophenoxy)propionic acid; ($C_{10}$-$C_{16}$) Alcohol ethoxylate, sulfated, sodium salt; ($C_{13}$-$C_{16}$)Alkyl ethoxylate sulfuric acid, ammonium saltethers, ammonium salts; ($C_{14}$-$C_{18}$) Dialkyldimethylammonium methyl sulfate; ($C_6$-$C_{12}$) Alkyl alcohol ethoxylate phosphoric acid; (N-Pantothenyl-amidoethyl)disulfide; (R,Z)-5-(1-Decenyl) Dihydro-2(3H) Furanone; (Z)-9-(E)-12-Tetradecadien-1-ol acetate; 0.11-0.04-0.08 Fertilizer, 1,1'-Oxydi-2-propanol; 1,1,1,2-Tetrafluoroethane; 1,1,1,3,3,5,5-Heptamethyltrisiloxane; 1,1-Difluoroethane (Hydrofluorocarbon 152A); 1,2 Butylene Oxide; 1,2,3-Trimethylbenzene; 1,2,4-Trimethylbenzene; 1,2-Benzisothiazolin-3-one; 1,2-Dimethoxyethane; 1,2-Ethanediamine, polymer with 2-(chloromethyl)oxirane and N-methylmethanamine; 1,2-Hexanediol; 1,3,5-Triazin-2(1H)-one, tetrahydro-; 1,3,5-Tris(trifluoropropyl)trimethylcyclotrisiloxane; 1,3-Butadiene; 1,3-Dichloro-5,5-dimethylhydantoin; 1,3-Dichloro-5-ethyl-5-methylhydantoin; 1,3-Dioxolane-2-propanoic acid; 1,3-Propanediol; 1,3-Propanediol, 2-ethyl-2-(hydroxymethyl)-, polymer with (chloromethyl)oxirane; 1,4-Anhydroxylitol; 1,4-Benzenediamine, N,N'-bis(1-methylpropyl)-; 1,4-Butanediol; 1,4-Dialkylaminoanthraquinone; 1,4-Dioxane; 1,5-Pentanediol; 1-(2-Methylcyclohexyl)-3-phenylurea; 1-Acetoxy-2-Methylnaphthalene; 1-Acetyl-2-phenylhydrazine; 1-Benzoylamino-7-(p-methyl-o-sulfophenylazo)-naphthalene-3,6-disulfonate, trisodium salt; 1-Bromo-3-chloro-5,5-dimethylhydantoin; 1-Butene, polymer with ethene; 1-Chloro-1,1-difluoroethane; 1-Decene, homopolymer, hydrogenated; 1-Decene, tetramer, with 1-decene trimer, hydrogenated; 1-Ethenyl-3-methylbenzene; 1-Ethenyl-4-methylbenzene; 1-Hydroxyethyl 4,5-diamino pyrazole sulfate; 1-hydroxyethylidene; 1-Methoxy-2-propanol; 1-Methoxy-2-propanol acetate; 1-Naphthol; 1-Nitropropane; 1-Octene, sulfurized; 1-Propanol, 2-(2-(benzoyloxy)propoxy)-, 1-benzoate; 1-Propanol-2-butoxy; 1-Propene, 2-methyl-, sulfurized; 1-Propoxy-2-propanol; 10-12-12 Fertilizer; 10-15-10 Fertilizer; 10-52-10 Fertilizer; 15-30-15 Fertilizer; 17-17-17 Fertilizer; 18-18-21 Fertilizer; 18-24-16 Fertilizer; 19-6-12 Fertilizer; 2(3H)-Furanone, 5-heptyldihydro-; 2,2,4,6,6-Pentamethylheptane; 2,2,4-Trimethyl-1,3-pentanediol; 2,2,4-Trimethyl-1,3-pentanediol isobutyrate; 2,2,4-Trimethylpentanediol-1,3-diisobutyrate; 2,2-Dimethylbutane; 2,2-Dimethylpentane; 2,2-Oxybis-ethanol dibenzoate; 2,3,4,5 Bis(2-butylene) tetrahydro 2-furaldehyde; 2,3-Dimethylbutane; 2,3-Dimethylpentane; 2,4,6-Triphenol (Dimethylaminomethyl); 2,4-D 2-Ethylhexyl ester; 2,4-D butoxyethyl ester; 2,4-D, isopropylamine salt; 2,4-Dichlorophenoxyacetic acid (2,4-D); 2,4-Dimethylpentane; 2,5-Diaminotoluene; 2,6-Di-t-butyl-p-cresol (BHT); 2,6-dimethylheptan-4-one; di-isobutyl ketone; 2-((Hydroxymethyl)amino)ethanol; 2-(2,4-Diaminophenoxy)ethanol dihydrochloride; 2-(2,4-Dichlorophenoxy)propionic acid; 2-(2,4-Dichlorophenoxy)propionic acid isooctyl ester; 2-(2-(2-(Octylphenoxy)ethoxy)ethoxy)ethanesulfonic acid, sodium salt; 2-(2-Methyl-4-chlorophenoxy)propionic acid; 2-(2H-Benzotriazol-2-yl)-4,6-ditertpentylphenol; 2-amino-1-propanol; 2-Amino-3-hydroxypyridine; 2-Amino-4-hydroxyethylaminoanisole sulfate; 2-Amino-6-chloro-4-nitrophenol; 2-Aminophenol; 2-Benzylheptanol; 2-Bromo-2-nitropropane-1,3-diol; 2-Butoxyethanol; 2-Butoxyethanol acetate; 2-Diethylaminoethanol; 2-Ethylhexanoic acid; 2-Ethylhexanol; 2-Ethylhexyl benzoate; 2-Ethylhexyl ester, acrylic acid polymer with styrene; 2-Ethylhexyl isononanoate; 2-Ethylhexyl nitrate; 2-Ethylhexyl salicylate; 2-Ethylhexyl stearate; 2-Ethylhexyltitanate; 2-Feb; 2-Hydroxyethyl octyl sulfide; 2-Hydroxyethyl starch (Tapioca); 2-Hydroxypropyl starch; 2-Imidazoline-1-ethanol, 2-(8-heptadecenyl)-; 2-Methoxy-1-propanol; 2-Methyl-1,3-Propanediol; 2-Methyl-5-hydroxyethylaminophenol; 2-Methylbutyl acetate; 2-Methylpentane; 2-Methylresorcinol; 2-N-octyl-4-isothiazolin-3-one; 2-Nitro-p-phenylenediamine; 2-Octadecenal; 2-Phenoxyethanol; 2-Phenyl ethyl propionate; 2-propenoic acid, 2,5-furandione polymer; 2-Propenoic acid, 2-methyl-, 2-(dimethylamino)ethyl ester, polymers with gamma-omega-perfluoro-$C_{10-16}$-alkyl acrylate and vinyl a; 2-Propenoic acid, 2-methyl-, butyl ester, polymer with butyl 2-propenoate and ethenylbenzene, 2-Propenoic acid, 2-methyl-, methyl ester, polymer with 1,1-dichloroethene and 2-propenenitrile; 2-Propenoic acid, 2-methyl-, polymer with butyl 2-methyl-2-propenoate and methyl 2-methyl-2-propenoate; 2-Propenoic acid, 2-methyl-, polymer with butyl 2-propenoate, ethenylbenzene, 2-ethylhexyl 2-propenoate and methyl 2-methyl-2-; 2-Propenoic acid, butyl ester, polymer with ethenylbenzene; 2-Propenoic acid, butyl ester, polymer with ethenylbenzene and 2-ethylhexyl 2-propenoate; 2-Propenoic acid, polymer with ethenylbenzene and 2-ethylhexyl 2-propenoate; 2-Propenoic acid, polymer with N-(1,1-dimethylethyl)-2-propenamide and ethyl 2-propenoate; 2-Propenoic acid, telomer with sodium sulfite (1:1), sodium salt; 2-Pyrrolidone; 3,3-Dimethylpentane; 3,6-diazaoctanethylenediamin; triethylenetetramine; 3,6-Dichloro-o-anisic acid (Dicambra); 3-(3,5-Dichlorophenyl)-5-ethenyl-5-methyl-2,4-oxazolidinedione; 3-(Dimethylamino) propylamine; 3-acetyl-6-methyl-2H-pyran-2,4(3H)-dione; dehydracetic acid; 3-Aminomethyl-3,5,5-trimethylcyclohexylamine; 3-Aminophenol; 3-Aminopropyltriethoxysilane; 3-Aminopropyltrimethoxysilane; 3-Decyloxysulfolane; 3-Hexenol; 3-Indolebutyric acid; 3-Iodo-2-propynylbutylcarbamate; 3-Isodecyloxypropaneamine, ethoxylated; 3-Methylpentane; 3-Phenylenediamine; 3-Xylene; 30-10-10 Fertilizer; 36-6-6 Fertilizer; 4,4'-Methylenebis(2,6-di-tert-butylphenol); 4,4-Isopropylidenediphenol; 4-(2,4-Dichlorophenoxy)butyric acid; 4-Amino-2-hydroxytoluene; 4-Amino-m-cresol; 4-Chloro-3,5-xylenol; 4-Chlorobenzotrifluoride; 4-Chlororesorcinol; 4-tert-Butylphenol; 5,5-Dimethyl-2,4-imidazolidinedione; 5-Diaminopyrazole sulfate; 5-Hydroxypoly(methyleneoxy)methyl-1-aza-3,7-dioxabicyclo-3,3-octa-ne; 5-Oxo-DL-proline, monosodium salt; 6-Hydroxyindole; 9,17-Octadecadienal (Z); 9-10-15 Fertilizer; A-17 Propellant (n-Butane@>95%/Isobutane@<5%); Abamectin; Abrasive (unspecified); *Acacia* flowers; *Acacia* Senegal Gum Extract; Acai Berry (*Euterpe Oleracea*) Extract; Acai Berry Extract; Acephate; *Acer Saccharinum* Extract (Sugar Maple); Acetaldehyde; Acetamide MEA; Acetamiprid [ISO]; Acetic acid; Acetic acid, 2-chloro-, sodium salt (1:1), reaction products with 4,5-dihydro-2-undecyl-1H-imidazole-1-ethanol and sodium hydrox; Acetic acid, $C_{11-14}$-branched alkyl esters, $C_{13}$-rich; Acetochlor; Acetone; Acetophenone; Acetyl Glucosamine; Acetyl Hexapeptide-8; Acetyl methoxycinnamate; Acetyl phosphate; Acetyl tributyl citrate; Acetylated lanolin; Acetylglucosamine; Acetyltriethyl citrate; Acid Blue 145; Acid Blue 182; Acid Blue 25; Acid Blue 40; Acid blue 7 (C.I. 42080); Acid Blue 87 (C.I. 74180); Acid blue 9 aluminum lake; Acid blue 9 dye (C.I. 42090); Acid Green 50; Acid Red 27 Aluminum Lake; Acid Red 289; Acid Red 52 (CI 45100); Acid Violet; Acid yellow 17 (C.I. 18965); Acid Yellow 23 Aluminum Lake; Acifluorfen-sodium; Acrawax C; Acriflavine; Acrylamide; Acrylamide/Sodium Acryloyldimethyltaurate Copolymer; Acrylate/carbamate copolymer; Acrylates copolymer; Acrylates copolymer (unspecified); Acrylates Crosspolymer; Acrylates/Beheneth-25 Methacrylate Copolymer; Acrylates/$C_{10}$-$C_{30}$ Alkyl acrylate crosspolymer; Acrylates/Dimethicone Copolymer; Acrylates/Octylacrylamide Copolymer; Acrylates/Steareth-20 Methacrylate copolymer; Acrylates/succinates/hydroxyesters; Acrylic acid; Acrylic acid butyl ester, acrylonitrile, styrene polymer; Acrylic acid polymer/copolymer; Acrylic acid sodium acrylate polymer; Acrylic acid, methacrylic acid polymer, sodium salt; Acrylic acid, styrene, (1-methylethenyl)benzene polymer, ammonium salt; Acrylic Copolymer Emulsion; Acrylic Emulsion Copolymer; Acrylic Impact Modifier; Acrylic Pigmented Polymer Emulsion; Acrylic polymer; Acrylic polymer emulsion; Acrylic polymer emulsion (unspecified); Acrylic polymer mixture/emulsion; Acrylic polymers; Acrylic Resin; Acrylic resin(s) (unspecified), Acrylic thermoset binder; Acrylic/Acrylate copolymer; Acrylonitrile; Acrylonitrile-butadiene-styrene (ABS) copolymer; Acrylonitrile/Methacrylonitrile/Methyl Methacrylate Copolymer; *Actinidia chinensis* extract; Active cationic salts; Acusol; Additive(s) (unspecified); Adhesive; Adipic acid; Adipic acid/Neopentyl glycol/Trimellitic anhydride copolymer; Aerosil R972; Aesthetic agent (unspecified); Agar; Alachlor; Alanine; Albumen; Alcohol Alkoxylate; Alcohol ethoxy sulfate (mixture); Alcohol ethoxylate; Alcohol ethoxylates ($C_{12}$-$C_{15}$); Alcohol ethoxylates AE7; Alcohol ethoxysulfate salt; Alcohol sulfate; Alcoholethoxy sulfate; Alcohols (unspecified); Alcohols, $C_{10-12}$, ethoxylated propoxylated; Alcohols, $C_{10-14}$, ethoxylated; Alcohols, $C_{10-16}$, ethoxylated; Alcohols, $C_{10-16}$, ethoxylated propoxylated; Alcohols, $C_{11-14}$-iso-, $C_{13}$-rich, ethoxylated; Alcohols, $C_{12-14}$, ethoxylated; Alcohols, $C_{12-14}$-secondary, ethoxylated; Alcohols, $C_{12-15}$-branched and linear, ethoxylated propoxylated; Alcohols, $C_{12-16}$, ethoxylated (Isureth-4); Alcohols, $C_{12-18}$, ethoxylated; Alcohols, $C_{12-18}$, ethoxylated propoxylated; Alcohols, $C_{14-18}$; Alcohols, $C_{16-18}$, ethoxylated; Alcohols, $C_{6-10}$, ethoxylated propoxylated, fumarated, sodium salts; Alcohols, $C_{6-12}$, ethoxylated; Alcohols, ethoxylated, sulfated, neutralized; Alcopol FL; *Aleurites moluccana* oil; Alfalfa extract; Algae extract; Alginic acid; Aliphatic Ethoxylated Alcohols; Aliphatic Glycol Acetate; Aliphatic petroleum distillate; Aliphatic petroleum distillate(s) (unspecified); Alkaline builders; Alkanes, $C_{14-16}$; Alkanes, $C_{6-18}$, chloro; Alkanes, $C_{7-10}$-iso; Alkanes, $C_{7-8}$-iso-; Alkanolamine (unspecified); Alkoxy Heterocyclic Ether; Alkyl (50% $C_{14}$, 40% $C_{12}$, 10% $C_{16}$) dimethyl benzyl ammonium saccharinate; Alkyl ($C_{10}$-$C_{14}$) dimethyl benzyl ammonium chloride; Alkyl ($C_{10}$-$C_{16}$) benzenesulfonic acid, sodium salt; Alkyl ($C_{10}$-$C_{16}$) glycidyl ether; Alkyl ($C_{12-15}$) benzoate; Alkyl ($C_{12}$-$C_{18}$) dimethyl benzyl ammonium chloride; Alkyl aryl polyethoxy alcohols; Alkyl benzene sulfonate; Alkyl dimethyl benzyl ammonium chloride; Alkyl glucoside; Alkyl polyethylene glycol ethers ($C_{10}$) mixture; Alkyl polyglucoside; Alkyl polyhydroxy-substituted ammonium chloride; Alkyl polymer (unspecified); Alkyl sulfonate; Alkyl($C_{12-16}$)dimethylbenzylammonium chloride; Alkyl($C_{12-18}$)dimethyl ethylbenzyl ammonium chloride; Alkyl($C_{12-18}$)dimethylbenzyldimethylethylbenzyl ammonium chlorides; Alkyl($C_{12}$-$C_{14}$)dimethyl ethyl benzyl ammonium chlorides; Alkylamine salts of phosphoric acid esters; Alkylamines (unspecified); Alkylarylsulfonate salt (proprietary); Alkyldicarboxylic acid (proprietary); Alkyldiol ethoxylate #1 (proprietary); Alkyldiol ethoxylate #2 (proprietary); Alkyldiol ethoxylate (proprietary); Alkylquarternaryamine salt (proprietary); Allantoin; *Allium Sativum* Bulb Oil; Allyl Cyclohexylpropionate; Allyl Methacrylates Crosspolymer; Almond oil; *Aloe* (unspecified); *Aloe barbadensis* extract; *Aloe Barbadensis* leaf juice; *Aloe barbadensis/vera* extract/gel; *Aloe* extract; *Aloe vera* leaf extract; alpha-Glucan oligosaccharide; alpha-Isomethyl ionone; alpha-Terpineol; Alpha-Terpineol; *Althaea Officinalis* Leaf/Root Extract; *Althea* extract; Alumina, activated; Alumina, cement bonded; Aluminosilicate; Aluminosilicates (Zeolites); Aluminum; Aluminum Calcium Sodium Silicate; Aluminum chloride; Aluminum chloride hexahydrate; Aluminum chlorohydrate; Aluminum chlorohydrate anhydrous; Aluminum distearate; Aluminum heptamolybdate; Aluminum hydroxide; Aluminum magnesium silicate; Aluminum monostearate; Aluminum nitrate nonahydrate; Aluminum oxide; Aluminum silicate; Aluminum silicate(s) (unspecified); Aluminum silicate, anhydrous; Aluminum silicate, hydrated; Aluminum starch octenylsuccinate; Aluminum stearate; Aluminum stearate benzoate complex; Aluminum sulfate; Aluminum sulfate anhydrous; Aluminum zirconium pentachlorohydrex GLY; Aluminum Zirconium Tetrachlorohydrex Gly; Aluminum zirconium tetrachlorohydrex gly; Aluminum zirconium tetrachlorohydrex gly [USAN:USP]; Aluminum zirconium trichlorohydrex gly: *Amaranthus Caudatus* Seed Extract; Amber; American *ginseng* extract; Amica extract; Amides, $C_{8-18}$ and $C_{18}$-unsatd, N,N-bis(hydroxyethyl); Amine oxide; Amines, $C_{12-14}$-alkyl, reaction products with hexanol, phosphorus oxide ($P_2O_5$), phosphorus sulfide ($P_2S_5$) and propylene oxide; Amines, $C_{12-18}$-alkyldimethyl; Amines, $C_{12-18}$-alkyldimethyl, N-oxides; Amines, coco alkyl; Amines, coco alkyl dimethyl, oxides; Amines, polyethylenepoly-, reaction products with succinic anhydride polyisobutenyl derivs.; Amino acids (unspecified); Amino alkyldiol (proprietary); Amino tri (methylene phosphonic acid), potassium salt; Aminoethyl ethanolamine; Aminoethylpiperazine; Aminoethylpropanol; Aminomethyl propanediol; Aminomethylpropanol; Aminopropyl Phenyl Trimethicone; Aminotrimethylene Phosphonic Acid; Amitraz; Amla oil; Ammonia; Ammoniacal nitrogen; Ammonium acetate; Ammonium acrylates copolymer; Ammonium Alcohol Ether Sulfate; Ammonium alcohol ethoxylate; Ammonium alcohol ethoxysulfate; Ammonium benzoate; Ammonium $C_{12-15}$ Pareth Sulfate; Ammonium $C_9$-$C_{10}$ perfluoroalkyl sulfonate; Ammonium chloride; Ammonium dodecylbenzenesulfonate; Ammonium fluoride; Ammonium glycolate; Ammonium glycyrrhizate; Ammonium hydrogen difluoride; Ammonium hydroxide; Ammonium lanolate; Ammonium laureth sulfate; Ammonium lauryl sulfate; Ammonium molybdate; Ammonium nitrate; Ammonium nonoxynol-4 sulfate; Ammonium oxalate; Ammonium peroxydisulfate; Ammonium phosphate, dibasic; Ammonium phosphate, monobasic; Ammonium polyacrylate; Ammonium Polyacryloyldimethyl Taurate; Ammonium polypropoxypolyethoxydecyl sulfate; Ammonium salt of polycarboxylic acid; Ammonium soaps of higher fatty acids; Ammonium sulfate; Ammonium tallate; Ammonium thiocyanate; Ammonium thiolactate; Ammonium trioxaundecanedioate; Ammonium xylenesulfonate; Ammonium zirconium carbonate; Amodimethicone; Amp-Isostearoyl Gelatin/Keratin Amino Acids/Lysine Hydroxypropyltrimonium Chloride; Amp-Isostearoyl Hydrolyzed Wheat Protein; Amyl acetate; Amyl alcohol; Amyl Cinnamal; Amylase; Amylcinnamyl Alcohol; Amylopectin, hydrogen phosphate, 2-hydroxypropyl ether; *Amyris Balsamifera* Bark Oil; Anatase titanium dioxide; Andrographolide; Androstadienone; *Angelica* extract; Anhydrite; *Anigozanthos flavidus* extract; *Anigozanthos Flavidus* Flower/Leaf Extract; *Anigozanthos Flavidus* Flower/Leaf Extract; Aniline; Animal blood, denatured; Animal glue; Animal protein (collagen), hydrolyzed; Anionic surfactant(s) (unspecified); Anise Alcohol; Anise extract; Annatto; *Anthemis Nobilis* Flower Extract; Anthophyllite asbestos; Anthraquinone; Anti-oxidant/Anti-wear dispersant; Antigorite; Antimony; Antimony (unspecified compound); Antimony diakyldithiocarbamate; Antimony trioxide; Antioxidant, anti-wear, or anti-redeposition agent (unspecified); Apple extract; Apricot extract; Apricot kernel oil; Aqueous acrylic emulsion; Aqueous Copolymer; Aqueous polymer (nonhazardous); Aqueous/emulsion diluent; Arachidic acid; Arachidyl alcohol; Arachidyl behenate; Araldite B; *Argania spinosa* kernel oil; Arginine; Arginine Hydrochloride; Armohib 31; Armoise oil (unspecified type); *Arnica montana*, ext.; Aromatic alcohol; Aromatic petroleum distillates (unspecified); Aromatic resin; Arsenic; *Artemisia pallens* oil; Arylesterase; Arylsulfonated Sodium Salt; Ascophyllum Nodosum Extract; Ascorbic acid; Ascorbic Acid (Vitamin C); Ascorbic acid polypeptide; Ascorbyl glucoside; Ascorbyl palmitate; Ashless dispersant and antioxidant; Aspartame; Aspartic acid; Aspartic acid, tetrasodium salt; Asphalt; Asphalt (unspecified type); Asphalt Extenda; Asphalt, oxidized; Atlox 3406-F; Atrazine; Attapulgite; Australian Silk Protein Extract; Australian wild peach extract; Avocado extract/oil; Avocado Oil PEG-11 Esters; Awapuhi extract; Azodicarbonamide; Bacillomycin; *Bacillus amyloliquefaciens; Bacillus licheniformis; Bacillus megaterium; Bacillus* spores; *Bacillus subtilis; Bacillus thuringiensis*; Bacteria, complex with amylase and proteinase; Balm mint extract; *Bambusa vulgaris*, ext.; Banana essence oils; Banana leaf extract; Barium as barium compounds (unspecified); Barium chloride; Barium petroleum sulfonate; Barium sulfate; Base lubricating oils mixture; Basic Blue 99; Basic brown 16; Basic brown 17; Basic yellow 57; Bees wax; Beeswax, synthetic; Behenamidopropyl dimethylamine; Behenamidopropyl Dimethylamine Behenate; Behenamidopropyl ethyldimonium ethosulfate; Behenic acid; Behentrimonium chloride; Behentrimonium methosulfate; Behenyl alcohol; Behenyl erucate; Behenyl trimonium methosulfite; Benfluralin; Bensulide; Bentonite; Benzaldehyde; Benzalkonium chloride; Benzene; Benzene, $C_{10-13}$-alkyl derivs.; Benzene, $C_{14-30}$-alkyl derivs.; Benzene, diethenyl-, polymer with 2-methyl-1,3-butadiene, hydrogenated; Benzenemethanaminium, N,N-dimethyl-N-tetradecyl-, saccharinate; Benzenesulfonic acid, 2,2'-(1E)-1,2-ethenediylbis(5-((4-(methylamino)-6-((4-((methylamino)carbonyl)phenyl)amino)-1,3,5-triaz; Benzenesulfonic acid, $C_{10}$-$C_{16}$-alkyl derivatives; Benzenesulfonic acid, $C_{15-30}$-alkyl derivs, sodium salts; Benzenesulfonic acid, dodecyl-, branched, compds. with 2-propanamine; Benzenesulfonic acid, mono-$C_{10-14}$-alkyl derivs., sodium salts; Benzenesulfonic acid, mono-$C_{10-16}$-alkyl derivs., compds. with ethanolamine; Benzenesulfonic acid, oxybis(decyl-, disodium salt; Benzethonium Chloride; Benzocaine; Benzoic acid; Benzoic acid, 2-((dioctadecylamino)carbonyl)-; Benzophenone; Benzophenone-1; Benzophenone-12; Benzophenone-2; Benzophenone-3 (Oxybenzone); Benzophenone-4; Benzophenone-9; Benzotriazole; Benzotriazolyl Dodecyl P-Cresol; Benzoyl peroxide; Benzyl acetate; Benzyl alcohol; Benzyl Benzoate; Benzyl chloride; Benzyl Cinnamate; Benzyl Salicylate; Benzyldiethyl[(2,6 xylyl carbamoyl) methyl ammonium *sacchari*; Benzylethyldimethylammonium chloride; Bergamot oil; Bergamot oil; *Bertholletia Excelsa* (Brazil Nut) Seed Oil; beta-Carotene; Beta-Methoxyethyl Cyanoacrylate; Betaine; Bifenthrin; Binding agent(s) (unspecified); Bioallethrin; Biodegradable fabric softening agents; Biodegradable soaps; Biotin; Bis(2-(dimethylamino)ethyl) ether; bis(2-Ethylhexyl)terephthalate; Bis (2-propylheptyl) phthalate; bis(Tributyltin) oxide; bis(Trioctyldodecylcitryl) dilinoleate; Bis-Aminopropyl Dimethicone; Bis-Diglyceryl Polyacyladipate-2; Bis-PEG/PPG-14/14; bis-PEG/PPG-14/14 dimethicone; Bis-PEG/PPG-16/16 PEG/PPG-16/16 Dimethicone; Bis-Phenylpropyl Dimethicone; Bisabolol; Bisacodyl; Bishydroxyethyl biscetyl malonamide; Bishydroxyethyl dihydroxypropyl stearaminium chloride; Bismuth; Bismuth oxychloride; Bisphenol A, epichlorohydrin polymer (epoxy); Bisphenol A, epichlorohydrin polymer, tall oil fatty acids ester; Bisphenol A, formaldehyde, epichlorohydrin polymer; Bisphenol A-epichlorohydrin copolymer acrylate; Bitter Orange flower extract; *Bixa Orellana* Seed Extract; Black colorant; Bladderwrack extract; Blast furnace slag; Bleach (unspecified); Blue Dye No. 1; Blysorbate-20; Boehmite; Bone Meal; Bone Meal, steamed; Borage extract; *Borago Officinalis* Seed Oil; Borate buffer salts (unspecified); Boric acid; Boric Acid, sodium salt; Boric acid, sodium salt, pentahydrate; Boron; Boron nitride; Boron oxide; Boron sodium oxide, tetrahydrate; Boron trifluoride; Boscalid; Branched-nonylphenol, ethoxylate; Brightener(s) (unspecified); Brodifacoum; Bromethalin; Bromochloro-5, 5-dimethylhydantoin; Bromochloro-5,5-dimethylhydantoin; Bronze pigment; Broom flower oil/extract; Bumper black; *Bupleurum Chinense* Root Extract; Butadiene, styrene, divinylbenzene polymer; Butan-2-one O,O'-(methoxymethylsilanediyl)dioxime; Butane; Butanol; Buteth-3; Butoxyethyl stearate; Butoxyethyl triclopyr; Butoxytriglycol; Buttermilk powder; Butyl 2-cyano-2-propenoate; Butyl acetate; Butyl benzyl phthalate; Butyl carbitol acetate; Butyl ether; Butyl mercaptan; Butyl methoxydibenzoylmethane (Avobenzone); Butyl rubber; Butyl stearate; Butylated hydroxyanisole (BHA); Butylene glycol; Butylene/ethylene/propylene copolymer; Butyloctanol; Butyloctyl Salicylate; Butylparaben; Butylphenyl Methylpropional-1; Butylphthalimide; Butyraldehyde, aniline reaction product; *Butyrospermum Parkii*; C.I. 11050; C.I. 12010; C.I. 12700; C.I. 26125; C.I. 74260; C.I. 77007; C.I. Acid Blue 80 (C.I. 61585); C.I. Acid Blue 93; C.I. Acid Orange 3; C.I. Acid Red 18 (C.I. 16255); C.I. Basic Green 4, oxalate; C.I. Direct Blue 199 (C.I. 74190); C.I. Direct Violet 107; C.I. Direct Yellow 173; C.I. Disperse Black 9; C.I. Disperse violet 1; C.I. Food Blue 3 (C.I. 42045); C.I. Pigment Black 11; C.I. Pigment Red 120; C.I. Pigment Red 48:4; C.I. Pigment yellow 35; C.I. Solvent Green 28; C.I. Solvent Yellow 14; 1-phenylazo-2-naphthol; $C_{10}$ Ethoxylated Alcohol 8EO; $C_{10-13}$ Isoparaffin; $C_{10-16}$ Alkylbenzene Sulfonic Acid; $C_{10-16}$-Alcohol sulfuric acid, triethanolamine salt; $C_{10-16}$-Alkyldimethylamines oxides; $C_{10-40}$ Isoalkylamidopropylethyldimonium Ethosulfate; $C_{10}$-$C_{18}$ Triglycerides; $C_{11-12}$ Isoparaffin; $C_{11-13}$ isoparaffin; $C_{11-15}$ Pareth-7; $C_{11-15}$ pareth-9; $C_{12-13}$ alkyl lactate; $C_{12-13}$ Pareth-15; $C_{12-14}$ isoparaffin; $C_{12-14}$-alkyl glycidyl ether; $C_{12-15}$ Alcohols; $C_{12-15}$ alkyl benzoate; $C_{12-15}$ Alkyl ethylhexanoate; $C_{12-15}$ alkyl lactate; $C_{12-15}$ alkyl octanoate; $C_{12-15}$ Pareth-11; $C_{12-15}$ pareth-12 carboxylic acid; $C_{12-15}$ Pareth-3; $C_{12-16}$ Alcohols; $C_{12-16}$ pareth-9; $C_{12-15}$ alcohols; $C_{12-18}$ alkyl oils; $C_{12-18}$ fatty acids, potassium salts; $C_{12-20}$ Isoparaffin; $C_{12-22}$ quaternary ammonium compounds; $C_{13-14}$ isoparaffin; $C_{13-15}$ Pareth-7; $C_{13-16}$ Isoparaffin; $C_{14-15}$ Pareth-7; $C_{18}$ polycarbamyl polyglycol ester; $C_{18-36}$ Acid Glycol Ester; $C_{18-36}$ acid triglyceride; $C_{18-36}$ acids; $C_{20-40}$ alcohols; $C_{20-40}$ pareth-10; $C_{20-40}$ pareth-40; $C_{6-10}$-Alkyl sulfates; $C_{6-8}$ paraffins & cycloparaffins; $C_{8-10}$ & $C_{10-16}$ Polyglycosides; $C_{8-18}$-Alkyldimethylbenzyl ammonium chlorides; $C_{8-9}$ isoparaffin; $C_{9-11}$ Alcohols; $C_{9-11}$ Isoparaffin; $C_{9-11}$ Pareth-3; $C_9$-Alkylated phenol; Cadmium; Cadmium compounds (unspecified); Cadmium selenide; Cadmium sulfide; Caffeine; Cajeput Oil; Calamine; Calcite; Calcium; Calcium acid methanearsonate; Calcium alkaryl sulfonate; Calcium aluminate; Calcium aluminum borosilicate; Calcium ammonium nitrate; Calcium bis(dihydrogen phosphate); Calcium carbonate; Calcium carbonate (Limestone); Calcium carbonate (unspecified CAS #); Calcium carrageenan; Calcium chlorate; Calcium chloride anhydrous; Calcium chloride dihydrate; Calcium dodecylbenzenesulfonate; Calcium fluoride; Calcium formate; Calcium Glycerophosphate; Calcium hydroxide; Calcium hypochlorite; Calcium magnesium carbonate; Calcium magnesium hydroxide (CaMg(OH)4); Calcium metasilicate, Calcium nitrate; Calcium oxide; Calcium pantothenate; Calcium peroxide; Calcium phosphate hydroxide; Calcium phosphate, tribasic; Calcium polysulfide; Calcium Pyrophosphate; Calcium silicate; Calcium sodium borosilicate; Calcium stearate; Calcium sulfate; Calcium sulfate dihydrate; Calcium sulfate hemihydrate; Calcium sulfonate; calcium sulphide; Calcium thioglycolate; Calcium/zinc polyvinyl methyl ether maleate; *Camellia oleifera*; Camphene; Camphor; Camphor benzalkonium methosulfate; Canadian balsam; *Canarium* Luzonicum Gum Nonvolatiles; Candelilla wax; Canola Oil; Capramide Dea; Capric acid; Capryleth-4; Caprylic acid; Caprylic Alcohol; Caprylic/Capric Glycerides; Caprylic/Capric triglyceride; Caprylic/capric triglyceride 1; Caprylyl glycol; Caprylyl Methicone; Caprylyl Pyrrolidone; Caprylyl/Myristyl Glucoside; Capsaicin; Captan; Captan derivatives; Caramel; Carbamic acid, N-((trimethoxysilyl)methyl)-, methyl ester; Carbaryl; Carbocysteine; Carbohydrate absorbent; Carbomer; Carbomer 934; Carbomer 940; Carbomer 951; Carbomer 954; Carbomer 956; Carbon; Carbon black; Carbon dioxide; Carbon tetrachloride; Carbonate derivative; Carbonic acid, compd. with guanidine (1:2); Carbopol; Carboxylated Polymer; Carboxylated styrene-butadiene polymer; Carboxylic acids, $C_{5-9}$; Carboxymethyl chitin; Carboxymethylcellulose; Carboxymethylcellulose sodium; Cardamom; Cardamom extract; Carfentrazone-ethyl; Carmine; Carnauba wax; Carnitine (L-form) hydrochloride; Carnosine; Carrageenan; Carrageenan, sodium salt; Carrot extract; Carrot oil; *Carum Petroselinum* Extract; Castor oil, hydrogenated (Trihydroxystearin); Castor oil, hydrogenated, lithium salt; Castor oil, oxidized; Castor oil, polymer with glycerol and sebacic acid; Castor oil, polymerized, oxidized; Castor oil, sulfated; Castoryl maleate; Caustics (unspecified); Cedarwood oil; Cedrol; Cellulase; Cellulose; Cellulose acetate butyrate; Cellulose ether; Cellulose, 2-hydroxyethyl ether, polymer with N,N-dimethyl-N-2-propenyl-2-propen-1-aminium chloride; Cellulose, microcrystalline; *Centella Asiatica* Extract, Ceramide 2; Ceramides; Ceresin (Ozokerite);

*Cereus Grandiflorius* (Cactus) Flower Extract; Cetamine oxide; Cetearyl Dimethicone Crosspolymer; Cetearyl ethylhexanoate; Cetearyl glucoside; Cetearyl isononanoate; Cetearyl isooctanoate; Cetearyl methicone; Ceteth-10; Ceteth-10 phosphate; Ceteth-2; Cetostearyl alcohol; Cetrimonium bromide; Cetrimonium chloride; Cetyl acetate; Cetyl alcohol; Cetyl betaine; Cetyl dimethicone; Cetyl dimethicone copolyol; Cetyl Esters, Cetyl esters (unspecified); Cetyl hydroxyethylcellulose; Cetyl Hydroxyethylcellulose; Cetyl lactate; Cetyl octanoate; Cetyl palmitate; Cetyl phosphate; Cetyl phosphate DEA; Cetyl ricinoleate; Cetylpyridinium chloride; Cetylpyridinium chloride [INN:BAN:JAN]; Chamomile extract; Chamomile oil; *Chamomilla Recutita (Matricaria)* Flower Extract; Charcoal, activated; Chelating agent(s); Chemical Not In Database; Cherry bark, wild, extract; *Chimaphila Umbellata* Leaf Extract; Chinese tea extract *(Camellia sinensis)*; Chitin; Chitosan glycolate; Chlorantraniliprole [ISO]; Chlorhexidine acetate; Chlorhexidine dihydrochloride; Chlorhexidine gluconate; Chloride phosphate; Chlorinated alpha-olefin; Chlorinated Paraffin, Chlorinated paraffin waxes; Chlorinated polyvinyl chloride (CPVC) resin; Chlorine; Chlorite (mineral group); Chloroacetic acid; Chlorobenzene; Chlorodifluoromethane; chloroethane; Chloroform; Chloromethane; Chlorophacinone; Chlorothalonil; Chlorothymol; Chlorphenesin; Chlorpyrifos; Cholecalciferol; Cholesterol; Cholesterol $C_{10}$-$C_{30}$/Lanosterol esters; Cholesteryl chloride; Cholesteryl isostearate; Cholesteryl nonanoate; Cholesteryl oleyl carbonate; Cholesteryl Oleyl Carbonate 1; Cholesteryl/behenyl/octyldodecyl lauroyl glutamate; Choleth-24; *Chondrus crispus*; Chromium; Chromium (III) oxide; Chromium III (unspecified compound); Chromium trihydroxide; *Chrysanthemum Parthenium* Extract; Chrysotile asbestos; CI 16230; CI 18050; CI Red Pigment 3; Cinnamaldehyde; Cinnamidopropyltrimonium Chloride; Cinnamon oil; Cinnamyl Alcohol; cis-1-(3-chloroallyl)-3,5,7-triaza-1-azoniaadamantane chloride; Citral; Citric acid; Citrine; Citronella oil; Citronellal; Citronellol; *Citrus aurantifolia* extract; *Citrus Aurantifolia* Oil; *Citrus Aurantium Amara* Leaf/Twig Extract; *Citrus Aurantium Bergamia* Fruit Oil; *Citrus* extract; *Citrus Gluaca* Fruit Extract; *Citrus* oils; *Citrus Sinensis* Peel Extract; *Citrus tangerina* extract; Clarifying agent; Clary extract; Clary Sage Oil; Clay; Clays (unspecified); Cleaning agent(s); Clinoptilolite; *Clintonia boreaalis* root extract; Cloransulam-methyl: Clove extract; Clove oil; Clover extract; Co-polymerized polymer; Coal tar pitch; Coating binder; Cobalt; Cobalt 2-ethylhexanoate; Cobalt acetate; Cobalt alkanoate; Cobalt aluminate blue spinel; Cobalt carboxylate(s); Cobalt naphthenate; Cobalt phosphate; Cobalt silicate; Cobaltous oxide; Cocamide; Cocamide DEA; Cocamide MEA; Cocamidopropyl betaine; Cocamidopropyl hydroxysultaine; Cocamidopropyl PG-dimonium chloride phosphate; Cocamidopropylamine oxide; Coceth-10; Coco diethanolamide; Coco-betaine; Coco-Caprylate/Caprate; Coco-glucoside, Coco-glucoside; Coco-glycerides; Coco-glycerides, hydrogenated; Cocoa butter; Cocoamidopropylbetaine; Cocoamphocarboxyglycinate, disodium salt; Cocobetaine; Cocodimonium hydroxypropyl hydrolyzed hair keratin; Cocodimonium hydroxypropyl hydrolyzed wheat protein; Coconut diethanolamide; Coconut diethylamide; Coconut fatty acid, aminoethylethanolamine imidazoline, di(methyl acrylate) alkylated, disodium salt; Coconut fatty acid, polyethylene glycol diester; Coconut fatty acids; Coconut fruit juice; Coconut isopropanolamide; Coconut oil; Coconut oil monoglycerides, ethoxylated; Coconut oil, diethanolamine condensate (Surfactant); Coconut-derived surfactant mixture; *Cocos Nucifera* Oil; Cocotrimonium Methosulfate; Cod liver oil; Collagen; Collagen Amino Acids; Collagen hydrolysate, sodium salt solution; Collagen, hydrolyzed; Collagen, hydrolyzed, ethyl ester; Color protection/processing agent; Color safe oxygen bleach (sodium perborate and bleach activator); Colorant/Pigment/Dye(s); Comfrey extract; *Commiphora* extract; *Commiphora Myrrha* Gum Extract; Complex mixture of petroleum hydrocarbons; Composted bark mulch; Composted green waste; Compressed air; Conditioners (trade secret); Coneflower extract; Copolymer alkyd resin; Copolymer emulsion (unspecified); Copper; Copper carbonate; Copper gluconate; Copper naphthenate; Copper phthalocyanine; Copper phthalocyanine, sulfamoyl sulfo derivs, sodium salts; Copper sulfate; Copper sulfate, pentahydrate; Copper triethanolamine; Copper(II) nitrate; *Corallina officinalis*, ext.; Coriander extract; *Coriandrum Sativum* Fruit Oil; Corn cobs, ground (ID: C 14032000); Corn gluten protein; Corn oil; Corn poppy extract; Corn starch/acrylamide/sodium acrylate copolymer; Cornflower extract; Corrosion inhibitor(s); Cotton; Cottonseed oil; Cottonseed oil, hydrogenated; Coumarin; Coupling agent; CPE resin; Cranberry *(Vaccinium macrocarpon)* Extract; *Crassula Argentea* Leaf Extract; *Crataegus monogina* fruit extract; Creatine; Cristobalite; Cube resins (unspecified); Cucumber extract; Cumene; Cumene hydroperoxide; *Cupressus Sempervirens* (Cypress) Bark Extract; Cupric acetylacetonate; Cupric oxide; Cuprous oxide; Custard apple extract; Cyanoacrylate; cyclic AMP (adenosine cyclic phosphate); Cyclocarboxypropyloleic Acid; Cyclodextrin; Cyclohex-1,2-ylenediamine; Cyclohexamine; Cyclohexane; Cyclohexanol; Cyclohexanone; Cyclohexasiloxane; Cyclohexene; Cyclohexylamine; Cyclomethicone; Cyclopentane; Cyclopentasiloxane; Cyclopentasiloxane, 2,4,6,8,10-pentamethyl-; Cyclopentasiloxane, decamethyl-; Cyclotetrasiloxane; Cyfluthrin; Cygon (Dimethoate); *Cymbopogon Citratus* Leaf; *Cymbopogon schoenanthus*; Cypermethrin; Cyphenothrin; Cystamine dihydrochloride; Cysteine; Cysteine Hcl; D & C Red no. 21; D&C Brown #1; D&C Green #3; D&C Green #5 (CI. 61570); D&C Green #6; D&C Green #8 (C.I. 59040); D&C Orange #2; D&C Orange #4; D&C Red #17; D&C Red #27 aluminum lake; D&C Red #28; D&C Red #30; D&C Red #33 (C.I. 17200); D&C Red #34 calcium lake; D&C Red #6; D&C Red #7; D&C Violet #2; D&C Yellow #11; D&C Yellow #8 (C.I. 45350); D-alpha-Tocopheryl acetate; d-cis,trans-Allethrin; D-Gluconic acid; D-Glucopyranose, oligomeric, $C_{10-16}$-alkyl glycosides; D-Glucopyranose, oligomeric, $C_{9-11}$-alkyl glycosides; D-Glucopyranose, oligomeric, decyl octyl glycosides; d-Limonene; d-Mecoprop; d-Methoprene; d-Phenothrin; d-trans Allethrin; d-trans-Allethrin; Daisy extract; Dakril 4B; Dandelion extract; DEA-Lauraminopropionate; DEA-methoxycinnamate; DEA-oleath-3 phosphate; DEA-oleth-7 phosphate; Decanedioic acid, 1,10-bis(1,2,2,6,6-pentamethyl-4-piperidinyl) ester; Decanoic acid, ester with 2-ethyl-2-(hydroxymethyl)-1,3-propanedioloctanoate; Decanoic acid, mixed diesters with octanoic acid and propylene glycol; Deceth-3; Decyl Alcohol; Decyl beta-D-glucopyranoside; Decyl dimethyl octyl ammonium chloride; Decyl glucoside; Decyl Glucoside; Decyl polyglucose; Decyl polyglucoside; Decyl(sulfophenoxy)benzenesulfonic acid disodium salt; Decylamine oxide; Decylene Glycol; Decyltetradecanol; Defoaming agent (unspecified); Dehydroacetic acid; Deltamethrin; Denatonium benzoate; Deodorizers (unspecified); Detergent engine oil package; Detergent/dispersant additive; Detergent/Inhibitor mixture; Dextrin; Di (C14-1S-alkyl) dimethyl methyl sulfate; Di tallow Dimethyl Ammonium Methyl Sulphate/EO Fatty Acid; Di($C_8$-$C_{10}$) branched alkyl phthalate; Di-2-ethylhexyl sebacate; Di-$C_{12-15}$ alkyl fumarate; Di-n-propyl isocinchomeronate; Di-PPG-2 myreth-10 adipate; Di-sec-octyl phthalate; Di-Syston; Diacetone alcohol; Dialkyl(C1-C14)dithiophosphoric acid, zinc salt; Diaminopolypropylene glycol; Diaminostilbene disulphonate disodium salt; Diaminostilbenedisulfonic acid; Diammonium molybdate; Diamond powder; Diatomaceous silica, calcined; Diatomite; Diazinon; Diazolidinylurea; Dibasic esters; Dibenzylidene sorbitol; Dibutoxy tetraglycol; Dibutoxydiacetoxysilane; Dibutyl ether; Dibutyl hydrogen phosphite; Dibutyl lauroyl glutamide; Dibutyl phthalate; Dibutyltin dilaurate; Dibutyltin oxide; Dicalcium phosphate; Dicalcium phosphate dihydrate; Dicalcium silicate; Dicambra, sodium salt; Dicapryl adipate; Dicaprylyl Carbonate; Dicaprylyl ether; Dicaprylyl maleate; Dicetyl Phosphate; Dicetyldimonium chloride; Dichlobenil; Dichloroacetic acid; Dichlorodimethylsilane Rx. with Silica; Dichlorofluoroethane; Dichlorprop-p-dimethylamine salt; Dichlorvos (DDVP); Dichromium trioxide; Dicyandiamide; Dicyclohexyl phthalate; Didecyl dimethyl ammonium chloride; Didodecyldimethylammonium chloride; DIDP; Diethanolamine; Diethanolamine tall oil acid amide; Diethyl ester dimethyl ammonium chloride; Diethyl phthalate; Diethylaminomethylcoumarin; Diethylbenzene; Diethylene glycol; Diethylene glycol ethyl ether; Diethylene glycol monobutyl ether; Diethylene glycol monohexyl ether; Diethylene glycol monolauryl ether sodium sulfate; Diethylene glycol monopropyl ether; Diethylenetriamine; Diethylenetriamine pentaacetic acid, sodium salt; Diethylenetriaminepentaacetic acid (DTPA); Diethylhexyl 2,6-Naphthalate; Diethylhexyl Carbonate; Difethialone; Diglycerol; Diglyceryl diisostearate; Diglycol/Cyclohexanedimethanol/Isophthalates/Sulfo; Diglycolamine; Dihydrate alkoxylate linear alcohol; Dihydro-5-pentyl-2(3H)-furanone; Dihydrogenated Tallowamidoethyl Hydroxyethylmonium; Dihydroxyacetone; Dihydroxyethyl tallow glycinate; Dihydroxypropyl PEG-5 linoleaminium chloride; Dihydroxypropyl PEG-5 Linoleammonium chloride; Dihydroxypropyltrimonium Chloride; Diisobutyl adipate; Diisodecyl phthalate; Diisoheptyl phthalate; Diisooctyl adipate; Diisopropanolamine; Diisopropyl adipate; Diisopropyl dimer dilinoleate; Diisopropyl dimerate; Diisopropyl sebacate; Diisostearoyl Trimethylolpropane Siloxy Silicate; Diisostearyl dimer dilinoleate; Diisostearyl fumarate; Dilauryl thiodipropionate; Dilinoleic acid; Dimethicone; Dimethicone bisamino hydroxypropyl copolyol; Dimethicone copolyol; Dimethicone copolyol meadowfoamate; Dimethicone Crosspolymer; Dimethicone PEG-8 Meadowfoamate; Dimethicone propyl PG-betaine; Dimethicone silylate; Dimethicone/Methicone Copolymer; Dimethicone/vinyl dimethicone crosspolymer; Dimethiconol; Dimethoxymethane; Dimethyl (1,2-phenylene)bis(iminocarbonothioyl)bis(carbamate);

Dimethyl adipate; Dimethyl benzyl ammonium chloride; Dimethyl ditallow ammonium chloride; Dimethyl ether; Dimethyl glutarate; Dimethyl lauramine isostearate; Dimethyl lauramine oleate; Dimethyl octyndiol; Dimethyl Oxazolidine; Dimethyl phenol; Dimethyl phthalate; Dimethyl polysiloxane; Dimethyl siloxane, reaction product with silica; Dimethyl siloxane, trimethoxysilyl-terminated; Dimethyl succinate; Dimethyl sulfoxide; Dimethyl Urea; Dimethylamine; Dimethylarsinic acid; Dimethylethanol amine; Dimethylpabamidopropyl laurdimonium tosylate; Dineca; Dinonylnaphthalene sulfonic acid, barium salt; Dinotefuran; Dioctyl adipate; Dioctyl dimethyl ammonium chloride; Dioctyl sebacate; Dioctyl sodium sufosuccinate; Dioctyl succinate; Dipalmethyl Hydroxyethylammoinum Methosulfate; Dipalmitoyl hydroxyproline; Dipentene; Diphosphonic acid; Dipotassium glycyrrhizate; Dipotassium phosphate; Dipropyl ethyl tetra amine; Dipropylene glycol; Dipropylene glycol dibenzoate; Dipropylene glycol methyl ether; Dipropylene glycol monobutyl ether; Dipropylene glycol monopropyl ether; Dipropylene glycol phenyl ether; Dipropylene Glycol Propyl Ether; Dipropylene glycol salicylate; Diquat dibromide; Diquaternium ethoxysulfate; Dishwasher/china protection agent(s); Disodium 2-sulfolaurate; Disodium C-(2-(2-(2-(dodecyloxy)ethoxy)ethoxy)ethyl) sulphonatosuccinate; Disodium capryloamphodipropionate; Disodium cocamid MIPA-sulfosuccinate; Disodium cocamido MEA sulfosuccinate; Disodium cocoyl glutamate; Disodium Decyl Phenyl Ether Disulfonate; Disodium Distyrylbiphenyl Disulfonate; Disodium EDTA; Disodium EDTA-copper; Disodium hydrogen citrate; Disodium Hydroxyethyliminodiacetate; Disodium laureth sulfosuccinate; Disodium lauroamphodiacetate; Disodium Lauryl Phenyl Ether Disulfonate; Disodium lauryl sulfosuccinate; Disodium octaborate tetrahydrate; Disodium oleamido MEA sulfosuccinate; Disodium phosphate; Disodium pocinoleamidomea sulfosuccinate; Disodium pyrophosphate; Disodium Stearoyl Glutamate; Disodium Wheat Germamido PEG-2 Sulfosuccinate; Disodium wheatgermamphodiacetate; Disodium zinc EDTA; Dispensing/stabilizing/buffering agent(s); Dispersant Inhibitor; Disperse Blue 1; Disperse Blue 3; Disperse Blue 377; Disteardimonium Hectorite; Disteareth 75 IPDI; Distearyl thiodipropionate; Distearyldimonium chloride; Distillates (petroleum), light distillate hydrotreating process, low-; Distillates (petroleum), steam-cracked, polymd.; Distillates (petroleum), sweetened middle; Distillates, petroleum, acid-treated heavy naphthenic; Distillates, petroleum, acid-treated light; Distillates, petroleum, acid-treated light paraffinic; Distillates, petroleum, clay-treated heavy paraffinic; Distillates, petroleum, hydrodesulfurized middle; Distillates, petroleum, hydrotreated heavy paraffinic; Distillates, petroleum, hydrotreated light; Distillates, petroleum, hydrotreated light paraffinic; Distillates, petroleum, hydrotreated middle; Distillates, petroleum, solvent-dewaxed heavy naphthenic; Distillates, petroleum, solvent-dewaxed heavy paraffinic; Distillates, petroleum, solvent-dewaxed light paraffinic; Distillates, petroleum, solvent-refined heavy naphthenic; Distillates, petroleum, solvent-refined light naphthenic; Distillates, petroleum, straight-run middle; Distyryl biphenyl derivative; Ditallow phthalic acid amide; Ditallowamine, hydrogenated; Dithiopyr; Ditrimethylolpropane tetrastearate; Diuron; DMA salt of 2,4-D (2,4-Dichlorophenoxyacetic acid); DMA salt of 2,4-DP (2-(2-methyl-4-chlorophenoxy) propanoic acid); DMA salt of Dicamba (3,6-dichloro-o-anisic acid); DMA salt of MCPA; DMA Salt Of Mecoprop (MCPP); DMDM hydantoin; Dodecamethylcyclohexasiloxane; Dodecamethylpentasiloxane; Dodecene; Dodecyl benzene sulfonic acid; Dodecyl dimethyl ammonium chloride; Dodecyl dimethyl ethylbenzyl ammonium chloride; Dodecylbenzenesulfonic acid, disodium salt; Dodecylphenoxypoly(ethyleneoxy)ethanol; Domiphen bromide; Dow Corning (R) Z-6040 Silane; Dow Corning 20 Release; Drainzyme (bacteria booster); Drometrizole; Dryer activated cloths; Dulse (*Rhodymenia palmata*) extract; Dye; Dye stabilizer; Dye transfer inhibition agent; Dye(s) (unspecified); *Ecklonia Radiata* Extract; Edelweiss extract; Edetate disodium; Edetate sodium tetrahydrate; Edible oils; EDTA tetrapotassium salt; Eicosapentaenoic Acid; *Elaesis Guineensis* Extract; Elastin; Elastin, hydrolyzed; Elder flower extract; Elderberry flowers extract; *Elettaria Cardamomum* Seed Oil; Emkarate 10079 (proprietary); Emollient(s) (unspecified); Emulsified waxes; Emulsifier H; Emulsifier(s) (unspecified); Enzyme (protease/amylase); Enzyme(s) (unspecified); Epichlorohydrin polyglycol resin polymer; *Epilobium Angustifolium* Extract; Epoxidized linseed oil; Epoxy polymer (unspecified/proprietary); Epoxy resin; Ergocalciferol; Esfenvalerate; Essential oils; Ester wax; Esters with triethanolamine; Ethane; Ethane, 1,1,1-trichloro-; Ethanol, 2,2'-((4-aminophenyl)imino)bis-, sulfate (salt); Ethanol/SD Alcohol 40; Ethanolamine tallate; Ethene, methoxy-, homopolymer; Ethenylbenzene, copolymer with (1-methylethenyl)benzene; Ethoxylated alcohol phosphate esters; Ethoxylated alcohols (unspecified); Ethoxylated aliphatic amines (unspecified); Ethoxylated long chain alkylamine alkylphosphite and metal sulfonate; Ethoxylated methyl beta-D-glucoside; Ethoxylated polyethyleneimine; Ethoxylated polyethylenepolyamine; Ethoxylated tallowamines; Ethoxylated-2,4,7,9-tetramethyl-5-decyne-4,7-diol; Ethoxytriglycol; Ethyl 2-cyanoacrylate; Ethyl 3-ethoxy propionate; Ethyl acetate; Ethyl acrylate; Ethyl alkyldiol (proprietary); Ethyl ester of PVM/MA copolymer; Ethyl ether; Ethyl glutamate; Ethyl lactate; Ethyl lactate; Ethyl Macadamiate; Ethyl sulfate; Ethyl tosylamide; Ethyl vinyl acetate; Ethyl, 1-hydroxy-; Ethylbenzene; Ethylene brassylate; Ethylene butyl ether; Ethylene carbonate; Ethylene glycol; Ethylene glycol methylene ether; Ethylene glycol monoethyl ether; Ethylene glycol monoethyl ether acetate; Ethylene glycol monopropyl ether; Ethylene glycol n-hexyl ether; Ethylene glycol, mono(2-ethylhexyl) ether; Ethylene oxide; Ethylene oxide-propylene oxide copolymer ether with trimethylolpropane; Ethylene-propylene copolymer; Ethylene/Acrylic Acid Copolymer; Ethylene/Methacrylate copolymer; Ethylene/propylene/diene terpolymer; Ethylene/Vinyl acetate co-polymer; Ethylenediaminetetraacetic acid (EDTA); Ethylhexyl Cocoate; Ethylhexyl glycerin; Ethylhexyl methacrylate; Ethylhexyl Methoxycinnamate; Ethylhexylglycerin; Ethylparaben; Ethyltoluene; Ethyltriacetoxysilane; Etidronic acid; Etocrylene; Etofenprox; Etridiazole; Eucalyptol; *Eucalyptus* extract; *Eucalyptus globulus* leaf; *Eucalyptus* oil; Eugenol; Euphrasia extract; Evangard DTB (proprietary); Evening primrose extract; Evergreen extract; *Evernia Furfuracea; Evernia* Prunastri; Exotic wood complex; Extract of orchid; Extract of strawberry; Extract of Sweet Clover; Extracts, petroleum, heavy naphtha solvent; Extracts, petroleum, middle distillate solvent; Fabric brightening agent; Fabric softening agent/static control; Fabric whitening agent(s); Fabric/Fiber protection agent; Farnesol; Fatty acid esters; Fatty acid soap, $C_{12-18}$, sodium salt; Fatty acid triglycerides; Fatty acids (unspecified); Fatty acids, $C_{12-18}$, compds. with ethanolamine; Fatty acids, $C_{14-18}$ and $C_{16-18}$-unsatd, sodium salts; Fatty acids, $C_{14-18}$, isopropyl esters; Fatty acids, $C_{16-18}$ and $C_{18}$-unsatd, polymers with p-tert-butylphenol, formaldehyde, glycerol; Fatty acids, $C_{18}$-unsatd, dimers, polymers w/ethylenediamine, pentaerythritol, phthalic anhydride & tall-oil fatty acids; Fatty acids, $C_{8-18}$ and $C_{18}$-unsatd.; Fatty acids, $C_{8-18}$ and $C_{18}$-unsatd., ammonium salts; Fatty acids, $C_8$-$C_{18}$ and $C_{18}$-unsaturated, sodium salts; Fatty acids, salts; Fatty acids, tall-oil, polymers with bisphenol A, diethylenetriamine, epichlorohydrin and tetraethylenepentamine; Fatty acids, tall-oil, reaction products with tetraethylenepentamine; Fatty acids, vegetable-oil, compds. with diethanolamine; Fatty alcohol ether sulfates; Fatty Ester Mixture Type 1; Fatty Ester Mixture Type 2; FD&C (or D&C) Yellow #10 (C.I. 47005); FD&C (or D&C) Yellow #5 (C.I. 19140); FD&C Blue #1; FD&C Green #3; FD&C Green #5; FD&C Red #33; FD&C Red #4 (C.I. 14700); FD&C Red #40; FD&C Red (unspecified number); FD&C Red No. 3; FD&C Yellow #6 (C.I. 15985); Feldspar-group minerals; Fennel extract; Fenoxycarb; Ferric ammonium ferrocyanide; Ferric chloride; Ferric chloride-Iron (III) chloride; Ferric Citrate; Ferric ferrocyanide; Ferric oxide; Ferric oxide hydrate; Ferric phosphate; Ferric sodium EDTA; Ferrite; Ferrosoferric oxide; Ferrous sulfate; Ferrous sulfate heptahydrate; Fertilizer 12-18-6; Fesco perlite board; Fiberousglass; Fig extract; Fillers; Film agent; Film formers; Fipronil; Fir needle oil; Fish oils; Flame retardant (proprietary/unspecified); Flavor(s); Fluazifop-p-butyl; Fluorinated acrylic copolymer; Fluoroaliphatic polymeric esters; Fluoroalkyl salts, mixed; Fluorophlogopite; Fluorosilicic acid; Flux core; Fly Ash; Foil facing; Foil/kraft, kraft, FSK, polyethylene, PSK, and various metal facings; Folic acid; Formaldehyde; Formaldehyde-Melamine-Sodium bisulfite copolymer; Formaldehyde-phenol-triethylenetetramine copolymer; Formic acid; Fragrance(s)/perfume(s); Frankincense; Freesia extract; Fructose; Fruit extracts; Fuels, diesel, no. 2; Fuller's earth; Fumed silica, crystalline-free; Furazolidone; Furfuryl alcohol; Galaxolid; gamma-(beta-Aminoethylamino)propylpolydimethylsiloxane, methoxyend blocked; gamma-Cyhalothrin; Gamma-Decalactone; gamma-Glycidoxypropyltrimethoxysilane; gamma-Hydroxybutyrolactone; gamma-Lactone; *Ganoderma Lucidum* Stem Extract; *Gardenia* oil; Garlic extract; Gasoline; Gasoline additive; Gelatin; Gelatin/Keratin Amino Acids/Lysine Hydroxypropyltrimonium Chloride; *Gelidiela acerosa* extract; *Gellidiela Acerosa* Extract; Gentisic acid; Geraniol; Geranium oil; Germali; Gilsonite; Ginger; Ginger extract; Ginger oil; Ginkgo extract; Glass beads; Glass, oxide chemicals (textile) (fibrous glass wool); Gluceptate Sodium; Gluconic acid; Gluconolactone; Glucosaminoglycans, hydrolyzed; Glucose; Glucose glutamate: Glucose oxidase; Glutamic Acid; Glutamine; Glutaraldehyde; Glycereth-18 ethylhexanoate; Glycereth-26; Glycereth-7 triacetate; Glycerides (unspecified); Glycerides, $C_{14-18}$ and $C_{16-18}$-unsatd. mono- and di-; Glycerides, $C_{14-18}$ mono- and di-; Glycerides, $C_{14-22}$-linear, mono-; Glycerides, $C_{16-18}$ and $C_{18}$-unsatd. mono- and di-; Glycerides, $C_{8-10}$ mono-, di- and tri-; Glycerides, $C_{8-21}$ and $C_{8-21}$-unsatd. mono- and di-; Glycerides, tallow mono- and di-, hydrogenated, ethoxylated; Glycerin; Glycerol ester of rosin; Glycerol Oleate; Glycerols (unspecified); Glyceryl Caprylate; Glyceryl Cocoate; Glyceryl dilaurate; Glyceryl distearate; Glyceryl hydroxystearate; Glyceryl lanolate; Glyceryl monostearate; Glyceryl monostearate SE (mixture); Glyceryl oleate; Glyceryl polyacrylate; Glyceryl polymethacrylate; Glyceryl rosinate; Glyceryl stearate; Glyceryl stearate citrate; Glyceryl Stearate Se; Glyceryl triacetyl hydroxystearate; *Glycine; Glycine soja; Glycine Soja* Germ Extract; Glycogen; Glycol derivatives; Glycol distearate; Glycol ether borate esters; Glycol ether(s) (unspecified); Glycol ethers (unspecified); Glycol stearate; Glycols, polyethylene; Glycosidase; Glycyrrhizic acid; Glyoxal; Glyoxal-sodium bisulfite; Glyphosate; Glyphosate, isopropylamine salt; Grape leaf extract; Grape, ext.; Grapefruit extract; Grapefruit oil; Graphite; Gray colorant; Green 3 (Cl 42053); Green mandarin; Green tea; Grotan BK; Guaiazulene; Guanine; Guar Gum; Guar hydroxypropyltrimonium chloride; Guava extract; Gum arabic (*Acacia*); Gypsum; Halofenozide; Halosulfuron-methyl; *Hamamelis virginiana*, ext.; HC Blue No 2; HC Orange no. 1; HC Red 3; HC Yellow No. 2; Heavy naphthenic distillate solvent extract; Hectorite; *Hedychium coronarium* extract; *Hedychium Coronarium* Flower/Leaf/Stem Extract; Henna extract; Heptakis(dipropyleneglycol) triphosphite; Heptane; Hesperidin Methyl Chalcone; Heterocyclic amine (unspecified); Hexabromocyclododecane; Hexadecane; Hexadecanol; Hexadimethrine chloride; Hexafluoron; Hexafluoropropene tetrafluoroethylene polymer; Hexakis(2-methyl-2-phenypropyl)distannoxane; Hexamethylcyclotrisiloxane; Hexamethyldisilazane; Hexamethylenetetramine hydrochloride; Hexane (mixed isomers); Hexane, 2-methyl-Hexane, 2-methyl-; Hexane, 3-methyl-; Hexanoic acid, 2-ethyl-, sodium salt (1:1); Hexyl Cinnamal; Hexyl Cinnamal-1; Hexyl laurate; Hexyl poly(oxyethylene) ether; Hexyl Salicylate; Hexyldecyl Stearate; Hexylene glycol; Hexyltrimethoxysilane; *Hibiscus sabdariffa* flower extract; Highly-refined petroleum lubricant oils; *Hippophae Rhamnoides* Extract; Histidine; Homosalate; Honey; Honey extract; Honeydew extract: Honeysuckle extract; Honeysuckle flower extract; Hops extract; Horse chestnut extract; Horsetail (*equisetium arvense*) extract; Hyaluronic acid; Hydramethylnon; Hydrated silica (Silica gel); Hydrazine monohydrochloride; Hydrocarbon propellant (unspecified); Hydrocarbon propellant blend (propane/isobutane/butane); Hydrocarbon resin; Hydrocarbon solvent (unspecified); Hydrocarbons, $C_{3-4}$-rich, petroleum distillates; Hydrocarbons, $C_{7-9}$ solvent; Hydrocarbons, terpene processing by-products Terpene processing by-products; Hydrochloric acid; Hydrocinnamic acid, 3,5-di-t-butyl-4-hydroxy-, octadecyl ester; Hydrocortisone; Hydrogel; Hydrogen bis(3,5-di-tert-butylsalicylato(2-)-O1,O2)chromate(1-); Hydrogen fluoride; Hydrogen peroxide; Hydrogen sulfide; Hydrogenated Coconut Oil; Hydrogenated Didecene; Hydrogenated Ethylene/Propylene/Styrene; Hydrogenated Jojoba Oil; Hydrogenated Methyl Abietate; Hydrogenated palm oil; Hydrogenated Poly($C_{6-20}$ Olefin); Hydrogenated soybean oil; Hydrogenated Starch Hydrolysate; Hydrogenated Styrene; Hydrogenated Tallow Glycerides; Hydrolyzed Corn Starch; Hydrolyzed Cranberry Fruit/Leaf Extract; Hydrolyzed Glycosaminoglycans; Hydrolyzed Human Hair Keratin; Hydrolyzed milk protein; Hydrolyzed Oat Protein; Hydrolyzed protein; Hydrolyzed Rice Protein; Hydrolyzed Wheat Protein PG Propyl Silanetriol; Hydrolyzed Wheat Starch; Hydroquinone; Hydrosulfite salts; Hydrotreated heavy naphthenic distillate solvent extract; Hydrotreated light naphthenic distillate solvent extract; Hydrotreated petroleum distillate (unspecified); Hydroxyacetic acid; Hydroxyalkyl Amine Oxides; Hydroxyalkyl methacrylate; Hydroxycaprylic acid; Hydroxycitronellal; Hydroxycitronellol; Hydroxyethyl Acrylate/Sodium Acryloyldimethyl Taurate Copolymer; Hydroxyethyl behenamidopropyl dimonium chloride; Hydroxyethyl cellulose; Hydroxyethyl cetyldimonium chloride; Hydroxyethyl cetyldimonium phosphate; Hydroxyethyl methacrylate; Hydroxyethyl stearamide MPA; Hydroxyethyl urea; Hydroxyethyl-3,4-Methylenedioxyaniline Hcl; Hydroxyisohexyl 3-Cyclohexene Carboxaldehyde; Hydroxylated alkane; Hydroxylated lanolin; Hydroxylated Lecithin; Hydroxymethylcellulose; Hydroxypropyl bis(N-hydroxyethyl-p-phenylenediamine) HCl; Hydroxypropyl cellulose; Hydroxypropyl distarch phosphate; Hydroxypropyl guar; Hydroxypropyl Guar Hydroxypropyltrimonium Chloride; Hydroxypropyl methylcellulose; Hydroxypropyl polysiloxane; Hydroxypropyltrimonium chloride; Hydroxypropyltrimonium hyaluronate; Hydroxypropyltrimonium hydrolyzed wheat starch/protein; Hydroxystearic acid; Hydrozincite; Hypnea musciformis extract; Icaridin; Imazapyr; Imazapyr, isopropylamine salt; Imidacloprid; Imidazolidinyl urea; Imidazoline monocarboxylate; Imiprothrin; Indaziflam [ISO]; Indian Cress extract; Indium; Indoxacarb; Inert ingredients (including petroleum distillates); Inert ingredients (unspecified); Inhibited paraffinic oil; Inhibitor package mixture; Inositol; Iodine; Iodopropynyl Butylcarbamate; Iodopropynyl carbamate; Ion exchange resins; Iron; Iron chloride; Iron oxide; Iron oxide(s) (un-specified); Iron Powder; Iron(II) sulfate, monohydrate; Iron (III) EDTA; Iron(III) oxide; Iron(III) oxide monohydrate (yellow pigment); Isoamyl acetate; Isoascorbic acid; Isobornyl acetate; Isobornyl methacrylate; Isobutane; Isobutane/Propane mixture; Isobutene; Isobutyl acetate; Isobutyl alcohol; Isobutyl isobuyrate; Isobutylparaben; Isobutylphenoxy epoxy resin; Isobutyraldehyde; Isoceteth-3 acetate; Isocetyl linoleoyl stearate; Isocetyl stearate; Isoctadecanoic acid, reaction products with tetraethylenepentamine; Isocyanate functional urethane resin; Isocyanic acid, polymethylenepolyphenylene ester, polymer with alpha-hydro-omega-hydroxypoly(oxy(methyl-1,2-ethanediyl)); Isocyanuric acid; Isodecyl oleate; Isododecane; Isoeicosane; Isoeugenol; Isohexadecane; Isolaureth-6; Isoleucine; Isononyl isononoate; Isooctadecanoic acid; Isooctane; Isooctyl ester of 2,4,-D acid; Isooctyl trimethoxy silane; Isoparaffinic hydrocarbon(s); Isopentane; Isophorone diisocyanate; Isophytol; Isopropanol; Isopropyl acetate; Isopropyl $C_{12-15}$-pareth-9 carboxylate; Isopropyl isostearate; Isopropyl lanolate; Isopropyl Lauroyl Sarcosinate; Isopropyl myristate; Isopropyl palmitate; Isopropyl stearate; Isopropyl titanium triisostearate; Isopropylamine Dodecylbenzene Sulfonate; Isopropylamine dodecylbenzenesulfonate; Isopropylparaben; Isopropylphthalimide; Isopulegol; Isostearamidopropyl Dimethylamine; Isostearamidopropyl ethyldimonium ethosulfate; Isostearamidopropyl morpholine lactate; Isosteareth-20; Isostearic acid; Isostearoyl Hydrolyzed Collagen; Isostearyl alcohol; Isostearyl behenate; Isostearyl citrate/glycolate/lactate/malate; Isostearyl neopentanoate; Isostearyl palmitate; Isotridecyl Isononanoate; Isoxaben; Jade Plant (*Crassula Argentea*) Extract; Japan wax; Japonilure; Jasmine extract; Jojoba extract; Jojoba wax; Juniper extract; *Juniperus Mexicana* Oil; *Juniperus Mexicana* Wood Oil; Kaolin clay; Kaolin clay (calcined); Kaolin, calcined; Kathon biocide; Kelp extract; Keratin; Keratin, hydrolyzed; Kerosine, petroleum, hydrodesulfurized; Kieselguhr; Kiwi seed; Kukui nut oil; Lactamidopropyl trimonium chloride; Lactic acid; Lactoperoxidase; Lactose; *Lagerstroemia indica* L., leaf and stem extract; lambda-Cyhalothrin *Laminaria Digitata* Extract; *Laminaria saccharina* extract; Laneth-25; Laneth-5; Lanolin; Lanolin acids; Lanolin alcohol; Lanolin alcohol, acetylated; Lanolin oil; Lanolin wax; Lanosterol; Lanthanum Chloride; Lanthanum sulfate; Lapyrium chloride; Lauramide diethanolamine (DEA); Lauramide MEA; Lauramide Mipa; Lauramidopropyl betaine; Lauramidopropylamine oxide; Lauramine oxide; Lauramine Oxide; Laurdimonium Hydroxypropyl Hydrolyzed Human Hair Keratin; Laureth-10; Laureth-12; Laureth-2 acetate; Laureth-23; Laureth-3; Laureth-4; Laureth-4; Laureth-4 carboxylic acid; Laureth-7: Laureth-9; Lauric acid; Lauric-Myristic monoethanolamide; Lauroyl lysine; Lauroyl sarcosine; Laurtrimonium Chloride; *Laurus Nobilis* Flower/Leaf/Stem Water; Lauryl alcohol; Lauryl aminopropylglycine; Lauryl diethylenediaminoglycine; Lauryl dimonium hydroxypropyl hydrolyzed wheat protein; Lauryl glucoside; Lauryl Hydroxysultaine; Lauryl Lactate; Lauryl Lactyl Lactate; Lauryl Methyl Gluceth 10 Hydroxypropyl Dimonium Chloride; Lauryl methyl gluceth-10 hydroxypropyladimonium chloride; Lauryl PCA; Lauryl polyglucose; Lauryl pyrrolidone; Lauryl sulfate DEA; Lauryldimethylbetaine; Laurylmethicone copolyol; *Lavandula Hybrida* Oil; Lavender extract; Lavender oil; Lead; Lead acetate; Lead compounds (unspecified); Lecithin; Lemon extract; Lemon oil; Lemongrass oil; *Lentinula Edodes* Extract; Lettuce extract; Leveling agent; Licorice oils; Lidocaine hydrochloride; Ligroin; Lime (chemical), dolomitic; Limnanthes Alba Seed Oil; Limonene fraction terpenes;

Linalool; Linden extract; Linear alkylaryl TEA sulfonate; Linear alkylbenzene; Linear($C_{12}$-$C_{14}$)alkanol, ethoxylated, sulfated, sodium salt; Linoleamide DEA; Linoleamide MEA; Linoleamidopropyl dimethylamine; Linoleamidopropyl dimethylamine dimer dilinoleate; Linoleamidopropyl PG-dimonium chloride phosphate; Linoleamidopropyl PGDimonium Chloride Phosphate; Linoleic acid; Linolenic acid; Linseed oil; Linseed oil, dicyclopentadiene copolymer; Linseed oil, phthalic anhydride, glycerin, vinyltoluene polymer; Linseed oil, polymer with maleic anhydride and pentaerythritol; Linseed oil, polymer with pentaerythritol, phthalic anhydride, soybean oil, styrene and vinyltoluene; Linseed oil, polymerized; Lipase, fungal; Liquefied petroleum gas mixture (unspecified); Liquitint Aquamarine; Liquitint Blue; Liquitint Bright Yellow Dye; Liquitint Brilliant Orange Dye; Liquitint Cyan 15; Liquitint green; Liquitint Orange; Liquitint Purple; Liquitint Red; Liquitint Sky Blue Dye; Liquitint Violet; Lithium; Lithium 12-hydroxystearate; Lithium carbonate; Lithium complex; Lithium grease; Lithium Magnesium Silicate; Lithium soap complex; Lithium stearate; Lithium trifluoromethanesulfonate; *Litsea Cubeba* Fruit Extract; Locust bean gum; Long oil alkyd resin; Low ash additive; Lube oil additive containing polybutylene in oil; Lubricating oils, petroleum, $C_{15\text{-}30}$, hydrotreated neutral oil-base; Lubricating oils, petroleum, hydrotreated spent; Lubricity additive mixture; Lyase, pectate; Lysine; Lysine HCL; m-Phenylenebis(methylamine); *Macadamia* oil; Magnesium aluminum silicate; Magnesium aluminum starch octenylsuccinate; Magnesium ascorbyl phosphate; Magnesium ascorbyl phosphate; Magnesium aspartate; Magnesium carbonate; Magnesium Carbonate Hydroxide; Magnesium chloride anhydrous; Magnesium Chloride Hexahydrate; Magnesium Citrate; Magnesium cocoate; Magnesium fluoride; Magnesium fluorosilicate (MgSiF6), hexahydrate; Magnesium Gluconate; Magnesium Hydroxide; Magnesium Isododecylbenzenesulfonate; Magnesium laurate; Magnesium lauryl sulfate; Magnesium Myristate; Magnesium nitrate; Magnesium oxide; Magnesium peroxide; Magnesium powder (pyrophoric); Magnesium silicate; Magnesium silicates, hydrated; Magnesium stearate; Magnesium sulfate; Magnesium sulfate; Magnesium sulfate heptahydrate; Magnesium tallowate; Magnesium Trisilicate; Magnetite ($Fe_3O_4$); *Magnolia* oil; Malachite green; Malathion; Maleic acid; Malic acid; Malic acid, L-; Mallow extract; Maltitol; Maltodextrin; Mancozeb; Mandarin oil; Mandarin orange, ext.; Manganese; Manganese 2-ethylhexanoate; Manganese acetate; Manganese compound/solution (unspecified); Manganese Dioxide; Manganese EDTA, disodium salt; Manganese ferrite black spinel; Manganese gluconate; Manganese naphthenate; Manganese oxalate; Manganese oxide; Manganese sesquioxide; Manganese sulfate anyhydrous; Manganese violet; Mango extract; Mannanase; Mannitol; Manure; Marigold (*calendula*) oil; Marigold extract; *Matricaria (chamomilla recutita)* extract; MDI (polymeric); MEA laureth sulfate; MEA-Oleate; Meadowfoam seed oil; Meadowseed (*Spiraea ulmaria*) extract; Meadowsweet extract; Mecoprop-dimethylammonium; Mecoprop-p; Mecoprop-P-potassium [ISO]; *Melaleuca alternifolia* extract (Tea tree oil); Melamine; Melamine, formaldehyde, toluenesulfonamide polymer; *Melia azedarach* Linn., extract; *Melissa Officinalis* Leaf Extract; Melon extract; *Mentha Aquatica* Flower/Leaf/Stem Extract; *Mentha arvensis* (peppermint) leaf oil; *Mentha citrata* (mint) oil; Menthol; Menthol (Racementhol); Menthol, L-; Menthyl anthranilate; Menthyl lactate; Mercaptobenzothiazole; Mercury; Mesitylene (1,3,5-Trimethylbenzene); Metalaxyl-M; Metaldehyde; Metaldehyde [BSI:ISO]; Methacrylate copolymer; Methacrylate polymer; Methacrylic acid; Methacrylic esters mixture; Methanol; Methanone, (1-hydroxycyclohexyl)phenyl-; Methenamine; Methicone; Methionine; Methoprene; Methoxychlor; Methoxydiglycol; Methoxyethanol; Methoxymethylbutanol; Methoxypropylgluconamide; Methoxysilyl capped polyether; Methoxytriglycol; Methyacrylate Copolymer; Methyl 2-Octynoate; Methyl acetate; Methyl anthranilate; Methyl benzoate; Methyl bis[ethyl(tallowate)]-2-hydroxyethyl ammonium-methyl sulfate; Methyl cyclohexane; Methyl D-tyrosinate HCl; Methyl derivatives of diazotized 4-aminoazobenzene coupled to x-heptyl-2-naphthol isomers and homologues; Methyl diisopropyl propionamide; Methylethyl ketone; Methylethyl ketone peroxide; Methylethyl ketoxime; Methyl glucose sesquistearate; Methyl isoamyl ketone; Methyl isobutyl ketone; Methyl methacrylate monomer (MMA); Methyl n-amyl ketone; Methyl nitrate; Methyl nonyl ketone; Methyl oleate; Methyl palmitate; Methyl Perfluoroisobutyl Ether; Methyl Propyl Ketone; Methyl salicylate; Methyl soyate; Methyl tri(ethylmethylketoxime) silane; Methyl-1H-benzotriazole; Methylcellulose; Methylchloroisothiazoline; Methylchloroisothiazolinone; Methylchloroisothiazolinone/Methylisothiazolinone (3/1) mixture; Methylcyclopentane; Methyldibromoglutaronitrile; Methyldihydrojasmonate; Methyldimethoxy polydime-siloxane; Methylene bis(thiocyanate); Methylene bisphenyl diisocyanate (MDI); Methylene blue; Methylene chloride; Methylene glycol; Methylene urea; Methylisothiazoline; Methylisothiazolinone; Methylisothiazolinone; Methylparaben; Methylpropanediol; Methylsilanol PEG-7 Glyceryl Cocoate; Methyltriacetoxysilane; Methyltrimethoxysilane; Metofluthrin; Metronidazole; Mica; Mica (unspecified type); Miconazole Nitrate; Microbial mixture; Microcrystalline cellulose (microfibers); Microcrystalline wax; Micronized Black 1080; Milk protein, casein, hydrolyzed; Milk Thistle extract; Milk, nonfat dry; *Mimosa* wax; Mineral colloid; Mineral filler(s); Mineral oil (unspecified); Mineral oil USP; Mineral oil, white; Mineral spirits; Mineral spirits (odorless, unspecified); Mineral spirits, odorless; Minoxidil; Mint oil, dementholized; Mixed alkyl borate esters; Mixed dialkyl ($C_8$-$C_{10}$) dimethyl ammonium chloride; Mixture Emulsion Asphalt; Mixture of polymers & polysiloxanes; Modified acrylic copolymer; Modified acrylic emulsion; Modified acrylic emulsion copolymer; Modified acrylic vinyl emulsion; Modified phthalic glycerol alkyd resins; Modified polyacrylate; Modified polymer emulsion; Modified Polymeric MDI; Modified polyurethane aqueous dispersion; Modified starch; Molasses; Molybdenum; Molybdenum disulfide; Molybdenum, N,N-bis($C_{11\text{-}14}$-branched and linear alkyl)carbamodithioate oxo thioxo complexes; Molybdic oxide; Monoethanolamine (MEA); Monoethanolamine borate; Monoethanolamine citrate; Monoisopropanolamine borate; Monosodium acid methanearsonate; Monosodium phosphate; Montan Cera; Montmorillonite; Moonflower; Morpholine; Morpholine, 4,4'-(oxydi-2,1-ethanediyl)bis-; MSDS: Contains no known hazardous ingredients.; MSDS: No reportable quantities of hazardous materials present; MSDS: Proprietary or trade secret ingredient(s); Mucopolysaccharides, hydrolyzed; Mucoprotein, soluble; Muguet (lily-of-the-valley oil); Mulberry extract; Multisterol extract; Muscovite; Mushroom oil; Musk(s); Mustard oil; Myclobutanil; Myrcene; *Myrciaria Dubia* Fruit Extract; Myreth-3 myristate; Myristalkonium Saccharinate; Myristamidopropylamine Oxide; Myristic acid; *Myristica Fragrans* Oil; Myristoyl hydrolyzed collagen; Myristyl alcohol; Myristyl dimethyl amine oxide; Myristyl dimethyl benzyl ammonium chloride; Myristyl lactate; Myristyl myristate; Myrrh; Myrtocyan (Bilberry extract); N,N'-(Piperazinediylbis(2,2,2-trichloroethylidene)) bis(formamide); N,N'-Disalicyclidene-1,2-propanediamine; N,N-bis(2-Hydroxyethyl)-p-phenylenediamine sulfate; N,N-Diethyl-meta-toluamide; N,N-Dimethylstearamide; N,N-Diphenylamine; N-(3-(Trimethoxysilyl)propyl)ethylenediamine; n-alkyl (50% $C_{12}$, 30% $C_{14}$, 17% $C_{16}$, 3% $C_{18}$) dimethyl benzyl ammonium chlorides; n-alkyl (50% $C_{12}$, 30% $C_{14}$, 17% $C_{16}$, 3% $C_{18}$) dimethyl ethylbenzyl ammonium chlorides; N-Alkyl ($C_{12-16}$) dimethylamine oxide(s); n-Alkyl ($C_{12}$, 68%, $C_{14}$, 32%) dimethyl ethylbenzyl ammonium chloride; n-Alkyl($C_{14}$, 60%; $C_{16}$, 30%; $C_{12}$, 5%; $C_{18}$, 5%) dimethylbenzyl ammonium chloride; N-Aminopropylmorpholine; n-butane; N-Dodecyl methacrylate; N-ethyl menthyl carboxamide; N-Ethyl perfluorooctane sulfonamide; N-Isotridecyloxypropyl trimethylenediamine; N-Methylolacrylamide; N-Methylpyrrolidone; N-Octyl bicycloheptene dicarboximide (MGK 264); N-Octylbicycloheptene dicarboximide; N-Phenyl-p-phenylenediamine; Naphtha (petroleum), light steam-cracked arom., polymer with light steam-cracked arom. petroleum naphtha piperylene conc. and m; Naphtha (petroleum), solvent-refined light; Naphtha (VM&P); Naphtha, medium aliphatic; Naphtha, petroleum, heavy alkylate; Naphtha, petroleum, heavy straight-run; Naphtha, petroleum, hydrotreated heavy; Naphtha, petroleum, hydrotreated light; Naphtha, petroleum, light alkylate; Naphthalene; Naphthalenesulfonic acid, dinonyl-, calcium salt; Naphthenic petroleum oil mixture (64742-53-6/64742-52-5); *Narcissus jonquilla* extract; Natural gum; Natural Methyl Ester; Neatsfoot oil; Nectarine; Neem oil; Neodecanoic acid, sodium salt; Neopentyl glycol dioctanoate; Nepheline syenite; Nettle extract; Neutralized heavy naphthenic petroleum distillates; Niacin; Niacinamide (Vitamin B); Nickel; Nicotine; Nitraline; Nitrate nitrogen; Nitric acid; Nitrocellulose; Nitroethane; Nitrofurazone; Nitrogen (propellant); Nitromethane; *Nitrosomonas*; Nitrosospira; Nitrospira; Nitrous oxide; NJTS 50173VE; No ingredients in this product are hazardous as defined by the Department of Labor.; No MSDS required; Non-hazardous ingredient(s); Nonane; Nonanoyloxy Benzene Sulfonate; Nonionic emulsifier; Nonionic surfactant(s) (unspecified); Nonoxynol; Nonoxynol-10; Nonoxynol-2; Nonoxynol-4; Nonoxynol-9; Nonoyl Nonoxynol-49; Nonpathogenic bacteria; Nonyl phenol; Nonylphenol; Nonylphenoxy poly(ethyleneoxy) ethanol, branched; Nonylphenyl polyethoxylate; Nonylphenyl polyethylene glycol ether (mixture); Novaluron; Nuisance dust; Nutmeg extract; Nylon (unspecified); Nylon-12; Nylon-6; *Nymphaea Alba* Flower Extract; O-Cresyl glycidyl ether; o-Dichlorobenzene; o-Phenylphenol; Oak moss absolute; Oat extract; Oat flour; Oat Kernel Oil; Oatmeal, colloidal; *Ocimum basilicum* (basil) oil; *Ocimum sanctum*, ext.; Octadecanoic acid; Octamethylcyclotetrasiloxane, silica reaction product; Octamethylcydotetrasiloxane; Octane improver; Octenyl succinate; Octocrylene; Octoxynol 9; Octoxynol-1; Octoxynol-13; Octrizole; Octyl cocoate; Octyl dimethyl PABA; Octyl ethoxycinnamate; Octyl hydroxystearate; Octyl isononanoate; Octyl methoxycinnamate; Octyl palmitate; Octyl phenyl ether; Octyl salicylate; Octyl stearate; Octyl triethoxy silane; Octyl/decyl alcohol, ethoxylated; Octylacrylamide/Acrylates copolymer; Octylacrylamide/acrylates/butylaminoethyl methacrylate copolymer; Octyldimethylamine oxide; Octyldodecanol; Octyldodecanol; Octyldodecyl myristate; Octyldodecyl neopentanoate; Octyldodecyl stearoyl stearate; Octylphenol polyethoxylate; Octylphenoxypoly(ethoxyethanol); Octylphosphonic acid; Octyltriethoxysilane; Odor eliminator derived from corn; Oil-100 sol. Neutral; Oil modified polyurethane; Oil of Lemon *Eucalyptus*; Oils, *eucalyptus, E. citriodora*; Oils, reclaimed; Oils, red pepper, paprika; Olealkonium chloride; Oleamide MIPA; Oleamidopropyl betaine; Oleamine Oxide; Olefin copolymer; Oleic acid; Oleth-10; Oleth-16; Oleth-2; Oleth-3; Oleth-3 phosphate; Oleth-5; Oleyl alcohol; Oleylpolyoxethylene glycol ether (Oleth-2); Olive oil; Opacifier; Orange (Citris aurantium *dulcis*) extract; Orange 5; Orange blossom oil; Orange colorant; Orange leaves; Orange oil; Orange peel wax; Orange roughy oil; Oregano (*Lippia* spp.); Organic acid(s) (unspecified); Organic ion exchange resin(s); Organo-Chromium compound (unspecified); Organofunctional silicon compound; ortho-Xylene; Other fragrance(s); Oxalic acid; Oxalic acid dihydrate; Oxirane, 2,2'-((1-methylethylidene)bis(4,1-phenyleneoxy(1-(butoxymethyl)-2,1-ethanediyl)oxymethylene))bis-; Oxirane, 2-methyl-, polymer with oxirane, mono(2-propylheptyl) ether; Oxirane, methyl-, polymer with oxirane, monohexyl ether; Oxybis(dodecyl benzenesulfonic acid), disodium salt; Oxychlorine compounds (unspecified); Oxyfluorfen; Ozokerite; p-Aminophenol; p-Anisic acid; p-Chloro-o-benzylphenol; P-Cymene; p-Dichlorobenzene; p-Menthane-3,8-diol; p-Methylaminophenol sulfate; p-Phenylenediamine; p-Phenylenediamine sulfate; p-Xylene; Palm acid; Palm glyceride; Palm kernel acid; Palm kernel oil; Palm Kernelamide Dea; Palm kernelate (unspecified type); Palmaria *palmata* extract; Palmarosa oil; Palmatine; Palmitamidohexadecanediol; Palmitic acid; Palmitoyl myristyl serinate; palmitoyl oligopeptide; Palmitoyl Pentapeptide-3; Palmitoyl Pentapeptide-4; Palmitoyl tetrapeptide; Palmitoyl tetrapeptide-7; Pancreatic Amylase; Pancreatin; Pantethine; Panthenol; Panthenol liposomes; Panthenol, DL-form; Panthenyl ethyl ether; Panthenyl Hydroxypropyl Steardimonium Chloride; Panthenyl Triacetate; Pantolactone; Pantothenic Acid; *Papaya* extract; Paper facing or substrate; Para Tertiary Amylphenol; para-Aramid fibrils; Paraben preservatives; Paraffin; Paraffin oil; Paraffin oils (petroleum), catalytic dewaxed light; Paraffin waxes, petroleum, clay-treated; Paraffin waxes, petroleum, hydrotreated; Paraffin(s) (unspecified); Paraffinic base oil (unspecified); Paraffinic oil, lightly refined; Paraffins, petroleum, normal $C_{5-20}$; Particulates not otherwise regulated; *Passiflora Incarnata* Extract; Passion flower extract; Passion fruit; Patchouli oil; PCMO additive; PE Color Conc Blue 1635C PEC; PE Color Conc Magenta 1435C PEC; Peach extract; Peanut butter; Peanut oil; Pear extract; Pearl Powder; Pectin; PEG 120; PEG 120 Methyl Glucose Dioleate; PEG 600; PEG 90 Diisostearate; PEG-100 Stearate; PEG-12 Dimethicone; PEG-10; PEG-10 Cocoate; PEG-10 Dimethicone; PEG-10 soya sterol; PEG-100; PEG-100 Stearate; PEG-12; PEG-12 Dimethicone; PEG-12 Dimethicone; PEG-12 distearate; PEG-120 Methyl glucose dioleate; PEG-120 methyl glucose trioleate; PEG-14M; PEG-15 cocamine; PEG-15 cocopolyamine; PEG-15 tallow polyamine; PEG-150; PEG-150 distearate; PEG-150 pentaerythrityl tetrastearate; Peg-150/Stearyl/SMDI Copolymer; PEG-16 soy sterol; PEG-18 Glyceryl Cocoate; PEG-18 glyceryl oleate/cocoate; PEG-180; PEG-2 Dimeadowfoamamidoethylmonium Methosulfate; PEG-2 Oleamine; PEG-2 Soyamine; PEG-2 sulfosuccinate; PEG-2 tallow amine; PEG-20 Almond glycerides; PEG-20 glycerides; PEG-20 methyl glucose sesquistearate; PEG-200; PEG-200 glyceryl tallowate; Peg-200 Hydrogenated Glyceryl Palmate; PEG-2M; PEG-3 Dioleoylamidoethylmonium methosulfate; PEG-30 Dipolyhydroxystearate; PEG-32; PEG-35 castor oil; PEG-4; PEG-4 Laurate; PEG-40; PEG-40 hydrogenated castor oil; PEG-40 stearate; PEG-5 cocoamide; PEG-5 soy sterol; PEG-5 stearamine; PEG-5 tallow amide; PEG-50 hydrogenated palmamide; PEG-50 Tallow amide;

PEG-55; PEG-5M; PEG-6; PEG-6 caprylic; PEG-6 Caprylic/capric glycerides; PEG-6 methyl ether; PEG-60 (Polysorbate 60); PEG-60 almond glycerides; PEG-60 lanolin; PEG-65 Lanolin oil; PEG-7; PEG-7 Glyceryl Cocoate; PEG-75; PEG-75 Lanolin oil; PEG-75 Soy glycerides; PEG-7M; PEG-8; PEG-8 dilaurate; PEG-8 Dimethicone; PEG-8 distearate; PEG-8 hydrogenated tallow amine; PEG-8/SMDI copolymer; PEG-80; PEG-80 Glyceryl cocoate; PEG-80 laurate; PEG-80 sorbitan laurate; PEG-80 Sorbitan Palmitate; PEG-90M; PEG/PPG 116/66 Copolymer; PEG/PPG 18/18 Dimethicone; PEG/PPG-17/6 copolymer; PEG/PPG-18/18 Dimethicone; Pei-14 PEG-10/PPG-7 Copolymer; Pelargonic acid; Pelvetia *Canaliculata* Extract; Pendimethalin; Pennyroyal oil; Pentadecalactone; Pentadecane; Pentaerythritol rosinate; Pentaerythritol tetra(2-ethylhexanoate); Pentaerythritol tetraisostearate; Pentaerythritol, phthalic anhydride, soybean oil polymer; Pentaerythrityl hydrogenated rosinate; Pentaerythrityl Tetra-Di-T-Butyl Hydroxyhydrocinnamate; Pentaerythrityl tetrabehenate; Pentaerythrityl tetracaprylate/caprate; Pentaerythrityl tetrastearate; Pentaethylene glycol; Pentaethylene glycol, monobutyl ether; Pentahydrosqualene; Pentane; Pentane, 1,1,1,2,2,3,4,5,5,5-decafluoro-; Pentapotassium triphosphate; Pentasodium pentetate; Pentasodium triphosphate; Pentasodium tripolyphosphate; Pentylene Glycol; Peony extract; Pepper oil; Peppermint extract; Peppermint oil; Peppermint oil; Perfluorooctyl triethoxysilane; Perfluoropolyether mixture; Perfume oils (mixture); *Perilla ocymoides* leaf extract; Perlite; Perlite; Permethrin; Petrolatum; Petroleum basestocks; Petroleum distillate(s) (unspecified); Petroleum distillate, steam-cracked, polymers with light steam-cracked petroleum naphtha; Petroleum distillates; Petroleum distillates (JP5 Jet fuel); Petroleum gases, liquefied; Petroleum gases, liquefied, sweetened; Petroleum lubricant; Petroleum oil; Petroleum oil (unspecified); Petroleum resins; Petroleum spirits; PG-Hydroxyethylcellulose cocodimonium chloride; PG-hydroxyethylcellulose stearyldimonium chloride; Phantolid; Phenol; Phenol, 4-methyl-, reaction products with dicyclopentadiene and; Phenol, polymer with formaldehyde, glycidyl ether; Phenolic resin; Phenolphthalein; Phenoxyisopropanol; Phenyl dimethicone; Phenyl Esters; Phenyl methyl pyrazolone; Phenyl trimethicone; Phenyl, propyl silicone resin; Phenylalanine; Phenylbenzimidazole sulfonic acid; Phenylenediamino Triazine; Phenylpropyl Ether Methicone; Phenylpropyldimethyl/Triethyl siloxysilicate; Phosphate; Phosphated polyol; Phospholipids (unspecified type); Phosphonobutanetricarboxylic Acid; Phosphoric acid; Phosphorus; Phosphorus acid; Phthalic anhydride/trimellitic anhydride/glycol copolymer; Phthalic anhydride/Trimellitic anhydride/Glycols copolymer; Phthalic/glycerol alkyl resin; Phytantriol; Phytantriol panthenol; Phytol; Phytosphingosine; Pigment (proprietary); Pigment Violet 23; Pine needle extract; Pine oil; Pineapple protease; Pinetree extract; *Pinus Palustris* Wood Tar; Piperine; Piperonyl butoxide; Plantain; Plantain extract; Plaster of paris; Plum extract; Polihexanide; Polishing powder; Polixetonium chloride; Poloxaflo 4370; Poloxamer; Poloxamer 124; Poloxamer 407; Poloxamine 1101; Poloxapol 1220; Poly(acrylamide-co-acrylic acid); Poly(alpha-olefins); Poly(oxy(methyl-1,2-ethanediyl)), alpha-(((3-; Poly(oxy(methyl-1,2-ethanediyl)), alpha-hydro-omega-hydroxy-, ether with 2,2-bis(hydroxymethyl)-1,3-propanediol (4:1), 2-hydroxy; Poly(oxy-1,2-ethanediyl); Poly(oxy-1,2-ethanediyl), alpha,alpha'-(((3-(decyloxy)propyl)methyliminio)di-2,1-ethanediyl)bis(omega-hydroxy-, branched; Poly(oxy-1,2-ethanediyl), alpha-(1,3-dimethyl-1-(2-methylpropyl)hexyl)-omega-hydroxy-; Poly(oxy-1,2-ethanediyl), alpha-(2-(bis(2-aminoethyl)methylammonio) ethyl)-omega-hydroxy-, N,N'-di-$C_{14-18}$ acyl derivs., Me sulfa; Poly(oxy-1,2-ethanediyl), alpha-(4-nonylphenyl)-omega-hydroxy-, branched; Poly(oxy-1,2-ethanediyl), alpha-isodecyl-omega-hydroxy-; Poly(oxy-1,2-ethanediyl), alpha-undecyl-omega-hydroxy-, branched and linear; Poly-TFE; Polyacrylamide; Polyacrylamidomethylpropane Sulfonic Acid; Polyacrylate-15; Polyacrylic acid emulsion; Polyacrylic emulsion; Polyalkenyl phenol; Polyalkylene glycol; Polyalkylmethacrylate; Polyamide resin; Polyamino sugar condensate; Polyaminopropyl biguanide stearate; Polyaspartic acid; Polybutadiene; Polybutene; Polybutene amine mixture; Polybutenylsuccinimide/amide; Polybutylene terephthalate; Polycyclopentadiene; Polydecene; Polydialkylsiloxanes; Polydimethylsiloxane; Polydimethylsiloxanes (Silicon oil); Polyester resin (proprietary); Polyether amine mixture; Polyether poly blend; Polyethylene; Polyethylene glycol (5) undecyl ether; Polyethylene glycol 1000 monocetyl ether; Polyethylene glycol ethyl ether; Polyethylene glycol, monobutyl ester; Polyethylene glycols (unspecified); Polyethylene oxide (crosslinked); Polyethylene oxide, dehydroabietylamine polymer; Polyethylene terephthalate; Polyethylene terephthalate (PET); Polyethylene, chlorosulfonated; Polyethylene, oxidized; Polyethylene-High Density; Polyethylene-polypropylene glycol; Polyethylene/polypropylene glycol ethyl ether; Polyethylene/Polypropylene Glycol Methyl Ether; Polyethyleneimine; Polyethyleneoxyethanol; Polyethylenepolyamine, dimer fatty acid condensate; Polyfunctional alcohol; Polyglyceryl-10 decaoleate; Polyglyceryl-10 Diisostearate; Polyglyceryl-10 Laurate; Polyglyceryl-2 oleyl ether; Polyglyceryl-3 Diisostearate; Polyglyceryl-3 diisostearate; Polyglyceryl-3 Laurate; Polyglyceryl-4 isostearate; Polyglyceryl-4 oleyl ether; Polyglyceryl-4-oleate; Polyglyceryl-6 Isostearate; Polyglyceryl-6 polyricinoleate; Polyglycerylmethacrylate; Polyglycol ester; Polyglycol oleate; Polyglycoside surfactant; Polyhydroxystearic Acid; Polyisobutane, hydrogenated; Polyisobutene; Polyisobutene, hydrogenated; Polyisocyanurate; Polymer coated sulfur coated urea; Polymer coated urea; Polymer JR; Polymer JR-400; Polymer mixture/emulsion; Polymer wax blend (unspecified); Polymer(s) (unspecified); Polymeric disperant solution; Polymeric mercaptan (Trade Secret); Polymeric Terpenes; Polymethacrylamidopropyltrimonium chloride; Polymethyl methacrylate; Polymethylenepolyphenylisocyanate, propoxylated glycerin polymer; Polymethylhydrogensiloxane; Polymethylsilsesquioxane; Polyol (proprietary); Polyolefin alkyl; Polyolefin mixture; Polyolefin phenolic amine; Polyolefin polyamine succinimide, Molybdenum complex; Polyox PEG 7m; Polyoxyethylated (6) isodecyl alcohol; Polyoxyethylated stearyl alcohol (Steareth-2); Polyoxyethylene hexaoleate; Polyoxyethylene isohexadecyl ether; Polyoxypropylene methylethyl ammonium chloride; Polyperfluoromethylisopropyl ether; Polyphosphoric acid; Polypropylene; Polypropylene, maleic anhydride polymer; Polypropyleneglycol diglycidyl ether; Polyquart Ampho 149; Polyquaternary amine in water; Polyquaternium-10; Polyquaternium-11; Polyquaternium-16; Polyquaternium-22; Polyquaternium-28; Polyquaternium-37; Polyquaternium-4; Polyquaternium-46; Polyquaternium-47; Polyquaternium-6; Polyquaternium-68; Polyquaternium-7; Polysaccharide(s); Polysilicone-15; Polysorbate 20; Polysorbate 80; Polysorbate 85; Polystyrene; Polystyrene resins; Polysulfides, di-tert-Bu; Polytetrafluoroethylene (PTFE); Polyurethane; Polyurethane oligimer; Polyurethane-11; Polyurethane-8; Polyvinyl acetate; Polyvinyl acetate emulsion; Polyvinyl alcohol;

Polyvinyl chloride (PVC); Polyvinylpyrrolidone (PVP); Poly[oxyethylene(dimethyliminio) ethylene(dimethyliminio)ethylene] dichloride; *Porphyra Umbilicalis* Extract; Portland cement; *Portulaca oleracea*, ext.; Potassium 2-ethylhexanoate; Potassium acesulfame; Potassium acrylinoleate; Potassium aspartate; Potassium bicarbonate; Potassium C9-C15 alkyl phosphate; Potassium carbonate; Potassium cetyl phosphate; Potassium chloride; Potassium cis-9-octadecenoic acid; Potassium Citrate; Potassium cocoate; Potassium cocoyl hydrolyzed collagen; Potassium Dodecylbenzenesulfonate; Potassium Gluconate; potassium hydrogensulphate; Potassium hydroxide; Potassium iodide; Potassium lactate; Potassium laurate; Potassium Laureth Phosphate; Potassium lauryl sulfate; Potassium magnesium sulfate; Potassium methyl siliconate; Potassium monopersulfate; Potassium myristate; Potassium nitrate; Potassium octoxynol-12 phosphate; Potassium oxalate monohydrate; Potassium oxide; Potassium palmitate; Potassium peroxymonosulfuric acid; Potassium persulfate; Potassium phosphate; Potassium phosphate, tribasic; Potassium polysilicate; Potassium siliconate; Potassium siliconate solution; Potassium soap of tall oil fatty acids (C18); Potassium soap of vegetable oil; Potassium sorbate; Potassium Sorbate [USAN]; Potassium stearate; Potassium sulfate; Potassium tallate; Potassium tallowate; Potassium thioglycolate; Pour point depressant; Povidone-Iodine; PPG 2 Isoceteth 20 Acetate; PPG-1 hydroxyethyl caprylamide; PPG-10 butanediol; PPG-10 glyceryl ether; PPG-10 Methyl Glucose Ether; PPG-10-Buteth-9; PPG-10-Laureth-7; PPG-11 stearyl ether; PPG-12 PEG-65 lanolin; PPG-12-Buleth-16; PPG-12-PEG-50 lanolin; PPG-12-PEG-65 Lanolin Oil; PPG-14 Butyl ether; PPG-17/ipdi/DMPA copolymer; PPG-2 ceteareth-9; PPG-2 Hydroxyethyl cocamide; PPG-2 Hydroxyethyl Coco/Isostearamide; PPG-2 myristyl ether propionate; PPG-24-glycereth-24; PPG-26 Oleate; PPG-3 hydroxyethyl soyamide; PPG-3 myristyl ether; PPG-30 Cetyl ether; PPG-4 Laureth-2; PPG-4 Laureth/Myreth-5; PPG-5 lanolin wax; PPG-5 Laureth-5; PPG-5-Ceteth-20; PPG-51/SMDI copolymer; PPG-6 C12-15 Pareth-12; PPG-66-glycereth-12; PPG-9 diethylmonium chloride; Prallethrin; Pramoxine hydrochloride; Pregnenolone acetate; Prepolymer of MDI and polyether polyol; Preservative(s) (unspecified); Process oil & Dispersant II; Processing aid(s); Prodiamine; Proline; Prometon; Propane; Propane, 2-methoxy-1-(2-methoxy-1-methylethoxy)-; Propane/Butane propellant; Propanoic acid, 2-hydroxy-, (2S)-; Propanol; Propellant (unspecified); Propellant blend; Propiconazole; Propionic acid; Propolis Extract; Propoxur; Propoxypropanol; Proprietary biocide; Proprietary coated mica; Proprietary Polyamine; Propyl acetate; Propyl gallate; Propylamine, 3-(isodecyloxy)-, acetate; Propylbenzene; Propylene carbonate; Propylene glycol; Propylene glycol 2-butyl ether; Propylene glycol alginate; Propylene glycol butyl ether; Propylene Glycol Ceteth-3 Acetate; Propylene glycol diacetate; Propylene glycol dicaprylate/dicaprate; Propylene glycol laurate; Propylene glycol monobutyl ether; Propylene glycol oleate; Propylene glycol phenyl ether; Propylene glycol stearate; Propylene glycol t-butyl ether; Propylene oxide; Propylene oxide, propylene glycol polymer (PPG-9); Propylidynetrimethyl trimethacrylate; Propylparaben; Protease enzyme (unspecified); Proteinase; *Prunus africana* extract; *Prunus amygdalus dulcis; Prunus Persica* Nectarina Fruit Extract; *Prunus Serrulata* Flower Extract; Prussian blue; *Psidium Guajava* Fruit Extract; *Pueraria thunbergiana* extract; Pullulan; Pumice; *Punica granatum* fruit juice; Punicaceae; Putrescent whole egg solids; PVM/MA copolymer; PVM/MA decadiene crosspolymer; PVP/Dimethylaminoethyl-methacrylate copolymer; PVP/Hexadecene copolymer; PVP/Hydrolyzed wheat protein crosspolymer; PVP/VA copolymer; Pyrethrin II; Pyrethrins; Pyrethrum; Pyrethrum (Pyrethrins) (unspecified CAS #); Pyridine, 3,5-diethyl-1,2-dihydro-1-phenyl-2-propyl-; Pyridoxine hydrochloride (Vitamin B6 hydrochloride); Pyriproxyfen; Pyronyl; Quality control agent(s); Quarbean powder; Quartz; Quartz; Quaternary ammonium bentonite; Quaternary ammonium compounds; Quaternary ammonium compounds, cocoalkylbis (hydroxyethyl)methyl, ethoxylated, chlorides; Quaternary ammonium compounds, Di-(C14-C18 Alkyl), Methyl sulfate surfactant blend; Quaternary ammonium montmorillonite; Quaternary fatty amine ethoxylate; Quaternium-15; Quaternium-18; Quaternium-18 bentonite; Quaternium-18 hectorite; Quaternium-22; Quaternium-52; Quaternium-53; Quaternium-79; Quaternium-79 hydrolyzed milk protein; Quaternium-80; Quaternium-84; *Quillaja saponaria* extract; Quince seed extract; Quinclorac; Quinine hydrochloride; Raffinates (petroleum), sorption process; Rare earth oxide; Raspberry leaf extract; Reacted urethane prepolymer, mixture; reaction mass of isomers of: $C_{7-9}$-alkyl 3-(3,5-di-tert-butyl-4-hydroxyphenyl)propionate; Red 30 Lake; Red 4; Red 40 Lake; Red dye; Refined coal tar pitch; Refractory ceramic fibers; Residual oils, (petroleum), solvent deasphalted; Residual oils, petroleum, hydrotreated; Residual oils, petroleum, solvent dewaxed; Residual oils, petroleum, solvent-refined; Resin (unspecified); Resin acids and Rosin acids, esters with triethylene glycol; Resin acids and rosin acids, hydrogenated, esters with pentaerythritol; Resin acids and Rosin acids, hydrogenated, esters with triethylene glycol; Resin acids and Rosin acids, sodium salts; Resmethrin; Resorcinol; Retinol (Vitamin A); Retinol A; Retinyl acetate; Retinyl palmitate; Retinyl Propionate; Rhatania root extract; Rhubarb extract; Rice bran oil; Rice bran wax; Ricinoleamidopropyl ethyldimonium ethosulfate; *Ricinus* oil (Castor oil); Ridomil; *Rosa centifolia* extract; Rose extract; Rosemary extract; Rosemary oil; Rosewood oil; Rosin; Rosin ester mixture; Rosin, polymerized; Rotenone; Rubber curing ingredients; Rubber, natural; Rubber, synthetic; *Russelia Equisetiformis* Leaf/Stem Extract; Rust inhibitor/preventive; Rutile (Titanium dioxide); Rutin; S-Bioallethrin; Saccharide isomerate; Saccharin; *Saccharomyces* lysate extract; *Saccharomyces*/Zinc ferment; *Saccharum Officinarum* Extract Sugar Cane; Safflower oil; Sage extract; Sage oil; Salicylic acid; Sandalwood oil/extract (unspecified); Sandoplast Violet; *Saponaria Officinalis* Leaf Extract; Sargassum extract; Sargassum Filipendula Extract; Sarsaparilla extract; Savinase 16L enzyme; Saw palmetto extract; Sawdust; *Saxifraga sarmentosa* extract; *Sclerocarya Birrea* Seed Oil; Scleroglucan; *Scutellaria baicalensis* extract; SD Alcohol 38B; SD Alcohol 39C; SD Alcohol 40C; Secondary alkane sulphonate; Sefa cottonate; Selenium; Selenium disulfide; Selenium sulfide; Sepiolite; Sequestrant; Serine; Sesame oil; Sethoxydim; Severely refined mineral oils (unspecified); Severely refined petroleum basestocks; Shale, expanded; Shale, expanded, aggregates; Shea butter; Shellac; Shellac wax; Silanamine, 1,1,1-trimethyl-N-(trimethylsilyl)-, hydrolysis products with silica; Silane (unspecified); Silane, dichlorodimethyl-, reaction products with silica; Silane, trimethoxy(2-methylpropyl)-; Silanol/Siloxane polymers; Silica (crystalline); Silica (unspecified); Silica and silicones (mixture); Silica Dimethicone Silylate; Silica dimethyl silylate; Silica fume, amorphous; Silica gel; Silica silylate; Silica, amorphous (Diatomaceous silica); Silica, crystaline; Silica, crystalline (unspecified type); Silica, crystalline-tridymite; Silica, hydrate; Silica, reaction product with chlorotrimethylsilane; Silicate; Silicate mineral (unspecified); Silicic acid; Silicic acid ($H_4SiO_4$), tetraethyl ester, hydrolysis products with chlorotrimethylsilane; Silicic acid, aluminum postassium salt (Feldspar); Silicic acid, aluminum salt; Silicic acid, diethoxyoctylsilyl trimethylsilyl ester; Silicic acid, disodium salt; Silicic acid, lithium salt; Siliconates (unspecified); Silicone emulsion/solution; Silicone fluid; Silicone glycol; Silicone quaternium-13; Silicone resin (unspecified); Silicones mixture; Silk Amino Acids; Silk peptide; Silk protein; Silk protein, hydrolyzed; Siloxanes and silicones; Siloxanes and Silicones, di-Me, hydroxy-terminated; Siloxanes and Silicones, di-Me, polymers with 3-((2-aminoethyl)amino)propyl silsesquioxanes, hydroxy-terminated; Silver; Silver chloride; Silyl terminated polyether; Simazine; Simethicone; Smectite; Snow floss; Soap (unspecified); Sodium 1-methyl 2-sulfolaurate; sodium 2-(nonanoyloxy)benzenesulfonate; sodium 2-biphenylate; 2-phenylphenol, sodium salt; Sodium 2-mercaptobenzothiazole; Sodium Acetate; Sodium acid sulfate; Sodium Acrylate/Sodium Acryloyldimethyl Taurate Copolymer; Sodium Acrylates Copolymer; Sodium Acrylic Acid/MA Copolymer; Sodium alcohol sulfate; Sodium Alkyl Aryl Ether Sulfate; Sodium alkyl glycerol sulfonate; Sodium alkyl phenoxybenzene disulfonate mixture; Sodium alkyl sulfate; Sodium alkylaryl sulfonates; Sodium alkylbenzenesulfonate; Sodium alpha-sulfo methyl ester; Sodium aluminosilicate; Sodium aryl sulfonate; Sodium ascorbyl phosphate; Sodium bentazon; Sodium benzoate; Sodium benzotriazolyl butylphenol sulfonate; Sodium Benzotriazolyl Butylphenol Sulfonate 1; Sodium bicarbonate; Sodium bifluoride; Sodium bisulfite; Sodium borate decahydrate (borax); Sodium bromide [USP:JAN]; Sodium $C_{12-15}$ Pareth Sulfate; Sodium $C_{12-18}$ fatty alcohol sulfate; Sodium $C_{14-16}$ olefin sulfonate; Sodium $C_{14-17}$ alcohol sulfonate; Sodium $C_{14-17}$ Alkyl Sec Sulfonate; Sodium $C_{8-16}$ isoalkylsuccinyl lactoglobulin sulfonate; Sodium cacodylate; Sodium caprylyl sulfonate; Sodium carbomer; Sodium carbonate; Sodium carbonate monohydrate; Sodium carbonate peroxide; Sodium Carboxymethyl Inulin; Sodium Carboxymethyl Starch; Sodium cetearyl sulfate; Sodium chlorate; Sodium chloride; Sodium chondroitin sulfate; Sodium citrate (Trisodium citrate); Sodium citrate dihydrate; Sodium coco PG-dimonium chloride phosphate; Sodium Coco-Sulfate; Sodium cocoamphoacetate; Sodium cocoamphopropionate; Sodium cocoate; Sodium cocoglyceryl ether sulfonate; Sodium Cocoyl Glycinate; Sodium cocoyl isethionate; Sodium cocoyl sarcosinate; Sodium cumenesulfonate; Sodium cumenesulphonate; Sodium decylglucosides hydroxypropyl phosphate; Sodium dehydroacetate; Sodium di-n-octyl sulfosuccinate; Sodium dichloroisocyanurate; Sodium dichloroisocyanurate dihydrate; Sodium diethylaminopropyl cocoaspartamide; Sodium dihydrogen citrate; Sodium dodecyl diphenyl oxide disulfonate; Sodium dodecylbenzenesulfonate; Sodium Ethylhexyl Sulfate; Sodium fluoride; Sodium Formate; Sodium glucoheptonate dihydrate; Sodium gluconate; Sodium glutamate; Sodium glycolate; Sodium hyaluronate; Sodium hydrosulfite; Sodium hydroxide; Sodium hydroxymethane sulfinic acid; Sodium hydroxymethane sulfonate; Sodium hydroxymethylglycinate; Sodium Hydroxypropyl Starch Phosphate; Sodium hypochlorite; Sodium isethionate; Sodium isostearoamphopropionate; Sodium isostearoyl lactylate; Sodium lactate; Sodium laurate; Sodium laureth sulfate; Sodium laureth-13 carboxylate; Sodium laureth-4 phosphate; Sodium laurimmodipropionate; Sodium lauroampho PG; Sodium lauroampho PG-acetate phosphate; Sodium lauroamphoacetate; Sodium lauroyl isethionate; Sodium lauroyl lactylate; Sodium Lauroyl Oat Amino Acids; Sodium lauroyl sarcosinate; Sodium lauryl sarcosinate; Sodium lauryl sulfate (SLS); Sodium lauryl sulfoacetate; Sodium MA/Diisobutylene Copolymer; Sodium magnesium silicate; Sodium metabisulfite; Sodium metasilicate; Sodium metasilicate pentahydrate; Sodium Methyl 2-Sulfolaurate; Sodium methyl cocoyl taurate; Sodium methylparaben; Sodium molybdate; Sodium monofluorophosphate; Sodium myreth sulfate; Sodium myristoyl sarcosinate; Sodium N-methyl-N-oleoyl-taurate; Sodium nitrate; Sodium nitrite; Sodium nonanoyloxybenzenesulfonate; Sodium Nonoxynol-9; Sodium Nonoxynol-9 Phosphate; Sodium octyl sulfonate; Sodium olefin sulfonate; Sodium oleth sulfate; Sodium oleth-7 phosphate; Sodium oxide; Sodium palm kernelate; Sodium Palmate; Sodium palmitate; Sodium PCA; Sodium PEG-4 lauramide carboxylate; Sodium perborate; Sodium perborate monohydrate; Sodium perborate tetrahydrate; Sodium percarbonate; Sodium persulfate; Sodium petroleum sulfonate; Sodium Phenoxide; Sodium phosphate; Sodium phosphate monobasic monohydrate; Sodium phosphate, tribasic; Sodium Polyacrylate; Sodium polymetaphosphate; Sodium Polymethacrylate; Sodium polynaphthalenesulfonate; Sodium polystyrene sulfonate; Sodium Potassium Aluminum Silicate; Sodium potassium aluminum silicate; Sodium saccharin; Sodium saccharin dihydrate; Sodium Salicylate; Sodium salt of polymeric carboxylic acid; Sodium sesquicarbonate; Sodium silicate; Sodium silicates; Sodium silicates (unspecified); Sodium silicates, hydrated; Sodium silicofluoride; Sodium sorbate; Sodium stannate; Sodium stearate; Sodium stearoyl lactylate; Sodium styrene/Acrylates/Divinylbenzene copolymer; Sodium sulfamate; Sodium sulfate; Sodium sulfate anhydrous; Sodium sulfate decahydrate; Sodium sulfite; Sodium tallate; Sodium tallowate; Sodium tetraborate anhydrous; Sodium tetraborate pentahydrate; Sodium thioglycolate; Sodium thiosulfate; Sodium thiosulfate anhydrous; Sodium Toluenesulfonate; Sodium trideceth sulfate; Sodium trideceth-7 carboxylate; Sodium tridecylbenzenesulfonate; Sodium undecylbenzenesulfonate; Sodium xylenesulfonate; Softening agent(s) (unspecified); Soil prevention agent; Soil suspending agent(s); Sokalan; Soluble Collagen; Solvent (unspecified); Solvent 140 (petroleum distillate); Solvent Blue 104; Solvent Blue 58; Solvent Blue 70; Solvent extracted mineral oil; Solvent naphtha, petroleum, heavy aliphatic; Solvent naphtha, petroleum, heavy aromatic; Solvent naphtha, petroleum, light aliphatic; Solvent naphtha, petroleum, light aromatic; Solvent naphtha, petroleum, medium aliphatic; Solvent Orange 3; Solvent(s) (unspecified); Solvent-refined heavy paraffinic distillate; Sorbic acid; Sorbitan isostearate; Sorbitan laurate; Sorbitan monooleate; Sorbitan oleate (emulsifier); Sorbitan sesquioleate; Sorbitan stearate; Sorbitan trioleate; Sorbitan tristearate; Sorbitol; Soy acids; Soy glyceride, hydrogenated: Soy protein; Soy protein, hydrolyzed; Soy sterol; Soyaethyl morpholinium ethosulfate; Soybean meal; Soybean oil; Soybean oil blend; Soybean oil, maleated; Soybean sterol; Soyethyldimonium ethosulfate; Soytrimonium chloride; Spearmint extract; Spearmint oil; Spermaceti; Sphinganine; Spice(s); Spike lavender oil; Spinosyn A; Spinosyn D; *Spirulina Platensis* Extract; Squalane (Polyquaternium-39); Squalene; St. Bartholomew's tea (Mate) (*Ilex paraguariensis*); Stabilizer; Stain remover (unspecified); Stainless Steel; Stannous chloride; Stannous fluoride; Starch; Starch (unspecified); Starch, acid-hydrolyzed; Starch, Sodium Octenyl Succinate; Static control agent(s) (unspecified); Steapyrium chloride; Stearalkonium bentonite; Stearalkonium chloride: Stearalkonium hectorite; Stearamide AMP; Stearamide MEA; Stearamidopropalkonium chloride; Stearamidopropyl diethylamine; Stearamidopropyl dimethylamine; Stearamidopropyl PG-dimonium chloride phosphate; Steareth-10; Steareth-10 Allyl Ether/Acrylates Copolymer; Steareth-10 Allyl Ether/Acrylates Copolymerl; Steareth-2; Steareth-21; Stearic acid; Stearic acid, aminoethylethanolamine amide-imidazoline, carboxymethylated sodium salt; Stearoxy dimethicone; Steartrimonium chloride; Stearyl alcohol; Stearyl dimethicone; Stearyl octyldimonium methosulfate; Stearyl propionate; Stearyl stearate; Stearyltrimonium hydroxyethyl; *Stevia rebandiana* extract; Stoddard solvent; Strawberry; Streptomycin sulfate; Strontium chloride; Strychnine alkaloid; Styrene; Styrene acrylic copolymer; Styrene acrylic emulsion; Styrene Acrylic Polymer; Styrene acrylic resin; Styrene, alpha-methylstyrene polymer, hydrogenated; Styrene, alpha-methylstyrene, vinyltoluene, indene, dicyclopentadiene polymer; Styrene, methyl methacrylate, methacrylic acid, 2-ethylhexyl acrylate polymer; Styrene-acrylic polymer; Styrene-butadiene latex; Styrene-ethylene/propylene block polymer; Styrene/1,3-Butadiene copolymer; Styrene/Acrylate copolymer; Styrene/acrylates copolymer; Styrene/Butadiene copolymer; Styrene/MA copolymer; Styrene/PVP copolymer; Substituted azonaphthalenesulfonate salt #1 (proprietary); Substituted naphthalenesulfonate salt #10 (proprietary); Subtilisin (proteolytic enzyme); Sucralose; Sucrose; Sucrose acetate isobutyrate; Sucrose benzoate; Sucrose cocoate; Sucrose esters of fatty acids; Sucrose octaacetate; Sucrose polybehenate; Sucrose Polycottonseedate; Sucrose polycottonseedate; Sucrose stearate; Sudsing agent; Sulfamic acid; Sulfated Ethoxylated Hexamethylenediamine Quaternized; Sulfentrazone; Sulfonated Fatty Acid Methyl Esters Sodium Salts; Sulfur; Sulfur dioxide; Sulfuric acid; Sulfuric acid, copper salt, basic; Sulfuric acid, mono-$C_{10-16}$-alkyl esters, sodium salts; Sulfuric acid, mono-$C_{14-18}$-alkyl esters, sodium salts; Sulfuric acid, mono-$C_{16-18}$-alkyl esters, sodium salts; Sulfurized diisobutylene; Sumithrin; Sunflower oil monoglycerides; Sunflower seed oil/extract; Superoxide dismutase; Superphosphates, concentrated; Surfactant(s); Surfactant(s) (unspecified); Surfactant, non-ionic ethoxylated fatty acid amide; Sweet orange peel extract; Sweet pea extract; *Swertia japonica* extract; SWS protein complex; Synthetic resin complex; Synthetic rubber; Syrups, corn, hydrogenated; t-Butyl alcohol; t-Butyl hydroquinone; t-Butylphenol diphosphate; TAED; Talc (non-fibrous); Tall oil fatty acid(s); Tall oil fatty acids, isophthalic acid, pentaerythritol polymer; Tall oil glycerides; Tall oil rosin ester; Tall oil, phthalic anhydride, pentaerythritol, ethylene glycol, vinyltoluene resin; Tallow; Tallow acid; Tallow glyceride, hydrogenated; Tallow, hydrogenated; Tallowtrimonium chloride; Tannic Acid; Tartaric acid; Tau-fluvalinate; Tea tree oil; TEA-acrylates/$C_{10-30}$ alkyl acrylate crosspolymer; TEA-carbomer; TEA-carbomer 940; TEA-carbomer 941; TEA-cocoyl glutamate; TEA-dodecylbenzenesulfonate; TEA-isostearate; TEA-lactate; TEA-lauryl sulfate; TEA-palmitate; TEA-salicylate; TEA-stearate; Tebuconazole; Teflon dispersion mixture; Terlon; Termamyl 330L enzyme; Terpene alcohol(s); Terpenes and Terpenoids, sweet orange-oil; Terpenes and Terpenoids, type *citrus* oil; Terpineol; Terpinolene; tert-Butyl peroxybenzoate; Tetraaluminium zirconium tetrachloride dodecahydroxide; Tetrabutyl phenyl hydroxybenzoate; Tetracalcium aluminoferrite; Tetrachloroethylene; Tetrachlorvinphos; Tetradecane; Tetradecene-1; Tetraethylene glycol; Tetraethylene glycol di(2-ethylhexoate); Tetraethylene glycol diethyl ether; Tetraethylene Glycol Monomethyl Ether; Tetraethylene glycol, monobutyl ether; Tetraethylenepentamine; Tetrahexyldecyl ascorbate; Tetrahydrofuran; Tetrahydrofurfuryl methacrylate; Tetrahydrolinalool; Tetrahydroxypropyl ethylenediamine; Tetrakis (Trimethylsiloxy) silane; Tetralithium 6-amino-4-hydroxy-3-[7-sulfonato-4-(5-sulfonato-2-naphthylazo)-1-napthylazo] naphthalene-2, 7-disulfonate; Tetramethrin; Tetrapotassium pyrophosphate (TKPP); Tetrasodium Dicarboxyethyl Stearyl Sulfosuccinamate; Tetrasodium EDTA; Tetrasodium etidronate; Tetrasodium Glutamate Diacetate; Tetrasodium pyrophosphate (TSPP); *Theobroma Cacao* Extract; Thermoset acrylic copolymer; Thiabendazole (Biogard); Thiamethoxam; Thiamine hydrochloride; Thianaphthene; Thiazolylalanine; Thickening agent(s) (unspecified); Thioctic Acid; Thiodiglycol; Thiodipropionic acid; Thiol alkane (unspecified); Thiolactic acid; Thiourea; Thiram; Thorium phosphate, Threonine; Thyme extract; Thyme oil; Thymol; Tiger lily; Tin; Tin dioxide; Tin oxide; Tin oxide (unspecified type); Titanium dioxide; Titanium tetrabutanolate; Titanium(4+) 2-methylpropan-2-olate; Tobacco; Tocopherol; Tocopherol acetate; Tocopherol linoleate; Tocopheryl acetate; Toluene; Toluene 2,4-diisocyanate; Toluene-2,5-diamine sulfate; Toluene-2,6-diisocyanate; Tolyltriazole, sodium salt; Tomato extract; Tonka beans resin; Tosylamide-formaldehyde resin; Tosylamide/Epoxy resin; Tourmaline; Toximul 3406F; Trade secret or proprietary formula; Tralomethrin; Trehalose; Tremolite (nonasbestiform); Tri-(2-chloroisopropyl)phosphate; Triacetin; Triadimefon; Triallate; Tribehenin; Tribenzoin; Tributoxyethyl phosphate; Tributyl citrate; Tributyl phosphate; Tricalcium silicate; Tricapryl citrate; Tricarbonyl(methylcyclopentadienyl)manganese; Triceteareth-4 phosphate; Tricetylmonium chloride; Trichlorfon; Trichloro-s-triazinetrione; Trichlorocarbanilide; Trichloroethylene; Trichlorofluoromethane; Trichloromelamine; Triclocarban; Triclopyr, triethylamine salt; Triclosan; Tricontanyl PVP; Tricresyl phosphate; Trideceth-12; Trideceth-2 carboxamide MEA; Trideceth-3; Trideceth-4; Tridecyl isononanoate; Tridecyl neopentanoate; Tridecyl salicylate; Tridecyl Trimellitate; Tridecyl trimellitate, Triethanolamine; Triethanolamine hydrochloride; Triethoxycaprylylsilane; Triethyl citrate; Triethylamine; Triethylene glycol; Triethylene glycol dibenzoate; Triethylene glycol dimethacrylate; Trifluoropropyl dimethicone; Trifluralin; Trihdroxystearin; Triisocetyl citrate; Triisopropanolamine; Triisostearyl Trilinoleate; Trilinoleic Acid; Trimellitic ester; Trimethoxyvinylsilane; Trimethylated silica; Trimethylbenzenes (mixed isomers); Trimethylhexane-1,6-diamine; Trimethylolpropane; Trimethylolpropane tricaprylate/tricaprate; Trimethylpentenyl diisobutyrate; Trimethylphenol; Trimethylsiloxy silicate; Trimethylsiloxyphenyl Dimethicone; Trimethylsiloxysilicate alcohol; Trimethylsilyl amodimethicone; Trimethylsilyl stearate; Trimethylsilylamodimethicone; Trioctyldodecyl citrate; Trioxaundecanedioic acid; Triphenyl phosphate; Tripropylene Glycol; Tripropylene glycol methyl ether; Tripropyleneglycol monomethyl ether; Tris(2,3-dibromopropyl)phosphate; Trisiloxane; Trisodium citrate dihydrate; Trisodium Dicarboxymethyl Alaninate; Trisodium EDTA; Trisodium EHDP; Trisodium Ethylenediamine Disuccinate; Trisodium etidronate; Trisodium HEDTA; Trisodium nitrilotriacetate; Trisodium phosphate (unspecified); Trisodium phosphate anhydrous; Triticonazole [ISO]; *Triticum Vulgare* Kernel Flour; Triundecanoin; Tromethamine; Tung oil; Turpentine; Ultramarine blue; Ultramarines; Ultramarines (unspecified); Umber; unassigned chemical; Undecylenoyl Phenylalanine; Unwoven cloth; Urea; Urea hydrochloride; Urea Peroxide; Urea phosphate; Urea, N,N'-bis(3-(dimethylamino)propyl)-; Urea, polymer with formaldehyde and phenol; Urea-formaldehyde resin; Urethane prepolymer Diphenylmethane-diisocyanate; Utramarines; UV Additives; VA/Crotonates/vinyl neodecanoate copolymer; Vancide-TH; *Vanilla fragrans*, ext.; *Vanilla* oil/extract; Vanillin; Vegetable emulsifying wax; Vegetable extract; Vegetable oil; Vegetable oil (unspecified); Vegetable oil, hydrogenated; Vegetable protein, hydrolyzed; Vegetable source ester-Quat derived from soy; *Verbena officinalis* extract; *Verbena* oil; Vermiculite; Vetiver; Vinyl acetate monomer; Vinyl acetate, dioctyl maleate copolymer; Vinyl acetate, n-butyl acrylate polymer; Vinyl acetate/acrylic copolymer; Vinyl acetate/Crotonic acid copolymer; Vinyl acrylic copolymer; Vinyl Acrylic Resin (unspecified); Vinyl alcohol-vinyl acetate copolymer; Vinyl Caprolactam/Vp/Dimethylaminoethyl Methacrylate Copolymer; Vinyl Oximinosilane; Vinyl polymer; Vinyl Terpolymer; Vinyl toluene alkyd copolymer; Vinylchloride, vinyl acetate, maleic anhydride polymer; Vinyltoluene; *Viola* tricolor extract; Viscosity improver; Vitamin B6 (Vitamin H); Vitamin E; Vitamin-protein complex; VP Hexadecene copolymer; VP/Dimethylaminoethylmethacrylate Copolymer; Vp/Eicosene Copolymer; Vp/Methacrylamide/Vinyl Imidazole Copolymer; VP/VA Copolymer; Walnut shell powder; Water; Water insoluble nitrogen; Water lily extract; Water softener(s); Water softeners (complex sodium phosphates/sodium carbonate); Water soluble cyan dye; Water soluble nitrogen; Water soluble organic solvents; Water soluble red dye; Water soluble yellow dye; Water spot prevention agent(s); Watercress extract; Wax emulsion; Wax(es) (unspecified); Wax-1 (proprietary); Wax-2 (proprietary); Wax-3 (proprietary); Wax/thickening agent(s); Western red cedar extract/dust; Wetable powder pyrethroid; Wetting agent(s) (unspecified); Wheat germ (*triticum vulgare*) protein; Wheat germ amidopropyl dimethylamine lactate; Wheat germ amidopropyl ethyldimonium ethosulfate; Wheat germ extract; Wheat germ glycerides; Wheat germ oil; Wheat germ, hydrolyzed; Wheat protein, hydrolyzed; Wheat starch, hydrolyzed; White birch extract; White ginger extract; White wax; Whole egg solids; Wild cherry extract; Wild yam (*Discoria villosa*) extract; Willow extract; WinSurf NLS-90; Wintergreen oil; Witch hazel extract; Wood fiber board; Wood floor; Wood flour; Xanthan gum; Ximenynic acid; Xylene (mixed isomers); Xylitol; Xylitylglucoside; Yarrow extract; Yeast extract; Yellow 1; Yellow 5; Yellow 6 Lake; Yellow gold colorant; Yellow iron oxide; Ylang-ylang oil; *Yucca* extract; *Zea Mays*; Zeolites, CaA; Zinc ammonium carbonate; Zinc borate; Zinc Carbonate; Zinc chloride; Zinc citrate; Zinc compound(s) (unspecified); Zinc dialkyldithiophosphate; Zinc dithiophosphate; Zinc dust; Zinc gluconate; Zinc Lactate; Zinc oxide; Zinc PCA; Zinc Phenolsulfonate; Zinc phosphate; Zinc phosphide; Zinc pyrithione; Zinc stearate; Zinc sulfate; Zinc sulfide; Zinc sulfide (ZnS), copper chloride-doped; Zinc yeast derivative; Zinc(2+), tetraammine-, (T-4)-, carbonate (1:1); Ziram; Zirconium 2-ethylhexanoate; Zirconium acetate; Zirconium and compounds; Zirconium compound/solution (unspecified); and Zirconium silicate.

In some embodiments, the cooling compositions described herein are incorporated into a home product. In some embodiments, the home product is selected from the list of: additive, adhesive, adhesive remover, air freshener, air sanitizer, all purpose cleaner, ammonia cleaner, antibacterial, aquarium sealant, automatic dishwashing aid, bar soap, bath and shower cleaner, bleach, blinds cleaner, bowl cleaner, brass polish, carpet/upholstery, carpet/upholstery care product, clay tile, cleaner, cleaner fluid, cleaner, antistatic, cleaner, antibacterial, cleaner, audio tape head, cleaner, contact, cleaner, disk drive, cleaner, flux, cleaner, mouse, cleaner-polish, cleaner/conditioner, cleaner/degreaser, cleaner/deodorizer, cleaner/polish, cleaner/protectant, cleaner/spot remover, cleanser, clear coat, cloth/wipe, concrete floor, conditioner, conditioner/protector, contact cement, cooktop cleaner, degreaser, dehumidifier, deodorant, deodorizer, detergent, detergent, automatic, detergent, hypo-allergenic, detergent, phosphate-free, detergent/soap, dish/wash, dishwash/automatic, dishwash/manual, dishwasher cleaner, dishwasher rinse, dishwasher, automatic, disinfectant, disinfectant cleaner, disinfectant wipes, drain cleaner/opener, dry cleaner, dry erase marker, dust mop treatment, dusting sheet, electrical tape, electronics cleaner, epoxy, epoxy enamel, fabric, fabric conditioner, fabric enhancer, fabric finish, fabric sizing, fabric softener, fabric/upholstery, fertilizer, fiberglass, filler putty, finish, finish, stain, fire starter, fixative, flea & tick control, floor, floor cleaner, floor cleaner/polish, floor polish, floor stripper, floor wax remover, floor wipes, flux, foam stamps, freshener, fungicidal, furniture, furniture polish, gel, glass, glass cleaner, glitter spray, glue stick, grease dissolver, grout, gum remover, hand cleaner, paint remover, head cleaner, ink, ink cartridge, ink/mark remover, insecticide, kitchen cleaner, laundry detergent, leaf cleaner, leaf shine, leather, lice killer, lime/rust/scale remover, marble/granite cleaner, marble/granite polish, metal polish, metallic finish, microwave cleaner, mildew remover, multipurpose cleaner, multipurpose cleanser, odor/stain remover, oven cleaner, pad, paint, paper, plastic, plastic bag/wrap, plastic cleaner, plastic stain remover, polish, polyurethane, pot/pan presoak, power wash, stain pre treatment, pre-stain, pre-stain conditioner, prewash, prewash/stain remover, primer, produce cleaner, protectant, protective coating, putty, refinisher, rinse agent, room freshener, rubber cement, rust preventer, sanitizer, scouring pad, scratch repair agent, sealant, sealer, shampoo, shoes, silver, soap scum remover, softener, solder, soldering flux, soldering torch, spot remover, spot/stain remover, spray, stain, stain remover, stain/finish, starch, stone, stove top, stove top cleaner, styrofoam, super glue, surface cleaner, tile, tile/grout cleaner, toilet bowl cleaner, toner, touch-up marker, transparency marker, tub/tile cleaner, varnish, vinyl flooring, washable, washing machine, water repellant, water treatment, water-based, waterless hand cleaner, waterproof, wax, wax remover, wax stripper, white board, window/door, wipes, wipes/pads, cleaning, wood, wood conditioner, prestain, and wood protectant. In some embodiments, the compositions disclosed herein are dispersed within a swimming pool, whirlpool, bathtub or spa.

In some embodiments, one or more of Compounds 101-105 or the cooling compositions described herein are incorporated into a personal care product. In some embodiments, the personal care product is selected from the list of: acne & blemish control; aftershave; antibacterial; antiperspirant; baby bath; baby lotion/ointment; baby powder; bar soap; bar soap, antibacterial; basecoat; bath oil/beads; blush; body hair bleach; body hair removal; body paints; body powder; body soap; body soap, antibacterial; body spray/mist; body wash; body wash, antibacterial; body wash/soap; body/hand moisturizer; body/hand moisturizer w/sunscreen; body/hand moisturizer, antibacterial.; bubble bath; cleaner; clipper lubricant; cologne/fragrance; concealer; conditioner; conditioner, dandruff; contact lens cleaner; cuticle treatment; denture adhesive; denture cleaner; deodorant; deodorant & antiperspirant, combination; diaper rash treatment; diapers; disinfectant; eye makeup remover; eye shadow; eyeliner/eyebrow pencil; face cleaner; face powder; facial cleaner; facial moisturizer; facial moisturizer, anti-aging; facial moisturizer, w/sunscreen; fade lotion/cream; foot care product; foundation/liquid makeup; foundation/liquid makeup w/SPF; fragrance; hair color; hair conditioner; hair lightener; hair relaxer; hair straightener; hair styling/sculpting;

haircolor; hand cleaner; hand cleaner, antibacterial; hand sanitizer; highlights; holding spray; insect repellent; itch relief; jewelry cleaner; kids; leather/fabric waterproofing; legs; lice shampoo; lip balm; lipcolor; lipcolor remover; liquid; mascara; moisturizer; mouthwash; nail polish/ enamel; nappies; night cream/lotion; pain relief/first aid; permanent wave compositions; polish remover; pre-lightener; preshave; protective hand cream; semi-permanent skin inks; shampoo; shampoo & conditioner combo; shampoo & conditioner, dandruff; shampoo, dandruff; shave cream/gel; shaving cream/gel; skin cleanser/wipes; sunscreen/sunblock; teeth whitener; tattoo ink; temporary tattoo; toner; toothpaste; under eye lotion/cream; and wipes.

In some embodiments, one or more of Compounds 101-105 or the cooling compositions described herein are incorporated into a pet product. In some embodiments, the pet product is selected from the list of: air freshener; algae control agent; ammonia cleaner; ammonia remover; animal repellent; cage cleaner; cat litter; dental hygiene compound; disease treatment; ear cleaner; ear mite treatment; fish health composition; flea & tick controler; fly repellent; fragrance; grooming aid; hand cleaner, antiseptic; insect repellent; medication; odor/stain remover; saddle and/or tack; sealant; shampoo; tank cleaner; terrarium cleaner; toothpaste; water conditioner/treatment; water treatment; and wound treatment.

Probiotic Supplements

In some embodiments, one or more of Compounds 101-105 or the cooling compositions described herein are incorporated, either alone or in combination with one or more of the additional compounds described herein, into a probiotic supplement. Suitable probiotic organisms include but are not limited to: *Bacteroides fragilis* ss. *Vulgatus, Collinsella aerofaciens, Bacteroides fragilis* ss. *Thetaiotaomicron, Peptostreptococcus productus* II, *Parabacteroidesdistasonis Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ss. A, *Eubacterium biforme, Bifidobacterium infantis, Eubacterium rectale* III-F, *Coprococcus comes, Pseudoflavonifractor capillosus, Ruminococcus albus, Dorea formicigenerans, Eubacterium haffii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ss. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ss. *ovatus*, -ss. d, -ss. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridliformis* ss. *clostridliformis, Bacteroides coagulans, Prevotella oralis, Prevotella ruminicola, Odoribacter splanchnicus, Desuifomonas pigra, Lactobacillus* G, *Succinivibrio* A, *Lactobacillus plantarum, Lactobacillus brevis, Lactobacillus acidophilus, Bifidobacterium bifidum, Lactobacillus casei, Lactobacillus bulgaricus, Streptococcus thermophiles, Lactobacillus acetotolerans, Lactobacillus acidifarinae, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustonrm, Lactobacillus curvatus, Lactobacillus delbrueckii* subsp. *bulgaricus, Lactobacillus delbrueckii* subsp. *delbrueckii, Lactobacillus delbrueckii* subsp. *lactis, Lactobacillus dextrinicus, Lactobacillus dioliovorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracasei, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus protectus, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae*, and *Lactobacillus zymae*.

In some embodiments, one or more of Compounds 101-105 or the cooling compositions described herein are incorporated, either alone or in combination with one or more of the additional compounds described herein, into a smoking article or vapor inhalation ("e-cigarette") device. Such articles and devices are well known in the art, including but not limited to, cigars, cigarettes, loose pipe tobacco, flavored cigars, flavored cigarettes, kretek cigarettes, bidis, and electronic cigarettes. In some embodiments, the cooling compositions described herein may be applied directly to a smoking article at any time during or after the manufacture of the smoking article. In some further embodiments, the cooling composition as described herein may be provided as a liquid, solid, or concentrate to be applied to a smoking article or vaporizer fluid. In some further embodiments, the cooling compositions disclosed herein can be incorporated into a vaporizer fluid. In some embodiments the vaporizer fluid further comprises propylene glycol, water, nicotine, glycerin, and/or polyethylene glycol. In some embodiments, the smoking article comprises tobacco. In some embodiments, the smoking article comprises marijuana, cloves, and/or tendu or temburni leaves.

One of ordinary skill will readily recognize that the compositions described herein can be provided in any form known in the art which functions to deliver the desired amount or functionality of each embodiment. In some embodiments, the compositions described herein are provided as a solid, powder, or paste. In some embodiments, the compositions described herein are provided as a liquid, syrup, or concentrate. In some embodiments, the compositions described herein are provided in ready-to-use form. In some embodiments, the compositions described herein are attached to a solid substrate.

Therapeutic Utilities

In some embodiments, compounds as disclosed and described herein, individually or in combination can be used for therapeutic purpose such as modulating a chemosensory receptor and/or its ligand to achieve therapeutic effect. For example, the therapeutic purpose may include modulating a chemosensory receptor and/or its ligand expressed in the body other than in the taste buds.

In some embodiments, the method includes modulation, treatment, and/or prophylactic measure of a condition associated with the gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g., inflammatory or infiltrative disorders, biochemical or genetic abnormalities, endocrine and metabolic disorders, protein-losing enteropathy, etc.), autoimmune diseases of the digestive tract (e.g., celiac disease, Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectial disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc. by administering compounds as disclosed and described herein, individually or in combination to an individual in need thereof.

In some embodiments, the method includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impairments associated with protein-energy malnutrition, etc.), obesity, secondary obesity (e.g., hypothyroidism, Cushing's disease, insulinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycemia, hyperlipoproteinemias, etc. by administering compounds as disclosed and described herein, individually or in combination to an individual in need thereof In some embodiments, the method includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human by administering compounds as disclosed and described herein, individually or in combination to an individual in need thereof.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastrointestinal tract, cold sensation of extremities, difficulty in concentration, impatience, sleep disorder, headache, general malaise, palpitation, night sweat, anxiety, dizziness, vertigo, hot flash, excess sweating, depression, etc.

In some embodiments, the method includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. by administering compounds as disclosed and described herein, individually or in combination to an individual in need thereof. In general, such promotion can be achieved either directly or via increasing the secretion of a regulatory entity, e.g., hormones, etc. by administering compounds as disclosed and described herein, individually or in combination to an individual in need thereof In some embodiments, the method includes increasing one or more gastrointestinal functions of a subject, e.g., to improve the quality of life or healthy state of an individual by administering compounds as disclosed and described herein, individually or in combination.

Some embodiments provide a pharmaceutical composition containing a therapeutically effective amount of one or more compounds as disclosed and described herein, or a salt, solvate, and/or prodrug thereof, optionally with a suitable amount of a pharmaceutically acceptable vehicle. In another embodiment, the pharmaceutical composition comprises a therapeutically effective amount of one or more compounds as disclosed and described herein, or a salt, solvate, and/or prodrug thereof; and a suitable amount of a pharmaceutically acceptable vehicle so as to provide the form for proper administration to a patient.

In one embodiment, when administered to a patient, the compounds as disclosed and described herein and the optional pharmaceutically acceptable vehicles are sterile. In one embodiment, water is a preferred vehicle when a compound as disclosed and described herein is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound as disclosed and described herein may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

In some embodiments, the pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, 20th Edition, 2000).

For topical administration a compound as disclosed and described herein may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, compounds as disclosed and described herein may be formulated in accordance with routine procedures as a pharmaceutical composition adapted for intravenous administration to human beings. Typically, compounds for intravenous administration are solutions in sterile isotonic aqueous buffer. For injection, a compound may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When a compound is administered by infusion, it can be dispensed, for example, with an infusion bottle containing sterile pharmaceutical grade water or saline. In some embodiments, an ampoule of sterile water for injection or saline can be provided so that the ingredients may be mixed prior to administration when a compound is administered by injection.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol)

oils, alcohols, slightly acidic buffers between pH 4 and pH 6 (e.g., acetate, citrate, ascorbate at between about 5 mM to about 50 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

In some embodiments, a compound as disclosed and described herein may also be formulated in rectal or vaginal pharmaceutical compositions such as suppositories or retention enemas, e.g., containing conventional suppository bases such as cocoa butter or other glycerides.

In addition to the formulations described previously, a compound as disclosed and described herein may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

A compound as disclosed and described herein, and/or pharmaceutical composition thereof, will generally be used in an amount effective to achieve the intended purpose. For use to treat or prevent diseases or disorders the compounds as disclosed and described herein and/or pharmaceutical compositions thereof, are administered or applied in a therapeutically effective amount.

In some embodiments, the dosage may be delivered in a pharmaceutical composition by a single administration, by multiple applications or controlled release. In some embodiments, the compounds as disclosed and described herein may be delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound as disclosed and described herein per kilogram body weight.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems.

In some embodiments, the dosage of a compound described herein will preferably be within a range of circulating concentrations that include an effective dose with little or no toxicity.

In certain embodiments, the compounds as disclosed and described herein and/or pharmaceutical compositions thereof can be used in combination therapy with at least one other agent. In some embodiments, a compound as disclosed and described herein and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

EXAMPLES

Example 1: Synthesis and Characterization

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P.G.M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

The starting materials used in preparing the compounds described herein are often known compounds, or can be synthesized by known methods described in the literature, or are commercially available from various sources well known to those of ordinary skill in the art.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive amination and the like.

Example 1.1: Synthesis and Characterization of N-(1H-pyrazol-3-yl)-N-(thiophen-2-ylmethyl)-2-(m-tolyloxy)acetamide (Compound 101)

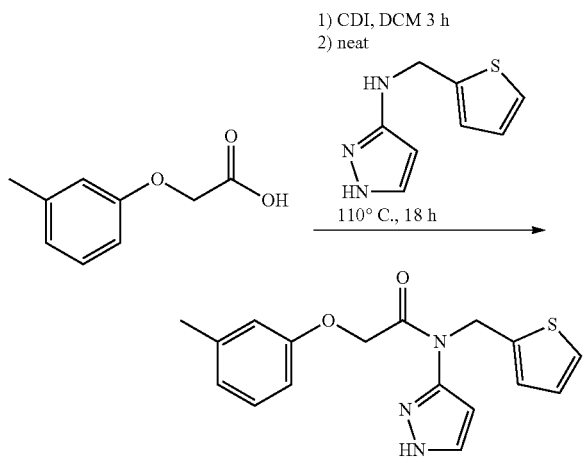

2-(m-tolyloxy)acetic acid (1.25 g, 7.52 mmol, 1 equiv) was suspended in anhydrous dichloromethane (DCM; 40 mL) under nitrogen and cooled to −45° C. CDI (1.26 g, 7.77 mmol, 1.03 equiv) was then added as a solution in anhydrous DCM (18 mL). The mixture was allowed to warm to room temperature and then stirred for 3 hours. Approximately 95% of the DCM solvent was then removed under vacuum to give a residue. To this residue was then added N-(thiophen-2-ylmethyl)-1H-pyrazol-3-amine (1.62 g, 9.04 mmol, 1.2 equiv) dissolved in anhydrous DCM (15 mL). The mixture was heated to a 110° C. in an oil bath, under nitrogen, set up in a way which allowed all the DCM to escape, to give a neat reaction mixture, which was stirred overnight. The resulting residue was then dissolved in MeOH and purified by HPLC using a 0.1% formic acid in water: ACN gradient (35% ACN to 45% ACN over 30 minutes). The pure fractions were combined, and sodium carbonate was added until basic, in order to neutralize all the formic acid. The ACN was then removed under vacuum, but the water layer was left behind and extracted with DCM. The DCM was then washed with brine, dried with magnesium sulfate, and concentrated to give a residue. The residue was dissolved in a mixture of EtOH and water, then frozen, and lyophilized to give the product as a solid. $^1$H NMR (DMSO-$d_6$, 400 MHz): 12.90 (s, 1H), 7.79 (s, 1H), 7.41 (m, 1H), 7.12 (t, J=7.6 Hz, 1H), 6.91 (m, 2H), 6.73 (m, 1H), 6.58 (m, 2H), 6.23 (s, 1H), 4.98 (s, 2H), 4.61 (s, 2H), 2.23 (s, 3H) ppm. MS=328 (MH$^+$).

Example 1.2: Synthesis and Characterization of 2-(4-flourophenoxy)-N-(1H-pyrazol-5-yl)-N-(thiophen-2-ylmethyl)acetamide (Compound 102)

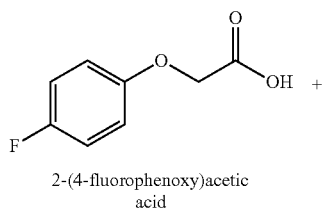

2-(4-fluorophenoxy)acetic acid

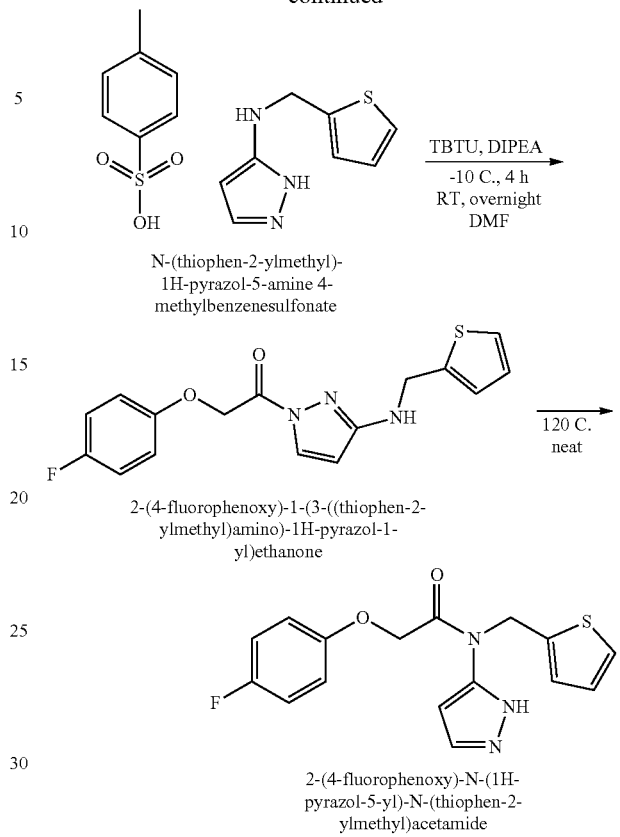

2-(4-fluorophenoxy)acetic acid (20.0 g, 117.6 mmol) was dissolved in 250 mL of anhydrous DMF. The solution was chilled to an internal temperature of below −10 degree Celsius. TBTU (45.2 g, 141.1 mmol) was added in portions while maintaining the internal temperature below −10 degree Celsius, followed by DIPEA (79 mL, 453 mmol). The reaction mixture was allowed to stir at or below −10 degrees Celsius for 30 minutes, then amine pTSA salt (43.4 g, 123.4 mmol) was added in portions over 10 minutes while maintaining the temperature at or below −10 degrees Celsius. The reaction was stirred at or below −10 degrees Celsius for 4 hours then allowed to warm to room temperature overnight. The reaction was diluted with 500 mL of ethyl acetate and washed with 500 mL of water. The aqueous layer was washed with ethyl acetate (500 mL×1, 250 mL×1), and the organic layers were combined and washed with saturated aqueous sodium bicarbonate solution (2×100 mL), water (200 mL), and then brine (2×250 mL). The organic layer was dried over sodium sulfate. 42 g of crude product were obtained and subjected to a silica plug (330 g), eluting with ethyl acetate. The fractions were concentrated into a 500 mL round bottom flask and dried thoroughly. The material was warmed and stirred at 120 degrees Celsius neat overnight. Upon completion by LC-MS, the reaction was diluted with 500 mL of ethyl acetate and cooled to room temperature. The solution was washed with 500 mL of 1.0N HCl(aq) and, the acidic aqueous layer was extracted with 300 mL of ethyl acetate. The combined organic layer was washed with 500 mL of 1.0N NaOH(aq). The aqueous basic layer was extracted with 300 mL of ethyl acetate. The organic layers were combined and washed with brine (250 mL) and dried over sodium sulfate. The crude material was purified by column chromatography (hexanes/ethyl acetate)

to give 34.2 g of material which was subjected to crystallization. 8 mL of ethyl acetate was added per gram of material, stirred and warmed to 45 degrees Celsius, and warm hexanes were added until the mixture became cloudy. Ethyl acetate was added in small amounts until solution was clear and homogenous again. After cooling to room temperature, 19 g of crystals were obtained and re-crystallized again to afford 17.4 g of a nice white solid in good purity (>97%). NMR Sample ID: 56451994, $^1$H NMR (400 MHz, DMSO-d6): δ, ppm: 4.64 (s, 2H), 4.98 (s, 2H), 6.23 (s, 1H), 6.81 (m, 2H), 6.91 (m, 2H), 7.08 (t, 2H, J=8.8 Hz), 7.40 (m, 1H), 7.77 (s, 1H), 12.84 (s, 1H). Analytical: MS(M+H, 332.1)

Example 1.3: Synthesis and Characterization of 2-(4-methoxyphenoxy)-N-(1H-pyrazol-3-yl)-N-(thiophen-2-ylmethyl)acetamide (Compound 103)

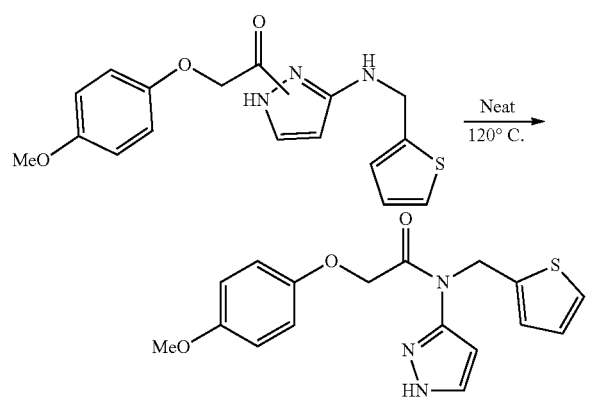

The mixture of 2-(4-methoxyphenoxy)-1-(3-((thiophen-2-ylmethyl)amino)-1H-pyrazol-1-yl)ethan-1-one and 2-(4-methoxyphenoxy)-1-(5-((thiophen-2-ylmethyl)amino)-1H-pyrazol-1-yl)ethanone (19.5 g, 56.8 mmol) was dissolved in a small amount of anhydrous DCM to aid in transferring it to a 500 mL round bottom flask. It was then heated under nitrogen in a 120° C. in an oil bath for 3 days, set up in a way which kept the reaction under nitrogen but allowed all the DCM to evaporate, which gave a neat reaction mixture. The product was then partially purified on a 340 gram silica column, running a gradient of 10% to 100% EtOAc/Hexanes. The fractions containing desired product were dissolved in a mixture of EtOH (185 mL), MeOH (250 mL), and hexanes (600 mL), and then water (400 mL) was added while stirring rapidly. The EtOH/MeOH/water layer (which contained mostly pure product) was then separated from the hexanes layer and a small amount of insoluble material. The solution was then concentrated under vacuum to remove the EtOH/MeOH/water and the residue was dissolved in EtOAc (100 mL), heated in a 45° C. oil bath, and heptane (90 mL) was added slowly. This clear and soluble solution was stirred rapidly while allowing it to slowly cool back down to room temperature. The white precipitated product was collected by filtration and dried under vacuum to give approximately 9.5 grams of material. The solid was further dried under high vacuum at 40° C. to give 9.3 grams of white product. $^1$H NMR (DMSO-d$_6$, 400 MHz): 12.88 (br, 1H), 7.78 (s, 1H), 7.41 (m, 1H), 6.91 (m, 2H), 6.81 (m, 2H), 6.73 (m, 2H), 6.23 (s, 1H), 4.98 (s, 2H), 4.56 (s, 2H), 3.68 (s, 3H) ppm. MS=344 (MH$^+$).

Example 1.4: Synthesis of Precursor 2-(4-methoxyphenoxy)-1-(3-((thiophen-2-ylmethyl)amino)-1H-pyrazol-1-yl)ethanone

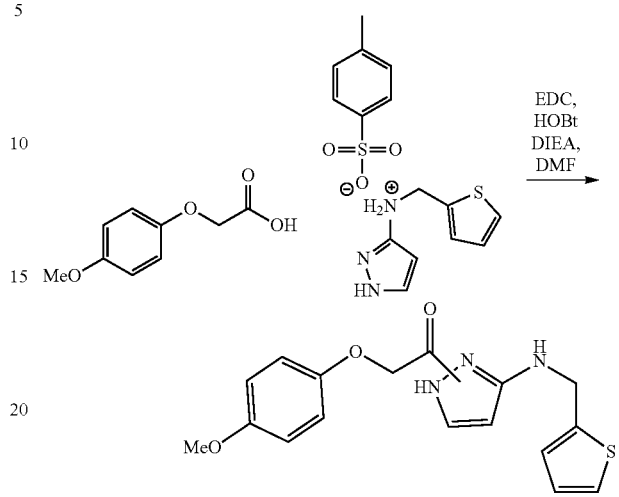

2-(4-methoxyphenoxy)acetic acid (18.3 g, 100 mmol, 1.5 equiv), EDC (19.3 g, 100 mmol, 1.5 equiv), HOBt (13.6 g, 100 mmol, 1.5 equiv), and DIEA (40.8 mL, 234 mmol, 3.5 equiv) were mixed in 240 mL anhydrous DMF under nitrogen and stirred at r.t. for 1.5 hours. The tosylate salt of N-(thiophen-2-ylmethyl)-1H-pyrazol-3-amine (26.7 g total weight, material estimated to be roughly 88% pure by mass) was then added and stirred for 3 days. The mixture was poured into 1300 mL ice water and the resultant solid material stuck to the sides of the flask and to the spatula. The water was decanted from the solid material and discarded. The solid material was dissolved in DCM, extracted once with water, then concentrated to give the product as a residue. This material was then partially purified on a 340 gram silica column running a gradient of 10% to 35% EtOAc/Hexanes to give 16.5 grams of product (a mixture of 2-(4-methoxyphenoxy)-1-(3-((thiophen-2-ylmethyl)amino)-1H-pyrazol-1-yl)ethan-1-one and 2-(4-methoxyphenoxy)-1-(5-((thiophen-2-ylmethyl)amino)-1H-pyrazol-1-yl)ethanone), in roughly 95% purity. This reaction was repeated again in order to provide more material. The product was then used in the next step without further purification.

Example 1.5: Synthesis and Characterization of 2-(4-ethylphenoxy)-N-(1H-pyrazol-3-yl)-N-(thiophen-2-ylmethyl)acetamide (Compound 104)

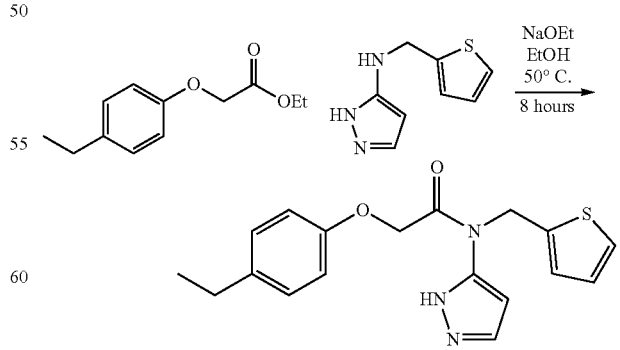

Ethyl 2-(4-ethylphenoxy)acetate (16.43 g, 78.9 mmol, 1.05 equiv) and N-(thiophen-2-ylmethyl)-1H-pyrazol-5-amine (13.47 g, 75.2 mmol, 1 equiv, purity roughly estimated between 80% and 90%), were combined in a flask under nitrogen, and sodium ethoxide (21% by weight, 2.679 M solution in Ethanol, 30.9 mL, 82.8 mmol, 1.1 equiv) was added. The mixture was heated under nitrogen in a 50° C. oil bath for 8 hours, then ethyl acetate (200 mL) was added while the reaction was still warm, followed by the addition of acetic acid (4.43 mL, 77.4 mmol, 1.03 equiv). After stirring for 10 minutes, an aqueous solution of 25% saturated NaCl was added (100 mL, made by combining 25 mL brine with 75 mL water), then the mixture was stirred and the layers separated. The organic layer was concentrated under vacuum, then the resultant residue was dissolved in DCM, dried with magnesium sulfate, filtered, and concentrated to give the crude product. At this point, another 8.4 grams of crude product was added to this batch, which was obtained from a separate reaction, but made using exactly the same protocol as this larger batch. This combined crude material was dissolved in a minimal amount of DCM, loaded onto a silica column, and an EtOAc/Hexanes gradient was run using a 10% EtOAc/Hexanes to 39% EtOAc/Hexanes gradient to provide 19.19 grams of product, roughly 95% pure by $^1$H NMR. The 19.19 grams was recrystallized twice from a solution of 22% Pentane, 36% EtOAc, 42% Heptane, to give 12.8 grams of product as a white solid. The 12.8 grams was dissolved in EtOH (50 mL), cooled to −78° C., then immediately put under vacuum and dried for 2 days, providing a white solid, 12.74 grams, 35.3% yield. $^1$H NMR (DMSO-$d_6$, 400 MHz): 12.89 (br, 1H), 7.78 (s, 1H), 7.40 (m, 1H), 7.08 (m, 2H), 6.91 (m, 2H), 6.69 (d, J=8.8 Hz, 2H), 6.24 (s, 1H), 4.98 (s, 2H), 4.60 (s, 2H), 2.51 (q, J=8.0 Hz, 2H), 1.13 (t, J=8.0 Hz, 3H) ppm. MS=342 (MH$^+$).

Example 1.5: Synthesis and Characterization of 2-(3,4-dimethylphenoxy)-N-(1H-pyrazol-3-yl)-N-(thiophen-2-ylmethyl)acetamide (Compound 105)

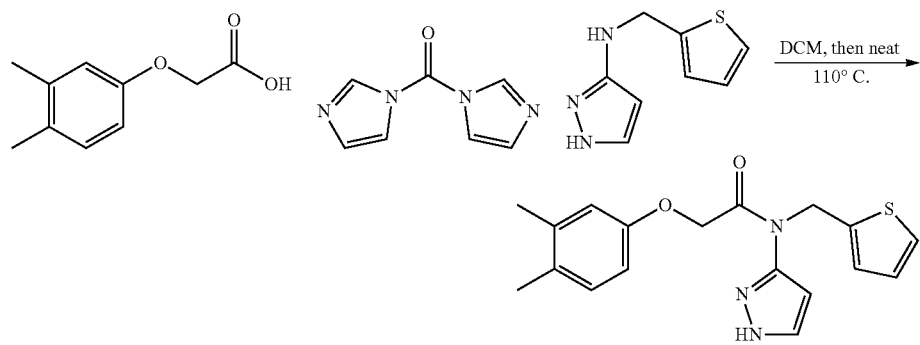

2-(3,4-dimethylphenoxy)acetic acid (2.65 g, 14.7 mmol, 1 equiv) was suspended in anhydrous DCM (75 mL) under nitrogen and cooled to −45° C., then CDI (2.46 g, 15.2 mmol, 1.03 equiv) was added as a solution in DCM (25 mL). After stirring for 3 hours at room temperature, the DCM was removed under vacuum, then N-(thiophen-2-ylmethyl)-1H-pyrazol-3-amine (3.17 g, 17.7 mmol, 1.2 equiv) was added as a solution in DCM (15 mL). The mixture was heated under nitrogen in a 110° C. oil bath for 17 hours, set up in a way which kept the reaction under nitrogen but allowed all the DCM to evaporate, to give a neat reaction mixture. The resultant residue was dissolved in DCM, extracted once with water, dried with magnesium sulfate, then partially purified on a 340 gram silica column (20% to 80% EtOAc/Hexanes).

The fractions containing desired product were concentrated, then dissolved in EtOAc (30 mL) and heated to 47° C. in an oil bath, after which pentane (50 mL) was added. The solution was then cooled in a −20° C. freezer for 2 hours, and the precipitate was collected by filtration, which gave 2.53 g of roughly 99% pure material. A second recrystallization gave 2.19 g of the product as a white solid $^1$H NMR (DMSO-$d_6$, 400 MHz): 12.89 (br, 1H), 7.78 (s, 1H), 7.41 (m, 1H), 6.97 (d, J=8.4 Hz, 1H), 6.91 (m, 2H), 6.57 (d, J=2.8 Hz, 1H), 6.48 (dd, J=2.4, 8.4 Hz, 1H), 6.22 (s, 1H), 4.98 (s, 1H), 4.57 (s, 1H), 2.14 (s, 3H), 2.11 (s, 3H) ppm. MS=342 (MH$^+$).

Example 2: Biological Assay of Compounds 101-105

A mammalian cell line derivative which stably expresses hTRPM8 was used in biological assays in association with testing the present compounds with cool-tasting or -feeling properties (Servant et al. US 2007/0259354 A1 and references cited therein). Typical compound concentrations tested were 100 µM, 30 µM, 10 µM, 3.3 µM, 1.1 µM, 0.37 µM, 0.12 µM, 0.04 µM, 0.01 µM and more dilutions for very potent compounds. The present compounds have shown strong activity as agonists of hTRPM8. Assay results for compounds are illustrated in Table 4 below and the respective EC$_{50}$ for each compound is compared to that of WS-3 and is reported as a ratio. For the sake of comparison, the EC$_{50}$ of Comparative Compound 1, which was previously disclosed in U.S. 2013/0324557 A1 and has the structure

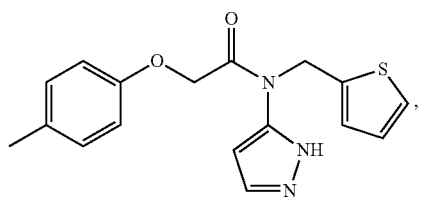 [SMILES: Cc1ccc(OCC(=O)N(Cc2cccs2)c2ccn[nH]2)cc1]

was also measured.

The results of these studies show that all of the present compounds show an improved EC$_{50}$ over WS-3. Additionally, based on the EC$_{50}$ ratio to WS-3, Compound 104 shows an unexpected improved potency that is significantly greater than the potency of Comparative Compound 1.

TABLE 4

| Compound | EC$_{50}$ (μM) | EC$_{50}$ WS-3 Ratio |
|---|---|---|
| Comparative Compound 1 | 0.0003 | 28648 |
| 101 | 0.0061 | 696.3 |
| 102 | 0.0107 | 495.4 |
| 103 | 0.0049 | 1050.9 |
| 104 | <0.001 | 1189444 |
| 105 | 0.0007 | 12169.3 |

Example 3: Sensory Studies of Compounds 101-105

A typical sensory study is described below followed by Table 5 summarizing sensory results of Compounds 101-105.

Cool Line Scale Test:

Formulation:

All samples made with Low Sodium Buffer (LSB) pH ~7.1 and contain 0.1% ethanol.

General Protocol:

Compounds are rated on a 15 point line scale where 45 μM WS-3 (N-Ethyl-p-menthane-3-carboxamide) is ranked as a 5 in cool intensity. In most cases, the compounds are tested to determine at what concentration the cooling intensity is equivalent to 45 μM WS-3. In each test, the panelist is presented with a 0 μM control sample, a 45 μM WS-3 control sample and the experimental compound sample and asked to rate the cooling intensity of each sample.

The results indicate an unexpected lingering effect for Compounds 103, 104, and 105.

TABLE 5

| Compound | Sensory Results |
|---|---|
| 101 | Panelists found 5 μM Compound 101 was equivalent to the cooling of 45 μM WS-3. |
| 102 | Panelists found that 5 μM of Compound 102 was equivalent to the cooling of 45 μM WS-3. |
| 103 | 5 μM Compound 103 was equivalent to the cooling 45 μM WS-3. |
| 104 | Panelists found that 5 μM of Compound 104 was significantly more cooling than 45 μM WS-3. |
| 105 | Panelists found that 5 μM of Compound 105 was equivalent to the cooling of 45 μM WS3. |

Example 4: Solubility Studies of Compounds 101-105

The solubility of Compounds 101-103 was measured and is reported in Table 6 below. For the sake of comparison, the solubility of Comparative Compound 1, which was previously disclosed in U.S. 2013/0324557 A1, was also measured. Compound 101 showed an unexpectedly superior solubility at pH 4.0 to that of the previously disclosed compound. Additionally, Compounds 102 and 103 showed unexpectedly superior solubility at pH 7.1.

TABLE 6

| Sample | Solubility (μM) (pH 4.0) | Solubility (μM) (pH 7.1) |
|---|---|---|
| Comparative Compound 1 | 106 | 171 |
| Compound 101 | 516.88 | 151.97 |
| Compound 102 | — | 503 |
| Compound 103 | — | 403 |

Example 5: Sensory Evaluation of Compounds 102-105

Compounds 102-105 and Comparative Compound 1 were evaluated using a quantitative descriptive evaluation technique. Ten panelists participated in the study. These panelists previously underwent extensive training in the use of standardized vocabulary to describe the appearance, aroma, flavor, and texture of a variety of products. Data collection was conducted over a period of seven days, with panelists evaluating two samples on each day of testing. Two evaluations were obtained from each panelist for each compound yielding a total of 20 evaluations per compound. During the data collection, the panelists were give a list of attributes and instructed to indicate the intensity of each attribute by indicating the intensity on a 15-point linescale. The intensity was evaluated for the following time periods: in-mouth, after expectoration, and 30 seconds, 1, 2, 5, 10, 15, 30, 45, and 60 minutes into the aftertaste period.

Compounds 102, 103, and 105 were prepared as 5 μM solutions and Compound 104 and Comparative Compound 1 were prepared in 3 μM solutions. 15 mL aliqouts of the test solutions were administered to Panelists in 1 oz. plastic cups coded with a random 3-digit code. The Panelists refrained from brushing their teeth, eating, and drinking one hour before each evaluation. Mean intensities were calculated based on the Panelists responses for each sensory characteristic. The sensory characteristics evaluated were bitter, icy cool in mouth, numbing, cooling breathe in, total burning, alcohol burning, pepperine/capsaicin, tingling, and total trigeminal impact. For each sensory characteristic, the scale of the intensity was designed to cover a range encompassing the universe of products having the indicated sensory characteristic.

After mean intensities for each attribute were calculated, statistical significance for each mean intensity was calculated using analysis of variance (ANOVA) followed by Duncan's multiple comparison test at an alpha level of 5%. Duncan's multiple comparison test provides a set of significance levels in which each the values in each level have been found not to be significantly different from one another while the values in one level will be statistically different from those in another level. In the results provided herein, the Duncan's levels are reported as Levels A, B, and C.

Numbing

Panelists were asked to assess the intensity of numbing sensation for Compounds 102 and 103 and Comparative Compound 1. The results are provided in Table 7 below. The average total numbing after expectoration to 60 minutes was lower for both 5 μM Compound 102 and 5 μM Compound 103 as compared to 3 μM Comparative Compound 1.

TABLE 7

Average Numbing (after expectoration to 60 minutes)

| Treatment | Average | Duncan's (5%) |
|---|---|---|
| 5 µM Compound 102 | 1.4 | AB |
| 5 µM Compound 103 | 1.3 | A |
| 3 µM Comparative Compound 1 | 1.5 | B |

Total Burning

Panelists were asked to assess the intensity of both capsaicin-like burning and Alcohol-like Burning sensations for Compounds 102 and 103 and Comparative Compound 1. Capsaicin-like burning is the sensation of warming or burning in the mouth, reminiscent of black pepper or hot sauce while alcohol-like burning is the sensation of warming or burning in the mouth, reminiscent of an alcohol burn. The combination of the intensity of these sensations was used to assess the total burning for the tested compounds. The results are provided in Table 8 below. The average total burning after expectoration to 60 minutes was lower for both 5 µM Compound 102 and 5 µM Compound 103 as compared to 3 µM Comparative Compound 1.

TABLE 8

Average Total Burning (after expectoration to 60 minutes)

| Treatment | Average | Duncan's (5%) |
|---|---|---|
| 5 µM Compound 102 | 0.9 | A |
| 5 µM Compound 103 | 0.9 | A |
| 3 µM Comparative Compound 1 | 1.1 | B |

Tingling

Panelists were asked to assess the intensity of tingling sensation for Compounds 102 and 103 and Comparative Compound 1. The results are provided in Table 9 below. The average total tingling after expectoration to 60 minutes was lower for both 5 µM Compound 102 and 5 µM Compound 103 as compared to 3 µM Comparative Compound 1.

TABLE 9

Average Tingling (after expectoration to 60 minutes)

| Treatment | Average | Duncan's (5%) |
|---|---|---|
| 5 µM Compound 102 | 0.6 | A |
| 5 µM Compound 103 | 0.6 | AB |
| 3 µM Comparative Compound 1 | 0.7 | BC |

Trigeminal Impact

The total intensity of trigeminal nerve feeling factors on the soft tissues of the mouth, including numbing, cooling (without breathing in), irritation, warming, burning, and tingling were determined for Compounds 102 and 103 and Comparative Compound 1. The results are provided in Table 10 below. The average total trigeminal impact after expectoration to 60 minutes was lower for both 5 µM Compound 102 and 5 µM Compound 103 as compared to 3 µM Comparative Compound 1.

TABLE 10

Average Total Trigeminal Impact (after expectoration to 60 minutes)

| Treatment | Average | Duncan's (5%) |
|---|---|---|
| 5 µM Compound 102 | 2.4 | A |
| 5 µM Compound 103 | 2.3 | A |
| 3 µM Comparative Compound 1 | 2.8 | B |

Icy Cool in Mouth (after Expectoration to 60 Minutes)

Icy cool in mouth is the sensation of coolness of the mouth, perceived with the mouth closed, not related to the temperature of the sample. Panelists were asked to assess the sensation of icy cool in mouth for Compound 104 and Compound 105 from the time immediately after expectoration of the sample through 60 minutes after expectoration. The results providing the average Icy Cool after expectoration to 60 minutes are provided in Table 11 below. The average Icy Cool after expectoration to 60 minutes was higher for both 5 µM Compound 105 and 3 µM Compound 104 as compared to 3 µM Comparative Compound 1.

TABLE 11

Average Icy Cool In Mouth (after expectoration to 60 minutes)

| Treatment | Average | Duncan's (5%) |
|---|---|---|
| 3 µM Compound 104 | 2.3 | C |
| 5 µM Compound 105 | 2.3 | C |
| 3 µM Comparative Compound 1 | 2.1 | B |

Icy Cool in Mouth (in Mouth and Immediately after Expectoration)

Panelists were additionally asked to assess the sensation of icy cool in mouth for Compound 104 and Compound 105 for the time while the sample was in the mouth and for the moment immediately after expectoration. The results for the average icy cool while in the mouth and after expectoration is also provided in Table 12 below. The average icy cool in mouth and immediately after expectoration was higher for both 5 µM Compound 105 and 3 µM Compound 104 as compared to 3 µM Comparative Compound 1.

TABLE 12

Average Icy Cool In Mouth and Immediately After Expectoration

| Treatment | Average | Duncan's (5%) |
|---|---|---|
| 3 µM Compound 104 | 2.0 | B |
| 5 µM Compound 105 | 1.9 | AB |
| 3 µM Comparative Compound 1 | 1.8 | AB |

Cooling Breath in (after Expectoration to 60 Minutes)

Cooling Breath In is the sensation of coolness of the mouth, when inhaling through the mouth, not related to the temperature of the sample. Panelists were asked to assess the sensation of Cooling Breath In for Compound 104 and Compound 105 from the time immediately after expectoration of the sample through 60 minutes after expectoration. The results are shown in Table 13 below. The average cooling breathe in after expectoration to 60 minutes was higher for both 5 µM Compound 105 and 3 µM Compound 104 as compared to 3 µM Comparative Compound 1.

TABLE 13

Average Cooling Breath In (after expectoration to 60 minutes)

| Treatment | Average | Duncan's (5%) |
|---|---|---|
| 3 μM Compound 104 | 2.7 | C |
| 5 μM Compound 105 | 2.7 | C |
| 3 μM Comparative Compound 1 | 2.5 | B |

Bitterness

Panelists assessed the bitterness of Compounds 102-105 and Comparative Compound 1 at the time point of 2 minutes after expectoration. The results are provided below in Table 14. The bitterness of each of 5 μM Compound 102, 5 μM Compound 103, 3 μM, Compound 104, and 5 μM Compound 105 was found to be lower than that of 3 μM Comparative Compound 1.

TABLE 14

Average Bitterness at 2 Minutes After Expectoration

| Sample | Bitterness Rating |
|---|---|
| 5 μM Compound 102 | 0.86 |
| 5 μM Compound 103 | 0.90 |
| 3 μM Compound 104 | 0.77 |
| 5 μM Compound 105 | 0.82 |
| 3 μM Comparative Compound 1 | 1.10 |

Although the foregoing has been described in some detail by way of illustrations and examples for purpose of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming within the true scope and spirit of the present disclosure.

What is claimed is:

1. A composition comprising:
   (a) at least one cooling agent compound selected from the group consisting of

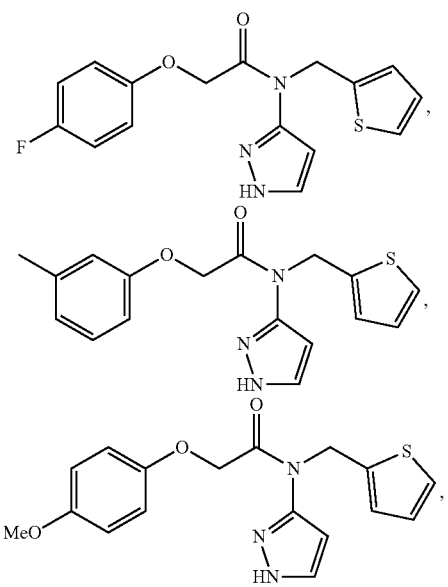

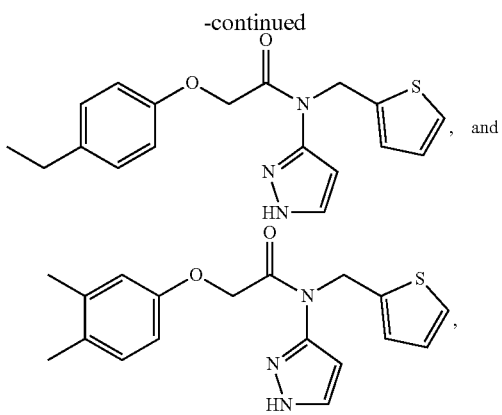

or a salt thereof, and
   (b) at least one additional cooling agent.

2. The composition of claim 1, wherein compound a) is

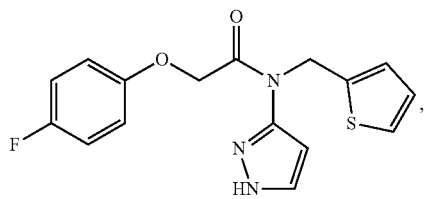 [SMILES: O=C(COc1ccc(F)cc1)N(Cc1cccs1)c1cc[nH]n1]

or a salt thereof.

3. The composition of claim 1, wherein compound a) is

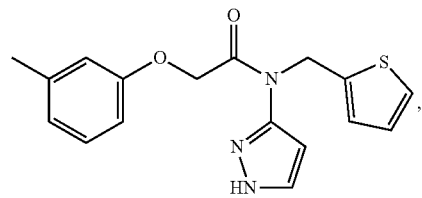 [SMILES: Cc1cccc(OCC(=O)N(Cc2cccs2)c2cc[nH]n2)c1]

or a salt thereof.

4. The composition of claim 1, wherein compound a) is

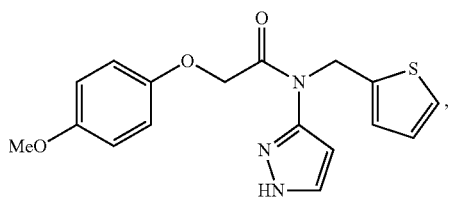

or a salt thereof.

5. The composition of claim 1, wherein compound a) is

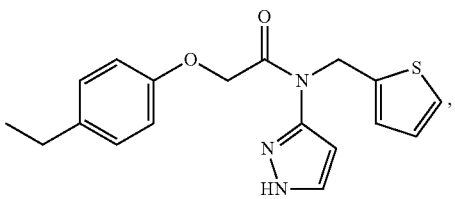 [SMILES: CCc1ccc(OCC(=O)N(Cc2cccs2)c2cc[nH]n2)cc1]

or a salt thereof.

6. The composition of claim 1, wherein compound a) is

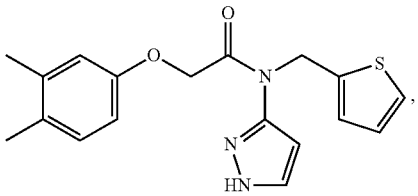 [SMILES: Cc1ccc(OCC(=O)N(Cc2cccs2)c2cc[nH]n2)cc1C]

or a salt thereof.

7. A composition, comprising a composition of claim 1 and at least one carrier.

8. The composition of claim 7, wherein the composition is an ingestible composition or a personal care product.

9. The composition of claim 7, wherein the composition is a food or beverage.

10. The composition of claim 7, wherein the composition is a topical personal care product.

11. The composition of claim 7, wherein composition is a solid, a semi-solid, a plaster, a solution, a suspension, a lotion, a cream, a foam, a gel, a paste, or an emulsion.

12. The composition of claim 7, wherein compound a) is in a concentration range of from about 0.0001 ppm to 100,000 ppm.

13. The composition of claim 7, wherein compound a) is in a concentration range of from about 1 to 500 ppm.

14. The composition of claim 7, which is a textile product or a packaging material.

15. A method of modulating transient receptor potential channel melastatin member 8 (TRPM8) comprising contacting the receptor with a composition of claim 1.

16. The method of claim 15, wherein component (a) of the composition of claim 1 is a TRPM8 receptor agonist.

17. The composition of claim 1, wherein compound b) is selected from the group consisting of: 2-isopropyl-N-2,3-trimethylbutyramide; N-ethyl-p-menthane-3-carboxamide; ethyl 3-(p-menthane-3-carboxamido)acetate; (1R,2S,5R)—N—O-methoxyphenyl)-p-menthanecarboxamide; N-ethyl-2,2-diisopropylbutanamide; N-cyclopropyl-5-methyl-2-isopropylcyclohexanecarboxamide; N-(1,1-dimethyl-2-hydroxyethyl)-2,2-diethylbutanamide); Menthoxy ethanol N-(4-cyanomethylphenyl)-p-menthanecarboxamide; N-(2-(Pyridin-2-yl)ethyl)-3-p-menthanecarboxamide; N-(2-Hydroxyethyl)-2-isopropyl-2,3-dimethylbutanamide; N-(4-(carbamoylmethyl)phenyl)-menthylcarboxamide; (1R,2S,5R)N-(4-Methoxyphenyl)-p-menthanecarboxamide; (2S,5R)—N-[4-(2-Amino-2-oxoethyl)phenyl]-p-menthanecarboxamide; 2-[(2-p-Menthoxy)ethoxy]ethanol; (2,6-Diethyl-5-isopropyl-2-methyltetrahydropyran; trans-4-tert-Butylcyclohexanol; 2-(p-tolyloxy)-N-(1H-pyrazol-5-yl)-N-((thiophen-2-yl)methyl)acetamide; Racemic N-isopropyl-5-methylcyclohexyl)cyclopropanecarboxamide; (−)-Menthol; (−)-Isopulegol; (−)-Menthyl lactate; 3-((−)-Menthoxy)propane-1,2-diol; (−)-Menthyl ethylene glycol carbonate; (−)-Menthone 1,2-glycerol ketal; DL-Menthone 1,2-glycerol ketal; (−)-Menthyl succinate; (−)-Menthyl 1&2 propylene glycol carbonates; (−)-Menthyl 1&2 propylene glycol carbonates; (−)-Menthyl glutarate; (+)-cis & (−)-trans p-menthane-3,8-diol; (−)-Menthyl pyrrolidone carboxylate; N,N-Dimethyl (−)-menthyl succinamide; (−)-Menthone (S)-lactic acid ketal; (−)-Menthyl (S)-3-hydroxybutyrate; (−)-Menthyl acetoacetate; (1R,2S,5R)—N-(4-(cyanomethyl) phenyl)menthylcarboxamide; (1R,4S,5R,6R,7S,10R)-7-isopropyl-4,10-dimethyl-tricyclo[4.4.0.0(1,5)]decan-4-ol; (1R,2S,5R)—N-(2-(pyridin-2-yl)ethyl)menthylcarboxamide; N-(2-Hydroxyethyl)-2,3-dimethyl-2-isopropylbutanamide; Di-(−)-menthyl glutarate; (1R,2S,5R)—N-(4-(carbamoylmethyl)phenyl)-menthylcarboxamide; 2-[2-(p-menthan-3-yloxy)ethoxy]ethanol; (1R,2R,4R)-1-(2-Hydroxy-4-methylcyclohexyl)ethanone; 2-(p-tolyloxy)-N-(1H-pyrazol-5-yl)-N-((thiophen-2-yl)methyl)acetamide; N-(2-hydroxyethyl)-2,3-dimethyl-2-isopropylbutyramide; ((1R,2S,5R)—N-(4-Methoxyphenyl)-p-menthanecarboxamide); (−)-Menthoxypropane-1,2-diol; 3-(1-Menthoxy)-2-methylpropane-1,2-diol; (−)-Isopulegol; (−)-Isopulegol; menthyl lactate and menthoxypropanediol; (cis)-p-Menthane-3,8-diol; (trans)-p-Menthane-3,8-diol; 2,3-dihydroxy-p-menthane; 3,3,5-trimethylcyclohexanone glycerol ketal; menthyl pyrrolidone carboxylate; (1R,3R,4S)-3-menthyl-3,6-dioxaheptanoate; (1R,2S,5R)-3-menthyl methoxyacetate; (1R,2S,5R)-3-menthyl 3,6,9-trioxadecanoate; (1R,2S,5R)-3-menthyl 3.6,9-trioxadecanoate; (1R,2S,5R)-3-menthyl (2-hydroxyethoxy)acetate; (1R,2S,5R)-menthyl 11-hydroxy-3,6,9-trioxaundecanoate; p-menthane carboxamides; (−)-Menthoxypropane-1,2-diol; 6-isopropyl-3,9-dimethyl-1,4-dioxaspiro[4.5]decan-2-one; N-benzo[1,3] dioxol-5-yl-3-p-menthanecarboxamide; N-benzooxazol-4-yl-3-p-menthanecarboxamide; N-4-([1,2,4]triazol-1-yl)-phenyl-3-p-menthanecarboxamide; N-4-(pyrazol-1-yl)-phenyl-3-p-menthanecarboxamide; N-(1-isopropyl-1,2-dimethylpropyl)-1,3-benzodioxole-5-carboxamide; L-Phenylephrine p-menthane carboxamide; 2,2,5,6,6-pentamethyl-2,3,6,6a-tetrahydropentalen-3 a(1H)-ol; 5-(2-hydroxy-2-methylpropyl)-3,4,4-trimethylcyclopent-2-en-1-one; (2S,5R)-2-isopropyl-5-methyl-N-(2-(pyridin-4-yl) ethyl)cyclohexanecarboxamide; 5-methyl-2-(propane-2-yl) cyclohexyl-N-ethyloxamate; (1R,2S,5R)-5-methyl-2-(propane-2-yl)cyclohexyl-N-ethyloxamate; 2,4-decadienoic acid-N-isobutylamide; N-[[5-methyl-2-(1-methylethyl)cyclohexyl]-carbonylglycine ethyl ester; menthyl-3-hydroxy butyrate; menthyl-3-oxo butyrate; menthyl-3-oxo pentanoate; menthyl lactate; menthone glycerine acetal; menthol glycol carbonate; menthol propyleneglycol carbonate; menthol glycerin carbonate; 1-menthyl-3-hydroxy butyrate; trans-pellitorin; cis-pellitorin; peppermint oil; 1,2-propylene glycol; diethyl malonate; N-ethyl-p-menthane-3-carboxamide; trimethyl isopropyl butanamide; 1S,2S,5R)—N-(4-(cyanomethyl)phenyl)-2-isopropyl-5-methylcyclohexanecarboxamide; (1S,2S,5R)-2-isopropyl-5-methylcyclohexyl-2(S)-acetoxypropanoate; 1-isopropyl-4-methyl-bicyclo[2.2.1oct-5-ene-2,3-dicarbinol; 4-methoxy-N-phenyl-N-[2-(pyridin-2-yl)ethyl]benzamide; 4-methoxy-N-phenyl-N-[2-(pyridin-2-yl)ethyl]benzenesulfonamide; 4-chloro-N-phenyl-N-[2-(pyridin-2-yl)ethyl]benzenesulfonamide; 4-cyano-N-phenyl-N-[2-(pyridin-2-yl)ethyl]benzenesulfonamide; 2,6-diethyl-5-isopropyl-2-methyl tetrahydropyran; 6-ethyl-5-isopropenyl-2-methyl-2-vinyltetrahydropyran; 2,6-dimethyl-5-isopropyl-2-ethyltetrahydropyran; 2,6-dimethyl-5-isopropenyl-2-vinyltetrahydropyran; 2,6-diethyl-5-sec-butyl-2-methyltetrahydropyran; 2,6-dimethyl-5-sec-butyl-2-ethyltetrahydropyran, 4-((benzhydrylamino)methyl)-2-methoxyphenol; 4-((bis(4-methoxyphenyl)-methylamino)-methyl)-2-methoxyphenol; 4-((1,2-diphenylethylamino) methyl)-2-methoxyphenol; 4-((benzhydryloxy)methyl)-2-methoxyphenol; 4-((9H-fluoren-9-ylamino)methyl)-2-methoxyphenol; 4-((benzhydrylamino)methyl)-2-ethoxyphenol; 1-(4-methoxyphenyl)-2-(1-methyl-1H-benzo [d]imidazol-2-yl)vinyl4-methoxybenzoate; 2-(1-isopropyl-6-methyl-1H-benzo[d]imidazol-2-yl)-1-(4-methoxyphenyl) vinyl4-methoxybenzoate; (Z)-2-(1-isoprop yl-5-methyl-1H- benzo[d]imidazol-2-yl)-1-(4-methoxy-phenyl)vinyl-4-methoxybenzoate; N-(1-methyl-1-isopropylbutyl) benzamide; fenchyl; D-bornyl; L-bornyl, exo-norbornyl; 2-methylisobornyl; 2-ethylfenchyl; 2-methylbornyl; cis-pinan-2-yl; verbanyl; isobornyl; menthyl oxamate and derivatives thereof; 4-oxo-4-((1R,2R,4R)-1,7,7-trimethylbicyclo[2.2.1]heptan-2-yloxy)butanoic acid; L-menthyl 3-oxobutyrate; L-menthyl 3-oxopentanoate; 3,4-methylenedioxycinnamic acid, N,N-diphenylamide; (−)-(R,2R,4S)-dihydroumbellulol; (1R,2R,5R)—N-ethyl-5-methyl-2-(prop-1-en-2-yl)cyclohexanecarboxamide; 3-menthoxy-1-propanol; 1-menthoxy-2-propanol; 1-[2-hydroxyphenyl]-4-[2-nitrophenyl-]-1,2,3,6-tetrahydropyrimidine-2-one); 4-methyl-3-(1-pyrrolidinyl)-2[5H]-furanone; 5-methyl-4-(1-pyrrolidinyl)-3-[2H]-furanone; 4,5-dimethyl-3-(1-pyrrolidinyl)-2[5H]-furanone; menthyl oxamate; menthyl N-methyl oxamate; menthyl N,N-dimethyl oxamate; menthyl N-ethyl oxamate; menthyl N,N-diethyl oxamate; menthyl N-propyl oxamate; menthyl N,N-dipropyl oxamate; menthyl N-isopropyl oxamate; menthyl N,N-diisopropyl oxamate; menthyl N-cyclopropyl oxamate; menthyl N-butyl oxamate; morpholin-4-yl-oxo-acetic acid; (1R,2S,5R)-2-isopropyl-5-methylcyclohexyl ester; menthyl N-(2-methoxyethyl)oxamate; menthyl N-(3-methoxypropanol) oxamate; menthyl N-(2-hydroxyethyl)oxamate; L-menthyl N-methyl oxamate; D-menthyl N-methyl oxamate; rac-menthyl N-methyl oxamate; L-menthyl N-ethyl oxamate; D-menthyl N-ethyl oxamate; rac-menthyl N-ethyl oxamate; menthyl N-(3-hydroxypropyl)oxamate; and combinations thereof.

18. The composition of claim 1, wherein compound b) is selected from the group consisting of: 5-methyl-2-(propane-2-yl)cyclohexyl-N-ethyloxamate; N-ethyl-p-menthane carboxamide; N-2,3-trimethyl-2-isopropyl butane amide; menthyl lactate; menthone glycerine acetal; mono-menthyl succinate; mono-menthyl glutarate; O-menthyl-glycerine; menthyl-N,N-dimethyl succinamate; N-(4-cyano methyl phenyl)-p-menthane carboxamide; N-(2 (pyridin-2-yl) ethyl)-3-p-menthane carboxamide menthol; L-menthol; D-menthol; racemic menthol; isomenthol; neoisomenthol; neomenthol; 1-menthoxy)-1,2-propanediol; (1-menthoxy)-2-methyl-1,2-propanediol; 1-menthyl-methyl ether; menthyl formiate; menthyl acetate; menthyl isobutyrate; menthyl lactates; L-menthyl-L-lactate; L-menthyl-D-lactate; menthyl-(2-methoxy)acetate; menthyl-(2-methoxy ethoxy)acetate; menthyl pyroglutamate; N-(4-cyano methyl phenyl)-p-menthane carboxamide; N-(2-(pyridin-2-yl)ethyl)-3-p-menthane carboxamides; menthyl propylene glycol carbonate; menthol ethylene glycol carbonate; menthyl glycerine carbonate; menthane carboxylic acid-N-ethylamide; N-alpha.-(menthane-carbonyl)glycine ethyl ester; menthane carboxylic acid-N-(4-cyanophenyl)amide; menthane carboxylic acid-N-(alkoxyalkyl)amide); menthone; L-menthone glycerine ketal; 2,3-dimethyl-2-(2-propyl)-butyric acid-N-methyl amide; isopulegol; 1-(−)-isopulegol; 1-(−)-isopulegol acetate; p-menthane-3,8-diol; N-(4-cyano methyl phenyl)-p-menthane carboxamides; N-(2-(pyridin-2-yl) ethyl)-3-p-menthane carboxamides; cubebol; 3-methyl-2(1-pyrrolidinyl)-2-cyclopentene-1-one; or tetrahydropyrimidine-2-one); N-(4-cyano methyl phenyl)-p-menthane carboxamide; N-(2-(pyridin-2-yl)ethyl)-3-p-menthane carboxamide; (1-menthoxy)-1,2-propanediol; (1-menthoxy)-2-methyl-1,2-propanediol; menthyl lactate; L-menthyl-L-lactate; L-menthyl-D-lactate; menthyl-(2-methoxy)acetate; menthyl-(2-methoxy ethoxy)acetate; menthyl pyroglutamate; menthyl propylene glycol carbonate; menthyl ethylene glycol carbonate; menthyl glycerine carbonate; mono-menthyl succinate; mono-menthyl glutarate; mono-menthyl malonate; O-menthyl succinic acid ester-N,N-(dimethyl) amide; O-menthyl succinic acid ester amide; 3,4-methylendioxycinnamic acid-N-cyclohexyl-N-2-pyridylamide; isopropyl-(5-methoxy-2-pyridin-2-yl-pyrimidin-4-yl)-amine; 3,4,6,7,11b,12-hexahydro-3,3-dimethyl-spiro[13H-dibenzo[a,f]quinolizine-1-3,2'-[1,3]dithiolan]-1(2H)-one; 5,6,10b,11-tetrahydro-3-methyl-spiro[12H-benzo[a]furo[3,4-f]quinolizine-1-2,2'-[1,3]dithiolan]-1(3H)-one; and combinations thereof.

19. The composition of claim 1, wherein compound b) is selected from the group consisting: of 5-methyl-2-(propane-2-yl)cyclohexyl-N-ethyloxamate; N-ethyl-p-menthane carboxamide; menthyl lactate; menthane glycerine acetal; N-(4-cyano methyl phenyl)-p-menthane carboxamide; (1-menthoxy)-1,2-propanediol; and combinations thereof.

20. The composition of claim 1, further comprising:
c) at least one pharmaceutically acceptable excipient.

21. A method of modulating a cooling sensation of a composition, the method comprising combining the composition with a composition of claim 1 to form a modified composition.

22. A method of inducing a cooling sensation in a human or an animal, the method comprising contacting the human or the animal with the composition of claim 1.

* * * * *